United States Patent
Busujima et al.

(10) Patent No.: US 9,035,059 B2
(45) Date of Patent: May 19, 2015

(54) NITROGEN-CONTAINING CONDENSED HETEROCYCLIC COMPOUND

(75) Inventors: Tsuyoshi Busujima, Toshima-ku (JP); Takahiro Oi, Toshima-ku (JP); Hiroaki Tanaka, Toshima-ku (JP); Yoshihisa Shirasaki, Toshima-ku (JP); Kanako Iwakiri, Toshima-ku (JP); Nagaaki Sato, Toshima-ku (JP); Shigeru Tokita, Toshima-ku (JP)

(73) Assignee: TAISHO PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/004,950

(22) PCT Filed: Mar. 14, 2012

(86) PCT No.: PCT/JP2012/056600
§ 371 (c)(1),
(2), (4) Date: Sep. 13, 2013

(87) PCT Pub. No.: WO2012/124744
PCT Pub. Date: Sep. 20, 2012

(65) Prior Publication Data
US 2014/0005382 A1 Jan. 2, 2014

(30) Foreign Application Priority Data
Mar. 14, 2011 (JP) ................................. 2011-056015

(51) Int. Cl.
C07D 401/14 (2006.01)
C07D 209/44 (2006.01)
(Continued)

(52) U.S. Cl.
CPC ............ *C07D 217/18* (2013.01); *C07D 209/44* (2013.01); *C07D 217/04* (2013.01); *C07D 217/06* (2013.01); *C07D 217/22* (2013.01); *C07D 223/16* (2013.01); *C07D 401/06* (2013.01); *C07D 401/10* (2013.01); *C07D 401/12* (2013.01); *C07D 403/12* (2013.01); *C07D 405/06* (2013.01); *C07D 413/12* (2013.01); *C07D 417/06* (2013.01); *A61K 9/1623* (2013.01); *A61K 9/2018* (2013.01); *A61K 9/4858* (2013.01); *C07D 217/20* (2013.01); *C07D 217/26* (2013.01); *C07D 405/12* (2013.01); *C07D 405/14* (2013.01);
(Continued)

(58) Field of Classification Search
None
See application file for complete search history.

(56) References Cited

U.S. PATENT DOCUMENTS

| 6,602,867 | B1* | 8/2003 | Starck et al. ............. 514/217.07 |
| 2005/0148631 | A1 | 7/2005 | Cheng et al. | |

(Continued)

FOREIGN PATENT DOCUMENTS

| JP | 9512275 | 12/1997 |
| JP | 2007514731 | 6/2007 |

(Continued)

OTHER PUBLICATIONS

STN Online, Registry File, RN=1350261-72-1, dated Dec. 7, 2011.
(Continued)

*Primary Examiner* — Zinna Northington Davis
(74) *Attorney, Agent, or Firm* — Sughrue Mion, PLLC

(57) ABSTRACT

There are provided compounds represented by the following general formula (I) or pharmaceutically acceptable salts of thereof, which have a superior monoacylglycerol acyltransferase 2 inhibitory action:

[Formula 1]

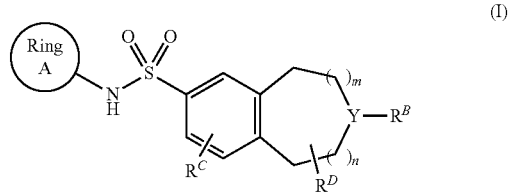

(I)

wherein
Ring A represents a partially saturated heteroaryl group, an aryl group or a heteroaryl group,
$R^B$ represents a $C_{4-18}$ alkyl group, a $C_{3-8}$ cycloalkyl group, a partially saturated aryl group, an aryl group, or the following formula (II):

[Formula 2]

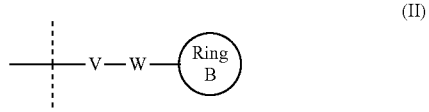

(II)

wherein
V represents the formula $-CR^{11}R^{12}-$, $-CO-$, $-CO-O-$, or $-CO-NH-$,
W represents a single bond or a $C_{1-3}$ alkylene group, and
Ring B represents a $C_{3-8}$ cycloalkyl group, a $C_{3-8}$ cycloalkenyl group, a partially saturated heteroaryl group, a saturated heterocyclyl group, an aryl group, or a heteroaryl group,
Y represents a nitrogen atom or the formula $N^+(R^F)$, $R^F$ represents a $C_{1-4}$ alkyl group, and
m and n, which may be the same or different, each represent an integer of 0 or 1.

15 Claims, No Drawings

(51) Int. Cl.

| | | |
|---|---|---|
| *C07D 217/04* | (2006.01) | |
| *C07D 223/16* | (2006.01) | |
| *C07D 405/12* | (2006.01) | |
| *C07D 409/06* | (2006.01) | |
| *C07D 413/06* | (2006.01) | |
| *C07D 417/10* | (2006.01) | |
| *A61K 31/4035* | (2006.01) | |
| *A61K 31/454* | (2006.01) | |
| *A61K 31/472* | (2006.01) | |
| *A61K 31/497* | (2006.01) | |
| *C07D 217/18* | (2006.01) | |
| *C07D 217/06* | (2006.01) | |
| *C07D 217/22* | (2006.01) | |
| *C07D 401/06* | (2006.01) | |
| *C07D 401/10* | (2006.01) | |
| *C07D 401/12* | (2006.01) | |
| *C07D 403/12* | (2006.01) | |
| *C07D 405/06* | (2006.01) | |
| *C07D 413/12* | (2006.01) | |
| *C07D 417/06* | (2006.01) | |
| *A61K 9/16* | (2006.01) | |
| *A61K 9/20* | (2006.01) | |
| *A61K 9/48* | (2006.01) | |
| *C07D 217/20* | (2006.01) | |
| *C07D 217/26* | (2006.01) | |
| *C07D 405/14* | (2006.01) | |
| *C07D 409/14* | (2006.01) | |
| *C07D 417/12* | (2006.01) | |
| *C07D 417/14* | (2006.01) | |
| *C07D 495/04* | (2006.01) | |
| *C07D 217/10* | (2006.01) | |
| *C07D 401/08* | (2006.01) | |

(52) U.S. Cl.
CPC ............ *C07D 409/06* (2013.01); *C07D 409/14* (2013.01); *C07D 413/06* (2013.01); *C07D 417/10* (2013.01); *C07D 417/12* (2013.01); *C07D 417/14* (2013.01); *C07D 495/04* (2013.01); *C07D 401/14* (2013.01); *C07D 217/10* (2013.01); *C07D 401/08* (2013.01)

(56) References Cited

U.S. PATENT DOCUMENTS

2010/0093771 A1 4/2010 Nakamura et al.
2011/0275647 A1 11/2011 Arakawa et al.

FOREIGN PATENT DOCUMENTS

| JP | 2008540539 | 11/2008 |
|---|---|---|
| WO | 9529159 | 11/1995 |
| WO | WO 2005/058328 A1 * | 6/2005 |
| WO | 2006051662 | 5/2006 |
| WO | 2006095822 | 9/2006 |
| WO | 2006122014 | 11/2006 |
| WO | 2008038768 | 4/2008 |
| WO | 2010095767 | 8/2010 |
| WO | 2012013716 | 2/2012 |

OTHER PUBLICATIONS

STN Online, Registry File, RN=1349442-17-6, dated Dec. 6, 2011.
STN Online, Registry File, RN=1349009-85-3, dated Dec. 5, 2011.
International Preliminary Report on Patentability for PCT/JP2012/056600 dated Sep. 17, 2013, with Written Opinion.
Communication for European Patent Application No. 12757861.5 dated Oct. 31, 2014, with Supplementary European Search Report (dated Oct. 1, 2014).

* cited by examiner

NITROGEN-CONTAINING CONDENSED HETEROCYCLIC COMPOUND

CROSS REFERENCE TO RELATED APPLICATIONS

This application is a National Stage of International Application No. PCT/JP2012/056600 filed Mar. 14, 2012, claiming priority based on Japanese Patent Application No. 2011-056015 filed Mar. 14, 2011, the contents of all of which are incorporated herein by reference in their entirety.

TECHNICAL FIELD

The present invention relates to compounds having an inhibitory action against monoacylglycerol acyltransferase 2 (hereinafter, sometimes abbreviated as MGAT2).

BACKGROUND ART

Neutral fats (sometimes referred to as triglycerol or triacylglycerol. Hereinafter, sometimes abbreviated as TG or TAG) are synthesized primarily in the small intestine, the liver and adipose tissues. Dietary-derived fats are degraded in the gastrointestinal tract and then taken up by small-intestinal epithelial cells. After resynthesis into neutral fats in the cells, the neutral fats are packaged into chylomicrons and secreted into the lymphatics. The secreted chylomicrons are degraded by lipoprotein lipase primarily into free fatty acids and chylomicron remnants. The free fatty acids are taken up by peripheral tissues such as skeletal muscles and utilized as energy, or an excess of the free fatty acids is taken up by adipose tissues, resynthesized into neutral fats, and then accumulates. On the other hand, the chylomicron remnants are taken up by chylomicron remnant receptors in the liver and degraded. In the liver, degraded fats are resynthesized into neutral fats, packaged into lipoproteins and secreted. In this way, living bodies sequentially metabolize fats primarily in the liver, the small intestine and adipose tissues to maintain the homeostasis of neutral fats in the blood.

However, the homeostasis is disrupted when dietary-derived fats excessively enter the body because of nutritional excess in recent years. As a result, neutral fat synthesis is excessively increased, which causes obesity. Further, enlarged fat cells characterized by obesity secrete malignant, physiologically active substances including TNFα, cause insulin resistance and gluconeogenesis, and induce type II diabetes.

Although superior antiobesity agents are desired, there is currently no drug satisfactory in terms of drug efficacy and safety. Orlistat, a fat absorption inhibitor, causes gastrointestinal symptoms including steatorrhea, and sibutramine, an anorexiant, has cardiovascular adverse effects. For these reasons, the development of drugs better in terms of both drug efficacy and safety is desired.

These days, the mechanisms of neutral fat synthesis and fat absorption in small-intestinal epithelial cells are being elucidated. 2-Monoacylglycerol and free fatty acids which are formed by degradation in the gastrointestinal tract by pancreatic lipase are each absorbed into small-intestinal epithelial cells. Next, the acyl group of the free fatty acid is transferred to 2-monoacylglycerol by monoacylglycerol acyltransferase. Further, diacylglycerol produced is converted into neutral fats by diacylglycerol acyltransferase (hereinafter, sometimes abbreviated as DGAT).

In 2003, the clonings of mouse MGAT2 and human MGAT2 were successively reported (see Non-Patent Documents 1 and 2). The enzyme was found to be expressed in small-intestinal epithelial cells and to exhibit MGAT activity that transfers an acyl group to 2-monoacylglycerol. Based on this finding, it was speculated that the enzyme might be responsible for MGAT activity in small-intestinal epithelial cells.

In 2004, high-fat feeding was reported to increase MGAT2 expression in the small intestine (see Non-Patent Document 3). In proportion thereto, the increase of MGAT activity in the small intestine was also observed.

In 2010, MGAT2 knockout mice were reported (see Non-Patent Document 4). The mice have been found to be free of abnormal general findings. Further, based on the finding that fat absorption was delayed in the mice, MGAT2 was confirmed as MGAT that plays a major role in fat absorption in small-intestinal epithelial cells. The knockout mice, when fed on a normal diet, had no difference in body weight from normal mice. However, in the MGAT2 knockout mice fed on a high-fat diet, body weight increase, which was observed in normal mice, was strongly inhibited. Moreover, increases of blood cholesterol and fatty liver, which are to be caused by high-fat feeding, were inhibited. Induction of impaired glucose tolerance was also inhibited.

Based on these findings, it is speculated that a substance inhibiting MGAT2 (hereinafter referred to as MGAT2-inhibiting substance or MGAT2 inhibitor) can inhibit neutral fat synthesis in small-intestinal epithelial cells and can inhibit or delay fat absorption. Further, in the modern society, which is characterized by nutritional excess and insufficient exercise, an MGAT2-inhibiting substance is expected to serve as an ideal antiobesity agent or antihyperlipidemic agent that has a strong body weight-lowering effect. An MGAT2-inhibiting substance is also expected to inhibit the progress of type II diabetes, which is induced by obesity. In addition, long-term administration of an MGAT2-inhibiting substance is expected to correct or prevent arteriosclerosis, fatty liver and hypertension.

As MGAT2 inhibitors, compounds having a bicyclic pyrimidine skeleton are reported (see Patent Documents 1 and 2). Further, as Na channel blockers unrelated to MGAT2 inhibitors, compounds having a nitrogen-containing condensed heterocyclic structure are reported; however, the compounds of the present invention as shown below are not disclosed (see Patent Document 3).

CITATION LIST

Patent Documents

Patent Document 1: WO 2008/038768
Patent Document 2: WO 2010/095767
Patent Document 3: WO 2006/122014

Non-Patent Documents

Non-Patent Document 1: The Journal of Biological Chemistry, 2003, 278, 16, 13860
Non-Patent Document 2: The Journal of Biological Chemistry, 2003, 278, 20, 18532
Non-Patent Document 3: The Journal of Biological Chemistry, 2004, 279, 18, 18878
Non-Patent Document 4: Nature Medicine, 2009, 15, 4, 442

SUMMARY OF INVENTION

Technical Problem

The present invention aims to provide novel compounds or pharmaceutically acceptable salts thereof which have a superior MGAT2 inhibitory action.

Solution to Problem

As a result of extensive and intensive studies to achieve the object mentioned above, the present inventors found that compounds represented by the following general formula (I) have a superior MGAT2 inhibitory action.

The present invention will be described below in detail. Embodiments of the present invention (hereinafter each referred to as "the inventive compound") are as follows. More specifically, (1) the present invention provides a compound represented by the following general formula (I) or a pharmaceutically acceptable salt thereof:

[Formula 1]

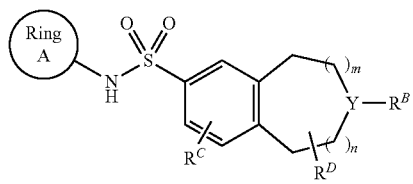

(I)

wherein
Ring A represents a partially saturated heteroaryl group which may be substituted by 1 or 2 substituents, which may be the same or different, selected from the group consisting of:
  a $C_{1-8}$ alkyl group, and
  an oxo group,
an aryl group or a heteroaryl group, which aryl group and heteroaryl group may be each substituted by 1 to 3 substituents, which may be the same or different, selected from the group consisting of (i) to (vii) below:
  (i) a halogen atom,
  (ii) a hydroxy group,
  (iii) a $C_{1-8}$ alkyl group which may be substituted by 1 to 3 substituents, which may be the same or different, selected from the group consisting of:
    a hydroxy group,
    a halogen atom,
    a $C_{1-8}$ alkoxy group which may be substituted by one saturated heterocyclyl group,
    a $C_{3-8}$ cycloalkyl group,
    a saturated heterocyclyl group, and
    an aryl group,
  (iv) a $C_{1-8}$ alkoxy group which may be substituted by 1 to 3 substituents, which may be the same or different, selected from the group consisting of:
    (iv-1) a halogen atom,
    (iv-2) an oxo group,
    (iv-3) a $C_{3-8}$ cycloalkyl group,
    (iv-4) a saturated heterocyclyl group which may be substituted by 1 or 2 substituents, which may be the same or different, selected from the group consisting of:
      a halogen atom,
      a $C_{1-8}$ alkyl group, and
      an oxo group,
    (iv-5) an aryl group,
    (iv-6) a heteroaryl group,
    (iv-7) a $C_{1-8}$ alkoxy group which may be substituted by 1 to 3 substituents, which may be the same or different, selected from the group consisting of:
      a halogen atom,
      a saturated heterocyclyl group, and
      a $C_{1-8}$ alkoxy group,
    (iv-8) a $C_{3-8}$ cycloalkyloxy group,
    (iv-9) an aryloxy group which may be substituted by one substituent selected from the group consisting of:
      a halogen atom,
      a $C_{1-8}$ alkyl group which may be substituted by 1 to 3 halogen atoms, and
      a $C_{1-8}$ alkoxy group,
    (iv-10) a $C_{1-8}$ alkylsulfonyl group, and
    (iv-11) an arylsulfonyl group,
  (v) a $C_{2-8}$ alkenyloxy group,
  (vi) a mono$C_{1-8}$ alkylamino group which may be substituted by one aryl group, and
  (vii) a di$C_{1-8}$ alkylamino group,
$R^B$ represents a $C_{4-18}$ alkyl group which may be substituted by 1 to 3 substituents, which may be the same or different, selected from the group consisting of:
  a halogen atom, and
  a $C_{3-8}$ cycloalkyl group,
a $C_{3-8}$ cycloalkyl group,
a partially saturated aryl group,
an aryl group, or
the following formula (II):

[Formula 2]

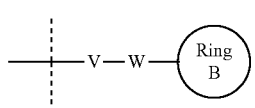

(II)

wherein
V represents the formula —$CR^{11}R^{12}$— (wherein $R^{11}$ and $R^{12}$, which may be the same or different, each represent a hydrogen atom or a $C_{1-4}$ alkyl group, or $R^{11}$ and $R^{12}$, taken together with the adjacent carbon atom, may form $C_{3-6}$ cycloalkane), —CO—, —CO—O— or —CO—NH—,
W represents a single bond or either a $C_{1-3}$ alkylene group which may be substituted by 1 or 2 substituents, which may be the same or different, selected from the group consisting of:
  a fluorine atom,
  an amino group which may be substituted by one $C_{1-4}$ alkyl group, and
  an oxo group, or
a $C_{1-3}$ alkylene group in which one carbon atom that forms the $C_{1-3}$ alkylene group may form a $C_{3-6}$ cycloalkane-1,1-diyl group, and
Ring B represents a $C_{3-8}$ cycloalkyl group which may be substituted by one $C_{1-8}$ alkyl group, a $C_{3-8}$ cycloalkenyl group which may be crosslinked with a $C_{1-4}$ alkanediyl group or may be substituted by one $C_{1-8}$ alkyl group,
a partially saturated heteroaryl group which may be substituted by 1 or 2 halogen atoms, a saturated heterocyclyl group, an aryl group or a heteroaryl group, which aryl group and heteroaryl group may be each substituted by 1 to 3 substituents, which may be the same or different, selected from the group consisting of:
  (a) a halogen atom,
  (b) a hydroxy group,
  (c) a $C_{1-8}$ alkyl group and a $C_{1-8}$ alkoxy group, which $C_{1-8}$ alkyl group and $C_{1-8}$ alkoxy group may be each substituted by 1 to 4 substituents, which may be the same or different, selected from the group consisting of:
    a halogen atom,
    a hydroxy group,
    a $C_{3-8}$ cycloalkyl group, and
    an aryl group,
  (d) a $C_{3-8}$ cycloalkyl group,
  (e) an aryl group and a heteroaryl group, which aryl group and heteroaryl group may be each substituted by 1 or 2 substituents, which may be the same or different, selected from the group consisting of:
    a halogen atom, and
    a $C_{1-8}$ alkyl group which may be substituted by 1 to 3 halogen atoms, and
  (f) a $C_{1-8}$ alkylsulfonyl group,
$R^C$ represents a hydrogen atom,
a halogen atom,
a $C_{1-4}$ alkyl group which may be substituted by 1 to 3 halogen atoms,
an aryl group, or
a heteroaryl group,
$R^D$ represents a hydrogen atom or a $C_{1-4}$ alkyl group which may be substituted by 1 to 3 halogen atoms,
Y represents a nitrogen atom or the formula $N^+(R^F)$,
$R^F$ represents a $C_{1-4}$ alkyl group, and
m and n, which may be the same or different, each represent an integer of 0 or 1, provided that the following compounds are excluded.
2-(4-fluorobenzoyl)-N-(thiazol-2-yl)isoindoline-5-sulfonamide,
2-(2-(1 H-indol-1-yl)propanoyl)-N-(thiazol-2-yl)isoindoline-5-sulfonamide,
2-(2-(6-chloro-3,4-dihydroquinolin-1(2 H)-yl)acetyl)-N-(pyrimidin-4-yl)isoindoline-5-sulfonamide,
2-(2-(7-chloro-1 H-indol-yl)acetyl)-N-(pyrimidin-4-yl)isoindoline-5-sulfonamide,
2-(2-(6-chloro-3,4-dihydroquinolin-1(2 H)-yl)propanoyl)-N-(1,2,4-thiadiazol-5-yl)isoindoline-5-sulfonamide,
(R)—N-(6-chloropyridazin-3-yl)-2-(2-(4-fluoro-1 H-indol-1-yl)propanoyl)isoindoline-5-sulfonamide,
(R)-2-(2-(4-fluoro-1 H-indol-1-yl)propanoyl)-N-(1,2,4-thiadiazol-5-yl)isoindoline-5-sulfonamide,
(S)-2-(2-(6-chloro-3,4-dihydroquinolin-1(2 H)-yl)propanoyl)-N-(5-methyl-1,3,4-thiadiazol-2-yl)isoindoline-5-sulfonamide,
(R)—N-(5-ethyl-1,3,4-thiadiazol-2-yl)-2-(2-(4-fluoro-1 H-indol-yl)propanoyl)isoindoline-5-sulfonamide,
2-(2-(6-chloro-3,4-dihydroquinolin-1(2 H)-yl)acetyl)-N-(1,2,4-thiadiazol-5-yl)isoindoline-5-sulfonamide,
(S)-2-(2-(4-fluoro-1 H-indol-1-yl)propanoyl)-N-(1,2,4-thiadiazol-5-yl)isoindoline-5-sulfonamide,
2-(3-(5-chloro-1 H-indol-1-yl)propanoyl)-N-(1,2,4-thiadiazol-5-yl)isoindoline-5-sulfonamide,
2-(2-(6-chloro-3,4-dihydroquinolin-1(2 H)-yl)propanoyl)-N-(5-ethyl-1,3,4-thiadiazol-2-yl)isoindoline-5-sulfonamide,
(S)-2-(2-(6-chloro-3,4-dihydroquinolin-1(2 H)-yl)propanoyl)-N-(6-chloropyridazin-3-yl)isoindoline-5-sulfonamide,
(S)-2-(2-(1 H-indol-1-yl)propanoyl)-N-(1,2,4-thiadiazol-5-yl)isoindoline-5-sulfonamide,
2-(3-(5-chloro-1 H-indol-1-yl)propanoyl)-N-(thiazol-2-yl)isoindoline-5-sulfonamide,
2-(2-(4-methoxyphenyl)acetyl)-N-(thiazol-2-yl)isoindoline-5-sulfonamide,
(S)-2-(2-(4-fluoro-1 H-indol-1-yl)propanoyl)-N-(pyrimidin-4-yl)isoindoline-5-sulfonamide,
(R)-2-(2-(1 H-indol-1-yl)propanoyl)-N-(1,2,4-thiadiazol-5-yl)isoindoline-5-sulfonamide,
2-(2-(7-chloro-1 H-indol-1-yl)acetyl)-N-(thiazol-2-yl)-1,2,3,4-tetrahydroisoquinoline-7-sulfonamide,
2-(2,4-difluorobenzoyl)-N-(thiazol-2-yl)-1,2,3,4-tetrahydroisoquinoline-7-sulfonamide,
2-(2,5-difluorobenzoyl)-N-(thiazol-2-yl)-1,2,3,4-tetrahydroisoquinoline-7-sulfonamide,
2-(4-fluorobenzoyl)-N-(thiazol-2-yl)-1,2,3,4-tetrahydroisoquinoline-7-sulfonamide,
2-(3-(5-chloro-1 H-indol-1-yl)propanoyl)-N-(thiazol-2-yl)-1,2,3,4-tetrahydroisoquinoline-7-sulfonamide,
2-(2-fluorobenzoyl)-N-(thiazol-2-yl)-1,2,3,4-tetrahydroisoquinoline-7-sulfonamide,
2-(2,4-dichlorobenzoyl)-N-(thiazol-2-yl)-1,2,3,4-tetrahydroisoquinoline-7-sulfonamide, and
2-(4-methoxybenzoyl)-N-(thiazol-2-yl)-1,2,3,4-tetrahydroisoquinoline-7-sulfonamide.

(2) Another embodiment of the present invention provides the compound of the general formula (I) above or pharmaceutically acceptable salt thereof according to (1) above, wherein Ring A is a partially saturated heteroaryl group which may be substituted by 1 or 2 substituents, which may be the same or different, selected from the group consisting of:
  a $C_{1-8}$ alkyl group, and
  an oxo group,
an aryl group or a heteroaryl group, which aryl group and heteroaryl group may be each substituted by 1 to 3 substituents, which may be the same or different, selected from the group consisting of:
  a halogen atom,
  a hydroxy group,
  a $C_{1-8}$ alkyl group which may be substituted by 1 to 3 substituents, which may be the same or different, selected from the group consisting of:
    a halogen atom,
    a $C_{3-8}$ cycloalkyl group, and
    an aryl group,
  a $C_{1-8}$ alkoxy group which may be substituted by 1 to 3 substituents, which may be the same or different, selected from the group consisting of:
    a halogen atom,
    an oxo group,
    a $C_{3-8}$ cycloalkyl group,
    a saturated heterocyclyl group which may be substituted by 1 or 2 substituents, which may be the same or different, selected from the group consisting of a $C_{1-8}$ alkyl group, and an oxo group,
    an aryl group,
    a heteroaryl group,
    a $C_{1-8}$ alkoxy group which may be substituted by one $C_{1-8}$ alkoxy group,
    a $C_{3-8}$ cycloalkyloxy group, and
    an aryloxy group which may be substituted by one substituent selected from the group consisting of a halogen atom, a $C_{1-8}$ alkyl group which may be substituted by 1 to 3 halogen atoms, and a $C_{1-8}$ alkoxy group,
    a $C_{2-8}$ alkenyloxy group, a mono$C_{1-8}$ alkylamino group which may be substituted by one aryl group, and a di$C_{1-8}$ alkylamino group, and $R^B$ is a $C_{4-18}$ alkyl group, a $C_{3-8}$ cycloalkyl group, a partially saturated aryl group, an aryl group, or the following formula (II):

[Formula 3]

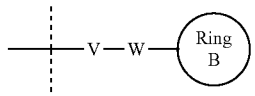

(II)

wherein

V represents the formula —$CR_{11}R^{12}$— (wherein $R^{11}$ and $R^{12}$ each represent a hydrogen atom or a $C_{1-4}$ alkyl group), —CO— or —CO—NH—, W represents a single bond or either a $C_{1-3}$ alkylene group which may be substituted by 1 or 2 substituents, which may be the same or different, selected from the group consisting of:

a fluorine atom, an amino group which may be substituted by one $C_{1-4}$ alkyl group, and an oxo group, or a $C_{1-3}$ alkylene group in which one carbon atom that forms the $C_{1-3}$ alkylene group may form a $C_{3-6}$ cycloalkane-1,1-diyl group, and Ring B represents a $C_{3-8}$ cycloalkyl group, a partially saturated heteroaryl group, an aryl group or a heteroaryl group, which aryl group and heteroaryl group may be each substituted by 1 to 3 substituents, which may be the same or different, selected from the group consisting of:

a halogen atom, a $C_{1-8}$ alkyl group and a $C_{1-8}$ alkoxy group, which $C_{1-8}$ alkyl group and $C_{1-8}$ alkoxy group may be each substituted by 1 to 3 substituents, which may be the same or different, selected from the group consisting of a halogen atom, a hydroxy group, and an aryl group, an aryl group, and a heteroaryl group, and Y is a nitrogen atom.

(3) Another embodiment of the present invention provides the compound of the general formula (I) above or pharmaceutically acceptable salt thereof according to (1) or (2) above, wherein $R^B$ is the formula (II).

(4) Another embodiment of the present invention provides the compound of the general formula (I) above or pharmaceutically acceptable salt thereof according to (1) above, wherein $R^B$ is the formula (II), V is the formula —$CR^{11}R^{12}$—, wherein $R^{11}$ and $R^{12}$, which may be the same or different, each represent a hydrogen atom or a $C_{1-4}$ alkyl group, or $R^{11}$ and $R^{12}$, taken together with the adjacent carbon atom, may form $C_{3-6}$ cycloalkane, m is 1, and n is 0.

(5) Another embodiment of the present invention provides the compound of the general formula (I) above or pharmaceutically acceptable salt thereof according to (3) above, wherein V is the formula —$CR^{11}R^{12}$—, wherein $R^{11}$ and $R^{12}$, which may be the same or different, each represent a hydrogen atom or a $C_{1-4}$ alkyl group, m is 1, and n is 0.

(6) Another embodiment of the present invention provides the compound of the general formula (I) above or pharmaceutically acceptable salt thereof according to (3) above, wherein V is the formula —CO—NH—, W is a single bond, m is 1, and n is 0.

(7) Another embodiment of the present invention provides the compound of the general formula (I) above or pharmaceutically acceptable salt thereof according to (3) above, wherein V is the formula —CO—NH—, W is a single bond, m is 0, and n is 0.

(8) Another embodiment of the present invention provides the compound of the general formula (I) above or pharmaceutically acceptable salt thereof according to any one of (1) to (7) above, wherein Ring A is an aryl group which may be substituted by 1 to 3 substituents, which may be the same or different, selected from the group consisting of (i) to (vii) below:

(i) a halogen atom, (ii) a hydroxy group, (iii) a $C_{1-8}$ alkyl group which may be substituted by 1 to 3 substituents, which may be the same or different, selected from the group consisting of:

a hydroxy group, a halogen atom, a $C_{1-8}$ alkoxy group which may be substituted by one saturated heterocyclyl group, a $C_{3-8}$ cycloalkyl group, a saturated heterocyclyl group, and an aryl group, (iv) a $C_{1-8}$ alkoxy group which may be substituted by 1 to 3 substituents, which may be the same or different, selected from the group consisting of:

(iv-1) a halogen atom, (iv-2) an oxo group, (iv-3) a $C_{3-8}$ cycloalkyl group, (iv-4) a saturated heterocyclyl group which may be substituted by 1 or 2 substituents, which may be the same or different, selected from the group consisting of:

a halogen atom, a $C_{1-8}$ alkyl group, and an oxo group, (iv-5) an aryl group, (iv-6) a heteroaryl group, (iv-7) a $C_{1-8}$ alkoxy group which may be substituted by 1 to 3 substituents, which may be the same or different, selected from the group consisting of:

a halogen atom, a saturated heterocyclyl group, and a $C_{1-8}$ alkoxy group, (iv-8) a $C_{3-8}$ cycloalkyloxy group, (iv-9) an aryloxy group which may be substituted by one substituent selected from the group consisting of:

a halogen atom, a $C_{1-8}$ alkyl group which may be substituted by 1 to 3 halogen atoms, and a $C_{1-8}$ alkoxy group, (iv-10) a $C_{1-8}$ alkylsulfonyl group, and
(iv-11) an arylsulfonyl group,
(v) a $C_{2-8}$ alkenyloxy group,
(vi) a mono$C_{1-8}$ alkylamino group which may be substituted by one aryl group, and
(vii) a di$C_{1-8}$ alkylamino group.
(9) Another embodiment of the present invention provides the compound of the general formula (I) above or pharmaceutically acceptable salt thereof according to any one of (1) to (8) above, wherein
Ring A is an aryl group which may be substituted by 1 to 3 substituents, which may be the same or different, selected from the group consisting of:
a halogen atom,
a hydroxy group,
a $C_{1-8}$ alkyl group which may be substituted by 1 to 3 substituents, which may be the same or different, selected from the group consisting of:
a halogen atom,
a $C_{3-8}$ cycloalkyl group, and
an aryl group,
a $C_{1-8}$ alkoxy group which may be substituted by 1 to 3 substituents, which may be the same or different, selected from the group consisting of:
a halogen atom,
an oxo group,
a $C_{3-8}$ cycloalkyl group,
a saturated heterocyclyl group which may be substituted by 1 or 2 substituents, which may be the same or different, selected from the group consisting of a $C_{1-8}$ alkyl group, and an oxo group,
an aryl group,
a heteroaryl group,
a $C_{1-8}$ alkoxy group which may be substituted by one $C_{1-8}$ alkoxy group,
a $C_{3-8}$ cycloalkyloxy group, and
an aryloxy group which may be substituted by one substituent selected from the group consisting of a halogen atom, a $C_{1-8}$ alkyl group which may be substituted by 1 to 3 halogen atoms, and a $C_{1-8}$ alkoxy group,
a $C_{2-8}$ alkenyloxy group, and
a di$C_{1-8}$ alkylamino group.
(10) Another embodiment of the present invention provides the compound of the general formula (I) above or pharmaceutically acceptable salt thereof according to any one of (1) to (9) above, wherein $R^C$ is a hydrogen atom or a $C_{1-4}$ alkyl group.
(11) Another embodiment of the present invention provides a medicament comprising, as an active ingredient, the compound or pharmaceutically acceptable salt thereof according to any one of (1) to (10) above.
(12) Another embodiment of the present invention provides a monoacylglycerol acyltransferase 2 inhibitor comprising, as an active ingredient, the compound or pharmaceutically acceptable salt thereof according to any one of (1) to (10) above.
(13) Another embodiment of the present invention provides a fat absorption inhibitor comprising, as an active ingredient, the compound or pharmaceutically acceptable salt thereof according to any one of (1) to (10) above.
(14) Another embodiment of the present invention provides a prophylactic or therapeutic agent for obesity comprising, as an active ingredient, the compound or pharmaceutically acceptable salt thereof according to any one of (1) to (10) above.
(15) Another embodiment of the present invention provides a prophylactic or therapeutic agent for lipid metabolism abnormality comprising, as an active ingredient, the compound or pharmaceutically acceptable salt thereof according to any one of (1) to (10) above.

Advantageous Effects of Invention

The present invention enables the provision of compounds having a superior MGAT2 inhibitory action.

DESCRIPTION OF EMBODIMENTS

The present invention provides compounds of general formula (I) or pharmaceutically acceptable salts thereof, which have a superior MGAT2 inhibitory action.

Hereinafter, the compounds of the present invention will be described in more detail, but the present invention is not limited to the compounds exemplified below in any case.

In the present invention, the term "n" refers to "normal", the term "i" to "iso", the term "s" or "sec" to "secondary", the term "t" or "tert" to "tertiary", the term "c" to "cyclo", the term "o" to "ortho", the term "m" to "meta", and the term "p" to "para".

The term "aryl group" refers to a monocyclic aromatic hydrocarbon group or condensed polycyclic aromatic hydrocarbon group which has 6 to 14 carbon atoms. Examples include a phenyl group, a naphthyl group, and the like.

The term "partially saturated aryl group" refers to a partially saturated monocyclic aromatic hydrocarbon group or partially saturated condensed polycyclic aromatic hydrocarbon group which has 6 to 14 carbon atoms. Examples include a tetrahydronaphthyl group and the like.

The term "heteroaryl group" refers to either a 5- or 7-membered monocyclic aromatic heterocyclic group consisting of one or more atoms, which may be the same or different, selected from the group consisting of an oxygen atom, a sulfur atom and a nitrogen atom and 1 to 6 carbon atoms or a condensed polycyclic aromatic heterocyclic group consisting of 9 to 14 atoms that consist of one or more atoms, which may be the same or different, selected from the group consisting of an oxygen atom, a sulfur atom and a nitrogen atom and 1 to 13 carbon atoms. Examples include a pyridyl group, a pyrazinyl group, a pyrimidinyl group, a furyl group, a thienyl group, an oxazolyl group, an isoxazolyl group, a thiazolyl group, an isothiazolyl group, an oxadiazolyl group, a thiadiazolyl group, a pyrrolyl group, a pyrazolyl group, a triazolyl group, a quinolyl group, an isoquinolyl group, a quinoxalinyl group, a 1 H-thieno[2,3-c]pyrazolyl group, and the like.

The term "partially saturated heteroaryl group" refers to either a 5- or 7-membered partially saturated monocyclic aromatic heterocyclic group consisting of one or more atoms, which may be the same or different, selected from the group consisting of an oxygen atom, a sulfur atom and a nitrogen atom and 1 to 6 carbon atoms or a partially saturated condensed polycyclic aromatic heterocyclic group consisting of 9 to 14 atoms that consist of one or more atoms, which may be the same or different, selected from the group consisting of an oxygen atom, a sulfur atom and a nitrogen atom and 1 to 13 carbon atoms. Examples include an oxazolidinyl group, a thiazolidinyl group, a dihydrobenzofuranyl group, a benzo[d][1,3]dioxolyl group, a dihydrobenzoxazolyl group, a tetrahydroisoquinolyl group, and the like.

The term "$C_{3-8}$ cycloalkyl group" refers to a cyclic alkyl group having 3 to 8 carbon atoms. The "$C_{3-8}$ cycloalkyl group" is a cyclopropyl group, a cyclobutyl group, a cyclopentyl group, a cyclohexyl group, a cycloheptyl group, or a cyclooctyl group.

The term "C$_{3-8}$ cycloalkenyl group" refers to a cyclic alkenyl group having 3 to 8 carbon atoms. The "C$_{3-8}$ cycloalkenyl group" is a cyclopropenyl group, a cyclobutenyl group, a cyclopentenyl group, a cyclohexenyl group, a cycloheptenyl group, or a cyclooctenyl group. Examples of a "C$_{3-8}$ cycloalkenyl group" crosslinked with a C$_{i-4}$ alkanediyl group include a bicyclo[2.2.1]heptenyl group.

The term "saturated heterocyclyl group" refers to either a 4- to 8-membered monocyclic saturated heterocyclic group consisting of one or more atoms, which may be the same or different, selected from the group consisting of an oxygen atom, a sulfur atom and a nitrogen atom and 1 to 7 carbon atoms or a condensed polycyclic saturated heterocyclic group consisting of 9 to 14 atoms that consist of one or more atoms, which may be the same or different, selected from the group consisting of an oxygen atom, a sulfur atom and a nitrogen atom and 1 to 13 carbon atoms. Examples include a tetrahydrofuranyl group, a tetrahydropyranyl group, a dioxanyl group, a pyrrolidinyl group, a piperidyl group, a piperazinyl group, and the like.

The term "halogen atom" refers to a fluorine atom, a chlorine atom, a bromine atom, or an iodine atom.

The term "C$_{1-4}$ alkyl group" means a straight-chain or branched-chain alkyl group having 1 to 4 carbon atoms, and is a methyl group, an ethyl group, a n-propyl group, an isopropyl group, a n-butyl group, an isobutyl group, a sec-butyl group, or a tert-butyl group.

The term "C$_{1-8}$ alkyl group" means a straight-chain or branched-chain alkyl group having 1 to 8 carbon atoms, and includes, for example, a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a 1-ethylpropyl group, a n-hexyl group, an isohexyl group, a neohexyl group, a n-heptyl group, a n-octyl group, and the like.

The term "C$_{4-18}$ alkyl group" means a straight-chain or branched-chain alkyl group having 4 to 18 carbon atoms, and includes, for example, a n-butyl group, an isobutyl group, a sec-butyl group, a tert-butyl group, a n-pentyl group, an isopentyl group, a neopentyl group, a tert-pentyl group, a 1-ethylpropyl group, a n-hexyl group, an isohexyl group, a neohexyl group, a 2-ethylbutyl group, a n-heptyl group, a n-octyl group, a n-nonyl group, a n-decyl group, a n-undecyl group, a n-dodecyl group, a n-tridecyl group, a n-tetradecyl group, a n-pentadecyl, a n-hexadecyl group, a n-heptadecyl group, a n-octadecyl group, and the like.

The term "C$_{1-8}$ alkoxy group" means a straight-chain or branched-chain alkoxy group having 1 to 8 carbon atoms, and includes, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a neopentyloxy group, a tert-pentyloxy group, a 1-ethylpropoxy group, a n-hexyloxy group, an isohexyloxy group, a neohexyloxy group, a 2-ethylbutoxy group, a n-heptyloxy group, a n-octyloxy group, and the like.

The term "C$_{2-8}$ alkenyloxy group" means a group obtained by the connection of a straight-chain or branched-chain alkenyl group having 2 to 8 carbon atoms to an oxy group, and includes, for example, an ethenyloxy group, an (E)-prop-1-en-1-yloxy group, a (Z)-prop-1-en-1-yloxy group, a prop-2-en-1-yloxy group, a (Z)-but-2-en-1-yloxy group, a (Z)-pent-3-en-1-yloxy group, a (Z)-hex-4-en-1-yloxy group, a (Z)-hept-5-en-1-yloxy group, a (Z)-oct-6-en-1-yloxy group, and the like.

The term "C$_{3-8}$ cycloalkyloxy group" refers to a group obtained by the connection of the aforementioned "C$_{3-8}$ cycloalkyl group" to an oxy group. The "C$_{3-8}$ cycloalkyloxy group" includes a cyclopropyloxy group, a cyclobutyloxy group, a cyclopentyloxy group, a cyclohexyloxy group, a cycloheptyloxy group, and a cyclooctyloxy group.

The term "aryloxy group" refers to a group obtained by the connection of the aforementioned "aryl group" to an oxy group. Examples include a phenoxy group and the like.

The term "monoC$_{1-8}$ alkylamino group" means an amino group having one aforementioned "C$_{1-8}$ alkyl group" as a substituent, and includes, for example, a methylamino group, an ethylamino group, a n-propylamino group, an isopropylamino group, a n-butylamino group, an isobutylamino group, a sec-butylamino group, a tert-butylamino group, a n-pentylamino group, a n-hexylamino group, a n-heptylamino group, a n-octylamino group, and the like.

The term "diC$_{1-8}$ alkylamino group" means an amino group having two aforementioned "C$_{1-8}$ alkyl groups" as substituents which may be the same or different, and includes, for example, a dimethylamino group, a di(n-propyl)amino group, a di(isopropyl)amino group, an ethylmethylamino group, a methyl(n-propyl)amino group, and the like.

The term "C$_{1-8}$ alkylsulfonyl group" refers to a group obtained by the attachment of the aforementioned "C$_{1-8}$ alkyl group" to a sulfonyl group. Examples include a methylsulfonyl group, an ethylsulfonyl group, a n-propylsulfonyl group, an isopropylsulfonyl group, a n-butylsulfonyl group, an isobutylsulfonyl group, a tert-butylsulfonyl group, a n-hexylsulfonyl group, and the like.

The term "arylsulfonyl group" refers to a group obtained by the attachment of the aforementioned "aryl group" to a sulfonyl group. Examples include a phenylsulfonyl group, a naphthylsulfonyl group, and the like.

The term "oxo group" refers to a substituent for substitution with an oxygen atom via a double bond (=O). Hence, when an oxo group attaches a carbon atom, the oxo group, taken together with the carbon atom, forms a carbonyl group; when one oxo group attaches a sulfur atom, the oxo group, taken together with the sulfur atom, forms a sulfinyl group; and when two oxo groups attach a sulfur atom, the oxo groups, taken together with the sulfur atom, form a sulfonyl group. In the present invention, specific examples of a saturated heterocyclyl group substituted by an oxo group include a 2-oxopyrrolidinyl group, a 2-oxopiperidinyl group, a 1,1-dioxidotetrahydrothiophenyl group, a 1-oxidotetrahydro-2 H-thiopyranyl group, a 1,1-dioxidotetrahydro-2 H-thiopyranyl group, a 1,1-dioxidoisothiazolidinyl group, a 2-oxo-1,3-oxazolidinyl group, a 6-oxo-1,1-dihydropyridazinyl group, a 3-oxo-3,4-dihydro-2 H-benzo[b][1,4]oxazinyl group, and the like.

The term "C$_{1-3}$ alkylene group" means a divalent group obtained by the removal of one hydrogen atom from an alkyl group having 1 to 3 carbon atoms, and includes, for example, a methylene group, an ethane-1,1-diyl group, an ethane-1,2-diyl group, a propane-1,3-diyl group, and the like.

The term "C$_{1-4}$ alkanediyl group" means a divalent group obtained by the removal of one hydrogen atom from an alkyl group having 1 to 4 carbon atoms, and includes, for example, a methylene group, an ethane-1,1-diyl group, an ethane-1,2-diyl group, a propane-1,3-diyl group, a butane-1,4-diyl group, and the like.

The term "C$_{3-6}$ cycloalkane-1,1-diyl group" means a divalent group obtained by the removal of one hydrogen atom from a cycloalkyl group having 3 to 6 carbon atoms, and is a cyclopropane-1,1-diyl group, a cyclobutane-1,1-diyl group, a cyclopentane-1,1-diyl group or a cyclohexane-1,1-diyl group.

The term "$C_{3-6}$ cycloalkane" refers to a cyclic alkane having 3 to 6 carbon atoms. The "$C_{3-6}$ cycloalkane" is a cyclopropane ring, a cyclobutane ring, a cyclopentane ring or a cyclohexane ring.

Preferred embodiments of the inventive compound are as follows.

Preferred embodiments of Ring A are shown in (1) to (3) below.

(1) Preferred Ring A is an aryl group or a heteroaryl group, which aryl group and heteroaryl group may be each substituted by 1 to 3 substituents, which may be the same or different, selected from the group consisting of:
  a halogen atom,
  a $C_{1-8}$ alkyl group which may be substituted by 1 to 3 substituents, which may be the same or different, selected from the group consisting of:
    a halogen atom,
    a hydroxy group,
    a $C_{1-8}$ alkoxy group which may be substituted by one saturated heterocyclyl group,
    a $C_{3-8}$ cycloalkyl group,
    a saturated heterocyclyl group, and
    an aryl group,
  a $C_{1-8}$ alkoxy group which may be substituted by 1 to 3 substituents, which may be the same or different, selected from the group consisting of:
    a halogen atom,
    an oxo group,
    a $C_{3-8}$ cycloalkyl group,
    a saturated heterocyclyl group which may be substituted by 1 or 2 substituents, which may be the same or different, selected from the group consisting of a halogen atom, a $C_{1-8}$ alkyl group, and an oxo group,
    an aryl group,
    a heteroaryl group,
    a $C_{1-8}$ alkoxy group which may be substituted by 1 to 3 substituents, which may be the same or different, selected from the group consisting of a halogen atom, a saturated heterocyclyl group, and a $C_{1-8}$ alkoxy group,
  a $C_{3-8}$ cycloalkyloxy group,
  an aryloxy group which may be substituted by one substituent selected from the group consisting of a halogen atom, a $C_{1-8}$ alkyl group which may be substituted by 1 to 3 halogen atoms, and a $C_{1-8}$ alkoxy group,
  a $C_{1-8}$ alkylsulfonyl group, and
  an arylsulfonyl group, and
  a $C_{2-8}$ alkenyloxy group.

(2) More preferred Ring A is an aryl group which may be substituted by 1 to 3 substituents, which may be the same or different, selected from the group consisting of:
  a halogen atom,
  a $C_{1-8}$ alkyl group which may be substituted by 1 to 3 substituents, which may be the same or different, selected from the group consisting of:
    a halogen atom,
    a hydroxy group,
    a $C_{1-8}$ alkoxy group which may be substituted by one saturated heterocyclyl group,
    a $C_{3-8}$ cycloalkyl group,
    a saturated heterocyclyl group, and
    an aryl group,
  a $C_{1-8}$ alkoxy group which may be substituted by 1 to 3 substituents, which may be the same or different, selected from the group consisting of:
    a halogen atom,
    an oxo group,
    a $C_{3-8}$ cycloalkyl group,
    a saturated heterocyclyl group which may be substituted by 1 or 2 substituents, which may be the same or different, selected from the group consisting of a halogen atom, a $C_{1-8}$ alkyl group, and an oxo group,
    an aryl group,
    a heteroaryl group,
    a $C_{1-8}$ alkoxy group which may be substituted by 1 to 3 substituents, which may be the same or different, selected from the group consisting of a halogen atom, a saturated heterocyclyl group, and a $C_{1-8}$ alkoxy group,
  a $C_{3-8}$ cycloalkyloxy group,
  an aryloxy group which may be substituted by one substituent selected from the group consisting of a halogen atom, a $C_{1-8}$ alkyl group which may be substituted by 1 to 3 halogen atoms, and a $C_{1-8}$ alkoxy group,
  a $C_{1-8}$ alkylsulfonyl group, and
  an arylsulfonyl group, and
  a $C_{2-8}$ alkenyloxy group.

(3) Yet more preferred Ring A is a phenyl group which has been substituted by a substituent selected from the following groups at the para position:
  an unsubstituted $C_{4-8}$ alkyl group,
  a substituted $C_{3-6}$ alkyl group which has been substituted by one substituent selected from the group consisting of a $C_{3-8}$ cycloalkyl group, a saturated heterocyclyl group, and an aryl group,
  an unsubstituted $C_{1-8}$ alkoxy group,
  a substituted $C_{2-5}$ alkoxy group which has been substituted by one substituent selected from the group consisting of:
    a $C_{3-8}$ cycloalkyl group,
    a saturated heterocyclyl group which may be substituted by 1 or 2 substituents, which may be the same or different, selected from the group consisting of a halogen atom, a $C_{1-8}$ alkyl group, and an oxo group,
    an aryl group,
    a heteroaryl group,
    a $C_{3-8}$ cycloalkyloxy group,
    an aryloxy group which may be substituted by one substituent selected from the group consisting of a halogen atom, a $C_{1-8}$ alkyl group which may be substituted by 1 to 3 halogen atoms, and a $C_{1-8}$ alkoxy group, and an arylsulfonyl group, and
  an unsubstituted $C_{3-8}$ alkenyloxy group, and
which phenyl group is optionally substituted by a halogen atom or a methoxy group (more preferably, a fluorine atom) at the ortho position.

Preferred $R^B$ is a structure represented by the following formula (II).

[Formula 4]

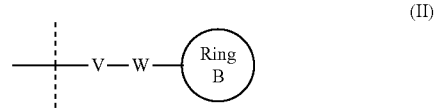

(II)

Preferred embodiments of the structure of formula (II) are as follows:

(1) One preferred V is the formula —$CR^{11}R^{12}$—, wherein preferred $R^{11}$ and $R^{12}$, which may be the same or different, each represent a hydrogen atom or a $C_{1-4}$ alkyl group or another preferred $R^{11}$ and $R^{12}$, taken together with the adjacent carbon atom, form $C_{3-6}$ cycloalkane, and in this case, preferred W is a single bond or either a $C_{1-3}$ alkylene group which may be substituted by 1 or 2 substituents, which may be the same or different, selected from the group consisting of:
  a fluorine atom,
  an amino group, and
  an oxo group, or a $C_{1-3}$ alkylene group in which one carbon atom that forms the $C_{1-3}$ alkylene group may form a $C_{3-6}$ cycloalkane-1,1-diyl group, in this case, preferred Ring B is an aryl group or a heteroaryl group, which aryl group and heteroaryl group may be each substituted by 1 to 3 substituents, which may be the same or different, selected from the group consisting of:
  a halogen atom,
  a $C_{1-8}$ alkyl group and a $C_{1-8}$ alkoxy group, which $C_{1-8}$ alkyl group and $C_{1-8}$ alkoxy group may be each substituted by 1 to 4 substituents, which may be the same or different, selected from the group consisting of a halogen atom, a hydroxy group, a $C_{3-8}$ cycloalkyl group, and an aryl group,
  a $C_{3-8}$ cycloalkyl group,
  an aryl group and a heteroaryl group, which aryl group and heteroaryl group may be each substituted by 1 or 2 substituents, which may be the same or different, selected from the group consisting of a halogen atom, and a $C_{1-8}$ alkyl group which may be substituted by 1 to 3 halogen atoms, and
  a $C_{1-8}$ alkylsulfonyl group,
a $C_{3-8}$ cycloalkyl group, or
a saturated heterocyclyl group, and more preferred Ring B is an aryl group, a heteroaryl group, which aryl group and heteroaryl group may be each substituted by 1 to 3 substituents, which may be the same or different, selected from the group consisting of:
  a halogen atom,
  a hydroxy group,
  a $C_{1-8}$ alkyl group and a $C_{1-8}$ alkoxy group, which $C_{1-8}$ alkyl group and $C_{1-8}$ alkoxy group may be each substituted by 1 to 4 substituents, which may be the same or different, selected from the group consisting of a halogen atom, a hydroxy group, a $C_{3-8}$ cycloalkyl group, and an aryl group,
  a $C_{3-8}$ cycloalkyl group,
  an aryl group and a heteroaryl group, which aryl group and heteroaryl group may be each substituted by 1 or 2 substituents, which may be the same or different, selected from the group consisting of a halogen atom, and a $C_{1-8}$ alkyl group which may be substituted by 1 to 3 halogen atoms, and
  a $C_{1-8}$ alkylsulfonyl group, or
a $C_{3-8}$ cycloalkyl group.

(2) Another preferred V is the formula —CO—NH—, and
in this case, preferred W is a single bond,
preferred Ring B is an aryl group, a heteroaryl group, which aryl group and heteroaryl group may be each substituted by 1 to 3 substituents, which may be the same or different, selected from the group consisting of:
  a halogen atom,
  a hydroxy group,
  a $C_{1-8}$ alkyl group and a $C_{1-8}$ alkoxy group, which $C_{1-8}$ alkyl group and $C_{1-8}$ alkoxy group may be each substituted by 1 to 4 substituents, which may be the same or different, selected from the group consisting of a halogen atom, a hydroxy group, a $C_{3-8}$ cycloalkyl group, and an aryl group,
  a $C_{3-8}$ cycloalkyl group,
  an aryl group and a heteroaryl group, which aryl group and heteroaryl group may be each substituted by 1 or 2 substituents, which may be the same or different, selected from the group consisting of a halogen atom, and a $C_{1-8}$ alkyl group which may be substituted by 1 to 3 halogen atoms, and
  a $C_{1-8}$ alkylsulfonyl group,
a $C_{3-8}$ cycloalkyl group, or
a saturated heterocyclyl group, and more preferred Ring B is an aryl group, a heteroaryl group, which aryl group and heteroaryl group may be each substituted by 1 to 3 substituents, which may be the same or different, selected from the group consisting of:
  a halogen atom,
  a hydroxy group,
  a $C_{1-8}$ alkyl group and a $C_{1-8}$ alkoxy group, which $C_{1-8}$ alkyl group and $C_{1-8}$ alkoxy group may be each substituted by 1 to 4 substituents, which may be the same or different, selected from the group consisting of a halogen atom, a hydroxy group,
  a $C_{3-8}$ cycloalkyl group, and an aryl group, a $C_{3-8}$ cycloalkyl group,
  an aryl group and a heteroaryl group, which aryl group and heteroaryl group may be each substituted by 1 or 2 substituents, which may be the same or different, selected from the group consisting of a halogen atom, and a $C_{1-8}$ alkyl group which may be substituted by 1 to 3 halogen atoms, and
  a $C_{1-8}$ alkylsulfonyl group, or
a $C_{3-8}$ cycloalkyl group.

(3) Another preferred V is the formula —CO—, and
in this case, preferred W is a single bond or an unsubstituted $C_{1-3}$ alkylene group,
in this case, preferred Ring B is an aryl group, a heteroaryl group, which aryl group and heteroaryl group may be each substituted by 1 to 3 substituents, which may be the same or different, selected from the group consisting of:
  a halogen atom,
  a hydroxy group,
  a $C_{1-8}$ alkyl group and a $C_{1-8}$ alkoxy group, which $C_{1-8}$ alkyl group and $C_{1-8}$ alkoxy group may be each substituted by 1 to 4 substituents, which may be the same or different, selected from the group consisting of a halogen atom, a hydroxy group,
  a $C_{3-8}$ cycloalkyl group, and an aryl group,
  a $C_{3-8}$ cycloalkyl group,
  an aryl group and a heteroaryl group, which aryl group and heteroaryl group may be each substituted by 1 or 2 substituents, which may be the same or different, selected from the group consisting of a halogen atom, and a $C_{1-8}$ alkyl group which may be substituted by 1 to 3 halogen atoms, and
  a $C_{1-8}$ alkylsulfonyl group,
a $C_{3-8}$ cycloalkyl group, or
a saturated heterocyclyl group, and more preferred Ring B is an aryl group, a heteroaryl group, which aryl group and heteroaryl group may be each substituted by 1 to 3 substituents, which may be the same or different, selected from the group consisting of:
  a halogen atom,
  a hydroxy group,
  a $C_{1-8}$ alkyl group and a $C_{1-8}$ alkoxy group, which $C_{1-8}$ alkyl group and $C_{1-8}$ alkoxy group may be each substituted by 1 to 4 substituents, which may be the same or different, selected from the group consisting of a halogen atom, a hydroxy group, a C$_{3-8}$ cycloalkyl group, and an aryl group, a C$_{3-8}$ cycloalkyl group, an aryl group and a heteroaryl group, which aryl group and heteroaryl group may be each substituted by 1 or 2 substituents, which may be the same or different, selected from the group consisting of a halogen atom, and a C$_{1-8}$ alkyl group which may be substituted by 1 to 3 halogen atoms, and a C$_{1-8}$ alkylsulfonyl group, or a C$_{3-8}$ cycloalkyl group.

Preferred R$^C$ is a hydrogen atom or a C$_{1-4}$ alkyl group.

Preferred R$^D$ is a hydrogen atom.

Preferred Y is a nitrogen atom.

One preferred m is 1, and in this case, preferred n is 0.

Another preferred m is 0, and in this case, preferred n is 0.

One preferred embodiment of the present invention is a compound represented by the following formula (III) or a pharmaceutically acceptable salt thereof.

[Formula 5]

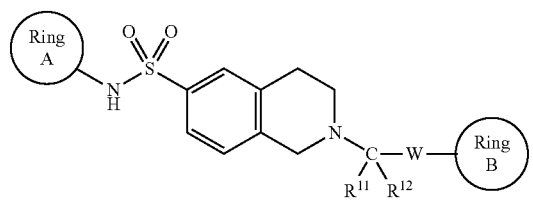

(III)

In this case, preferred embodiments of Ring A are as described in (1) to (3) above and preferred embodiments of Ring B, R$^{11}$, R$^{12}$ and W are as described in the preferred embodiment (1) for the aforementioned structure of formula (II).

Another preferred embodiment of the present invention is a compound represented by the following formula (IV) or a pharmaceutically acceptable salt thereof.

[Formula 6]

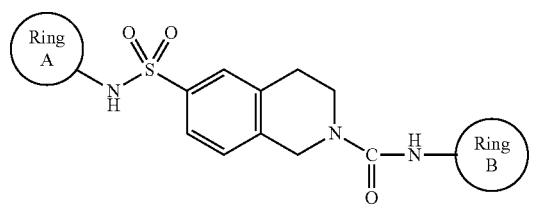

(IV)

In this case, preferred embodiments of Ring A are as described in (1) to (3) above and preferred embodiments of Ring B are as described in the preferred embodiment (2) for the aforementioned structure of formula (II).

Another preferred embodiment of the present invention is a compound represented by the following formula (V) or a pharmaceutically acceptable salt thereof.

[Formula 7]

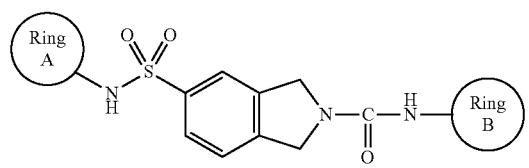

(V)

In this case, preferred embodiments of Ring A are as described in (1) to (3) above and preferred embodiments of Ring B are as described in the preferred embodiment (2) for the aforementioned structure of formula (II).

Another preferred embodiment of the present invention is a compound represented by the following formula (VI) or a pharmaceutically acceptable salt thereof.

[Formula 8]

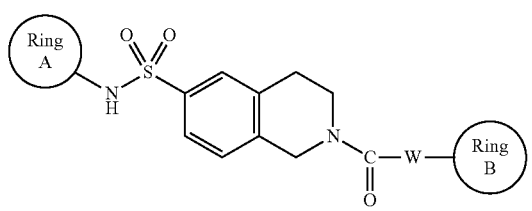

(VI)

In this case, preferred embodiments of Ring A are as described in (1) to (3) above and preferred embodiments of Ring B and W are as described in the preferred embodiment (3) for the aforementioned structure of formula (II).

Another embodiment of the inventive compound is as follows (this embodiment is also applied to formulae (III), (IV), (V) and (VI) above).

Ring A is an aryl group or a heteroaryl group, which aryl group and heteroaryl group may be each substituted by 1 to 3 substituents, which may be the same or different, selected from the group consisting of:

a halogen atom, a C$_{1-8}$ alkyl group which may be substituted by 1 to 3 substituents, which may be the same or different, selected from the group consisting of a halogen atom, a C$_{3-8}$ cycloalkyl group, and an aryl group, and a C$_{1-8}$ alkoxy group which may be substituted by 1 to 3 substituents, which may be the same or different, selected from the group consisting of:

a halogen atom, a C$_{3-8}$ cycloalkyl group, a saturated heterocyclyl group which may be substituted by 1 or 2 substituents, which may be the same or different, selected from the group consisting of a C$_{1-8}$ alkyl group, and an oxo group, an aryl group, a heteroaryl group, a C$_{1-8}$ alkoxy group which may be substituted by one C$_{1-8}$ alkoxy group, a C$_{3-8}$ cycloalkyloxy group, an aryloxy group which may be substituted by one substituent selected from the group consisting of a halogen atom, a $C_{1-8}$ alkyl group which may be substituted by 1 to 3 halogen atoms, and a $C_{1-8}$ alkoxy group, and $R^B$ is a structure represented by the following formula (II).

[Formula 9]

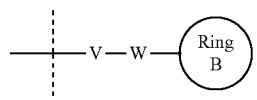

(II)

One embodiment of V is the formula —$CR^{11}R^{12}$—, wherein
$R^{11}$ and $R^{12}$, which may be the same or different, each represent a hydrogen atom or a $C_{1-4}$ alkyl group, and
in this case, W is a single bond or
either a $C_{1-3}$ alkylene group which may be substituted by 1 or 2 substituents, which may be the same or different, selected from the group consisting of:
  a fluorine atom,
  an amino group, and
  an oxo group, or
a $C_{1-3}$ alkylene group in which one carbon atom that forms the $C_{1-3}$ alkylene group may form a $C_{3-6}$ cycloalkane-1,1-diyl group, and
in this case, Ring B is an aryl group or a heteroaryl group, which aryl group and heteroaryl group may be each substituted by 1 to 3 substituents, which may be the same or different, selected from the group consisting of:
  a halogen atom,
  a $C_{1-8}$ alkyl group and a $C_{1-8}$ alkoxy group, which $C_{1-8}$ alkyl group and $C_{1-8}$ alkoxy group may be each substituted by 1 to 3 substituents, which may be the same or different, selected from the group consisting of a halogen atom, a hydroxy group, and an aryl group, and
  an aryl group,
another embodiment of V is the formula —CO—NH—, and
in this case, W is a single bond,
in this case, Ring B is an aryl group or a heteroaryl group, which aryl group and heteroaryl group may be each substituted by 1 to 3 substituents, which may be the same or different, selected from the group consisting of:
  a halogen atom,
  a $C_{1-8}$ alkyl group and a $C_{1-8}$ alkoxy group, which $C_{1-8}$ alkyl group and $C_{1-8}$ alkoxy group may be each substituted by 1 to 3 substituents, which may be the same or different, selected from the group consisting of a halogen atom, a hydroxy group, and an aryl group, and
  an aryl group,
$R^C$ is a hydrogen atom or a $C_{1-4}$ alkyl group,
$R^D$ is a hydrogen atom,
Y is a nitrogen atom,
one embodiment of m is 1, and in this case, n is 0, and
another embodiment of m is 0, and in this case, n is 0.

The compound of the present invention is a compound having a condensed heterocycle or may be a pharmaceutically acceptable salt of the compound (hereinafter referred to as "the compound of the present invention" as appropriate).

Examples of the pharmaceutically acceptable salt include acid addition salts such as mineral acid salts such as hydrochloride, hydrobromide, hydroiodide, phosphate, sulfate and nitrate; sulfonates such as methanesulfonate, ethanesulfonate, benzenesulfonate, p-toluenesulfonate and trifluoromethanesulfonate; and organic acid salts such as oxalate, tartrate, citrate, maleate, succinate, acetate, benzoate, mandelate, ascorbate, lactate, gluconate and malate; amino acid salts such as glycine salt, lysine salt, arginine salt, ornithine salt, glutamate and aspartate; inorganic salts such as lithium salt, sodium salt, potassium salt, calcium salt and magnesium salt; and salts with organic bases such as ammonium salt, triethylamine salt, diisopropylamine salt and cyclohexylamine salt. It is to be noted that such salts include hydrate salts.

The term "pharmaceutically acceptable salt" also includes a case where, in a compound of the present invention where Y represents the formula $N^+(R^F)$, one equivalent of anion is attached to the positive charge of the nitrogen atom to form a quaternary ammonium salt. In this case, the anion includes mineral acid ions such as chloride ion, bromide ion, iodide ion, phosphate ion, sulfate ion and nitrate ion; sulfonate ions such as methanesulfonate ion, p-toluenesulfonate ion and trifluoromethanesulfonate ion; acetate ion; amino acid anion such as glutamic acid ion; and the like. In particular, halide ions such as chloride ion, bromide ion and iodide ion are preferred. It is to be noted that such anions may also be converted to preferred anions as appropriate by a common ion-exchange reaction.

The compounds of the present invention have an asymmetric center in some cases, in which they occur as various optical isomers. Hence, the compounds of the present invention may occur in separate optically active forms with (R) and (S) configurations or may occur as racemates or (RS) mixtures. In the case of compounds having two or more asymmetric centers, diastereomers may also occur owing to optical isomerism of each asymmetric center. The compounds of the present invention include compounds containing all of these forms in any proportions. For example, diastereomers can be separated by methods well known to the skilled person (e.g., fractional crystallization) and optically active forms can be obtained by techniques in organic chemistry that are well known for this purpose. Further, the compounds of the present invention occur as geometric isomers in some cases, such as cis forms or trans forms. The compounds of the present invention include these isomers and compounds containing the isomers in any proportions.

Since the inventive compounds have an MGAT2 inhibitory action, they are effective as prophylactic or therapeutic agents for diseases attributable to MGAT2-related lipid metabolism abnormality. For example, the inventive compounds can inhibit neutral fat synthesis in small-intestinal epithelial cells and can inhibit or delay fat absorption; hence, the compounds can be used as fat absorption inhibitors. Further, the inventive compounds have a strong body weight-lowering effect owing to the fat absorption-inhibiting action mentioned above, and they are expected to serve as ideal antiobesity agents or antihyperlipidemic agents. The inventive compounds are also expected to serve as antidiabetic agents that inhibit the enlargement of fat cells, thereby inhibiting the secretion of malignant, physiologically active substances including TNFα and correcting insulin resistance. Moreover, long-term administration of the compounds is expected to correct or prevent arteriosclerosis, fatty liver and hypertension.

Further, the inventive compounds can be used as new drugs that are different in mechanism of action from existing antiobesity agents, antihyperlipidemic agents, and the like. Hence, the inventive compounds may also be used in combination with an agent having a mechanism of action different from MGAT2 inhibitory action, such as an antiobesity agent, an antihyperlipidemic agent, an antidiabetic agent, a therapeutic agent for diabetic complications, an antihypertensive agent, or an antiarteriosclerotic agent. A combination of a compound of the present invention and another agent is expected to bring about additive effects, as compared with effects obtained from each agent alone, in the diseases mentioned above.

Examples of the antiobesity agent and antihyperlipidemic agent that can be used in combination with the inventive compounds include mazindol, sibutramine, phentermine, pancreatic lipase inhibitors (e.g., orlistat, cetilistat), cannabinoid receptor antagonists (e.g., rimonabant, taranabant), MTP inhibitors (e.g., JTT-130, Usistapide), MCH receptor antagonists (e.g., AMG-076), statin drugs (e.g., atorvastatin), squalene synthase inhibitors (e.g., TAK-475), bile acid adsorbents (e.g., colestimide), CETP inhibitors (e.g., anacetrapib, dalcetrapib), cholesterol absorption inhibitors (e.g., ezetimibe), fibrates (e.g., bezafibrate), nicotinic acid derivatives (e.g., niacin), PYY agonists (e.g., AC-162352), IBAT inhibitors, ACAT inhibitors, DGAT inhibitors, LXR agonists, and the like.

Examples of the antidiabetic agent, therapeutic agent for diabetic complications, antihypertensive agent and antiarteriosclerotic agent that can be used in combination with the inventive compounds include insulin preparations, DPP-IV inhibitors, SGLT inhibitors, GLP-1 agonists, PPAR agonists, α glucosidase inhibitors, biguanides, insulin secretagogues, amylin agonists, GPR119 receptor agonists, GK activators, ACC inhibitors, 11β-HSD1 inhibitors, glucagon receptor antagonists, angiotensin converting enzyme inhibitors, angiotensin receptor antagonists, diuretics, calcium antagonists, endothelin converting enzyme inhibitors, endothelin receptor antagonists, aldose reductase inhibitors, warfarin, Factor Xa inhibitors, and the like.

The inventive compounds may be administered either alone or together with a pharmacologically or pharmaceutically acceptable carrier or diluent. When the inventive compounds are used as MGAT2-inhibiting substances or the like, they may be directly administered orally or parenterally. Alternatively, the inventive compounds may be administered orally or parenterally as formulations containing the inventive compounds as an active ingredient. The parenteral administration includes intravenous, transnasal, transdermal, subcutaneous, intramuscular and sublingual administrations.

The dosage of the inventive compounds varies depending on subjects to be treated, administration routes, diseases and symptoms to be treated, and the like. For example, in the case of oral administration to adult patients with diabetes, the compounds are administered in an amount of generally about 0.01 mg to about 1000 mg per dose, preferably 0.1 mg to 100 mg per dose, and the frequency of administration of the dose is desirably once to three times a day.

The MGAT2 inhibitory action of the compounds of the present invention may be evaluated in accordance with known techniques such as the methods described in Test Examples as shown herein.

The methods of producing the compounds according to the present invention will be described below in detail but are not limited to those exemplified below in any case. The solvents that are used in reactions may be any solvents that do not interfere with the respective reactions and are not limited to the following description in any case.

Hereinafter, methods of producing compounds (I) will be described. Compounds (I) may be produced by a combination of methods known per se, for example, Production Methods 1 to 7 as shown below or modified versions of the methods. It is to be noted that starting materials may be used as salts in the respective production methods shown below, such as the "pharmaceutically acceptable salts" described above.

Among compounds (I) of the present invention, compounds (1-g), (1-h) and (1-i) may be produced by, for example, Production Method 1 as shown below or a modified version of the method.

Production Method 1:

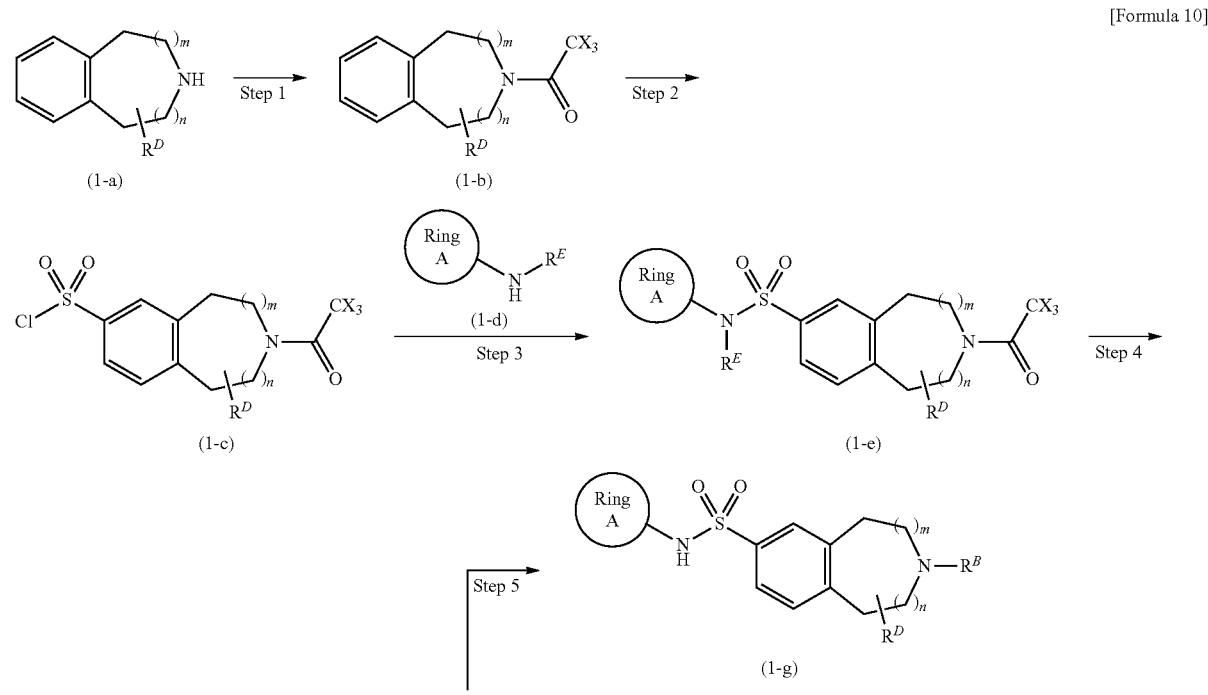

[Formula 10]

(In this scheme, Ring A, Ring B, $R^B$, $R^D$, W, m and n are as defined above; X represents a hydrogen atom, a fluorine atom or a chlorine atom; $R^E$ represents a hydrogen atom or Pro$^1$.) Pro$^1$, which is represented by $R^E$, is a protecting group for an amino group and preferably represents a benzyl group, a 4-methoxybenzyl group, a 2,4-dimethoxybenzyl group, or the like.

[Step 1]

This step is a process in which compound (1-a) is used to produce compound (1-b).

The step may be performed by a known method such as the method described in the Journal of Organic Chemistry, 1980, 23, 837, U.S. Pat. No. 4,315,935, WO 1996/033993 or WO 2006/122014 or a modified version of the method.

Examples of a reagent for use in the step include an acid anhydride such as trifluoroacetic anhydride, an acid chloride such as trichloroacetylchloride, and the like. The amount of the reagent for use in the step is 1 to 5 equivalents, preferably 1 to 3 equivalents, relative to 1 equivalent of compound (1-a).

Examples of a base used generally in the step include triethylamine, pyridine, N,N-dimethyl-4-aminopyridine, N,N-diisopropylethylamine, aqueous sodium hydroxide solution, aqueous sodium hydrogen carbonate solution, and the like. The amount of the base for use in the step is generally 1 to 5 equivalents, preferably 1 to 3 equivalents, relative to 1 equivalent of compound (1-a).

Examples of a reaction solvent for use in the step include solvents that do not interfere with the reaction, such as chloroform, dichloromethane, diethyl ether, tetrahydrofuran, 1,4-dioxane, methanol, ethanol, ethyl acetate, and acetonitrile. These solvents may be mixed and used in appropriate proportions.

This reaction may be generally performed at 0° C. to reflux temperature for 1 to 24 hr.

[Step 2]

This step is a process in which compound (1-b) and chlorosulfonic acid are reacted to produce compound (1-c).

The amount of chlorosulfonic acid for use in this reaction is 1 to 20 equivalents, preferably 1 to 7 equivalents, relative to 1 equivalent of compound (1-b).

Examples of a solvent for use in the reaction include solvents that do not interfere with the reaction, such as chloroform and dichloromethane. These solvents may be mixed and used in appropriate proportions.

This reaction may be generally performed at −78° C. to reflux temperature for 1 to 24 hr.

[Step 3]

This step is a process in which compound (1-c) and compound (1-d) are reacted in the presence of a base to produce compound (1-e).

The amount of compound (1-d) for use in this reaction is 0.5 to 3 equivalents, preferably 1 to 2 equivalents, relative to 1 equivalent of compound (1-c).

Examples of the base used generally in the reaction include triethylamine, pyridine, N,N-dimethyl-4-aminopyridine, N,N-diisopropylethylamine, and the like. The amount of the base for use in the reaction is generally 1 to 5 equivalents, preferably 1 to 3 equivalents, relative to 1 equivalent of compound (1-c).

Examples of a reaction solvent for use in the reaction include solvents that do not interfere with the reaction, such as chloroform, dichloromethane, diethyl ether, tetrahydrofuran, 1,4-dioxane, ethyl acetate, and acetonitrile. These solvents may be mixed and used in appropriate proportions.

This reaction may be generally performed at 0° C. to room temperature for 1 to 24 hr.

[Step 4]

This step is a process in which compound (1-e) is subjected to a reaction in the presence of a base to produce compound (1-f).

Examples of the base used generally in this reaction include aqueous lithium hydroxide solution, aqueous sodium hydroxide solution, aqueous potassium hydroxide solution, aqueous potassium carbonate solution, and the like. The amount of the base for use in the reaction is 1 to 10 equivalents, preferably 1 to 3 equivalents, relative to 1 equivalent of compound (1-e).

Examples of a reaction solvent for use in the reaction include solvents that do not interfere with the reaction, such as tetrahydrofuran, 1,4-dioxane, methanol, ethanol, and water.

These solvents may be mixed and used in appropriate proportions.

This reaction may be generally performed at 0° C. to room temperature for 1 to 24 hr.

[Step 5]

This step is a process in which compound (1-f) is used to produce compound (1-g).

Examples of a reagent for use in the step include aldehyde, ketone, carboxylic acid, acid chloride, acid anhydride, alkyl halide, alkyl sulfonate, aryl halide, aryl sulfonate, and the like, which correspond to $R^B$.

When the reagent for use in the step is aldehyde or ketone, the reaction may be performed using a reductive amination reaction.

The amount of aldehyde or the like for use in the reductive amination reaction in the step is 1 to 5 equivalents, preferably 1 to 3 equivalents, relative to 1 equivalent of compound (1-f). Examples of a reducing agent for use in the reaction include sodium triacetoxyborohydride, sodium cyanoborohydride, sodium borohydride, 2-picoline borane, and the like. The amount of the reducing agent for use in the reaction is 0.5 to 5 equivalents, preferably 1 to 3 equivalents, relative to 1 equivalent of compound (1-f).

In the reductive amination reaction, an acid may also be used. Examples of the acid used generally in the reaction include acetic acid and the like. The amount of the acid for use in the reaction is 1 equivalent to the amount of solvent, preferably 1 to 3 equivalents, relative to 1 equivalent of compound (1-f).

Examples of a reaction solvent for use in the reaction include solvents that do not interfere with the reaction, such as chloroform, dichloromethane, 1,2-dichloroethane, tetrahydrofuran, methanol, and ethanol. These solvents may be mixed and used in appropriate proportions. This reaction may be generally performed at room temperature to reflux temperature for 1 to 24 hr.

When the reagent for use in the step is carboxylic acid, the reaction may be performed by a known method, such as conversion into an amide compound using a condensing agent in the presence or absence of a base and an activator followed by a reduction reaction of the amide bond.

The amount of carboxylic acid for use in a condensation reaction in the step is 1 to 5 equivalents, preferably 1 to 3 equivalents, relative to 1 equivalent of compound (1-f).

Examples of the condensing agent include 1-ethyl-3-(3-dimethylaminopropyl)carbodiimide hydrochloride, N,N'-dicyclohexylcarbodiimide, diethyl cyanophosphonate, and the like. The amount of the condensing agent for use in the reaction is 1 to 5 equivalents, preferably 1 to 3 equivalents, relative to 1 equivalent of compound (1-f).

Examples of the activator include N-hydroxybenzotriazole monohydrate, N-hydroxysuccinimide, and the like. The amount of the activator for use in the reaction is 1 to 5 equivalents, preferably 1 to 2 equivalents, relative to 1 equivalent of compound (1-f). Examples of the base include tertiary aliphatic amines such as N,N-diisopropylethylamine and triethylamine, pyridine, and the like. The amount of the base for use in the reaction is 1 to 5 equivalents, preferably 1 to 2 equivalents, relative to 1 equivalent of compound (1-f). Examples of a reaction solvent for use in the reaction include solvents that do not interfere with the reaction, such as N,N-dimethylformamide, dichloromethane, chloroform, 1,2-dichloroethane, toluene, tetrahydrofuran, and water. These solvents may be mixed and used in appropriate proportions.

This reaction may be generally performed at 0° C. to reflux temperature for 1 to 24 hr.

Examples of a reducing agent in the reduction reaction of the amide bond include a borane-tetrahydrofuran complex, a borane-dimethylsulfide complex, and the like. The amount of the reducing agent for use in this reaction is 1 to 5 equivalents, preferably 1 to 3 equivalents, relative to 1 equivalent of compound (1-f).

Examples of a reaction solvent for use in this reaction include solvents that do not interfere with the reaction, such as tetrahydrofuran and diethyl ether. These solvents may be mixed and used in appropriate proportions.

This reaction may be generally performed at room temperature to reflux temperature for 1 to 24 hr.

When the reagent for use in the step is an acid chloride or an acid anhydride, the reaction may be performed using an acylation reaction for conversion into an amide compound followed by a reduction reaction of the amide bond.

The amount of the acid chloride or the like for use in the step is 1 to 5 equivalents, preferably 1 to 3 equivalents, relative to 1 equivalent of compound (1-f).

Examples of a base used generally in the acylation reaction in the step include triethylamine, pyridine, N,N-dimethyl-4-aminopyridine, N,N-diisopropylethylamine, and the like. The amount of the base for use in the reaction is generally 1 to 5 equivalents, preferably 1 to 3 equivalents, relative to 1 equivalent of compound (1-f).

Examples of a reaction solvent for use in the reaction include solvents that do not interfere with the reaction, such as chloroform, dichloromethane, diethyl ether, tetrahydrofuran, N,N-dimethylformamide, ethyl acetate, and acetonitrile. These solvents may be mixed and used in appropriate proportions.

This reaction may be generally performed at 0° C. to room temperature for 1 to 24 hr.

The reduction reaction of the amide bond may be performed in accordance with the method described in the paragraph for the foregoing case where "the reagent for use in the step is carboxylic acid".

When the reagent for use in the step is an alkyl halide or an alkyl sulfonate, the reaction may be performed in the presence of a base.

The amount of the alkyl halide or the like for use in an alkylation reaction in the step is 1 to 5 equivalents, preferably 1 to 3 equivalents, relative to 1 equivalent of compound (1-f).

Examples of the base used generally in the alkylation reaction in the step include tertiary aliphatic amines such as triethylamine, N,N-diisopropylethylamine and 1,8-diazabicyclo[4,3,0]undec-7-ene, alkali metal hydrides such as sodium hydride, alkali metal hydroxides such as potassium hydroxide, alkali metal carbonates such as cesium carbonate, potassium carbonate and sodium carbonate, alkali metal alkoxides such as potassium tert-butoxide, and the like. The amount of the base for use in the reaction is 1 to 5 equivalents, preferably 1 to 3 equivalents, relative to 1 equivalent of compound (1-f).

Examples of a reaction solvent for use in the reaction include solvents that do not interfere with the reaction, such as tetrahydrofuran, dimethyl sulfoxide, N,N-dimethylformamide, N,N-dimethylacetamide, and N-methylpyrrolidone. These solvents may be mixed and used in appropriate proportions.

This reaction may be generally performed at room temperature to reflux temperature for 1 to 24 hr.

When the reagent for use in the step is an aryl halide or an aryl sulfonate, the reaction may be performed by a known method (Angewandte Chemie International Edition, 1998, 37, 2046) such as a method of performing a reaction in a solvent that does not interfere with a coupling reaction in the presence of a palladium catalyst and a base.

The amount of the aryl halide or the like for use in a coupling reaction in the step is 1 to 3 equivalents, preferably 1 to 2 equivalents, relative to 1 equivalent of compound (1-f). Examples of the palladium catalyst include palladium(II) acetate, dichlorobis(triphenylphosphine)palladium(II), tetrakis(triphenylphosphine)palladium(0), and the like. The amount of the palladium catalyst for use in the reaction is generally 0.01 to 1 equivalent, preferably 0.1 to 0.5 equivalent, relative to 1 equivalent of compound (1-f).

Examples of the base include alkali metal carbonates such as potassium carbonate, cesium carbonate and sodium carbonate, alkali metal phosphates such as potassium phosphate, and the like. The amount of the base for use in the reaction is 1 to 10 equivalents, preferably 1 to 5 equivalents, relative to 1 equivalent of compound (1-f).

Examples of the reaction solvent include solvents that do not interfere with the reaction, such as toluene, 1,2-dimethoxyethane, N,N-dimethylformamide, and dimethyl sulfoxide. These solvents may be mixed and used in appropriate proportions.

This reaction may be generally performed at room temperature to 200° C. for 1 to 24 hr.

When $R^E$ is $Pro^1$ in the step, a deprotection reaction may be performed under an acidic condition in the presence or absence of anisole.

Examples of an acid for use in the reaction include trifluoroacetic acid and the like. The amount of the acid for use in the reaction is 1 equivalent to the amount of solvent, preferably 1 to 10 equivalents, relative to 1 equivalent of compound (1-f).

The amount of anisole for use in the reaction is 1 equivalent to the amount of solvent, preferably 1 to 10 equivalents, relative to 1 equivalent of compound (1-f).

The thus obtained compound (1-g) may be isolated and purified by a known separation and purification means, such as concentration, vacuum concentration, reprecipitation, solvent extraction, crystallization, or chromatography.

[Step 6]

This step is a process in which compound (1-f) is reacted with carboxylic acid or an acid chloride or an acid anhydride, which corresponds to $R^B$, to produce compound (1-h).

When a reagent for use in this step is carboxylic acid, the reaction may be performed by a known method such as a method using a condensing agent in the presence or absence of a base and an activator.

The amount of carboxylic acid for use in the step is 1 to 5 equivalents, preferably 1 to 3 equivalents, relative to 1 equivalent of compound (1-f).

Examples of the condensing agent include 1-ethyl-3-(3-dimethylaminopropyl)carbodiimide hydrochloride, N,N'-dicyclohexylcarbodiimide, diethyl cyanophosphonate, and the like.

The amount of the condensing agent for use in the reaction is 1 to 5 equivalents, preferably 1 to 3 equivalents, relative to 1 equivalent of compound (1-f).

Examples of the activator include N-hydroxybenzotriazole monohydrate, N-hydroxysuccinimide, and the like. The amount of the activator for use in the reaction is 1 to 5 equivalents, preferably 1 to 2 equivalents, relative to 1 equivalent of compound (1-f).

Examples of the base include tertiary aliphatic amines such as N,N-diisopropylethylamine and triethylamine, pyridine, and the like. The amount of the base for use in the reaction is 1 to 5 equivalents, preferably 1 to 2 equivalents, relative to 1 equivalent of compound (1-f). Examples of a solvent for use in the reaction include solvents that do not interfere with the reaction, such as N,N-dimethylformamide, dichloromethane, chloroform, 1,2-dichloroethane, toluene, tetrahydrofuran, and water. These solvents may be mixed and used in appropriate proportions.

This reaction may be generally performed at 0° C. to reflux temperature for 1 to 24 hr.

When a reagent for use in the step is an acid chloride or an acid anhydride, the reaction may be performed using an acylation reaction.

The amount of the acid chloride or the like for use in this step is 1 to 5 equivalents, preferably 1 to 3 equivalents, relative to 1 equivalent of compound (1-f).

Examples of a base used generally in the reaction include triethylamine, pyridine, N,N-dimethyl-4-aminopyridine, N,N-diisopropylethylamine, and the like. The amount of the base for use in the reaction is generally 1 to 5 equivalents, preferably 1 to 3 equivalents, relative to 1 equivalent of compound (1-f).

Examples of a reaction solvent for use in the reaction include solvents that do not interfere with the reaction, such as chloroform, dichloromethane, diethyl ether, tetrahydrofuran, ethyl acetate, N,N-dimethylformamide, and acetonitrile. These solvents may be mixed and used in appropriate proportions.

This reaction may be generally performed at 0° C. to room temperature for 1 to 24 hr. When $R^E$ is $Pro^1$ in the step, a deprotection reaction may be performed under an acidic condition in the presence or absence of anisole.

Examples of an acid for use in the reaction include trifluoroacetic acid and the like. The amount of the acid for use in the reaction is 1 equivalent to the amount of solvent, preferably 1 to 10 equivalents, relative to 1 equivalent of compound (1-f).

The amount of anisole for use in the reaction is 1 equivalent to the amount of solvent, preferably 1 to 10 equivalents, relative to 1 equivalent of compound (1-f).

The thus obtained compound (1-h) may be isolated and purified by a known separation and purification means, such as concentration, vacuum concentration, reprecipitation, solvent extraction, crystallization, or chromatography.

[Step 7]

This step is a process in which compound (1-f) is reacted with isocyanate or amine, which corresponds to $R^B$, to produce compound (1-i).

When a reagent for use in this step is isocyanate, the reaction may be performed in a solvent that does not interfere with the reaction in the presence or absence of a base. The amount of isocyanate for use in the step is 1 to 5 equivalents, preferably 1 to 3 equivalents, relative to 1 equivalent of compound (1-f).

Examples of the base used generally in the reaction include triethylamine, pyridine, N,N-dimethyl-4-aminopyridine, N,N-diisopropylethylamine, and the like. The amount of the base for use in the reaction is generally 1 to 5 equivalents, preferably 1 to 3 equivalents, relative to 1 equivalent of compound (1-f).

Examples of the reaction solvent include solvents that do not interfere with the reaction, such as chloroform, dichloromethane, diethyl ether, tetrahydrofuran, ethyl acetate, N,N-dimethylformamide, and dimethyl sulfoxide. These solvents may be mixed and used in appropriate proportions.

This reaction may be generally performed at 0° C. to room temperature for 1 to 24 hr.

When a reagent for use in the step is amine, the reaction may be performed by allowing 4-nitrophenyl chloroformate to act in the presence of a base in a solvent that does not interfere with the reaction.

The amount of amine for use in the step is 1 to 5 equivalents, preferably 1 to 3 equivalents, relative to 1 equivalent of compound (1-f).

Examples of the base used generally in the reaction include triethylamine, pyridine, N,N-dimethyl-4-aminopyridine, N,N-diisopropylethylamine, and the like. The amount of the base for use in the reaction is generally 1 to 5 equivalents, preferably 1 to 3 equivalents, relative to 1 equivalent of compound (1-f).

The amount of 4-nitrophenyl chloroformate for use in the reaction is 1 to 5 equivalents, preferably 1 to 3 equivalents, relative to 1 equivalent of compound (1-f).

Examples of the reaction solvent include solvents that do not interfere with the reaction, such as chloroform, dichloromethane, diethyl ether, tetrahydrofuran, ethyl acetate, and acetonitrile. These solvents may be mixed and used in appropriate proportions.

This reaction may be generally performed at 0° C. to reflux temperature for 1 to 24 hr.

When $R^E$ is $Pro^1$ in the step, a deprotection reaction may be performed under an acidic condition in the presence or absence of anisole.

Examples of an acid for use in the reaction include trifluoroacetic acid and the like. The amount of the acid for use in the reaction is 1 equivalent to the amount of solvent, preferably 1 to 10 equivalents, relative to 1 equivalent of compound (1-f).

The amount of anisole for use in the reaction is 1 equivalent to the amount of solvent, preferably 1 to 10 equivalents, relative to 1 equivalent of compound (1-f).

The thus obtained compound (1-i) may be isolated and purified by a known separation and purification means, such as concentration, vacuum concentration, reprecipitation, solvent extraction, crystallization, or chromatography.

Compound (1-a) and compound (1-d), which are used as starting materials in Production Method 1 as described above, may be produced by methods known per se.

Production Method 2:

[Formula 11]

(In this scheme, Ring A, $R^D$, X, m, n and $R^E$ are as defined above.)

[Step 1]

This step is a process in which compound (2-a) is used to produce compound (2-b).

This reaction may be performed in accordance with the method described in Step 1 of Production Method 1.

[Step 2]

This step is a process in which compound (2-b) is used to produce compound (2-c).

This reaction may be performed in accordance with the method described in Step 2 of Production Method 1.

[Step 3]

This step is a process in which compound (2-c) and compound (1-d) are reacted to produce compound (2-d).

This reaction may be performed in accordance with the method described in Step 3 of Production Method 1.

[Step 4]

This step is a process in which compound (2-d) is used to produce compound (1-e).

The step may be performed in accordance with a known method such as the method described in Synthesis, 1980, 425, Tetrahedron Letters, 2002, 43, 7247 or a modified version of the method.

This reaction is peformed by a method of performing a reaction in a solvent that does not interfere with the reaction in the presence of a metal and a hydrogen source, in the presence or absence of a base.

Examples of the metal include palladium and the like. The amount of the metal for use in the reaction is 0.1 to 1 equivalent, preferably 0.1 to 0.5 equivalent, relative to 1 equivalent of compound (2-d).

Hydrogen pressure for use in the reaction is normal pressure to 10 atm, preferably normal pressure to 4 atm.

Examples of the base used generally in the reaction include triethylamine, ethylenediamine, dimethylamine, and the like. The amount of the base for use in the reaction is generally 1 to 5 equivalents, preferably 1 to 3 equivalents, relative to 1 equivalent of compound (2-d).

Examples of the reaction solvent include methanol, ethanol, water, tetrahydrofuran, chloroform, dichloromethane, ethyl acetate, and the like. These solvents may be mixed and used in appropriate proportions.

This reaction may be generally performed at room temperature to reflux temperature for 1 to 24 hr.

The thus obtained compound (1-e) may be used to produce compounds (1-g), (1-h) and (1-i) as shown in Production Method 1 above by modified versions of the processes of Step 4 onwards in Production Method 1.

Compound (2-a) and compound (1-d), which are used as starting materials in Production Method 2 as described above, may be produced by methods known per se.

Production Method 3:

[Formula 12]

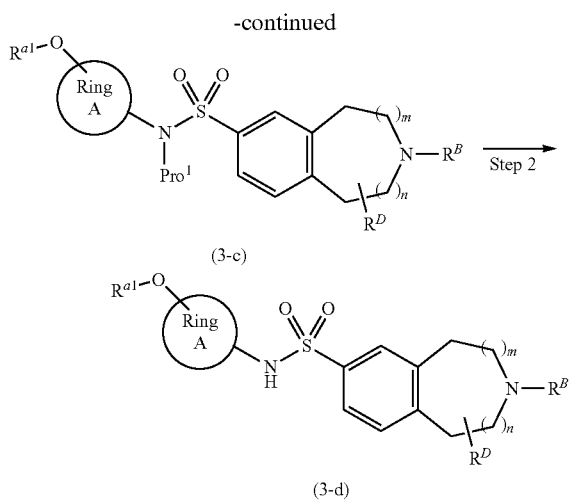

(In this scheme, Ring A, $R^B$, $R^D$, m, n and $Pro^1$ are as defined above; $R^{a1}$ represents a $C_{1-8}$ alkyl group; Ua represents a leaving group or a hydroxy group.)

The $C_{1-8}$ alkyl group represented by $R^{a1}$ may be substituted by 1 to 3 substituents, which may be the same or different, selected from the group consisting of:
a halogen atom,
an oxo group,
a $C_{3-8}$ cycloalkyl group,
a saturated heterocyclyl group which may be substituted by 1 or 2 substituents, which may be the same or different, selected from the group consisting of a $C_{1-8}$ alkyl group, and an oxo group,
an aryl group,
a heteroaryl group,
a $C_{1-8}$ alkyl group,
a $C_{1-8}$ alkoxy group which may be substituted by 1 to 3 substituents, which may be the same or different, selected from the group consisting of a halogen atom, a saturated heterocyclyl group, and a $C_{1-8}$ alkoxy group,
a $C_{3-8}$ cycloalkyloxy group,
an aryloxy group which may be substituted by one substituent selected from the group consisting of a halogen atom, a $C_{1-8}$ alkyl group which may be substituted by 1 to 3 halogen atoms, and a $C_{1-8}$ alkoxy group,
a $C_{1-8}$ alkylsulfonyl group, and
an arylsulfonyl group.

Examples of the "leaving group" represented by Ua include a chlorine atom, a bromine atom, an iodine atom, a methylsulfonyloxy group, a p-toluenesulfonyloxy group, a trifluoromethylsulfonyloxy group, a phenylsulfonyloxy group, and the like.

[Step 1]
This step is a process in which compound (3-a) and compound (3-b) are reacted to produce compound (3-c).

When Ua contained in compound (3-b) is a leaving group, the reaction may be performed in the presence of a base.

The amount of compound (3-b) for use in the step is 1 to 5 equivalents, preferably 1 to 3 equivalents, relative to 1 equivalent of compound (3-a).

Examples of the base used generally in the reaction include tertiary aliphatic amines such as triethylamine, N,N-diisopropylethylamine and 1,8-diazabicyclo[4,3,0]undec-7-ene, alkali metal hydrides such as sodium hydride, alkali metal hydroxides such as potassium hydroxide, alkali metal carbonates such as cesium carbonate, potassium carbonate and sodium carbonate, alkali metal alkoxides such as potassium tert-butoxide, and the like. The amount of the base for use in the reaction is 1 to 5 equivalents, preferably 1 to 3 equivalents, relative to 1 equivalent of compound (3-a).

Examples of a reaction solvent for use in the reaction include solvents that do not interfere with the reaction, such as tetrahydrofuran, dimethyl sulfoxide, N,N-dimethylformamide, N,N-dimethylacetamide, and N-methylpyrrolidone. These solvents may be mixed and used in appropriate proportions.

This reaction may be generally performed at room temperature to reflux temperature for 1 to 24 hr.

When Ua contained in compound (3-b) is a hydroxy group, the reaction may be performed by a so-called Mitsunobu reaction (Synthesis, 1981, 1), which is a known method. The amount of compound (3-b) for use in the step is 1 to 5 equivalents, preferably 1 to 3 equivalents, relative to 1 equivalent of compound (3-a).

Examples of an azo compound used generally in the reaction include diethyl azodicarboxylate, diisopropyl azodicarboxylate, 1,1'-azobis(N,N-dimethylformamide), and the like. The amount of the azo compound for use in the reaction is 1 to 5 equivalents, preferably 1 to 3 equivalents, relative to 1 equivalent of compound (3-a).

Examples of a phosphine compound used generally in the reaction include triphenylphosphine, tributylphosphine, and the like. The amount of the phosphine compound for use in the reaction is 1 to 5 equivalents, preferably 1 to 3 equivalents, relative to 1 equivalent of compound (3-a).

Examples of a reaction solvent for use in the reaction include solvents that do not interfere with the reaction, such as tetrahydrofuran, dioxane, diethyl ether, chloroform, dichloromethane, toluene, N,N-dimethylformamide, and dimethyl sulfoxide. These solvents may be mixed and used in appropriate proportions.

This reaction may be generally performed at room temperature to reflux temperature for 1 to 24 hr.

Alternatively, the Mitsunobu reaction in the step may be performed by a method described in another document (Tetrahedron Letters, 1995, 36, 2531 or Tetrahedron Letters, 1996, 37, 2463). Examples of a reagent for use in the Mitsunobu reactions described in the documents mentioned above include cyanomethylene trimethylphosphorane, cyanomethylene tributylphosphorane, and the like. The amount of the reagent for use in the reaction is 1 to 5 equivalents, preferably 1 to 3 equivalents, relative to 1 equivalent of compound (3-a).

Examples of a reaction solvent for use in the reaction include the same solvents as those listed in relation to the Mitsunobu reaction mentioned above.

This reaction may be generally performed at room temperature to reflux temperature for 1 to 24 hr.

[Step 2]
This step is a process in which compound (3-c) is subjected to a reaction under an acidic condition in the presence or absence of anisole to produce compound (3-d).

Examples of an acid for use in the reaction include trifluoroacetic acid and the like. The amount of the acid for use in the reaction is 1 equivalent to the amount of solvent, preferably 1 to 10 equivalents, relative to 1 equivalent of compound (3-c).

The amount of anisole for use in the reaction is 1 equivalent to the amount of solvent, preferably 1 to 10 equivalents, relative to 1 equivalent of compound (3-c).

The thus obtained compound (3-d) may be isolated and purified by a known separation and purification means, such as concentration, vacuum concentration, reprecipitation, solvent extraction, crystallization, or chromatography.

It is to be noted that compound (3-a) and compound (3-b), which are used as starting materials in Production Method 3 as described above, may be produced by Production Methods 1 and 2 as described above or modified versions of the methods or methods known per se.

Production Method 4:

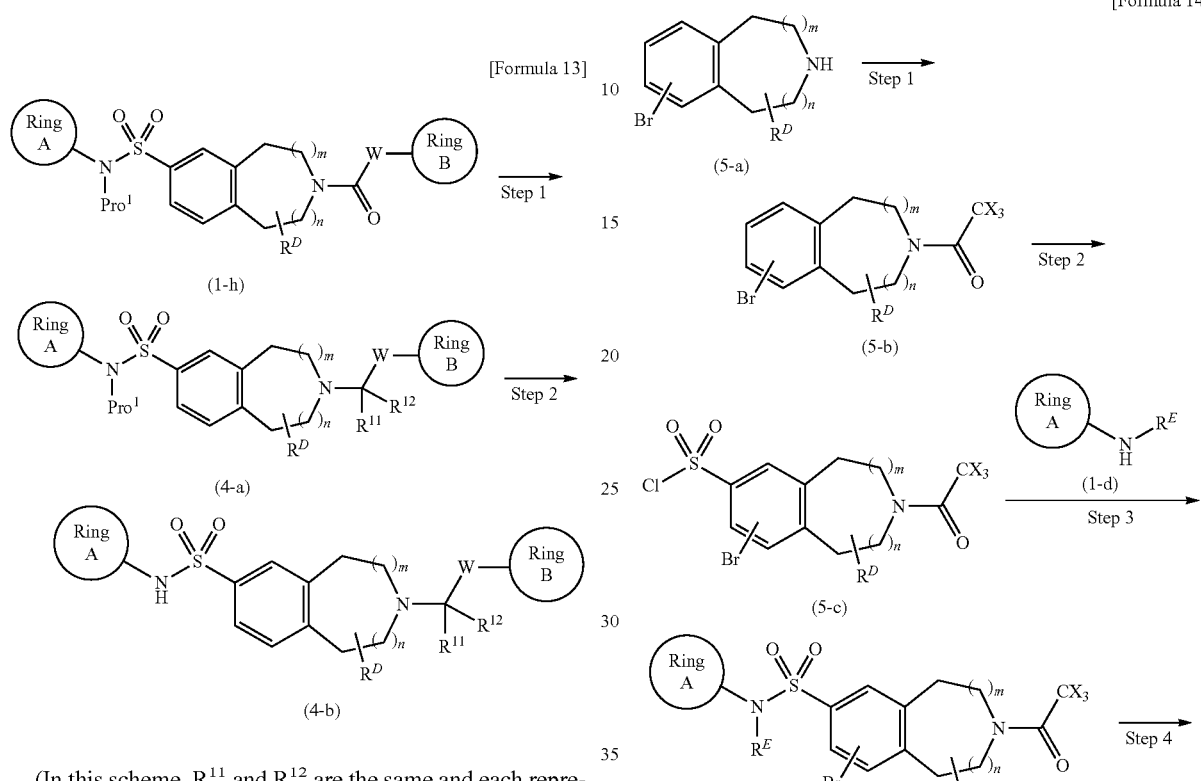

(In this scheme, $R^{11}$ and $R^{12}$ are the same and each represent a $C_{1-4}$ alkyl group; Ring A, Ring B, $R^D$, W, m, n and $Pro^1$ are as defined above.)

[Step 1]

This step is a process in which compound (1-h) is used to produce compound (4-a). The step may be performed by a known method such as the method described in Synlett, 1999, 55 or a modified version of the method.

This reaction is performed by a method of performing a reaction in a solvent that does not interfere with the reaction in the presence of a Lewis acid using a Grignard reagent having $C_{1-4}$ alkyl groups which correspond to $R^{11}$ and $R^{12}$.

The amount of the Grignard reagent for use in the reaction is generally 1 to 5 equivalents, preferably 1 to 3 equivalents, relative to 1 equivalent of compound (1-h).

Examples of the Lewis acid for use in the reaction include titanium tetrachloride, zirconium tetrachloride, tetraisopropyl orthotitanate, and the like. The amount of the Lewis acid for use in the reaction is 0.5 to 5 equivalents, preferably 1 to 3 equivalents, relative to 1 equivalent of compound (1-h).

Examples of the solvent for use in the reaction include tetrahydrofuran, diethyl ether, and the like, and these solvents may be mixed and used in appropriate proportions.

This reaction may be generally performed at room temperature to 50° C. for 1 to 24 hr.

[Step 2]

This step is a process in which compound (4-a) is used to produce compound (4-b).

This reaction may be performed in accordance with the method described in Step 2 of Production Method 3.

It is to be noted that compound (1-h), which is used as a starting material in Production Method 4 as described above, may be produced by Production Methods 1 to 3 as described above or modified versions of the methods.

Production Method 5:

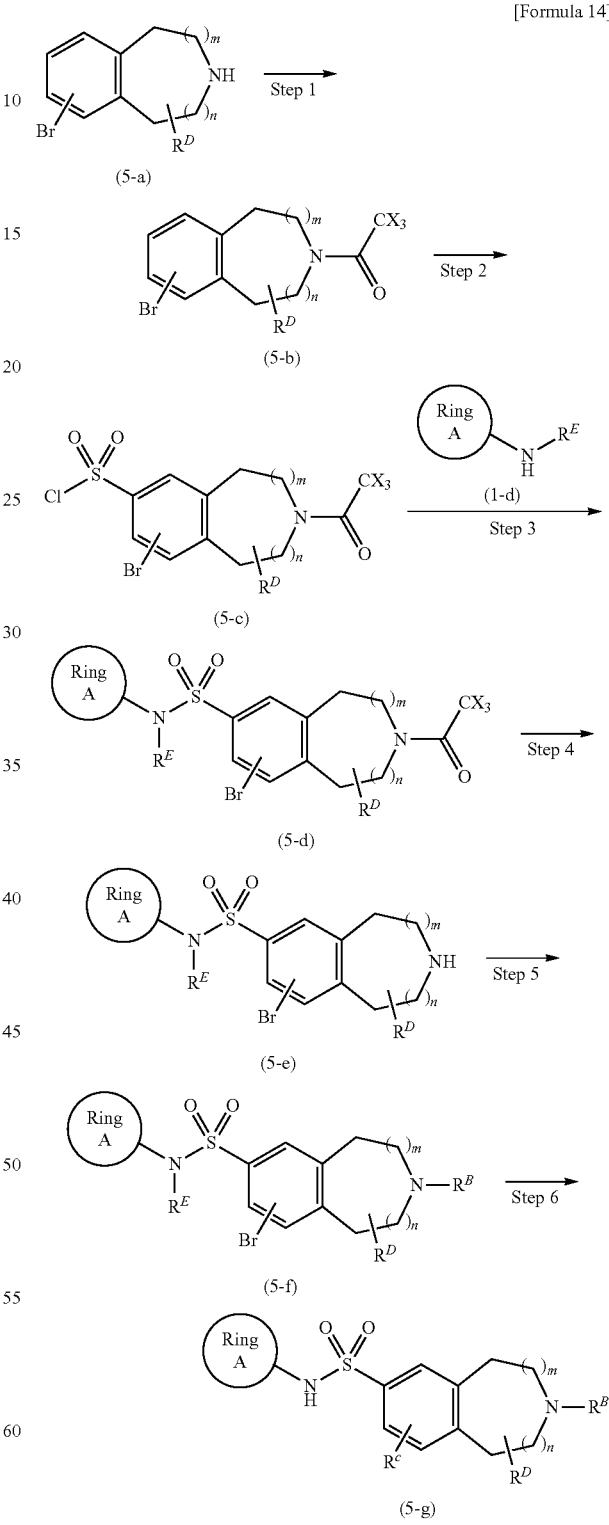

(In this scheme, Ring A, $R^B$, $R^E$, m, n and X are as defined above.)

[Step 1]
This step is a process in which compound (5-a) is used to produce compound (5-b).
This reaction may be performed in accordance with the method described in Step 1 of Production Method 1.

[Step 2]
This step is a process in which compound (5-b) is used to produce compound (5-c).
This reaction may be performed in accordance with the method described in Step 2 of Production Method 1.

[Step 3]
This step is a process in which compound (5-c) is used to produce compound (5-d).
This reaction may be performed in accordance with the method described in Step 3 of Production Method 1.

[Step 4]
This step is a process in which compound (5-d) is used to produce compound (5-e).
This reaction may be performed in accordance with the method described in Step 4 of Production Method 1.

[Step 5]
This step is a process in which compound (5-e) is used to produce compound (5-f).
This reaction may be performed in accordance with the method described in Step 5, 6 or 7 of Production Method 1.

[Step 6]
This step is a process in which compound (5-f) is used to produce compound (5-g).
This reaction, which is a so-called Suzuki-Miyaura coupling reaction, may be performed in the presence of a palladium catalyst and a base by the method described in a document (
Tetrahedron Letters, 1979, 20, 3437 or Chemical reviews, 1995, 95, 2457) or a modified version of the method.
The amount of a boronic acid or boronic acid ester for use in the step is 1 to 5 equivalents, preferably 1 to 3 equivalents, relative to 1 equivalent of compound (5-f).
Examples of the palladium catalyst include tetrakis(triphenylphosphine)palladium(0), [1,1'-bis(diphenylphosphino)ferrocene]palladium(II)dichloride dichloromethane complex, bis(triphenylphosphine)palladium(II)dichloride, and the like.
The amount of the palladium catalyst for use in the reaction is generally 0.01 to 0.5 equivalent, preferably 0.05 to 0.3 equivalent, relative to 1 equivalent of compound (5-f).
Examples of the base include alkali metal carbonates such as potassium carbonate, cesium carbonate and sodium carbonate or aqueous solutions thereof, potassium fluoride, cesium fluoride, triethylamine, and the like.
The amount of the base for use in the reaction is generally 1 to 5 equivalents, preferably 1 to 3 equivalents, relative to 1 equivalent of compound (5-f).
Examples of a reaction solvent for use in the reaction include solvents that do not interfere with the reaction, such as N,N-dimethylformamide, dimethyl sulfoxide, toluene, dioxane, tetrahydrofuran, 1,2-dimethoxyethane, and ethanol. These solvents may be mixed and used in appropriate proportions.
This reaction may be generally performed at room temperature to 180° C. for 1 to 24 hr, and may also be performed under microwave irradiation.
When $R^E$ is $Pro^I$ in the step, a deprotection reaction may be performed under an acidic condition in the presence or absence of anisole.
Examples of an acid for use in the reaction include trifluoroacetic acid and the like.
The amount of the acid for use in the reaction is 1 equivalent to the amount of solvent, preferably 1 to 10 equivalents, relative to 1 equivalent of compound (5 f).
The amount of anisole for use in the reaction is 1 equivalent to the amount of solvent, preferably 1 to 10 equivalents, relative to 1 equivalent of compound (5 f).
Compound (5-a) and compound (1-d), which are used as starting materials in Production Method 5 as described above, may be produced by methods known per se.

Production Method 6:

[Formula 15]

(In this scheme, $R^{11}$ represents a $C_{1-4}$ alkyl group; Ring A, Ring B, $R^D$, W, m, n and $Pro^1$ are as defined above.)

[Step 1]
This step is a process in which compound (1-f) is used to produce compound (6-a).
The step may be performed by a known method such as the method described in Synthesis, 2002, 199 or a modified version of the method.
This reaction is performed by a method of performing a reaction in a solvent that does not interfere with the reaction in the presence of benzotriazole monohydrate using an aldehyde represented by the structural formula OHC—W-Ring B and a Grignard reagent having a $C_{1-4}$ alkyl group which corresponds to $R^{11}$.
The amount of the aldehyde for use in the step is 1 to 5 equivalents, preferably 1 to 3 equivalents, relative to 1 equivalent of compound (1-f). The amount of the Grignard reagent for use in the step is generally 1 to 5 equivalents, preferably 1 to 3 equivalents, relative to 1 equivalent of compound (1-f). The amount of benzotriazole monohydrate for use in the step is 0.5 to 5 equivalents, preferably 1 to 3 equivalents, relative to 1 equivalent of compound (1-f).
Examples of the solvent for use in the reaction include chloroform, tetrahydrofuran, diethyl ether, and the like, and these solvents may be mixed and used in appropriate proportions. This reaction may be generally performed at room temperature to 50° C. for 1 to 24 hr.

[Step 2]

This step is a process in which compound (6-a) is used to produce compound (6-b).

This reaction may be performed in accordance with the method described in Step 2 of Production Method 3.

It is to be noted that compound (1-f), which is used as a starting material in Production Method 6 as described above, may be produced by Production Methods 1 to 5 as described above or modified versions of the methods.

Production Method 7:

[Formula 16]

(In this scheme, Ring A, $R^B$, $R^C$, $R^D$, m, n and $R^F$ are as defined above.)

[Step 1]

This step is a process in which compound (5-g) is used to produce compound (7-a).

The step may be performed by a known method such as the method described in Bioorganic & Medicinal Chemistry, 2005, 13, 1201 or a modified version of the method. This reaction is performed by a method of performing a reaction in a solvent that does not interfere with the reaction by using an alkyl halide or alkyl sulfonate which corresponds to $R^F$.

The amount of the alkyl halide or the like for use in the step is 1 to 20 equivalents, preferably 1 to 10 equivalents, relative to 1 equivalent of compound (5-g). Examples of the solvent for use in the reaction include acetonitrile, dichloromethane, and the like, and these solvents may be mixed and used in appropriate proportions.

This reaction may be generally performed at room temperature to reflux temperature for 1 to 24 hr.

It is to be noted that compound (5-g), which is used as a starting material in Production Method 7 as described above, may be produced by Production Methods 1 to 6 as described above or modified versions of the methods.

EXAMPLES

The present invention will be described in more detail by means of Reference Examples, Working Examples, Test Examples and Formulation Examples, but these Examples are in no way intended to limit the scope of the present invention, and modifications may be made without departing from the scope of the present invention.

The microwave reaction apparatus used in Reference Examples and Working Examples as described below was Initiator from Biotage.

In Reference Examples and Working Examples below, the term "NH silica gel column chromatography" refers to separation and purification by column chromatography using an NH2 type silica gel (Chromatorex NH2 type from Fuji Silysia Chemical). Unless otherwise indicated, a ratio of an elution solvent indicates a volumetric ratio.

The abbreviations used herein mean the following:
s: singlet
d: doublet
t: triplet
q: quartet
dd: double doublet
dt: double triplet
m: multiplet
br: broad
J: coupling constant
Hz: hertz
$CDCl_3$: deuterated chloroform
DMSO-$d_6$: deuterated dimethyl sulfoxide
$CD_3OD$: deuterated methanol $^1$H-NMR (proton nuclear magnetic resonance spectra) was measured by the following Fourier transform NMR.
200 MHz: Gemini 2000 (Agilent Technologies)
300 MHz: Inova 300 (Agilent Technologies)
600 MHz: JNM-ECA 600 (JEOL Ltd.)

In the analyses, ACD/SpecManager ver. 12.01 (trade name) and the like were used. No description of too broad peaks from protons in a hydroxyl group, an amino group and the like is provided herein.

MS (mass spectra) were measured with the following apparatuses:
Platform LC (Waters)
LCMS-2010 EV (Shimadzu Corp.)
LCMS-IT-TOF (Shimadzu Corp.)

As an ionization method, the ESI (Electrospray Ionization) method or a dual ionization method combining the ESI method and the APCI (Atmospheric Pressure Chemical Ionization) method was used. The data show measured values as "found". In general, a molecular ion peak is observed; however, in the case of a compound having a hydroxyl group (—OH), a peak after elimination of $H_2O$ may be observed as a fragment peak. In the case of a salt, a molecular ion peak or fragment ion peak of free form is generally observed.

In Reference Examples and Working Examples below, preparative high performance liquid chromatography (HPLC) was used to perform purification under the conditions shown below. It should be noted that when trifluoroacetic acid was used in this procedure for a compound having a basic functional group, a neutralization procedure or the like was performed to obtain the compound in free form in some cases.

Apparatus: Preparative HPLC system from Gilson, Inc.
Condition 1
Column: Capcell pak C18 MGII 5 μm 20×150 mm from Shiseido Co., Ltd.
Flow rate: 20 mL/min, Detection method: UV 254 nm
Solvent: A-liquid (0.1% trifluoroacetic acid-containing water), B-liquid (0.1% trifluoroacetic acid-containing acetonitrile)
Gradient: 0 min (A-liquid/B-liquid=90/10), 2 min (A-liquid/B-liquid=90/10), 22 min (A-liquid/B-liquid=20/80), 25 min (A-liquid/B-liquid=10/90)
Condition 2
Column: Waters SunFire™ Prep C18, OBD™ 5 μm (30 mm×50 mm)
Flow rate: 40 mL/min, Detection method: UV 254 nm Solvent: A-liquid (0.1% trifluoroacetic acid-containing water), B-liquid (0.1% trifluoroacetic acid-containing acetonitrile)

Gradient: 0 min (A-liquid/B-liquid=90/10), 2 min (A-liquid/B-liquid=90/10), 12 min (A-liquid/B-liquid=20/80), 13.5 min (A-liquid/B-liquid=5/95), 15 min (A-liquid/B-liquid=5/95)

In Reference Examples and Working Examples below, the following conditions were used for high performance liquid chromatography mass spectra (LCMS).

Condition 1-1

Instrument: Platform LC from Waters and Agilent 1100 from Agilent

Column: SunFire™ C18, 2.5 µm 4.6×50 mm from Waters

Flow rate: 1 mL/min, Detection method: 254 nm

Ionization method: Electron impact ionization method (Electron Spray Ionization: ESI)

Solvent: A-liquid (0.1% trifluoroacetic acid-containing water), B-liquid (0.1% trifluoroacetic acid-containing acetonitrile)

Condition 1-1-1

Gradient: 0 min (A-liquid/B-liquid=90/10), 0.5 min (A-liquid/B-liquid=90/10), 5.5 min (A-liquid/B-liquid=20/80), 6.0 min (A-liquid/B-liquid=1/99), 6.3 min (A-liquid/B-liquid=1/99)

Condition 1-1-2

Gradient: 0 min (A-liquid/B-liquid=90/10), 0.5 min (A-liquid/B-liquid=90/10), 5.5 min (A-liquid/B-liquid=20/80), 6.0 min (A-liquid/B-liquid=1/99), 7.3 min (A-liquid/B-liquid=1/99)

Condition 1-1-3

Gradient: 0 min (A-liquid/B-liquid=90/10), 0.5 min (A-liquid/B-liquid=90/10), 5.0 min (A-liquid/B-liquid=1/99), 7.3 min (A-liquid/B-liquid=1/99)

Condition 1-2

Instrument: LCQ Deca XP from ThermoFisher Scientific, and LC-10AD series from Shimadzu Corp.

Column: SunFire™ C18, 2.5 µm 4.6×50 mm from Waters

Flow rate: 1 mL/min, Detection method: 254 nm and 210 nm

Ionization method: Electron impact ionization method (Electron Spray Ionization: ESI)

Solvent: A-liquid (0.1% trifluoroacetic acid-containing water), B-liquid (0.1% trifluoroacetic acid-containing acetonitrile)

Condition 1-2-1

Gradient: 0 min (A-liquid/B-liquid=90/10), 0.5 min (A-liquid/B-liquid=90/10), 5.5 min (A-liquid/B-liquid=20/80), 6.0 min (A-liquid/B-liquid=1/99), 6.3 min (A-liquid/B-liquid=1/99)

Condition 1-2-2

Gradient: 0 min (A-liquid/B-liquid=90/10), 0.5 min (A-liquid/B-liquid=90/10), 5.5 min (A-liquid/B-liquid=20/80), 6.0 min (A-liquid/B-liquid=1/99), 7.3 min (A-liquid/B-liquid=1/99)

Condition 1-2-3

Gradient: 0 min (A-liquid/B-liquid=90/10), 0.5 min (A-liquid/B-liquid=90/10), 5.0 min (A-liquid/B-liquid=1/99), 7.3 min (A-liquid/B-liquid=1/99)

Condition 2

Instrument: Agilent 2900 and Agilent 6150, both from Agilent

Column: Acquity CSH C18, 1.7 µm 2.1×50 mm from Waters

Flow rate: 0.8 mL/min, Detection method: 254 nm

Ionization method: Electron impact ionization method (Electron Spray Ionization: ESI)

Solvent: A-liquid (0.1% formic acid-containing water), B-liquid (0.1% formic acid-containing acetonitrile)

Gradient: 0 min (A-liquid/B-liquid=80/20), 1.2 min (A-liquid/B-liquid=1/99), 1.4 min (A-liquid/B-liquid=1/99), 1.5 min (A-liquid/B-liquid=1/99)

Condition 3

Instrument: LC-MS 2010 EV and LC-20AD series, both from Shimadzu Corp.

Column: XR-ODS, 2.2 µm 2.0×30 mm from Shimadzu Corp.

Flow rate: 0.6 mL/min, Detection method: 254 nm

Ionization method: Dual ionization method combining Electron impact ionization method (Electron Spray Ionization: ESI) and Atmospheric Pressure Chemical Ionization (APCI)

Solvent: A-liquid (0.1% formic acid-containing water), B-liquid (0.1% formic acid-containing acetonitrile)

Gradient: 0 min (A-liquid/B-liquid=90/10), 1.0 min (A-liquid/B-liquid=60/40), 2.0 min (A-liquid/B-liquid=0/100), 3.5 min (A-liquid/B-liquid=0/100)

Condition 4

Instrument: LCQ Deca XP from ThermoFisher Scientific, and LC-30AD series from Shimadzu Corp.

Column: Acquity HSS C18, 1.8 µm 2.1×50 mm from Waters

Flow rate: 1 mL/min, Detection method: 254 nm

Ionization method: Electron impact ionization method (Electron Spray Ionization: ESI)

Solvent: A-liquid (0.1% trifluoroacetic acid-containing water), B-liquid (0.1% trifluoroacetic acid-containing acetonitrile)

Condition 4-1

Gradient: 0 min (A-liquid/B-liquid=90/10), 1.1 min (A-liquid/B-liquid=20/80), 1.3 min (A-liquid/B-liquid=1/99), 1.5 min (A-liquid/B-liquid=1/99)

Condition 4-2

Gradient: 0 min (A-liquid/B-liquid=90/10), 1.1 min (A-liquid/B-liquid=1/99), 1.5 min (A-liquid/B-liquid=1/99)

Condition 5

Instrument: LCQ Deca XP from ThermoFisher Scientific, and LC-30AD series from Shimadzu Corp.

Column: Acquity CSH C18, 1.7 µm 2.1×50 mm from Waters

Flow rate: 1 mL/min, Detection method: 254 nm

Ionization method: Electron impact ionization method (Electron Spray Ionization: ESI)

Solvent: A-liquid (0.1% trifluoroacetic acid-containing water), B-liquid (0.1% trifluoroacetic acid-containing acetonitrile)

Condition 5-1

Gradient: 0 min (A-liquid/B-liquid=90/10), 1.1 min (A-liquid/B-liquid=20/80), 1.3 min (A-liquid/B-liquid=1/99), 1.5 min (A-liquid/B-liquid=1/99)

Condition 5-2

Gradient: 0 min (A-liquid/B-liquid=90/10), 1.1 min (A-liquid/B-liquid=1/99), 1.5 min (A-liquid/B-liquid=1/99)

In Reference Examples and Working Examples below, the following conditions were used for high performance liquid chromatography (HPLC).

Condition 6

Instrument: Waters 2695 Separations Module

Column: Daicel Corporation CHIRALPAK AD-H 5 µm 4.6×250 mm

Flow rate: 1.0 mL/min, Detection method: 254 nm, Temperature: 40° C.

Solvent: hexane:ethanol:diethylamine=90:10:0.1

The phase separator used herein was ISOLUTE (registered trademark) Phase Separator from Biotage.

In Reference Examples and Working Examples below, compounds were named in accordance with ACD/Name (ACD/Labs 12.01, Advanced Chemistry Development Inc.)

Reference Example 1-1

7-Bromo-1-(trifluoromethyl)-1,2,3,4-tetrahydroisoquinoline

[Formula 17]

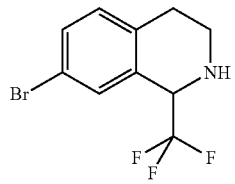

(1) N-[2-(4-Bromophenyl)ethyl]-2,2,2-trifluoroacetamide (4.0 g, 13.5 mmol) which was synthesized in accordance with the method described in a document (Tetrahedron Letters, 1996, 37, 5453) was dissolved in chloroform (40 mL), and 2-chloropyridine and trifluoromethane sulfonic acid anhydride were added thereto. The mixture was stirred at 140° C. for 5 min using a microwave reaction apparatus (Initiator Sixt™ (trade name) from Biotage) under microwave irradiation. To the reaction mixture was added triethylamine (1.1 mL), followed by concentration under reduced pressure. The resulting residue was purified by silica gel column chromatography (hexane only→hexane:ethyl acetate=9:1), powdered with hexane and then collected by filtration to afford 7-bromo-1-(trifluoromethyl)-3,4-dihydroisoquinoline as a colorless powder (1.7 g).

(2) 7-Bromo-1-(trifluoromethyl)-3,4-dihydroisoquinoline obtained (1.9 g, 6.83 mmol) was dissolved in methanol, sodium borohydride (258 mg, 6.83 mmol) was added portionwise thereto and the mixture was stirred at room temperature for 2 hr. Sodium borohydride (516 mg, 13.7 mmol) was further added thereto, followed by heating to reflux for 2 hr. Sodium borohydride (258 mg, 6.83 mmol) was still further added thereto and the mixture was heated to reflux for 4 hr. Thereafter, sodium borohydride (258 mg, 6.83 mmol) was added thereto and the mixture was heated to reflux for 4 hr. The reaction mixture was concentrated and the residue was diluted and extracted with water and ethyl acetate. The organic layer was washed with brine, concentrated under reduced pressure and then purified by silica gel column chromatography (hexane:ethyl acetate) to afford the title compound as a colorless powder (0.85 g)
$^1$H NMR (300 MHz, CDCl$_3$) δ ppm 1.98 (br. s., 1 H), 2.72-2.88 (m, 2 H), 3.02-3.12 (m, 1 H), 3.24-3.36 (m, 1 H), 4.43 (q, J=8.3 Hz, 1 H), 7.05 (d, J=8.7 Hz, 1 H), 7.36-7.42 (m, 1 H), 7.46 (s, 1 H).

Reference Example 2-1

N-(4-Fluorophenyl)-2-(trifluoroacetyl)-2,3-dihydro-1 H-isoindole-5-sulfonamide

[Formula 18]

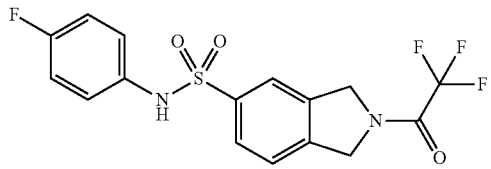 [SMILES: Cc1cc(F)ccc1NS(=O)(=O)c1ccc2c(c1)CN(C(=O)C(F)(F)F)C2]

(1) Pyridine (6.56 mL, 81.1 mmol) and dimethylaminopyridine (248 mg, 2.03 mmol) were added to a solution of isoindoline (8.08 g, 40.6 mmol) in chloroform (120 mL) at room temperature and the mixture was cooled in ice. Trifluoroacetic acid anhydride (6.77 mL, 48.7 mmol) was added dropwise thereto and the reaction mixture was warmed to room temperature and stirred for 4 hr. The reaction mixture was concentrated under reduced pressure and the residue was diluted with ethyl acetate. The mixture was washed with 1 mol/L hydrochloric acid, saturated aqueous sodium hydrogen carbonate solution and brine. The organic layer was dried over anhydrous magnesium sulfate and then the desiccant was filtered off, followed by concentration under reduced pressure. The resulting residue was purified by silica gel column chromatography (hexane:ethyl acetate=9:1) to afford 1-(1,3-dihydro-2 H-isoindol-2-yl)-2,2,2-trifluoroethanone as a brownish red powder (8.66 g).

(2) A solution of 1-(1,3-dihydro-2 H-isoindol-2-yl)-2,2,2-trifluoroethanone obtained (5.00 g, 23.2 mmol) in chloroform (80 mL) was cooled at an external temperature of −78° C., and chlorosulfonic acid (10.1 mL, 152 mmol) was added dropwise thereto. The reaction mixture was warmed to room temperature and stirred overnight. The reaction mixture was poured into ice water for separation into an organic layer and an aqueous layer. The aqueous layer was extracted twice with chloroform, and the combined organic layer was washed with water. The organic layer was dried over anhydrous magnesium sulfate and then the desiccant was filtered off, followed by concentration under reduced pressure. The resulting residue was dried under reduced pressure to afford 2-(trifluoroacetyl)-2,3-dihydro-1 H-isoindole-5-sulfonyl chloride as a brown oil (5.15 g).

(3) Pyridine (2.57 mL, 31.9 mmol) and dimethylaminopyridine (195 mg, 1.59 mmol) were added to a solution of 4-fluoroaniline (1.86 g, 16.7 mmol) in chloroform (46 mL) at room temperature and the mixture was cooled in ice. 2-(Trifluoroacetyl)-2,3-dihydro-1 H-isoindole-5-sulfonyl chloride (5.00 g, 15.9 mmol) was added thereto and the mixture was warmed to room temperature and stirred for 15 hr. The reaction mixture was concentrated under reduced pressure and the residue was diluted with ethyl acetate. The mixture was washed with 1 mol/L hydrochloric acid and brine, the organic layer was dried over anhydrous magnesium sulfate, and then the desiccant was filtered off, followed by concentration under reduced pressure. The resulting residue was powdered with diethyl ether and collected by filtration to afford the title compound as a pale pink powder (5.85 g).
$^1$H NMR (300 MHz, DMSO-d$_6$) δ ppm 4.86 (s, 2 H), 5.06 (s, 2 H), 7.04-7.14 (m, 4 H), 7.47-7.59 (m, 1 H), 7.64-7.72 (m, 1 H), 7.75-7.82 (m, 1 H), 10.31 (br. s., 1 H).
MS ESI/APCI Dual nega: 387[M−H]$^-$.

The compounds of Reference Examples 2-2 to 2-26 were obtained by using the compound obtained in Reference Example 2-1(2) and the corresponding anilines obtained in Reference Examples 15, 16, 17, 18, 21, 24, 26, 27 and the likein accordance with the process of Reference Example 2-1(3).

Reference Example 2-2

$^1$H NMR (300 MHz, DMSO-d$_6$) δ ppm 4.81-4.93 (m, 2 H), 5.03-5.13 (m, 2 H), 6.98-7.07 (m, 1 H), 7.18-7.29 (m, 2 H), 7.52-7.61 (m, 1 H), 7.63-7.71 (m, 1 H), 7.73-7.78 (m, 1 H), 10.20 (s, 1 H).
MS ESI/APCI Dual nega: 405[M−H]$^-$.

Reference Example 2-3

$^1$H NMR (300 MHz, CDCl$_3$) δ ppm 3.63 (s, 3 H), 4.87-5.08 (m, 4 H), 6.46-6.53 (m, 1 H), 6.59-6.69 (m, 1 H), 6.80 (s, 1 H), 7.29-7.42 (m, 1 H), 7.45-7.53 (m, 1 H), 7.65-7.76 (m, 2 H).
MS ESI/APCI Dual nega: 417[M−H]$^-$.

Reference Example 2-4

¹H NMR (300 MHz, CDCl₃) δ ppm 1.23-1.30 (m, 3 H), 3.82 (q, J=6.9 Hz, 2 H), 4.86-5.07 (m, 4 H), 6.42-6.49 (m, 1 H), 6.59-6.67 (m, 1 H), 6.78-6.82 (m, 1 H), 7.29-7.41 (m, 1 H), 7.46-7.54 (m, 1 H), 7.62-7.74 (m, 2 H).

Reference Example 2-5

¹H NMR (300 MHz, CDCl₃) δ ppm 0.92 (t, J=7.4 Hz, 3 H), 1.60-1.73 (m, 2 H), 3.71 (t, J=6.6 Hz, 2 H), 4.86-5.06 (m, 4 H), 6.44-6.50 (m, 1 H), 6.59-6.67 (m, 1 H), 6.76-6.80 (m, 1 H), 7.29-7.39 (m, 1 H), 7.47-7.55 (m, 1 H), 7.63-7.73 (m, 2 H).

Reference Example 2-6

¹H NMR (300 MHz, DMSO-d₆) δ ppm 4.84-4.93 (m, 2 H), 5.05-5.14 (m, 2 H), 7.16-7.26 (m, 2 H), 7.53-7.62 (m, 1 H), 7.66-7.81 (m, 2 H), 10.1 (br. s., 1 H).
MS ESI/APCI Dual nega: 423[M−H]⁻.

Reference Example 2-7

¹H NMR (300 MHz, CDCl₃) δ ppm 1.99-2.05 (m, 3 H), 4.86-5.12 (m, 4 H), 6.17 (s, 1 H), 6.78-6.91 (m, 2 H), 7.12-7.21 (m, 1 H), 7.33-7.46 (m, 1 H), 7.59-7.74 (m, 2 H).
MS ESI/APCI Dual nega: 401[M−H]⁻.

Reference Example 2-8

¹H NMR (300 MHz, CDCl₃) δ ppm 4.70-4.85 (m, 4 H), 4.87-5.03 (m, 2 H), 6.52-6.60 (m, 1 H), 6.64-6.76 (m, 2 H), 7.09-7.16 (m, 2 H), 7.21-7.32 (m, 1 H), 7.34-7.41 (m, 2 H), 7.51-7.66 (m, 3 H).
MS ESI/APCI Dual nega: 493[M−H]⁻.

Reference Example 2-9

¹H NMR (300 MHz, CDCl₃) δ ppm 4.88-5.09 (m, 4 H), 6.79 (s, 1 H), 6.97-7.07 (m, 2 H), 7.31-7.44 (m, 1 H), 7.63-7.74 (m, 3 H).
MS ESI/APCI Dual nega: 421[M−H]⁻.

Reference Example 2-10

¹H NMR (300 MHz, CDCl₃) δ ppm 3.56 (s, 3 H), 3.76 (s, 3 H), 4.85-4.94 (m, 2 H), 4.98-5.06 (m, 2 H), 6.27-6.32 (m, 1 H), 6.41-6.48 (m, 1 H), 6.67 (s, 1 H), 7.28-7.39 (m, 1 H), 7.41-7.48 (m, 1 H), 7.62-7.74 (m, 2 H).
MS ESI/APCI Dual nega: 429[M−H]⁻.

Reference Example 2-11

¹H NMR (300 MHz, CDCl₃) δ ppm 3.76 (s, 3 H), 4.84-5.14 (m, 4 H), 6.37 (s, 1 H), 6.46-6.56 (m, 1 H), 6.65-6.76 (m, 1 H), 7.30-7.55 (m, 2 H), 7.63-7.74 (m, 2 H).
MS ESI/APCI Dual nega: 417[M−H]⁻.

Reference Example 2-12

¹H NMR (300 MHz, CDCl₃) δ ppm 0.87-0.98 (m, 3 H), 1.31-1.48 (m, 4 H), 1.68-1.82 (m, 2 H), 3.89 (t, J=6.6 Hz, 2 H), 4.86-5.09 (m, 4 H), 6.22 (s, 1 H), 6.77 (d, J=8.1 Hz, 2 H), 6.91-7.00 (m, 2 H), 7.31-7.43 (m, 1 H), 7.60-7.70 (m, 2 H).
MS ESI/APCI Dual nega: 455[M−H]⁻.

Reference Example 2-13

¹H NMR (300 MHz, CDCl₃) δ ppm 0.88-0.95 (m, 3 H), 1.33-1.44 (m, 4 H), 1.69-1.82 (m, 2 H), 3.88 (t, J=6.5 Hz, 2 H), 4.87-5.09 (m, 4 H), 6.34 (s, 1 H), 6.44-6.53 (m, 1 H), 6.63-6.70 (m, 1 H), 7.30-7.51 (m, 2 H), 7.62-7.72 (m, 2 H).
MS ESI/APCI Dual nega: 473[M−H]⁻.

Reference Example 2-14

¹H NMR (300 MHz, CDCl₃) δ ppm 2.91 (s, 6 H), 4.91 (d, J=10.6 Hz, 2 H), 5.03 (d, J=10.6 Hz, 2 H), 6.25-6.31 (m, 1 H), 6.43 (s, 1 H), 6.45-6.51 (m, 2 H), 7.01-7.09 (m, 1 H), 7.26-7.43 (m, 1 H), 7.68-7.81 (m, 2 H).
MS ESI/APCI Dual posi: 414[M+H]⁺.

Reference Example 2-15

¹H NMR (300 MHz, CDCl₃) δ ppm 1.07 (t, J=7.6 Hz, 3 H), 2.40 (q, J=7.6 Hz, 2 H), 4.92 (s, 1 H), 4.96 (s, 1 H), 5.03 (s, 1 H), 5.09 (s, 1 H), 6.18 (s, 1 H), 6.79-6.92 (m, 2 H), 7.12-7.18 (m, 1 H), 7.35-7.46 (m, 1 H), 7.63-7.74 (m, 2 H).
MS ESI/APCI Dual nega: 415[M−H]⁻.

Reference Example 2-16

¹H NMR (300 MHz, CDCl₃) δ ppm 0.86 (t, J=7.3 Hz, 3 H), 1.38-1.48 (m, 2 H), 2.27-2.35 (m, 2 H), 4.91 (s, 1 H), 4.96 (s, 1 H), 5.03 (s, 1 H), 5.08 (s, 1 H), 6.18 (s, 1 H), 6.78-6.88 (m, 2 H), 7.15-7.22 (m, 1 H), 7.35-7.46 (m, 1 H), 7.62-7.74 (m, 2 H).
MS ESI/APCI Dual nega: 429[M−H]⁻.

Reference Example 2-17

¹H NMR (300 MHz, CDCl₃) δ ppm 3.63 (s, 3 H), 4.92-5.18 (m, 4 H), 6.07 (s., 1 H), 6.32-6.58 (m, 2 H), 7.35-7.52 (m, 1 H), 7.71-7.91 (m, 2 H).
MS ESI/APCI Dual nega: 435[M−H]⁻.

Reference Example 2-18

¹H NMR (300 MHz, CDCl₃) δ ppm 2.82 (s, 6 H), 4.89-5.10 (m, 4 H), 6.27-6.32 (m, 1 H), 6.34-6.41 (m, 1 H), 6.62-6.69 (m, 1 H), 6.78-6.89 (m, 1 H), 7.32-7.45 (m, 1 H), 7.64-7.75 (m, 2 H).
MS ESI/APCI Dual posi: 432[M+H]⁺.

Reference Example 2-19

¹H NMR (300 MHz, CDCl₃) δ ppm 1.48 (s, 9 H), 2.75 (t, J=5.8 Hz, 2 H), 3.60 (t, J=5.8 Hz, 2 H), 4.49 (s, 2 H), 4.89-5.10 (m, 4 H), 6.52-6.57 (m, 1 H), 6.81-7.01 (m, 3 H), 7.33-7.45 (m, 1 H), 7.68-7.79 (m, 2 H).
MS ESI/APCI Dual nega: 524[M−H]⁻.

Reference Example 2-20

¹H NMR (300 MHz, CDCl₃) δ ppm 2.92 (s, 6 H), 4.86-5.08 (m, 4 H), 6.34-6.44 (m, 1 H), 6.58-6.63 (m, 1 H), 6.76-6.85 (m, 1 H), 6.90-6.96 (m, 1 H), 7.31-7.42 (m, 1 H), 7.68-7.79 (m, 2 H).
MS ESI/APCI Dual posi: 432[M+H]⁺.

Reference Example 2-21

$^1$H NMR (300 MHz, CDCl$_3$) δ ppm 2.71 (s, 6 H), 3.52-3.57 (m, 3 H), 4.86-5.06 (m, 4 H), 6.57-6.64 (m, 1 H), 6.89-6.94 (m, 1 H), 7.09-7.16 (m, 1 H), 7.32-7.43 (m, 1 H), 7.75-7.86 (m, 2 H).
MS ESI/APCI Dual posi: 444[M+H]$^+$.

Reference Example 2-22

$^1$H NMR (300 MHz, CDCl$_3$) δ ppm 3.55 (s, 3 H), 3.77 (s, 3 H), 4.92-5.11 (m, 4 H), 5.96 (s, 1 H), 6.16 (s, 1 H), 6.22-6.31 (m, 1 H), 7.34-7.46 (m, 1 H), 7.73-7.84 (m, 2 H).
MS ESI/APCI Dual nega: 447[M−H]$^−$.

Reference Example 2-23

$^1$H NMR (300 MHz, CDCl$_3$) δ ppm 2.83 (s, 6 H), 4.90-5.09 (m, 4 H), 6.46 (s, 1 H), 6.64-6.74 (m, 1 H), 7.09-7.18 (m, 1 H), 7.33-7.44 (m, 1 H), 7.65-7.74 (m, 2 H).
MS ESI/APCI Dual posi: 450[M+H]$^+$.

Reference Example 2-24

$^1$H NMR (300 MHz, DMSO-d$_6$) δ ppm 3.20 (s, 3 H), 4.27 (s, 2 H), 4.87 (s, 2 H), 5.08 (s, 2 H), 6.90-7.00 (m, 3 H), 7.49-7.59 (m, 1 H), 7.66-7.74 (m, 1 H), 7.76-7.84 (m, 1 H), 9.92 (br. s., 1 H).
MS ESI/APCI Dual nega: 454[M−H]$^−$.

Reference Example 2-25

$^1$H NMR (300 MHz, CDCl$_3$) δ ppm 4.92 (d, J=17 Hz, 2 H), 5.00 (s, 2 H), 5.04 (d, J=14 Hz, 2 H), 6.48 (s, 1 H), 6.52-6.63 (m, 1 H), 6.72-6.80 (m, 1 H), 7.30-7.41 (m, 6 H), 7.42-7.51 (m, 1 H), 7.63-7.72 (m, 2 H).

Reference Example 2-26

$^1$H NMR (300 MHz, DMSO-d$_6$) 3.56 (s, 3 H), 3.70 (s, 3 H), 4.56 (s, 2 H), 4.92 (d, J=12 Hz, 2 H), 5.13 (d, J=12 Hz, 2 H), 6.32-6.56 (m, 4 H), 6.68-6.80 (m, 1 H), 7.08 (d, J=8.9 Hz, 1 H), 7.53-7.73 (m, 2 H), 7.78 (d, J=5.1 Hz, 1 H), 10.05 (s, 1 H).

The structures of the compounds of Reference Examples 2-2 to 2-26 are shown in Tables 1-1 and 1-2.

TABLE 1-1

| Reference Ex. | Structure |
|---|---|
| 2-2 | 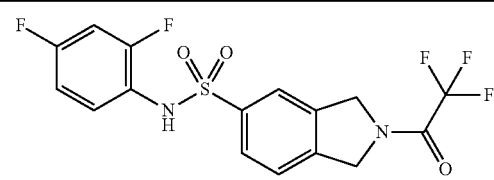 |
| 2-3 | 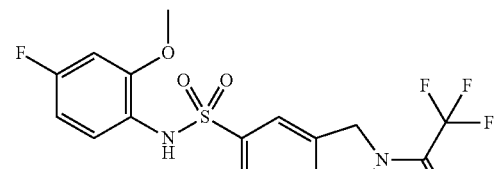 |
| 2-4 | 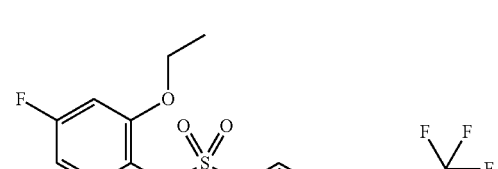 |
| 2-5 | 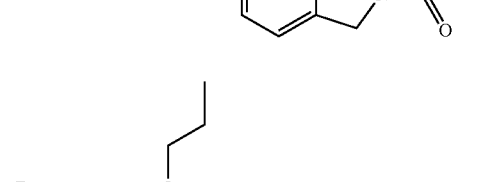 |

TABLE 1-1-continued
| Reference Ex. | Structure |
|---|---|
| 2-6 | 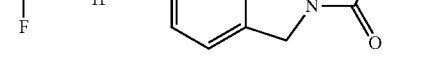 |
| 2-7 | 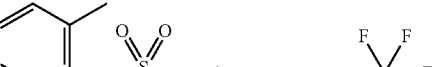 |
| 2-8 | 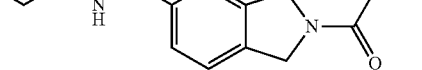 |
| 2-9 | 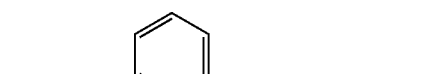 |
| 2-10 | 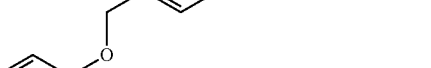 |
| 2-11 | 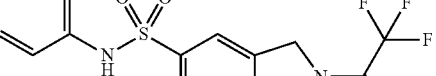 |
| 2-12 | 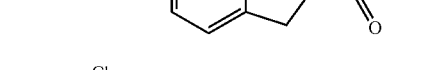 |
| 2-13 | 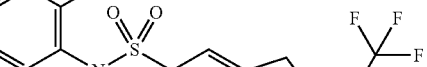 |

TABLE 1-1-continued
| Reference Ex. | Structure |
|---|---|
| 2-14 | 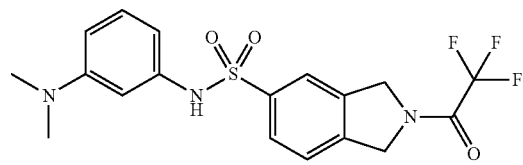 [SMILES: CN(C)c1cccc(NS(=O)(=O)c2ccc3c(c2)CN(C(=O)C(F)(F)F)C3)c1] |
| 2-15 | 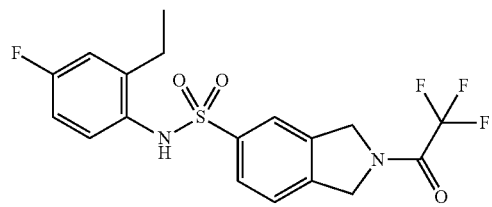 [SMILES: CCc1cc(F)ccc1NS(=O)(=O)c1ccc2c(c1)CN(C(=O)C(F)(F)F)C2] |
TABLE 1-2
| Reference Ex. | Structure |
|---|---|
| 2-16 | 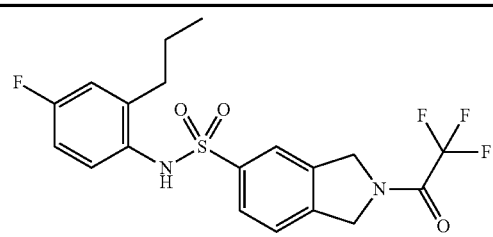 |
| 2-17 | 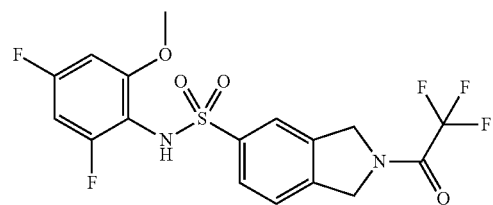 [SMILES: COc1cc(F)cc(F)c1NS(=O)(=O)c1ccc2c(c1)CN(C(=O)C(F)(F)F)C2] |
| 2-18 | 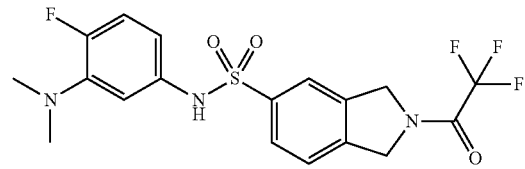 [SMILES: CN(C)c1cc(NS(=O)(=O)c2ccc3c(c2)CN(C(=O)C(F)(F)F)C3)ccc1F] |
| 2-19 | 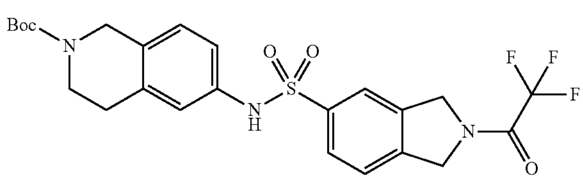 [SMILES: CC(C)(C)OC(=O)N1CCc2cc(NS(=O)(=O)c3ccc4c(c3)CN(C(=O)C(F)(F)F)C4)ccc2C1] |
| 2-20 | 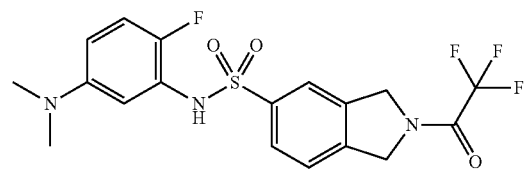 [SMILES: CN(C)c1ccc(F)c(NS(=O)(=O)c2ccc3c(c2)CN(C(=O)C(F)(F)F)C3)c1] |

TABLE 1-2-continued
| Reference Ex. | Structure |
|---|---|
| 2-21 | 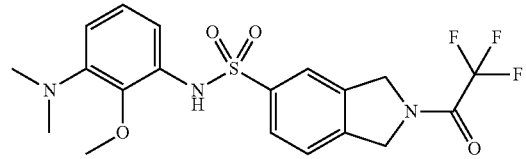 [SMILES: COc1c(NS(=O)(=O)c2ccc3c(c2)CN(C(=O)C(F)(F)F)C3)cccc1N(C)C] |
| 2-22 | 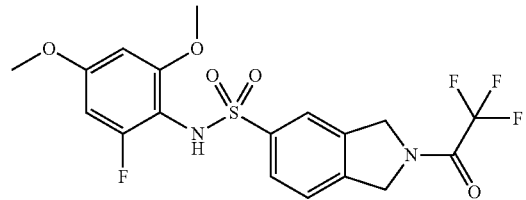 [SMILES: COc1cc(F)c(NS(=O)(=O)c2ccc3c(c2)CN(C(=O)C(F)(F)F)C3)c(OC)c1] |
| 2-23 | 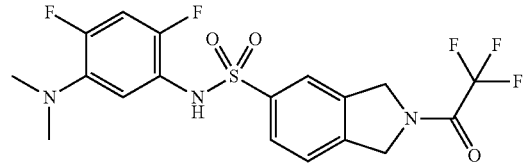 [SMILES: CN(C)c1cc(NS(=O)(=O)c2ccc3c(c2)CN(C(=O)C(F)(F)F)C3)c(F)cc1F] |
| 2-24 | 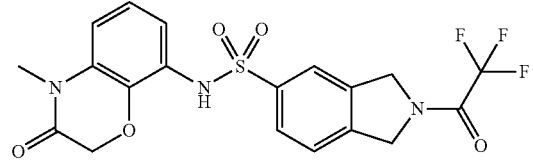 [SMILES: CN1C(=O)COc2c(NS(=O)(=O)c3ccc4c(c3)CN(C(=O)C(F)(F)F)C4)cccc21] |
| 2-25 | 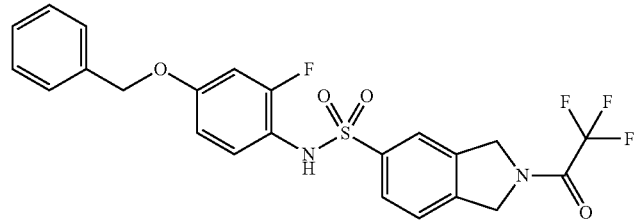 [SMILES: O=C(N1Cc2ccc(S(=O)(=O)Nc3ccc(OCc4ccccc4)cc3F)cc2C1)C(F)(F)F] |
| 2-26 | 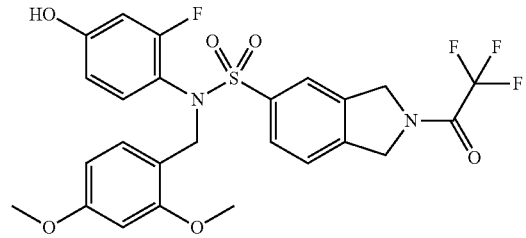 [SMILES: COc1ccc(CN(c2ccc(O)cc2F)S(=O)(=O)c2ccc3c(c2)CN(C(=O)C(F)(F)F)C3)c(OC)c1] |

Reference Example 3-1

N-(4-Fluorophenyl)-1,2,3,4-tetrahydroisoquinoline-6-sulfonamide

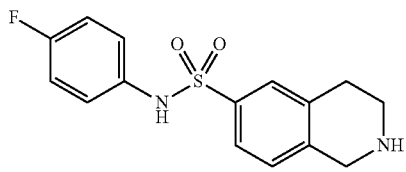

[Formula 19]

(1) Pyridine (18.2 mL, 226 mmol) and 4-dimethylaminopyridine (184 mg, 1.51 mmol) were added to a solution of 7-bromo-1,2,3,4-tetrahydroisoquinoline (32.0 g, 151 mmol) in chloroform (280 mL), and trifluoroacetic acid anhydride (21.9 mL, 158 mmol) was added dropwise thereto while cooling in ice. The mixture was warmed to room temperature and stirred for 20 hr. The mixture was concentrated under reduced pressure, 1 mol/L hydrochloric acid was added thereto, and the mixture was extracted with ethyl acetate. The organic layer was washed with saturated aqueous sodium hydrogen carbonate solution and brine and dried over anhydrous magnesium sulfate and then the desiccant was filtered off, followed by concentration under reduced pressure. The resulting residue was purified by silica gel column chromatography (hexane:ethyl acetate=9:1→7:3) to afford 1-(7-bromo-3,4-dihydroisoquinolin-2(1 H)-yl)-2,2,2-trifluoroethanone as a pale yellow oil (42.4 g).

(2) Chlorosulfonic acid (35.6 mL) was added dropwise to a solution of 1-(7-bromo-3,4-dihydroisoquinolin-2(1 H)-yl)-2,2,2-trifluoroethanone obtained (25.4 g, 82.3 mmol) in chloroform (35 mL) while cooling in ice, and the mixture was stirred at room temperature for 1 hr and at 60° C. for 4 hr. After cooling, the reaction mixture was added dropwise to ice water and the mixture was extracted with chloroform. The organic layer was dried over anhydrous magnesium sulfate and then the desiccant was filtered off, followed by concentration under reduced pressure. The concentrate was powdered with hexane and ethyl acetate (5:1) and then collected by filtration to afford 7-bromo-2-(trifluoroacetyl)-1,2,3,4-tetrahydroisoquinoline-6-sulfonyl chloride as a pale yellow powder (22.7 g).

(3) Pyridine (3.09 mL, 38.4 mmol) was added to a solution of 4-fluoroaniline (3.73 g, 33.6 mmol) in chloroform (107 mL), and 7-bromo-2-(trifluoroacetyl)-1,2,3,4-tetrahydroisoquinoline-6-sulfonyl chloride (13.0 g, 32.0 mmol) was added thereto while cooling in ice. The mixture was warmed to room temperature and stirred for 13 hr. To the mixture was added 1 mol/L hydrochloric acid, and the mixture was extracted with chloroform. The organic layer was concentrated under reduced pressure and the concentrate was powdered with hexane and ethyl acetate (4:1) and then collected by filtration to afford 7-bromo-N-(4-fluorophenyl)-2-(trifluoroacetyl)-1,2,3,4-tetrahydroisoquinoline-6-sulfonamide as an orange powder (14.5 g).

(4) To a solution of 7-bromo-N-(4-fluorophenyl)-2-(trifluoroacetyl)-1,2,3,4-tetrahydroisoquinoline-6-sulfonamide obtained (14.5 g, 30.2 mmol) in methanol (200 mL) and ethyl acetate (100 mL) was added 10% palladium activated carbon (4.36 g), and the mixture was stirred under a hydrogen atmosphere at room temperature for 15 hr. The mixture was filtered through Celite (registered trademark) and the filtrate was concentrated under reduced pressure. The resulting residue was powdered with ethanol and then collected by filtration to afford N-(4-fluorophenyl)-2-(trifluoroacetyl)-1,2,3,4-tetrahydroisoquinoline-6-sulfonamide as a colorless powder (10.6 g).

(5) An aqueous solution (10 mL) of potassium hydroxide (2.24 g, 40.0 mmol) was added to a suspension of N-(4-fluorophenyl)-2-(trifluoroacetyl)-1,2,3,4-tetrahydroisoquinoline-6-sulfonamide obtained (8.05 g, 20.0 mmol) in ethanol (40 mL), and the mixture was stirred at room temperature for 15 hr. The mixture was concentrated under reduced presseure and then diluted with water. While cooling in ice, 3 mol/L hydrochloric acid was added dropwise thereto to adjust the pH to 7 to 8. A precipitated solid was collected by filtration to afford the title compound as a colorless powder (6.04 g).

[1] H NMR (300 MHz, DMSO-$d_6$) δ ppm 2.65-2.72 (m, 2 H), 2.87-2.94 (m, 2 H), 3.84 (s, 2 H), 7.05-7.10 (m, 4 H), 7.16 (d, J=8.1 Hz, 1 H), 7.38-7.45 (m, 2 H).

MS ESI/APCI Dual posi: 307[M+H]$^+$.

Compound 18-5, which was obtained in Reference Example 18, was used to afford the compound of Reference Example 3-2 in accordance with the processes of Reference Example 3-1(3) and (4).

Reference Example 3-2

[1] H NMR (300 MHz, DMSO-$d_6$) δ ppm 2.90-3.10 (m, 2 H), 3.54 (s, 3 H), 3.69 (s, 3 H), 3.80-3.91 (m, 2 H), 4.54 (s, 2 H), 4.83-4.93 (m, 2 H), 6.37-6.53 (m, 4 H), 6.75-6.80 (m, 1 H), 7.04-7.13 (m, 1 H), 7.43-7.63 (m, 3 H), 10.05 (br. s, 1 H).

LCMS retention time: 4.92 min. (Condition 1-1-3)

MS (ESI nega) m/z: 681 [M+$CF_3CO_2$]$^-$.

The compounds of Reference Examples 3-3 to 3-29 were obtainted by using the compound obtained in Reference Example 1-1 and the corresponding anilines obtained in Reference Examples 15, 18, 19, 20, 22, 23, 25, 28 and the like in accordance with the process of Reference Example 3-1.

Reference Example 3-3

[1] H NMR (300 MHz, $CDCl_3$) δ ppm 1.97-2.16 (m, 2 H), 2.71-2.86 (m, 4 H), 3.11-3.20 (m, 2 H), 3.57 (s, 3 H), 3.75 (s, 3 H), 3.83-3.89 (m, 2 H), 4.08 (s, 2 H), 4.67 (s, 2 H), 6.26-6.28 (m, 1 H), 6.35-6.40 (m, 1 H), 6.43-6.51 (m, 2 H), 6.86-6.94 (m, 1 H), 7.06-7.34 (m, 7 H), 7.44-7.52 (m, 2 H).

MS ESI/APCI Dual posi: 591[M+H]$^+$.

Reference Example 3-4

[1] H NMR (300 MHz, $CDCl_3$) δ ppm 0.85-0.94 (m, 3 H), 1.24-1.50 (m, 4 H), 1.63-1.81 (m, 4 H), 2.82 (t, J=5.8 Hz, 2 H), 3.16 (t, J=5.8 Hz, 2 H), 3.57 (s, 3 H), 3.75 (s, 3 H), 3.86 (t, J=6.5 Hz, 2 H), 4.08 (s, 2 H), 4.67 (s, 2 H), 6.27 (d, J=2.3 Hz, 1 H), 6.37 (dd, J=8.2, 2.3 Hz, 1 H), 6.43-6.52 (m, 2 H), 6.84-6.94 (m, 1 H), 7.08-7.13 (m, 1 H), 7.20-7.27 (m, 1 H), 7.44-7.52 (m, 2 H).

MS ESI/APCI Dual posi: 557[M+H]$^+$.

Reference Example 3-5

[1] H NMR (300 MHz, DMSO-$d_6$) δ ppm 0.79-0.92 (m, 3 H), 1.20-1.45 (m, 6 H), 1.56-1.73 (m, 2 H), 2.63-2.72 (m, 2 H), 2.87-2.96 (m, 2 H), 3.83-3.93 (m, 4 H), 6.60-6.67 (m, 1 H), 6.70-6.77 (m, 1 H), 6.96-7.06 (m, 1 H), 7.10-7.17 (m, 1 H), 7.31-7.41 (m, 2 H).

MS ESI/APCI Dual posi: 407[M+H]$^+$.

Reference Example 3-6

¹H NMR (300 MHz, CDCl₃) δ ppm 2.84 (t, J=5.8 Hz, 2 H), 3.19 (t, J=5.8 Hz, 2 H), 3.58 (s, 3 H), 3.75 (s, 3 H), 4.10 (s, 2 H), 4.67 (s, 2 H), 6.27 (d, J=2.3 Hz, 1 H), 6.36-6.41 (m, 1 H), 6.83-6.98 (m, 4 H), 7.12 (d, J=8.4 Hz, 1 H), 7.22 (d, J=8.4 Hz, 1 H), 7.36-7.41 (m, 2 H).
MS ESI/APCI Dual posi: 457[M+H]⁺.

Reference Example 3-7

¹H NMR (300 MHz, DMSO-d₆) δ ppm 2.78 (t, J=6.0 Hz, 2 H), 3.07 (t, J=6.0 Hz, 2 H), 3.99 (s, 2 H), 6.87-6.98 (m, 2 H), 7.09 (t, J=75.0 Hz, 1 H), 7.13-7.24 (m, 2 H), 7.42-7.48 (m, 2 H).
MS ESI/APCI Dual posi: 373[M+H]⁺.

Reference Example 3-8

¹H NMR (300 MHz, DMSO-d₆) δ ppm 0.93-1.09 (m, 2 H), 1.17-1.29 (m, 2 H), 1.40-1.60 (m, 6 H), 1.63-1.78 (m, 3 H), 2.65-2.75 (m, 2 H), 2.90-2.97 (m, 2 H), 3.88 (s, 2 H), 6.87-6.99 (m, 2 H), 7.05-7.19 (m, 2 H), 7.37-7.44 (m, 2 H).
MS ESI/APCI Dual posi: 417[M+H]⁺.

Reference Example 3-9

¹H NMR (300 MHz, DMSO-d₆) δ ppm 0.80-0.88 (m, 3 H), 1.15-1.30 (m, 8 H), 1.42-1.56 (m, 2 H), 2.64-2.75 (m, 2 H), 2.90-2.98 (m, 2 H), 3.88 (s, 2 H), 6.86-6.99 (m, 2 H), 7.05-7.19 (m, 2 H), 7.36-7.44 (m, 2 H).
MS ESI/APCI Dual posi: 405[M+H]⁺.

Reference Example 3-10

¹H NMR (300 MHz, DMSO-d₆) δ ppm 0.73-0.88 (m, 2 H), 1.01-1.26 (m, 5 H), 1.42-1.73 (m, 6 H), 2.65-2.75 (m, 2 H), 2.90-3.00 (m, 2 H), 3.89 (s, 2 H), 6.86-7.02 (m, 2 H), 7.05-7.20 (m, 2 H), 7.34-7.46 (m, 2 H).
MS ESI/APCI Dual posi: 431[M+H]⁺.

Reference Example 3-11

¹H NMR (300 MHz, DMSO-d₆) δ ppm 1.18-1.33 (m, 2 H), 1.46-1.64 (m, 4 H), 2.65-2.74 (m, 2 H), 2.90-2.99 (m, 2 H), 3.89 (s, 2 H), 6.85-7.00 (m, 2 H), 7.05-7.19 (m, 5 H), 7.21-7.29 (m, 2 H), 7.38-7.46 (m, 2 H).
MS ESI/APCI Dual posi: 453[M+H]⁺.

Reference Example 3-12

¹H NMR (300 MHz, DMSO-d₆) δ ppm 1.90-2.04 (m, 2 H), 2.66-2.75 (m, 2 H), 2.85-2.95 (m, 2 H), 3.16-3.25 (m, 2 H), 3.88-3.96 (m, 2 H), 4.16 (s, 2 H), 6.67-6.83 (m, 2 H), 7.01-7.12 (m, 1 H), 7.14-7.34 (m, 6 H), 7.43-7.51 (m, 2 H).
MS ESI/APCI Dual posi: 441[M+H]⁺.

Reference Example 3-13

¹H NMR (300 MHz, CDCl₃) δ ppm 1.72-1.83 (m, 4 H), 2.61-2.73 (m, 2 H), 2.76-2.86 (m, 2 H), 3.15 (t, J=6.0 Hz, 2 H), 3.57 (s, 3 H), 3.75 (s, 3 H), 3.83-3.91 (m, 2 H), 4.07 (s, 2 H), 4.67 (s, 2 H), 6.27 (d, J=2.4 Hz, 1 H), 6.37 (dd, J=8.5, 2.4 Hz, 1 H), 6.43-6.46 (m, 1 H), 6.47-6.50 (m, 1 H), 6.86-6.93 (m, 1 H), 7.09 (d, J=8.5 Hz, 1 H), 7.14-7.33 (m, 6 H), 7.44-7.51 (m, 2 H).
MS ESI/APCI Dual posi: 605[M+H]⁺.

Reference Example 3-14

¹H NMR (300 MHz, CD₃OD) δ ppm 2.83-2.94 (m, 2 H), 3.10-3.20 (m, 2 H), 4.05 (s, 2 H), 6.94 (d, J=8.1 Hz, 1 H), 7.22 (d, J=7.5 Hz, 1 H), 7.46-7.56 (m, 2 H), 7.69 (br. s., 1 H), 7.77 (br. s., 1 H).
MS ESI/APCI Dual posi: 308[M+H]⁺.

Reference Example 3-15

¹H NMR (300 MHz, DMSO-d₆) δ ppm 1.89-2.02 (m, 2 H), 2.64-2.74 (m, 2 H), 2.75-2.84 (m, 2 H), 3.05 (t, J=6.1 Hz, 2 H), 3.86 (t, J=6.4 Hz, 2 H), 3.99 (s, 2 H), 6.76-6.83 (m, 2 H), 6.93-7.01 (m, 2 H), 7.13-7.31 (m, 6 H), 7.40-7.47 (m, 2 H).
LCMS retention time: 4.27 min. (Condition 1-1-1)
MS (ESI posi) m/z: 423[M+H]⁺.

Reference Example 3-16

¹H NMR (300 MHz, DMSO-d₆) δ ppm 2.66-2.75 (m, 2 H), 2.90-2.98 (m, 2 H), 3.89 (s, 2 H), 4.25-4.33 (m, 2 H), 4.34-4.41 (m, 2 H), 6.71-6.78 (m, 1 H), 6.85 (dd, J=12.2, 2.7 Hz, 1 H), 7.02-7.11 (m, 1 H), 7.17 (d, J=7.8 Hz, 1 H), 7.24-7.41 (m, 4 H), 7.48-7.58 (m, 1 H).
MS ESI/APCI Dual posi: 511[M+H]⁺.

Reference Example 3-17

¹H NMR (300 MHz, DMSO-d₆) δ ppm 1.97 (dd, J=9.1, 6.5 Hz, 2 H), 2.65-2.78 (m, 4 H), 2.94-3.00 (m, 2 H), 3.86-3.98 (m, 4 H), 7.07 (d, J=9.5 Hz, 1 H), 7.14-7.23 (m, 4 H), 7.24-7.31 (m, 2 H), 7.35 (dd, J=8.9, 3.1 Hz, 1 H), 7.52-7.59 (m, 2 H), 7.87 (d, J=2.6 Hz, 1 H).
MS ESI/APCI Dual posi: 424[M+H]⁺.

Reference Example 3-18

¹H NMR (300 MHz, CDCl₃) δ ppm 1.97-2.11 (m, 2 H), 2.68-2.78 (m, 2 H), 2.83-2.94 (m, 2 H), 3.17-3.30 (m, 2 H), 4.11-4.24 (m, 4 H), 6.64 (d, J=8.9 Hz, 1 H), 7.08 (d, J=7.9 Hz, 1 H), 7.12-7.20 (m, 3 H), 7.21-7.30 (m, 2 H), 7.35-7.50 (m, 3 H), 7.70 (d, J=2.8 Hz, 1 H).
MS ESI/APCI Dual posi: 424[M+H]⁺.

Reference Example 3-19

¹H NMR (300 MHz, CDCl₃) δ ppm 1.87-1.99 (m, 2 H), 2.64-2.73 (m, 2 H), 2.80-2.86 (m, 2 H), 3.17 (t, J=6.1 Hz, 2 H), 3.35-3.46 (m, 2 H), 4.08 (s, 2 H), 7.09-7.23 (m, 5 H), 7.27-7.30 (m, 1 H), 7.42-7.49 (m, 2 H), 7.91-7.94 (m, 2 H).
MS ESI/APCI Dual posi: 424[M+H]⁺.

Reference Example 3-20

¹H NMR (300 MHz, DMSO-d₆) δ ppm 0.80-0.88 (m, 3 H), 1.15-1.32 (m, 8 H), 1.55-1.67 (m, 2 H), 2.61-2.69 (m, 2 H), 2.87 (t, J=5.4 Hz, 2 H), 3.16 (t, J=5.8 Hz, 2 H), 4.07 (s, 2 H), 7.16-7.22 (m, 1 H), 7.46-7.54 (m, 2 H), 8.17 (s, 2 H).
MS ESI/APCI Dual posi: 389[M+H]⁺.

Reference Example 3-21

¹H NMR (300 MHz, DMSO-d₆) δ ppm 0.71-0.93 (m, 3 H), 1.14-1.32 (m, 8 H), 1.54 (s, 2 H), 2.44 (t, J=7.2 Hz, 2 H), 2.70-2.79 (m, 2 H), 2.96-3.04 (m, 2 H), 3.89 (s, 2 H), 6.99-7.06 (m, 1 H), 7.46-7.53 (m, 2 H), 7.70 (s, 1 H), 7.80 (s, 1 H).
MS ESI/APCI Dual posi: 389[M+H]$^+$.

Reference Example 3-22

$^1$H NMR (600 MHz, CDCl$_3$) δ ppm 0.86-0.91 (m, 3 H), 1.22-1.36 (m, 8 H), 1.38-1.46 (m, 2 H), 1.70-1.78 (m, 2 H), 2.78 (t, J=5.8 Hz, 2 H), 3.12 (t, J=5.8 Hz, 2 H), 3.87 (t, J=6.6 Hz, 2 H), 4.03 (s, 2 H), 6.49 (dd, J=12.0, 2.9 Hz, 1 H), 6.62-6.66 (m, 1 H), 7.04 (d, J=8.3 Hz, 1 H), 7.39-7.47 (m, 3 H).
MS ESI/APCI Dual posi: 435[M+H]$^+$.

Reference Example 3-23

$^1$H NMR (600 MHz, DMSO-d$_6$) δ ppm 2.63-2.74 (m, 2 H), 2.86-2.97 (m, 2 H), 3.48 (s, 3 H), 3.85 (s, 2 H), 6.63-6.75 (m, 1 H), 6.78-6.87 (m, 1 H), 7.10-7.20 (m, 2 H), 7.32-7.40 (m, 2 H).
MS ESI/APCI Dual posi: 337[M+H]$^+$.

Reference Example 3-24

$^1$H NMR (200 MHz, CDCl$_3$) δ ppm 2.74-2.94 (m, 2 H), 3.08-3.23 (m, 2 H), 3.51 (s, 3 H), 3.55 (s, 3 H), 3.74 (s, 3 H), 4.08 (s, 2 H), 4.43-4.77 (m, 2 H), 6.17-6.42 (m, 4 H), 7.04-7.18 (m, 2 H), 7.51-7.69 (m, 2 H).
MS ESI/APCI Dual posi: 505[M+H]$^+$.

Reference Example 3-25

$^1$H NMR (600 MHz, CDCl$_3$) δ ppm 0.89-1.00 (m, 2 H), 1.11-1.30 (m, 4 H), 1.40-1.50 (m, 1 H), 1.54-1.77 (m, 6 H), 2.79-2.86 (m, 2 H), 3.15-3.17 (m, 2 H), 3.57 (s, 3 H), 3.75 (s, 3 H), 3.85-3.95 (m, 2 H), 4.08 (s, 2 H), 4.67 (s, 2 H), 6.25-6.29 (m, 1 H), 6.35-6.40 (m, 1 H), 6.45-6.52 (m, 2 H), 6.87-6.93 (m, 1 H), 7.07-7.12 (m, 1 H), 7.19-7.25 (m, 1 H), 7.46-7.50 (m, 2 H).
LCMS retention time: 4.66 min. (Condition 1-1-3)
MS (ESI posi) m/z: 583[M+H]$^+$.

Reference Example 3-26

LCMS retention time: 3.29 min. (Condition 1-1-3)
MS (ESI posi) m/z: 375[M+H]$^+$.

Reference Example 3-27

$^1$H NMR (300 MHz, CDCl$_3$) δ ppm 1.39-1.55 (m, 2 H), 1.60-1.86 (m, 4 H), 2.58-2.68 (m, 2 H), 2.73-2.83 (m, 2 H), 3.11 (t, J=5.9 Hz, 2 H), 3.87 (t, J=6.5 Hz, 2 H), 4.02 (s, 2 H), 6.48 (dd, J=12.1, 2.7 Hz, 1 H), 6.60-6.66 (m, 1 H), 7.04 (d, J=8.1 Hz, 1 H), 7.14-7.22 (m, 3 H), 7.23-7.33 (m, 2 H), 7.37-7.48 (m, 3 H).
MS ESI/APCI Dual posi: 469[M+H]$^+$.

Reference Example 3-28

$^1$H NMR (300 MHz, CDCl$_3$) δ ppm 0.79-0.98 (m, 2 H), 1.03-1.37 (m, 6 H), 1.58-1.82 (m, 7 H), 2.80 (t, J=5.8 Hz, 2 H), 3.09-3.19 (m, 2 H), 3.85 (t, J=6.6 Hz, 2 H), 4.04 (s, 2 H), 6.49 (dd, J=12.0, 2.8 Hz, 1 H), 6.61-6.66 (m, 1 H), 7.05 (d, J=7.8 Hz, 1 H), 7.37-7.49 (m, 3 H).
MS ESI/APCI Dual posi: 447[M+H]$^+$.

Reference Example 3-29

LCMS retention time: 3.31 min. (Condition 1-1-3)
MS (ESI posi) m/z: 473[M+H]$^+$.

The compounds of Reference Examples 3-30 to 3-35 were obtained by using the corresponding commercially available amines, the corresponding anilines obtained in Reference Examples 15 and 18 and the corresponding commercially available anilines in accordance with the processes of Reference Example 3-1(1), (2), (3) and (5).

Reference Example 3-30

$^1$H NMR (300 MHz, DMSO-d$_6$) δ ppm 2.61-2.69 (m, 2 H), 2.86-2.92 (m, 2 H), 3.82 (s, 2 H), 7.04-7.11 (m, 4 H), 7.47 (s, 1 H), 7.74 (s, 1 H).
MS ESI/APCI Dual posi: 385, 387[M+H]$^+$.

Reference Example 3-31

$^1$H NMR (300 MHz, DMSO-d$_6$) δ ppm 4.55 (br. s., 4 H), 7.06-7.14 (m, 4 H), 7.54-7.61 (m, 1 H), 7.69-7.75 (m, 1 H), 7.80 (s, 1 H), 10.37 (s, 1 H).
MS ESI/APCI Dual posi: 293[M+H]$^+$.

Reference Example 3-32

$^1$H NMR (300 MHz, CDCl$_3$) δ ppm 3.58 (s, 3 H), 3.75 (s, 3 H), 4.27 (s, 2 H), 4.31 (s, 2 H), 4.68 (s, 2 H), 6.26-6.29 (m, 1 H), 6.36-6.41 (m, 1 H), 6.83-6.98 (m, 4 H), 7.22 (d, J=8.4 Hz, 1 H), 7.31-7.35 (m, 1 H), 7.48-7.54 (m, 2 H).
MS ESI/APCI Dual posi: 443[M+H]$^+$.

Reference Example 3-33

$^1$H NMR (300 MHz, DMSO-d$_6$) δ ppm 2.66-2.73 (m, 2 H), 2.87-2.94 (m, 2 H), 3.82 (s, 2 H), 7.05-7.09 (m, 4 H), 7.18-7.23 (m, 1 H), 7.37-7.44 (m, 2 H).
MS ESI/APCI Dual posi: 307[M+H]$^+$.

Reference Example 3-34

$^1$H NMR (300 MHz, DMSO-d$_6$) δ ppm 2.75-2.83 (m, 4 H), 2.84-2.93 (m, 4 H), 7.04-7.11 (m, 4 H), 7.26 (d, J=7.9 Hz, 1 H), 7.39-7.48 (m, 2 H).
MS ESI/APCI Dual posi: 321[M+H]$^+$.

Reference Example 3-35

$^1$H NMR (300 MHz, DMSO-d$_6$) δ ppm 1.90-2.02 (m, 2 H), 2.66-2.80 (m, 6 H), 2.81-2.92 (m, 4 H), 3.90 (t, J=6.4 Hz, 2 H), 6.62-6.70 (m, 1 H), 6.71-6.79 (m, 1 H), 6.97-7.06 (m, 1 H), 7.14-7.32 (m, 6 H), 7.33-7.40 (m, 2 H).
MS ESI/APCI Dual posi: 455[M+H]$^+$.

The compounds of Reference Examples 3-36 to 3-48 were obtained by using the corresponding commercially available anilines and the corresponding anilines obtained in Reference Examples 15, 18, 31 to 35 and the like in accordance with the process of Reference Example 3-1.

Reference Example 3-36

$^1$H NMR (300 MHz, CDCl$_3$) δ ppm 2.83 (m, 2 H), 3.06-3.21 (m, 2 H), 3.54-3.60 (m, 3 H), 3.75 (s, 3 H), 4.07 (s, 2 H), 4.62 (s, 2 H), 4.67-4.77 (m, 2 H), 6.27 (m, 1 H), 6.32-6.43 (m, 1 H), 6.88-7.15 (m, 4 H), 7.22 (m, 1 H), 7.42-7.53 (m, 2 H).
LCMS retention time: 0.79 min. (Condition 4-2)
MS (ESI posi) m/z: 487[M+H]$^+$.

Reference Example 3-37

¹ H NMR (300 MHz, CDCl₃) δ ppm 2.80-2.89 (m, 2 H), 3.14-3.24 (m, 2 H), 3.76 (s, 3 H), 4.10 (s, 2 H), 6.22 (d, J=2.3 Hz, 1 H), 7.07 (d, J=7.8 Hz, 1 H), 7.19 (d, J=2.3 Hz, 1 H), 7.52 (s, 2 H).
MS ESI/APCI Dual posi: 293[M+H]⁺.

Reference Example 3-38

¹ H NMR (300 MHz, DMSO-d₆) δ ppm 1.19 (s, 9 H), 2.89-3.05 (m, 2 H), 3.25-3.39 (m, 2 H), 4.22 (s, 2 H), 5.90 (s, 1 H), 7.26 (d, J=8.1 Hz, 1 H), 7.52-7.63 (m, 2 H).
MS ESI/APCI Dual posi: 336[M+H]⁺.

Reference Example 3-39

¹ H NMR (300 MHz, CDCl₃) δ ppm 1.18 (s, 9 H), 2.89 (t, J=6.0 Hz, 2 H), 3.18 (t, J=6.0 Hz, 2 H), 4.09 (s, 2 H), 5.25 (s, 1 H), 7.13 (d, J=9.0 Hz, 1 H), 7.67-7.74 (m, 2 H).
MS ESI/APCI Dual posi: 335[M+H]⁺.

Reference Example 3-40

¹ H NMR (300 MHz, DMSO-d₆) δ ppm 1.16 (s, 9 H), 2.85-2.94 (m, 2 H), 3.13-3.23 (m, 2 H), 4.10 (s, 2 H), 6.25 (s, 1 H), 7.24 (d, J=8.2 Hz, 1 H), 7.58 (s, 2 H).
MS ESI/APCI Dual nega: 350[M−H]⁻.

Reference Example 3-41

¹ H NMR (300 MHz, DMSO-d₆) δ ppm 1.19 (d, J=10.7 Hz, 2 H), 1.52-1.69 (m, 4 H), 2.83-2.94 (m, 2 H), 3.13-3.24 (m, 5 H), 3.81 (d, J=12.1 Hz, 2 H), 3.96 (t, J=6.1 Hz, 2 H), 4.16 (s, 2 H), 6.66-6.84 (m, 2 H), 7.06 (t, J=9.1 Hz, 1 H), 7.31 (d, J=7.8 Hz, 1 H), 7.43-7.53 (m, 2 H).
MS ESI/APCI Dual posi: 435[M+H]⁺.

Reference Example 3-42

¹ H NMR (300 MHz, CDCl₃) δ ppm 2.25-2.43 (m, 2 H), 2.77-2.86 (m, 2 H), 2.95 (s, 3 H), 3.10-3.27 (m, 4 H), 3.97-4.10 (m, 4 H), 6.47-6.55 (m, 1 H), 6.61-6.67 (m, 1 H), 7.06 (d, J=7.8 Hz, 1 H), 7.39-7.51 (m, 3 H).
LCMS retention time: 0.87 min. (Condition 3)
MS ESI/APCI Dual posi: 443[M+H]⁺.

Reference Example 3-43

¹ H NMR (300 MHz, DMSO-d₆) δ ppm 1.21 (t, J=7.5 Hz, 3 H), 2.03-2.15 (m, 2H), 2.79-2.88 (m, 2 H), 3.04-3.25 (m, 6 H), 3.97-4.14 (m, 4 H), 6.68-6.84 (m, 2 H), 7.04-7.11 (m, 1 H), 7.26 (d, J=7.6 Hz, 1 H), 7.40-7.49 (m, 2 H).
MS ESI/APCI Dual posi: 457[M+H]⁺.

Reference Example 3-44

¹ H NMR (300 MHz, DMSO-d₆) δ ppm −0.05-0.03 (m, 2 H), 0.32-0.39 (m, 2 H), 0.55-0.69 (m, 1 H), 1.36-1.46 (m, 2 H), 2.55-2.63 (m, 2 H), 2.80-2.88 (m, 2 H), 3.11-3.18 (m, 2 H), 4.10 (s, 2 H), 6.90-7.03 (m, 2 H), 7.07-7.16 (m, 1 H), 7.25-7.31 (m, 1 H), 7.45-7.51 (m, 2 H).
LCMS retention time: 3.01 min. (Condition 1-2-3)
MS (ESI posi) m/z: 375[M+H]⁺.

Reference Example 3-45

¹ H NMR (300 MHz, DMSO-d₆) δ ppm 0.99-1.16 (m, 2 H), 1.37-1.79 (m, 9 H), 2.45-2.56 (m, 2 H), 2.80-2.89 (m, 2 H), 3.09-3.20 (m, 2 H), 4.10 (s, 2 H), 6.90-7.03 (m, 2 H), 7.06-7.16 (m, 1 H), 7.28 (d, J=8.7 Hz, 1 H), 7.45-7.53 (m, 2 H).
LCMS retention time: 1.70 min. (Condition 3)
MS ESI/APCI Dual posi: 403[M+H]⁺.

Reference Example 3-46

¹ H NMR (300 MHz, DMSO-d₆) δ ppm 0.78-0.95 (m, 2 H), 1.05-1.25 (m, 4 H), 1.34-1.44 (m, 2 H), 1.55-1.74 (m, 5 H), 2.47-2.56 (m, 2 H), 2.81-2.89 (m, 2 H), 3.12-3.20 (m, 2 H), 4.11 (s, 2 H), 6.90-7.02 (m, 2 H), 7.07-7.15 (m, 1 H), 7.25-7.31 (m, 1 H), 7.46-7.51 (m, 2 H).
LCMS retention time: 4.04 min. (Condition 1-2-3)
MS (ESI posi) m/z: 417[M+H]⁺.

Reference Example 3-47

¹ H NMR (300 MHz, DMSO-d₆) δ ppm −0.07-−0.01 (m, 2 H), 0.33-0.40 (m, 2 H), 0.59-0.72 (m, 1 H), 1.09-1.19 (m, 2 H), 1.54-1.66 (m, 2 H), 2.48-2.57 (m, 2 H), 2.81-2.89 (m, 2 H), 3.12-3.20 (m, 2 H), 4.10 (s, 2 H), 6.91-7.03 (m, 2 H), 7.08-7.16 (m, 1 H), 7.26-7.32 (m, 1 H), 7.46-7.52 (m, 2 H).
LCMS retention time: 1.61 min. (Condition 3)
MS ESI/APCI Dual posi: 389[M+H]⁺.

Reference Example 3-48

¹ H NMR (300 MHz, DMSO-d₆) δ ppm 0.81-1.58 (m, 9 H), 2.97-3.06 (m, 2 H), 3.17-3.42 (m, 6 H), 3.75-3.85 (m, 2 H), 4.34 (s, 2 H), 6.92-7.04 (m, 2 H), 7.09-7.17 (m, 1 H), 7.40 (d, J=7.9 Hz, 1 H), 7.54-7.61 (m, 2 H).
LCMS retention time: 1.46 min. (Condition 3)
MS ESI/APCI Dual posi: 433[M+H]⁺.

The structures of the compounds of Reference Examples 3-2 to 3-48 are shown in Tables 2-1 to 2-4.

TABLE 2-1

| Reference Ex. | Structure |
|---|---|
| 3-2 | 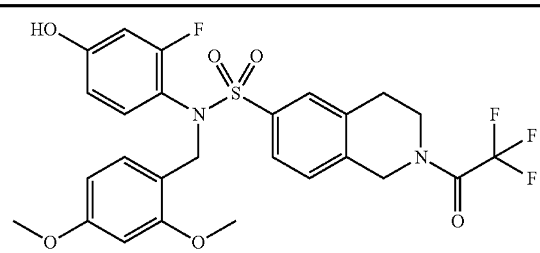 |

TABLE 2-1-continued

| Reference Ex. | Structure |
|---|---|
| 3-3 | 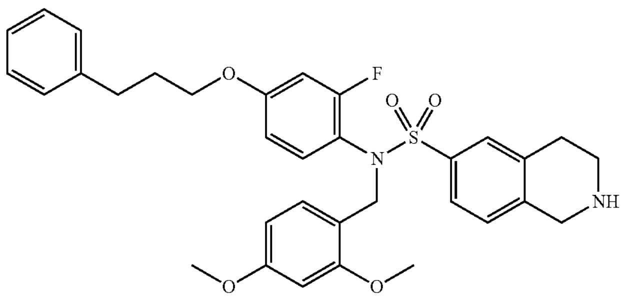 [SMILES: COc1ccc(CN(c2ccc(OCCCc3ccccc3)cc2F)S(=O)(=O)c2ccc3c(c2)CCNC3)c(OC)c1] |
| 3-4 | 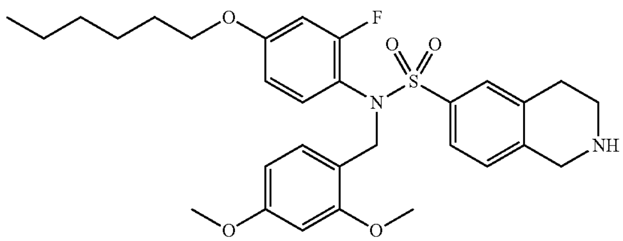 [SMILES: CCCCCCOc1ccc(N(Cc2ccc(OC)cc2OC)S(=O)(=O)c2ccc3c(c2)CCNC3)c(F)c1] |
| 3-5 | 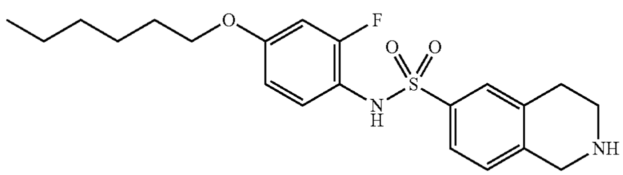 [SMILES: CCCCCCOc1ccc(NS(=O)(=O)c2ccc3c(c2)CCNC3)c(F)c1] |
| 3-6 | 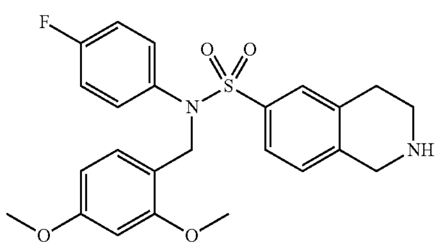 [SMILES: COc1ccc(CN(c2ccc(F)cc2)S(=O)(=O)c2ccc3c(c2)CCNC3)c(OC)c1] |
| 3-7 | 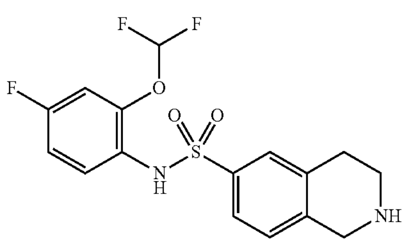 [SMILES: O=S(=O)(Nc1ccc(F)cc1OC(F)F)c1ccc2c(c1)CCNC2] |
| 3-8 | 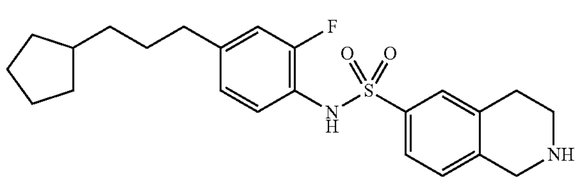 [SMILES: O=S(=O)(Nc1ccc(CCCC2CCCC2)cc1F)c1ccc2c(c1)CCNC2] |
| 3-9 | 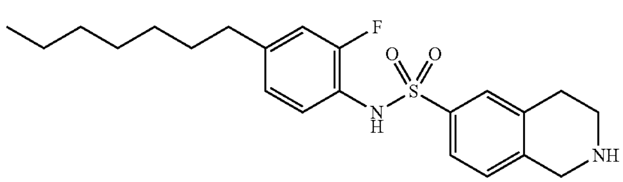 [SMILES: CCCCCCCc1ccc(NS(=O)(=O)c2ccc3c(c2)CCNC3)c(F)c1] |

TABLE 2-1-continued
| Reference Ex. | Structure |
|---|---|
| 3-10 | 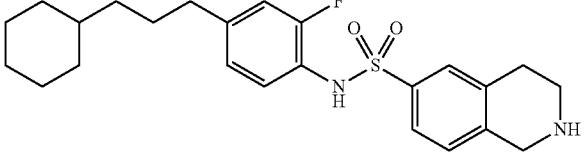 |
| 3-11 | 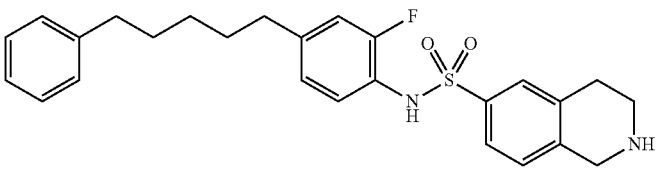 [SMILES: O=S(=O)(Nc1ccc(CCCCCc2ccccc2)cc1F)c1ccc2c(c1)CCNC2] |
| 3-12 | 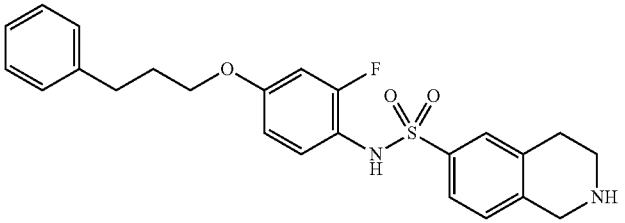 [SMILES: O=S(=O)(Nc1ccc(OCCCc2ccccc2)cc1F)c1ccc2c(c1)CCNC2] |
| 3-13 | 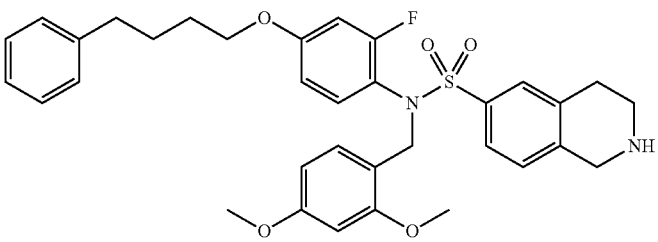 [SMILES: COc1ccc(CN(c2ccc(OCCCCc3ccccc3)cc2F)S(=O)(=O)c2ccc3c(c2)CCNC3)c(OC)c1] |
| 3-14 | 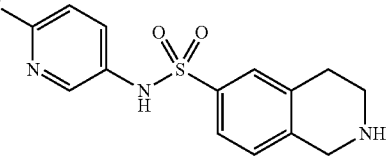 |
| 3-15 | 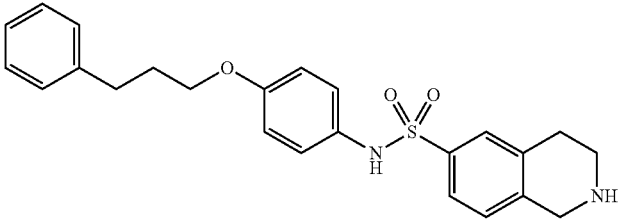 [SMILES: O=S(=O)(Nc1ccc(OCCCc2ccccc2)cc1)c1ccc2c(c1)CCNC2] |

TABLE 2-2

| Reference Ex. | Structure |
|---|---|
| 3-16 | 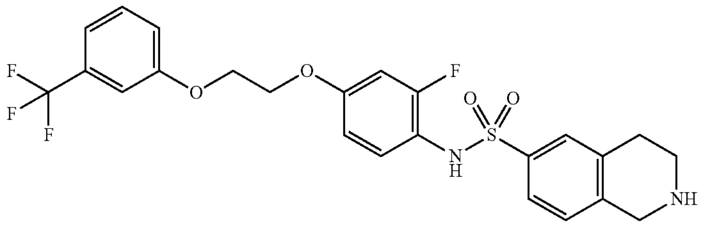 [SMILES: O=S(=O)(Nc1ccc(OCCOc2cccc(C(F)(F)F)c2)cc1F)c1ccc2c(c1)CCNC2] |
| 3-17 | 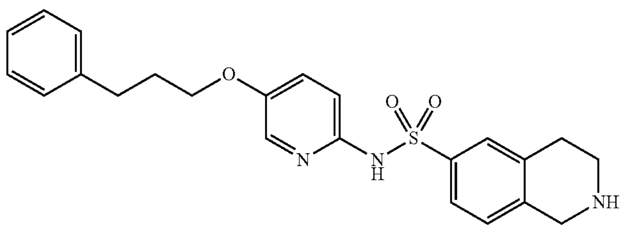 [SMILES: O=S(=O)(Nc1ccc(OCCCc2ccccc2)cn1)c1ccc2c(c1)CCNC2] |
| 3-18 | 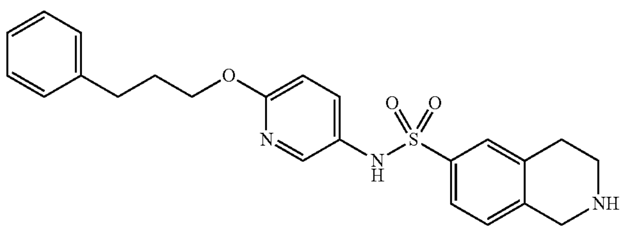 |
| 3-19 | 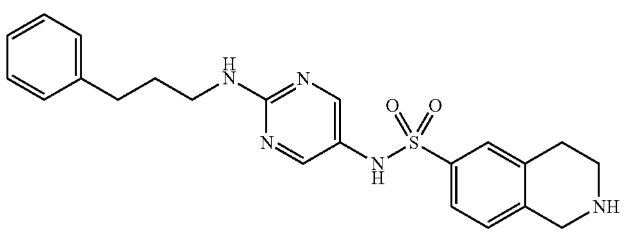 [SMILES: O=S(=O)(Nc1cnc(NCCCc2ccccc2)nc1)c1ccc2c(c1)CCNC2] |
| 3-20 | 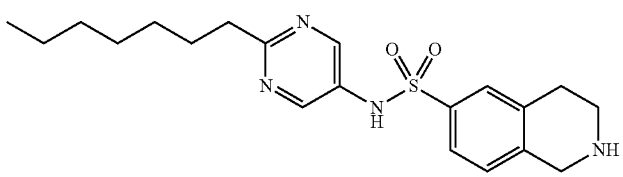 [SMILES: CCCCCCCc1ncc(NS(=O)(=O)c2ccc3c(c2)CCNC3)cn1] |
| 3-21 | 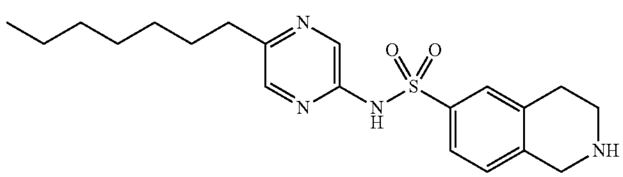 [SMILES: CCCCCCCc1cnc(NS(=O)(=O)c2ccc3c(c2)CCNC3)cn1] |
| 3-22 | 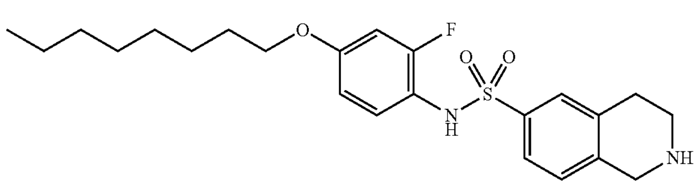 [SMILES: CCCCCCCCOc1ccc(NS(=O)(=O)c2ccc3c(c2)CCNC3)c(F)c1] |

TABLE 2-2-continued

| Reference Ex. | Structure |
|---|---|
| 3-23 | 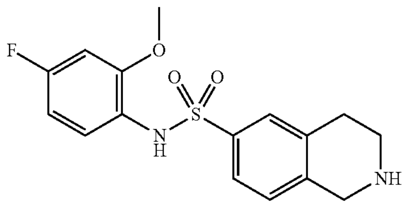 [SMILES: COc1cc(F)ccc1NS(=O)(=O)c1ccc2c(c1)CCNC2] |
| 3-24 | 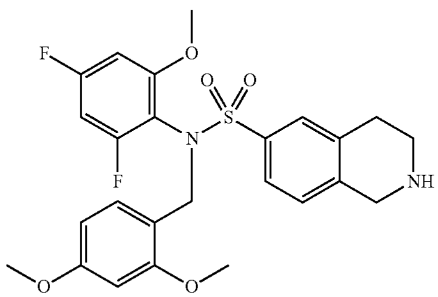 [SMILES: COc1ccc(CN(c2c(F)cc(F)cc2OC)S(=O)(=O)c2ccc3c(c2)CCNC3)c(OC)c1] |
| 3-25 | 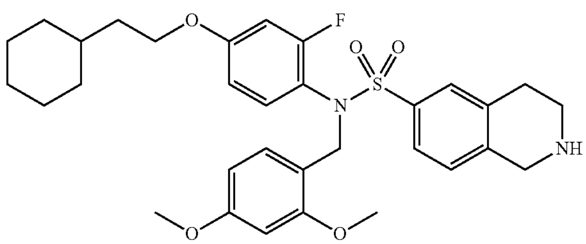 [SMILES: COc1ccc(CN(c2ccc(OCCC3CCCCC3)cc2F)S(=O)(=O)c2ccc3c(c2)CCNC3)c(OC)c1] |
| 3-26 | 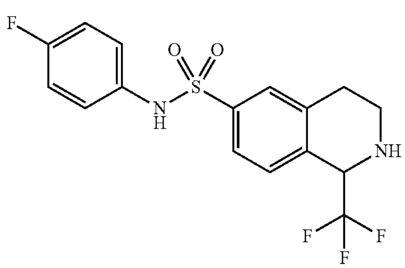 [SMILES: O=S(=O)(Nc1ccc(F)cc1)c1ccc2c(c1)CCNC2C(F)(F)F] |
| 3-27 | 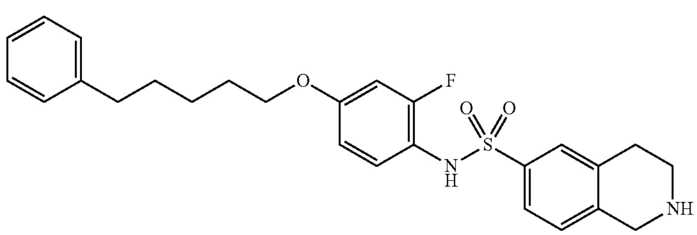 [SMILES: O=S(=O)(Nc1ccc(OCCCCCc2ccccc2)cc1F)c1ccc2c(c1)CCNC2] |
| 3-28 | 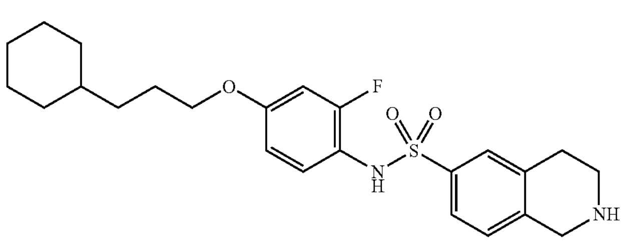 [SMILES: O=S(=O)(Nc1ccc(OCCCC2CCCCC2)cc1F)c1ccc2c(c1)CCNC2] |

TABLE 2-2-continued
| Reference Ex. | Structure |
|---|---|
| 3-29 | 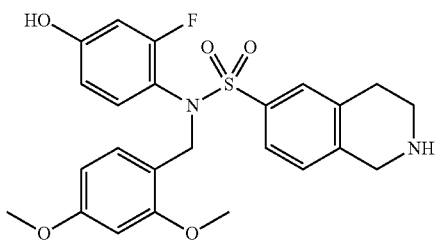 [SMILES: COc1ccc(CN(c2ccc(O)cc2F)S(=O)(=O)c2ccc3c(c2)CCNC3)c(OC)c1] |
TABLE 2-3
| Reference Ex. | Structure |
|---|---|
| 3-30 | 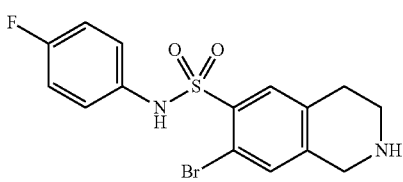 [SMILES: O=S(=O)(Nc1ccc(F)cc1)c1cc2c(cc1Br)CNCC2] |
| 3-31 | 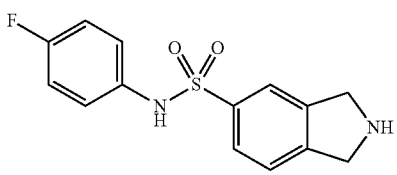 [SMILES: O=S(=O)(Nc1ccc(F)cc1)c1ccc2c(c1)CNC2] |
| 3-32 | 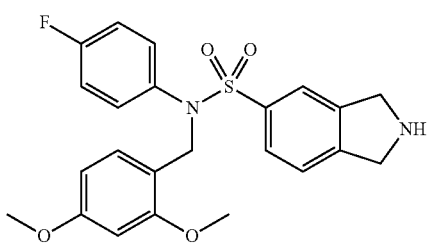 [SMILES: COc1ccc(CN(c2ccc(F)cc2)S(=O)(=O)c2ccc3c(c2)CNC3)c(OC)c1] |
| 3-33 | 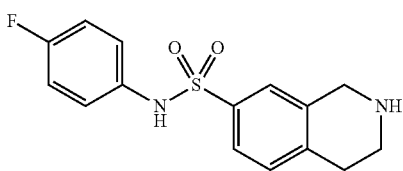 [SMILES: O=S(=O)(Nc1ccc(F)cc1)c1ccc2c(c1)CNCC2] |
| 3-34 | 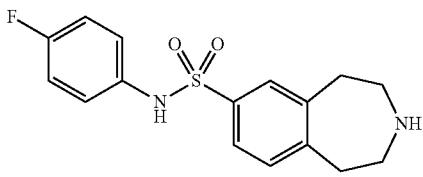 [SMILES: O=S(=O)(Nc1ccc(F)cc1)c1ccc2c(c1)CCNCC2] |

TABLE 2-3-continued
| Reference Ex. | Structure |
|---|---|
| 3-35 | 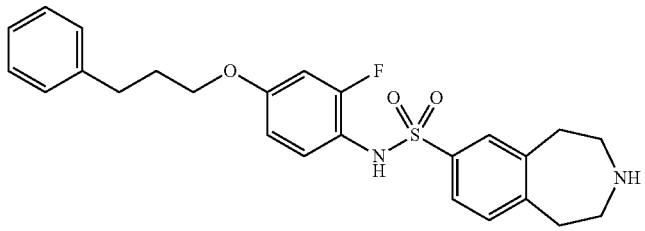 [SMILES: O=S(=O)(Nc1ccc(OCCCc2ccccc2)cc1F)c1ccc2c(c1)CCNCC2] |
TABLE 2-4
| Reference Ex. | Structure |
|---|---|
| 3-36 | 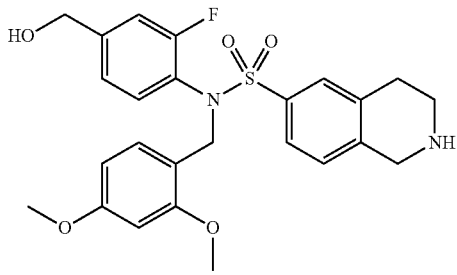 [SMILES: COc1ccc(CN(c2ccc(CO)cc2F)S(=O)(=O)c2ccc3c(c2)CCNC3)c(OC)c1] |
| 3-37 | 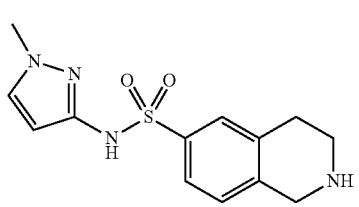 [SMILES: Cn1ccc(NS(=O)(=O)c2ccc3c(c2)CCNC3)n1] |
| 3-38 | 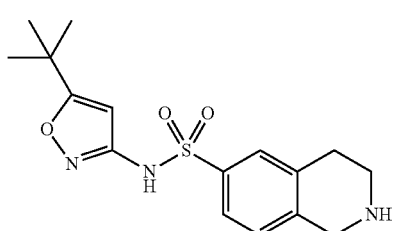 |
| 3-39 | 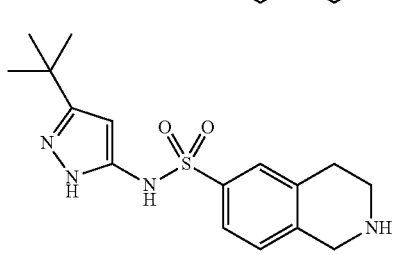 |
| 3-40 | 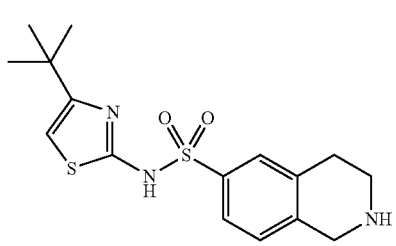 [SMILES: CC(C)(C)c1csc(NS(=O)(=O)c2ccc3c(c2)CCNC3)n1] |

TABLE 2-4-continued
| Reference Ex. | Structure |
|---|---|
| 3-41 | 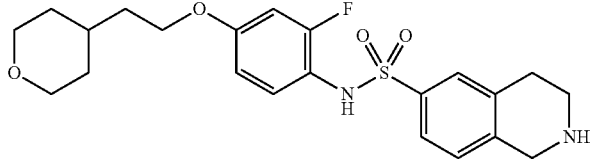 [SMILES: O=S(=O)(Nc1ccc(OCCC2CCOCC2)cc1F)c1ccc2c(c1)CCNC2] |
| 3-42 | 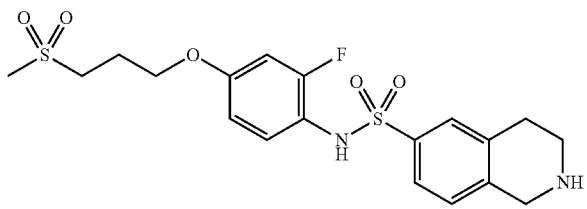 [SMILES: CS(=O)(=O)CCCOc1ccc(NS(=O)(=O)c2ccc3c(c2)CCNC3)c(F)c1] |
| 3-43 | 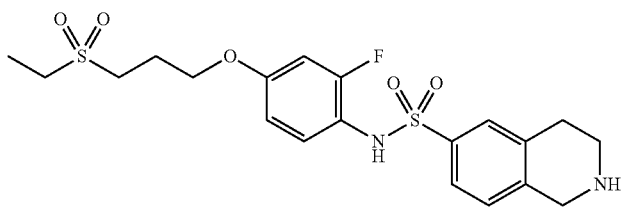 [SMILES: CCS(=O)(=O)CCCOc1ccc(NS(=O)(=O)c2ccc3c(c2)CCNC3)c(F)c1] |
| 3-44 | 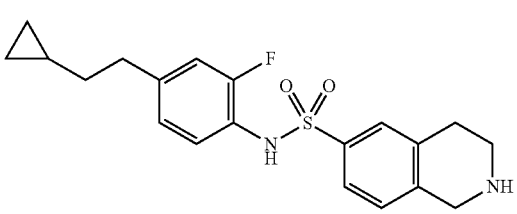 [SMILES: O=S(=O)(Nc1ccc(CCC2CC2)cc1F)c1ccc2c(c1)CCNC2] |
| 3-45 | 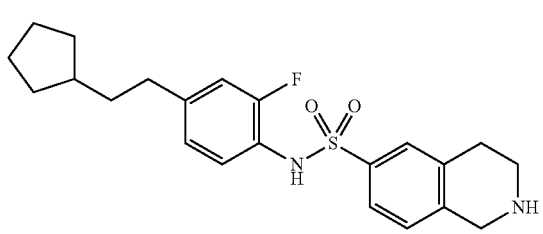 [SMILES: O=S(=O)(Nc1ccc(CCC2CCCC2)cc1F)c1ccc2c(c1)CCNC2] |
| 3-46 | 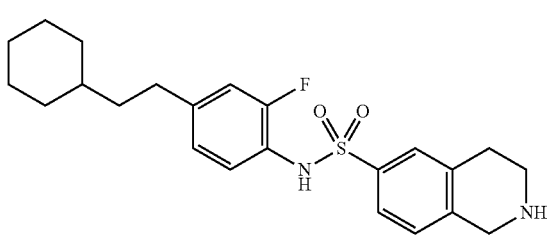 [SMILES: O=S(=O)(Nc1ccc(CCC2CCCCC2)cc1F)c1ccc2c(c1)CCNC2] |
| 3-47 | 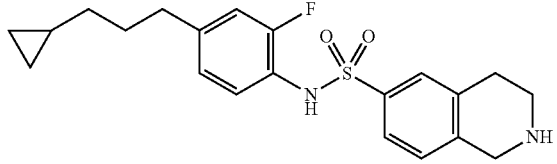 [SMILES: O=S(=O)(Nc1ccc(CCCC2CC2)cc1F)c1ccc2c(c1)CCNC2] |

TABLE 2-4-continued

| Reference Ex. | Structure |
|---|---|
| 3-48 | 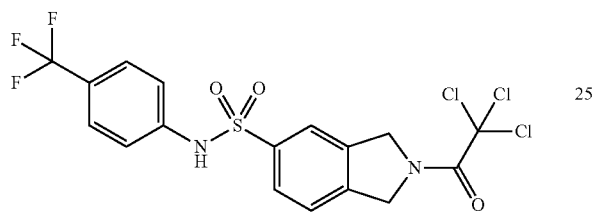 |

Reference Example 4-1

2-(Trichloroacetyl)-N-[4-(trifluoromethyl)phenyl]-2,3-dihydro-1 H-isoindole-5-sulfonamide

[Formula 20]

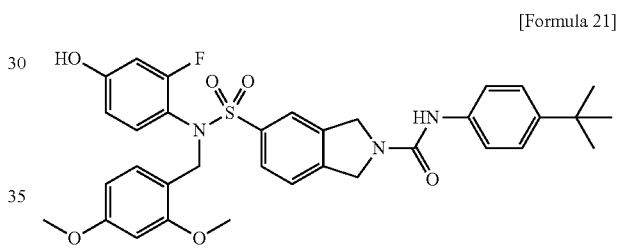

(1) Triethylamine (3.48 mL, 25.0 mmol) was added to a solution of isoindoline (4.98 g, 25.0 mmol) in chloroform (100 mL) at room temperature and the mixture was cooled in ice. Trichloroacetic acid chloride (2.79 mL, 25.0 mmol) was added dropwise thereto and the reaction mixture was warmed to room temperature and stirred for 1 hr. The reaction mixture was concentrated under reduced pressure and the resulting residue was purified by silica gel column chromatography (hexane:ethyl acetate=4:1) to afford 2,2,2-trichloro-1-(1,3-dihydro-2 H-isoindol-2-yl)ethanone as a purple powder (6.59 g).

(2) Chlorosulfonic acid (5.22 mL, 78.5 mmol) was cooled to −78° C. and 2,2,2-trichloro-1-(1,3-dihydro-2 H-isoindol-2-yl)ethanone (1.32 g, 5.00 mmol) was added thereto. The reaction mixture was warmed to room temperature and stirred for 30 min. The reaction mixture was poured into ice water and the mixture was extracted three times with ethyl acetate. The organic layer was concentrated under reduced pressure, and the resulting residue was powdered with hexane and collected by filtration to afford 2-(trichloroacetyl)-2,3-dihydro-1 H-isoindole-5-sulfonyl chloride as a pale green powder (1.38 g).

(3) To a solution of 4-trifluoromethyl aniline (213 μL, 1.70 mmol) in pyridine (270 μL) was added 2-(trichloroacetyl)-2,3-dihydro-1 H-isoindole-5-sulfonyl chloride (617 mg, 1.70 mmol) at room temperature, and the mixture was stirred at 60° C. for 1.5 hr. The reaction mixture was allowed to cool to room temperature and diluted with ethyl acetate. The mixture was washed with 1 mol/L hydrochloric acid, brine and water. The organic layer was dried over anhydrous sodium sulfate and then the desiccant was filtered off, followed by concentration under reduced pressure. The resulting residue was purified by silica gel column chromatography (hexane:ethyl acetate=4:1→2:1) to afford the title compound as a colorless powder (586 mg).

[1] H NMR (300 MHz, CDCl$_3$) δ ppm 4.95-5.04 (m, 2 H), 5.29-5.38 (m, 2 H), 6.87-6.95 (m, 1 H), 7.17-7.24 (m, 2 H), 7.36-7.49 (m, 1 H), 7.50-7.56 (m, 2 H), 7.74-7.86 (m, 2 H).

MS ESI/APCI Dual nega: 485, 487[M−H]$^-$.

Reference Example 5-1

N-(4-tert-Butylphenyl)-5-[(2,4-dimethoxybenzyl)(2-fluoro-4-hydroxyphenyl)sulfamoyl]-1,3-dihydro-2 H-isoindole-2-carboxamide

[Formula 21]

To a solution of compound 2-26 as obtained in Reference Example 2 (14.3 g, 25.8 mmol) in an ethanol/water mixture (9/1) (200 mL) was added potassium hydroxide (3.18 g, 56.7 mmol) at room temperature, and the mixture was stirred for 3 hr just after the addition. The reaction mixture was distilled off under reduced pressure and water was added to the resulting residue. To the mixture, 1 mol/L hydrochloric acid was added to adjust the pH to 8, and the mixture was extracted three times with ethyl acetate. The organic layer was washed with brine, dried over anhydrous magnesium sulfate, and filtered. Thereafter, the solvent was distilled off under reduced pressure to give a residue as a colorless powder (7.10 g). The residue (6.30 g) was dissolved in a chloroform/DMSO mixture (9/1) (80 mL) and then triethylamine (19.1 mL, 137 mmol) and 4-tert-butylphenyl isocyanate (26.9 mL, 15.1 mmol) were added thereto at room temperature. The mixture was stirred for 14 hr. To the reaction mixture was added saturated aqueous ammonium chloride solution, and the mixture was extracted twice with ethyl acetate. After the organic layer was dried over anhydrous magnesium sulfate and filtered, the solvent was distilled off under reduced pressure. The resulting residue was purified by silica gel column chromatography (hexane:ethyl acetate=50:50→ethyl acetate only) to afford the title compound as a colorless powder (4.8 g).

[1] H NMR (300 MHz, DMSO-d$_6$) δ ppm 1.23 (s, 9 H), 3.56 (s, 3 H), 3.70 (s, 3 H), 4.56 (s, 2 H), 4.84 (d, J=12 Hz, 4 H), 6.32-6.56 (m, 4 H), 6.69-6.80 (m, 1 H), 7.04-7.11 (m, 1H), 7.28 (d, J=8.6 Hz, 2 H), 7.46 (d, J=8.6 Hz, 2 H), 7.51-7.78 (m, 3 H), 8.35 (s, 1 H), 10.04 (br. s, 1 H).

Reference Example 6-1

N-{2-Fluoro-4-[2-(pyridin-2-yl)ethoxy]phenyl}-1,2,3,4-tetrahydroisoquinoline-6-sulfonamide

[Formula 22]

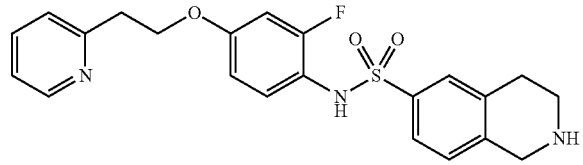

(1) To a tetrahydrofuran solution (5 mL) of compound 3-2 (224 mg) obtained in Reference Example 3-1,2-pyridine ethanol (89 μL, 0.788 mmol) and cyanomethylene tributylphosphorane (258 μL, 0.985 mmol) were successively added at room temperature, and the mixture was stirred at room temperature over two nights and stirred under reflux for 9 hr. 2-Pyridine ethanol (89 μL, 0.788 mmol) and cyanomethylene tributylphosphorane (258 μL, 0.985 mmol) were further added thereto and the mixture was stirred under reflux for 2 hr. 2-Pyridine ethanol (89 μL, 0.788 mmol) and cyanomethylene tributylphosphorane (258 μL, 0.985 mmol) were still further added thereto and the mixture was stirred under reflux for 14 hr and stirred at room temperature for 5 hr. 2-Pyridine ethanol (89 μL, 0.788 mmol) and cyanomethylene tributylphosphorane (258 μL, 0.985 mmol) were still further added thereto and the mixture was stirred under reflux for 2 hr. The reaction mixture was cooled to room temperature and water was added thereto, followed by extraction with ethyl acetate. The organic layer was washed with brine and dried over anhydrous magnesium sulfate. The desiccant was filtered off, followed by concentration under reduced pressure. The resulting residue was purified by NH silica gel column chromatography (hexane:ethyl acetate=80:20→65:35) to afford N-(2,4-dimethoxybenzyl)-N-[2-fluoro-4-[2-(pyridin-2-yl)ethoxy]phenyl]-2-(trifluoroacetyl)-1,2,3,4-tetrahydroisoquinoline-6-sulfonamide as a yellow oil (350 mg).

(2) Trifluoroacetic acid (1 mL) was added to a solution of N-(2,4-dimethoxybenzyl)-N-{2-fluoro-4-[2-(pyridin-2-yl)ethoxy]phenyl}-2-(trifluoroacetyl)-1,2,3,4-tetrahydroisoquinoline-6-sulfonamide obtained (350 mg) in a mixture of anisole (5 mL) and chloroform (5 mL) while cooling in ice, and the mixture was stirred at room temperature for 16 hr. To the reaction mixture was added saturated aqueous sodium hydrogen carbonate solution while cooling in ice, and the mixture was extracted with ethyl acetate. The organic layer was washed with brine and dried over anhydrous magnesium sulfate and then the desiccant was filtered off, followed by concentration under reduced pressure. The resulting residue was purified by NH silica gel column chromatography (hexane:ethyl acetate=70:30→chloroform:methanol=95:5) to afford N-{2-fluoro-4-[2-(pyridin-2-yl)ethoxy]phenyl}-2-(trifluoroacetyl)-1,2,3,4-tetrahydroisoquinoline-6-sulfonamide as a colorless oil (12 mg).

(3) Powdered potassium hydroxide (2 mg, 36.2 μmol) was added to a solution of N-{2-fluoro-4-[2-(pyridin-2-yl)ethoxy]phenyl}-2-(trifluoroacetyl)-1,2,3,4-tetrahydroisoquinoline-6-sulfonamide obtained (10 mg) in an ethanol-water mixture (9:1) (2 mL), and the mixture was stirred at room temperature for 3 hr. The reaction mixture was concentrated under reduced pressure and water was added thereto. The mixture was extracted with ethyl acetate and the organic layer was washed with brine and dried over anhydrous magnesium sulfate. Thereafter, the desiccant was filtered off, followed by concentration under reduced pressure to afford the title compound as a colorless solid (10 mg).

$^1$H NMR (300 MHz, CDCl$_3$) δ ppm 2.72-2.83 (m, 2 H), 3.07-3.16 (m, 2 H), 3.22 (t, J=6.7 Hz, 2 H), 4.02 (s, 2 H), 4.29 (t, J=6.7 Hz, 2 H), 6.45-6.54 (m, 1 H), 6.61-6.67 (m, 1 H), 7.03 (d, J=7.9 Hz, 1 H), 7.13-7.19 (m, 1 H), 7.21-7.25 (m, 1 H), 7.35-7.48 (m, 3 H), 7.62 (dt, J=7.6, 1.9 Hz, 1 H), 8.52-8.57 (m, 1 H).

MS ESI/APCI Dual posi: 428[M+H]$^+$.

Reference Example 7-1

(4-tert-Butylphenyl)acetaldehyde

[Formula 23]

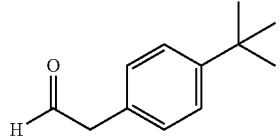

(1) A solution of 2-(4-tert-butylphenyl)ethanol (5.35 g, 30.0 mmol) in chloroform (150 mL) was cooled in ice and Dess-Martin periodinane (16.5 g, 39.0 mmol) was added thereto. The mixture was warmed to room temperature and stirred for 3 hr. The reaction mixture was diluted with chloroform (150 mL), followed by cooling in ice. Thereafter, saturated aqueous sodium thiosulfate solution was added thereto and the mixture was stirred for 5 min. The mixture was extracted three times with chloroform and then the organic layer was washed with brine and dried over anhydrous magnesium sulfate. The desiccant was filtered off and then the filtrate was concentrated under reduced pressure. The resulting precipitate was filtered again, followed by washing with chloroform. The filtrate was concentrated under reduced pressure and the resulting residue was purified by silica gel column chromatography (hexane:ethyl acetate=9:1) to afford the title compound as a yellow oil (4.24 g).

$^1$H NMR (300 MHz, CDCl$_3$) δ ppm 1.32 (d, J=0.6 Hz, 9 H), 3.66 (d, J=2.5 Hz, 2 H), 7.16 (d, J=8.2 Hz, 2 H), 7.40 (d, J=8.2 Hz, 2 H), 9.69-9.81 (m, 1 H).

Reference Example 8-1

4-(1-Hydroxy-2-methylpropan-2-yl)benzaldehyde

[Formula 24]

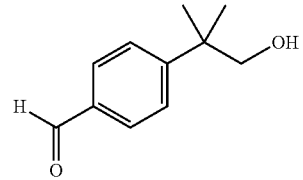

(1) A reaction was performed by the method described in JP 2008-1635 A to afford 2-(4-bromophenyl)-2-methylpropan-1-ol as a colorless oil (8.32 g).

(2) To a solution of 2-(4-bromophenyl)-2-methylpropan-1-ol obtained (8.32 g, 36.3 mmol) in N,N-dimethylformamide (73 mL) were added imidazole (2.97 g, 43.6 mmol) and tert-butyldimethylchlorosilane (6.57 g, 43.6 mmol), and the mixture was stirred at room temperature for 5 hr. Water was added thereto and the mixture was extracted with hexane. The organic layer was washed with water and brine and dried over anhydrous sodium sulfate. The desiccant was filtered off, followed by concentration under reduced pressure.

Thereafter, the resulting residue was purified by silica gel column chromatography (hexane only) to afford [2-(4-bromophenyl)-2-methylpropoxy](tert-butyl)dimethylsilane as a colorless oil (11.1 g).

(3) A solution of [2-(4-bromophenyl)-2-methylpropoxy](tert-butyl)dimethylsilane (3.43 g, 10.0 mmol) in tetrahydrofuran (30 mL) was cooled to −78° C. under a nitrogen atmosphere, n-butyllithium (2.64 mol/L hexane solution, 5.70 mL, 15.0 mmol) was added dropwise thereto, and the mixture was stirred at the same temperature for 30 min. To the reaction mixture, N,N-dimethylformamide (3.89 mL, 50.0 mmol) was added dropwise, and the mixture was stirred at the same temperature for 30 min. After warming to room temperature, the reaction mixture was poured into aqueous ammonium chloride solution and the mixture was extracted with ethyl acetate. The organic layer was washed with brine and dried over anhydrous magnesium sulfate and then the desiccant was filtered off, followed by concentration under reduced pressure. The resulting residue was purified by silica gel column chromatography (hexane only→hexane:ethyl acetate=9:1) to afford 4-(1-{[tert-butyl(dimethyl)silyl]oxy}-2-methylpropan-2-yl)benzaldehyde as a colorless oil (2.88 g).

(4) To a solution of 4-(1-{[tert-butyl(dimethyl)silyl]oxy}-2-methylpropan-2-yl)benzaldehyde (530 mg, 1.81 mmol) in 1,4-dioxane (5 mL) was added a 4 mol/L hydrogen chloride-1,4-dioxane solution (4.5 mL), and the mixture was stirred at room temperature for 15 hr. Water was added thereto and the mixture was extracted with chloroform. The organic layer was concentrated under reduced pressure and the resulting residue was purified by silica gel column chromatography (hexane:ethyl acetate=9:1→1:1) to afford the title compound as a colorless oil (303 mg).

$^1$H NMR (300 MHz, CDCl$_3$) δ ppm 1.38 (s, 6 H), 3.68 (s, 2 H), 7.57 (d, J=8.3 Hz, 2 H), 7.86 (d, J=8.3 Hz, 2 H), 10.00 (s, 1 H).

Reference Example 9-1

6-tert-Butylpyridine-2-carbaldehyde

[Formula 25]

(1) Silver nitrate (4.43 g, 28.8 mmol) was added to a suspension of pivalic acid (1.96 g, 19.2 mmol), 3-cyanopyridine (2.00 g, 19.2 mmol) and ammonium peroxodisulfate (6.58 g, 28.8 mmol) in water (40 mL). The mixture was stirred at room temperature for 10 min and then stirred at an external temperature of 80° C. for 2 hr. After cooling, the reaction mixture was diluted with ethyl acetate and the resulting insoluble matter was removed by filtration through Celite (registered trademark). The aqueous layer was separated from the filtrate, followed by extraction with ethyl acetate. The organic layer was washed with water and brine and dried over anhydrous magnesium sulfate. The desiccant was filtered off and then the solvent was distilled off under reduced pressure. The resulting residue was purified by silica gel column chromatography (hexane only→hexane:ethyl acetate=4:1) to afford 6-tert-butylpyridine-2-carbonitrile as a yellow oil (2.71 g).

(2) Diisobutylaluminum hydride (1.02 mol/L toluene solution, 23.5 mL, 24.1 mmol) was added to a solution of 6-tert-butylpyridine-2-carbonitrile obtained (2.57 g, 16.0 mmol) in tetrahydrofuran (20 mL) under a nitrogen atmosphere at −78° C., and the mixture was stirred for 1.5 hr while cooling in ice. To the reaction mixture was added 1 mol/L hydrochloric acid, and the mixture was diluted with ethyl acetate and stirred at room temperature for 45 min. The organic layer was washed with brine and dried over anhydrous magnesium sulfate. The desiccant was filtered off and then the solvent was distilled off under reduced pressure. The resulting residue was purified by silica gel column chromatography (hexane only→hexane:ethyl acetate=4:1) to afford the title compound as a yellow oil (1.71 g).

$^1$H NMR (200 MHz, CDCl$_3$) δ ppm 1.40 (s, 9 H), 7.46-7.57 (m, 1 H), 8.04-8.15 (m, 1 H), 8.95-9.04 (m, 1 H), 10.08 (s, 1 H).

MS ESI/APCI Dual posi: 164[M+H]$^+$.

The compounds of Reference Examples 9-2 to 9-5A were obtained by using the corresponding commercially available cyano compounds in accordance with the process of Reference Example 9-1.

Reference Example 9-2

$^1$H NMR (200 MHz, CDCl$_3$) δ ppm 1.45 (s, 9 H), 8.79-8.82 (m, 1 H), 9.08-9.10 (m, 1 H), 10.14 (s, 1 H).

MS ESI/APCI Dual posi: 165[M+H]$^+$.

Reference Example 9-3

$^1$H NMR (200 MHz, CDCl$_3$) δ ppm 1.42 (s, 9 H), 7.48 (d, J=5.3 Hz, 1 H), 8.87 (d, J=5.3 Hz, 1 H), 10.11 (s, 1 H).

MS ESI/APCI Dual posi: 165[M+H]$^+$.

Reference Example 9-4

$^1$H NMR (200 MHz, CDCl$_3$) δ ppm 1.45 (s, 9 H), 8.99 (s, 2 H), 10.11 (s, 1 H).

MS ESI/APCI Dual posi: 165[M+H]$^+$.

Reference Example 9-5

$^1$H NMR (600 MHz, CDCl$_3$) δ ppm 1.42 (s, 9 H), 7.48-7.53 (m, 1 H), 7.73-7.77 (m, 1 H), 8.82 (d, J=5.0 Hz, 1 H), 10.08 (s, 1 H).

MS ESI/APCI Dual posi: 164[M+H]$^+$.

The structures of the compounds of Reference Examples 9-2 to 9-5 are shown in Tables 3-1 and 3-2.

TABLE 3-1

| Reference Ex. | Structure |
|---|---|
| 9-2 | (5-tert-butylpyrazine-2-carbaldehyde structure) |
| 9-3 | (4-tert-butylpyrimidine-2-carbaldehyde structure) |
| 9-4 | (5-tert-butylpyrimidine-2-carbaldehyde structure) |

TABLE 3-2

| Reference Ex. | Structure |
|---|---|
| 9-5 | (2-tert-butylpyridine-4-carbaldehyde structure) |

Reference Example 10-1

(6-tert-Butylpyridin-3-yl)acetaldehyde

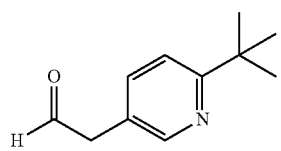

[Formula 26]

(1) (Methoxymethyl)triphenylphosphonium chloride (10.1 g, 29.4 mmol) was suspended in tetrahydrofuran (100 mL) under a nitrogen atmosphere, and sodium hexamethyldisilazane (tetrahydrofuran solution, 1.09 mol/L) (27.0 mL, 29.4 mmol) was added dropwise thereto at 0° C. and then the mixture was stirred for 10 min. A tetrahydrofuran solution (20 mL) of the compound of Reference Example 9-1 (4.0 g, 24.5 mmol) was added dropwise to the suspension, and the mixture was warmed to room temperature and stirred for 2.5 hr. Saturated aqueous ammonium chloride solution (3 mL) was added to the reaction mixture, followed by concentration under reduced pressure. The residue was diluted with water and ethyl acetate for separation into phases. The aqueous layer was extracted with ethyl acetate. The combined organic layer was filtered through a phase separator and then, the filtrate was concentrated and the residue was purified by NH silica gel column chromatography (hexane only→hexane: ethyl acetate=17:3) to afford 2-tert-butyl-5-[(E/Z)-2-methoxyethenyl]pyridine as a colorless oil (4.46 g).

(2) 2-tert-Butyl-5-[(E/Z)-2-methoxyethenyl]pyridine obtained (4.23 g, 22.12 mmol) was dissolved in a mixture of tetrahydrofuran (85 mL) and water (43 mL), and concentrated hydrochloric acid was added thereto, followed by stirring at room temperature for 5 hr. To the reaction mixture was added sodium hydrogen carbonate (39 g) and the mixture was diluted with water (300 mL) to adjust the pH to 4. Ethyl acetate (150 mL) was added thereto for separation into phases. The aqueous layer was extracted twice with ethyl acetate (150 mL) and the extract was mixed with the organic layer. The mixture was dried over anhydrous magnesium sulfate, filtered and then concentrated. The residue was purified by silica gel column chromatography (hexane:ethyl acetate=49:1→1:1) to afford the title compound as a pale yellow oil (635 mg).

$^1$H NMR (300 MHz, CDCl$_3$) δ ppm 1.37 (s, 9 H), 3.68-3.72 (m, 2 H), 7.33-7.37 (m, 1 H), 7.46-7.50 (m, 1 H), 8.41-8.47 (m, 1 H), 9.75-9.82 (m, 1 H).

LCMS retention time: 1.49 min. (Condition 1-1-1)

MS (ESI posi) m/z: 178[M+H]$^+$.

The compounds of Reference Examples 10-2 to 10-8 were obtained by using the corresponding commercially available aldehydes and the aldehydes obtained in Reference Examples 8-1 and 9-5 in accordance with the process of Reference Example 10-1.

Reference Example 10-2

$^1$H NMR (300 MHz, CDCl$_3$) δ ppm 3.89 (s, 1 H), 7.67-7.81 (m, 2 H), 8.56-8.61 (m, 1 H), 9.86 (t, J=1.4 Hz, 1 H).

LCMS retention time: 3.27 min. (Condition 1-1-1)

MS (ESI posi) m/z: 190[M+H]$^+$.

Reference Example 10-3

$^1$H NMR (300 MHz, CDCl$_3$) δ ppm 1.42 (s, 9 H), 3.72-3.75 (m, 2 H), 8.55 (s, 2 H), 9.82-9.86 (m, 1 H).

LCMS retention time: 2.77 min. (Condition 1-1-1)

MS (ESI posi) m/z: 179[M+H]$^+$.

Reference Example 10-4

$^1$H NMR (300 MHz, CDCl$_3$) δ ppm 1.31-1.36 (m, 6 H), 3.57-3.70 (m, 4 H), 7.09-7.43 (m, 4 H), 9.73-9.77 (m, 1 H).

Reference Example 10-5

$^1$H NMR (300 MHz, CDCl$_3$) δ ppm 1.49-1.67 (m, 9 H), 3.56 (d, J=2.2 Hz, 2 H), 7.37-7.59 (m, 2 H), 9.71 (t, J=2.2 Hz, 1 H).

LCMS retention time: 0.60 min. (Condition 5-1)

MS (ESI posi) m/z: 167[M+H]$^+$.

Reference Example 10-6

$^1$H NMR (200 MHz, CDCl$_3$) δ ppm 1.44 (s, 9 H), 3.86-3.92 (m, 2 H), 7.45-7.51 (m, 1 H), 9.75 (t, J=1.8 Hz, 1 H).

MS ESI/APCI Dual posi: 184[M+H]$^+$.

Reference Example 10-7

$^1$H NMR (600 MHz, CDCl$_3$) δ ppm 1.37 (s, 9 H), 3.70 (d, J=2.1 Hz, 2 H), 6.95-6.99 (m, 1 H), 7.17-7.20 (m, 1 H), 8.54 (d, J=5.0 Hz, 1 H), 9.75-9.78 (m, 1 H).

MS ESI/APCI Dual posi: 178[M+H]$^+$.

Reference Example 10-8

$^1$H NMR (300 MHz, CDCl$_3$) δ ppm 3.71 (d, J=2.0 Hz, 2 H), 6.89-6.96 (m, 2 H), 7.05 (d, J=8.1 Hz, 1 H), 9.76 (t, J=2.0 Hz, 1 H).

MS ESI/APCI Dual nega: 199[M−H]$^−$.

The structures of the compounds of Reference Examples 10-2 to 10-8 are shown in Tables 4-1 and 4-2.

TABLE 4-1

| Reference Ex. | Structure |
|---|---|
| 10-2 | 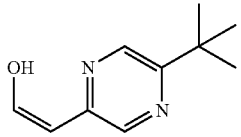 |
| 10-3 | 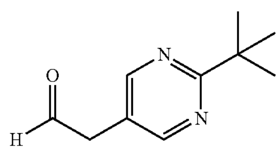 |
| 10-4 | 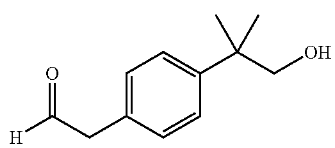 |

TABLE 4-2

| Reference Ex. | Structure |
|---|---|
| 10-5 | 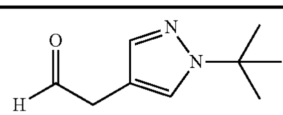 |
| 10-6 | 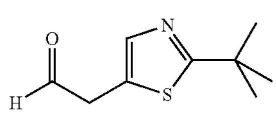 |
| 10-7 | 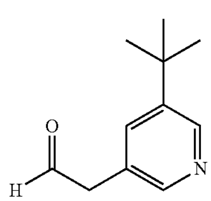 |

TABLE 4-2-continued

| Reference Ex. | Structure |
|---|---|
| 10-8 | 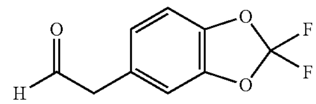 [SMILES: O=CCc1ccc2c(c1)OC(F)(F)O2] |

Reference Example 11-1

(Z)-2-(5-tert-Butylpyrazin-2-yl)ethenol

[Formula 27]

(1) Sodium hexamethyldisilazane (tetrahydrofuran solution, 1.07 mmol/L) (4.4 mL, 4.70 mmol) was added dropwise to a suspension of 2-(trimethylsilyl)ethoxymethyltriphenylphosphonium chloride (2.02 g, 4.70 mmol) in tetrahydrofuran (16 mL) under a nitrogen atmosphere while cooling in ice, and the mixture was stirred for 20 min. A solution of compound 9-2 (643 mg, 3.91 mmol) obtained in Reference Example 9 in tetrahydrofuran (4 mL) was added dropwise to the reaction mixture, followed by stirring at room temperature for 2 hr. To the reaction mixture was added saturated aqueous ammonium chloride solution, and the mixture was extracted twice with ethyl acetate. The organic layer was washed with brine and dried over anhydrous magnesium sulfate. The desiccant was filtered off and then the solvent was distilled off under reduced pressure. The resulting residue was purified by silica gel column chromatography (hexane only→hexane:ethyl acetate=9:1) to afford 2-tert-butyl-5-{(E/Z)-2-[2-(trimethylsilyl)ethoxy]ethenyl}pyrazine as a yellow oil (0.93 g).

(2) A boron trifluoride-ethyl ether complex (0.85 mL, 6.67 mmol) was added dropwise to a solution of 2-tert-butyl-5-{(E/Z)-2-[2-(trimethylsilyl)ethoxy]ethenyl}pyrazine obtained (0.93 g, 3.33 mmol) in chloroform (20 mL) under a nitrogen atmosphere while cooling in ice, and the mixture was stirred at room temperature for 2.5 hr. A boron trifluoride-ethyl ether complex (0.41 mL, 3.33 mmol) was added dropwise to the reaction mixture, followed by stirring at room temperature for 18 hr. To the reaction mixture was added saturated aqueous sodium hydrogen carbonate solution, and the mixture was extracted with chloroform. The organic layer was washed with brine and dried over anhydrous magnesium sulfate. After the desiccant was filtered off, the solvent was distilled off under reduced pressure. The resulting residue was purified by silica gel column chromatography (hexane only→hexane:ethyl acetate=4:1) to afford the title compound as a brown solid (322 mg).

$^1$H NMR (200 MHz, CDCl$_3$) δ ppm 1.41 (s, 9 H), 5.88 (d, J=5.3 Hz, 1 H), 7.31-7.50 (m, 1 H), 8.16-8.25 (m, 1 H), 8.66-8.75 (m, 1 H).

MS ESI/APCI Dual posi: 179[M+H]$^+$.

The compounds of Reference Examples 11-2 to 11-4 were obtained by using the commercially available aldehydes and the compounds obtained in Reference Example 9 in accordance with the process of Reference Example 11-1.

Reference Example 11-2

$^1$H NMR (200 MHz, CDCl$_3$) δ ppm 1.42 (s, 9 H), 6.01 (d, J=5.3 Hz, 1 H), 7.37-7.55 (m, 1 H), 8.45-8.55 (m, 1 H), 8.99-9.06 (m, 1 H).

MS ESI/APCI Dual posi: 179[M+H]$^+$.

Reference Example 11-3

$^1$H NMR (200 MHz, CDCl$_3$) δ ppm 1.38 (s, 9 H), 5.97 (d, J=5.3 Hz, 1 H), 7.30-7.55 (m, 2 H), 8.38-8.53 (m, 1 H).

MS ESI/APCI Dual posi: 179[M+H]$^+$.

Reference Example 11-4

$^1$H NMR (200 MHz, CDCl$_3$) δ ppm 5.90 (d, J=5.3 Hz, 1 H), 7.30-7.53 (m, 2 H), 8.03-8.20 (m, 1 H), 8.70 (s, 1 H).

MS ESI/APCI Dual posi: 190[M+H]$^+$.

The structures of the compounds of Reference Examples 11-2 to 11-4 are shown in Table 5-1.

TABLE 5-1

| Reference Ex. | Structure |
|---|---|
| 11-2 | ![structure] |
| 11-3 | ![structure] |
| 11-4 | ![structure] |

Reference Example 12-1

1-(4-tert-Butylphenyl)propan-2-one

[Formula 28]

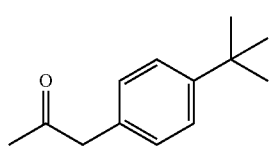

(1) To a solution of 4-tert-butylphenyl acetic acid methyl ester (10.0 g, 48.5 mmol) in a mixture of tetrahydrofuran (50 mL) and methanol (50 mL) was added 6 mol/L aqueous sodium hydroxide solution (16.2 mL, 97.0 mmol), and the mixture was stirred at room temperature for 3 hr. The mixture was concentrated under reduced pressure and 6 mol/L hydrochloric acid was added thereto while cooling in ice, to adjust the pH to 4 to 5. A precipitated solid was collected by filtration to afford (4-tert-butylphenyl)acetic acid as a colorless powder (9.32 g).

(2) To a solution of (4-tert-butylphenyl)acetic acid obtained (5.00 g, 26.0 mmol) in chloroform (50 mL) were added N,O-dimethylhydroxylamine hydrochloride (2.79 g, 28.6 mmol), triethylamine (4.35 mL, 31.2 mmol), 1-hydroxybenzotriazole monohydrate (5.18 g, 33.8 mmol) and 1-ethyl-3-(3-dimethylaminopropyl)carbodiimide hydrochloride (6.48 g, 33.8 mmol) successively. The mixture was stirred at room temperature for 20 hr. Water was added thereto and the mixture was extracted with chloroform. The organic layer was dried over anhydrous magnesium sulfate and then the desiccant was filtered off, followed by concentration under reduced pressure. The resulting residue was purified by silica gel column chromatography (hexane:ethyl acetate=4:1→3:2) to afford 2-(4-tert-butylphenyl)-N-methoxy-N-methylacetamide as a colorless oil (5.62 g).

(3) A solution of 2-(4-tert-butylphenyl)-N-methoxy-N-methylacetamide obtained (200 mg, 0.850 mmol) in tetrahydrofuran (5 mL) was cooled in ice under a nitrogen atmosphere, methylmagnesium bromide (1 mol/L tetrahydrofuran solution, 1.70 mL, 1.70 mmol) was added dropwise thereto, and the mixture was stirred at the same temperature for 30 min. Aqueous ammonium chloride solution was added thereto and the mixture was extracted with ethyl acetate. The organic layer was washed with brine and dried over anhydrous sodium sulfate. Thereafter, the desiccant was filtered off, followed by concentration under reduced pressure. The resulting residue was purified by silica gel column chromatography (hexane:ethyl acetate=4:1→3:2) to afford the title compound as a colorless oil (157 mg).

$^1$H NMR (300 MHz, CDCl$_3$) δ ppm 1.31 (s, 9 H), 2.16 (s, 3 H), 3.66 (s, 2 H), 7.11-7.16 (m, 2 H), 7.33-7.38 (m, 2 H).

MS ESI/APCI Dual posi: 191[M+H]$^+$.

The compounds of Reference Examples 12-2 and 12-3 were obtained by using the corresponding Grignard reagents in accordance with the process of Reference Example 12-1 (3).

Reference Example 12-2

$^1$H NMR (300 MHz, CDCl$_3$) δ ppm 1.03 (t, J=7.3 Hz, 3 H), 1.31 (s, 9 H), 2.48 (q, J=7.3 Hz, 2 H), 3.65 (s, 2 H), 7.11-7.16 (m, 2 H), 7.31-7.37 (m, 2 H).

Reference Example 12-3

$^1$H NMR (300 MHz, CDCl$_3$) δ ppm 0.88 (t, J=7.4 Hz, 3 H), 1.31 (s, 9 H), 1.55-1.63 (m, 2 H), 2.43 (t, J=7.4 Hz, 2 H), 3.64 (s, 2 H), 7.10-7.17 (m, 2 H), 7.31-7.37 (m, 2 H).

MS ESI/APCI Dual posi: 219[M+H]$^+$.

The structures of the compounds of Reference Examples 12-2 and 12-3 are shown in Table 6-1.

TABLE 6-1

| Reference Ex. | Structure |
|---|---|
| 12-2 | ![structure] |
| 12-3 | ![structure] |

Reference Example 13-1

1-(1-Bromoethyl)-4-tert-butylbenzene

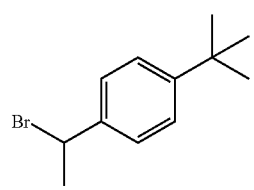

[Formula 29]

(1) Methylmagnesium bromide (3 mol/L diethyl ether solution, 5 mL, 15.0 mmol) was added dropwise to a solution of 4-tert-butylbenzaldehyde (1.62 g, 10.0 mmol) in diethyl ether (20 mL) while cooling in ice, and the mixture was stirred at the same temperature for 30 min. Aqueous ammonium chloride solution was added thereto and the mixture was extracted with diethyl ether. The organic layer was washed with brine and dried over anhydrous magnesium sulfate. The desiccant was filtered off and then the filtrate was concentrated under reduced pressure to afford 1-(4-tert-butylphenyl)ethanol as a colorless solid (1.84 g).

(2) A solution of 1-(4-tert-butylphenyl)ethanol obtained (934 mg, 5.24 mmol) in diethyl ether (10 mL) was cooled in ice under a nitrogen atmosphere, phosphorus tribromide (852 µL, 9.07 mmol) was added dropwise thereto, and the mixture was stirred at the same temperature for 2 hr. Aqueous ammonium chloride solution was added thereto and the mixture was extracted with diethyl ether. The organic layer was washed with brine and dried over anhydrous magnesium sulfate. The desiccant was filtered off and then the filtrate was concentrated under reduced pressure to afford the title compound as a pale yellow oil (1.19 g).

$^1$H NMR (300 MHz, CDCl$_3$) δ ppm 1.31 (s, 9 H), 2.05 (d, J=7.0 Hz, 3 H), 5.23 (q, J=7.0 Hz, 1 H), 7.37 (s, 4 H).

The compounds of Reference Examples 13-2 to 13-4 were obtained by using the compound synthesized in Reference Example 9-1 or the corresponding Grignard reagents in accordance with the process of Reference Example 13-1.

Reference Example 13-2

$^1$H NMR (300 MHz, CDCl$_3$) δ ppm 1.36 (s, 9 H), 2.05 (d, J=7.0 Hz, 3 H), 5.21 (q, J=7.0 Hz, 1 H), 7.31-7.36 (m, 1 H), 7.68-7.74 (m, 1 H), 8.57-8.60 (m, 1 H).

Reference Example 13-3

$^1$H NMR (300 MHz, CDCl$_3$) δ ppm 1.01 (t, J=7.2 Hz, 3 H), 1.31 (s, 9 H), 2.08-2.38 (m, 2 H), 4.85-4.94 (m, 1 H), 7.28-7.39 (m, 4 H).

Reference Example 13-4

$^1$H NMR (300 MHz, CDCl$_3$) δ ppm 0.91-0.98 (m, 3 H), 1.31 (s, 9 H), 1.34-1.60 (m, 2 H), 2.03-2.35 (m, 2 H), 4.95-5.02 (m, 1 H), 7.30-7.37 (m, 4 H). The structures of the compounds of Reference Examples 13-2 to 13-4 are shown in Table 7-1.

TABLE 7-1

| Reference Ex. | Structure |
|---|---|
| 13-2 | ![structure] |
| 13-3 | ![structure] |
| 13-4 | ![structure] |

Reference Example 14-1

2-Bromo-1-(4-tert-butylphenyl)ethanone

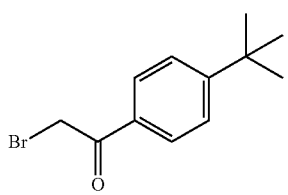

[Formula 30]

(1) Manganese dioxide (17.4 g, 200 mmol) was added to a solution of the compound obtained in Reference Example 13-1(1) (3.57 g, 20.0 mmol) in chloroform (67 mL), and the mixture was heated to an external temperature of 65° C. and stirred for 1 hr. After cooling, the mixture was filtered through Celite (registered trademark) and the filtrate was concentrated under reduced pressure. The resulting residue was purified by silica gel column chromatography (hexane only→hexane:ethyl acetate=9:1) to afford 1-(4-tert-butylphenyl)ethanone as a pale yellow oil (3.31 g).

(2) Pyrrolidone trihydrobromide (3.27 g, 10.0 mmol) was added to a solution of 1-(4-tert-butylphenyl)ethanone obtained (1.61 g, 9.13 mmol) in tetrahydrofuran (30 mL) and the mixture was heated to an external temperature of 60° C. and stirred for 30 min. After cooling, water was added thereto and the mixture was extracted with ethyl acetate. The organic layer was washed with brine and dried over anhydrous magnesium sulfate and then the desiccant was filtered off, followed by concentration under reduced pressure. The resulting residue was purified by silica gel column chromatography (hexane only→hexane:ethyl acetate=9:1) to afford the title compound as a colorless oil (472 mg).

$^1$ H NMR (300 MHz, CDCl$_3$) δ ppm 1.35 (s, 9 H), 4.44 (s, 2 H), 7.48-7.53 (m, 2 H), 7.91-7.96 (m, 2 H).
MS ESI/APCI Dual posi: 255, 257[M+H]$^+$.

Reference Example 15-1

2-Fluoro-4-(3-phenylpropoxy)aniline

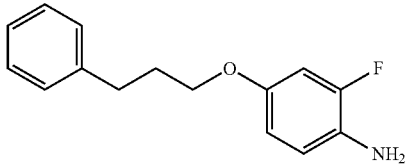

[Formula 31]

(1) Potassium carbonate (20.7 g, 150 mmol) and 3-phenylpropyl bromide (18.2 mL, 120 mmol) were added to a solution of 3-fluoro-4-nitrophenol (15.7 g, 100 mmol) in N,N-dimethylformamide (200 mL) at room temperature and the mixture was stirred at 85° C. for 6 hr. After cooling to room temperature, water was added to the reaction mixture and the mixture was extracted three times with ethyl acetate. The organic layer was washed with 1 mol/L hydrochloric acid and brine and dried over anhydrous sodium sulfate and then the desiccant was filtered off, followed by concentration under reduced pressure. The resulting residue was dried under reduced pressure to afford 2-fluoro-1-nitro-4-(3-phenylpropoxy)benzene as a brown oil (33.2 g).

(2) To a solution of 2-fluoro-1-nitro-4-(3-phenylpropoxy) benzene obtained (33.2 g) in ethanol (150 mL) was added 10% palladium activated carbon (2.75 g) at room temperature, and the mixture was stirred overnight under a hydrogen atmosphere. The reaction mixture was filtered through Celite (registered trademark) and the filtrate was concentrated under reduced pressure. The resulting residue was purified by silica gel column chromatography (hexane:ethyl acetate=9:1) to afford the title compound as a brown oil (9.64 g).

$^1$ H NMR (300 MHz, CDCl$_3$) δ ppm 1.95-2.14 (m, 2 H), 2.74-2.83 (m, 2 H), 3.42 (br. s., 2 H), 3.87 (t, J=6.3 Hz, 2 H), 6.48-6.77 (m, 3 H), 7.12-7.34 (m, 5 H).

The compounds of Reference Examples 15-2 to 15-20 were obtained by using the corresponding phenols and alkyl halides or alkyl tosylates in accordance with the process of Reference Example 15-1.

It is to be noted that the aforementioned corresponding phenols and alkyl halides and alkyl tosylates are either available by the methods of Reference Examples as shown herein or methods described in publications or commercially available.

Reference Example 15-2

$^1$ H NMR (300 MHz, CDCl$_3$) δ ppm 0.85-0.96 (m, 3 H), 1.24-1.50 (m, 6 H), 1.67-1.80 (m, 2 H), 3.42 (br. s., 2 H), 3.86 (dt, J=1.2, 6.6 Hz, 2 H), 6.48-6.76 (m, 3 H).

Reference Example 15-3

$^1$ H NMR (300 MHz, CDCl$_3$) δ ppm 1.75-1.82 (m, 4 H), 2.60-2.72 (m, 2 H), 3.82-3.92 (m, 2 H), 6.48-6.55 (m, 1 H), 6.56-6.74 (m, 2 H), 7.14-7.22 (m, 3 H), 7.23-7.32 (m, 2 H).
MS ESI/APCI Dual posi: 260[M+H]$^+$.

Reference Example 15-4

$^1$ H NMR (300 MHz, CDCl$_3$) δ ppm 2.00-2.13 (m, 2 H), 2.74-2.84 (m, 2 H), 3.89 (t, J=6.4 Hz, 2 H), 6.60-6.77 (m, 4 H), 7.15-7.32 (m, 5 H).
MS ESI/APCI Dual posi: 228[M+H]$^+$.

Reference Example 15-5

$^1$ H NMR (300 MHz, CDCl$_3$) δ ppm 4.23-4.35 (m, 4 H), 6.54-6.63 (m, 1 H), 6.64-6.79 (m, 2 H), 7.12 (dd, J=8.4, 2.3 Hz, 1 H), 7.17-7.25 (m, 2 H), 7.35-7.45 (m, 1 H).
MS ESI/APCI Dual posi: 316[M+H]$^+$.

Reference Example 15-6

$^1$ H NMR (300 MHz, CDCl$_3$) δ ppm 2.01-2.14 (m, 2 H), 2.74-2.85 (m, 2 H), 3.92 (t, J=6.3 Hz, 2 H), 6.47 (dd, J=8.9, 0.8 Hz, 1 H), 7.09 (dd, J=8.9, 2.9 Hz, 1 H), 7.15-7.25 (m, 3 H), 7.26-7.33 (m, 2 H), 7.77 (d, J=2.9 Hz, 1 H).
MS ESI/APCI Dual posi: 229[M+H]$^+$.

Reference Example 15-7

$^1$ H NMR (300 MHz, CDCl$_3$) δ ppm 0.77-0.98 (m, 3 H), 1.19-1.50 (m, 10 H), 1.65-1.84 (m, 2 H), 3.86 (t, J=6.6 Hz, 2 H), 6.50-6.56 (m, 1 H), 6.62 (dd, J=12.5, 2.7 Hz, 1 H), 6.70 (dd, J=10.0, 8.7 Hz, 1 H).
MS ESI/APCI Dual posi: 240[M+H]$^+$.

Reference Example 15-8

$^1$ H NMR (200 MHz, CDCl$_3$) δ ppm 3.61 (br. s., 2 H), 3.83 (s, 3 H), 6.40-6.70 (m, 3 H).
MS ESI/APCI Dual posi: 142[M+H]$^+$.

Reference Example 15-9

$^1$ H NMR (300 MHz, CDCl$_3$) δ ppm 3.55 (br. s., 2 H), 3.85 (s, 3 H), 6.32-6.52 (m, 2 H).

Reference Example 15-10

$^1$ H NMR (300 MHz, CDCl$_3$) δ ppm 0.84-1.05 (m, 2 H), 1.09-1.34 (m, 3 H), 1.40-1.53 (m, 1 H), 1.57-1.81 (m, 7 H), 3.41 (br. s., 2 H), 3.90 (t, J=6.7 Hz, 2 H), 6.48-6.76 (m, 3 H).
MS ESI/APCI Dual posi: 238[M+H]$^+$.

Reference Example 15-11

$^1$ H NMR (300 MHz, CDCl$_3$) δ ppm 1.44 (t, J=7.0 Hz, 3 H), 4.03 (q, J=7.0 Hz, 2 H), 6.44-6.66 (m, 3 H).
MS ESI/APCI Dual posi: 156[M+H]$^+$.

Reference Example 15-12

$^1$H NMR (300 MHz, CDCl$_3$) δ ppm 1.05 (t, J=7.4 Hz, 3 H), 1.77-1.92 (m, 2 H), 3.92 (t, J=6.5 Hz, 2 H), 6.43-6.66 (m, 3 H).
MS ESI/APCI Dual posi: 170[M+H]$^+$.

Reference Example 15-13

$^1$H NMR (300 MHz, CDCl$_3$) δ ppm 1.36 (d, J=6.1 Hz, 6 H), 4.49 (m, 1 H), 6.38-6.70 (m, 3 H).
MS ESI/APCI Dual posi: 170[M+H]$^+$.

Reference Example 15-14

$^1$H NMR (300 MHz, CDCl$_3$) δ ppm 3.40 (br. s., 2 H), 3.73 (s, 3 H), 6.44-6.80 (m, 3 H).
MS ESI/APCI Dual posi: 142[M+H]$^+$.

Reference Example 15-15

$^1$H NMR (300 MHz, CDCl$_3$) δ ppm 1.40-1.85 (m, 6 H), 2.58-2.68 (m, 2 H), 3.86 (t, J=6.5 Hz, 2 H), 6.49-6.54 (m, 1 H), 6.61 (dd, J=12.6, 2.6 Hz, 1 H), 6.70 (dd, J=10.1, 8.6 Hz, 1 H), 7.14-7.32 (m, 5 H).
MS ESI/APCI Dual posi: 274[M+H]$^+$.

Reference Example 15-16

$^1$H NMR (300 MHz, CDCl$_3$) δ ppm 0.80-1.00 (m, 2 H), 1.06-1.39 (m, 6 H), 1.59-1.82 (m, 7 H), 3.84 (t, J=6.7 Hz, 2 H), 6.50-6.55 (m, 1 H), 6.61 (dd, J=12.6, 2.6 Hz, 1 H), 6.70 (dd, J=10.1, 8.6 Hz, 1 H).
MS ESI/APCI Dual posi: 252[M+H]$^+$.

Reference Example 15-17

$^1$H NMR (300 MHz, CDCl$_3$) δ ppm 0.84-1.00 (m, 3 H), 1.29-1.49 (m, 4 H), 1.67-1.81 (m, 2 H), 3.41 (br. s., 2 H), 3.86 (t, J=6.5 Hz, 2 H), 6.48-6.76 (m, 3 H).
MS ESI/APCI Dual posi: 198[M+H]$^+$.

Reference Example 15-18

$^1$H NMR (300 MHz, CDCl$_3$) δ ppm 1.24-1.45 (m, 2 H), 1.48-1.90 (m, 5 H), 3.40 (dt, J=11.9, 2.3 Hz, 3 H), 3.85-4.04 (m, 3 H), 6.50-6.56 (m, 1 H), 6.61 (dd, J=12.5, 2.7 Hz, 1 H), 6.71 (dd, J=10.0, 8.8 Hz, 1 H).
MS ESI/APCI Dual posi: 240[M+H]$^+$.

Reference Example 15-19

$^1$H NMR (300 MHz, CDCl$_3$) δ ppm 1.38-1.48 (m, 3 H), 2.23-2.38 (m, 2 H), 3.03 (q, J=7.5 Hz, 2 H), 3.12-3.22 (m, 2 H), 4.02 (t, J=5.8 Hz, 2 H), 6.49-6.55 (m, 1 H), 6.61 (dd, J=12.4, 2.7 Hz, 1 H), 6.72 (dd, J=9.8, 8.9 Hz, 1 H).

Reference Example 15-20

$^1$H NMR (300 MHz, CDCl$_3$) δ ppm 2.23-2.38 (m, 2 H), 2.95 (s, 3 H), 3.19-3.28 (m, 2 H), 4.02 (t, J=5.8 Hz, 2 H), 6.50-6.55 (m, 1 H), 6.61 (dd, J=12.2, 2.7 Hz, 1 H), 6.71 (dd, J=10.0, 8.7 Hz, 1 H).
MS ESI/APCI Dual posi: 248[M+H]$^+$.

The structures of the compounds of Reference Examples 15-2 to 15-20 are shown in Tables 8-1 to 8-3.

TABLE 8-1

| Reference Ex. | Structure |
|---|---|
| 15-2 | 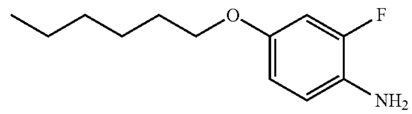 |
| 15-3 | 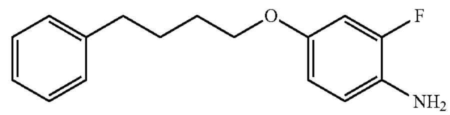 [SMILES: Nc1ccc(OCCCCc2ccccc2)cc1F] |
| 15-4 | 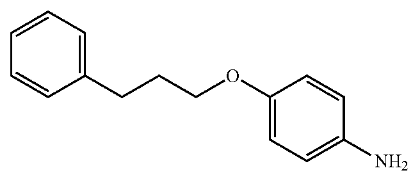 [SMILES: Nc1ccc(OCCCc2ccccc2)cc1] |
| 15-5 | 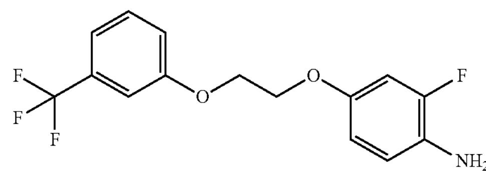 [SMILES: Nc1ccc(OCCOc2cccc(C(F)(F)F)c2)cc1F] |
| 15-6 | 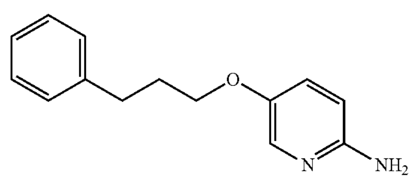 [SMILES: Nc1ccc(OCCCc2ccccc2)cn1] |
| 15-7 | 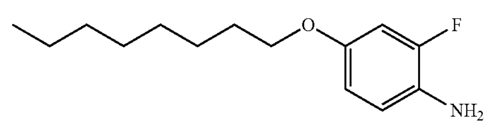 [SMILES: CCCCCCCCOc1ccc(N)c(F)c1] |
| 15-8 | 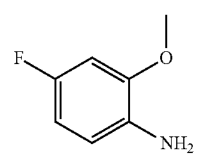 |
| 15-9 | 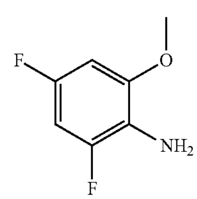 |
| 15-10 | 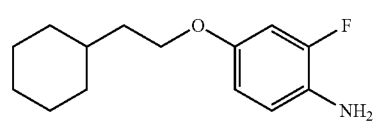 [SMILES: Nc1ccc(OCCC2CCCCC2)cc1F] |
| 15-11 | 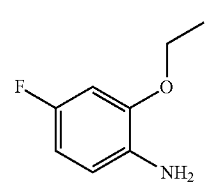 |

TABLE 8-1-continued

| Reference Ex. | Structure |
|---|---|
| 15-12 | 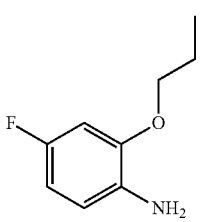 |
| 15-13 | 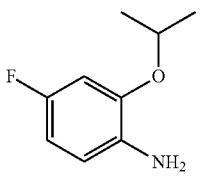 |
| 15-14 | 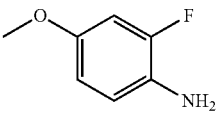 |
| 15-15 | 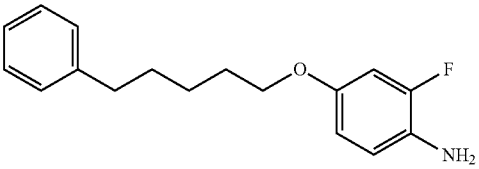 [SMILES: Nc1ccc(OCCCCCc2ccccc2)cc1F] |

TABLE 8-2

| Reference Ex. | Structure |
|---|---|
| 15-16 | 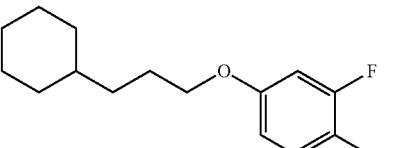 |
| 15-17 | 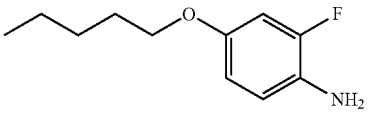 |

TABLE 8-3

| Reference Ex. | Structure |
|---|---|
| 15-18 | 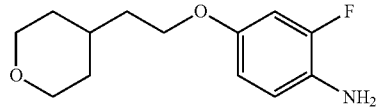 [SMILES: Nc1ccc(OCCC2CCOCC2)cc1F] |

TABLE 8-3-continued

| Reference Ex. | Structure |
|---|---|
| 15-19 | 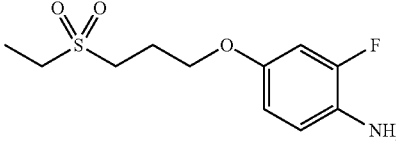 |
| 15-20 | 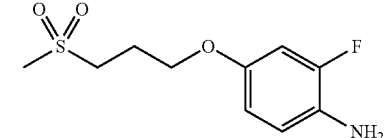 |

Reference Example 16-1

2-(Benzyloxy)-4-fluoroaniline

[Formula 32]

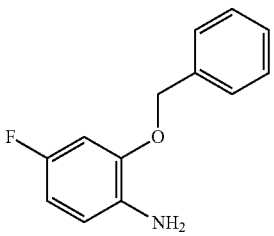

(1) Potassium carbonate (2.07 g, 15.0 mmol) and benzyl bromide (1.43 mL, 12.0 mmol) were added to a solution of 5-fluoro-2-nitrophenol (1.57 g, 10.0 mmol) in N,N-dimethylformamide (30 mL) at room temperature and the mixture was stirred for 2 hr. Water was added to the reaction mixture and the mixture was extracted three times with ethyl acetate. The organic layer was washed with 1 mol/L hydrochloric acid and brine and dried over anhydrous magnesium sulfate and then the desiccant was filtered off, followed by concentration under reduced pressure. The resulting residue was dried under reduced pressure to afford 2-(benzyloxy)-4-fluoro-1-nitrobenzene as a pale yellow oil (2.76 g).

(2) To an ethanol (25 mL)-water (25 mL) mixture containing 2-(benzyloxy)-4-fluoro-1-nitrobenzene obtained were added iron (2.79 g, 50.0 mmol) and ammonium chloride (535 mg, 10.0 mmol) at room temperature, and the mixture was stirred at 100° C. for 1 hr. After cooling to room temperature, the reaction mixture was filtered through Celite (registered trademark) and the filtrate was concentrated under reduced pressure. Saturated aqueous sodium hydrogen carbonate solution was added to the resulting residue, and the mixture was extracted three times with ethyl acetate. The organic layer was washed with brine and dried over anhydrous magnesium sulfate and then the desiccant was filtered off, followed by concentration under reduced pressure. The resulting residue was purified by silica gel column chromatography (hexane:ethyl acetate=9:1) to afford the title compound as a brownish red oil (1.26 g).

$^1$H NMR (300 MHz, CDCl$_3$) δ ppm 5.05 (s, 2 H), 6.47-6.57 (m, 1 H), 6.58-6.72 (m, 2 H), 7.29-7.48 (m, 5 H).

MS ESI/APCI Dual posi: 218[M+H]$^+$.

Reference Example 17-1

4-(Benzyloxy)-2-fluoroaniline

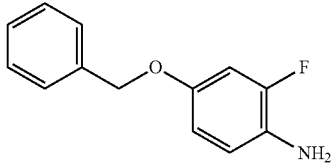

[Formula 33]

(1) In N,N-dimethylformamide (70 mL), 3-fluoro-4-nitrophenol was dissolved, and benzyl bromide (6.53 g, 38.2 mmol) and potassium carbonate (6.59 g, 47.7 mmol) were added thereto and the mixture was stirred at room temperature for 18 hr. Water (100 mL) was added to the reaction mixture and the mixture was extracted three times with ethyl acetate (100 mL). The combined organic layer was washed with 1 mol/L hydrochloric acid and brine. The mixture was dried over anhydrous magnesium sulfate and filtered, and the solvent was distilled off under reduced pressure. The resulting solid was washed with hexane to afford 4-(benzyloxy)-2-fluoro-1-nitrobenzene as a yellow solid (7.47 g).

(2) In methanol (120 mL), 4-(benzyloxy)-2-fluoro-1-nitrobenzene obtained (6.00 g) was dissolved, platinum carbon (0.600 g) was added thereto, and the mixture was stirred under a hydrogen atmosphere at room temperature for 5 hr. The reaction mixture was filtered through Celite (registered trademark), followed by washing with methanol. Thereafter, the solvent was distilled off from the filtrate under reduced pressure. The residue was purified by silica gel column chromatography (hexane only→hexane:ethyl acetate=7:3) to afford the title compound as a yellow oil (4.43 g).

$^1$H NMR (300 MHz, CDCl$_3$) δ ppm 3.37 (br. s, 2 H), 4.97 (s, 2 H), 6.46-6.84 (m, 3 H), 7.16-7.51 (m, 5 H).

Reference Example 18-1

N-(2,4-Dimethoxybenzyl)-4-fluoroaniline

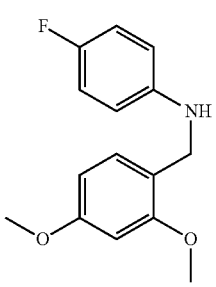

[Formula 34]

To a solution of 4-fluoroaniline (3.85 g, 34.7 mmol) in tetrahydrofuran (100 mL) were added 2,4-dimethoxybenzaldehyde (6.34 g, 38.2 mmol) and acetic acid (11.9 mL, 208 mmol). After stirring at room temperature for 15 min, sodium triacetoxyborohydride (22.1 g, 104 mmol) was added thereto and the mixture was stirred at the same temperature for 15 hr. The mixture was concentrated under reduced pressure, diluted with ethyl acetate, and then washed with 2 mol/L aqueous sodium hydroxide solution and brine successively. The organic layer was dried over anhydrous sodium sulfate and then the desiccant was filtered off, followed by concentration under reduced pressure. The resulting residue was purified by silica gel column chromatography (hexane:ethyl acetate=5:1) to afford the title compound as a pale yellow solid (7.37 g).

$^1$H NMR (300 MHz, CDCl$_3$) δ ppm 3.79 (s, 3 H), 3.83 (s, 3 H), 4.20 (s, 2 H), 6.40-6.48 (m, 2 H), 6.55-6.60 (m, 2 H), 6.83-6.90 (m, 2 H), 7.17 (d, J=8.2 Hz, 1 H).

The compounds of Reference Examples 18-2 to 18-9 were obtained by using either the compounds obtained in Reference Example 15 or the corresponding commercially available compounds as well as the corresponding aldehydes in accordance with the process of Reference Example 18-1.

Reference Example 18-2

$^1$H NMR (300 MHz, CDCl$_3$) δ ppm 1.99-2.11 (m, 2 H), 2.73-2.82 (m, 2 H), 3.79 (s, 3 H), 3.81-3.89 (m, 5 H), 4.03 (br. s., 1 H), 4.23 (s, 2 H), 6.38-6.73 (m, 5 H), 7.14-7.22 (m, 4 H), 7.25-7.32 (m, 2 H).

Reference Example 18-3

$^1$H NMR (300 MHz, CDCl$_3$) δ ppm 0.84-0.96 (m, 3 H), 1.26-1.48 (m, 6 H), 1.64-1.81 (m, 2 H), 3.74-3.94 (m, 8 H), 4.01 (br. s., 1 H), 4.23 (s, 2 H), 6.32-6.78 (m, 5 H), 7.17 (d, J=8.2 Hz, 1 H).

Reference Example 18-4

$^1$H NMR (300 MHz, CDCl$_3$) δ ppm 1.70-1.84 (m, 4 H), 2.62-2.73 (m, 2 H), 3.79 (s, 3 H), 3.83 (s, 3 H), 3.84-3.89 (m, 2 H), 4.23 (s, 2 H), 6.42 (dd, J=8.2, 2.3 Hz, 1 H), 6.47 (d, J=2.3 Hz, 1 H), 6.50-6.71 (m, 3 H), 7.13-7.32 (m, 6 H).

Reference Example 18-5

$^1$H NMR (300 MHz, CDCl$_3$) δ ppm 3.79 (s, 3 H), 3.83 (s, 3 H), 4.22 (s, 2 H), 6.42 (dd, J=8.3, 2.3 Hz, 1 H), 6.45-6.67 (m, 4 H), 7.17 (d, J=8.3 Hz, 1 H).
MS ESI/APCI Dual nega: 276[M−H]$^-$.

Reference Example 18-6

$^1$H NMR (300 MHz, CDCl$_3$) δ ppm 3.77 (s, 6 H), 3.82 (s, 3 H), 4.27 (s, 1 H), 6.28-6.45 (m, 4 H), 7.05 (d, J=8.2 Hz, 1 H).

Reference Example 18-7

$^1$H NMR (300 MHz, CDCl$_3$) δ ppm 0.84-1.06 (m, 2 H), 1.07-1.34 (m, 3 H), 1.36-1.87 (m, 8 H), 3.69-3.96 (m, 8 H), 4.01 (br. s., 1 H), 4.23 (s, 2 H), 6.34-6.76 (m, 5 H), 7.17 (d, J=8.2 Hz, 1 H).

Reference Example 18-8

$^1$H NMR (300 MHz, CDCl$_3$) δ ppm 3.77-3.81 (m, 3 H), 3.82-3.87 (m, 3 H), 4.29 (s, 2 H), 4.53 (s, 2 H), 6.36-6.50 (m, 2 H), 6.63-6.76 (m, 1 H), 6.89-7.04 (m, 2 H), 7.17 (d, J=8.2 Hz, 1 H).
LCMS retention time: 1.33 min. (Condition 4-1)
MS (ESI posi) m/z: 292[M+H]$^+$.

Reference Example 18-9

$^1$H NMR (300 MHz, CDCl$_3$) δ ppm 3.80 (s, 3 H), 4.23 (s, 2 H), 6.44-6.51 (m, 1 H), 6.53-6.63 (m, 2 H), 6.88 (d, J=8.7

Hz, 2 H), 7.24-7.33 (m, 2 H). The structures of the compounds of Reference Examples 18-2 to 18-9 are shown in Tables 9-1 and 9-2.

TABLE 9-1

| Reference Ex. | Structure |
|---|---|
| 18-2 | 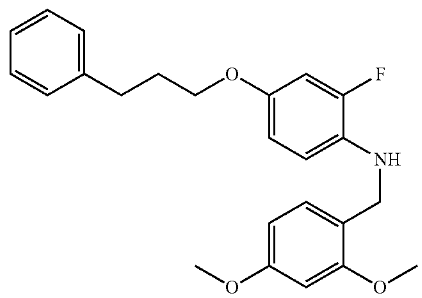 [SMILES: COc1ccc(CNc2ccc(OCCCc3ccccc3)cc2F)c(OC)c1] |
| 18-3 | 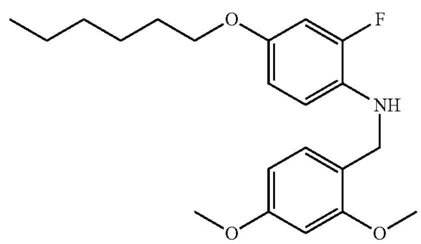 [SMILES: CCCCCCOc1ccc(NCc2ccc(OC)cc2OC)c(F)c1] |
| 18-4 | 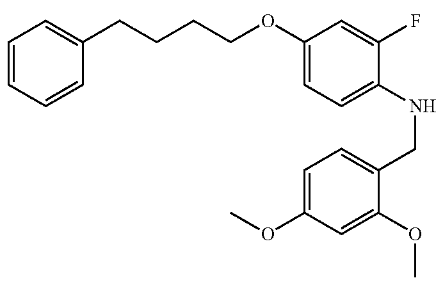 [SMILES: COc1ccc(CNc2ccc(OCCCCc3ccccc3)cc2F)c(OC)c1] |
| 18-5 | 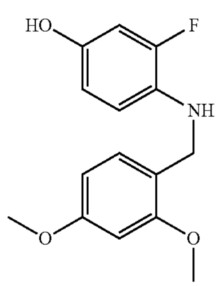 |
| 18-6 | 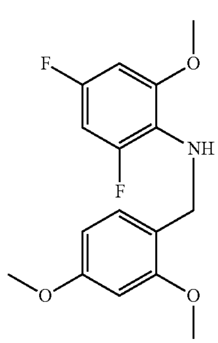 |

TABLE 9-1-continued

| Reference Ex. | Structure |
|---|---|
| 18-7 | 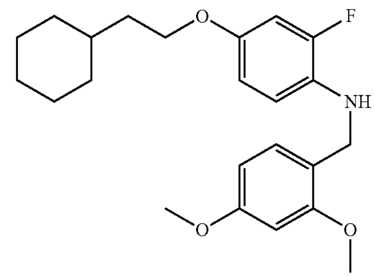 [SMILES: COc1ccc(CNc2ccc(OCCC3CCCCC3)cc2F)c(OC)c1] |

TABLE 9-2

| Reference Ex. | Structure |
|---|---|
| 18-8 | 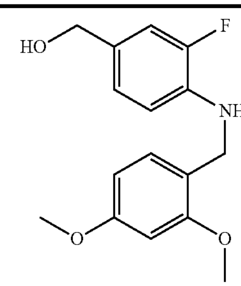 |
| 18-9 | 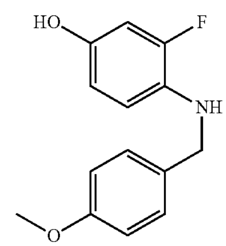 [SMILES: COc1ccc(CNc2ccc(O)cc2F)cc1] |

Reference Example 19-1

2-(Difluoromethoxy)-4-fluoroaniline

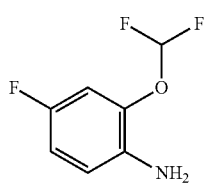

[Formula 35]

(1) Potassium carbonate (2.42 g, 17.5 mmol) was added to a solution of 5-fluoro-2-nitrophenol (785 mg, 5.00 mmol) in N,N-dimethylformamide (10 mL), and the mixture was stirred at room temperature for 20 min. Chlorodifluoroacetic acid methyl ester (1.33 mL, 12.5 mmol) was added dropwise to the reaction mixture, and the mixture was stirred at room temperature for 30 min and then stirred at an external temperature of 90° C. for 3 hr. After cooling, water was added thereto and the mixture was extracted with ethyl acetate. The organic layer was washed with water and brine and dried over anhydrous magnesium sulfate and then the desiccant was filtered off, followed by concentration under reduced pressure. The resulting residue was purified by silica gel column chromatography (hexane:ethyl acetate=9:1→4:1) to afford 2-(difluoromethoxy)-4-fluoro-1-nitrobenzene as a pale yellow oil (745 mg).

(2) To a solution of 2-(difluoromethoxy)-4-fluoro-1-nitrobenzene obtained (745 mg, 3.60 mmol) in ethanol (15 mL) was added 10% palladium activated carbon (75 mg), and the mixture was stirred under a hydrogen atmosphere at room temperature for 15 hr. The mixture was filtered through Celite (registered trademark) and the filtrate was concentrated under reduced pressure to afford the title compound as a pale orange oil (561 mg).

$^1$H NMR (300 MHz, CDCl$_3$) δ ppm 3.60-3.83 (m, 2 H), 6.47 (t, J=73.5 Hz, 1 H), 6.68-6.86 (m, 3 H).

MS ESI/APCI Dual posi: 178[M+H]$^+$.

Reference Example 20-1

4-[(1E)-3-Cyclopentylprop-1-en-1-yl]-2-fluoroaniline

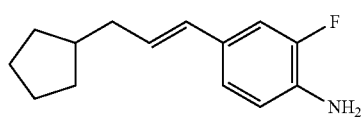

[Formula 36]

1,4-Dioxane (5 mL) and water (1.2 mL) were added to 4-bromo-2-fluoroaniline (285 mg, 1.50 mmol), trans-3-(cyclopentyl)propenylboronic acid pinacol ester (425 mg, 1.80 mmol), tris(dibenzylidene acetone)dipalladium (137 mg, 0.15 mmol), tri-2-furylphosphine (210 mg, 0.90 mmol) and cesium carbonate (976 mg, 3.00 mmol). The mixture was heated to an external temperature of 100° C. and stirred for 6 hr, under a nitrogen atmosphere. After cooling, the mixture was diluted with ethyl acetate and washed with brine. The organic layer was dried over anhydrous magnesium sulfate and then the desiccant was filtered off, followed by concentration under reduced pressure. The resulting residue was purified by silica gel column chromatography (hexane only→hexane:ethyl acetate=9:1) to afford the title compound as a pale yellow oil (302 mg).

$^1$H NMR (300 MHz, CDCl$_3$) δ ppm 1.10-1.24 (m, 2 H), 1.44-1.67 (m, 4 H), 1.69-1.82 (m, 2 H), 1.83-2.00 (m, 1 H), 2.12-2.22 (m, 2 H), 3.68 (br. s., 2 H), 5.96-6.09 (m, 1 H), 6.17-6.28 (m, 1 H), 6.64-6.74 (m, 1 H), 6.86-6.94 (m, 1 H), 6.96-7.05 (m, 1 H).

MS ESI/APCI Dual posi: 220[M+H]$^+$.

The compounds of Reference Examples 20-2 to 20-4 were obtained by using the corresponding commercially available compounds in accordance with the process of Reference Example 20-1.

Reference Example 20-2

$^1$H NMR (300 MHz, CDCl$_3$) δ ppm 0.86-0.94 (m, 3 H), 1.24-1.50 (m, 6 H), 2.10-2.21 (m, 2 H), 3.67 (br. s., 2 H), 5.97-6.08 (m, 1 H), 6.18-6.27 (m, 1 H), 6.65-6.73 (m, 1 H), 6.88-6.93 (m, 1 H), 6.97-7.04 (m, 1 H).

MS ESI/APCI Dual posi: 208[M+H]$^+$.

Reference Example 20-3

$^1$H NMR (300 MHz, CDCl$_3$) δ ppm 1.72-1.84 (m, 2 H), 2.17-2.26 (m, 2 H), 2.61-2.70 (m, 2 H), 3.69 (br. s., 2 H), 5.97-6.09 (m, 1 H), 6.20-6.30 (m, 1 H), 6.66-6.73 (m, 1 H), 6.88-6.93 (m, 1 H), 6.97-7.04 (m, 1 H).

MS ESI/APCI Dual posi: 256[M+H]$^+$.

Reference Example 20-4

$^1$H NMR (300 MHz, CDCl$_3$) δ ppm 0.84-0.95 (m, 3 H), 1.28-1.38 (m, 4 H), 1.43-1.53 (m, 2 H), 2.18-2.27 (m, 2 H), 6.31-6.39 (m, 1 H), 6.48-6.62 (m, 1 H), 7.90-7.97 (m, 2 H).

LCMS retention time: 1.81 min. (Condition 1-1-1)

MS (ESI posi) m/z: 192[M+H]$^+$.

The structures of the compounds of Reference Examples 20-2 to 20-4 are shown in Table 10-1.

TABLE 10-1

| Reference Ex. | Structure |
|---|---|
| 20-2 | ![structure] |
| 20-3 | ![structure] |
| 20-4 | ![structure] |

Reference Example 21-1

2-Ethyl-4-fluoroaniline

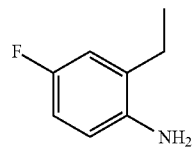

[Formula 37]

(1) Tetrakis(triphenylphosphine)palladium (289 mg, 0.250 mmol), potassium carbonate (829 mg, 6.00 mmol), water (4 mL) and 2,4,6-trivinylcyclotriboroxane-pyridine complex (722 mg, 3.00 mmol) were successively added to a solution of 2-bromo-4-fluoroaniline (950 mg, 5.00 mmol) in 1,2-dimethoxyethane (10 mL) under an argon atmosphere. The mixture was heated to an external temperature of 105° C. and stirred for 7 hr. The mixture was diluted with ethyl acetate, washed with brine and dried over anhydrous sodium sulfate. Thereafter, the desiccant was filtered off, followed by concentration under reduced pressure. The resulting residue was purified by silica gel column chromatography (hexane:ethyl acetate=9:1→2:1) to afford 2-ethenyl-4-fluoroaniline as a reddish brown oil (458 mg).

(2) To a solution of 2-ethenyl-4-fluoroaniline obtained (458 mg) in ethyl acetate (10 mL) and ethanol (10 mL) was added 10% palladium activated carbon (46 mg), and the mixture was stirred under a hydrogen atmosphere at room temperature for 4 hr. The mixture was filtered through Celite (registered trademark) and then the filtrate was concentrated under reduced pressure to afford the title compound as a reddish brown oil (516 mg).

$^1$H NMR (300 MHz, CDCl$_3$) δ ppm 1.25 (t, J=7.5 Hz, 3 H), 2.49 (q, J=7.5 Hz, 2 H), 3.48 (br. s., 2 H), 6.57-6.63 (m, 1 H), 6.69-6.83 (m, 2 H).

MS ESI/APCI Dual posi: 140[M+H]$^+$.

The compound of Reference Example 21-2 was obtained by using the corresponding boronic acid in accordance with the process of Reference Example 21-1.

Reference Example 21-2

$^1$H NMR (300 MHz, CDCl$_3$) δ ppm 1.01 (t, J=7.3 Hz, 3 H), 1.62-1.75 (m, 2 H), 2.54-2.61 (m, 2 H), 6.76-7.00 (m, 3 H).

MS ESI/APCI Dual posi: 154[M+H]$^+$.

The structure of the compound of Reference Example 21-2 is shown in Table 11-1.

TABLE 11-1

| Reference Ex. | Structure |
|---|---|
| 21-2 | 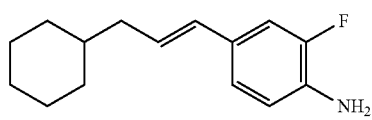 |

Reference Example 22-1

4-[(1E)-3-Cyclohexylprop-1-en-1-yl]-2-fluoroaniline

[Formula 38]

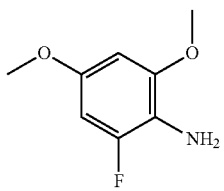

Toluene (5 mL) was added to 4-bromo-2-fluoroaniline (950 mg, 5.00 mmol), allylcyclohexane (1.15 mL, 7.50 mmol), palladium acetate (112 mg, 0.50 mmol), tris(2-methylphenyl)phosphine (457 mg, 1.50 mmol) and triethylamine (2.09 mL, 15.0 mmol), and the mixture was stirred, followed by heating to reflux for 10 hr. After cooling, ethyl acetate was added thereto, the mixture was filtered through Celite (registered trademark), and then the filtrate was concentrated under reduced pressure. The resulting residue was purified by silica gel column chromatography (hexane only→hexane:ethyl acetate=9:1) to afford the title compound as a pale yellow oil (805 mg).

$^1$H NMR (300 MHz, CDCl$_3$) δ ppm 0.82-1.02 (m, 2 H), 1.03-1.44 (m, 5 H), 1.58-1.80 (m, 4 H), 2.01-2.10 (m, 2 H), 3.67 (br. s., 2 H), 5.96-6.07 (m, 1 H), 6.16-6.24 (m, 1 H), 6.65-6.72 (m, 1 H), 6.87-6.93 (m, 1 H), 6.96-7.04 (m, 1 H).

MS ESI/APCI Dual posi: 234[M+H]$^+$.

Reference Example 23-1

2-[(1E)-Hept-1-en-1-yl]pyrimidin-5-amine

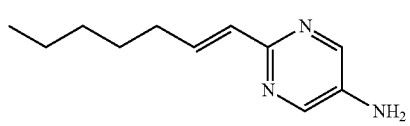

[Formula 39]

(1) Sodium iodide (846 mg, 5.64 mmol) and hydrogen iodide (40 μL) were successively added to an acetone solution of 2-chloro-5-nitropyrimidine (300 mg, 1.88 mmol) and the mixture was stirred at room temperature for 5 hr. An iron powder (525 mg, 9.40 mmol) and saturated aqueous ammonium chloride solution (200 μL) were added thereto at room temperature and the mixture was stirred under reflux for 1.5 hr. The reaction mixture was cooled to room temperature and filtered through Celite (registered trademark) and then the filtrate was concentrated under reduced pressure. The resulting residue was purified by silica gel column chromatography (hexane:ethyl acetate=9:1→3:2) to afford 2-iodopyrimidin-5-amine as a brown solid (180 mg).

(2) The same process as that of Reference Example 20-1 was performed using 2-iodopyrimidin-5-amine obtained (146 mg, 661 μmol) to afford the title compound as a yellow solid (180 mg).

$^1$H NMR (300 MHz, CDCl$_3$) δ ppm 0.84-0.94 (m, 3 H), 1.27-1.40 (m, 6 H), 2.20-2.31 (m, 2 H), 6.41-6.53 (m, 1 H), 6.82-6.94 (m, 1 H), 8.16 (s, 2 H).

LCMS retention time: 1.61 min. (Condition 1-1-1)
MS (ESI posi) m/z: 192[M+H]$^+$.

Reference Example 24-1

2-Fluoro-4,6-dimethoxyaniline

[Formula 40]

(1) Sodium methoxide (25% wt methanol solution) (259 mg, 1.20 mmol) was added to a methanol (5 mL) solution of the compound obtained in accordance with the process of Reference Example 15-1(1) (1,5-difluoro-3-methoxy-2-nitrobenzene) (189 mg, 1.00 mmol) at room temperature and the mixture was stirred overnight. The reaction mixture was concentrated under reduced pressure, water was added to the residue, and the mixture was extracted three times with ethyl acetate. The organic layer was washed with brine and dried over anhydrous sodium sulfate and then the desiccant was filtered off, followed by concentration under reduced pressure. The resulting residue was purified by silica gel column chromatography (hexane:ethyl acetate=9:1) to afford 1-fluoro-3,5-dimethoxy-2-nitrobenzene as a pale yellow powder (46.5 mg).

(2) The same process as that of Reference Example 15-1(2) was performed using 1-fluoro-3,5-dimethoxy-2-nitrobenzene obtained (51.4 mg, 0.256 mmol) to afford the title compound as a colorless oil (27.6 mg).

$^1$H NMR (300 MHz, CDCl$_3$) δ ppm 3.43 (br. s., 2 H), 3.74 (s, 3 H), 3.84 (s, 3 H), 6.21-6.32 (m, 2 H).

MS ESI/APCI Dual posi: 172[M+H]$^+$.

Reference Example 25-1

6-(3-Phenylpropoxy)pyridin-3-amine

[Formula 41]

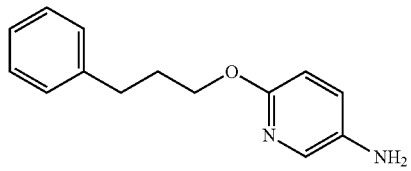

(1) Sodium hydride (99 mg, 4.14 mmol) was added to a solution of 3-phenyl-1-propanol (564 μL, 4.14 mmol) in N,N-dimethylformamide (15 mL) while cooling in ice, and the mixture was stirred for 30 min while cooling in ice. A solution of 2-fluoro-5-nitropyridine (500 mg, 3.45 mmol) in N,N-dimethylformamide (5 mL) was added thereto. The mixture was warmed to room temperature and stirred for 19 hr. Subsequently, sodium hydride (99 mg, 4.14 mmol) was added thereto and the mixture was stirred at room temperature for 2 hr. Thereafter, the mixture was heated to 85° C., stirred for 1.5 hr, and further stirred at room temperature for 2 hr. Water was added to the reaction mixture while cooling in ice, and the mixture was extracted with ethyl acetate. The organic layer was washed with 1 mol/L hydrochloric acid and dried over anhydrous magnesium sulfate. The desiccant was filtered off, followed by concentration under reduced pressure. The resulting residue was purified by silica gel column chromatography (hexane:ethyl acetate=19:1) to afford 5-nitro-2-(3-phenylpropoxy)pyridine as a brown solid (440 mg).

(2) The same process as that of Reference Example 15-1(2) was performed using 5-nitro-2-(3-phenylpropoxy)pyridine obtained (440 mg, 1.70 mmol) to afford the title compound as an orange oil (310 mg).

$^1$H NMR (300 MHz, CDCl$_3$) δ ppm 2.01-2.13 (m, 2 H), 2.74-2.82 (m, 2 H), 4.22 (t, J=6.5 Hz, 2 H), 6.60 (dd, J=8.7, 0.7 Hz, 1 H), 7.03 (dd, J=8.7, 3.0 Hz, 1 H), 7.14-7.32 (m, 5 H), 7.64 (dd, J=3.0, 0.7 Hz, 1 H).

MS ESI/APCI Dual posi: 229[M+H]$^+$.

Reference Example 26-1

8-Amino-4-methyl-2 H-1,4-benzoxazin-3(4 H)-one

[Formula 42]

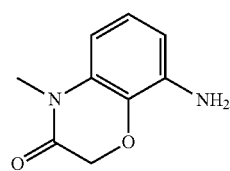

(1) A solution of 2,6-dinitrophenol (6.31 g, 27.4 mmol) in ethyl acetate (50 mL) was cooled to 0° C., 10% palladium activated carbon (250 mg) was added thereto, and the mixture was stirred under a hydrogen atmosphere for 5 hr. The reaction mixture was filtered through Celite (registered trademark) and the filtrate was concentrated under reduced pressure. The resulting residue was diluted with chloroform, anhydrous sodium sulfate was added thereto, and the mixture was stirred for 15 min. Anhydrous sodium sulfate was filtered off, followed by concentration under reduced pressure. The resulting residue was powdered with hexane and collected by filtration to afford 2-amino-6-nitrophenol as a brown amorphous substance (2.41 g).

(2) Sodium hydrogen carbonate (6.30 g, 75.0 mmol) and water (75 mL) were added to a solution of 2-amino-6-nitrophenol obtained (5.77 g, 37.5 mmol) in ethyl acetate (75 mL) while cooling in ice, and chloroacetic acid chloride (3.58 mL, 45.0 mmol) was added dropwise thereto. After stirring at room temperature for 1.5 hr, the reaction mixture was cooled in ice, saturated aqueous ammonium chloride solution was added thereto, and the mixture was extracted with ethyl acetate. The organic layer was washed with brine and dried over anhydrous sodium sulfate. The desiccant was filtered off, followed by concentration under reduced pressure. The resulting residue was purified by silica gel column chromatography (hexane:ethyl acetate=9:1→1:1) to afford 2-chloro-N-(2-hydroxy-3-nitrophenyl)acetamide as a pale yellow powder (5.70 g).

(3) Potassium carbonate (4.10 g, 29.7 mmol) was added to a solution of 2-chloro-N-(2-hydroxy-3-nitrophenyl)acetamide obtained (5.70 g, 24.7 mmol) in N,N-dimethylformamide (150 mL) while cooling in ice, and the mixture was stirred at room temperature for 5 hr. The mixture was diluted with ethyl acetate, washed with water and brine, and then dried over anhydrous sodium sulfate. The desiccant was filtered off, followed by concentration under reduced pressure. The resulting residue was powdered with chloroform and collected by filtration to afford 8-nitro-2 H-1,4-benzoxazin-3(4 H)-one as a pale orange powder (4.32 g).

(4) Sodium hydride (60%) (300 mg, 7.50 mmol) was added to a solution of 8-nitro-2 H-1,4-benzoxazin-3(4 H)-one (971 mg, 5.00 mmol) in N,N-dimethylformamide (15 mL) at room temperature, the mixture was stirred for 10 min, and then methyl iodide (374 μL, 6.00 mmol) was added dropwise thereto. The mixture was stirred at room temperature for 3 hr and water was added to the reaction mixture. The resulting precipitate was collected by filtration, washed with ethyl acetate and water, and then dried at 60° C. under reduced pressure to afford 4-methyl-8-nitro-2 H-1,4-benzoxazin-3(4 H)-one as a pale yellow amorphous substance (453 mg).

(5) To a solution of 4-methyl-8-nitro-2 H-1,4-benzoxazin-3(4 H)-one (415 mg, 1.99 mmol) in ethanol (10 mL) was added 10% palladium activated carbon (415 mg) at room temperature, and the mixture was stirred overnight under a hydrogen atmosphere. The reaction mixture was filtered through Celite (registered trademark), followed by washing with ethanol. The filtrate was concentrated under reduced pressure. The resulting residue was dried under reduced pressure to afford the title compound as a gray powder (314 mg).

$^1$H NMR (300 MHz, CDCl$_3$) δ ppm 3.34 (s, 3 H), 3.84 (br. s., 2 H), 4.63 (s, 2 H), 6.39-6.52 (m, 2 H), 6.80-6.88 (m, 1 H).

MS ESI/APCI Dual posi: 179[M+H]$^+$.

Reference Example 27-1

4-Fluoro-$N^3,N^3$-dimethylbenzene-1,3-diamine

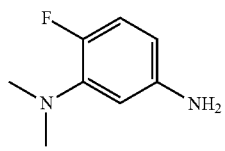

[Formula 43]

(1) Potassium carbonate (4.15 g, 30 mmol) and methyl iodide (1.49 mL, 24.0 mmol) were added to a solution of 2-fluoro-5-nitroaniline (1.56 g, 10.0 mmol) in N,N-dimethylformamide (30 mL) at room temperature and the mixture was stirred at 100° C. for 6 hr. After cooling to room temperature, water was added to the reaction mixture and the mixture was extracted three times with ethyl acetate. The organic layer was washed with 1 mol/L hydrochloric acid and brine and dried over anhydrous magnesium sulfate and then the desiccant was filtered off, followed by concentration under reduced pressure. The resulting residue was purified by silica gel column chromatography (hexane:ethyl acetate=9:1) to afford 2-fluoro-N,N-dimethyl-5-nitroaniline as a pale yellow oil (290 mg).

(2) The same process as that of Reference Example 15-1(2) was performed using 2-fluoro-N,N-dimethyl-5-nitroaniline obtained (275 mg, 1.78 mmol) to afford the title compound as a pale yellow oil (154 mg).

$^1$H NMR (300 MHz, CDCl$_3$) δ ppm 2.81 (s, 6 H), 3.49 (br. s., 2 H), 6.12-6.26 (m, 2 H), 6.75-6.84 (m, 1 H).

MS ESI/APCI Dual posi: 155[M+H]$^+$.

The compounds of Reference Examples 27-2 to 27-4 were obtained by using the compound obtained in Reference Example 26-1(1) or the corresponding commercially available compounds in accordance with the process of Reference Example 27-1.

Reference Example 27-2

$^1$H NMR (300 MHz, CDCl$_3$) δ ppm 2.86 (s, 6 H), 3.64 (br. s., 2 H), 6.04-6.11 (m, 1 H), 6.14-6.20 (m, 1 H), 6.80-6.90 (m, 1 H).

MS ESI/APCI Dual posi: 155[M+H]$^+$.

Reference Example 27-3

$^1$H NMR (300 MHz, CDCl$_3$) δ ppm 2.80 (s, 6 H), 3.76-3.84 (m, 5 H), 6.29-6.41 (m, 2 H), 6.77-6.85 (m, 1 H).

MS ESI/APCI Dual posi: 167[M+H]$^+$.

Reference Example 27-4

$^1$H NMR (300 MHz, CDCl$_3$) δ ppm 2.75 (s, 6 H), 3.51 (br. s., 2 H), 6.28-6.42 (m, 1 H), 6.67-6.80 (m, 1 H).

MS ESI/APCI Dual posi: 173[M+H]$^+$.

The structures of the compounds of Reference Examples 27-2 to 27-4 are shown in Table 12-1.

TABLE 12-1

| Reference Ex. | Structure |
|---|---|
| 27-2 | ![structure] |
| 27-3 | ![structure] |
| 27-4 | ![structure] |

Reference Example 28-1

$N^2$-(3-Phenylpropyl)pyrimidine-2,5-diamine

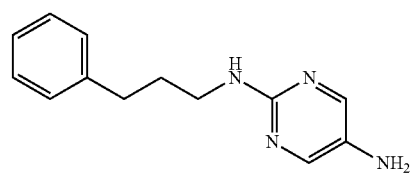

[Formula 44]

(1) 2-Chloro-5-nitropyrimidine (100 mg, 0.627 mmol) and triethylamine (96 µL, 0.690 mmol) were added successively to a solution of 3-phenylpropylamine (98 µL, 0.690 mmol) in tetrahydrofuran, and the mixture was stirred at room temperature for 18 hr. Water was added to the reaction mixture and the mixture was extracted with ethyl acetate. The organic layer was washed with brine and 0.5 mol/L hydrochloric acid and dried over anhydrous magnesium sulfate. Thereafter, the desiccant was filtered off, followed by concentration under reduced pressure. The resulting residue was purified by silica gel column chromatography (hexane:ethyl acetate=9:1) to afford 5-nitro-N-(3-phenylpropyl)pyrimidin-2-amine as a colorless solid (108 mg).

(2) To a solution of 5-nitro-N-(3-phenylpropyl)pyrimidin-2-amine obtained (108 mg) in a mixture of methanol (2 mL), ethanol (1 mL) and ethyl acetate (1 mL) was added 10% palladium activated carbon (13 mg), and the mixture was stirred under a hydrogen atmosphere at room temperature for 18 hr. The reaction mixture was filtered through Celite (registered trademark) and the filtrate was concentrated under reduced pressure. The resulting residue was purified by silica gel column chromatography (hexane:ethyl acetate=7:3→chloroform:methanol=49:1) to afford the title compound (79 mg) as a brown solid.

$^1$H NMR (300 MHz, CDCl$_3$) δ ppm 1.85-1.99 (m, 2 H), 2.65-2.78 (m, 2 H), 3.33-3.45 (m, 2 H), 7.13-7.33 (m, 5 H), 7.94 (s, 2 H).

MS ESI/APCI Dual posi: 229[M+H]$^+$.

Reference Example 29-1

N-[4-(3-Cyclopentylpropyl)-2-fluorophenyl]-N-(4-methoxybenzyl)-1,2,3,4-tetrahydroisoquinoline-6-sulfonamide

[Formula 45]

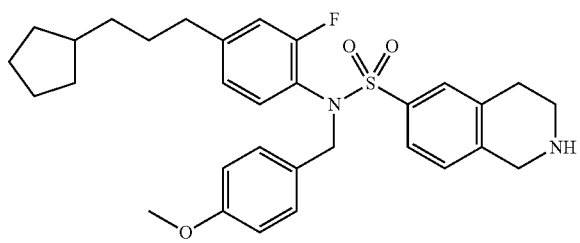

(1) Potassium carbonate (1.36 g, 9.84 mmol) and 4-methoxybenzyl chloride (0.98 mL, 7.21 mmol) were added to a N,N-dimethylformamide (16 mL) solution of a compound obtained using the aniline of Reference Example 20-1 in accordance with the processes of Reference Example 3-1(1) to (4) (N-[4-(3-cyclopentylpropyl)-2-fluorophenyl]-2-(trifluoroacetyl)-1,2,3,4-tetrahydroisoquinoline-6-sulfonamide) (3.36 g, 6.56 mmol). The mixture was stirred at 60° C. for 2 hr. Saturated aqueous ammonium chloride solution was added to the reaction mixture and the mixture was extracted with ethyl acetate. The organic layer was washed with saturated aqueous ammonium chloride solution and brine and dried over anhydrous magnesium sulfate. Thereafter, the desiccant was filtered off, followed by concentration under reduced pressure. The resulting residue was purified by silica gel column chromatography (hexane only→hexane:ethyl acetate=3:2) to afford N-[4-(3-cyclopentylpropyl)-2-fluorophenyl]-N-(4-methoxybenzyl)-2-(trifluoroacetyl)-1,2,3,4-tetrahydroisoquinoline-6-sulfonamide as a colorless oil (4.07 g).

(2) An aqueous solution (10 mL) of ethanol (20 mL) and potassium hydroxide (730 mg, 12.86 mmol) was added to a solution of N-[4-(3-cyclopentylpropyl)-2-fluorophenyl]-N-(4-methoxybenzyl)-2-(trifluoroacetyl)-1,2,3,4-tetrahydroisoquinoline-6-sulfonamide obtained (4.07 g, 6.43 mmol) in tetrahydrofuran (10 mL), and the mixture was stirred at room temperature for 15 hr. The mixture was diluted with water and extracted with chloroform. The organic layer was concentrated under reduced pressure, a mixed solvent of hexane and ethyl acetate (6:1) was added to the residue, and a precipitated solid was collected by filtration to afford the title compound as a colorless powder (3.11 g).

$^1$ H NMR (300 MHz, CDCl$_3$) δ ppm 0.95-1.12 (m, 2 H), 1.21-1.32 (m, 2 H), 1.45-1.64 (m, 6 H), 1.66-1.79 (m, 3 H), 2.46-2.55 (m, 2 H), 2.76-2.86 (m, 2 H), 3.12-3.20 (m, 2 H), 3.74 (s, 3 H), 4.08 (s, 2 H), 4.63 (s, 2 H), 6.69-6.82 (m, 4 H), 6.88-6.98 (m, 1 H), 7.07-7.16 (m, 3 H), 7.42-7.51 (m, 2 H).

LCMS retention time: 4.35 min. (Condition 1-2-3)

MS (ESI posi) m/z: 537[M+H]$^+$.

The compound of Reference Example 29-2 was obtained by using the corresponding aniline obtained in Reference Example 15 in accordance with the process of Reference Example 29-1.

Reference Example 29-2

$^1$ H NMR (600 MHz, CDCl$_3$) δ ppm 1.44-1.49 (m, 2 H), 1.64-1.70 (m, 2 H), 1.73-1.80 (m, 2 H), 2.61-2.65 (m, 2 H), 2.80-2.84 (m, 2 H), 3.13-3.18 (m, 2 H), 3.74 (s, 3 H), 3.84 (t, J=6.4 Hz, 2 H), 4.08 (s, 2 H), 4.61 (s, 2 H), 6.43-6.50 (m, 2 H), 6.72-6.76 (m, 2 H), 6.87-6.91 (m, 1 H), 7.09-7.14 (m, 3 H), 7.15-7.20 (m, 3 H), 7.24-7.30 (m, 2 H), 7.45-7.49 (m, 2 H).

MS ESI/APCI Dual posi: 589[M+H]$^+$.

The structure of the compound of Reference Example 29-2 is shown in Table 13-1.

TABLE 13-1

| Reference Ex. | Structure |
|---|---|
| 29-2 | 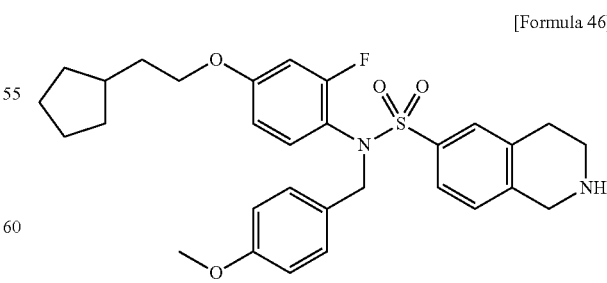 |

Reference Example 30-1

N-[4-(2-Cyclopentylethoxy)-2-fluorophenyl]-N-(4-methoxybenzyl)-1,2,3,4-tetrahydroisoquinoline-6-sulfonamide

[Formula 46]

(1) Potassium carbonate (51 mg, 0.37 mmol) and 2-cyclopentylethyl 4-methylbenzenesulfonate (55 mg, 0.20 mmol) which was synthesized in accordance with the method described in a document (Journal of Medicinal Chemistry, 2008, 51, 3065) were added to an N,N-dimethylformamide (3 mL) solution of a compound obtained using compound 18-9 as obtained in Reference Example 18 in accordance with the processes of Reference Example 3-1(1), (2), (3) and (4) (N-(2-fluoro-4-hydroxyphenyl)-N-(4-methoxybenzyl)-2-(trifluoroacetyl)-1,2,3,4-tetrahydroisoquinoline-6-sulfonamide) (100 mg, 0.19 mmol). The mixture was stirred at 60° C. for 2 hr. Saturated aqueous ammonium chloride solution was added to the reaction mixture and the mixture was extracted with ethyl acetate. The organic layer was washed with saturated aqueous ammonium chloride solution and brine, and was dried over anhydrous magnesium sulfate. Thereafter, the desiccant was filtered off, followed by concentration under reduced pressure. The resulting residue was purified by silica gel column chromatography (hexane:ethyl acetate=4:1→ethyl acetate only) to afford N-[4-(2-cyclopentylethoxy)-2-fluorophenyl]-N-(4-methoxybenzyl)-2-(trifluoroacetyl)-1,2,3,4-tetrahydroisoquinoline-6-sulfonamide as a colorless amorphous substance (100 mg).

(2) An aqueous solution (1 mL) of potassium hydroxide (29 mg, 0.51 mmol) was added to a solution of N-[4-(2-cyclopentylethoxy)-2-fluorophenyl]-N-(4-methoxybenzyl)-2-(trifluoroacetyl)-1,2,3,4-tetrahydroisoquinoline-6-sulfonamide obtained (163 mg, 0.26 mmol) in ethanol (4 mL), and the mixture was stirred at room temperature for 15 hr. The mixture was diluted with water and extracted with chloroform. The organic layer was concentrated under reduced pressure to afford the title compound as a colorless oil (145 mg).

$^1$H NMR (300 MHz, CDCl$_3$) δ ppm 1.06-1.20 (m, 2 H), 1.48-1.98 (m, 9 H), 2.80-2.88 (m, 2 H), 3.13-3.21 (m, 2 H), 3.75 (s, 3 H), 3.87 (t, J=6.8 Hz, 2 H), 4.09 (s, 2 H), 4.61 (s, 2 H), 6.43-6.52 (m, 2 H), 6.71-6.78 (m, 2 H), 6.85-6.93 (m, 1 H), 7.09-7.16 (m, 3 H), 7.44-7.50 (m, 2 H).

LCMS retention time: 1.90 min. (Condition 3)
MS ESI/APCI Dual posi: 539[M+H]$^+$.

The compounds of Reference Examples 30-2 to 30-11 were obtained by using the corresponding alkyl halides or alkyl tosylates in accordance with the process of Reference Example 30-1.

It is to be noted that the aforementioned corresponding alkyl halides or alkyl tosylates are either available by the methods of Reference Examples as shown herein or methods described in publications or commercially available.

Reference Example 30-2

$^1$H NMR (600 MHz, CDCl$_3$) δ ppm 1.22-1.36 (m, 1 H), 1.42-1.72 (m, 4 H), 1.80-1.92 (m, 1 H), 2.80-2.86 (m, 2 H), 3.13-3.20 (m, 2 H), 3.40-3.56 (m, 4 H), 3.75 (s, 3 H), 3.77-3.85 (m, 2 H), 3.96-4.13 (m, 5 H), 4.61 (s, 2 H), 6.45-6.55 (m, 2 H), 6.70-6.78 (m, 2 H), 6.84-6.94 (m, 1 H), 7.08-7.15 (m, 3 H), 7.42-7.51 (m, 2 H).

LCMS retention time: 0.70 min. (Condition 2)
MS (ESI posi) m/z: 585[M+H]$^+$.

Reference Example 30-3

$^1$H NMR (600 MHz, CDCl$_3$) δ ppm 1.54-1.66 (m, 1 H), 1.81-2.00 (m, 3 H), 2.80-2.86 (m, 2 H), 3.13-3.20 (m, 2 H), 3.48-3.59 (m, 2 H), 3.72-3.91 (m, 7 H), 4.00-4.12 (m, 5 H), 4.61 (s, 2 H), 6.46-6.55 (m, 2 H), 6.71-6.77 (m, 2 H), 6.86-6.93 (m, 1 H), 7.07-7.15 (m, 3 H), 7.43-7.50 (m, 2 H).

LCMS retention time: 0.65 min. (Condition 2)
MS (ESI posi) m/z: 571[M+H]$^+$.

Reference Example 30-4

$^1$H NMR (600 MHz, CDCl$_3$) δ ppm 1.52-1.63 (m, 1 H), 1.77-1.91 (m, 2 H), 2.05-2.14 (m, 1 H), 2.30-2.41 (m, 1 H), 2.79-2.87 (m, 2 H), 3.13-3.20 (m, 2 H), 3.37-3.43 (m, 1 H), 3.72-3.79 (m, 4 H), 3.84-3.97 (m, 4 H), 4.05-4.12 (m, 2 H), 4.61 (s, 2 H), 6.43-6.52 (m, 2 H), 6.70-6.79 (m, 2 H), 6.87-6.94 (m, 1 H), 7.09-7.16 (m, 3 H), 7.44-7.52 (m, 2 H).

LCMS retention time: 0.66 min. (Condition 2)
MS (ESI posi) m/z: 541[M+H]$^+$.

Reference Example 30-5

$^1$H NMR (600 MHz, CDCl$_3$) δ ppm 1.46-1.55 (m, 1 H), 1.58-2.01 (m, 4 H), 2.80-2.89 (m, 2 H), 3.13-3.21 (m, 2 H), 3.36-3.56 (m, 2 H), 3.75 (s, 3 H), 3.89-4.04 (m, 3 H), 4.05-4.18 (m, 3 H), 4.44-4.65 (m, 3 H), 6.42-6.54 (m, 2 H), 6.71-6.78 (m, 2 H), 6.86-6.95 (m, 1 H), 7.08-7.17 (m, 3 H), 7.44-7.53 (m, 2 H).

LCMS retention time: 0.68 min. (Condition 2)
MS (ESI posi) m/z: 573[M+H]$^+$.

Reference Example 30-6

$^1$H NMR (600 MHz, CDCl$_3$) δ ppm 1.36-1.50 (m, 1 H), 1.54-1.98 (m, 3 H), 2.11-2.20 (m, 1 H), 2.82-2.92 (m, 2 H), 3.16-3.43 (m, 3 H), 3.75 (s, 3 H), 3.83-4.01 (m, 4 H), 4.03-4.16 (m, 3 H), 4.19-4.34 (m, 1 H), 4.61 (s, 2 H), 6.44-6.53 (m, 2 H), 6.71-6.78 (m, 2 H), 6.87-6.94 (m, 1 H), 7.09-7.16 (m, 3 H), 7.45-7.51 (m, 2 H).

LCMS retention time: 0.70 min. (Condition 2)
MS (ESI posi) m/z: 573[M+H]$^+$.

Reference Example 30-7

$^1$H NMR (600 MHz, CDCl$_3$) δ ppm 1.99-2.08 (m, 2 H), 2.80-2.87 (m, 2 H), 3.14-3.20 (m, 2 H), 3.72-3.77 (m, 5 H), 3.77-3.85 (m, 2 H), 3.97 (t, J=6.0 Hz, 2 H), 4.09 (s, 2 H), 4.61 (s, 2 H), 6.42-6.54 (m, 2 H), 6.71-6.79 (m, 2 H), 6.86-6.95 (m, 1 H), 7.08-7.16 (m, 3 H), 7.44-7.51 (m, 2 H).

LCMS retention time: 1.76 min. (Condition 3)
MS ESI/APCI Dual posi: 583[M+H]$^+$.

Reference Example 30-8

$^1$H NMR (600 MHz, CDCl$_3$) δ ppm 1.14-1.34 (m, 6 H), 1.49-1.58 (m, 1 H), 1.68-1.79 (m, 1 H), 1.86-1.96 (m, 2 H), 2.79-2.88 (m, 2 H), 3.12-3.20 (m, 2 H), 3.25-3.34 (m, 1 H), 3.71-3.79 (m, 5 H), 3.97-4.03 (m, 2 H), 4.09 (s, 2 H), 4.61 (s, 2 H), 6.47-6.55 (m, 2 H), 6.70-6.77 (m, 2 H), 6.85-6.93 (m, 1 H), 7.07-7.15 (m, 3 H), 7.43-7.50 (m, 2 H).

LCMS retention time: 1.83 min. (Condition 3)
MS ESI/APCI Dual posi: 569[M+H]$^+$.

Reference Example 30-9

$^1$H NMR (600 MHz, CDCl$_3$) δ ppm 1.44-1.54 (m, 2 H), 1.56-1.75 (m, 6 H), 1.91-2.02 (m, 2 H), 2.79-2.87 (m, 2 H), 3.14-3.20 (m, 2 H), 3.50 (t, J=6.2 Hz, 2 H), 3.75 (s, 3 H), 3.83-3.89 (m, 1 H), 3.95 (t, J=6.4 Hz, 2 H), 4.09 (s, 2 H), 4.61 (s, 2 H), 6.43-6.54 (m, 2 H), 6.71-6.78 (m, 2 H), 6.86-6.93 (m, 1 H), 7.09-7.15 (m, 3 H), 7.44-7.50 (m, 2 H).

LCMS retention time: 1.82 min. (Condition 3)
MS ESI/APCI Dual posi: 569[M+H]$^+$.

Reference Example 30-10

$^1$H NMR (300 MHz, DMSO-d$_6$) δ ppm 1.86-2.01 (m, 2 H), 2.78-2.88 (m, 2 H), 3.02-3.11 (m, 2 H), 3.37-3.48 (m, 2 H), 3.68 (s, 3 H), 3.95 (t, J=6.1 Hz, 2 H), 4.04 (s, 2 H), 4.56 (s, 2 H), 6.58 (d, J=9.2 Hz, 1 H), 6.71 (d, J=12.6 Hz, 1 H), 6.75-

6.91 (m, 3 H), 7.09 (d, J=8.1 Hz, 2 H), 7.26-7.33 (m, 1 H), 7.39-7.51 (m, 2 H), 7.60-7.79 (m, 3 H), 7.86-7.94 (m, 2 H).
LCMS retention time: 0.95 min. (Condition 4-1)
MS (ESI posi) m/z: 625[M+H]⁺.
Reference Example 30-11
¹H NMR (300 MHz, DMSO-$d_6$) δ ppm 1.11-1.26 (m, 1 H), 1.37-1.48 (m, 3 H), 1.53-1.62 (m, 1 H), 1.71-1.81 (m, 3 H), 2.86-2.94 (m, 2 H), 3.12-3.42 (m, 4 H), 3.68 (s, 3 H), 3.79-3.87 (m, 1 H), 3.91-4.03 (m, 2 H), 4.13 (s, 2 H), 4.57 (s, 2 H), 6.60-6.67 (m, 1 H), 6.72-6.90 (m, 4 H), 7.07-7.13 (m, 2 H), 7.32-7.37 (m, 1 H), 7.44-7.50 (m, 1 H), 7.52-7.56 (m, 1 H).
LCMS retention time: 1.72 min. (Condition 3)
MS ESI/APCI Dual posi: 555[M+H]⁺.
The structures of the compounds of Reference Examples 30-2 to 30-11 are shown in Table 14-1.
TABLE 14-1
| Reference Ex. | Structure |
|---|---|
| 30-2 | 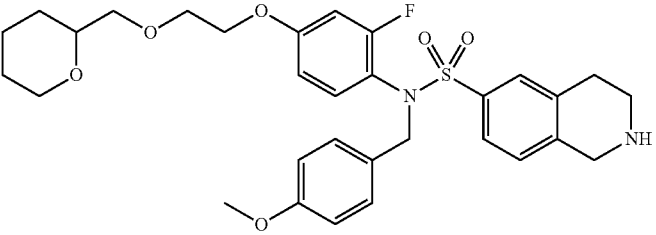 [SMILES: COc1ccc(CN(c2ccc(OCCOCC3CCCCO3)cc2F)S(=O)(=O)c2ccc3c(c2)CCNC3)cc1] |
| 30-3 | 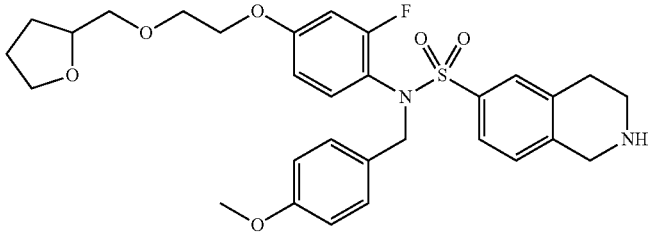 [SMILES: COc1ccc(CN(c2ccc(OCCOCC3CCCO3)cc2F)S(=O)(=O)c2ccc3c(c2)CCNC3)cc1] |
| 30-4 | 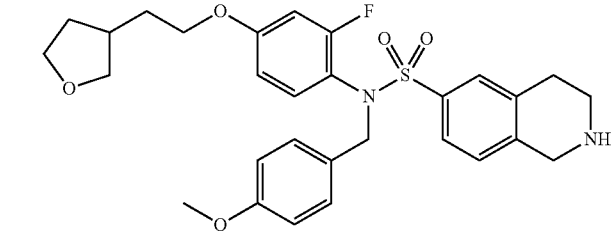 [SMILES: COc1ccc(CN(c2ccc(OCCC3CCOC3)cc2F)S(=O)(=O)c2ccc3c(c2)CCNC3)cc1] |
| 30-5 | 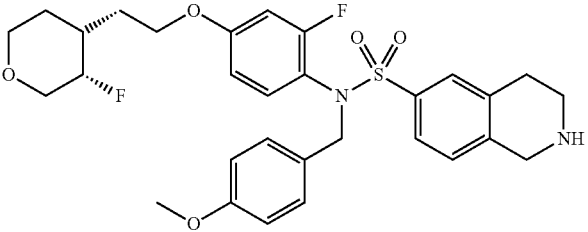 |
| 30-6 | 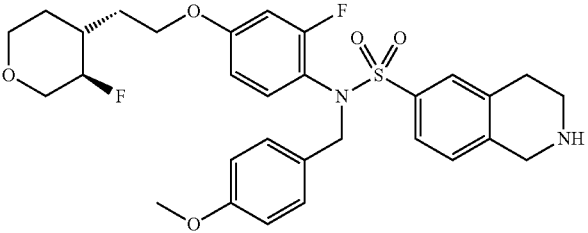 |

TABLE 14-1-continued
| Reference Ex. | Structure |
|---|---|
| 30-7 | 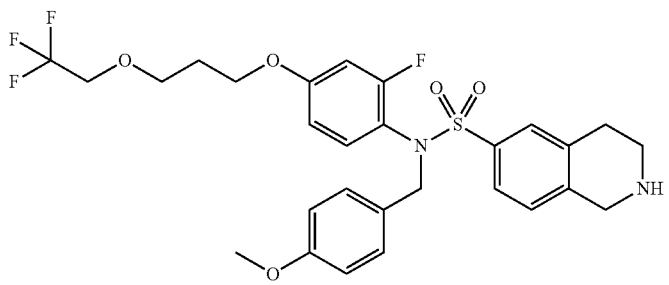 [SMILES: COc1ccc(CN(c2ccc(OCCCOCC(F)(F)F)cc2F)S(=O)(=O)c2ccc3c(c2)CCNC3)cc1] |
| 30-8 | 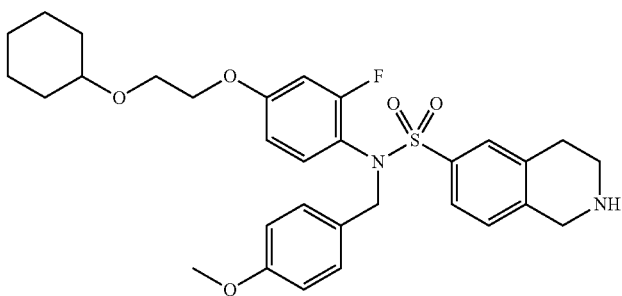 [SMILES: COc1ccc(CN(c2ccc(OCCOC3CCCCC3)cc2F)S(=O)(=O)c2ccc3c(c2)CCNC3)cc1] |
| 30-9 | 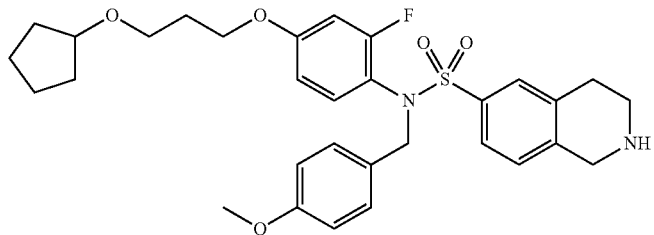 [SMILES: COc1ccc(CN(c2ccc(OCCCOC3CCCC3)cc2F)S(=O)(=O)c2ccc3c(c2)CCNC3)cc1] |
| 30-10 | 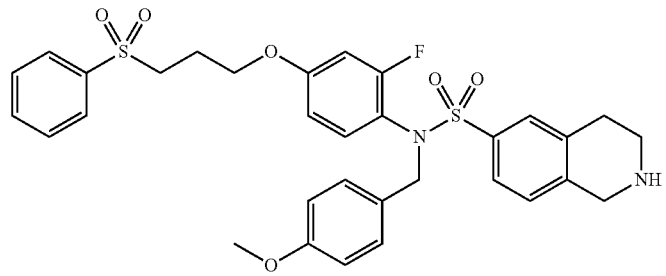 [SMILES: COc1ccc(CN(c2ccc(OCCCS(=O)(=O)c3ccccc3)cc2F)S(=O)(=O)c2ccc3c(c2)CCNC3)cc1] |
| 30-11 | 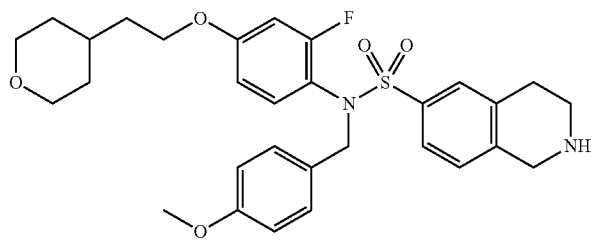 [SMILES: COc1ccc(CN(c2ccc(OCCC3CCOCC3)cc2F)S(=O)(=O)c2ccc3c(c2)CCNC3)cc1] |

Reference Example 31-1

4-(2-Cyclopropylethyl)-2-fluoroaniline

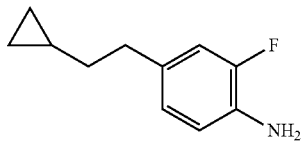

[Formula 47]

(1) 4-[(E)-2-Cyclopropylethenyl]-2-fluoroaniline was obtained as a brown oil (12.5 g) by using the corresponding commercially available compound in accordance with the process of Reference Example 20-1.

(2) To a solution of 4-[(E)-2-cyclopropylethenyl]-2-fluoroaniline obtained (12.5 g, 25.0 mmol) in ethanol (85 mL) was added 10% palladium activated carbon (1.25 g), and the mixture was stirred under a hydrogen atmosphere at room temperature for 15 hr. The mixture was filtered through Celite (registered trademark) and the filtrate was concentrated under reduced pressure. The resulting residue was purified by silica gel column chromatography (hexane:ethyl acetate=9:1) to afford the title compound as a pale orange oil (3.74 g).

$^1$H NMR (300 MHz, CDCl$_3$) δ ppm −0.06-0.09 (m, 2 H), 0.32-0.48 (m, 2 H), 0.60-0.74 (m, 1 H), 1.39-1.51 (m, 2 H), 2.54-2.64 (m, 2 H), 6.64-6.87 (m, 3 H).

Reference Example 32-1

4-(2-Cyclohexylethyl)-2-fluoroaniline

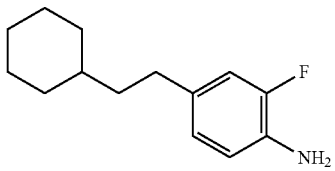

[Formula 48]

(1) Isopropanol (60 mL) was added to PEPPSI™-IPr catalyst (161 mg, 0.24 mmol) and tert-butoxy potassium (2.65 g, 23.6 mmol) under an argon atmosphere, and the mixture was stirred at room temperature for 15 min. To the reaction mixture were added trans-(2-cyclohexylvinyl)boronic acid (2.00 g, 13.0 mmol) and 4-bromo-2-fluoroaniline (2.24 g, 11.8 mmol) successively and the mixture was stirred at room temperature for 15 hr. Water was added thereto, the mixture was extracted with ethyl acetate, and the organic layer was washed with brine and dried over anhydrous magnesium sulfate. The desiccant was filtered off and the filtrate was concentrated under reduced pressure to afford 4-[(E)-2-cyclohexylethenyl]-2-fluoroaniline as a reddish brown oil (2.58 g).

(2) 4-[(E)-2-Cyclohexylethenyl]-2-fluoroaniline obtained (2.58 g, 11.8 mmol) was used to afford the title compound as a brown oil (2.47 g) in accordance with the process of Reference Example 31-1(2).

(3) To a solution of the title compound (2.47 g) in ethyl acetate (30 mL) was added 4 mol/L hydrogen chloride-ethyl acetate (5 mL), and the mixture was stirred at room temperature for 3 hr. The resulting precipitate was collected by filtration to afford the monohydrochloride of the title compound as a colorless powder (2.32 g).

$^1$H NMR (300 MHz, DMSO-d$_6$) δ ppm 0.81-0.97 (m, 2 H), 1.06-1.26 (m, 4 H), 1.38-1.48 (m, 2 H), 1.56-1.76 (m, 5 H), 2.53-2.60 (m, 2 H), 6.95-7.03 (m, 1 H), 7.09-7.25 (m, 2 H).

LCMS retention time: 4.24 min. (Condition 1-2-3)
MS (ESI posi) m/z: 222[M+H]$^+$.

Reference Example 33-1

4-(2-Cyclopentylethyl)-2-fluoroaniline

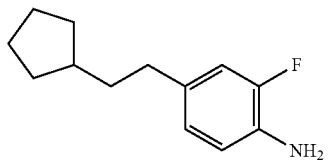

[Formula 49]

(1) 9-Borabicyclo[3,3,1]nonane (9-BBN) (tetrahydrofuran solution, 0.5 mol/L, 33 mL, 16.5 mmol) was added dropwise to a solution of vinylcyclopentane (1.59 g, 16.5 mmol) in tetrahydrofuran (7.5 mL) at 0° C. under a nitrogen atomosphere. The mixture was warmed gradually to room temperature and stirred for 15 hr. To the reaction mixture were added dichloro[1,1'-bis(diphenylphosphino)ferrocene]palladium (II) (367 mg, 0.45 mmol), 4-bromo-2-fluoroaniline (2.85 g, 15.0 mmol) and 3 mol/L aqueous sodium hydroxide solution (15 mL, 45.0 mmol), and the mixture was heated to reflux for 10 hr. After cooling, ethyl acetate was added thereto, the mixture was filtered through Celite (registered trademark), and the filtrate was concentrated under reduced pressure. Water was added thereto, the mixture was extracted with ethyl acetate, and the organic layer was washed with brine. After drying over anhydrous magnesium sulfate, the desiccant was filtered off, followed by concentration under reduced pressure. The resulting residue was purified by silica gel column chromatography (hexane:ethyl acetate=9:1) to afford the title compound as a pale yellow oil (3.01 g).

(2) To a solution of the obtained title compound (3.01 g) in ethyl acetate (75 mL) was added 4 mol/L hydrogen chloride-ethyl acetate (8 mL), and the mixture was stirred at room temperature for 3 hr. The resulting precipitate was collected by filtration to afford the monohydrochloride of the title compound as a colorless powder (2.34 g).

$^1$H NMR (300 MHz, DMSO-d$_6$) δ ppm 1.02-1.17 (m, 2 H), 1.40-1.79 (m, 9 H), 2.53-2.60 (m, 2 H), 6.99-7.04 (m, 1 H), 7.11-7.27 (m, 2 H).

LCMS retention time: 2.44 min. (Condition 3)
MS ESI/APCI Dual posi: 208[M+H]$^+$.

Reference Example 34-1

6-(2,2,2-Trifluoroethoxy)pyridine-3-carbaldehyde

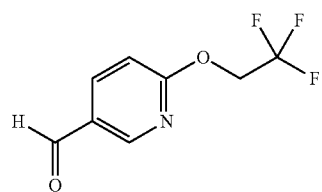

[Formula 50]

(1) N-Methoxy-N-methyl-6-(2,2,2-trifluoroethoxy)pyridine-3-carboxamide was obtained as a colorless oil (432 mg) by using the corresponding commercially available carboxylic acid in accordance with the process of Reference Example 12-1(2).

(2) Diisobutylaluminum hydride (toluene solution, 1.01 mol/L, 1.95 mL, 1.97 mmol) was added dropwise to a solution of N-methoxy-N-methyl-6-(2,2,2-trifluoroethoxy)pyridine-3-carboxamide obtained (432 mg, 1.64 mmol) in toluene (11 mL) at −78° C. under a nitrogen atmosphere. The mixture was stirred at the same temperature for 1 hr. Methanol (5 mL) was added dropwise to the reaction mixture, the mixture was warmed to room temperature, and 50% aqueous Rochelle salt solution (10 mL) was added thereto, followed by stirring for 1.5 hr. The mixture was extracted with chloroform and the organic layer was concentrated under reduced pressure. The resulting residue was purified by silica gel column chromatography (hexane:ethyl acetate=9:1→7:3) to afford the title compound as a colorless solid (287 mg).

$^1$ H NMR (300 MHz, CDCl$_3$) δ ppm 4.86 (q, J=8.4 Hz, 2 H), 6.97-7.02 (m, 1 H), 8.16 (dd, J=8.6, 2.3 Hz, 1 H), 8.62-8.66 (m, 1 H), 10.00 (d, J=0.6 Hz, 1 H).

LCMS retention time: 1.86 min. (Condition 3)

MS ESI/APCI Dual posi: 206[M+H]$^+$.

The compound of Reference Example 34-2 was obtained by using the corresponding commercially available carboxylic acid in accordance with the process of Reference Example 34-1.

Reference Example 34-2

$^1$ H NMR (300 MHz, DMSO-d$_6$) δ ppm 7.94-7.99 (m, 1 H), 8.07 (dd, J=11.0, 1.6 Hz, 1 H), 8.33-8.40 (m, 1 H), 10.09 (d, J=1.6 Hz, 1 H).

The structure of the compound of Reference Example 34-2 is shown in Table 15-1.

TABLE 15-1

| Reference Ex. | Structure |
| --- | --- |
| 34-2 | ![F, NO2, H, O structure] |

Reference Example 35-1

4-(3-Cyclopropylpropyl)-2-fluoroaniline

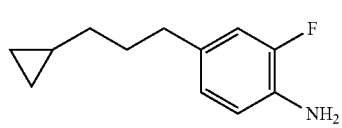

[Formula 51]

(1) Iodine (3.05 g, 24.0 mmol) and imidazole (1.63 g, 24.0 mmol) were added to a solution of triphenylphosphine (6.29 g, 24.0 mmol) in chloroform (50 mL) at 0° C. under a nitrogen atmosphere, and the mixture was stirred at the same temperature for 15 min. A solution of 2-cyclopropylethanol (1.72 g, 20.0 mmol) in chloroform (50 mL) was added dropwise to the reaction mixture and the mixture was stirred at room temperature for 3 hr. To the reaction mixture were added saturated aqueous sodium thiosulfate solution and water, and the mixture was extracted with chloroform. The organic layer was concentrated under reduced pressure and the residue was purified by silica gel column chromatography (hexane only) to afford (2-iodoethyl)cyclopropane as a pale yellow oil (2.14 g).

(2) Triphenylphosphine (2.86 g, 10.9 mmol) was added to a solution of (2-iodoethyl)cyclopropane obtained (2.14 g, 10.9 mmol) in acetonitrile (5 mL), and the mixture was heated to reflux for 15 hr. After cooling, diethyl ether was added thereto and a precipitaed solid was collected by filtration to afford (2-cyclopropylethyl)(triphenyl)phosphonium iodide as a colorless powder (3.87 g).

(3) (2-Cyclopropylethyl)(triphenyl)phosphonium iodide obtained (3.83 g, 8.36 mmol) was suspended in tetrahydrofuran (60 mL) under a nitrogen atmosphere. Potassium hexamethyldisilazane (toluene solution, 0.5 mol/L) (16.7 mL, 8.36 mmol) was added dropwise thereto at 0° C. and then the mixture was stirred at room temperature for 1 hr. The mixture was cooled to 0° C. again, a solution of compound 34-2 as obtained in Reference Example 34 (1.23 g, 7.27 mmol) in tetrahydrofuran (10 mL) was added dropwise to the reaction mixture, and the mixture was warmed to room temperature and stirred for 1 hr. Saturated aqueous ammonium chloride solution was added to the reaction mixture and the mixture was extracted with ethyl acetate. The organic layer was washed with brine and dried over anhydrous magnesium sulfate. The desiccant was filtered off, followed by concentration under reduced pressure. The residue was purified by silica gel column chromatography (hexane only→hexane:ethyl acetate=4:1) to afford 4-[3-cyclopropylprop-1-en-1-yl]-2-fluoro-1-nitrobenzene as a brown oil (1.42 g).

(4) 4-[3-Cyclopropylprop-1-en-1-yl]-2-fluoro-1-nitrobenzene obtained (1.42 g, 6.42 mmol) was used to afford the title compound as a brown oil (709 mg) in accordance with the process of Reference Example 31-1(2).

$^1$ H NMR (300 MHz, CDCl$_3$) δ ppm −0.04-0.02 (m, 2 H), 0.36-0.43 (m, 2 H), 0.60-0.73 (m, 1 H), 1.16-1.25 (m, 2 H), 1.60-1.72 (m, 2 H), 2.48-2.55 (m, 2 H), 6.65-6.77 (m, 2 H), 6.78-6.85 (m, 1 H).

LCMS retention time: 1.14 min. (Condition 4-2)

MS (ESI posi) m/z: 194[M+H]$^+$.

Reference Example 36-1

2-Fluoro-4-[3-(tetrahydro-2 H-pyran-4-yl)propyl]aniline

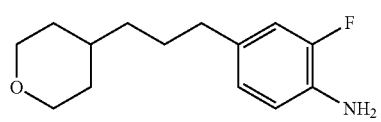

[Formula 52]

(1) Methyltriphenylphosphonium bromide (2.18 g, 6.10 mmol) was suspended in tetrahydrofuran (50 mL) under an argon atmosphere, and potassium hexamethyldisilazane (toluene solution, 0.5 mol/L) (11.0 mL, 5.49 mmol) was added dropwise thereto at room temperature, followed by stirring for 1 hr. The reaction mixture was cooled to −78° C., a solution of (tetrahydropyran-4-yl)acetaldehyde (391 mg, 3.05 mmol) in tetrahydrofuran (10 mL) was added dropwise thereto, and the mixture was warmed to room temperature, followed by stirring for 1 hr. Saturated aqueous ammonium chloride solution was added to the reaction mixture and the mixture was extracted with diethyl ether. The organic layer was washed with brine and dried over anhydrous magnesium sulfate. The desiccant was filtered off, followed by concentration under reduced pressure. The residue was purified by silica gel column chromatography (hexane only→hexane: ethyl acetate=9:1) to afford 4-(prop-2-en-1-yl)tetrahydro-2 H-pyran as a pale yellow oil (245 mg).

(2) 4-(Prop-2-en-1-yl)tetrahydro-2 H-pyran obtained (719 mg, 5.70 mmol) was used to afford the title compound as a colorless solid (419 mg) in accordance with the process of Reference Example 33-1(1).

$^1$ H NMR (300 MHz, CDCl$_3$) δ ppm 1.20-1.32 (m, 5 H), 1.40-1.64 (m, 4 H), 2.48 (t, J=7.6 Hz, 2 H), 3.30-3.41 (m, 2 H), 3.59 (br. s., 2 H), 3.89-3.98 (m, 2 H), 6.66-6.76 (m, 2 H), 6.77-6.84 (m, 1 H).

LCMS retention time: 1.96 min. (Condition 3)
MS ESI/APCI Dual posi: 238[M+H]$^+$.

Reference Examples 37-1 and 37-2

(±)-cis Ethyl(3-fluorotetrahydro-2 H-pyran-4-yl) acetate and (±)-trans ethyl(3-fluorotetrahydro-2 H-pyran-4-yl)acetate

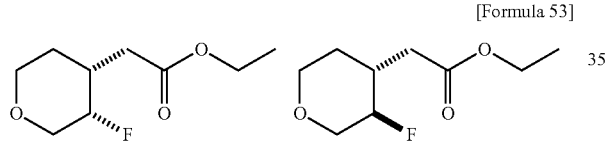

[Formula 53]

(1) A solution of triethyl phosphonoacetate (1.04 g, 4.66 mmol) in tetrahydrofuran (5 mL) was added to a mixture of sodium hydride (203 mg, 4.66 mmol) and tetrahydrofuran (5 mL) under a nitrogen atmosphere while cooling in ice, and the mixture was stirred at room temperature for 30 min. A solution of 3-fluorodihydro-2 H-pyran-4(3 H)-one (0.50 g, 4.23 mmol) in tetrahydrofuran (5 mL) was added to the reaction mixture and the mixture was stirred at 40° C. for 2 hr. After cooling, water and saturated aqueous ammonium chloride solution were added to the reaction mixture and the mixture was extracted with ethyl acetate. The organic layer was dried over anhydrous magnesium sulfate, the desiccant was filtered off, and then the solvent was distilled off under reduced pressure. The resulting residue was purified by silica gel column chromatography (hexane only→hexane:ethyl acetate=3:2) to afford (±)-ethyl(2E/Z)-(3-fluorotetrahydro-4 H-pyran-4-ylidene)ethanoate (0.76 g, a mixture of E/Z forms) as a colorless oil.

(2) To a solution of (±)-ethyl(2E/Z)-(3-fluorotetrahydro-4 H-pyran-4-ylidene)ethanoate obtained (0.76 g, 4.02 mmol) in ethanol (20 mL) was added 10% palladium activated carbon (76 mg), and the mixture was stirred under a hydrogen atmosphere at room temperature for 3 hr. The mixture was filtered through Celite (registered trademark) and the filtrate was concentrated under reduced pressure. The resulting residue was purified by silica gel column chromatography (hexane only→hexane:ethyl acetate=3:2) to afford the compound of Reference Example 37-1 (cis form) (0.26 g) and the compound of Reference Example 37-2 (trans form) (45 mg) as colorless oils.

Reference Example 37-1

Cis Form $^1$ H NMR (600 MHz, CDCl$_3$) δ ppm 1.27 (t, J=7.2 Hz, 3 H), 1.47-1.55 (m, 1 H), 1.74-1.86 (m, 1 H), 2.13-2.27 (m, 1 H), 2.33 (dd, J=16.0, 6.8 Hz, 1 H), 2.55 (dd, J=16.0, 7.4 Hz, 1 H), 3.42-3.58 (m, 2 H), 4.00 (dd, J=11.0, 4.3 Hz, 1 H), 4.08-4.20 (m, 3 H), 4.49-4.64 (m, 1 H).

MS ESI/APCI Dual posi: 191[M+H]$^+$.

Reference Example 37-2

Trans Form $^1$ H NMR (600 MHz, CDCl$_3$) δ ppm 1.24-1.29 (m, 3 H), 1.39-1.48 (m, 1 H), 1.87-1.95 (m, 1 H), 2.19-2.27 (m, 2 H), 2.70-2.77 (m, 1 H), 3.24-3.31 (m, 1 H), 3.35-3.44 (m, 1 H), 3.83-3.89 (m, 1 H), 4.05-4.10 (m, 1 H), 4.10-4.18 (m, 2 H), 4.19-4.33 (m, 1 H).

MS ESI/APCI Dual posi: 191[M+H]$^+$.

Reference Example 38-1

(±)-cis-2-(3-Fluorotetrahydro-2 H-pyran-4-yl)ethyl 4-methylbenzene sulfonate

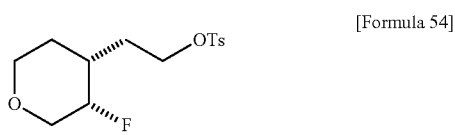 [SMILES: Cc1ccc(S(=O)(=O)OCC[C@H]2CCOC[C@H]2F)cc1]

[Formula 54]

(1) Aluminum lithium hydride (104 mg, 2.73 mmol) was added to a solution of the compound of Reference Example 37-1 (0.26 g, 1.37 mmol) in tetrahydrofuran (20 mL), and the mixture was stirred under reflux for 3 hr. Water and 1M hydrochloric acid were added to the reaction mixture while cooling in ice, and the mixture was extracted with ethyl acetate and chloroform. The organic layer was dried over anhydrous magnesium sulfate, the desiccant was filtered off, and then the solvent was distilled off under reduced pressure to afford (±)-cis-2-(3-fluorotetrahydro-2 H-pyran-4-yl)ethanol (198 mg) as a yellow oil.

(2) Trimethylamine hydrochloride (128 mg, 1.34 mmol) and triethylamine (0.39 mL, 2.81 mmol) were added to a solution of (±)-cis-2-(3-fluorotetrahydro-2 H-pyran-4-yl) ethanol obtained (198 mg, 1.34 mmol) in toluene (5 mL). Subsequently, p-toluenesulfonyl chloride (382 mg, 2.00 mmol) was added thereto while cooling in ice, and the mixture was stirred for 1 hr. Water was added to the reaction mixture and the mixture was extracted with ethyl acetate. The organic layer was washed with brine and dried over anhydrous magnesium sulfate. After the desiccant was filtered off, the solvent was distilled off under reduced pressure. The resulting residue was purified by silica gel column chromatography (hexane only→hexane:ethyl acetate=1:1) to afford the title compound (354 mg) as a colorless oil.

$^1$ H NMR (600 MHz, CDCl$_3$) δ ppm 1.35-1.42 (m, 1 H), 1.64-1.75 (m, 2 H), 1.80-1.94 (m, 2 H), 2.46 (s, 3 H), 3.34-

3.50 (m, 2 H), 3.96 (dd, J=11.4, 4.3 Hz, 1 H), 4.05-4.19 (m, 3 H), 4.32-4.45 (m, 1 H), 7.36 (d, J=8.3 Hz, 2 H), 7.80 (d, J=8.3 Hz, 2 H).

MS ESI/APCI Dual posi: 325 [M+Na]+.

The compound of Reference Example 37-2 was used to afford the compound of Reference Example 38-2 in accordance with the process of Reference Example 38-1.

Reference Example 38-2

$^1$H NMR (200 MHz, CDCl$_3$) δ ppm 1.13-1.49 (m, 2 H), 1.50-1.85 (m, 2 H), 1.95-2.18 (m, 1 H), 2.46 (s, 3 H), 3.08-3.41 (m, 2 H), 3.76-4.34 (m, 5 H), 7.30-7.41 (m, 2 H), 7.75-7.84 (m, 2 H).

MS ESI/APCI Dual posi: 325 [M+Na]+.

The structure of the compound of Reference Example 38-2 is shown in Table 16-1.

TABLE 16-1

| Reference Ex. | Structure |
|---|---|
| 38-2 | 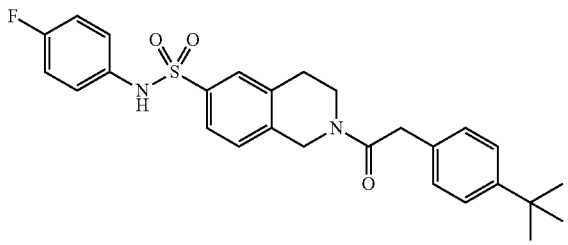 |

Working Example 1-1

2-[(4-tert-Butylphenyl)acetyl]-N-(4-fluorophenyl)-1,2,3,4-tetrahydroisoquinoline-6-sulfonamide

[Formula 55]

To a suspension of the compound obtained in Reference Example 3-1 (153 mg, 0.50 mmol) in chloroform (10 mL) and N,N-dimethylformamide (1.5 mL) were added the compound obtained in Reference Example 12-1(1) (105 mg, 0.55 mmol), 1-hydroxybenzotriazole monohydrate (100 mg, 0.65 mmol) and 1-ethyl-3-(3-dimethylaminopropyl)carbodiimide hydrochloride (125 mg, 0.65 mmol) successively, and the mixture was stirred at room temperature for 15 hr. Water was added thereto and the mixture was extracted with ethyl acetate. The organic layer was washed with brine and dried over anhydrous magnesium sulfate and then the desiccant was filtered off, followed by concentration under reduced pressure. The resulting residue was purified by silica gel column chromatography (hexane:ethyl acetate=3:1→2:3) and ethyl acetate, isopropyl ether and hexane were added thereto. The mixture was powedered and then collected by filtration to afford the title compound as a colorless powder (142 mg).

$^1$H NMR (300 MHz, DMSO-d$_6$) δ ppm 1.26 (s, 9 H), 2.73-2.83 (m, 2 H), 3.62-3.76 (m, 4 H), 4.62-4.78 (m, 2 H), 7.04-7.19 (m, 6 H), 7.24-7.39 (m, 3 H), 7.47-7.56 (m, 2 H), 10.20 (br. s., 1 H).

MS ESI/APCI Dual posi: 481[M+H]+.

The compounds of Working Examples 1-2 to 1-8 were obtained by using the corresponding compounds obtained in Reference Example 3 and either the carboxylic acid obtained in Reference Example 12-1(1) or the commercially available carboxylic acid in accordance with the process of Working Example 1-1.

Working Example 1-2

$^1$H NMR (300 MHz, DMSO-d$_6$) δ ppm 1.23-1.29 (m, 9 H), 3.67 (s, 2 H), 4.67 (s, 2 H), 4.92 (s, 2 H), 7.04-7.11 (m, 4 H), 7.16-7.22 (m, 2 H), 7.29-7.36 (m, 2 H), 7.45-7.55 (m, 1 H), 7.58-7.67 (m, 1 H), 7.68-7.77 (m, 1 H).

MS ESI/APCI Dual posi: 467[M+H]+.

Working Example 1-3

$^1$H NMR (300 MHz, DMSO-d$_6$) δ ppm 1.26 (s, 9 H), 2.75-2.83 (m, 2 H), 3.62-3.75 (m, 4 H), 4.62-4.78 (m, 2 H), 7.06-7.10 (m, 4 H), 7.13-7.19 (m, 2 H), 7.25-7.35 (m, 3 H), 7.45-7.54 (m, 1 H), 7.56-7.60 (m, 1 H), 10.21 (br. s., 1 H).

MS ESI/APCI Dual posi: 481[M+H]+.

Working Example 1-4

$^1$H NMR (600 MHz, DMSO-d$_6$) δ ppm 0.96-1.04 (m, 2 H), 1.20-1.26 (m, 2 H), 1.31 (s, 9 H), 1.40-1.56 (m, 6 H), 1.64-1.75 (m, 3 H), 2.45-2.54 (m, 2 H), 2.82-2.93 (m, 2 H), 3.28-3.35 (m, 2 H), 3.48-3.66 (m, 1 H), 4.61-4.87 (m, 1 H), 6.92 (d, J=8.3 Hz, 1 H), 6.98 (d, J=11.2 Hz, 1 H), 7.08-7.14 (m, 1 H), 7.35-7.59 (m, 7 H), 9.99 (s, 1 H).

LCMS retention time: 6.04 min. (Condition 1-2-3)

MS (ESI posi) m/z: 577[M+H]+.

Working Example 1-5

$^1$H NMR (300 MHz, DMSO-d$_6$) δ ppm 0.92-1.09 (m, 2 H), 1.18-1.29 (m, 2 H), 1.38-1.59 (m, 6 H), 1.62-1.77 (m, 3 H), 2.85-2.99 (m, 2 H), 3.28-3.36 (m, 2 H), 3.49-3.93 (m, 2 H), 4.62-4.91 (m, 2 H), 6.89-7.03 (m, 2 H), 7.07-7.16 (m, 1 H), 7.41-7.61 (m, 3 H), 8.02 (d, J=7.9 Hz, 1 H), 8.14-8.25 (m, 1 H), 8.82-8.91 (m, 1 H), 10.02 (s, 1 H).

LCMS retention time: 5.61 min. (Condition 1-2-3)

MS (ESI posi) m/z: 589[M+H]+.

Working Example 1-6

$^1$H NMR (600 MHz, CDCl$_3$) δ ppm 0.86 (s, 9 H), 0.99-1.10 (m, 5 H), 1.24-1.32 (m, 2 H), 1.46-1.62 (m, 8 H), 1.68-1.91 (m, 7 H), 2.40-2.49 (m, 1 H), 2.52 (t, J=7.6 Hz, 2 H), 2.78-2.92 (m, 2 H), 3.68-3.84 (m, 2 H), 4.65-4.78 (m, 2 H), 6.52 (br. s., 1 H), 6.78 (d, J=11.2 Hz, 1 H), 6.91 (d, J=7.8 Hz, 1 H), 7.18 (d, J=8.3 Hz, 1 H), 7.43-7.49 (m, 1 H), 7.50-7.60 (m, 2 H).

LCMS retention time: 6.09 min. (Condition 1-2-3)

MS (ESI posi) m/z: 583[M+H]+.

Working Example 1-7

$^1$H NMR (600 MHz, CDCl$_3$) δ ppm 0.84 (s, 9 H), 0.95-1.07 (m, 3 H), 1.24-1.33 (m, 2 H), 1.45-1.62 (m, 12 H), 1.66-1.77 (m, 3 H), 1.88-2.00 (m, 2 H), 2.52 (t, J=7.8 Hz, 2 H), 2.78-2.90 (m, 3 H), 3.61-3.83 (m, 2 H), 4.58-4.77 (m, 2 H), 6.50-6.54

(m, 1 H), 6.76-6.81 (m, 1 H), 6.91 (d, J=7.8 Hz, 1 H), 7.11-7.20 (m, 1 H), 7.43-7.48 (m, 1 H), 7.50-7.58 (m, 2 H).
LCMS retention time: 6.25 min. (Condition 1-2-3)
MS (ESI posi) m/z: 583[M+H]$^+$.

Working Example 1-8

$^1$H NMR (300 MHz, CDCl$_3$) δ ppm 0.94-1.13 (m, 2 H), 1.22-1.34 (m, 2 H), 1.46-1.59 (m, 6 H), 1.61 (s, 9 H), 1.73 (br. s., 3 H), 2.52 (t, J=7.8 Hz, 2 H), 2.93 (t, J=5.8 Hz, 2 H), 3.92 (t, J=5.8 Hz, 2 H), 4.88 (s, 2 H), 6.50-6.57 (m, 1 H), 6.78 (d, J=12.4 Hz, 1 H), 6.92 (d, J=9.5 Hz, 1 H), 7.42-7.60 (m, 3 H), 7.69 (s, 1 H), 7.94 (s, 1 H).
LCMS retention time: 1.03 min. (Condition 4-1)
MS (ESI posi) m/z: 567[M+H]$^+$.

The structures of the compounds of Working Examples 1-2 to 1-8 are shown in Tables 17-1 and 17-2.

TABLE 17-1

| Working Ex. | Structure |
|---|---|
| 1-2 | 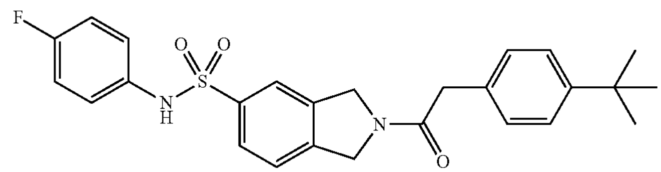 [SMILES: CC(C)(C)c1ccc(CC(=O)N2Cc3ccc(S(=O)(=O)Nc4ccc(F)cc4)cc3C2)cc1] |
| 1-3 | 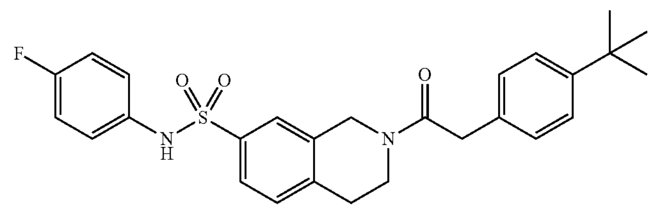 [SMILES: CC(C)(C)c1ccc(CC(=O)N2CCc3ccc(S(=O)(=O)Nc4ccc(F)cc4)cc3C2)cc1] |

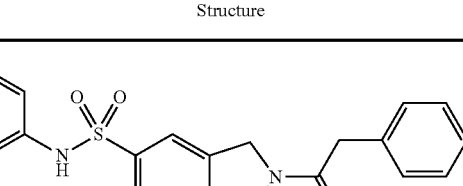

TABLE 17-2

| Working Ex. | Structure |
|---|---|
| 1-4 | 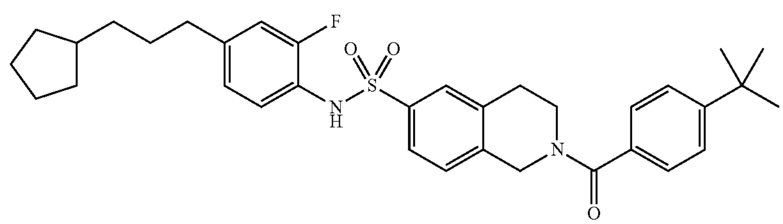 [SMILES: CC(C)(C)c1ccc(C(=O)N2CCc3cc(S(=O)(=O)Nc4ccc(CCCC5CCCC5)cc4F)ccc3C2)cc1] |
| 1-5 | 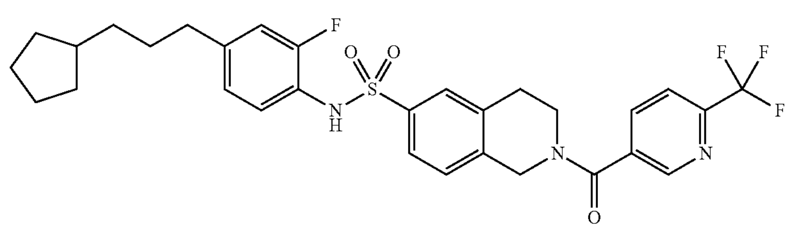 [SMILES: O=C(c1ccc(C(F)(F)F)nc1)N1CCc2cc(S(=O)(=O)Nc3ccc(CCCC4CCCC4)cc3F)ccc2C1] |
| 1-6 | 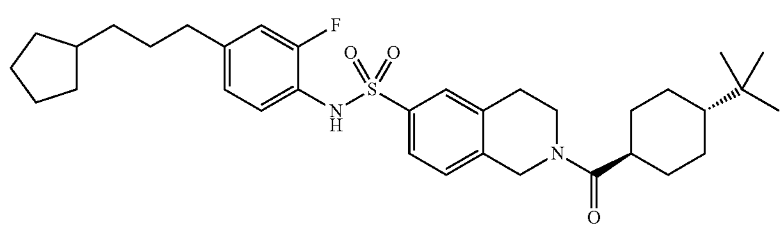 [SMILES: CC(C)(C)[C@H]1CC[C@H](C(=O)N2CCc3cc(S(=O)(=O)Nc4ccc(CCCC5CCCC5)cc4F)ccc3C2)CC1] |

| Working Ex. | Structure |
|---|---|
| 1-7 | 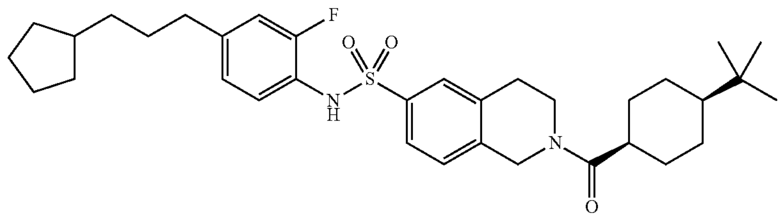 [SMILES: CC(C)(C)[C@H]1CC[C@@H](C(=O)N2CCc3cc(S(=O)(=O)Nc4ccc(CCCC5CCCC5)cc4F)ccc3C2)CC1] |
| 1-8 | 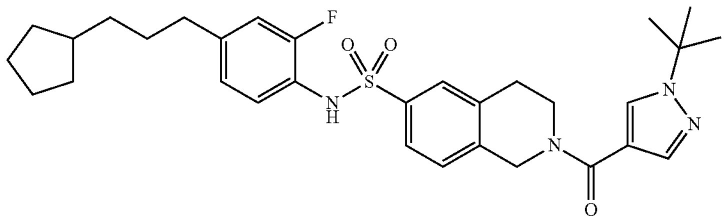 [SMILES: CC(C)(C)n1cc(C(=O)N2CCc3cc(S(=O)(=O)Nc4ccc(CCCC5CCCC5)cc4F)ccc3C2)cn1] |

Working Example 2-1

2-[2-(4-tert-Butylphenyl)ethyl]-N-(4-fluorophenyl)-1,2,3,4-tetrahydroisoquinoline-6-sulfonamide

[Formula 56]

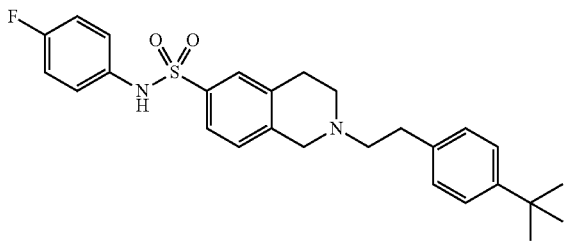

(1) A borane-tetrahydrofuran complex (0.9 mol/L tetrahydrofuran solution, 0.55 mL, 0.50 mmol) was added to a solution of the compound obtained in Working Example 1-1 (120 mg, 0.25 mmol) in tetrahydrofuran (10 mL) while cooling in ice, and the mixture was heated to 90° C. and heated to reflux for 5 hr. After cooling, 6 mol/L hydrochloric acid (6 mL) was added thereto and the mixture was heated to 100° C. and stirred for 3 hr. After cooling, the mixture was cooled in ice, 6 mol/L aqueous sodium hydroxide solution was added thereto to adjust the pH to 8 to 9, and the mixture was extracted with ethyl acetate. The organic layer was washed with brine and dried over anhydrous magnesium sulfate and then the desiccant was filtered off, followed by concentration under reduced pressure. The resulting residue was purified by NH silica gel column chromatography (chloroform only→chloroform:methanol=19:1) to afford the title compound as a colorless amorphous substance (115 mg).

$^1$ H NMR (300 MHz, CDCl$_3$) δ ppm 1.31 (s, 9 H), 2.72-2.99 (m, 8 H), 3.67-3.81 (m, 2 H), 6.37 (br. s., 1 H), 6.90-7.05 (m, 4 H), 7.09 (d, J=8.1 Hz, 1 H), 7.13-7.20 (m, 2 H), 7.30-7.35 (m, 2 H), 7.39-7.45 (m, 1 H), 7.46-7.50 (m, 1 H).

MS ESI/APCI Dual posi: 467[M+H]$^+$.

(2) To a solution of the title compound in ethyl acetate (4 mL) was added 4 mol/L hydrogen chloride-ethyl acetate (1 mL), and the mixture was stirred at room temperature overnight. The resulting precipitate was collected by filtration to afford the monohydrochloride of the title compound as a colorless powder (115 mg).

MS ESI/APCI Dual posi: 467[M+H]$^+$.

Compounds 1-2, 1-3 and 1-8 as obtained in Working Example 1 were used to afford the compounds of Working Examples 2-2 to 2-4 in accordance with the process of Working Example 2-1.

Working Example 2-2

$^1$ H NMR (600 MHz, DMSO-d$_6$) δ ppm 1.27 (s, 9 H), 2.95-3.02 (m, 2 H), 3.49-3.65 (m, 2 H), 4.51-4.70 (m, 2 H), 4.78-4.98 (m, 2 H), 7.04-7.15 (m, 4 H), 7.22 (d, J=8.3 Hz, 2 H), 7.36 (d, J=8.3 Hz, 2 H), 7.53-7.62 (m, 1 H), 7.70-7.76 (m, 1 H), 7.79 (s, 1 H), 10.38 (s, 1 H), 11.32 (br. s., 1 H).

MS ESI/APCI Dual posi: 453[M+H]$^+$.

Working Example 2-3

MS ESI/APCI Dual posi: 467[M+H]$^+$.

Working Example 2-4

$^1$ H NMR (600 MHz, DMSO-d$_6$) δ ppm 0.95-1.07 (m, 2 H), 1.18-1.29 (m, 2 H), 1.39-1.58 (m, 15 H), 1.65-1.77 (m, 3 H), 3.10-3.28 (m, 5 H), 3.62-3.72 (m, 1 H), 4.25-4.41 (m, 3 H), 4.45-4.48 (m, 1 H), 6.91-7.01 (m, 2 H), 7.09-7.15 (m, 1 H), 7.42 (d, J=8.3 Hz, 1 H), 7.54-7.68 (m, 3 H), 8.01 (s, 1 H), 10.10 (br. s., 1 H).

LCMS retention time: 1.89 min. (Condition 3)

MS ESI/APCI Dual posi: 553[M+H]$^+$.

The compounds of Working Examples 2-5 to 2-11 were obtained by using the corresponding compounds obtained in Reference Example 3 and the corresponding carboxylic acids in accordance with the processes of Working Examples 1-1 and 2-1. It is to be noted that the aforementioned corresponding carboxylic acids are either available by the methods of Reference Examples as shown herein or methods described in publications or commercially available.

Working Example 2-5

$^1$H NMR (600 MHz, DMSO-d$_6$) δ ppm 0.94-1.07 (m, 2 H), 1.18-1.28 (m, 2 H), 1.36-1.59 (m, 12 H), 1.62-1.77 (m, 3 H), 3.06-3.28 (m, 5 H), 3.60-3.70 (m, 1 H), 4.24-4.59 (m, 5 H), 6.91-7.02 (m, 2 H), 7.08-7.14 (m, 1 H), 7.42 (d, J=8.3 Hz, 1 H), 7.54-7.67 (m, 3 H), 7.96 (s, 1 H), 10.10 (s, 1 H).
LCMS retention time: 1.89 min. (Condition 3)
MS ESI/APCI Dual posi: 539[M+H]$^+$.

Working Example 2-6

$^1$H NMR (600 MHz, DMSO-d$_6$) δ ppm 0.84 (d, J=6.6 Hz, 6 H), 0.95-1.07 (m, 2 H), 1.20-1.28 (m, 2 H), 1.40-1.59 (m, 6 H), 1.64-1.77 (m, 3 H), 2.10 (dt, J=13.6, 6.8 Hz, 1 H), 3.06-3.27 (m, 3 H), 3.61-3.65 (m, 1 H), 3.80-4.10 (m, 4 H), 4.27-4.36 (m, 3 H), 4.40-4.47 (m, 1 H), 6.92-7.02 (m, 2 H), 7.08-7.14 (m, 1 H), 7.40 (d, J=8.3 Hz, 1 H), 7.55-7.61 (m, 2 H), 7.65 (s, 1 H), 7.92 (s, 1 H), 10.10 (s, 1 H).
LCMS retention time: 1.93 min. (Condition 3)
MS ESI/APCI Dual posi: 553[M+H]$^+$.

Working Example 2-7

$^1$H NMR (600 MHz, DMSO-d$_6$) δ ppm 0.34-0.41 (m, 2 H), 0.50-0.58 (m, 2 H), 0.94-1.07 (m, 2 H), 1.19-1.28 (m, 3 H), 1.40-1.59 (m, 6 H), 1.65-1.77 (m, 3 H), 3.06-3.29 (m, 5 H), 3.64-3.68 (m, 1 H), 4.00 (d, J=7.0 Hz, 2 H), 4.27-4.53 (m, 4 H), 6.91-7.02 (m, 2 H), 7.09-7.15 (m, 1 H), 7.41 (d, J=8.3 Hz, 1 H), 7.55-7.66 (m, 3 H), 7.98 (s, 1 H), 10.10 (s, 1 H).
LCMS retention time: 1.91 min. (Condition 3)
MS ESI/APCI Dual posi: 551[M+H]$^+$.

Working Example 2-8

$^1$H NMR (600 MHz, DMSO-d$_6$) δ ppm 0.76-0.88 (m, 3 H), 0.94-1.07 (m, 2 H), 1.19-1.28 (m, 2 H), 1.39-1.59 (m, 6 H), 1.63-1.86 (m, 5 H), 3.04-3.28 (m, 5 H), 3.60-3.68 (m, 1 H), 4.04-4.13 (m, 2 H), 4.26-4.38 (m, 3 H), 4.41-4.50 (m, 1 H), 6.91-7.01 (m, 2 H), 7.08-7.14 (m, 1 H), 7.38-7.43 (m, 1 H), 7.55-7.69 (m, 3 H), 7.93 (s, 1 H), 10.10 (s, 1 H).
LCMS retention time: 1.89 min. (Condition 3)
MS ESI/APCI Dual posi: 539[M+H]$^+$.

Working Example 2-9

$^1$H NMR (600 MHz, DMSO-d$_6$) δ ppm 0.81-0.86 (m, 3 H), 0.96-1.06 (m, 2 H), 1.20-1.27 (m, 2 H), 1.40-1.58 (m, 6 H), 1.65-1.83 (m, 5 H), 3.07-3.28 (m, 5 H), 3.63-3.67 (m, 1 H), 4.06-4.13 (m, 2 H), 4.29-4.37 (m, 3 H), 4.41-4.50 (m, 1 H), 6.90-7.03 (m, 2 H), 7.08-7.15 (m, 1 H), 7.37-7.44 (m, 1 H), 7.53-7.70 (m, 3 H), 7.93 (s, 1 H), 10.10 (s, 1 H).
LCMS retention time: 1.90 min. (Condition 3)
MS ESI/APCI Dual posi: 551[M+H]$^+$.

Working Example 2-10

$^1$H NMR (600 MHz, DMSO-d$_6$) δ ppm 1.15-1.24 (m, 2 H), 1.53 (s, 9 H), 1.54-1.72 (m, 3 H), 3.06-3.30 (m, 7 H), 3.63-3.67 (m, 1 H), 3.81 (dd, J=11.4, 2.9 Hz, 2 H), 3.96 (t, J=6.4 Hz, 2 H), 4.26-4.40 (m, 3 H), 4.41-4.50 (m, 1 H), 6.67-6.82 (m, 2 H), 7.02-7.08 (m, 1 H), 7.42 (d, J=8.3 Hz, 1 H), 7.52-7.59 (m, 2 H), 7.66 (s, 1 H), 8.02 (s, 1 H), 9.90 (s, 1 H).
LCMS retention time: 1.55 min. (Condition 3)
MS ESI/APCI Dual posi: 571[M+H]$^+$.

Working Example 2-11

$^1$H NMR (600 MHz, DMSO-d$_6$) δ ppm 0.96-1.06 (m, 2 H), 1.20-1.28 (m, 2 H), 1.37 (s, 9 H), 1.41-1.58 (m, 6 H), 1.65-1.76 (m, 3 H), 3.09-3.30 (m, 4 H), 3.33-3.99 (m, 6 H), 4.39-4.52 (m, 1 H), 4.67-4.81 (m, 1 H), 6.92-7.03 (m, 2 H), 7.09-7.16 (m, 1 H), 7.34 (s, 1 H), 7.36-7.42 (m, 1 H), 7.57-7.66 (m, 2 H), 10.11 (s, 1 H).
LCMS retention time: 0.98 min. (Condition 2)
MS (ESI posi) m/z: 584[M+H]$^+$.

The structures of the compounds of Working Examples 2-2 to 2-11 are shown in Tables 18-1 and 18-2.

TABLE 18-1

| Working Ex. | Structure |
|---|---|
| 2-2 | 4-fluorophenyl-NH-SO$_2$-isoindoline-N-CH$_2$CH$_2$-(4-tert-butylphenyl) |
| 2-3 | 4-fluorophenyl-NH-SO$_2$-(1,2,3,4-tetrahydroisoquinolin-7-yl)-N-CH$_2$CH$_2$-(4-tert-butylphenyl) |

TABLE 18-2
| Working Ex. | Structure |
|---|---|
| 2-4 | 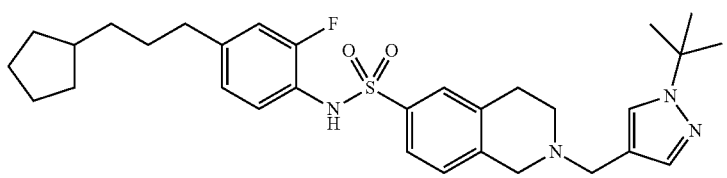 [SMILES: CC(C)(C)n1cc(CN2CCc3cc(S(=O)(=O)Nc4ccc(CCCC5CCCC5)cc4F)ccc3C2)cn1] |
| 2-5 | 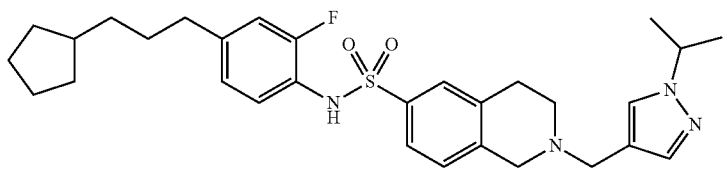 [SMILES: CC(C)n1cc(CN2CCc3cc(S(=O)(=O)Nc4ccc(CCCC5CCCC5)cc4F)ccc3C2)cn1] |
| 2-6 | 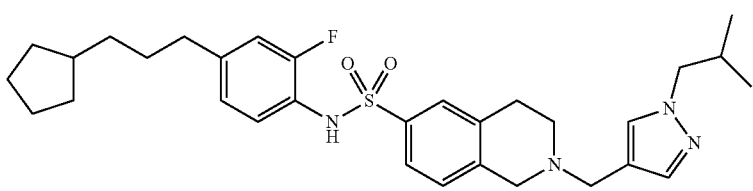 [SMILES: CC(C)Cn1cc(CN2CCc3cc(S(=O)(=O)Nc4ccc(CCCC5CCCC5)cc4F)ccc3C2)cn1] |
| 2-7 | 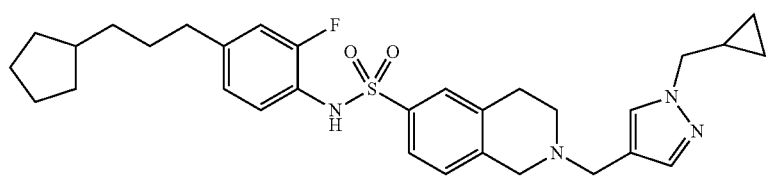 [SMILES: O=S(=O)(Nc1ccc(CCCC2CCCC2)cc1F)c1ccc2c(c1)CCN(Cc1cnn(CC3CC3)c1)C2] |
| 2-8 | 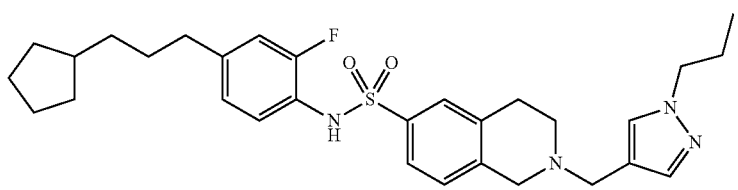 [SMILES: CCCn1cc(CN2CCc3cc(S(=O)(=O)Nc4ccc(CCCC5CCCC5)cc4F)ccc3C2)cn1] |
| 2-9 | 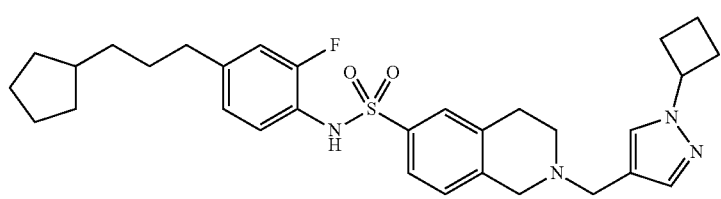 [SMILES: O=S(=O)(Nc1ccc(CCCC2CCCC2)cc1F)c1ccc2c(c1)CCN(Cc1cnn(C3CCC3)c1)C2] |
| 2-10 | 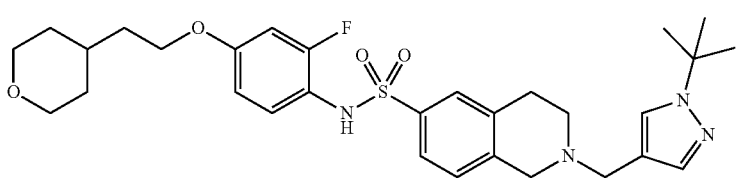 [SMILES: CC(C)(C)n1cc(CN2CCc3cc(S(=O)(=O)Nc4ccc(OCCC5CCOCC5)cc4F)ccc3C2)cn1] |
| 2-11 | 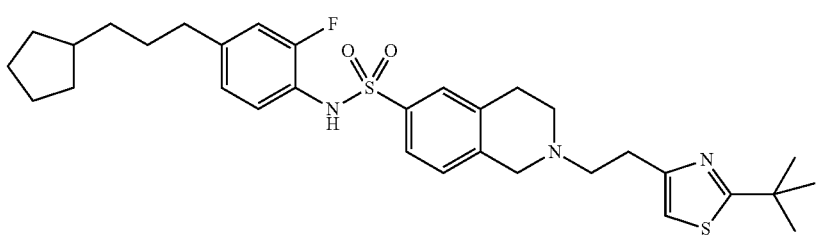 [SMILES: CC(C)(C)c1nc(CCN2CCc3cc(S(=O)(=O)Nc4ccc(CCCC5CCCC5)cc4F)ccc3C2)cs1] |

Working Example 3-1

N-(4-Fluorophenyl)-2-{2-[4-(trifluoromethyl)phenyl]ethyl}-1,2,3,4-tetrahydroisoquinoline-6-sulfonamide

[Formula 57]

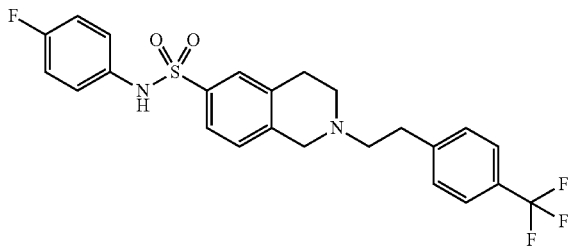

The compound obtained in Reference Example 3-1 (50 mg, 0.16 mmol) and 4-(trifluoromethyl)phenyl acetic acid (37 mg, 0.18 mmol) were dissolved in N,N-dimethylformamide (0.80 mL), and O-(7-azabenzotriazol-1-yl)-N,N,N',N'-tetramethyl uronium hexafluorophosphate (68 mg, 0.18 mmol) was added thereto, followed by stirring at room temperature for 19 hr. Water and ethyl acetate were added to the reaction mixture for separation into phases. The organic layer was washed with saturated aqueous sodium hydrogen carbonate solution and the solvent was distilled off under reduced pressure. The resulting residue was dissolved in tetrahydrofuran (2.0 mL), a borane-tetrahydrofuran complex (0.9 mol/L tetrahydrofuran solution, 0.257 mL, 0.285 mmol) was added thereto, and the mixture was heated at 95° C. for 3 hr. The reaction mixture was concentrated under reduced pressure, methanol (1 mL) and 6 mol/L hydrochloric acid (1 mL) were added thereto, and the mixture was heated at 95° C. for 6 hr. Potassium carbonate was added to the reaction mixture to adjust the pH to 8, the mixture was diluted with dimethyl sulfoxide and then filtered, and the filtrate was purified by HPLC to afford the trifluoroacetate of the title compound as a colorless powder (26 mg).

LCMS retention time: 3.82 min. (Condition 1-1-3)
MS (ESI posi) m/z: 479[M+H]$^+$.

The compounds of Working Examples 3-2 to 3-39 were obtained by using the corresponding compounds obtained in Reference Example 3 and the corresponding commercially available carboxylic acids in accordance with the process of Working Example 3-1.

Working Example 3-2

LCMS retention time: 4.32 min. (Condition 1-1-3)
MS (ESI posi) m/z: 495[M+H]$^+$.

Working Example 3-3

LCMS retention time: 3.93 min. (Condition 1-1-3)
MS (ESI posi) m/z: 493[M+H]$^+$.

Working Example 3-4

LCMS retention time: 3.72 min. (Condition 1-1-3)
MS (ESI posi) m/z: 465[M+H]$^+$.

Working Example 3-5

LCMS retention time: 3.83 min. (Condition 1-1-3)
MS (ESI posi) m/z: 479[M+H]$^+$.

Working Example 3-6

LCMS retention time: 3.75 min. (Condition 1-1-3)
MS (ESI posi) m/z: 479[M+H]$^+$.

Working Example 3-7

LCMS retention time: 3.91 min. (Condition 1-1-3)
MS (ESI posi) m/z: 495[M+H]$^+$.

Working Example 3-8

LCMS retention time: 3.51 min. (Condition 1-1-3)
MS (ESI posi) m/z: 441[M+H]$^+$.

Working Example 3-9

LCMS retention time: 3.50 min. (Condition 1-1-3)
MS (ESI posi) m/z: 453[M+H]$^+$.

Working Example 3-10

LCMS retention time: 3.97 min. (Condition 1-1-3)
MS (ESI posi) m/z: 453[M+H]$^+$.

Working Example 3-11

LCMS retention time: 2.85 min. (Condition 1-1-3)
MS (ESI posi) m/z: 488[M+H]$^+$.

Working Example 3-12

LCMS retention time: 3.63 min. (Condition 1-1-3)
MS (ESI posi) m/z: 425[M+H]$^+$.

Working Example 3-13

LCMS retention time: 3.67 min. (Condition 1-1-3)
MS (ESI posi) m/z: 445[M+H]$^+$.

Working Example 3-14

LCMS retention time: 3.98 min. (Condition 1-1-3)
MS (ESI posi) m/z: 487[M+H]$^+$.

Working Example 3-15

LCMS retention time: 4.57 min. (Condition 1-1-3)
MS (ESI posi) m/z: 503[M+H]$^+$.

Working Example 3-16

LCMS retention time: 3.80 min. (Condition 1-1-3)
MS (ESI posi) m/z: 459[M+H]$^+$.

Working Example 3-17

LCMS retention time: 3.28 min. (Condition 1-1-3)
MS (ESI posi) m/z: 474[M+H]$^+$.

Working Example 3-18

LCMS retention time: 3.63 min. (Condition 1-1-3)
MS (ESI posi) m/z: 516[M+H]$^+$.

Working Example 3-19

LCMS retention time: 3.65 min. (Condition 1-1-3)
MS (ESI posi) m/z: 546[M+H]$^+$.

Working Example 3-20

LCMS retention time: 3.88 min. (Condition 1-1-3)
MS (ESI posi) m/z: 560[M+H]$^+$.

Working Example 3-21

LCMS retention time: 3.51 min. (Condition 1-1-3)
MS (ESI posi) m/z: 403[M+H]+.

Working Example 3-22

LCMS retention time: 3.72 min. (Condition 1-1-3)
MS (ESI posi) m/z: 417[M+H]+.

Working Example 3-23

LCMS retention time: 3.95 min. (Condition 1-1-3)
MS (ESI posi) m/z: 431[M+H]+.

Working Example 3-24

LCMS retention time: 3.57 min. (Condition 1-1-3)
MS (ESI posi) m/z: 480[M+H]+.

Working Example 3-25

LCMS retention time: 3.42 min. (Condition 1-1-3)
MS (ESI posi) m/z: 481[M+M]+.

Working Example 3-26

LCMS retention time: 4.19 min. (Condition 1-1-3)
MS (ESI posi) m/z: 481[M+H]+.

Working Example 3-27

LCMS retention time: 4.15 min. (Condition 1-1-3)
MS (ESI posi) m/z: 493[M+H]+.

Working Example 3-28

LCMS retention time: 4.26 min. (Condition 1-1-3)
MS (ESI posi) m/z: 507[M+H]+.

Working Example 3-29

LCMS retention time: 4.36 min. (Condition 1-1-3)
MS (ESI posi) m/z: 521[M+H]+.

Working Example 3-30

LCMS retention time: 4.49 min. (Condition 1-1-3)
MS (ESI posi) m/z: 535[M+H]+.

Working Example 3-31

LCMS retention time: 3.58 min. (Condition 1-1-3)
MS (ESI posi) m/z: 463[M+H]+.

Working Example 3-32

LCMS retention time: 3.77 min. (Condition 1-1-3)
MS (ESI posi) m/z: 513[M+H]+.

Working Example 3-33

LCMS retention time: 3.67 min. (Condition 1-1-3)
MS (ESI posi) m/z: 496[M+H]+.

Working Example 3-34

LCMS retention time: 3.67 min. (Condition 1-1-3)
MS (ESI posi) m/z: 474[M+H]+.

Working Example 3-35

LCMS retention time: 4.62 min. (Condition 1-1-3)
MS (ESI posi) m/z: 579[M+H]+.

Working Example 3-36

LCMS retention time: 4.65 min. (Condition 1-1-3)
MS (ESI posi) m/z: 597[M+H]+.

Working Example 3-37

LCMS retention time: 4.80 min. (Condition 1-1-3)
MS (ESI posi) m/z: 647[M+H]+.

Working Example 3-38

LCMS retention time: 4.66 min. (Condition 1-1-3)
MS (ESI posi) m/z: 597[M+H]+.

Working Example 3-39

LCMS retention time: 5.90 min. (Condition 1-1-3)
MS (ESI posi) m/z: 535[M+H]+.

The structures of the compounds of Working Examples 3-2 to 3-39 are shown in Tables 19-1 to 19-3.

TABLE 19-1

| Working Ex. | Structure |
|---|---|
| 3-2 | 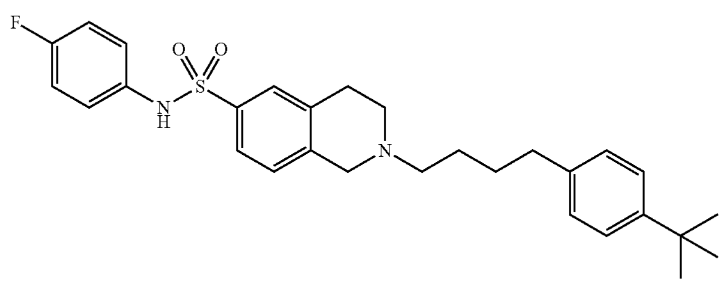 [SMILES: CC(C)(C)c1ccc(CCCCN2CCc3cc(S(=O)(=O)Nc4ccc(F)cc4)ccc3C2)cc1] |

TABLE 19-1-continued
| Working Ex. | Structure |
|---|---|
| 3-3 | 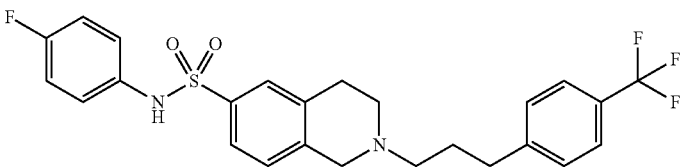 [SMILES: O=S(=O)(Nc1ccc(F)cc1)c1ccc2c(c1)CCN(CCCc1ccc(C(F)(F)F)cc1)C2] |
| 3-4 | 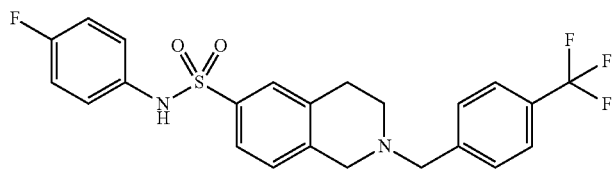 |
| 3-5 | 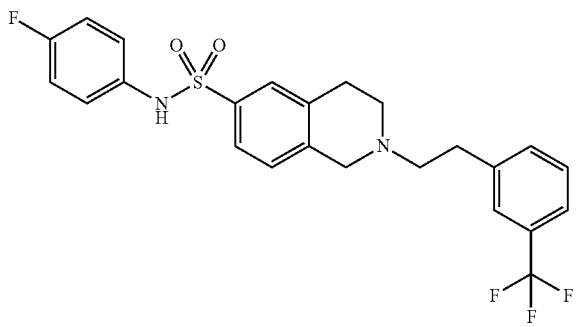 [SMILES: O=S(=O)(Nc1ccc(F)cc1)c1ccc2c(c1)CCN(CCc1cccc(C(F)(F)F)c1)C2] |
| 3-6 | 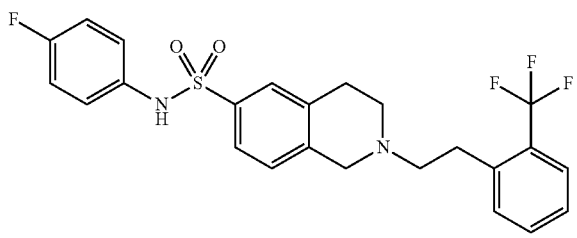 [SMILES: O=S(=O)(Nc1ccc(F)cc1)c1ccc2c(c1)CCN(CCc1ccccc1C(F)(F)F)C2] |
| 3-7 | 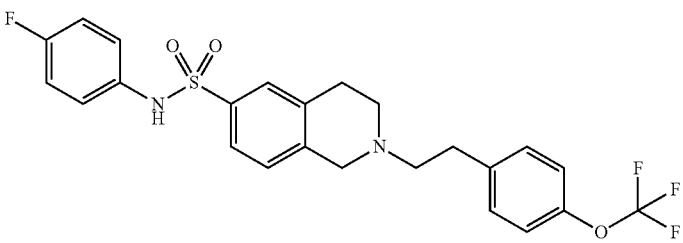 [SMILES: O=S(=O)(Nc1ccc(F)cc1)c1ccc2c(c1)CCN(CCc1ccc(OC(F)(F)F)cc1)C2] |
| 3-8 | 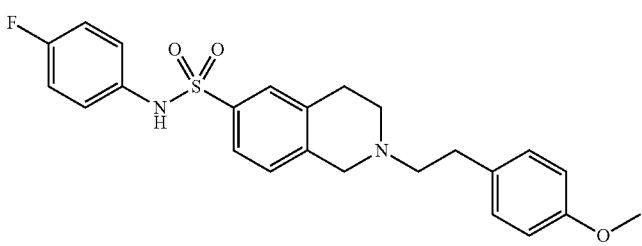 [SMILES: COc1ccc(CCN2CCc3cc(S(=O)(=O)Nc4ccc(F)cc4)ccc3C2)cc1] |

TABLE 19-1-continued
| Working Ex. | Structure |
|---|---|
| 3-9 | 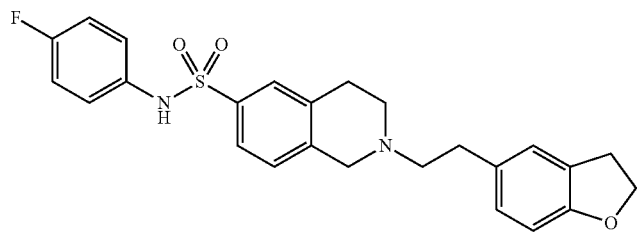 [SMILES: O=S(=O)(Nc1ccc(F)cc1)c1ccc2c(c1)CCN(CCc1ccc3c(c1)CCO3)C2] |
| 3-10 | 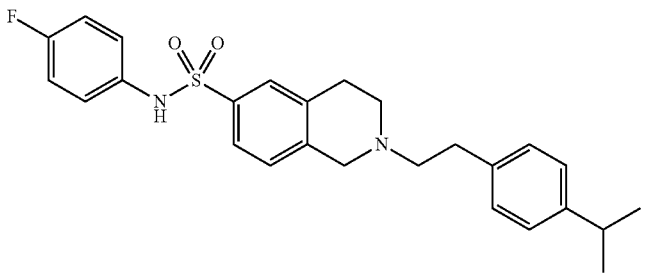 [SMILES: CC(C)c1ccc(CCN2CCc3cc(S(=O)(=O)Nc4ccc(F)cc4)ccc3C2)cc1] |
| 3-11 | 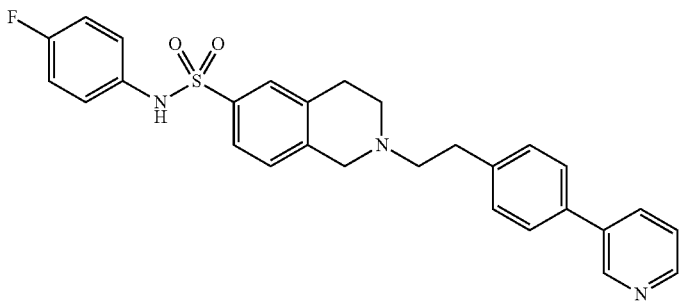 [SMILES: O=S(=O)(Nc1ccc(F)cc1)c1ccc2c(c1)CCN(CCc1ccc(-c3cccnc3)cc1)C2] |
| 3-12 | 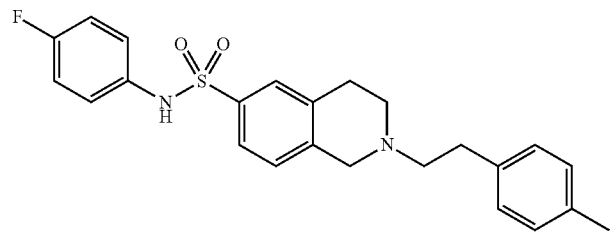 [SMILES: Cc1ccc(CCN2CCc3cc(S(=O)(=O)Nc4ccc(F)cc4)ccc3C2)cc1] |
| 3-13 | 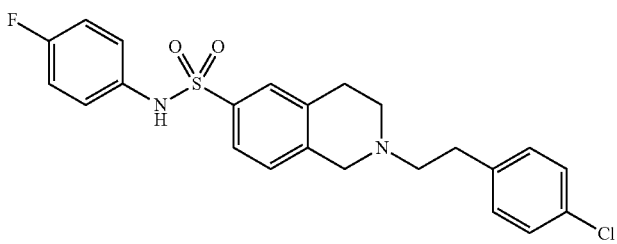 [SMILES: O=S(=O)(Nc1ccc(F)cc1)c1ccc2c(c1)CCN(CCc1ccc(Cl)cc1)C2] |

TABLE 19-1-continued
| Working Ex. | Structure |
|---|---|
| 3-14 | 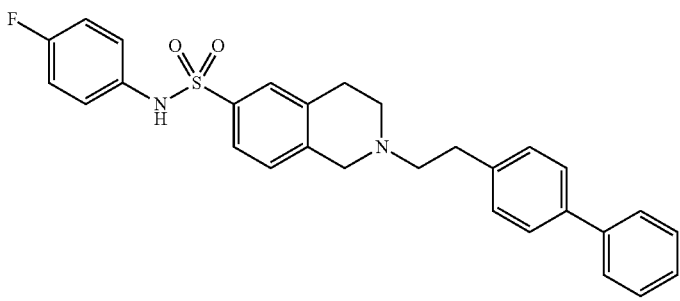 [SMILES: O=S(=O)(Nc1ccc(F)cc1)c1ccc2c(c1)CCN(CCc1ccc(-c3ccccc3)cc1)C2] |
| 3-15 | 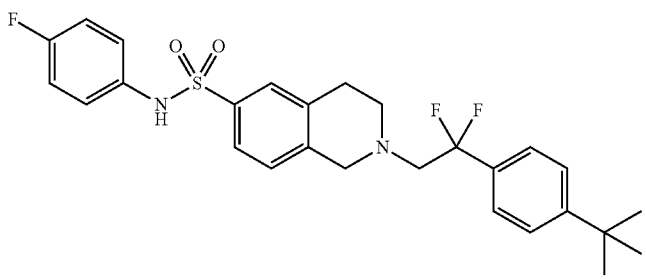 [SMILES: CC(C)(C)c1ccc(C(F)(F)CN2CCc3cc(S(=O)(=O)Nc4ccc(F)cc4)ccc3C2)cc1] |
TABLE 19-2
| Working Ex. | Structure |
|---|---|
| 3-16 | 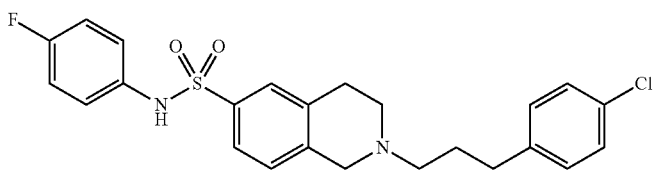 [SMILES: O=S(=O)(Nc1ccc(F)cc1)c1ccc2c(c1)CCN(CCCc1ccc(Cl)cc1)C2] |
| 3-17 | 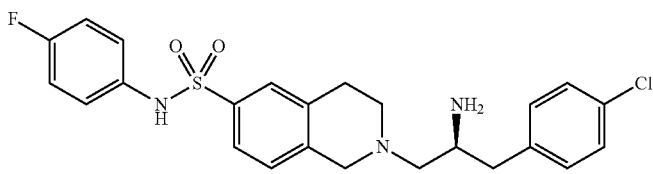 [SMILES: N[C@@H](Cc1ccc(Cl)cc1)CN1CCc2cc(S(=O)(=O)Nc3ccc(F)cc3)ccc2C1] |
| 3-18 | 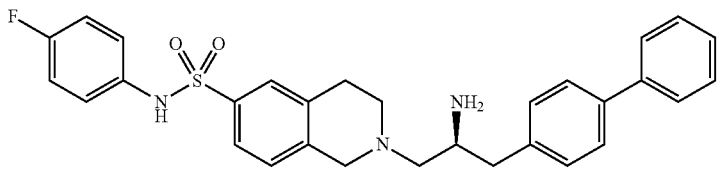 [SMILES: N[C@@H](Cc1ccc(-c2ccccc2)cc1)CN1CCc2cc(S(=O)(=O)Nc3ccc(F)cc3)ccc2C1] |
| 3-19 | 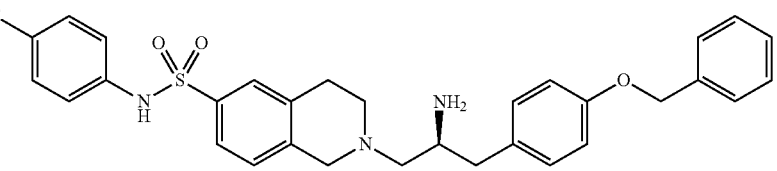 |

TABLE 19-2-continued
| Working Ex. | Structure |
|---|---|
| 3-20 | 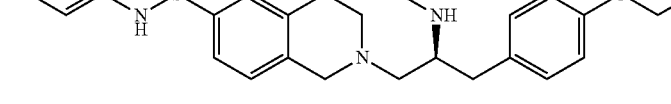 |
| 3-21 | 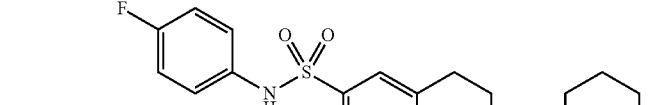 |
| 3-22 | 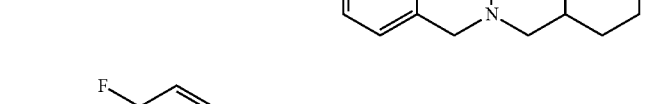 |
| 3-23 | 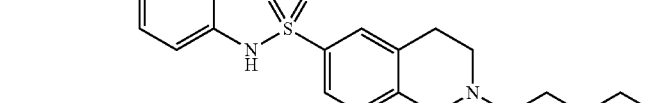 |
| 3-24 | 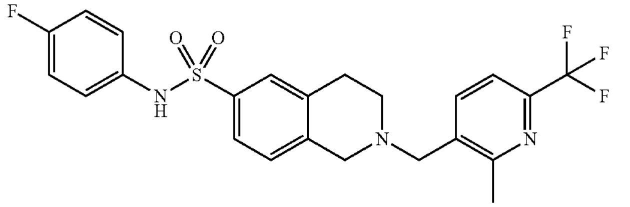 [SMILES: Cc1nc(C(F)(F)F)ccc1CN1CCc2cc(S(=O)(=O)Nc3ccc(F)cc3)ccc2C1] |
| 3-25 | 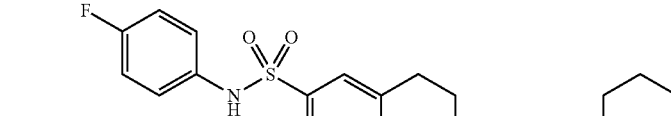 |
| 3-26 | 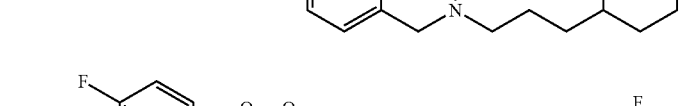 |

TABLE 19-2-continued
| Working Ex. | Structure |
|---|---|
| 3-27 | 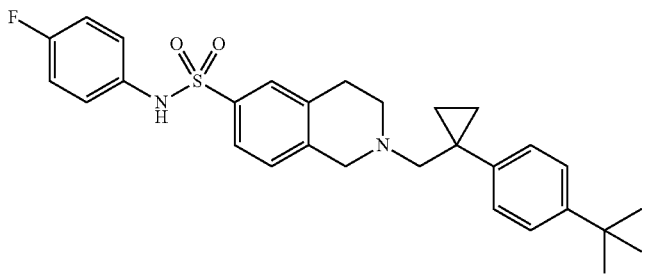 [SMILES: CC(C)(C)c1ccc(C2(CN3CCc4cc(S(=O)(=O)Nc5ccc(F)cc5)ccc4C3)CC2)cc1] |
| 3-28 | 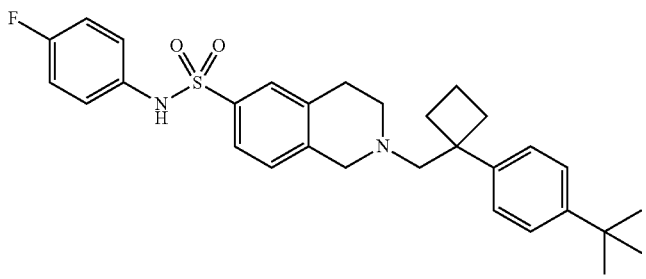 [SMILES: CC(C)(C)c1ccc(C2(CN3CCc4cc(S(=O)(=O)Nc5ccc(F)cc5)ccc4C3)CCC2)cc1] |
| 3-29 | 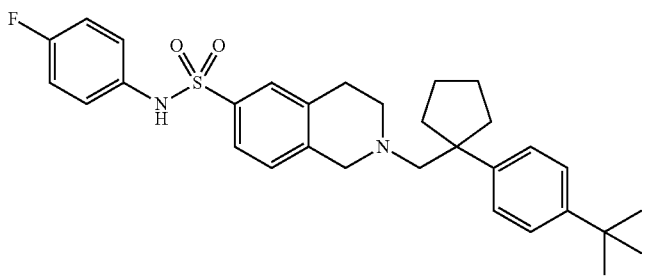 [SMILES: CC(C)(C)c1ccc(C2(CN3CCc4cc(S(=O)(=O)Nc5ccc(F)cc5)ccc4C3)CCCC2)cc1] |
TABLE 19-3
| Working Ex. | Structure |
|---|---|
| 3-30 | 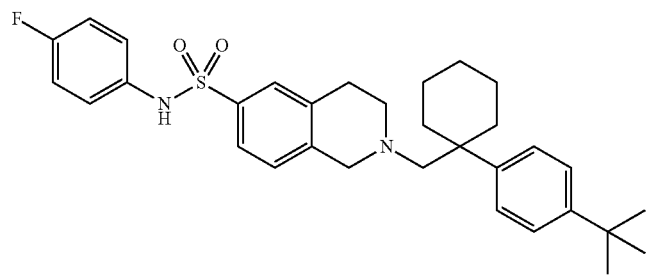 [SMILES: CC(C)(C)c1ccc(C2(CN3CCc4cc(S(=O)(=O)Nc5ccc(F)cc5)ccc4C3)CCCCC2)cc1] |
| 3-31 | 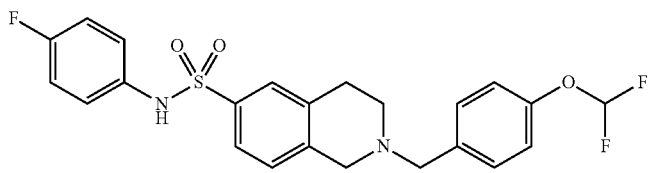 [SMILES: O=S(=O)(Nc1ccc(F)cc1)c1ccc2c(c1)CCN(Cc1ccc(OC(F)F)cc1)C2] |

TABLE 19-3-continued

| Working Ex. | Structure |
|---|---|
| 3-32 | (structure) |
| 3-33 | (structure) |
| 3-34 | (structure) |
| 3-35 | (structure) |
| 3-36 | (structure) |
| 3-37 | (structure) |

TABLE 19-3-continued

| Working Ex. | Structure |
|---|---|
| 3-38 | (structure shown) |
| 3-39 | (structure shown) |

Working Example 4-1

2-[(4-tert-Butylphenyl)acetyl]-N-[4-(2-cyclohexylethoxy)-2-fluorophenyl]-1,2,3,4-tetrahydroisoquinoline-6-sulfonamide

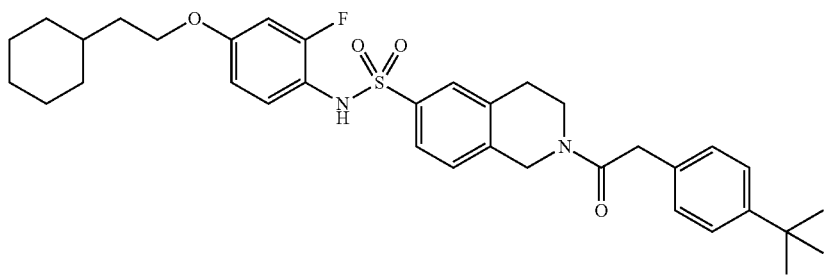

[Formula 58]

(1) Compound 3-25 as obtained in Reference Example 3 (468 mg, 0.80 mmol) and the compound obtained in Reference Example 12-1(1) (132 mg, 0.88 mmol) were dissolved in N,N-dimethylformamide (5 mL), and 1-hydroxybenzotriazole monohydrate (207 mg, 1.04 mmol) was added thereto. Thereafter, 1-ethyl-3-(3-dimethylaminopropyl)carbodiimide hydrochloride (199 mg, 1.04 mmol) was added thereto and the mixture was stirred at room temperature for 19 hr. The reaction mixture was concentrated under reduced pressure and ethyl acetate and water were added thereto for separation into phases. The organic layer was washed with saturated aqueous sodium hydrogen carbonate solution and saturaed brine and dried over anhydrous magnesium sulfate and the solvent was distilled off under reduced pressure. The resulting residue was purified by silica gel column chromatography (hexane only→hexane:ethyl acetate=3:7) to afford 2-[(4-tert-butylphenyl)acetyl]-N-[4-(2-cyclohexylethoxy)-2-fluorophenyl]-N-(2,4-dimethoxybenzyl)-1,2,3,4-tetrahydroisoquinoline-6-sulfonamide as a colorless powder (530 mg).

(2) 2-[(4-tert-Butylphenyl)acetyl]-N-[4-(2-cyclohexylethoxy)-2-fluorophenyl]-N-(2,4-dimethoxybenzyl)-1,2,3,4-tetrahydroisoquinoline-6-sulfonamide obtained (500 mg, 0.66 mmol) was dissolved in chloroform (1.8 mL), and trifluoroacetic acid (1.8 mL) was added thereto, followed by stirring at room temperature for 1 hr. The reaction mixture was concentrated under reduced pressure and the residue was washed with hexane and ethyl acetate to afford the title compound as a colorless powder (270 mg).

$^1$H NMR (300 MHz, CDCl$_3$) δ ppm 0.80-1.01 (m, 2 H), 1.03-1.31 (m, 12 H), 1.32-1.48 (m, 1 H), 1.49-1.80 (m, 7 H), 2.69-2.86 (m, 2 H), 3.60-4.01 (m, 6 H), 4.65-4.83 (m, 2 H), 6.63-6.71 (m, 1 H), 6.73-6.83 (m, 1 H), 6.96-7.09 (m, 1 H), 7.10-7.20 (m, 2 H), 7.22-7.52 (m, 5 H), 9.69-9.85 (m, 1 H).

LCMS retention time: 6.13 min. (Condition 1-1-3)

MS (ESI posi) m/z: 607[M+H]$^+$.

Working Example 5-1

2-[2-(4-tert-Butylphenyl)ethyl]-N-[4-(2-cyclohexylethoxy)-2-fluorophenyl]-1,2,3,4-tetrahydroisoquinoline-6-sulfonamide

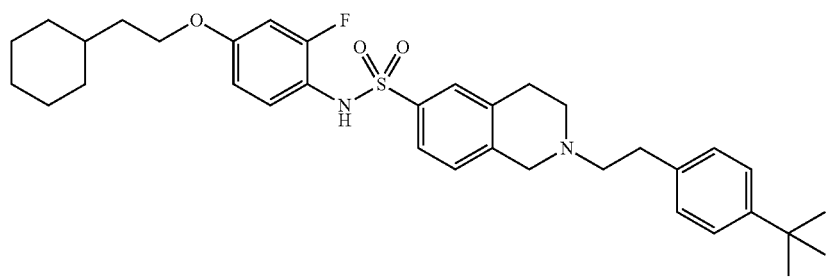

[Formula 59]

(1) The compound obtained in Working Example 4-1 (250 mg, 0.41 mmol) was dissolved in tetrahydrofuran (20 mL), a borane-tetrahydrofuran complex (0.9 mol/L tetrahydrofuran solution, 0.742 mL, 0.824 mmol) was added thereto at room temperature, and the mixture was heated to reflux at 95° C. for 3 hr. A borane-tetrahydrofuran complex (0.9 mol/L tetrahydrofuran solution, 0.742 mL, 0.824 mmol) was further added thereto and the mixture was heated to reflux at 95° C. for 3 hr. To the reaction mixture was added 6 mol/L hydrochloric acid (12 mL) and the mixture was heated to reflux at 95° C. for 6 hr. To the reaction mixture were added 6 mol/L aqueous sodium hydroxide solution and saturated aqueous sodium hydrogen carbonate solution to adjust the pH to 8 and the mixture was extracted three times with ethyl acetate. The organic layer was concentrated under reduced pressure and the resulting residue was purified by NH silica gel column chromatography (chloroform only→chloroform:methanol=9:1) and further purified by NH silica gel column chromatography (hexane only→ethyl acetate only→chloroform only→chloroform:methanol=9:1) to afford the title compound as a colorless amorphous substance (120 mg).

(2) To a solution of the title compound in ethyl acetate (1 mL) was added 4 mol/L hydrogen chloride-ethyl acetate (0.20 mL), and the mixture was stirred at room temperature for 5 min. The solvent was distilled off under reduced pressure and the residue was suspended in ethyl acetate, collected by filtration and washed with ethyl acetate to afford the monohydrochloride of the title compound as a colorless powder (108 mg).

$^1$H NMR (600 MHz, DMSO-$d_6$) δ ppm 0.88-0.98 (m, 2 H), 1.08-1.34 (m, 4 H), 1.27 (s, 9 H), 1.36-1.46 (m, 1 H), 1.52-1.74 (m, 7 H), 3.04-3.17 (m, 3 H), 3.18-3.50 (m, 3 H), 3.75-3.84 (m, 1 H), 3.87-4.01 (m, 2 H), 4.38-4.49 (m, 1 H), 4.67-4.78 (m, 1 H), 6.66-6.74 (m, 1 H), 6.75-6.82 (m, 1 H), 7.02-7.09 (m, 1 H), 7.18-7.28 (m, 2 H), 7.32-7.44 (m, 3 H), 7.52-7.64 (m, 2 H), 9.90 (br. s, 1 H), 10.79 (br. s, 1 H).

LCMS retention time: 5.01 min. (Condition 1-1-3)
MS (ESI posi) m/z: 593[M+H]$^+$.

Compound 3-24 as obtained in Reference Example 3 was used to afford the compound of Working Example 5-2 in accordance with the processes of Examples 4-1 and 5-1.

Working Example 5-2

$^1$H NMR (600 MHz, DMSO-$d_6$) δ ppm 1.28 (s, 9 H), 3.03-3.51 (m, 10 H), 3.75-3.88 (m, 1 H), 4.39-4.53 (m, 1 H), 4.67-4.80 (m, 1 H), 6.74-6.81 (m, 1 H), 6.82-6.91 (m, 1 H), 7.18-7.27 (m, 2 H), 7.34-7.45 (m, 3 H), 7.53-7.62 (m, 2 H), 9.48 (s, 1 H), 10.89 (br. s., 1 H).

MS ESI/APCI Dual posi: 515[M+H]$^+$.

The structure of the compound of Working Example 5-2 is shown in Table 20-1.

TABLE 20-1

| Working Ex. | Structure |
|---|---|
| 5-2 | (structure shown) |

Working Example 6-1

2-[2-(4-tert-Butylphenyl)ethyl]-N-(4-fluoro-2-methoxyphenyl)-1,2,3,4-tetrahydroisoquinoline-6-sulfonamide

[Formula 60]

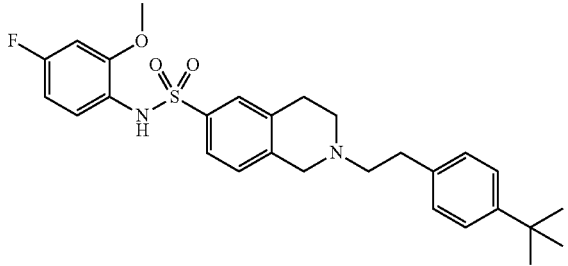 [SMILES: COc1cc(F)cc(F)c1NS(=O)(=O)c1ccc2c(c1)CCN(CCc1ccc(C(C)(C)C)cc1)C2]

(1) To a 1,2-dichloroethane suspension (50 mL) of compound 3-23 as obtained in Reference Example 3 (5.05 g, 15.0 mmol) and the compound obtained in Reference Example 7-1 (2.91 g, 16.5 mmol) was added sodium triacetoxyborohydride (4.77 g, 22.5 mmol), and the mixture was stirred at room temperature for 17 hr. Saturated aqueous sodium hydrogen carbonate solution was added to the reaction mixture and the mixture was extracted twice with chloroform. The organic layer was dried over anhydrous magnesium sulfate and filtered and then the solvent was distilled off under reduced pressure. The resulting residue was purified by silica gel column chromatography (chloroform only→chloroform:methanol=19:1) to afford the title compound as a colorless powder (6.87 g).

$^1$H NMR (600 MHz, CDCl$_3$) δ ppm 1.31 (s, 9H), 2.74-2.81 (m, 4 H), 2.83-2.92 (m, 4 H), 3.60 (s, 3 H), 3.70 (s, 2 H), 6.44-6.50 (m, 1 H), 6.58-6.64 (m, 1 H), 6.74 (s, 1 H), 7.06 (d, J=7.8 Hz, 1 H), 7.16 (d, J=8.3 Hz, 2 H), 7.32 (d, J=8.3 Hz, 2 H), 7.42-7.50 (m, 3 H).

MS ESI/APCI Dual posi: 497[M+H]$^+$.

(2) A suspension of the title compound in ethyl acetate (21 mL) was dissolved at 77° C. To this solution was added 4 mol/L hydrogen chloride-ethyl acetate (20 mL), and the mixture was stirred at room temperature for 16 hr. The resulting precipitate was collected by filtration and washed with ethyl acetate to afford the monohydrochloride of the title compound as a colorless powder (5.71 g).

$^1$H NMR (600 MHz, DMSO-d$_6$) δ ppm 1.27 (s, 9 H), 3.05-3.17 (m, 3 H), 3.20-3.54 (m, 7 H), 3.71-3.85 (m, 1 H), 4.35-4.48 (m, 1 H), 4.63-4.75 (m, 1 H), 6.66-6.76 (m, 1 H), 6.79-6.88 (m, 1 H), 7.14-7.27 (m, 3 H), 7.30-7.42 (m, 3 H), 7.47-7.60 (m, 2 H), 9.54 (s, 1 H), 11.18 (br. s., 1 H).

MS ESI/APCI Dual posi: 497[M+H]$^+$.

The compounds of Working Examples 6-2 to 6-8 were obtained by using the corresponding compounds obtained in Reference Example 3 and the aldehydes and ketone obtained in Reference Examples 7-1, 8-1, 9-1 and 12-1 as well as the aldehydes obtained in WO 2010/011375 in accordance with the process of Working Example 6-1(1).

Working Example 6-2

$^1$H NMR (300 MHz, CDCl$_3$) δ ppm 1.33 (s, 9 H), 3.87 (s, 2 H), 3.92 (br. s., 4 H), 6.40 (s, 1 H), 6.88-7.03 (m, 4 H), 7.17-7.40 (m, 5 H), 7.48-7.55 (m, 2 H).
MS ESI/APCI Dual posi: 439[M+H]$^+$.

Working Example 6-3

$^1$H NMR (300 MHz, CDCl$_3$) δ ppm 1.08 (d, J=6.4 Hz, 3 H), 1.32 (s, 9 H), 2.42-2.55 (m, 1 H), 2.89-3.03 (m, 1 H), 3.05-3.15 (m, 1 H), 4.02-4.16 (m, 4 H), 6.50 (br. s., 1 H), 6.90-7.03 (m, 4 H), 7.10-7.16 (m, 2 H), 7.24-7.35 (m, 3 H), 7.51-7.60 (m, 2 H).
MS ESI/APCI Dual posi: 467[M+H]$^+$.

Working Example 6-4

$^1$H NMR (600 MHz, CDCl$_3$) δ ppm 1.31 (s, 9 H), 1.89-1.96 (m, 2 H), 2.67-2.72 (m, 2 H), 2.76-2.97 (m, 6 H), 3.38-3.44 (m, 3 H), 3.76 (br. s., 2 H), 5.21 (t, J=5.7 Hz, 1 H), 7.12-7.15 (m, 1 H), 7.16-7.21 (m, 6 H), 7.26-7.30 (m, 1 H), 7.31-7.35 (m, 2 H), 7.45 (dd, J=8.3, 1.8 Hz, 1 H), 7.48-7.51 (m, 1 H), 7.94 (s, 2 H).
LCMS retention time: 4.83 min. (Condition 1-1-1)
MS (ESI posi) m/z: 584[M+H]$^+$.

Working Example 6-5

$^1$H NMR (300 MHz, DMSO-d$_6$) δ ppm 1.30 (s, 9 H), 1.90-2.03 (m, 2 H), 2.66-2.75 (m, 2 H), 2.84-2.96 (m, 4 H), 3.60 (s, 2 H), 3.88-3.95 (m, 2 H), 6.65-6.71 (m, 1 H), 6.72-6.79 (m, 1 H), 6.97-7.04 (m, 1 H), 7.13-7.22 (m, 3 H), 7.23-7.31 (m, 3 H), 7.35-7.41 (m, 3 H), 7.63-7.68 (m, 1 H), 8.40-8.43 (m, 1 H).
MS ESI/APCI Dual posi: 602[M+H]$^+$.

Working Example 6-6

$^1$H NMR (300 MHz, CDCl$_3$) δ ppm 1.59 (s, 6 H), 2.02-2.12 (m, 2 H), 2.69-2.81 (m, 4 H), 2.82-2.89 (m, 2 H), 3.62 (s, 2 H), 3.66 (s, 2 H), 3.87 (t, J=6.2 Hz, 2 H), 6.44-6.53 (m, 2 H), 6.59-6.65 (m, 1 H), 7.01 (d, J=8.2 Hz, 1 H), 7.15-7.23 (m, 3 H), 7.24-7.36 (m, 4 H), 7.37-7.50 (m, 5 H).

Working Example 6-7

$^1$H NMR (300 MHz, DMSO-d$_6$) δ ppm 0.82-0.90 (m, 3 H), 1.23-1.45 (m, 12 H), 1.60-1.71 (m, 2 H), 2.63-2.70 (m, 2 H), 2.77-2.86 (m, 2 H), 3.58 (s, 2 H), 3.90 (t, J=6.5 Hz, 2 H), 4.96 (s, 1 H), 6.64-6.71 (m, 1 H), 6.73-6.81 (m, 1 H), 6.98-7.06 (m, 1 H), 7.19 (d, J=8.1 Hz, 1 H), 7.26 (d, J=8.1 Hz, 2 H), 7.34-7.46 (m, 4 H).

Working Example 6-8

$^1$H NMR (300 MHz, DMSO-d$_6$) δ ppm 0.82-0.90 (m, 3 H), 1.17-1.42 (m, 12 H), 1.59-1.71 (m, 2 H), 2.62-2.70 (m, 2 H), 2.78-2.85 (m, 2 H), 3.37-3.44 (m, 2 H), 3.55-3.63 (m, 4 H), 3.85-3.94 (m, 2 H), 4.61-4.68 (m, 1 H), 6.64-6.70 (m, 1 H), 6.73-6.80 (m, 1 H), 6.97-7.06 (m, 1 H), 7.19 (d, J=8.1 Hz, 1 H), 7.22-7.28 (m, 2 H), 7.29-7.43 (m, 4 H), 9.74 (s, 1 H).
MS ESI/APCI Dual posi: 569[M+H]$^+$.

The compounds of Working Examples 6-9 to 6-90 were obtained by using the corresponding compounds obtained in Reference Examples 3 and 6-1 and either the aldehydes obtained in Reference Examples 7-1, 9 and 10 or the corresponding commercially available aldehydes in accordance with the processes of Working Example 6-1(1) and (2).

Working Example 6-9

$^1$H NMR (300 MHz, DMSO-d$_6$) δ ppm 1.27 (s, 9 H), 3.01-3.46 (m, 8 H), 4.35-4.48 (m, 1 H), 4.65-4.76 (m, 1 H), 7.10-7.16 (m, 1 H), 7.19-7.24 (m, 2 H), 7.33-7.44 (m, 3 H), 7.60-7.66 (m, 1 H), 7.67-7.75 (m, 2 H), 7.89-7.93 (m, 1 H), 10.69 (s, 1 H).
LCMS retention time: 1.87 min. (Condition 1-1-1)
MS (ESI posi) m/z: 468[M+H]$^+$.

Working Example 6-10

MS ESI/APCI Dual nega: 586[M−H]$^-$.

Working Example 6-11

$^1$ H NMR (300 MHz, DMSO-d$_6$) δ ppm 1.27 (s, 9 H), 1.89-2.02 (m, 3 H), 2.25-2.29 (m, 1 H), 2.66-2.75 (m, 3 H), 2.98-3.21 (m, 5 H), 3.36-3.48 (m, 2 H), 3.87 (t, J=6.5 Hz, 2 H), 6.79-6.83 (m, 2 H), 6.96-7.01 (m, 2 H), 7.14-7.31 (m, 8 H), 7.34-7.40 (m, 2 H), 7.54-7.64 (m, 2 H), 10.00 (s, 1 H).
LCMS retention time: 5.39 min. (Condition 1-1-1)
MS (ESI posi) m/z: 583[M+H]$^+$.

Working Example 6-12

MS ESI/APCI Dual posi: 533[M+H]$^+$.

Working Example 6-13

MS ESI/APCI Dual posi: 599[M+H]$^+$.

Working Example 6-14

$^1$ H NMR (300 MHz, DMSO-d$_6$) δ ppm 1.27 (s, 9 H), 2.99-3.24 (m, 5 H), 3.35-3.54 (m, 3 H), 3.72-3.86 (m, 1 H), 4.27-4.42 (m, 4 H), 4.67-4.80 (m, 1 H), 6.77 (dd, J=8.2, 3.1 Hz, 1 H), 6.87 (dd, J=12.0, 2.8 Hz, 1 H), 7.06-7.14 (m, 1 H), 7.17-7.45 (m, 8 H), 7.49-7.64 (m, 3 H), 9.96 (s, 1 H).
LCMS retention time: 5.42 min. (Condition 1-1-1)
MS (ESI posi) m/z: 671[M+H]$^+$.

Working Example 6-15

$^1$ H NMR (300 MHz, DMSO-d$_6$) δ ppm 1.27 (s, 9 H), 1.90-2.03 (m, 3 H), 2.23-2.31 (m, 1 H), 2.64-2.75 (m, 3 H), 3.00-3.12 (m, 3 H), 3.13-3.25 (m, 3 H), 3.89-3.98 (m, 2 H), 4.63-4.77 (m, 1 H), 7.05-7.11 (m, 1 H), 7.14-7.31 (m, 7 H), 7.34-7.42 (m, 4 H), 7.68-7.78 (m, 2 H), 7.83-7.89 (m, 1 H).
LCMS retention time: 5.11 min. (Condition 1-1-1)
MS (ESI posi) m/z: 584[M+H]$^+$.

Working Example 6-16

$^1$ H NMR (300 MHz, DMSO-d$_6$) δ ppm 1.27 (s, 9 H), 1.90-2.04 (m, 3 H), 2.63-2.75 (m, 3 H), 3.02-3.13 (m, 3 H), 3.14-3.23 (m, 2 H), 3.70-3.88 (m, 1 H), 4.13 (t, J=6.7 Hz, 2 H), 4.35-4.52 (m, 1 H), 4.64-4.78 (m, 1 H), 6.76 (dd, J=8.9, 0.5 Hz, 1 H), 7.16-7.31 (m, 7 H), 7.32-7.45 (m, 4 H), 7.55-7.66 (m, 2 H), 7.78 (dd, J=2.8, 0.3 Hz, 1 H), 10.19 (s, 1 H).
LCMS retention time: 5.26 min. (Condition 1-1-1)
MS (ESI posi) m/z: 584[M+H]$^+$.

Working Example 6-17

$^1$ H NMR (600 MHz, CDCl$_3$) δ ppm 0.99-1.08 (m, 2 H), 1.24-1.33 (m, 11 H), 1.44-1.62 (m, 6 H), 1.68-1.77 (m, 3 H), 2.52 (t, J=7.8 Hz, 2 H), 2.94-3.03 (m, 1 H), 3.16-3.39 (m, 5 H), 3.54-3.64 (m, 1 H), 3.69-3.78 (m, 1 H), 3.97-4.07 (m, 1 H), 4.68-4.76 (m, 1 H), 6.79-6.83 (m, 1 H), 6.89-6.92 (m, 1 H), 7.05 (s, 1 H), 7.12 (d, J=8.3 Hz, 1 H), 7.18 (d, J=8.3 Hz, 2 H), 7.34 (d, J=8.3 Hz, 2 H), 7.37-7.41 (m, 1 H), 7.61-7.67 (m, 2 H).
LCMS retention time: 2.12 min. (Condition 3)
MS ESI/APCI Dual posi: 577[M+H]$^+$.

Working Example 6-18

LCMS retention time: 5.42 min. (Condition 1-1-3)
MS (ESI posi) m/z: 565[M+H]$^+$.

Working Example 6-19

$^1$ H NMR (600 MHz, DMSO-d$_6$) δ ppm 0.77-0.86 (m, 2 H), 1.05-1.23 (m, 6 H), 1.27 (s, 9 H), 1.48-1.54 (m, 2 H), 1.56-1.68 (m, 5 H), 2.44-2.53 (m, 2 H), 3.04-3.17 (m, 3 H), 3.19-3.48 (m, 4 H), 3.75-3.83 (m, 1 H), 4.40-4.48 (m, 1 H), 4.68-4.75 (m, 1 H), 6.92-6.96 (m, 1 H), 6.97-7.02 (m, 1 H), 7.10-7.14 (m, 1 H), 7.20-7.25 (m, 2 H), 7.34-7.43 (m, 3 H), 7.57-7.65 (m, 2 H), 10.10 (s, 1 H).
LCMS retention time: 4.40 min. (Condition 1-2-3)
MS (ESI posi) m/z: 591[M+H]$^+$.

Working Example 6-20

LCMS retention time: 5.21 min. (Condition 1-1-1)
MS (ESI posi) m/z: 565[M+H]$^+$.

Working Example 6-21

LCMS retention time: 5.03 min. (Condition 1-1-1)
MS (ESI posi) m/z: 566[M+H]$^+$.

Working Example 6-22

MS ESI/APCI Dual posi: 600[M+H]$^+$.

Working Example 6-23

$^1$ H NMR (600 MHz, DMSO-d$_6$) δ ppm 0.79-0.93 (m, 3 H), 1.21-1.43 (m, 6 H), 1.60-1.73 (m, 2 H), 3.11-3.44 (m, 5 H), 3.48-3.63 (m, 2 H), 3.75-3.86 (m, 1 H), 3.91 (t, J=6.4 Hz, 2 H), 4.38-4.54 (m, 1 H), 4.64-4.79 (m, 1 H), 6.64-6.83 (m, 2 H), 6.99-7.11 (m, 1 H), 7.34-7.46 (m, 1 H), 7.52-7.66 (m, 2 H), 7.87-7.98 (m, 1 H), 8.02-8.11 (m, 1 H), 8.75 (s, 1 H), 9.91 (br. s., 1 H), 10.72 (br. s., 1 H).
MS ESI/APCI Dual posi: 580[M+H]$^+$.

Working Example 6-24

$^1$ H NMR (600 MHz, DMSO-d$_6$) δ ppm 0.84 (t, J=7.1 Hz, 3 H), 1.18-1.33 (m, 8 H), 1.27 (s, 17 H), 1.63-1.70 (m, 2 H), 2.77 (t, J=7.6 Hz, 2 H), 3.03-3.12 (m, 2 H), 3.13-3.27 (m, 2 H), 3.30-3.45 (m, 3 H), 3.74-3.82 (m, 1 H), 4.43 (dd, J=15.2, 8.0 Hz, 1 H), 4.71 (d, J=15.2 Hz, 1 H), 7.22 (d, J=8.3 Hz, 2 H), 7.35-7.38 (m, 2 H), 7.43 (d, J=8.3 Hz, 1 H), 7.67 (dd, J=8.0, 1.6 Hz, 1 H), 7.71-7.74 (m, 1 H), 8.43 (s, 2 H).
LCMS retention time: 5.31 min. (Condition 1-1-1)
MS (ESI posi) m/z: 549[M+H]$^+$.

Working Example 6-25

$^1$ H NMR (600 MHz, DMSO-d$_6$) δ ppm 0.82-0.87 (m, 3 H), 1.20-1.32 (m, 16 H), 1.27 (s, 9 H), 1.54-1.64 (m, 2 H), 2.60-2.65 (m, 2 H), 3.01-3.48 (m, 8 H), 3.76-3.84 (m, 1 H), 4.44 (dd, J=15.9, 8.0 Hz, 1 H), 4.71 (d, J=15.9 Hz, 1 H), 7.22 (d, J=8.3 Hz, 2 H), 7.37 (d, J=8.7 Hz, 2 H), 7.43 (d, J=8.3 Hz, 1 H), 7.81 (dd, J=8.0, 1.6 Hz, 1 H), 7.85 (s, 1 H), 8.12 (s, 1 H), 8.30 (s, 1 H).
LCMS retention time: 5.40 min. (Condition 1-1-1)
MS (ESI posi) m/z: 549[M+H]$^+$.

Working Example 6-26

$^1$H NMR (600 MHz, DMSO-d$_6$) δ ppm 1.35 (s, 9 H), 1.94-2.00 (m, 2 H), 2.68-2.72 (m, 2 H), 3.03-3.27 (m, 4 H), 3.92 (t, J=6.2 Hz, 2 H), 4.35-4.58 (m, 4 H), 6.70 (dd, J=9.0, 2.9 Hz, 1 H), 6.77 (dd, J=12.2, 2.9 Hz, 1 H), 7.05 (t, J=9.0 Hz, 1 H), 7.15-7.23 (m, 3 H), 7.25-7.31 (m, 2 H), 7.41 (d, J=8.3 Hz, 1 H), 7.53 (d, J=8.3 Hz, 1 H), 7.57 (s, 1 H), 7.60-7.67 (m, 1 H), 8.06 (br. s., 1 H), 8.73 (br. s., 1 H), 9.88 (s, 1 H).
LCMS retention time: 4.43 min. (Condition 1-1-1)
MS (ESI posi) m/z: 588[M+H]$^+$.

Working Example 6-27

$^1$H NMR (600 MHz, DMSO-d$_6$) δ ppm 0.84-0.88 (m, 3 H), 1.23-1.32 (m, 5 H), 1.36 (s, 9 H), 1.62-1.69 (m, 2 H), 3.04-3.37 (m, 5 H), 3.90 (t, J=6.4 Hz, 2 H), 4.36-4.57 (m, 4 H), 6.66-6.71 (m, 1 H), 6.76 (dd, J=11.9, 2.8 Hz, 1 H), 7.03 (t, J=8.9 Hz, 1 H), 7.40 (d, J=8.7 Hz, 1 H), 7.52 (dd, J=8.3, 1.4 Hz, 1 H), 7.57 (s, 1 H), 7.62-7.69 (m, 1 H), 8.13 (br. s., 1 H), 8.77 (br. s., 1 H), 9.87 (s, 1 H).
LCMS retention time: 4.59 min. (Condition 1-1-1)
MS (ESI posi) m/z: 554[M+H]$^+$.

Working Example 6-28

LCMS retention time: 5.34 min. (Condition 1-1-3)
MS (ESI posi) m/z: 613[M+H]$^+$.

Working Example 6-29

LCMS retention time: 5.28 min. (Condition 1-1-2)
MS (ESI posi) m/z: 587[M+H]$^+$.

Working Example 6-30

LCMS retention time: 1.61 min. (Condition 3)
MS ESI/APCI Dual posi: 583[M+H]$^+$.

Working Example 6-31

LCMS retention time: 4.55 min. (Condition 1-1-3)
MS (ESI posi) m/z: 564[M+H]$^+$.

Working Example 6-32

LCMS retention time: 4.53 min. (Condition 1-1-3)
MS (ESI posi) m/z: 552[M+H]$^+$.

Working Example 6-33

LCMS retention time: 1.81 min. (Condition 3)
MS ESI/APCI Dual posi: 582[M+H]$^+$.

Working Example 6-34

LCMS retention time: 1.73 min. (Condition 3)
MS ESI/APCI Dual posi: 616[M+H]$^+$.

Working Example 6-35

LCMS retention time: 1.82 min. (Condition 3)
MS ESI/APCI Dual posi: 594[M+H]$^+$.

Working Example 6-36

$^1$H NMR (600 MHz, DMSO-d$_6$) δ ppm 0.83-0.92 (m, 6 H), 1.21-1.42 (m, 17 H), 1.61-1.69 (m, 2 H), 1.70-1.81 (m, 2 H), 3.06-3.24 (m, 4 H), 3.66-3.76 (m, 1 H), 3.91 (t, J=6.4 Hz, 2 H), 4.29-4.40 (m, 1 H), 4.59-4.67 (m, 1 H), 6.69 (dd, J=9.0, 2.8 Hz, 1 H), 6.77 (dd, J=12.0, 2.8 Hz, 1 H), 7.04-7.08 (m, 1 H), 7.39 (d, J=7.8 Hz, 1 H), 7.52-7.61 (m, 2 H), 9.90 (s, 1 H).
LCMS retention time: 1.72 min. (Condition 3)
MS ESI/APCI Dual posi: 519[M+H]$^+$.

Working Example 6-37

$^1$H NMR (600 MHz, DMSO-d$_6$) δ ppm 0.79-0.92 (m, 6 H), 1.19-1.41 (m, 27 H), 1.61-1.69 (m, 2 H), 1.69-1.79 (m, 2 H), 3.03-3.24 (m, 4 H), 3.66-3.77 (m, 1 H), 3.91 (t, J=6.6 Hz, 2 H), 4.29-4.40 (m, 1 H), 4.57-4.69 (m, 1 H), 6.69 (dd, J=9.2, 2.5 Hz, 1 H), 6.77 (dd, J=12.2, 2.5 Hz, 1 H), 7.03-7.09 (m, 1 H), 7.36-7.41 (m, 1 H), 7.52-7.62 (m, 2 H), 9.89 (s, 1 H).
LCMS retention time: 1.95 min. (Condition 3)
MS ESI/APCI Dual posi: 589[M+H]$^+$.

Working Example 6-38

MS ESI/APCI Dual posi: 481[M+H]$^+$.

Working Example 6-39

MS ESI/APCI Dual posi: 468[M+H]$^+$.

Working Example 6-40

MS ESI/APCI Dual posi: 615[M+H]$^+$.

Working Example 6-41

$^1$H NMR (600 MHz, DMSO-d$_6$) δ ppm 1.38 (s, 9 H), 3.04-3.30 (m, 2 H), 3.35-3.85 (m, 2 H), 4.45-4.67 (m, 4 H), 7.03-7.15 (m, 4 H), 7.39 (d, J=8.3 Hz, 1 H), 7.53-7.61 (m, 1 H), 7.63 (s, 1 H), 8.80-8.88 (m, 2 H), 10.33 (s, 1 H), 11.28 (br. s., 1 H).
MS ESI/APCI Dual posi: 455[M+H]$^+$.

Working Example 6-42

$^1$H NMR (600 MHz, DMSO-d$_6$) δ ppm 1.38 (s, 9 H), 3.02-3.39 (m, 4 H), 4.34-4.43 (m, 2 H), 4.47-4.57 (m, 2 H), 7.03-7.14 (m, 4 H), 7.38 (d, J=8.3 Hz, 1 H), 7.51-7.60 (m, 1 H), 7.63 (s, 1 H), 7.67-7.77 (m, 1 H), 8.24 (br. s., 1 H), 8.82 (br. s., 1 H), 10.31 (s, 1 H), 11.43 (br. s., 1 H).
MS ESI/APCI Dual posi: 454[M+H]$^+$.

Working Example 6-43

$^1$H NMR (600 MHz, DMSO-d$_6$) δ ppm 1.37 (s, 9 H), 3.12-3.29 (m, 2 H), 3.61-3.96 (m, 2 H), 4.56-4.79 (m, 4 H), 7.06-7.17 (m, 4 H), 7.39 (d, J=8.3 Hz, 1 H), 7.56-7.62 (m, 1 H), 7.66 (s, 1 H), 8.97 (s, 2 H), 10.36 (s, 1 H), 10.98 (br. s., 1 H).
MS ESI/APCI Dual posi: 455[M+H]$^+$.

Working Example 6-44

LCMS retention time: 3.67 min. (Condition 1-1-3)
MS (ESI posi) m/z: 568[M+H]$^+$.

Working Example 6-45

LCMS retention time: 3.58 min. (Condition 1-1-3)
MS (ESI posi) m/z: 602[M+H]$^+$.

Working Example 6-46

LCMS retention time: 4.19 min. (Condition 1-1-3)
MS (ESI posi) m/z: 614[M+H]$^+$.

Working Example 6-47

$^1$H NMR (600 MHz, DMSO-d$_6$) δ ppm 0.97-1.04 (m, 2 H), 1.20-1.26 (m, 2 H), 1.30 (s, 9 H), 1.40-1.57 (m, 6 H), 1.65-1.75 (m, 3 H), 2.43-2.55 (m, 2 H), 3.07-3.21 (m, 2 H), 3.25-3.38 (m, 1 H), 3.61-3.68 (m, 1 H), 4.36-4.46 (m, 4 H), 6.92-6.95 (m, 1 H), 6.96-7.01 (m, 1 H), 7.09-7.14 (m, 1 H), 7.39-7.43 (m, 1 H), 7.49-7.61 (m, 6 H), 10.07 (s, 1 H).
LCMS retention time: 4.81 min. (Condition 1-2-3)
MS (ESI posi) m/z: 563[M+H]$^+$.

Working Example 6-48

$^1$H NMR (600 MHz, DMSO-d$_6$) δ ppm 0.97-1.05 (m, 2 H), 1.21-1.27 (m, 2 H), 1.40 (s, 9 H), 1.42-1.57 (m, 6 H), 1.65-1.76 (m, 3 H), 2.45-2.53 (m, 2 H), 3.09-3.24 (m, 2 H), 3.26-3.37 (m, 1 H), 3.65-3.76 (m, 1 H), 4.36-4.49 (m, 2 H), 4.69-4.76 (m, 2 H), 6.92-6.95 (m, 1 H), 6.97-7.01 (m, 1 H), 7.09-7.13 (m, 1 H), 7.41-7.44 (m, 1 H), 7.55-7.61 (m, 2 H), 7.89 (s, 1 H), 10.08 (s, 1 H).
LCMS retention time: 4.52 min. (Condition 1-2-3)
MS (ESI posi) m/z: 570[M+H]$^+$.

Working Example 6-49

$^1$H NMR (600 MHz, DMSO-d$_6$) δ ppm 0.93 (t, J=7.4 Hz, 3 H), 0.97-1.06 (m, 2 H), 1.21-1.27 (m, 2 H), 1.31-1.39 (m, 2 H), 1.41-1.58 (m, 6 H), 1.66-1.77 (m, 5 H), 2.44-2.55 (m, 2 H), 3.06-3.24 (m, 4 H), 3.25-3.38 (m, 1 H), 3.67-3.75 (m, 1 H), 4.30-4.39 (m, 1 H), 4.59-4.65 (m, 1 H), 6.93-6.96 (m, 1 H), 6.97-7.02 (m, 1 H), 7.09-7.15 (m, 1 H), 7.37-7.41 (m, 1 H), 7.56-7.63 (m, 2 H), 10.09 (s, 1 H).
LCMS retention time: 4.37 min. (Condition 1-2-3)
MS (ESI posi) m/z: 473[M+H]$^+$.

Working Example 6-50

$^1$H NMR (600 MHz, DMSO-d$_6$) δ ppm 0.85-0.91 (m, 3 H), 0.97-1.06 (m, 2 H), 1.21-1.36 (m, 8 H), 1.41-1.58 (m, 6 H), 1.65-1.78 (m, 5 H), 2.44-2.55 (m, 2 H), 3.06-3.23 (m, 4 H), 3.25-3.35 (m, 1 H), 3.67-3.74 (m, 1 H), 4.30-4.39 (m, 1 H), 4.58-4.66 (m, 1 H), 6.93-6.96 (m, 1 H), 6.98-7.02 (m, 1 H), 7.10-7.14 (m, 1 H), 7.36-7.42 (m, 1 H), 7.56-7.63 (m, 2 H), 10.09 (s, 1 H).
LCMS retention time: 4.63 min. (Condition 1-2-3)
MS (ESI posi) m/z: 501[M+H]$^+$.

Working Example 6-51

$^1$H NMR (600 MHz, DMSO-d$_6$) δ ppm 0.85-0.89 (m, 3 H), 0.98-1.06 (m, 2 H), 1.20-1.35 (m, 12 H), 1.41-1.58 (m, 6 H), 1.65-1.79 (m, 5 H), 2.44-2.55 (m, 2 H), 3.05-3.22 (m, 4 H), 3.25-3.36 (m, 1 H), 3.67-3.74 (m, 1 H), 4.30-4.38 (m, 1 H), 4.58-4.66 (m, 1 H), 6.93-6.96 (m, 1 H), 6.98-7.01 (m, 1 H), 7.10-7.14 (m, 1 H), 7.36-7.41 (m, 1 H), 7.57-7.62 (m, 2 H), 10.09 (s, 1 H).
LCMS retention time: 5.65 min. (Condition 1-2-1)
MS (ESI posi) m/z: 529[M+H]$^+$.

Working Example 6-52

$^1$H NMR (600 MHz, DMSO-d$_6$) δ 0.84-0.88 (m, 3 H), 0.98-1.05 (m, 2 H), 1.21-1.35 (m, 16 H), 1.41-1.58 (m, 6 H), 1.66-1.78 (m, 5 H), 2.45-2.53 (m, 2 H), 3.05-3.23 (m, 4 H), 3.27-3.35 (m, 1 H), 3.67-3.73 (m, 1 H), 4.30-4.38 (m, 1 H), 4.59-4.65 (m, 1 H), 6.92-6.96 (m, 1 H), 6.97-7.02 (m, 1 H), 7.10-7.14 (m, 1 H), 7.37-7.42 (m, 1 H), 7.57-7.63 (m, 2 H), 10.09 (s, 1 H).
LCMS retention time: 5.17 min. (Condition 1-2-3)
MS (ESI posi) m/z: 557[M+H]$^+$.

Working Example 6-53

$^1$H NMR (600 MHz, DMSO-d$_6$) δ ppm 0.96-1.05 (m, 2 H), 1.21-1.26 (m, 2 H), 1.41-1.57 (m, 6 H), 1.65-1.75 (m, 3 H), 2.45-2.55 (m, 2 H), 3.08-3.25 (m, 2 H), 3.28-3.41 (m, 1 H), 3.65-3.74 (m, 1 H), 4.37-4.46 (m, 2 H), 4.51-4.64 (m, 2 H), 6.92-6.95 (m, 1 H), 6.97-7.01 (m, 1 H), 7.09-7.14 (m, 1 H), 7.37-7.42 (m, 1 H), 7.53-7.62 (m, 2 H), 7.80-7.93 (m, 4 H), 10.08 (s, 1 H).
LCMS retention time: 4.58 min. (Condition 1-2-3)
MS (ESI posi) m/z: 575[M+H]$^+$.

Working Example 6-54

$^1$H NMR (600 MHz, DMSO-d$_6$) δ ppm 0.96-1.05 (m, 2 H), 1.20-1.27 (m, 2 H), 1.40-1.57 (m, 6 H), 1.65-1.75 (m, 3 H), 2.43-2.55 (m, 2 H), 3.06-3.44 (m, 3 H), 3.69-3.79 (m, 1 H), 4.37-4.50 (m, 2 H), 4.54-4.73 (m, 2 H), 6.92-6.95 (m, 1 H), 6.97-7.01 (m, 1 H), 7.09-7.13 (m, 1 H), 7.32-7.42 (m, 1 H), 7.50-7.65 (m, 2 H), 8.01-8.12 (m, 1 H), 8.30-8.42 (m, 1 H), 8.92-9.02 (m, 1 H), 10.07 (s, 1 H).
LCMS retention time: 4.47 min. (Condition 1-2-3)
MS (ESI posi) m/z: 576[M+H]$^+$.

Working Example 6-55

$^1$H NMR (600 MHz, DMSO-d$_6$) δ ppm 0.83-0.88 (m, 3 H), 0.97-1.06 (m, 2 H), 1.20-1.34 (m, 20 H), 1.41-1.58 (m, 6 H), 1.66-1.78 (m, 5 H), 2.45-2.54 (m, 2 H), 3.05-3.24 (m, 3 H), 3.26-3.37 (m, 2 H), 3.65-3.75 (m, 1 H), 4.29-4.38 (m, 1 H), 4.57-4.66 (m, 1 H), 6.92-6.96 (m, 1 H), 6.97-7.02 (m, 1 H), 7.10-7.14 (m, 1 H), 7.36-7.41 (m, 1 H), 7.57-7.62 (m, 2 H), 10.09 (s, 1 H).
LCMS retention time: 2.25 min. (Condition 3)
MS ESI/APCI Dual posi: 585[M+H]$^+$.

Working Example 6-56

$^1$H NMR (600 MHz, DMSO-d$_6$) δ ppm 0.84-0.89 (m, 3 H), 0.97-1.04 (m, 2 H), 1.21-1.35 (m, 10 H), 1.37-1.57 (m, 8 H), 1.65-1.75 (m, 5 H), 2.44-2.54 (m, 2 H), 3.06-3.38 (m, 3 H), 3.61-3.67 (m, 1 H), 3.97-4.02 (m, 2 H), 4.31-4.42 (m, 4 H), 6.92-6.95 (m, 1 H), 6.97-7.04 (m, 3 H), 7.08-7.13 (m, 1 H), 7.36-7.41 (m, 1 H), 7.47-7.61 (m, 4 H), 10.08 (s, 1 H).
LCMS retention time: 2.31 min. (Condition 3)
MS ESI/APCI Dual posi: 635[M+H]$^+$.

Working Example 6-57

$^1$H NMR (600 MHz, DMSO-d$_6$) δ ppm 0.86-0.90 (m, 3 H), 0.97-1.04 (m, 2 H), 1.20-1.26 (m, 2 H), 1.28-1.34 (m, 4 H), 1.38-1.57 (m, 8 H), 1.65-1.75 (m, 5 H), 2.44-2.53 (m, 2 H), 3.07-3.21 (m, 2 H), 3.24-3.37 (m, 1 H), 3.61-3.67 (m, 1 H), 3.97-4.02 (m, 2 H), 4.32-4.43 (m, 4 H), 6.92-6.95 (m, 1 H), 6.97-7.05 (m, 3 H), 7.09-7.13 (m, 1 H), 7.37-7.41 (m, 1 H), 7.47-7.52 (m, 2 H), 7.53-7.61 (m, 2 H), 10.08 (s, 1 H).
LCMS retention time: 2.17 min. (Condition 3)
MS ESI/APCI Dual posi: 607[M+H]$^+$.

Working Example 6-58

$^1$H NMR (600 MHz, DMSO-d$_6$) δ ppm 0.84-0.89 (m, 3 H), 0.97-1.05 (m, 2 H), 1.21-1.36 (m, 8 H), 1.38-1.57 (m, 8 H), 1.64-1.75 (m, 5 H), 2.45-2.55 (m, 2 H), 3.06-3.22 (m, 2 H), 3.24-3.39 (m, 1 H), 3.60-3.68 (m, 1 H), 3.95-4.04 (m, 2 H), 4.30-4.45 (m, 4 H), 6.91-6.95 (m, 1 H), 6.96-7.05 (m, 3 H), 7.08-7.14 (m, 1 H), 7.35-7.43 (m, 1 H), 7.45-7.63 (m, 4 H), 10.07 (s, 1 H).
LCMS retention time: 2.24 min. (Condition 3)
MS ESI/APCI Dual posi: 621[M+H]$^+$.

Working Example 6-59

$^1$H NMR (600 MHz, DMSO-d$_6$) δ ppm 0.96-1.05 (m, 2 H), 1.21-1.27 (m, 2 H), 1.40-1.57 (m, 6 H), 1.65-1.75 (m, 3 H), 2.46-2.55 (m, 2 H), 3.07-3.25 (m, 2 H), 3.27-3.40 (m, 1 H), 3.63-3.72 (m, 1 H), 4.36-4.44 (m, 2 H), 4.45-4.56 (m, 2 H), 6.94 (d, J=8.3 Hz, 1 H), 6.98 (d, J=11.6 Hz, 1 H), 7.09-7.13 (m, 1 H), 7.38-7.43 (m, 1 H), 7.47-7.62 (m, 4 H), 7.72-7.78 (m, 2 H), 10.08 (s, 1 H).
LCMS retention time: 4.65 min. (Condition 1-2-3)
MS (ESI posi) m/z: 591[M+H]$^+$.

Working Example 6-60

$^1$H NMR (600 MHz, DMSO-d$_6$) δ ppm 0.97-1.05 (m, 2 H), 1.21-1.26 (m, 2 H), 1.41-1.57 (m, 6 H), 1.66-1.75 (m, 3 H), 2.46-2.53 (m, 2 H), 3.06-3.36 (m, 3 H), 3.60-3.67 (m, 1 H), 4.28-4.39 (m, 4 H), 6.85 (d, J=8.3 Hz, 2 H), 6.92-6.95 (m, 1 H), 6.96-7.01 (m, 1 H), 7.07-7.15 (m, 1 H), 7.34-7.43 (m, 3 H), 7.51-7.62 (m, 2 H), 9.83 (s, 1 H), 10.08 (s, 1 H).
LCMS retention time: 4.17 min. (Condition 1-2-3)
MS (ESI posi) m/z: 523[M+H]$^+$.

Working Example 6-61

$^1$H NMR (600 MHz, DMSO-d$_6$) δ ppm 0.37-0.48 (m, 2 H), 0.63-0.73 (m, 2 H), 0.96-1.06 (m, 2 H), 1.13-1.28 (m, 3 H), 1.41-1.58 (m, 6 H), 1.65-1.77 (m, 3 H), 2.45-2.54 (m, 2 H), 3.05-3.24 (m, 4 H), 3.27-3.37 (m, 1 H), 3.72-3.80 (m, 1 H), 4.36-4.46 (m, 1 H), 4.61-4.72 (m, 1 H), 6.93-6.96 (m, 1 H), 6.98-7.02 (m, 1 H), 7.10-7.15 (m, 1 H), 7.39-7.46 (m, 1 H), 7.55-7.65 (m, 2 H), 10.09 (s, 1 H).
LCMS retention time: 4.17 min. (Condition 1-2-3)
MS (ESI posi) m/z: 471[M+H]$^+$.

Working Example 6-62

$^1$H NMR (600 MHz, DMSO-d$_6$) δ ppm 0.96-1.05 (m, 2 H), 1.21-1.26 (m, 2 H), 1.36 (s, 9 H), 1.40-1.57 (m, 6 H), 1.65-1.74 (m, 3 H), 2.46-2.54 (m, 2 H), 3.08-3.26 (m, 2 H), 3.30-3.40 (m, 1 H), 3.66-3.73 (m, 1 H), 4.38-4.44 (m, 2 H), 4.46-4.58 (m, 2 H), 6.91-6.95 (m, 1 H), 6.97-7.01 (m, 1 H), 7.09-7.14 (m, 1 H), 7.38-7.41 (m, 2 H), 7.54-7.58 (m, 1 H), 7.60 (s, 1 H), 7.72 (d, J=8.3 Hz, 2 H), 8.03 (d, J=8.3 Hz, 2 H), 10.08 (s, 1 H).
LCMS retention time: 5.04 min. (Condition 1-2-3)
MS (ESI posi) m/z: 646[M+H]$^+$.

Working Example 6-63

$^1$H NMR (600 MHz, DMSO-d$_6$) δ ppm 0.98-1.03 (m, 2 H), 1.20-1.28 (m, 2 H), 1.37 (s, 9 H), 1.41-1.59 (m, 7 H), 1.65-1.77 (m, 3 H), 3.08-3.29 (m, 8 H), 3.75-3.83 (m, 1 H), 4.40-4.48 (m, 1 H), 4.52-4.79 (m, 1 H), 6.91-7.04 (m, 2 H), 7.09-7.17 (m, 1 H), 7.41 (d, J=8.3 Hz, 1 H), 7.57-7.65 (m, 2 H), 7.82-8.15 (m, 2 H), 8.60 (br. s., 1 H), 10.11 (s, 1 H).
LCMS retention time: 3.71 min. (Condition 1-2-3)
MS (ESI posi) m/z: 578[M+H]$^+$.

Working Example 6-64

$^1$H NMR (600 MHz, DMSO-d$_6$) δ ppm 0.98-1.03 (m, 2 H), 1.20-1.28 (m, 2 H), 1.34 (s, 9 H), 1.39-1.59 (m, 6 H), 1.64-1.77 (m, 3 H), 3.10-3.21 (m, 3 H), 3.40-3.59 (m, 5 H), 3.65-3.75 (m, 4 H), 6.92-7.02 (m, 2 H), 7.10-7.15 (m, 1 H), 7.40 (d, J=8.3 Hz, 1 H), 7.58-7.65 (m, 2 H), 8.83 (s, 2 H), 10.10 (s, 1 H).
LCMS retention time: 4.37 min. (Condition 1-2-3)
MS (ESI posi) m/z: 579[M+H]$^+$.

Working Example 6-65

LCMS retention time: 4.88 min. (Condition 1-2-3)
MS (ESI posi) m/z: 672[M+H]$^+$.

Working Example 6-66

$^1$H NMR (600 MHz, DMSO-d$_6$) δ ppm 0.81-0.92 (m, 2 H), 1.11-1.37 (m, 12 H), 1.51-1.73 (m, 5 H), 3.07-3.29 (m, 2 H), 3.60-3.69 (m, 1 H), 3.76-3.85 (m, 2 H), 3.96 (t, J=6.4 Hz, 2 H), 4.42 (br. s., 4 H), 6.70 (dd, J=8.7, 2.7 Hz, 1 H), 6.78 (dd, J=12.0, 2.7 Hz, 1 H), 7.01-7.08 (m, 1 H), 7.41 (d, J=8.3 Hz, 1 H), 7.46-7.62 (m, 6 H), 9.89 (s, 1 H).
LCMS retention time: 3.73 min. (Condition 1-2-3)
MS (ESI posi) m/z: 581[M+H]$^+$.

Working Example 6-67

$^1$H NMR (600 MHz, DMSO-d$_6$) δ ppm 1.14-1.25 (m, 2 H), 1.53-1.70 (m, 6 H), 3.08-3.30 (m, 5 H), 3.70-3.85 (m, 2 H), 3.96 (t, J=6.4 Hz, 2 H), 4.50-4.58 (m, 2 H), 4.71-4.79 (m, 2 H), 6.68-6.82 (m, 2 H), 7.03-7.09 (m, 1 H), 7.36-7.40 (m, 1 H), 7.51-7.56 (m, 1 H), 7.59 (s, 1 H), 7.89 (d, J=8.2 Hz, 1 H), 8.41 (dd, J=8.2, 1.9 Hz, 1 H), 9.09 (s, 1 H), 9.91 (s, 1 H).
LCMS retention time: 3.40 min. (Condition 1-2-3)
MS (ESI posi) m/z: 594[M+H]$^+$.

Working Example 6-68

$^1$H NMR (600 MHz, DMSO-d$_6$) δ ppm 1.14-1.24 (m, 2 H), 1.36 (s, 9 H), 1.54-1.73 (m, 5 H), 3.05-3.38 (m, 6 H), 3.76-3.85 (m, 2 H), 3.96 (t, J=6.4 Hz, 2 H), 4.37-4.59 (m, 4 H), 6.66-6.83 (m, 2 H), 7.01-7.06 (m, 1 H), 7.41 (d, J=8.3 Hz, 1 H), 7.53 (d, J=8.3 Hz, 1 H), 7.56-7.60 (m, 2 H), 8.05-8.13 (m, 1 H), 8.75 (s., 1 H), 9.89 (s, 1 H).
LCMS retention time: 3.00 min. (Condition 1-2-3)
MS (ESI posi) m/z: 582[M+H]$^+$.

Working Example 6-69

$^1$H NMR (600 MHz, DMSO-d$_6$) δ ppm 1.14-1.26 (m, 2 H), 1.35 (s., 9 H), 1.53-1.72 (m, 5 H), 3.10-3.40 (m, 9 H), 3.75-3.84 (m, 3 H), 3.97 (t, J=6.2 Hz, 2 H), 4.40-4.51 (m, 1 H), 4.69-4.77 (m, 1 H), 6.67-6.85 (m, 2 H), 7.05-7.09 (m, 1 H), 7.41 (d, J=8.3 Hz, 1 H), 7.53-7.63 (m, 2 H), 7.73-8.16 (m, 2 H), 8.53-8.59 (m, 1 H), 9.92 (s, 1 H).
LCMS retention time: 2.84 min. (Condition 1-2-3)
MS (ESI posi) m/z: 596[M+H]$^+$.

Working Example 6-70

$^1$H NMR (600 MHz, DMSO-d$_6$) δ ppm 1.15-1.24 (m, 2 H), 1.40 (s, 9 H), 1.53-1.72 (m, 5 H), 3.07-3.35 (m, 5 H), 3.65-3.73 (m, 1 H), 3.75-3.86 (m, 2 H), 3.96 (t, J=6.4 Hz, 2 H), 4.32-4.54 (m, 2 H), 4.69-4.77 (m, 2 H), 6.70 (dd, J=8.9, 2.3 Hz, 1 H), 6.78 (dd, J=12.2, 2.7 Hz, 1 H), 7.01-7.08 (m, 1 H), 7.42 (d, J=7.8 Hz, 1 H), 7.50-7.62 (m, 2 H), 7.89 (s., 1 H), 9.90 (s, 1 H).
LCMS retention time: 3.39 min. (Condition 1-2-3)
MS (ESI posi) m/z: 588[M+H]$^+$.

Working Example 6-71

$^1$H NMR (600 MHz, DMSO-d$_6$) δ ppm −0.03-0.01 (m, 2 H), 0.33-0.38 (m, 2 H), 0.59-0.67 (m, 1 H), 1.27 (s, 9 H), 1.38-1.44 (m, 2 H), 2.57-2.63 (m, 2 H), 3.03-3.26 (m, 4 H), 3.27-3.48 (m, 3 H), 3.75-3.84 (m, 1 H), 4.40-4.49 (m, 1 H), 4.68-4.76 (m, 1 H), 6.94-6.98 (m, 1 H), 6.99-7.03 (m, 1 H), 7.10-7.15 (m, 1 H), 7.19-7.26 (m, 2 H), 7.34-7.43 (m, 3 H), 7.56-7.66 (m, 2 H), 10.10 (s, 1 H).
LCMS retention time: 3.79 min. (Condition 1-2-3)
MS (ESI posi) m/z: 535[M+H]$^+$.

Working Example 6-72

$^1$H NMR (600 MHz, DMSO-d$_6$) δ ppm 0.83-0.93 (m, 2 H), 1.07-1.21 (m, 4 H), 1.27 (s, 9 H), 1.36-1.43 (m, 2 H), 1.57-1.72 (m, 5 H), 2.48-2.54 (m, 2 H), 3.03-3.48 (m, 7 H), 3.75-3.84 (m, 1 H), 4.40-4.49 (m, 1 H), 4.67-4.76 (m, 1 H), 6.93-6.96 (m, 1 H), 6.97-7.01 (m, 1 H), 7.09-7.15 (m, 1 H), 7.20-7.24 (m, 2 H), 7.34-7.43 (m, 3 H), 7.57-7.66 (m, 2 H), 10.10 (s, 1 H).
LCMS retention time: 4.23 min. (Condition 1-2-3)
MS (ESI posi) m/z: 577[M+H]$^+$.

Working Example 6-73

$^1$H NMR (600 MHz, DMSO-d$_6$) δ ppm 1.04-1.12 (m, 2 H), 1.27 (s, 9 H), 1.41-1.60 (m, 6 H), 1.63-1.74 (m, 3 H), 2.45-2.55 (m, 2 H), 3.05-3.16 (m, 3 H), 3.20-3.46 (m, 4 H), 3.74-3.83 (m, 1 H), 4.40-4.48 (m, 1 H), 4.66-4.76 (m, 1 H), 6.93-6.97 (m, 1 H), 6.98-7.03 (m, 1 H), 7.09-7.15 (m, 1 H), 7.20-7.24 (m, 2 H), 7.35-7.42 (m, 3 H), 7.57-7.64 (m, 2 H), 10.10 (s, 1 H).
LCMS retention time: 1.11 min. (Condition 4-2)
MS (ESI posi) m/z: 563[M+H]$^+$.

Working Example 6-74

$^1$H NMR (600 MHz, DMSO-d$_6$) δ ppm 0.97-1.03 (m, 2 H), 1.18-1.29 (m, 2 H), 1.38-1.59 (m, 6 H), 1.63-1.77 (m, 3 H), 3.05-3.25 (m, 4 H), 3.63-3.72 (m, 2 H), 4.29-4.59 (m, 4 H), 6.91-7.01 (m, 2 H), 7.08-7.14 (m, 1 H), 7.33-7.74 (m, 6 H), 10.08 (br. s., 1 H).
LCMS retention time: 1.30 min. (Condition 4-2)
MS (ESI posi) m/z: 587[M+H]$^+$.

Working Example 6-75

$^1$H NMR (600 MHz, DMSO-d$_6$) δ ppm 1.04-1.12 (m, 2 H), 1.14-1.20 (m, 2 H), 1.27 (s, 9 H), 1.38-1.47 (m, 1 H), 1.49-1.56 (m, 4 H), 3.02-3.26 (m, 6 H), 3.28-3.48 (m, 5 H), 3.75-3.84 (m, 3 H), 4.41-4.49 (m, 1 H), 4.69-4.76 (m, 1 H), 6.93-6.97 (m, 1 H), 6.99-7.03 (m, 1 H), 7.10-7.15 (m, 1 H), 7.19-7.26 (m, 2 H), 7.33-7.44 (m, 3 H), 7.55-7.68 (m, 2 H), 10.11 (s, 1 H).
LCMS retention time: 1.86 min. (Condition 3)
MS ESI/APCI Dual posi: 593[M+H]$^+$.

Working Example 6-76

$^1$H NMR (600 MHz, DMSO-d$_6$) δ ppm 0.97-1.03 (m, 2 H), 1.21-1.28 (m, 2 H), 1.40-1.59 (m, 6 H), 1.65-1.77 (m, 3 H), 3.11-3.48 (m, 9 H), 3.72-3.79 (m, 1 H), 4.42-4.47 (m, 1 H), 4.66-4.72 (m, 1 H), 6.92-7.03 (m, 2 H), 7.09-7.20 (m, 2 H), 7.36-7.45 (m, 3 H), 7.57-7.66 (m, 2 H), 10.11 (br. s., 1 H).
LCMS retention time: 1.51 min. (Condition 4-2)
MS (ESI posi) m/z: 601[M+H]$^+$.

Working Example 6-77

$^1$H NMR (600 MHz, DMSO-d$_6$) δ ppm 1.27 (s, 9 H), 2.07-2.14 (m, 2 H), 3.00 (s, 3 H), 3.03-3.25 (m, 7 H), 3.36-3.50 (m, 2 H), 3.76-3.83 (m, 1 H), 4.05 (t, J=6.2 Hz, 2 H), 4.41-4.51 (m, 1 H), 4.70-4.76 (m, 1 H), 6.73 (dd, J=9.1, 2.7 Hz, 1 H), 6.80 (dd, J=12.0, 2.7 Hz, 1 H), 7.07-7.13 (m, 1 H), 7.23 (d, J=7.4 Hz, 2 H), 7.33-7.44 (m, 3 H), 7.53-7.64 (m, 2 H), 9.95 (br. s., 1 H).
LCMS retention time: 1.37 min. (Condition 4-1)
MS (ESI posi) m/z: 603[M+H]$^+$.

Working Example 6-78

$^1$H NMR (600 MHz, DMSO-d$_6$) δ ppm 0.96-1.05 (m, 2 H), 1.20-1.27 (m, 2 H), 1.40-1.57 (m, 6 H), 1.65-1.75 (m, 3 H), 2.46-2.57 (m, 2 H), 3.02-3.27 (m, 3 H), 3.70-3.89 (m, 1 H), 4.30-4.82 (m, 4 H), 6.91-6.95 (m, 1 H), 6.96-7.01 (m, 1 H), 7.08-7.13 (m, 1 H), 7.28-7.39 (m, 1 H), 7.49-7.65 (m, 2 H), 9.17-9.37 (m, 2 H), 10.06 (s, 1 H).
LCMS retention time: 1.30 min. (Condition 4-2)
MS (ESI posi) m/z: 577[M+H]$^+$.

Working Example 6-79

$^1$H NMR (600 MHz, DMSO-d$_6$) δ ppm 0.96-1.06 (m, 2 H), 1.20-1.27 (m, 2 H), 1.40-1.58 (m, 6 H), 1.65-1.76 (m, 3 H), 2.46-2.54 (m, 2 H), 3.08-3.62 (m, 3 H), 3.71-4.00 (m, 1 H), 4.41-5.09 (m, 4 H), 6.93-6.97 (m, 1 H), 6.98-7.03 (m, 1 H), 7.09-7.16 (m, 1 H), 7.30-7.38 (m, 1 H), 7.51-7.66 (m, 2 H), 9.42 (s, 2 H), 10.09 (s, 1 H).
LCMS retention time: 1.28 min. (Condition 4-2)
MS (ESI posi) m/z: 577[M+H]$^+$.

Working Example 6-80

$^1$H NMR (600 MHz, DMSO-d$_6$) δ ppm 1.21 (t, J=7.4 Hz, 3 H), 1.27 (s, 9 H), 2.06-2.13 (m, 2 H), 2.99-3.25 (m, 8 H), 3.35-3.50 (m, 3 H), 3.76-3.83 (m, 1 H), 4.01-4.09 (m, 2 H), 4.40-4.50 (m, 1 H), 4.71-4.75 (m, 1 H), 6.73 (dd, J=8.7, 2.7 Hz, 1 H), 6.80 (dd, J=12.0, 2.7 Hz, 1 H), 7.06-7.12 (m, 1 H), 7.23 (d, J=7.8 Hz, 2 H), 7.33-7.44 (m, 3 H), 7.54-7.64 (m, 2 H), 9.94 (br. s., 1 H).
LCMS retention time: 1.02 min. (Condition 4-1)
MS (ESI posi) m/z: 617[M+H]$^+$.

Working Example 6-81

$^1$H NMR (600 MHz, DMSO-d$_6$) δ ppm −0.05-−0.02 (m, 2 H), 0.33-0.40 (m, 2 H), 0.62-0.70 (m, 1 H), 1.11-1.18 (m, 2

H), 1.27 (s, 9 H), 1.56-1.64 (m, 2 H), 2.44-2.57 (m, 2 H), 3.02-3.49 (m, 7 H), 3.75-3.84 (m, 1 H), 4.40-4.49 (m, 1 H), 4.68-4.76 (m, 1 H), 6.92-7.03 (m, 2 H), 7.10-7.16 (m, 1 H), 7.19-7.26 (m, 2 H), 7.35-7.43 (m, 3 H), 7.56-7.66 (m, 2 H), 10.11 (s, 1 H).
LCMS retention time: 1.11 min. (Condition 4-2)
MS (ESI posi) m/z: 549[M+H]$^+$.

Working Example 6-82

$^1$H NMR (600 MHz, DMSO-d$_6$) δ ppm 0.96-1.05 (m, 2 H), 1.21-1.27 (m, 2 H), 1.38 (t, J=7.1 Hz, 3 H), 1.41-1.57 (m, 6 H), 1.65-1.76 (m, 3 H), 3.06-3.27 (m, 5 H), 3.61-3.67 (m, 1 H), 4.16 (q, J=7.1 Hz, 2 H), 4.27-4.39 (m, 3 H), 4.41-4.49 (m, 1 H), 6.91-7.02 (m, 2 H), 7.08-7.14 (m, 1 H), 7.41 (d, J=7.8 Hz, 1 H), 7.53-7.67 (m, 3 H), 7.94 (s., 1 H), 10.10 (br. s., 1 H).
LCMS retention time: 1.01 min. (Condition 4-1)
MS (ESI posi) m/z: 525[M+H]$^+$.

Working Example 6-83

$^1$H NMR (600 MHz, DMSO-d$_6$) δ ppm 1.14-1.24 (m, 2 H), 1.54-1.70 (m, 5 H), 3.04-3.86 (m, 9 H), 3.93-3.99 (m, 2 H), 4.35-4.79 (m, 3 H), 6.67-6.72 (m, 1 H), 6.75-6.82 (m, 1 H), 7.01-7.07 (m, 1 H), 7.26-7.63 (m, 3 H), 9.17-9.36 (m, 2 H), 9.87 (s, 1 H).
LCMS retention time: 1.90 min. (Condition 3)
MS ESI/APCI Dual posi: 595[M+H]$^+$.

Working Example 6-84

$^1$H NMR (600 MHz, DMSO-d$_6$) δ ppm 0.97-1.04 (m, 2 H), 1.21-1.26 (m, 2 H), 1.40-1.57 (m, 6 H), 1.65-1.75 (m, 3 H), 2.45-2.54 (m, 2 H), 3.07-3.14 (m, 1 H), 3.18-3.35 (m, 2 H), 3.65-3.72 (m, 1 H), 4.34-4.53 (m, 4 H), 5.00-5.08 (m, 2 H), 6.92-6.95 (m, 1 H), 6.97-7.01 (m, 1 H), 7.08-7.14 (m, 2 H), 7.40 (d, J=8.7 Hz, 1 H), 7.54-7.57 (m, 1 H), 7.60 (s, 1 H), 8.07-8.10 (m, 1 H), 8.40-8.42 (m, 1 H), 10.09 (s, 1 H).
LCMS retention time: 2.12 min. (Condition 3)
MS ESI/APCI Dual posi: 606[M+H]$^+$.

Working Example 6-85

$^1$H NMR (600 MHz, DMSO-d$_6$) δ ppm 0.95-1.06 (m, 2 H), 1.20-1.27 (m, 2 H), 1.36 (s, 9 H), 1.39-1.58 (m, 7 H), 1.64-1.75 (m, 3 H), 3.01-4.61 (m, 9 H), 6.91-7.03 (m, 2 H), 7.08-7.15 (m, 1 H), 7.34-7.86 (m, 5 H), 8.66 (d, J=5.0 Hz, 1 H), 10.10 (br. s., 1 H).
LCMS retention time: 1.08 min. (Condition 5-1)
MS (ESI posi) m/z: 564[M+H]$^+$.

Working Example 6-86

$^1$H NMR (600 MHz, DMSO-d$_6$) δ ppm 0.96-1.06 (m, 2 H), 1.19-1.28 (m, 3 H), 1.33 (s, 9 H), 1.40-1.58 (m, 7 H), 1.64-1.77 (m, 4 H), 3.15-3.23 (m, 3 H), 4.51-4.80 (m, 4 H), 6.93-7.02 (m, 2 H), 7.12-7.16 (m, 1 H), 7.42 (d, J=8.3 Hz, 1 H), 7.57-7.67 (m, 3 H), 8.83 (d, J=5.4 Hz, 1 H), 10.12 (s, 1 H).
LCMS retention time: 1.17 min. (Condition 5-1)
MS (ESI posi) m/z: 565[M+H]$^+$.

Working Example 6-87

$^1$H NMR (600 MHz, DMSO-d$_6$) δ ppm 0.96-1.05 (m, 2 H), 1.20-1.27 (m, 2 H), 1.32 (s, 9 H), 1.41-1.58 (m, 6 H), 1.64-1.76 (m, 3 H), 3.08-3.25 (m, 2 H), 3.34-3.87 (m, 2 H), 4.45-4.64 (m, 2 H), 4.72-5.47 (m, 4 H), 6.91-7.03 (m, 2 H), 7.07-7.15 (m, 1 H), 7.39-7.44 (m, 1 H), 7.49 (s, 1 H), 7.55-7.63 (m, 2 H), 10.11 (s, 1 H).
LCMS retention time: 1.39 min. (Condition 2)
MS (ESI posi) m/z: 570[M+H]$^+$.

Working Example 6-88

$^1$H NMR (600 MHz, DMSO-d$_6$) δ ppm 0.96-1.07 (m, 2 H), 1.20-1.28 (m, 2 H), 1.36 (s, 9 H), 1.42-1.58 (m, 6 H), 1.65-1.77 (m, 3 H), 3.08-3.28 (m, 2 H), 3.32-3.55 (m, 5 H), 3.74-4.25 (m, 3 H), 4.39-4.48 (m, 1 H), 4.67-4.74 (m, 1 H), 6.91-7.03 (m, 2 H), 7.09-7.16 (m, 1 H), 7.35-7.43 (m, 1 H), 7.54 (s, 1 H), 7.58-7.65 (m, 2 H), 10.12 (s, 1 H).
LCMS retention time: 0.98 min. (Condition 2)
MS (ESI posi) m/z: 584[M+H]$^+$.

Working Example 6-89

$^1$H NMR (600 MHz, DMSO-d$_6$) δ ppm 0.97-1.06 (m, 2 H), 1.20-1.29 (m, 2 H), 1.37 (s, 9 H), 1.41-1.58 (m, 6 H), 1.65-1.77 (m, 3 H), 3.10-3.90 (m, 6 H), 4.45-4.88 (m, 4 H), 6.92-7.03 (m, 2 H), 7.09-7.17 (m, 1 H), 7.36-7.43 (m, 1 H), 7.54-7.65 (m, 2 H), 8.98 (s, 2 H), 10.10 (s, 1 H).
LCMS retention time: 0.98 min. (Condition 2)
MS (ESI posi) m/z: 565[M+H]$^+$.

Working Example 6-90

$^1$H NMR (600 MHz, DMSO-d$_6$) δ ppm 0.95-1.07 (m, 2 H), 1.19-1.29 (m, 2 H), 1.37-1.58 (m, 15 H), 1.64-1.77 (m, 3 H), 2.82-3.94 (m, 10 H), 4.40-4.51 (m, 1 H), 4.64-4.75 (m, 1 H), 6.90-7.05 (m, 2 H), 7.08-7.16 (m, 1 H), 7.36-7.45 (m, 1 H), 7.54-7.96 (m, 4 H), 8.60-8.74 (m, 1 H), 10.12 (s, 1 H).
LCMS retention time: 1.80 min. (Condition 3)
MS ESI/APCI Dual posi: 578[M+H]$^+$.

The structures of the compounds of Working Examples 6-2 to 6-90 are shown in Tables 21-1 to 21-8.

TABLE 21-1

| Working Ex. | Structure |
|---|---|
| 6-2 | 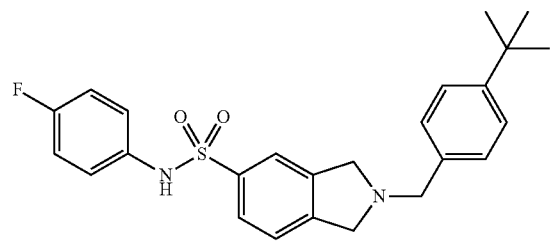 [SMILES: CC(C)(C)c1ccc(CN2Cc3ccc(S(=O)(=O)Nc4ccc(F)cc4)cc3C2)cc1] |

TABLE 21-1-continued

| Working Ex. | Structure |
|---|---|
| 6-3 | 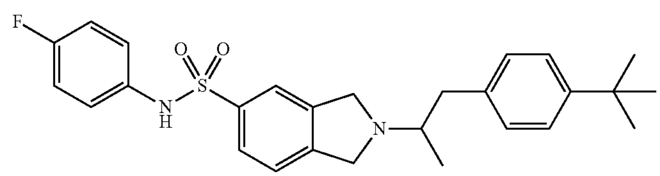 [SMILES: CC(Cc1ccc(C(C)(C)C)cc1)N1Cc2ccc(S(=O)(=O)Nc3ccc(F)cc3)cc2C1] |
| 6-4 | 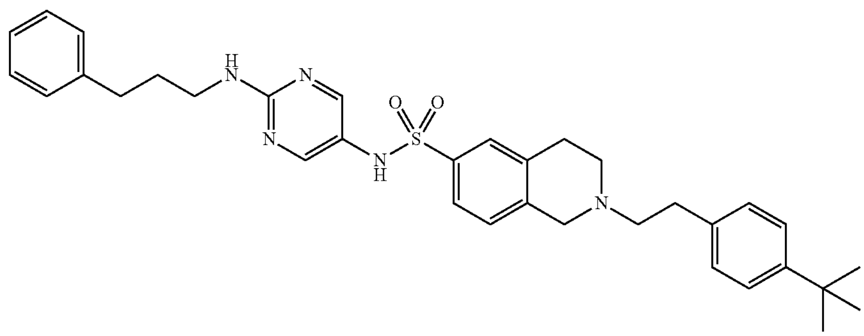 [SMILES: CC(C)(C)c1ccc(CCN2CCc3cc(S(=O)(=O)Nc4cnc(NCCCc5ccccc5)nc4)ccc3C2)cc1] |
| 6-5 | 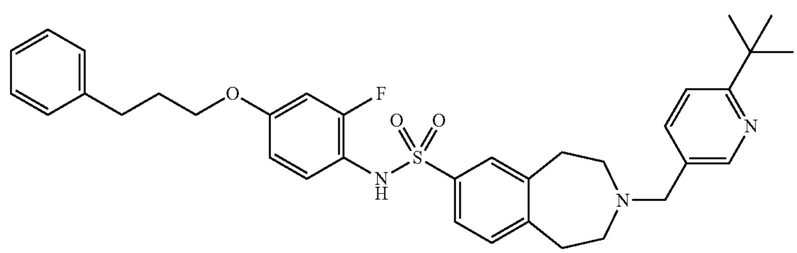 [SMILES: CC(C)(C)c1ccc(CN2CCc3ccc(S(=O)(=O)Nc4ccc(OCCCc5ccccc5)cc4F)cc3CC2)cn1] |
| 6-6 | 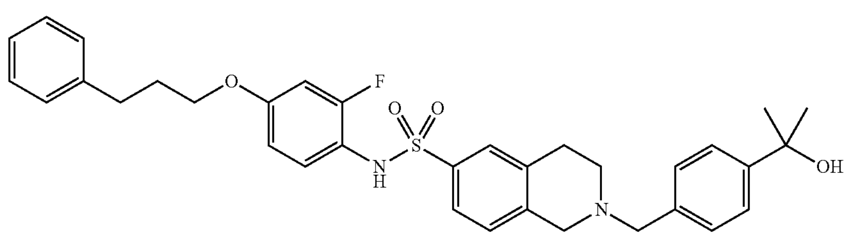 [SMILES: CC(C)(O)c1ccc(CN2CCc3cc(S(=O)(=O)Nc4ccc(OCCCc5ccccc5)cc4F)ccc3C2)cc1] |
| 6-7 | 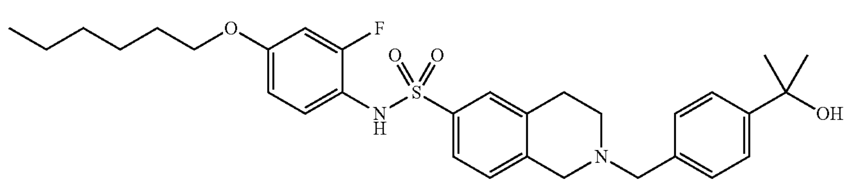 [SMILES: CCCCCCOc1ccc(NS(=O)(=O)c2ccc3c(c2)CCN(Cc2ccc(C(C)(C)O)cc2)C3)c(F)c1] |
| 6-8 | 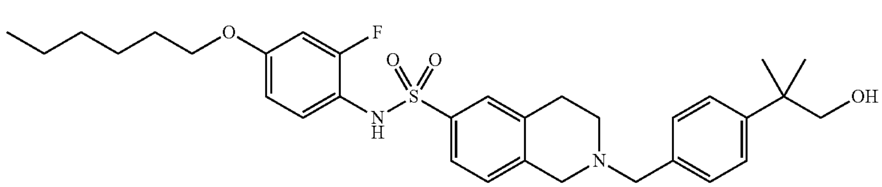 [SMILES: CCCCCCOc1ccc(NS(=O)(=O)c2ccc3c(c2)CCN(Cc2ccc(C(C)(C)CO)cc2)C3)c(F)c1] |

TABLE 21-1-continued
| Working Ex. | Structure |
|---|---|
| 6-9 | 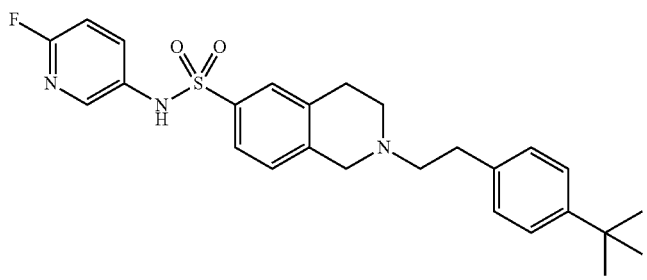 [SMILES: CC(C)(C)c1ccc(CCN2CCc3cc(S(=O)(=O)Nc4ccc(F)nc4)ccc3C2)cc1] |
| 6-10 | 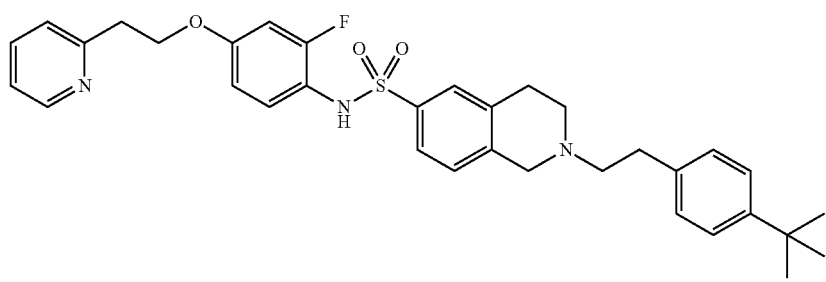 [SMILES: CC(C)(C)c1ccc(CCN2CCc3cc(S(=O)(=O)Nc4ccc(OCCc5ccccn5)cc4F)ccc3C2)cc1] |
| 6-11 | 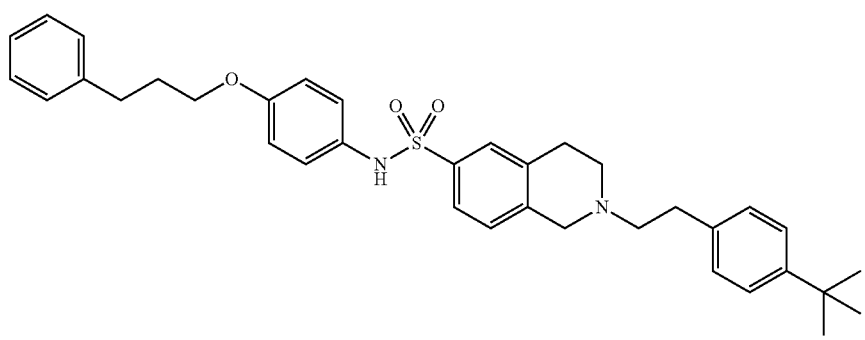 |
| 6-12 | 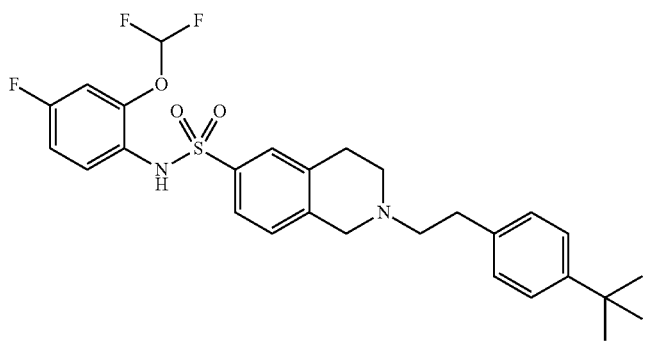 [SMILES: CC(C)(C)c1ccc(CCN2CCc3cc(S(=O)(=O)Nc4ccc(F)cc4OC(F)F)ccc3C2)cc1] |
| 6-13 | 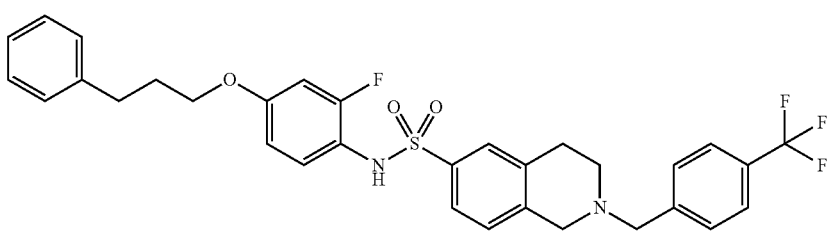 [SMILES: O=S(=O)(Nc1ccc(OCCCc2ccccc2)cc1F)c1ccc2c(c1)CCN(Cc1ccc(C(F)(F)F)cc1)C2] |

TABLE 21-1-continued
| Working Ex. | Structure |
|---|---|
| 6-14 | 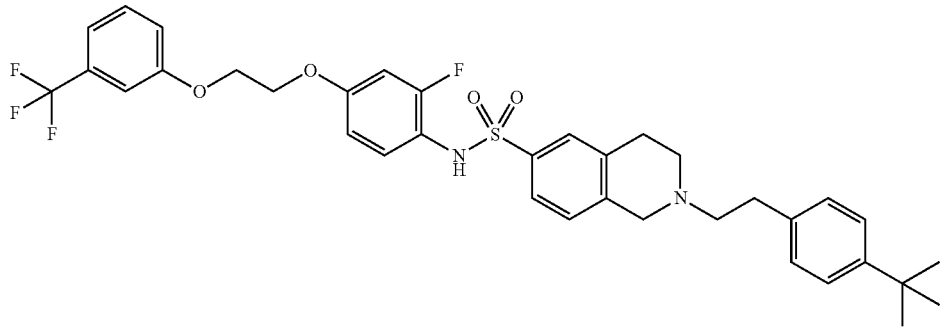 [SMILES: CC(C)(C)c1ccc(CCN2CCc3cc(S(=O)(=O)Nc4ccc(OCCOc5cccc(C(F)(F)F)c5)cc4F)ccc3C2)cc1] |
| 6-15 | 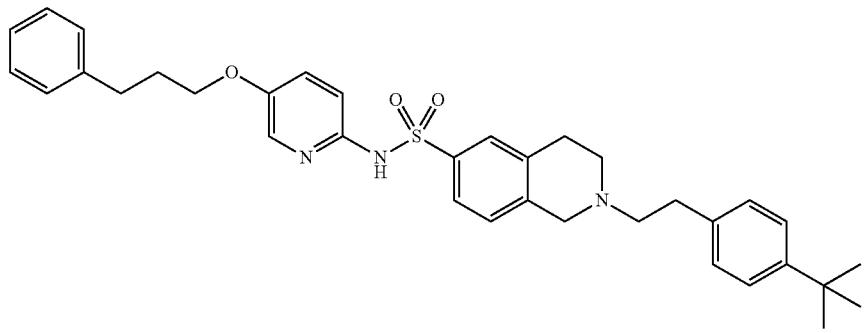 [SMILES: CC(C)(C)c1ccc(CCN2CCc3cc(S(=O)(=O)Nc4ccc(OCCCc5ccccc5)cn4)ccc3C2)cc1] |
TABLE 21-2
| Working Ex. | Structure |
|---|---|
| 6-16 | 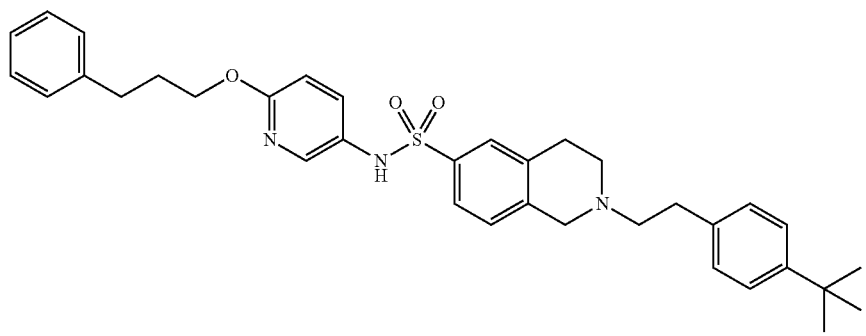 |
| 6-17 | 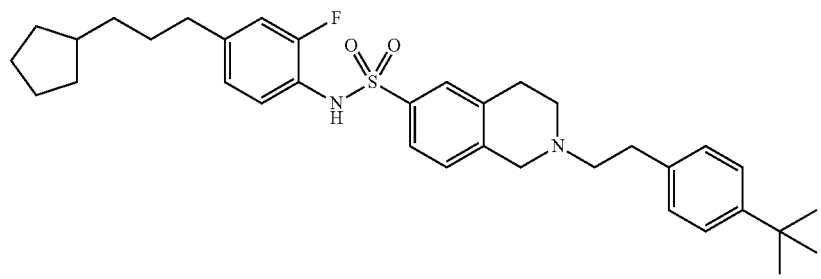 [SMILES: CC(C)(C)c1ccc(CCN2CCc3cc(S(=O)(=O)Nc4ccc(CCCC5CCCC5)cc4F)ccc3C2)cc1] |

TABLE 21-2-continued
| Working Ex. | Structure |
|---|---|
| 6-18 | 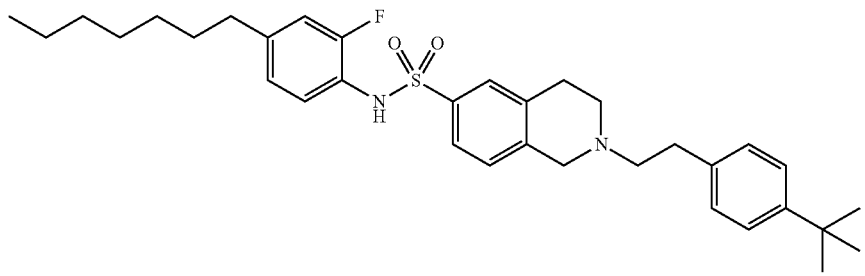 [SMILES: CCCCCCCc1ccc(NS(=O)(=O)c2ccc3c(c2)CCN(CCc2ccc(C(C)(C)C)cc2)C3)c(F)c1] |
| 6-19 | 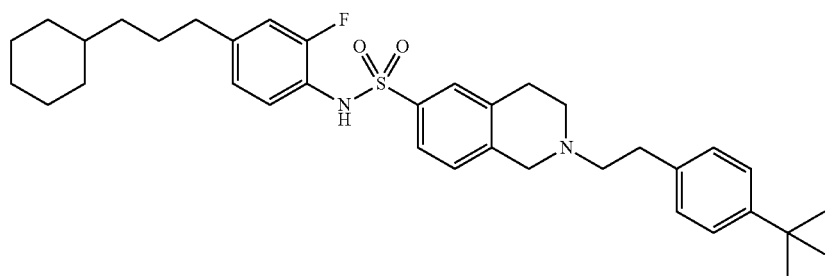 [SMILES: CC(C)(C)c1ccc(CCN2CCc3cc(S(=O)(=O)Nc4ccc(CCCC5CCCCC5)cc4F)ccc3C2)cc1] |
| 6-20 | 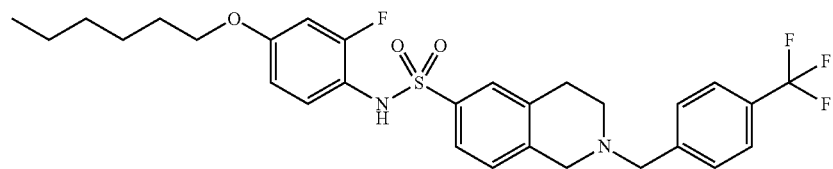 [SMILES: CCCCCCOc1ccc(NS(=O)(=O)c2ccc3c(c2)CCN(Cc2ccc(C(F)(F)F)cc2)C3)c(F)c1] |
| 6-21 | 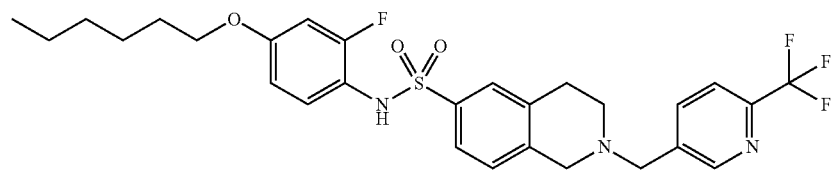 [SMILES: CCCCCCOc1ccc(NS(=O)(=O)c2ccc3c(c2)CCN(Cc2ccc(C(F)(F)F)nc2)C3)c(F)c1] |
| 6-22 | 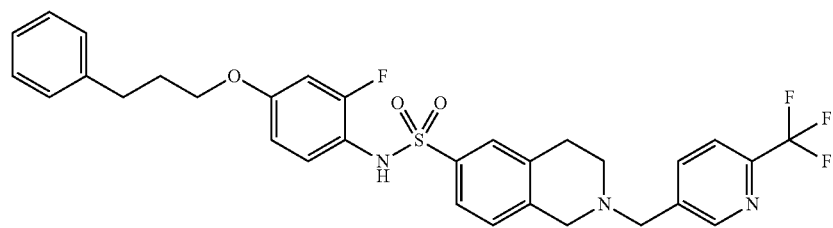 |
| 6-23 | 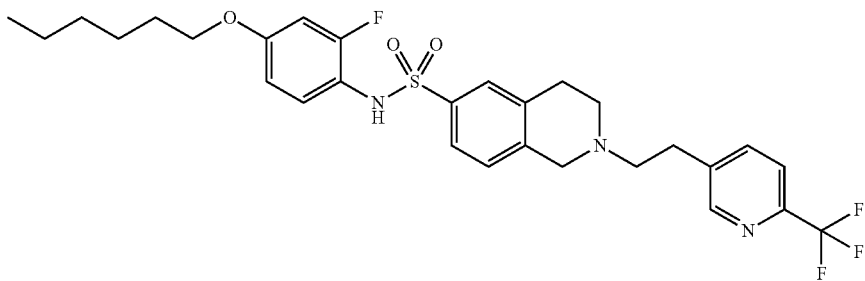 [SMILES: CCCCCCOc1ccc(NS(=O)(=O)c2ccc3c(c2)CCN(CCc2ccc(C(F)(F)F)nc2)C3)c(F)c1] |

TABLE 21-2-continued
| Working Ex. | Structure |
|---|---|
| 6-24 | 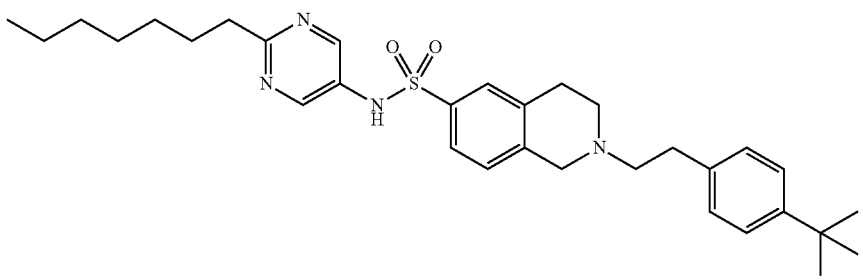 [SMILES: CCCCCCCc1ncc(NS(=O)(=O)c2ccc3c(c2)CCN(CCc2ccc(C(C)(C)C)cc2)C3)cn1] |
| 6-25 | 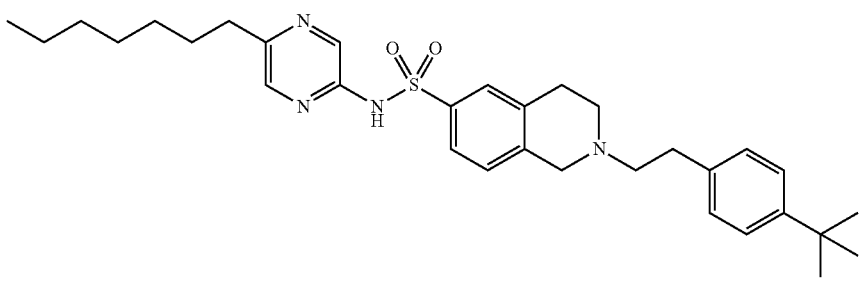 [SMILES: CCCCCCCc1cnc(NS(=O)(=O)c2ccc3c(c2)CCN(CCc2ccc(C(C)(C)C)cc2)C3)cn1] |
| 6-26 | 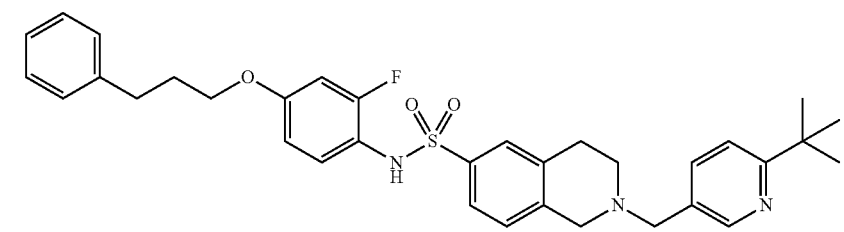 |
| 6-27 | 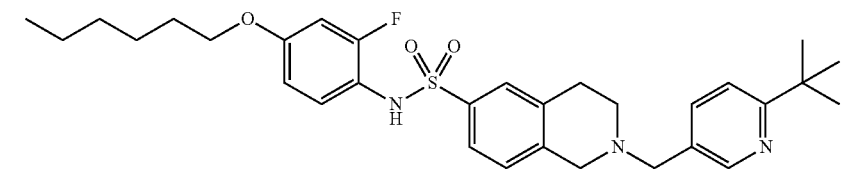 [SMILES: CCCCCCOc1ccc(NS(=O)(=O)c2ccc3c(c2)CCN(Cc2ccc(C(C)(C)C)nc2)C3)c(F)c1] |
| 6-28 | 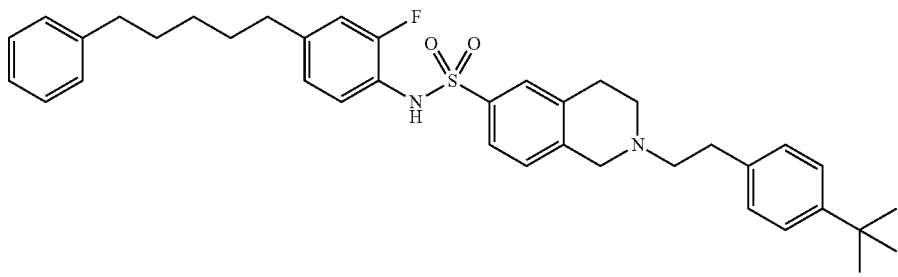 [SMILES: CC(C)(C)c1ccc(CCN2CCc3cc(S(=O)(=O)Nc4ccc(CCCCCc5ccccc5)cc4F)ccc3C2)cc1] |
| 6-29 | 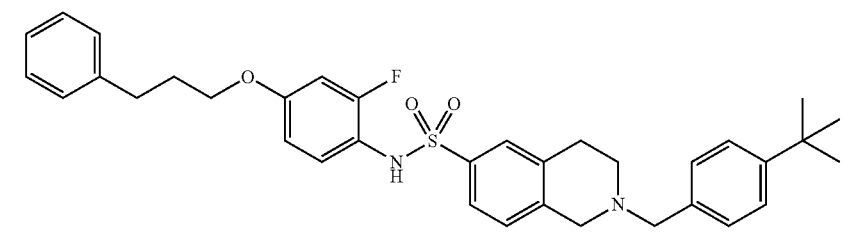 [SMILES: CC(C)(C)c1ccc(CN2CCc3cc(S(=O)(=O)Nc4ccc(OCCCc5ccccc5)cc4F)ccc3C2)cc1] |

TABLE 21-3

| Working Ex. | Structure |
|---|---|
| 6-30 | (structure) |
| 6-31 | (structure) |
| 6-32 | (structure) |
| 6-33 | (structure) |
| 6-34 | (structure) |
| 6-35 | (structure) |
| 6-36 | (structure) |

TABLE 21-3-continued

| Working Ex. | Structure |
|---|---|
| 6-37 | 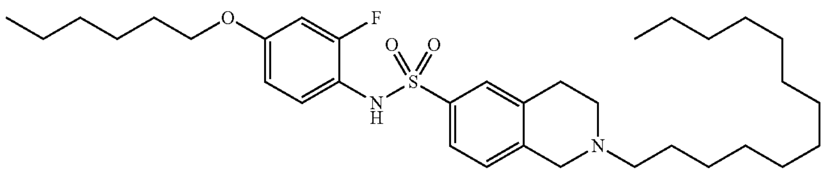 [SMILES: CCCCCCCCCCCCCN1CCc2cc(S(=O)(=O)Nc3ccc(OCCCCCC)cc3F)ccc2C1] |
| 6-38 | 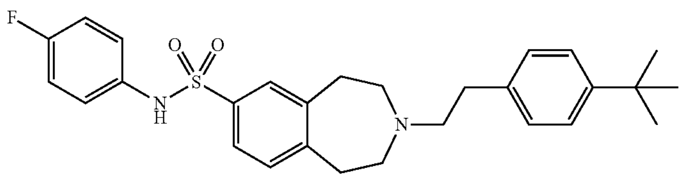 [SMILES: CC(C)(C)c1ccc(CCN2CCc3ccc(S(=O)(=O)Nc4ccc(F)cc4)cc3CC2)cc1] |
| 6-39 | 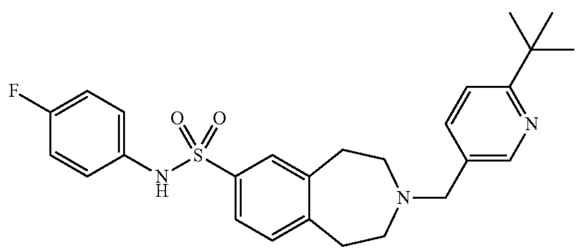 [SMILES: CC(C)(C)c1ccc(CN2CCc3ccc(S(=O)(=O)Nc4ccc(F)cc4)cc3CC2)cn1] |
| 6-40 | 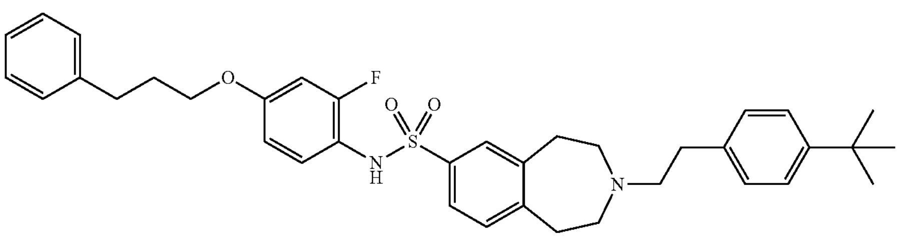 [SMILES: CC(C)(C)c1ccc(CCN2CCc3ccc(S(=O)(=O)Nc4ccc(OCCCc5ccccc5)cc4F)cc3CC2)cc1] |
| 6-41 | 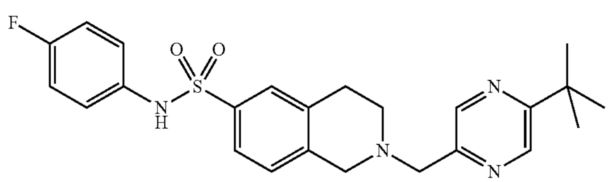 [SMILES: CC(C)(C)c1cnc(CN2CCc3cc(S(=O)(=O)Nc4ccc(F)cc4)ccc3C2)cn1] |
| 6-42 | 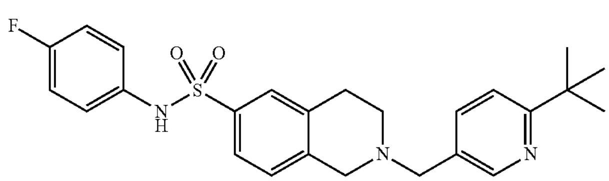 [SMILES: CC(C)(C)c1ccc(CN2CCc3cc(S(=O)(=O)Nc4ccc(F)cc4)ccc3C2)cn1] |
| 6-43 | 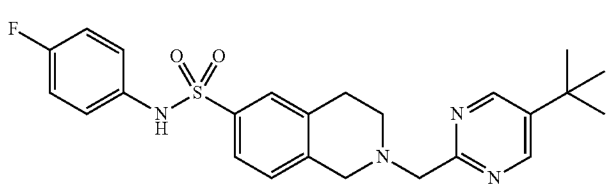 [SMILES: CC(C)(C)c1cnc(CN2CCc3cc(S(=O)(=O)Nc4ccc(F)cc4)ccc3C2)nc1] |

TABLE 21-4
| Working Ex. | Structure |
|---|---|
| 6-44 | 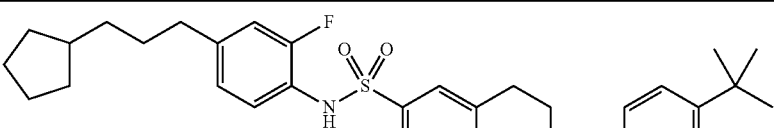 |
| 6-45 | 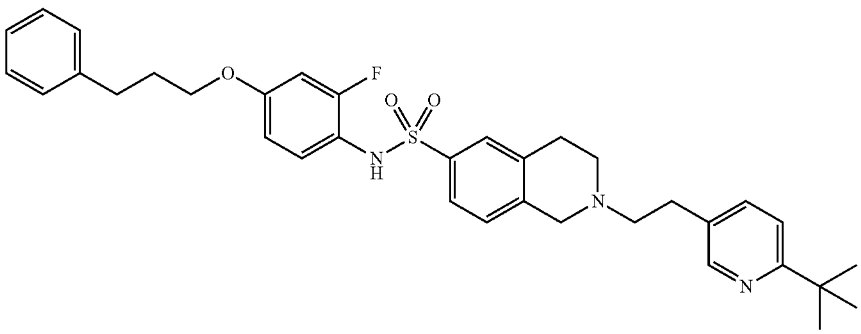 [SMILES: CC(C)(C)c1ccc(CCN2CCc3cc(S(=O)(=O)Nc4ccc(OCCCc5ccccc5)cc4F)ccc3C2)cn1] |
| 6-46 | 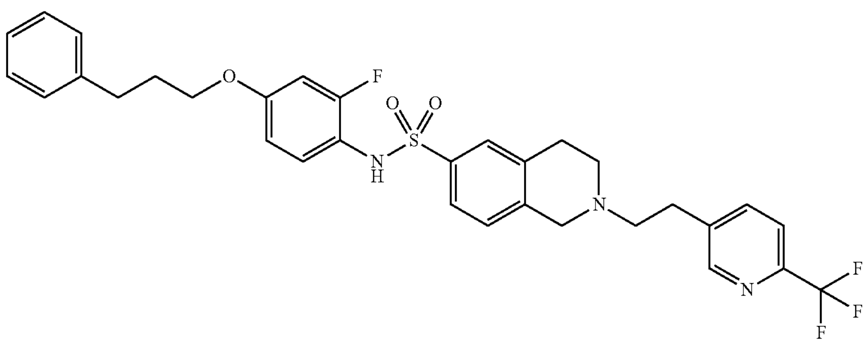 [SMILES: O=S(=O)(Nc1ccc(OCCCc2ccccc2)cc1F)c1ccc2c(c1)CCN(CCc1ccc(C(F)(F)F)nc1)C2] |
TABLE 21-5
| Working Ex. | Structure |
|---|---|
| 6-47 | 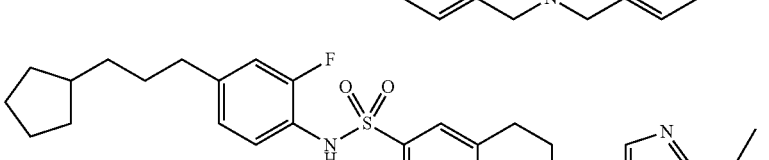 |
| 6-48 | 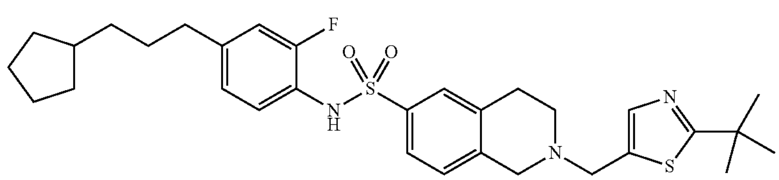 [SMILES: CC(C)(C)c1ncc(CN2CCc3cc(S(=O)(=O)Nc4ccc(CCCC5CCCC5)cc4F)ccc3C2)s1] |

US 9,035,059 B2
TABLE 21-5-continued
| Working Ex. | Structure |
|---|---|
| 6-49 | 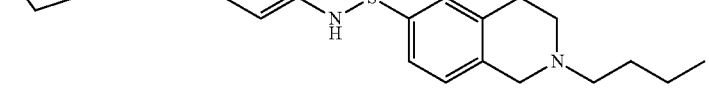 |
| 6-50 | 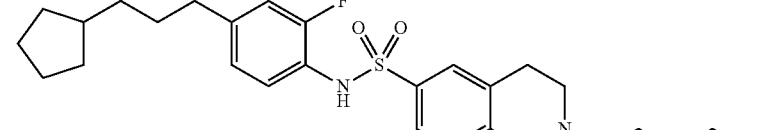 |
| 6-51 | 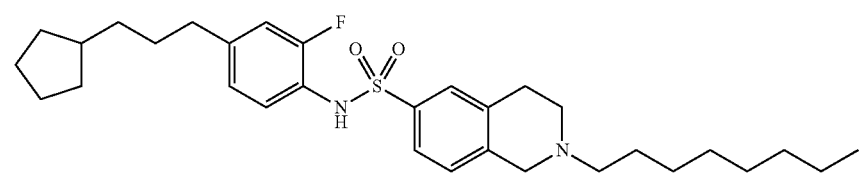 [SMILES: CCCCCCCCN1CCc2cc(S(=O)(=O)Nc3ccc(CCCC4CCCC4)cc3F)ccc2C1] |
| 6-52 | 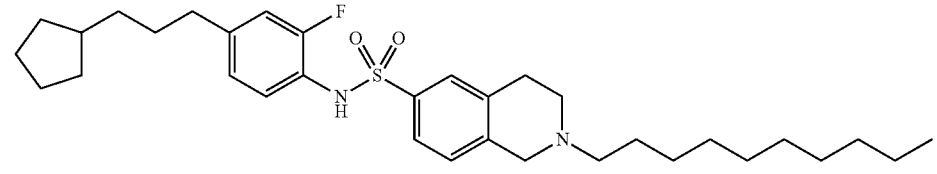 [SMILES: CCCCCCCCCCN1CCc2cc(S(=O)(=O)Nc3ccc(CCCC4CCCC4)cc3F)ccc2C1] |
| 6-53 | 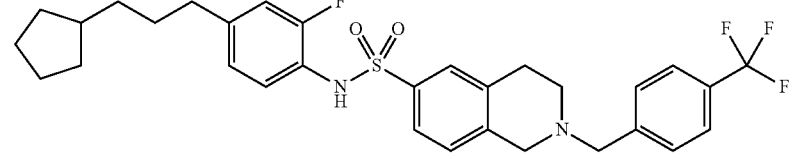 |
| 6-54 | 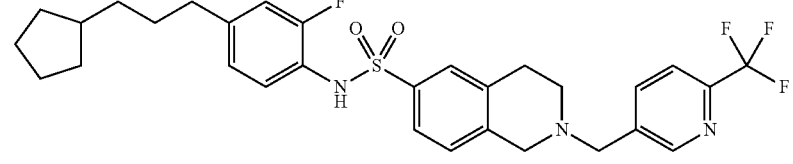 |
| 6-55 | 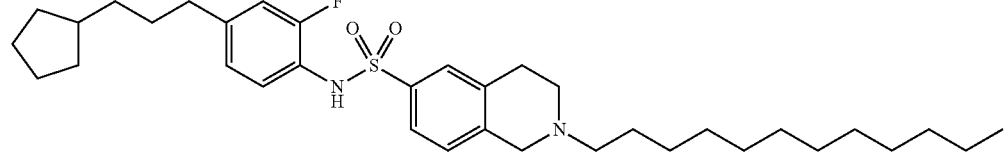 |
| 6-56 | 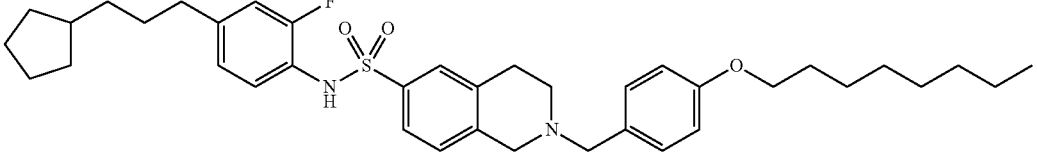 |

TABLE 21-5-continued
| Working Ex. | Structure |
|---|---|
| 6-57 | 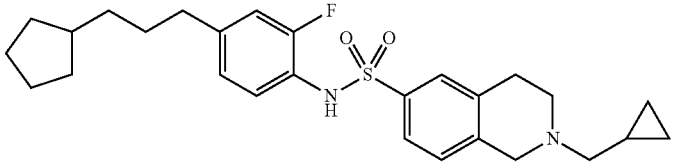 |
| 6-58 | 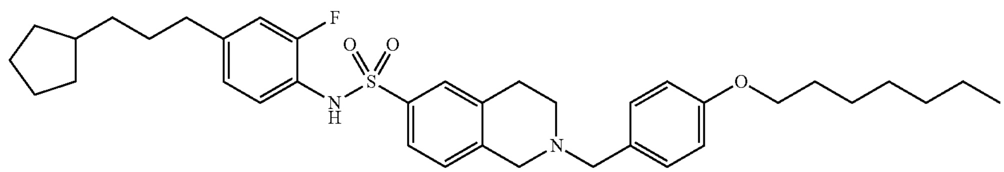 [SMILES: CCCCCCCOc1ccc(CN2CCc3cc(S(=O)(=O)Nc4ccc(CCCC5CCCC5)cc4F)ccc3C2)cc1] |
| 6-59 | 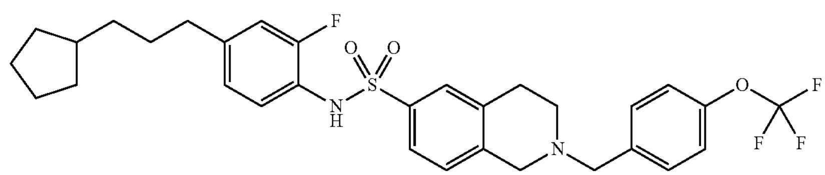 [SMILES: O=S(=O)(Nc1ccc(CCCC2CCCC2)cc1F)c1ccc2c(c1)CCN(Cc1ccc(OC(F)(F)F)cc1)C2] |
| 6-60 | 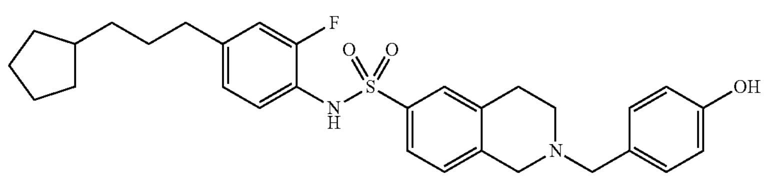 [SMILES: O=S(=O)(Nc1ccc(CCCC2CCCC2)cc1F)c1ccc2c(c1)CCN(Cc1ccc(O)cc1)C2] |
TABLE 21-6
| Working Ex. | Structure |
|---|---|
| 6-61 | 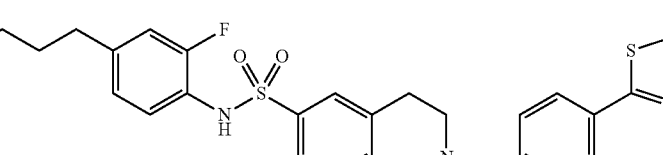 |
| 6-62 | 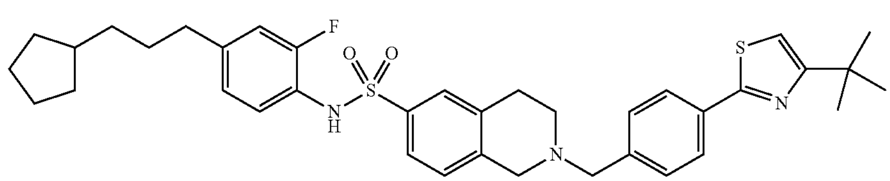 [SMILES: CC(C)(C)c1csc(-c2ccc(CN3CCc4cc(S(=O)(=O)Nc5ccc(CCCC6CCCC6)cc5F)ccc4C3)cc2)n1] |
| 6-63 | 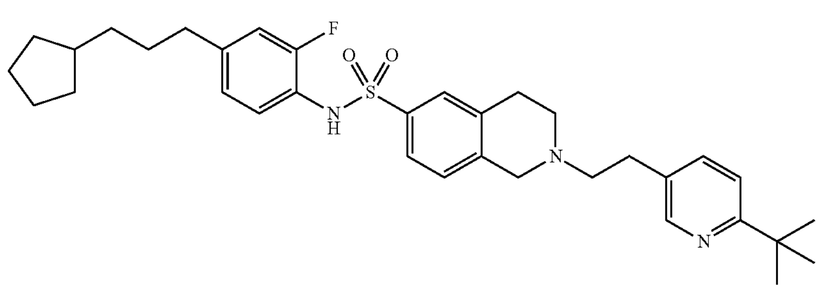 [SMILES: CC(C)(C)c1ccc(CCN2CCc3cc(S(=O)(=O)Nc4ccc(CCCC5CCCC5)cc4F)ccc3C2)cn1] |

TABLE 21-6-continued

| Working Ex. | Structure |
|---|---|
| 6-64 | 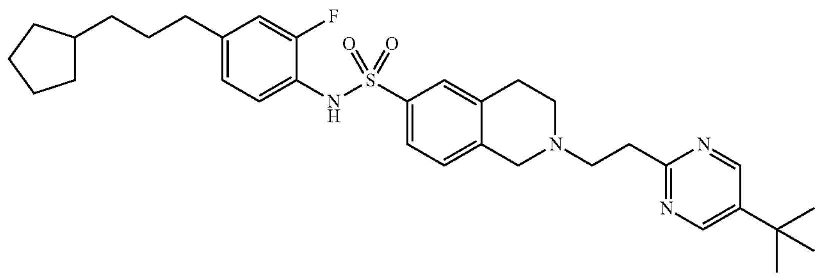 [SMILES: CC(C)(C)c1cnc(CCN2CCc3cc(S(=O)(=O)Nc4ccc(CCCC5CCCC5)cc4F)ccc3C2)nc1] |
| 6-65 | 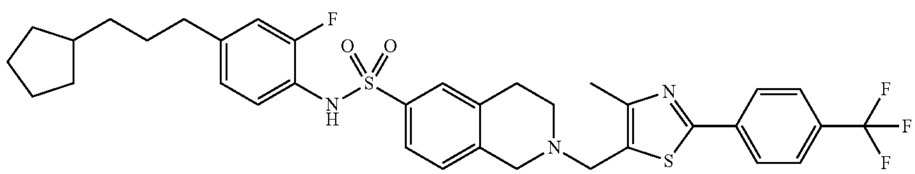 [SMILES: Cc1nc(-c2ccc(C(F)(F)F)cc2)sc1CN1CCc2cc(S(=O)(=O)Nc3ccc(CCCC4CCCC4)cc3F)ccc2C1] |
| 6-66 | 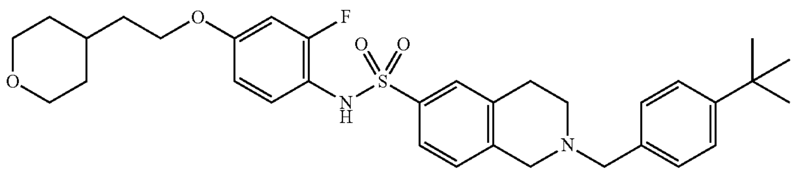 [SMILES: CC(C)(C)c1ccc(CN2CCc3cc(S(=O)(=O)Nc4ccc(OCCC5CCOCC5)cc4F)ccc3C2)cc1] |
| 6-67 | 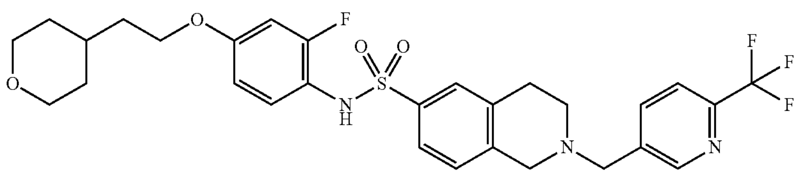 [SMILES: O=S(=O)(Nc1ccc(OCCC2CCOCC2)cc1F)c1ccc2c(c1)CCN(Cc1ccc(C(F)(F)F)nc1)C2] |
| 6-68 | 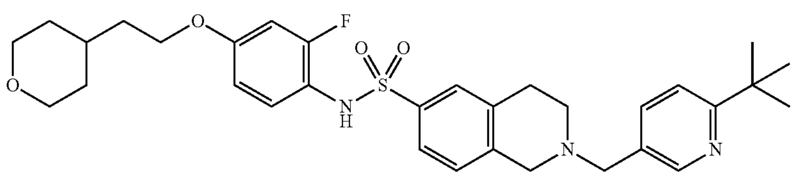 |
| 6-69 | 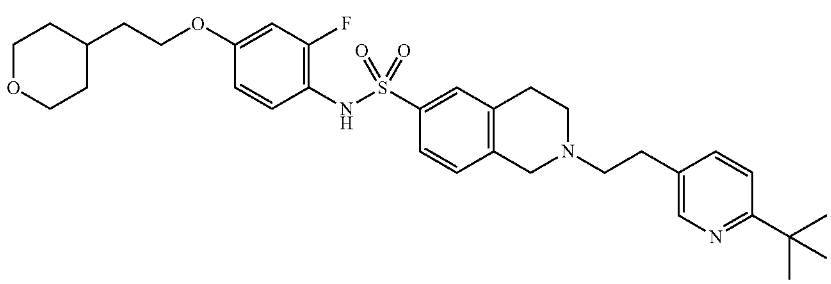 [SMILES: CC(C)(C)c1ccc(CCN2CCc3cc(S(=O)(=O)Nc4ccc(OCCC5CCOCC5)cc4F)ccc3C2)cn1] |
| 6-70 | 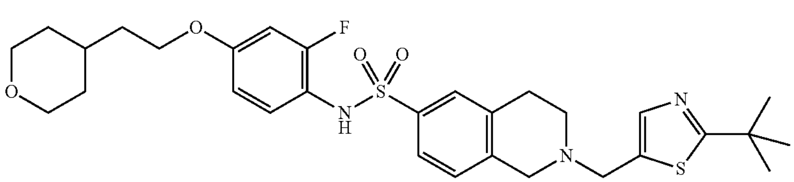 [SMILES: CC(C)(C)c1ncc(CN2CCc3cc(S(=O)(=O)Nc4ccc(OCCC5CCOCC5)cc4F)ccc3C2)s1] |

TABLE 21-6-continued

| Working Ex. | Structure |
|---|---|
| 6-71 | 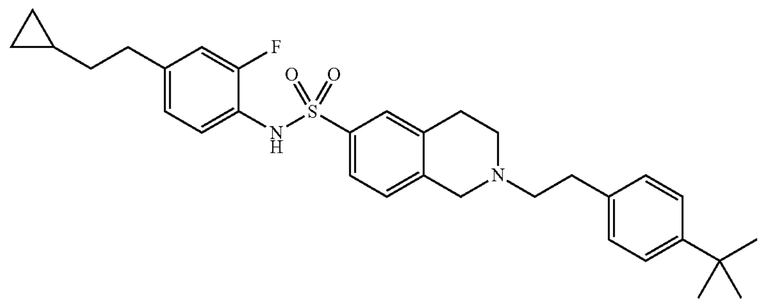 [SMILES: CC(C)(C)c1ccc(CCN2CCc3cc(S(=O)(=O)Nc4ccc(CCC5CC5)cc4F)ccc3C2)cc1] |
| 6-72 | 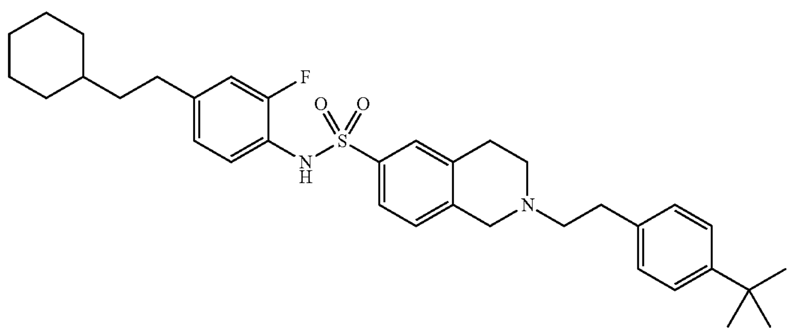 [SMILES: CC(C)(C)c1ccc(CCN2CCc3cc(S(=O)(=O)Nc4ccc(CCC5CCCCC5)cc4F)ccc3C2)cc1] |
| 6-73 | 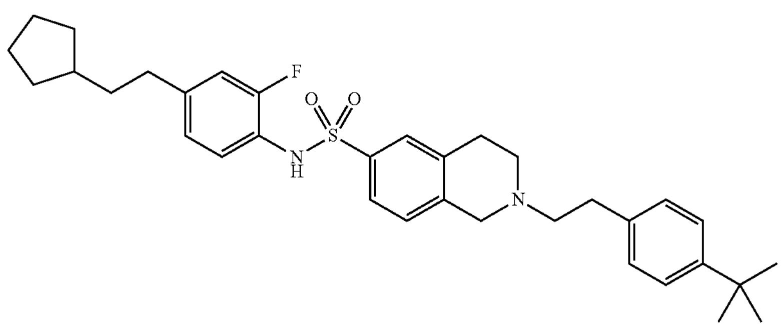 [SMILES: CC(C)(C)c1ccc(CCN2CCc3cc(S(=O)(=O)Nc4ccc(CCC5CCCC5)cc4F)ccc3C2)cc1] |
| 6-74 | 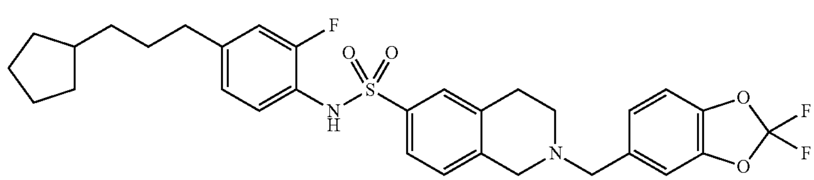 [SMILES: O=S(=O)(Nc1ccc(CCCC2CCCC2)cc1F)c1ccc2c(c1)CCN(Cc1ccc3c(c1)OC(F)(F)O3)C2] |

TABLE 21-7

| Working Ex. | Structure |
|---|---|
| 6-75 | 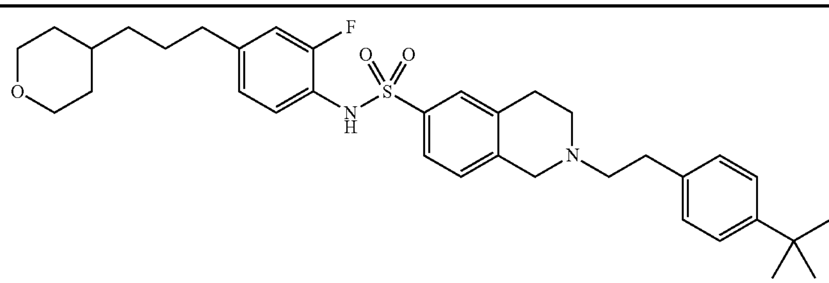 |

TABLE 21-7-continued

| Working Ex. | Structure |
|---|---|
| 6-76 | 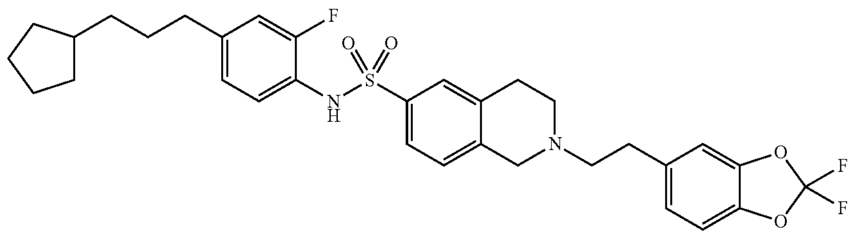 [SMILES: O=S(=O)(Nc1ccc(CCCC2CCCC2)cc1F)c1ccc2c(c1)CCN(CCc1ccc3c(c1)OC(F)(F)O3)C2] |
| 6-77 | 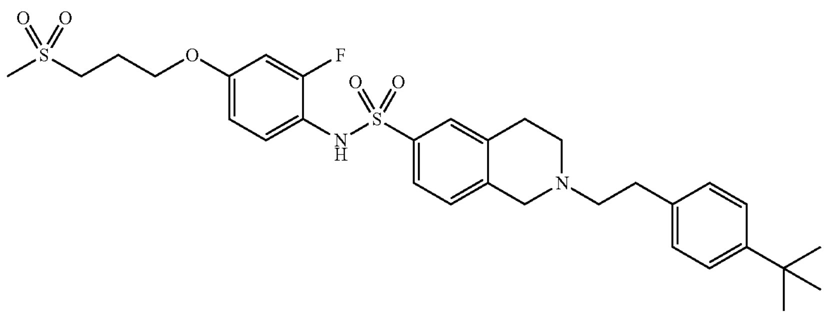 [SMILES: CC(C)(C)c1ccc(CCN2CCc3cc(S(=O)(=O)Nc4ccc(OCCCS(C)(=O)=O)cc4F)ccc3C2)cc1] |
| 6-78 | 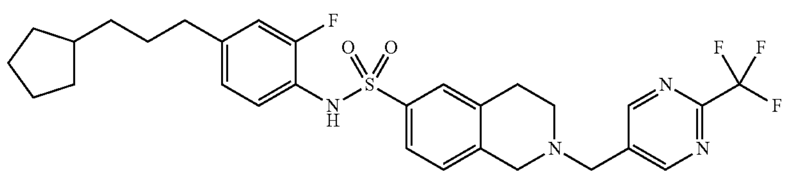 [SMILES: O=S(=O)(Nc1ccc(CCCC2CCCC2)cc1F)c1ccc2c(c1)CCN(Cc1cnc(C(F)(F)F)nc1)C2] |
| 6-79 | 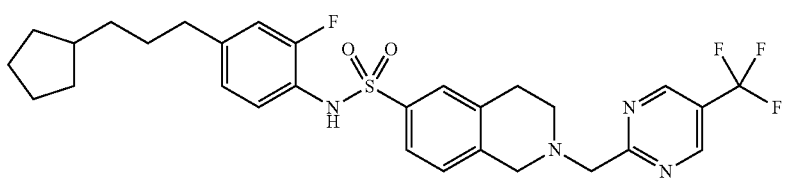 [SMILES: O=S(=O)(Nc1ccc(CCCC2CCCC2)cc1F)c1ccc2c(c1)CCN(Cc1ncc(C(F)(F)F)cn1)C2] |
| 6-80 | 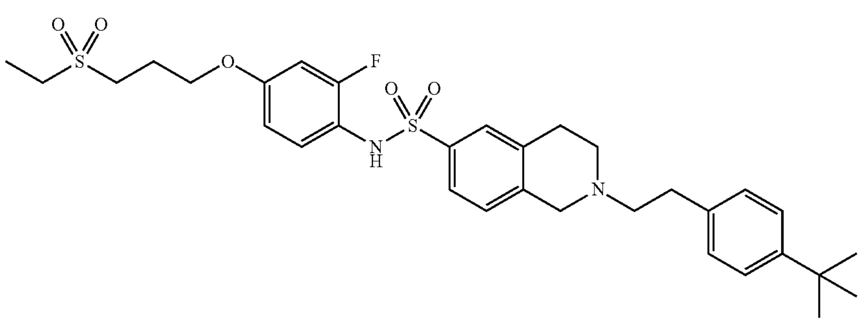 [SMILES: CCS(=O)(=O)CCCOc1ccc(NS(=O)(=O)c2ccc3c(c2)CCN(CCc2ccc(C(C)(C)C)cc2)C3)c(F)c1] |
| 6-81 | 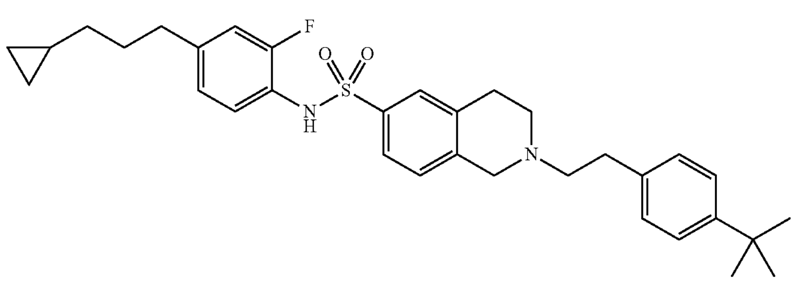 [SMILES: CC(C)(C)c1ccc(CCN2CCc3cc(S(=O)(=O)Nc4ccc(CCCC5CC5)cc4F)ccc3C2)cc1] |

TABLE 21-7-continued

| Working Ex. | Structure |
|---|---|
| 6-82 | 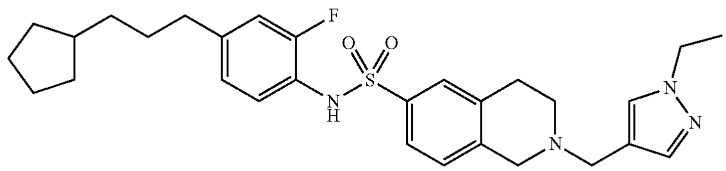 [SMILES: CCn1cc(CN2CCc3cc(S(=O)(=O)Nc4ccc(CCCC5CCCC5)cc4F)ccc3C2)cn1] |
| 6-83 | 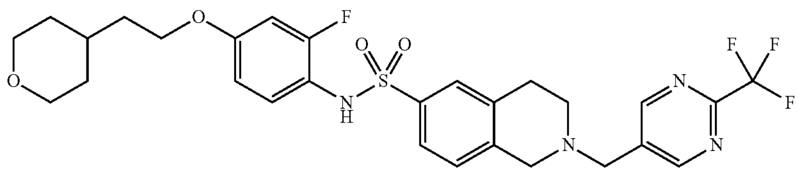 [SMILES: O=S(=O)(Nc1ccc(OCCC2CCOCC2)cc1F)c1ccc2c(c1)CCN(Cc1cnc(C(F)(F)F)nc1)C2] |
| 6-84 | 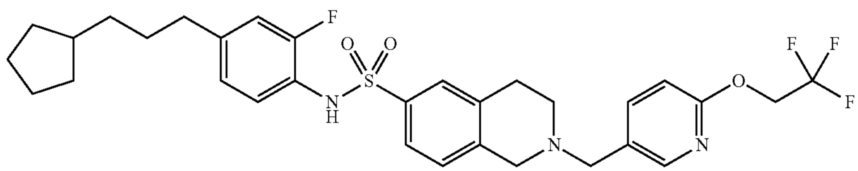 [SMILES: O=S(=O)(Nc1ccc(CCCC2CCCC2)cc1F)c1ccc2c(c1)CCN(Cc1ccc(OCC(F)(F)F)nc1)C2] |
| 6-85 | 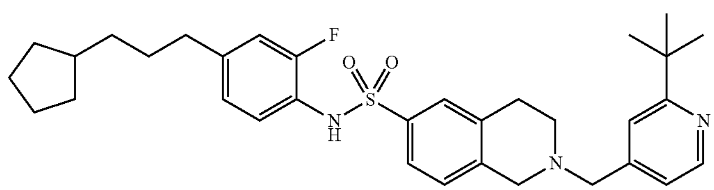 [SMILES: CC(C)(C)c1cc(CN2CCc3cc(S(=O)(=O)Nc4ccc(CCCC5CCCC5)cc4F)ccc3C2)ccn1] |
| 6-86 | 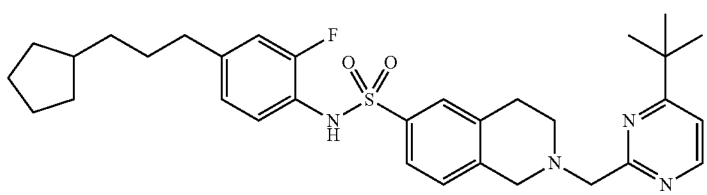 [SMILES: CC(C)(C)c1ccnc(CN2CCc3cc(S(=O)(=O)Nc4ccc(CCCC5CCCC5)cc4F)ccc3C2)n1] |
| 6-87 | 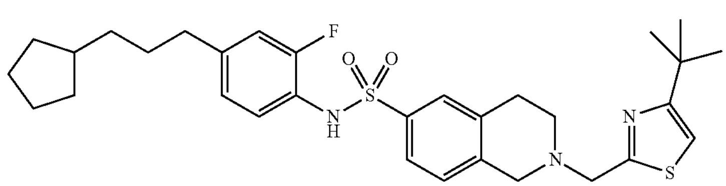 [SMILES: CC(C)(C)c1csc(CN2CCc3cc(S(=O)(=O)Nc4ccc(CCCC5CCCC5)cc4F)ccc3C2)n1] |
| 6-88 | 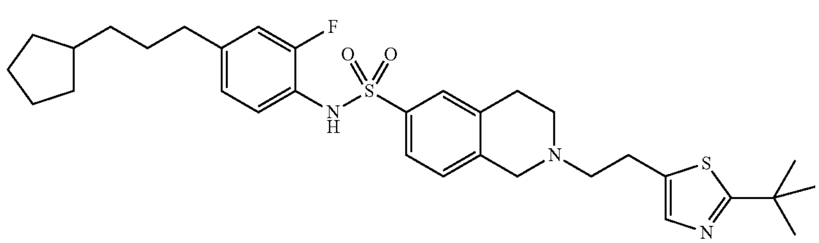 [SMILES: CC(C)(C)c1ncc(CCN2CCc3cc(S(=O)(=O)Nc4ccc(CCCC5CCCC5)cc4F)ccc3C2)s1] |

TABLE 21-8

| Working Ex. | Structure |
|---|---|
| 6-89 | ![structure] |
| 6-90 | ![structure] |

Working Example 7-1

2-[2-(2-tert-Butyl)pyrimidin-5-yl)ethyl]-N-[2-fluoro-4-(hexyloxy)phenyl]-1,2,3,4-tetrahydroisoquinoline-6-sulfonamide

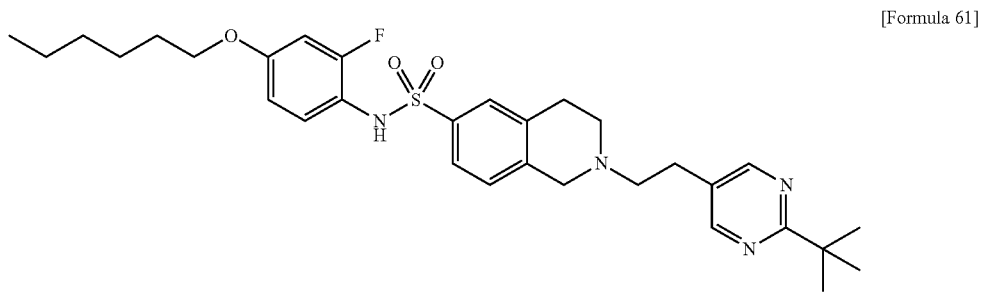 [SMILES: CCCCCCOc1ccc(NS(=O)(=O)c2ccc3c(c2)CCN(CCc2cnc(C(C)(C)C)nc2)C3)c(F)c1]

[Formula 61]

(1) Sodium triacetoxyborohydride (159 mg, 0.75 mmol) was added to a chloroform suspension (2.0 mL) of compound 3-5 as obtained in Reference Example 3 (102 mg, 0.25 mmol) and compound 10-3 as obtained in Reference Example 10 (98 mg, 0.55 mmol), and the mixture was stirred at room temperature for 19 hr. Saturated aqueous sodium hydrogen carbonate solution was added to the reaction mixture and the mixture was extracted with chloroform. The solvent was distilled off from the organic layer under reduced pressure and HPLC was performed for purification to afford the trifluoroacetate of the title compound as a colorless amorphous substance.

(2) The trifluoroacetate of the title compound was dissolved in ethyl acetate (1 mL), and 4 mol/L hydrogen chloride-ethyl acetate (0.5 mL) was added thereto, followed by concentration under reduced pressure. The residue was washed with ethyl acetate and hexane to afford the monohydrochloride of the title compound as a colorless powder (91 mg).

LCMS retention time: 4.41 min. (Condition 1-1-3)
MS (ESI posi) m/z: 569[M+H]$^+$.

The compounds of Working Examples 7-2 to 7-24 were obtained by using the corresponding compounds obtained in Reference Example 3 and either the aldehydes obtained in Reference Example 10 or the corresponding commercially available aldehydes in accordance with the process of Working Example 7-1(1).

Working Example 7-2

LCMS retention time: 3.41 min. (Condition 1-1-3)
MS (ESI posi) m/z: 427[M+H]$^+$.

Working Example 7-3

LCMS retention time: 3.78 min. (Condition 1-1-3)
MS (ESI posi) m/z: 481[M+H]$^+$.

Working Example 7-4

LCMS retention time: 3.29 min. (Condition 1-1-3)
MS (ESI posi) m/z: 449[M+H]$^+$.

Working Example 7-5

LCMS retention time: 3.56 min. (Condition 1-1-3)
MS (ESI posi) m/z: 441[M+H]$^+$.

Working Example 7-6

LCMS retention time: 4.05 min. (Condition 1-1-3)
MS (ESI posi) m/z: 453[M+H]$^+$.

Working Example 7-7

LCMS retention time: 3.48 min. (Condition 1-1-3)
MS (ESI posi) m/z: 466[M+H]$^+$.

Working Example 7-8

LCMS retention time: 3.73 min. (Condition 1-1-3)
MS (ESI posi) m/z: 454[M+H]$^+$.

Working Example 7-9

LCMS retention time: 2.81 min. (Condition 1-1-3)
MS (ESI posi) m/z: 468[M+H]$^+$.

Working Example 7-10

LCMS retention time: 3.46 min. (Condition 1-1-3)
MS (ESI posi) m/z: 480[M+H]$^+$.

Working Example 7-11

LCMS retention time: 3.47 min. (Condition 1-1-3)
MS (ESI posi) m/z: 455[M+H]$^+$.

Working Example 7-12

LCMS retention time: 3.42 min. (Condition 1-1-3)
MS (ESI posi) m/z: 469[M+H]$^+$.

Working Example 7-13

LCMS retention time: 3.46 min. (Condition 1-1-3)
MS (ESI posi) m/z: 466[M+H]$^+$.

Working Example 7-14

LCMS retention time: 4.66 min. (Condition 1-1-3)
MS (ESI posi) m/z: 583[M+H]$^+$.

Working Example 7-15

LCMS retention time: 4.70 min. (Condition 1-1-3)
MS (ESI posi) m/z: 533[M+H]$^+$.

Working Example 7-16

LCMS retention time: 4.72 min. (Condition 1-1-3)
MS (ESI posi) m/z: 533[M+H]$^+$.

Working Example 7-17

LCMS retention time: 4.65 min. (Condition 1-1-3)
MS (ESI posi) m/z: 533[M+H]$^+$.

Working Example 7-18

LCMS retention time: 4.64 min. (Condition 1-1-3)
MS (ESI posi) m/z: 515[M+H]$^+$.

Working Example 7-19

LCMS retention time: 4.46 min. (Condition 1-1-3)
MS (ESI posi) m/z: 560[M+H]$^+$.

Working Example 7-20

LCMS retention time: 4.54 min. (Condition 1-1-3)
MS (ESI posi) m/z: 565[M+H]$^+$.

Working Example 7-21

LCMS retention time: 4.56 min. (Condition 1-1-3)
MS (ESI posi) m/z: 565[M+H]$^+$.

Working Example 7-22

LCMS retention time: 4.60 min. (Condition 1-1-3)
MS (ESI posi) m/z: 583[M+H]$^+$.

Working Example 7-23

LCMS retention time: 4.66 min. (Condition 1-1-3)
MS (ESI posi) m/z: 583[M+H]$^+$.

Working Example 7-24

LCMS retention time: 4.62 min. (Condition 1-1-3)
MS (ESI posi) m/z: 583[M+H]$^+$.

The compounds of Working Examples 7-25 and 7-26 were obtained by using the corresponding compounds obtained in Reference Example 3 and either the aldehydes obtained in Reference Example 10 or the corresponding commercially available aldehydes in accordance with the processes of Working Example 7-1(1) and (2).

Working Example 7-25

LCMS retention time: 4.25 min. (Condition 1-1-3)
MS (ESI posi) m/z: 603[M+H]$^+$.

Working Example 7-26

LCMS retention time: 3.04 min. (Condition 1-1-3)
MS (ESI posi) m/z: 460[M+H]$^+$.

The compounds of Working Examples 7-27 to 7-91 were obtained by using the corresponding compounds obtained in Reference Example 3 and either the aldehydes obtained in Reference Example 10 or the corresponding commercially available aldehydes in accordance with the process of Working Example 7-1(1).

Working Example 7-27

$^1$H NMR (600 MHz, DMSO-d$_6$) δ ppm 0.84 (t, J=7.0 Hz, 3 H), 1.18-1.27 (m, 13 H), 1.32 (s, 9 H), 1.49 (dt, J=14.7, 7.5 Hz, 2 H), 3.08-3.15 (m, 2 H), 3.60-3.69 (m, 1 H), 4.39-4.47 (m, 3 H), 6.93 (dd, J=8.2, 1.5 Hz, 1 H), 6.98 (dd, J=11.4, 1.5 Hz, 1 H), 7.05-7.13 (m, 1 H), 7.37-7.63 (m, 7 H).
LCMS retention time: 4.83 min. (Condition 1-2-3)
MS (ESI posi) m/z: 551[M+H]$^+$.

Working Example 7-28

$^1$H NMR (600 MHz, DMSO-d$_6$) δ ppm 0.83 (t, J=7.0 Hz, 3 H), 1.16-1.29 (m, 8 H), 1.45-1.53 (m, 2 H), 3.08-3.17 (m, 2 H), 3.55-3.76 (m, 1 H), 4.32-4.70 (m, 7 H), 6.93 (dd, J=8.1, 1.6 Hz, 1 H), 6.98 (dd, J=11.2, 1.6 Hz, 1 H), 7.09-7.14 (m, 1 H), 7.30-7.99 (m, 7 H), 10.07 (br. s., 1 H).
LCMS retention time: 4.67 min. (Condition 1-2-3)
MS (ESI posi) m/z: 563[M+H]$^+$.

Working Example 7-29

LCMS retention time: 4.51 min. (Condition 1-2-3)
MS (ESI posi) m/z: 564[M+H]$^+$.

Working Example 7-30

$^1$H NMR (600 MHz, DMSO-d$_6$) δ ppm 0.78-0.93 (m, 6 H), 1.16-1.28 (m, 12 H), 1.29-1.35 (m, 4 H), 1.37-1.54 (m, 4 H), 1.66-1.76 (m, 2 H), 3.08-3.15 (m, 2 H), 3.60-3.69 (m, 1 H), 3.95-4.02 (m, 2 H), 4.35-4.42 (m, 3 H), 6.89-7.07 (m, 4 H), 7.09-7.15 (m, 1 H), 7.34-7.65 (m, 5 H), 10.08 (br. s., 1 H).
LCMS retention time: 5.14 min. (Condition 1-2-3)
MS (ESI posi) m/z: 595[M+H]$^+$.

Working Example 7-31

$^1$H NMR (600 MHz, DMSO-d$_6$) δ ppm 0.80-0.90 (m, 7 H), 1.14-1.35 (m, 20 H), 1.36-1.44 (m, 3 H), 1.45-1.54 (m, 2 H), 1.65-1.76 (m, 3 H), 3.08-3.15 (m, 2 H), 3.61-3.68 (m, 1 H), 3.90-4.03 (m, 1 H), 4.33-4.42 (m, 1 H), 6.84-6.91 (m, 1 H), 6.92-7.07 (m, 2 H), 7.10-7.12 (m, 1 H), 7.21 (dd, J=17.3, 8.7 Hz, 1 H), 7.35-7.63 (m, 5 H), 10.08 (br. s., 1 H).
LCMS retention time: 5.38 min. (Condition 1-2-3)
MS (ESI posi) m/z: 623[M+H]$^+$.

Working Example 7-32

$^1$H NMR (600 MHz, DMSO-d$_6$) δ ppm 0.84 (t, J=7.0 Hz, 3 H), 1.18-1.29 (m, 8 H), 1.39 (s, 9 H), 1.46-1.53 (m, 2 H), 2.99-3.18 (m, 4 H), 3.59-3.98 (m, 2 H), 4.15-5.08 (m, 4 H), 6.91-7.01 (m, 2 H), 7.07-7.15 (m, 1 H), 7.49-7.60 (m, 4 H), 10.05 (br. s., 1 H).
LCMS retention time: 4.57 min. (Condition 1-2-3)
MS (ESI posi) m/z: 558[M+H]$^+$.

Working Example 7-33

$^1$H NMR (600 MHz, DMSO-d$_6$) δ ppm 0.78-0.93 (m, 6 H), 1.15-1.36 (m, 18 H), 1.37-1.45 (m, 2 H), 1.46-1.53 (m, 2 H), 1.68-1.75 (m, 2 H), 3.05-3.16 (m, 2 H), 3.61-3.68 (m, 1 H), 3.95-4.03 (m, 2 H), 4.32-4.45 (m, 3 H), 6.90-7.07 (m, 4 H), 7.05-7.14 (m, 1 H), 7.35-7.64 (m, 5 H), 10.08 (br. s., 1 H).
LCMS retention time: 5.17 min. (Condition 1-2-3)
MS (ESI posi) m/z: 609[M+H]$^+$.

Working Example 7-34

$^1$H NMR (600 MHz, DMSO-d$_6$) δ ppm 0.84 (t, J=7.0 Hz, 3 H), 0.93 (t, J=7.4 Hz, 3 H), 1.17-1.30 (m, 8 H), 1.31-1.40 (m, 2 H), 1.46-1.53 (m, 2 H), 1.65-1.74 (m, 2 H), 3.06-3.25 (m, 7 H), 3.65-3.74 (m, 1 H), 4.29-4.39 (m, 1 H), 4.60-4.69 (m, 1 H), 6.92-7.02 (m, 2 H), 7.11-7.16 (m, 1 H), 7.39 (d, J=7.8 Hz, 1 H), 7.57-7.65 (m, 2 H), 10.09 (br. s., 1 H).
LCMS retention time: 4.27 min. (Condition 1-2-3)
MS (ESI posi) m/z: 461[M+H]$^+$.

Working Example 7-35

$^1$H NMR (600 MHz, DMSO-d$_6$) δ ppm 0.76-0.94 (m, 6 H), 1.14-1.40 (m, 14 H), 1.45-1.54 (m, 2 H), 1.69-1.76 (m, 2 H), 3.04-3.25 (m, 7 H), 3.67-3.75 (m, 1 H), 4.32-4.39 (m, 1 H), 4.57-4.70 (m, 1 H), 6.94 (dd, J=8.1, 1.6 Hz, 1 H), 6.99 (dd, J=11.2, 1.6 Hz, 1 H), 7.10-7.15 (m, 1 H), 7.39 (d, J=7.8 Hz, 1 H), 7.54-7.66 (m, 2 H), 10.09 (br. s., 1 H).
LCMS retention time: 4.52 min. (Condition 1-2-3)
MS (ESI posi) m/z: 489[M+H]$^+$.

Working Example 7-36

$^1$H NMR (600 MHz, DMSO-d$_6$) δ ppm 0.78-0.94 (m, 6 H), 1.13-1.39 (m, 18 H), 1.45-1.54 (m, 2 H), 1.66-1.75 (m, 2 H), 3.03-3.24 (m, 7 H), 3.68-3.74 (m, 1 H), 4.30-4.44 (m, 1 H), 4.59-4.71 (m, 1 H), 6.92-7.01 (m, 2 H), 7.10-7.15 (m, 1 H), 7.39 (d, J=7.8 Hz, 1 H), 7.56-7.65 (m, 2 H), 10.09 (s, 1 H).
LCMS retention time: 4.77 min. (Condition 1-2-3)
MS (ESI posi) m/z: 517[M+H]$^+$.

Working Example 7-37

$^1$H NMR (600 MHz, DMSO-d$_6$) δ ppm 0.76-0.92 (m, 6 H), 1.10-1.38 (m, 22 H), 1.45-1.54 (m, 2 H), 1.66-1.74 (m, 2 H), 3.01-3.25 (m, 7 H), 3.68-3.75 (m, 1 H), 4.32-4.39 (m, 1 H), 4.59-4.71 (m, 1 H), 6.91-7.02 (m, 2 H), 7.11-7.15 (m, 1 H), 7.37-7.41 (m, 1 H), 7.59-7.63 (m, 2 H), 10.09 (br. s., 1 H).
LCMS retention time: 5.04 min. (Condition 1-2-3)
MS (ESI posi) m/z: 545[M+H]$^+$.

Working Example 7-38

$^1$H NMR (600 MHz, DMSO-d$_6$) δ ppm 0.82-0.89 (m, 6 H), 1.16-1.36 (m, 26 H), 1.45-1.54 (m, 2 H), 1.66-1.74 (m, 2 H), 3.06-3.25 (m, 7 H), 3.67-3.74 (m, 1 H), 4.32-4.39 (m, 1 H), 4.61-4.65 (m, 1 H), 6.91-7.01 (m, 2 H), 7.11-7.15 (m, 1 H), 7.37-7.41 (m, 1 H), 7.59-7.63 (m, 2 H), 10.09 (br. s., 1 H).
LCMS retention time: 5.33 min. (Condition 1-2-3)
MS (ESI posi) m/z: 573[M+H]$^+$.

Working Example 7-39

$^1$H NMR (600 MHz, DMSO-d$_6$) δ ppm 0.78-0.89 (m, 3 H), 1.11-1.32 (m, 8 H), 1.45-1.54 (m, 2 H), 3.09-3.16 (m, 5 H), 3.65-3.75 (m, 2 H), 4.35-4.66 (m, 3 H), 6.91-7.01 (m, 2 H), 7.09-7.15 (m, 1 H), 7.34-7.76 (m, 7 H), 10.09 (br. s., 1 H).
LCMS retention time: 4.61 min. (Condition 1-2-3)
MS (ESI posi) m/z: 579[M+H]$^+$.

Working Example 7-40

$^1$H NMR (600 MHz, DMSO-d$_6$) δ ppm 0.84 (t, J=7.0 Hz, 3 H), 1.14-1.28 (m, 8 H), 1.34 (s, 9 H), 1.45-1.54 (m, 2 H), 3.09-3.17 (m, 5 H), 3.62-3.71 (m, 1 H), 4.39-4.43 (m, 4 H), 6.90-7.02 (m, 2 H), 7.03-7.17 (m, 3 H), 7.36-7.49 (m, 3 H), 7.52-7.65 (m, 2 H), 10.09 (s, 1 H).
LCMS retention time: 4.63 min. (Condition 1-2-3)
MS (ESI posi) m/z: 567[M+H]$^+$.

Working Example 7-41

$^1$H NMR (600 MHz, DMSO-d$_6$) δ ppm 0.80-0.91 (m, 9 H), 1.17-1.29 (m, 8 H), 1.31-1.40 (m, 3 H), 1.41-1.54 (m, 3 H), 1.78-1.90 (m, 1 H), 3.04-3.23 (m, 7 H), 3.73-3.77 (m, 1 H), 4.32-4.41 (m, 1 H), 4.62-4.69 (m, 1 H), 6.90-7.03 (m, 2 H), 7.11-7.17 (m, 1 H), 7.40 (d, J=8.3 Hz, 1 H), 7.55-7.67 (m, 2 H), 10.11 (s, 1 H).
LCMS retention time: 4.40 min. (Condition 1-2-3)
MS (ESI posi) m/z: 489[M+H]$^+$.

Working Example 7-42

$^1$H NMR (600 MHz, DMSO-d$_6$) δ ppm 0.84 (t, J=7.0 Hz, 3 H), 0.90 (t, J=7.4 Hz, 3 H), 1.16-1.29 (m, 10 H), 1.31-1.39 (m, 2 H), 1.46-1.54 (m, 2 H), 1.58-1.62 (m, 2 H), 2.20-2.26

(m, 2 H), 2.79-2.85 (m, 2 H), 2.97-3.03 (m, 2 H), 3.19-3.27 (m, 2 H), 3.96-4.01 (m, 2 H), 6.91-7.02 (m, 2 H), 7.09-7.13 (m, 1 H), 7.23 (d, J=8.7 Hz, 1 H), 7.42-7.47 (m, 2 H), 9.95 (s, 1 H).
LCMS retention time: 5.87 min. (Condition 1-2-3)
MS (ESI posi) m/z: 557[M+H]$^+$.

Working Example 7-43

$^1$H NMR (600 MHz, DMSO-d$_6$) δ ppm 0.77-0.92 (m, 6 H), 1.13-1.36 (m, 16 H), 1.44-1.55 (m, 2 H), 1.56-1.66 (m, 2 H), 2.17-2.28 (m, 2 H), 2.79-2.87 (m, 2 H), 2.96-3.04 (m, 2 H), 3.21-3.62 (m, 2 H), 3.95-4.01 (m, 2 H), 6.91-7.01 (m, 2 H), 7.09-7.13 (m, 1 H), 7.23 (d, J=8.7 Hz, 1 H), 7.43-7.47 (m, 2 H), 9.95 (s, 1 H).
LCMS retention time: 5.89 min. (Condition 1-2-3)
MS (ESI posi) m/z: 585[M+H]$^+$.

Working Example 7-44

$^1$H NMR (600 MHz, DMSO-d$_6$) δ ppm 0.84 (t, J=7.0 Hz, 3 H), 0.95 (t, J=7.2 Hz, 3 H), 1.16-1.29 (m, 10 H), 1.46-1.54 (m, 2 H), 1.60-1.68 (m, 2 H), 2.18-2.24 (m, 2 H), 2.82-3.30 (m, 6 H), 3.82-4.01 (m, 2 H), 6.92-7.02 (m, 2 H), 7.09-7.13 (m, 1 H), 7.23 (d, J=8.7 Hz, 1 H), 7.43-7.48 (m, 2 H), 9.95 (s, 1 H).
LCMS retention time: 5.81 min. (Condition 1-2-3)
MS (ESI posi) m/z: 543[M+H]$^+$.

Working Example 7-45

$^1$H NMR (600 MHz, DMSO-d$_6$) δ ppm 0.95-1.05 (m, 2 H), 1.21-1.26 (m, 2 H), 1.28 (d, J=5.8 Hz, 6 H), 1.36-1.60 (m, 6 H), 1.62-1.79 (m, 3 H), 3.05-3.18 (m, 2 H), 3.25-3.70 (m, 5 H), 4.30-4.45 (m, 3 H), 4.62-4.70 (m, 1 H), 6.90-7.05 (m, 4 H), 7.09-7.14 (m, 1 H), 7.36-7.47 (m, 3 H), 7.53-7.63 (m, 2 H), 10.08 (s, 1 H).
LCMS retention time: 4.53 min. (Condition 1-2-3)
MS (ESI posi) m/z: 565[M+H]$^+$.

Working Example 7-46

$^1$H NMR (600 MHz, DMSO-d$_6$) δ ppm 0.90-1.08 (m, 8 H), 1.20-1.32 (m, 2 H), 1.39-1.62 (m, 6 H), 1.64-1.78 (m, 3 H), 2.15-2.23 (m, 1 H), 3.00-3.23 (m, 7 H), 3.70-3.76 (m, 1 H), 4.33-4.40 (m, 1 H), 4.61-4.68 (m, 1 H), 6.92-7.03 (m, 2 H), 7.12-7.17 (m, 1 H), 7.40 (d, J=8.3 Hz, 1 H), 7.58-7.65 (m, 2 H), 10.11 (s, 1 H).
LCMS retention time: 4.21 min. (Condition 1-2-3)
MS (ESI posi) m/z: 473[M+H]$^+$.

Working Example 7-47

$^1$H NMR (600 MHz, DMSO-d$_6$) δ ppm 0.95-1.05 (m, 2 H), 1.16-1.28 (m, 8 H), 1.39-1.57 (m, 6 H), 1.64-1.76 (m, 3 H), 2.92-3.45 (m, 7 H), 3.65-3.80 (m, 1 H), 4.38-4.50 (m, 3 H), 6.90-7.01 (m, 2 H), 7.09-7.15 (m, 1 H), 7.31-7.63 (m, 7 H), 9.99-10.13 (m, 1 H).
LCMS retention time: 4.65 min. (Condition 1-2-3)
MS (ESI posi) m/z: 549[M+H]$^+$.

Working Example 7-48

$^1$H NMR (600 MHz, DMSO-d$_6$) δ ppm 0.89 (t, J=7.0 Hz, 3 H), 0.94-1.06 (m, 5 H), 1.12-1.58 (m, 12 H), 1.65-1.75 (m, 3 H), 2.01-2.09 (m, 1 H), 3.00-3.22 (m, 7 H), 3.71-3.76 (m, 1 H), 4.31-4.42 (m, 1 H), 4.60-4.70 (m, 1 H), 6.92-7.02 (m, 2 H), 7.11-7.17 (m, 1 H), 7.41 (d, J=8.3 Hz, 1 H), 7.58-7.65 (m, 2 H), 10.10 (s, 1 H).
LCMS retention time: 4.45 min. (Condition 1-2-3)
MS (ESI posi) m/z: 501[M+H]$^+$.

Working Example 7-49

$^1$H NMR (600 MHz, DMSO-d$_6$) δ ppm 0.89 (t, J=7.0 Hz, 3 H), 0.94-1.08 (m, 5 H), 1.10-1.59 (m, 12 H), 1.65-1.77 (m, 3 H), 2.01-2.09 (m, 1 H), 3.00-3.22 (m, 3 H), 3.71-3.76 (m, 1 H), 4.31-4.42 (m, 1 H), 4.60-4.70 (m, 1 H), 6.92-7.02 (m, 2 H), 7.12-7.17 (m, 1 H), 7.40 (d, J=7.8 Hz, 1 H), 7.58-7.65 (m, 2 H), 10.10 (s, 1 H).
LCMS retention time: 4.04 min. (Condition 1-2-3)
MS (ESI posi) m/z: 501[M+H]$^+$.

Working Example 7-50

$^1$H NMR (600 MHz, DMSO-d$_6$) δ ppm 0.96-1.05 (m, 2 H), 1.18-1.27 (m, 2 H), 1.38-1.58 (m, 6 H), 1.63-1.76 (m, 3 H), 3.05-3.20 (m, 7 H), 3.65-3.76 (m, 1 H), 4.29-4.65 (m, 3 H), 6.71-7.01 (m, 3 H), 7.09-7.15 (m, 1 H), 7.32-7.74 (m, 6 H), 9.99-10.22 (m, 1 H).
LCMS retention time: 4.55 min. (Condition 1-2-3)
MS (ESI posi) m/z: 623[M+H]$^+$.

Working Example 7-51

$^1$H NMR (600 MHz, DMSO-d$_6$) δ ppm 0.87 (d, J=6.6 Hz, 6 H), 0.97-1.05 (m, 2 H), 1.19-1.27 (m, 2 H), 1.40-1.57 (m, 6 H), 1.63-1.75 (m, 3 H), 1.80-1.90 (m, 1 H), 3.08-3.15 (m, 7 H), 3.62-3.69 (m, 2 H), 4.38-4.47 (m, 3 H), 6.91-7.01 (m, 2 H), 7.09-7.14 (m, 1 H), 7.25-7.32 (m, 2 H), 7.35-7.50 (m, 3 H), 7.52-7.64 (m, 2 H), 9.98-10.16 (m, 1 H).
LCMS retention time: 4.80 min. (Condition 1-2-3)
MS (ESI posi) m/z: 563[M+H]$^+$.

Working Example 7-52

$^1$H NMR (600 MHz, DMSO-d$_6$) δ ppm 0.97-1.06 (m, 2 H), 1.20-1.26 (m, 2 H), 1.40-1.57 (m, 6 H), 1.65-1.75 (m, 3 H), 3.05-3.16 (m, 4 H), 3.40-3.75 (m, 3 H), 4.29-4.64 (m, 3 H), 6.91-7.01 (m, 2 H), 7.09-7.15 (m, 1 H), 7.28-7.89 (m, 6 H).
LCMS retention time: 4.65 min. (Condition 1-2-3)
MS (ESI posi) m/z: 609[M+H]$^+$.

Working Example 7-53

$^1$H NMR (600 MHz, DMSO-d$_6$) δ ppm 0.96-1.07 (m, 2 H), 1.15-1.29 (m, 4 H), 1.39-1.78 (m, 14 H), 3.10-3.16 (m, 3 H), 3.25-3.40 (m, 6 H), 3.71-3.77 (m, 1 H), 3.82-3.87 (m, 2 H), 4.32-4.39 (m, 1 H), 4.65-4.70 (m, 1 H), 6.92-7.02 (m, 2 H), 7.11-7.16 (m, 1 H), 7.38-7.42 (m, 1 H), 7.58-7.64 (m, 2 H), 10.09 (s, 1 H).
LCMS retention time: 4.12 min. (Condition 1-2-3)
MS (ESI posi) m/z: 529[M+H]$^+$.

Working Example 7-54

$^1$H NMR (600 MHz, DMSO-d$_6$) δ ppm 0.98-1.05 (m, 3 H), 1.20-1.30 (m, 3 H), 1.39-1.60 (m, 8 H), 1.64-1.77 (m, 4 H), 1.95-2.03 (m, 3 H), 3.10-3.18 (m, 3 H), 3.72-3.79 (m, 1 H), 4.38-4.45 (m, 1 H), 4.65-4.72 (m, 1 H), 6.91-7.02 (m, 2 H), 7.10-7.16 (m, 1 H), 7.38-7.42 (m, 1 H), 7.59-7.65 (m, 2 H), 10.05-10.15 (m, 1 H).
LCMS retention time: 4.32 min. (Condition 1-2-3)
MS (ESI posi) m/z: 527[M+H]$^+$.

Working Example 7-55

$^1$H NMR (600 MHz, DMSO-$d_6$) δ ppm 0.88-1.07 (m, 4 H), 1.09-1.36 (m, 7 H), 1.39-1.77 (m, 17 H), 3.09-3.38 (m, 5 H), 3.68-3.75 (m, 1 H), 4.31-4.38 (m, 1 H), 4.60-4.67 (m, 1 H), 6.92-7.02 (m, 2 H), 7.11-7.15 (m, 1 H), 7.39 (d, J=7.8 Hz, 1 H), 7.56-7.64 (m, 2 H), 10.08 (br. s., 1 H).
LCMS retention time: 4.60 min. (Condition 1-2-3)
MS (ESI posi) m/z: 527[M+H]$^+$.

Working Example 7-56

$^1$H NMR (600 MHz, DMSO-$d_6$) δ ppm 0.95-1.05 (m, 2 H), 1.18-1.28 (m, 2 H), 1.37 (s, 9 H), 1.41-1.59 (m, 6 H), 1.64-1.76 (m, 3 H), 2.85-3.10 (m, 5 H), 4.15-4.50 (m, 5 H), 6.90-7.01 (m, 2 H), 7.09-7.14 (m, 1 H), 7.22-7.54 (m, 3 H), 8.81-8.92 (m, 2 H), 10.03 (br. s., 1 H).
LCMS retention time: 4.47 min. (Condition 1-2-3)
MS (ESI posi) m/z: 565[M+H]$^+$.

Working Example 7-57

$^1$H NMR (600 MHz, DMSO-$d_6$) δ ppm 0.98-1.03 (m, 2 H), 1.19-1.30 (m, 4 H), 1.40-1.77 (m, 12 H), 1.87-1.91 (m, 2 H), 2.29-2.39 (m, 2 H), 3.08-3.26 (m, 7 H), 3.71-3.77 (m, 1 H), 4.35-4.42 (m, 1 H), 4.62-4.70 (m, 1 H), 6.93-7.02 (m, 2 H), 7.12-7.16 (m, 1 H), 7.40 (d, J=8.3 Hz, 1 H), 7.58-7.65 (m, 2 H), 10.10 (s, 1 H).
LCMS retention time: 4.33 min. (Condition 1-2-3)
MS (ESI posi) m/z: 499[M+H]$^+$.

Working Example 7-58

$^1$H NMR (600 MHz, DMSO-$d_6$) δ ppm 0.93-1.08 (m, 2 H), 1.19-1.30 (m, 2 H), 1.39-1.59 (m, 6 H), 1.63-1.78 (m, 3 H), 3.05-3.72 (m, 6 H), 3.87 (s, 3 H), 4.24-4.55 (m, 4 H), 6.91-7.01 (m, 2 H), 7.10-7.14 (m, 1 H), 7.41 (d, J=8.3 Hz, 1 H), 7.54-7.62 (m, 3 H), 7.88 (s, 1 H), 10.08 (s, 1 H).
LCMS retention time: 4.00 min. (Condition 1-2-3)
MS (ESI posi) m/z: 511[M+H]$^+$.

Working Example 7-59

$^1$H NMR (600 MHz, DMSO-$d_6$) δ ppm 0.62-0.68 (m, 1 H), 0.96-1.08 (m, 2 H), 1.20-1.59 (m, 11 H), 1.65-1.77 (m, 3 H), 1.96-2.05 (m, 1 H), 2.80-3.21 (m, 9 H), 3.71-3.78 (m, 1 H), 4.34-4.40 (m, 1 H), 4.62-4.73 (m, 1 H), 5.99-6.05 (m, 1 H), 6.23-6.29 (m, 1 H), 6.93-7.02 (m, 2 H), 7.12-7.16 (m, 1 H), 7.40 (d, J=8.3 Hz, 1 H), 7.58-7.65 (m, 2 H), 10.09 (s, 1 H).
LCMS retention time: 4.43 min. (Condition 1-2-3)
MS (ESI posi) m/z: 523[M+H]$^+$.

Working Example 7-60

$^1$H NMR (600 MHz, DMSO-$d_6$) δ ppm 0.96-1.05 (m, 2 H), 1.20-1.26 (m, 2 H), 1.38 (s, 9 H), 1.41-1.58 (m, 5 H), 1.63-1.76 (m, 3 H), 3.09-3.15 (m, 6 H), 4.31-4.78 (m, 5 H), 6.91-7.01 (m, 2 H), 7.10-7.14 (m, 1 H), 7.34-7.39 (m, 1 H), 7.52-7.62 (m, 2 H), 8.73 (s, 1 H), 8.83 (s., 1 H), 10.06 (br. s., 1 H).
LCMS retention time: 4.48 min. (Condition 1-2-3)
MS (ESI posi) m/z: 565[M+H]$^+$.

Working Example 7-61

LCMS retention time: 1.37 min. (Condition 4-1)
MS (ESI posi) m/z: 583[M+H]$^+$.

Working Example 7-62

LCMS retention time: 1.36 min. (Condition 4-1)
MS (ESI posi) m/z: 589[M+H]$^+$.

Working Example 7-63

LCMS retention time: 1.35 min. (Condition 4-1)
MS (ESI posi) m/z: 573[M+H]$^+$.

Working Example 7-64

LCMS retention time: 1.31 min. (Condition 4-1)
MS (ESI posi) m/z: 590[M+H]$^+$.

Working Example 7-65

LCMS retention time: 1.35 min. (Condition 4-1)
MS (ESI posi) m/z: 604[M+H]$^+$.

Working Example 7-66

LCMS retention time: 1.39 min. (Condition 4-1)
MS (ESI posi) m/z: 587[M+H]$^+$.

Working Example 7-67

LCMS retention time: 1.34 min. (Condition 4-1)
MS (ESI posi) m/z: 574[M+H]$^+$.

Working Example 7-68

LCMS retention time: 1.36 min. (Condition 4-1)
MS (ESI posi) m/z: 590[M+H]$^+$.

Working Example 7-69

LCMS retention time: 1.35 min. (Condition 4-1)
MS (ESI posi) m/z: 590[M+H]$^+$.

Working Example 7-70

LCMS retention time: 1.29 min. (Condition 4-1)
MS (ESI posi) m/z: 587[M+H]$^+$.

Working Example 7-71

LCMS retention time: 1.30 min. (Condition 4-1)
MS (ESI posi) m/z: 601[M+H]$^+$.

Working Example 7-72

LCMS retention time: 1.27 min. (Condition 4-1)
MS (ESI posi) m/z: 574[M+H]$^+$.

Working Example 7-73

LCMS retention time: 1.32 min. (Condition 4-1)
MS (ESI posi) m/z: 574[M+H]$^+$.

Working Example 7-74

LCMS retention time: 1.37 min. (Condition 4-1)
MS (ESI posi) m/z: 624[M+H]$^+$.

Working Example 7-75

LCMS retention time: 1.39 min. (Condition 4-1)
MS (ESI posi) m/z: 608[M+H]$^+$.

Working Example 7-76

LCMS retention time: 1.33 min. (Condition 4-1)
MS (ESI posi) m/z: 587[M+H]$^+$.

Working Example 7-77

LCMS retention time: 1.34 min. (Condition 4-1)
MS (ESI posi) m/z: 582[M+H]$^+$.

Working Example 7-78

LCMS retention time: 1.25 min. (Condition 4-1)
MS (ESI posi) m/z: 512[M+H]$^+$.

Working Example 7-79

LCMS retention time: 1.26 min. (Condition 4-1)
MS (ESI posi) m/z: 528[M+H]$^+$.

Working Example 7-80

LCMS retention time: 1.36 min. (Condition 4-1)
MS (ESI posi) m/z: 615[M+H]$^+$.

Working Example 7-81

LCMS retention time: 1.43 min. (Condition 4-1)
MS (ESI posi) m/z: 668[M+H]$^+$.

Working Example 7-82

LCMS retention time: 1.20 min. (Condition 4-1)
MS (ESI posi) m/z: 539[M+H]$^+$.

Working Example 7-83

LCMS retention time: 1.36 min. (Condition 4-1)
MS (ESI posi) m/z: 661[M+H]$^+$.

Working Example 7-84

LCMS retention time: 1.37 min. (Condition 4-1)
MS (ESI posi) m/z: 661[M+H]$^+$.

Working Example 7-85

LCMS retention time: 1.32 min. (Condition 4-1)
MS (ESI posi) m/z: 610[M+H]$^+$.

Working Example 7-86

LCMS retention time: 1.26 min. (Condition 4-1)
MS (ESI posi) m/z: 590[M+H]$^+$.

Working Example 7-87

LCMS retention time: 1.34 min. (Condition 4-1)
MS (ESI posi) m/z: 635[M+H]$^+$.

Working Example 7-88

LCMS retention time: 1.12 min. (Condition 4-1)
MS (ESI posi) m/z: 601[M+H]$^+$.

Working Example 7-89

LCMS retention time: 1.21 min. (Condition 5-1)
MS (ESI posi) m/z: 633[M+H]$^+$.

Working Example 7-90

LCMS retention time: 1.29 min. (Condition 5-1)
MS (ESI posi) m/z: 569[M+H]$^+$.

Working Example 7-91

LCMS retention time: 1.18 min. (Condition 5-1)
MS (ESI posi) m/z: 567[M+H]$^+$.

The structures of the compounds of Working Examples 7-2 to 7-91 are shown in Tables 22-1 to 22-7.

TABLE 22-1

| Working Ex. | Structure |
|---|---|
| 7-2 | [Structure: N-(4-fluorophenyl)-2-(4-methoxybenzyl)-1,2,3,4-tetrahydroisoquinoline-6-sulfonamide] |
| 7-3 | [Structure: N-(4-fluorophenyl)-2-(4-(trifluoromethoxy)benzyl)-1,2,3,4-tetrahydroisoquinoline-6-sulfonamide] |

TABLE 22-1-continued
| Working Ex. | Structure |
|---|---|
| 7-4 | 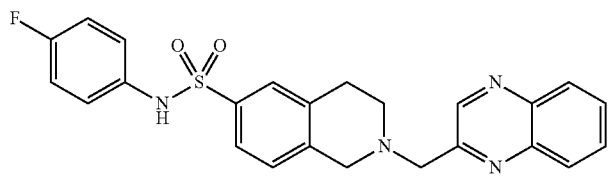 [SMILES: O=S(=O)(Nc1ccc(F)cc1)c1ccc2c(c1)CCN(Cc1cnc3ccccc3n1)C2] |
| 7-5 | 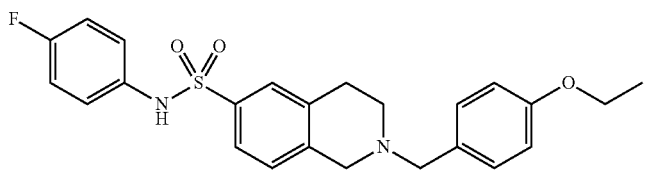 [SMILES: CCOc1ccc(CN2CCc3cc(S(=O)(=O)Nc4ccc(F)cc4)ccc3C2)cc1] |
| 7-6 | 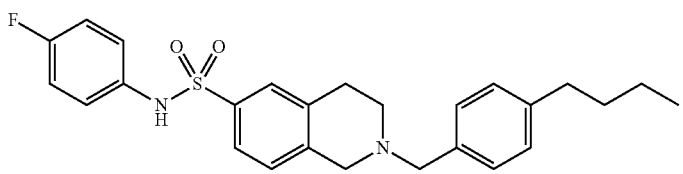 [SMILES: CCCCc1ccc(CN2CCc3cc(S(=O)(=O)Nc4ccc(F)cc4)ccc3C2)cc1] |
| 7-7 | 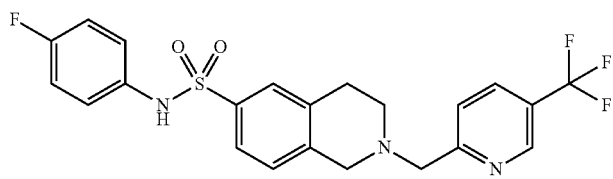 [SMILES: O=S(=O)(Nc1ccc(F)cc1)c1ccc2c(c1)CCN(Cc1ccc(C(F)(F)F)cn1)C2] |
| 7-8 | 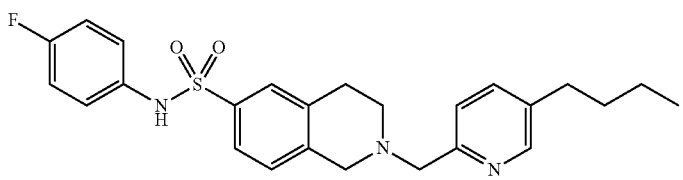 [SMILES: CCCCc1ccc(CN2CCc3cc(S(=O)(=O)Nc4ccc(F)cc4)ccc3C2)nc1] |
| 7-9 | 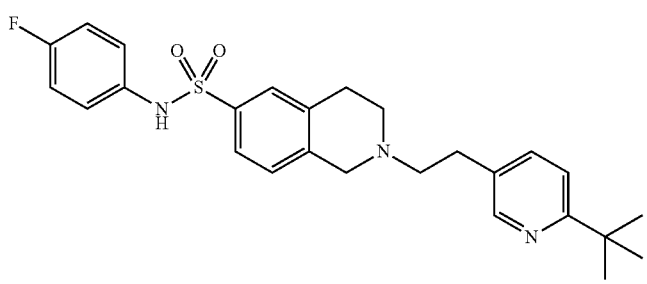 [SMILES: CC(C)(C)c1ccc(CCN2CCc3cc(S(=O)(=O)Nc4ccc(F)cc4)ccc3C2)cn1] |
| 7-10 | 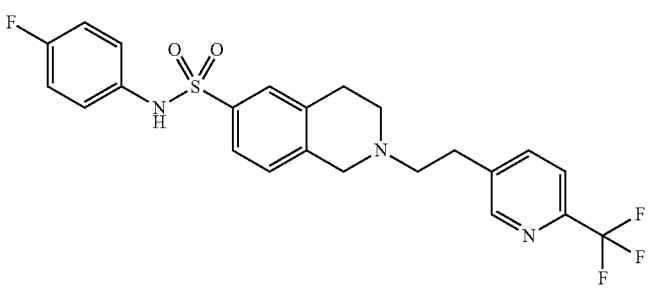 [SMILES: O=S(=O)(Nc1ccc(F)cc1)c1ccc2c(c1)CCN(CCc1ccc(C(F)(F)F)nc1)C2] |

TABLE 22-1-continued

| Working Ex. | Structure |
|---|---|
| 7-11 | (4-fluorophenyl)-N-sulfonamide of 2-((2-tert-butylpyrimidin-5-yl)methyl)-1,2,3,4-tetrahydroisoquinoline-6-sulfonamide |
| 7-12 | (4-fluorophenyl)-N-sulfonamide of 2-(2-(2-tert-butylpyrimidin-5-yl)ethyl)-1,2,3,4-tetrahydroisoquinoline-6-sulfonamide |
| 7-13 | (4-fluorophenyl)-N-sulfonamide of 2-((6-(trifluoromethyl)pyridin-3-yl)methyl)-1,2,3,4-tetrahydroisoquinoline-6-sulfonamide |
| 7-14 | N-(2-fluoro-4-(pentyloxy)phenyl)-2-(3-fluoro-5-(trifluoromethyl)benzyl)-1,2,3,4-tetrahydroisoquinoline-6-sulfonamide |
| 7-15 | 2-(3,4-difluorobenzyl)-N-(2-fluoro-4-(pentyloxy)phenyl)-1,2,3,4-tetrahydroisoquinoline-6-sulfonamide |

TABLE 22-2

| Working Ex. | Structure |
|---|---|
| 7-16 | 2-(3,5-difluorobenzyl)-N-(2-fluoro-4-(pentyloxy)phenyl)-1,2,3,4-tetrahydroisoquinoline-6-sulfonamide |
| 7-17 | 2-(2,4-difluorobenzyl)-N-(2-fluoro-4-(pentyloxy)phenyl)-1,2,3,4-tetrahydroisoquinoline-6-sulfonamide |

TABLE 22-2-continued

| Working Ex. | Structure |
|---|---|
| 7-18 | 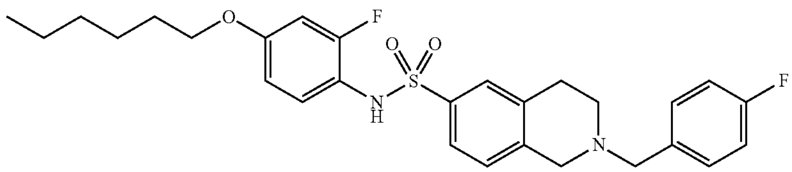 [SMILES: CCCCCCOc1ccc(NS(=O)(=O)c2ccc3c(c2)CCN(Cc2ccc(F)cc2)C3)c(F)c1] |
| 7-19 | 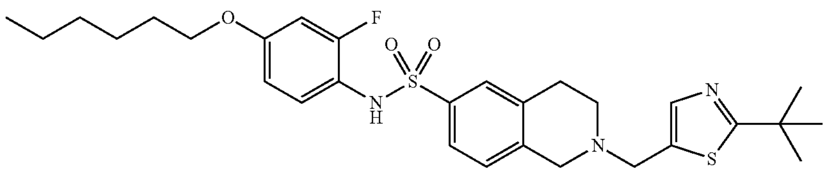 [SMILES: CCCCCCOc1ccc(NS(=O)(=O)c2ccc3c(c2)CCN(Cc2cnc(C(C)(C)C)s2)C3)c(F)c1] |
| 7-20 | 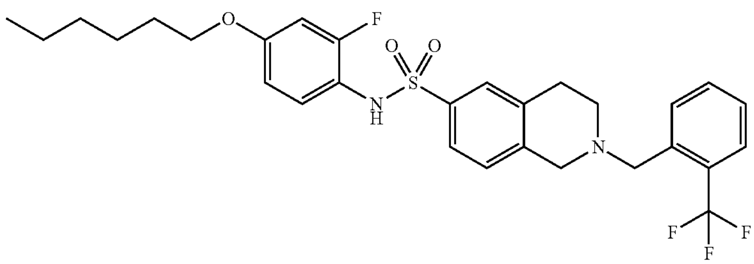 [SMILES: CCCCCCOc1ccc(NS(=O)(=O)c2ccc3c(c2)CCN(Cc2ccccc2C(F)(F)F)C3)c(F)c1] |
| 7-21 | 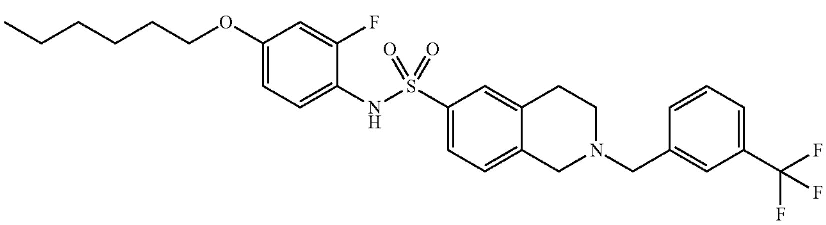 [SMILES: CCCCCCOc1ccc(NS(=O)(=O)c2ccc3c(c2)CCN(Cc2cccc(C(F)(F)F)c2)C3)c(F)c1] |
| 7-22 | 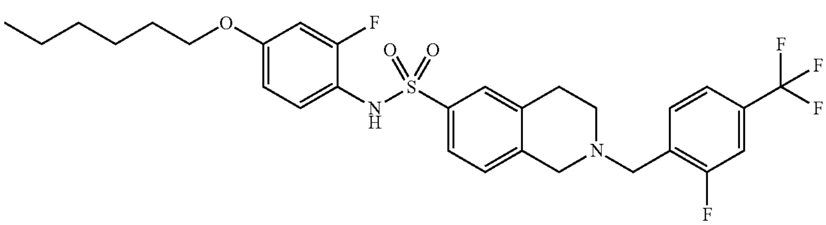 [SMILES: CCCCCCOc1ccc(NS(=O)(=O)c2ccc3c(c2)CCN(Cc2ccc(C(F)(F)F)cc2F)C3)c(F)c1] |
| 7-23 | 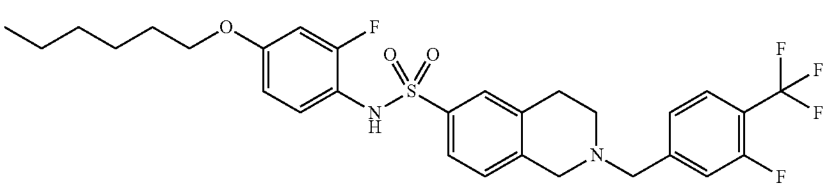 [SMILES: CCCCCCOc1ccc(NS(=O)(=O)c2ccc3c(c2)CCN(Cc2ccc(C(F)(F)F)c(F)c2)C3)c(F)c1] |
| 7-24 | 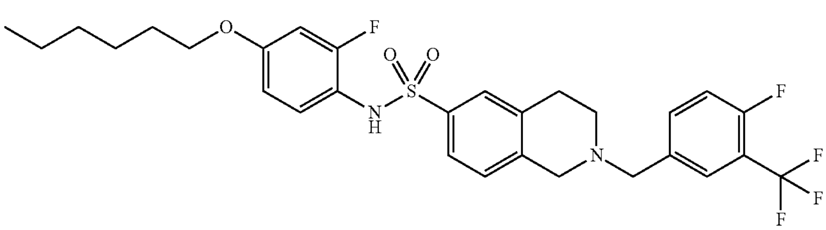 [SMILES: CCCCCCOc1ccc(NS(=O)(=O)c2ccc3c(c2)CCN(Cc2ccc(F)c(C(F)(F)F)c2)C3)c(F)c1] |

TABLE 22-2-continued
| Working Ex. | Structure |
|---|---|
| 7-25 | 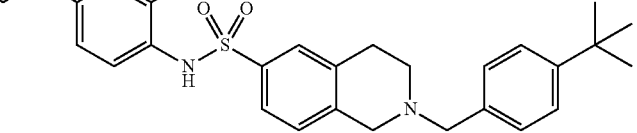 |
| 7-26 | 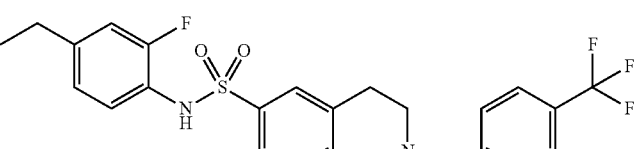 |
TABLE 22-3
| Working Ex. | Structure |
|---|---|
| 7-27 | 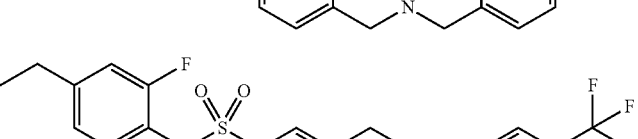 |
| 7-28 | 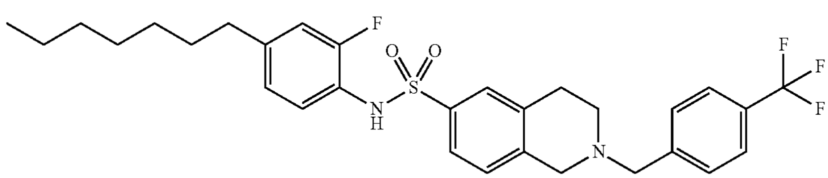 [SMILES: CCCCCCCc1ccc(NS(=O)(=O)c2ccc3c(c2)CCN(Cc2ccc(C(F)(F)F)cc2)C3)c(F)c1] |
| 7-29 | 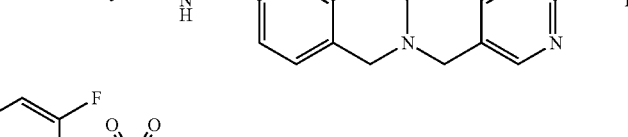 |
| 7-30 | 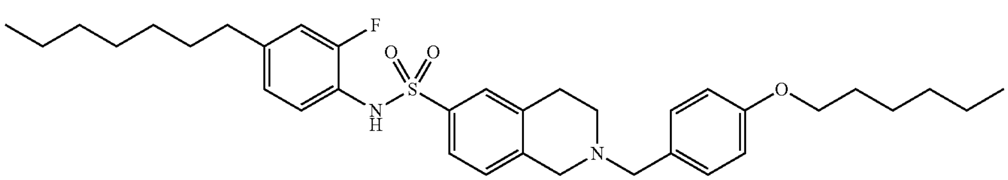 [SMILES: CCCCCCCc1ccc(NS(=O)(=O)c2ccc3c(c2)CCN(Cc2ccc(OCCCCCC)cc2)C3)c(F)c1] |
| 7-31 | 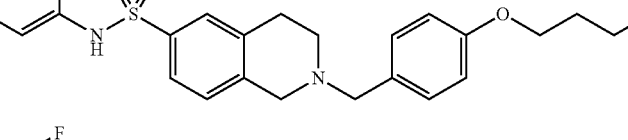 |

TABLE 22-3-continued
| Working Ex. | Structure |
|---|---|
| 7-32 | 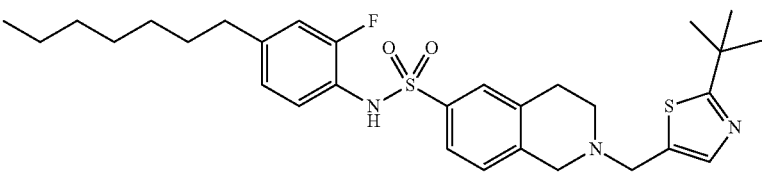 [SMILES: CCCCCCCc1ccc(NS(=O)(=O)c2ccc3c(c2)CCN(Cc2cnc(C(C)(C)C)s2)C3)c(F)c1] |
| 7-33 | 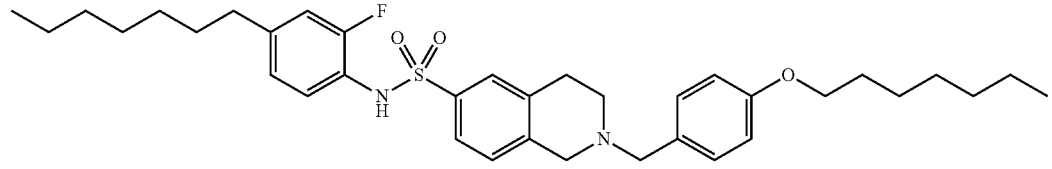 [SMILES: CCCCCCCOc1ccc(CN2CCc3cc(S(=O)(=O)Nc4ccc(CCCCCCC)cc4F)ccc3C2)cc1] |
| 7-34 | 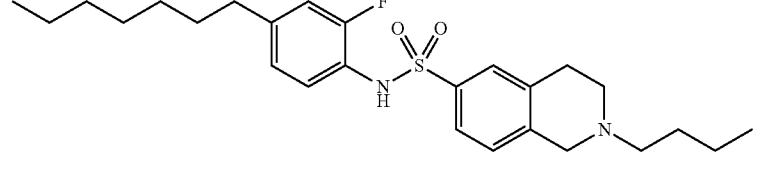 |
| 7-35 | 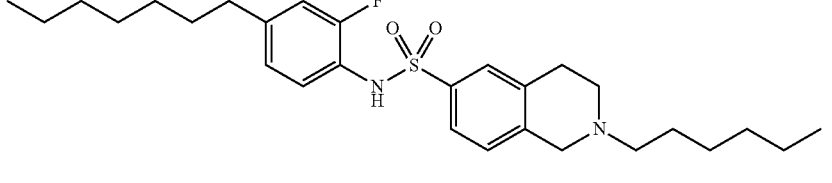 |
| 7-36 | 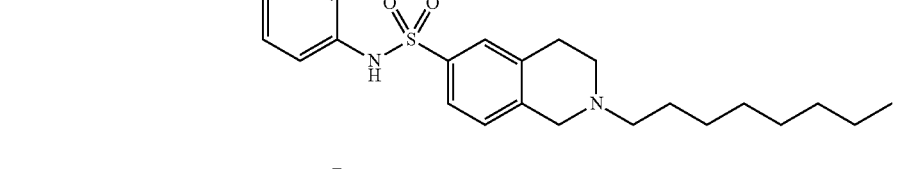 |
| 7-37 | 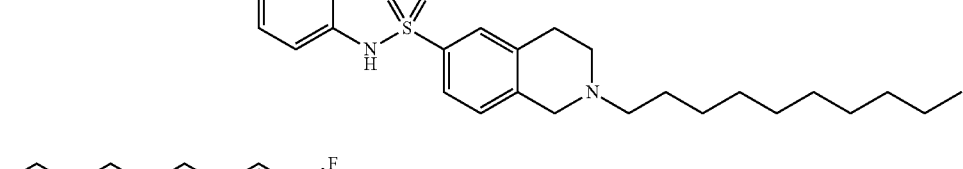 |
| 7-38 | 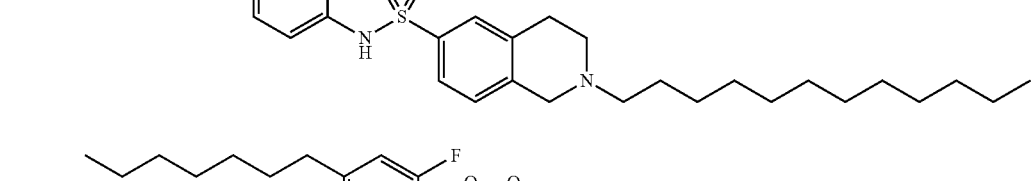 |
| 7-39 | 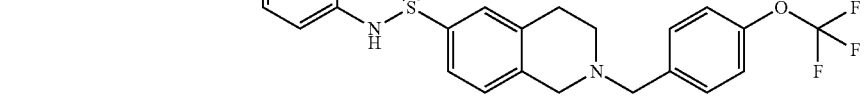 |

TABLE 22-3-continued
| Working Ex. | Structure |
|---|---|
| 7-40 | 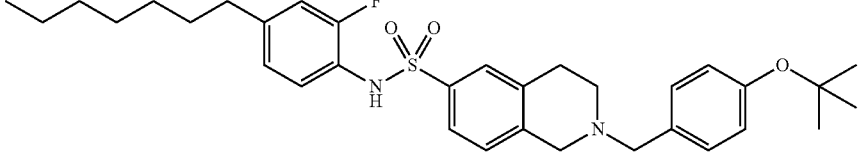 |
TABLE 22-4
| Working Ex. | Structure |
|---|---|
| 7-41 | 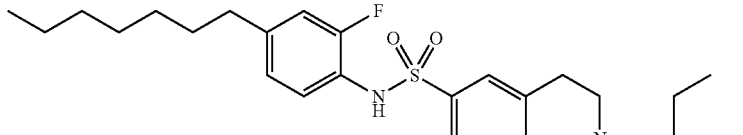 |
| 7-42 | 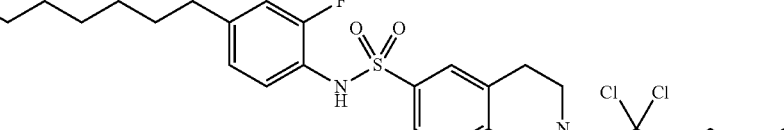 |
| 7-43 | 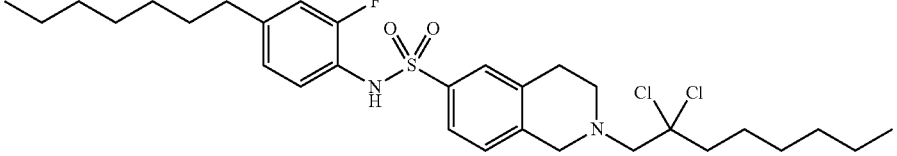 |
| 7-44 | 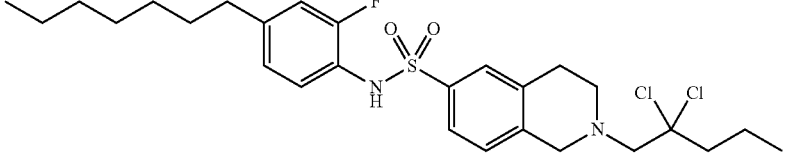 |
| 7-45 | 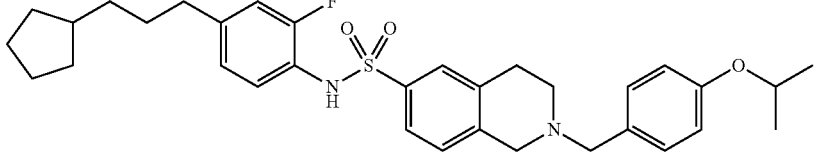 |
| 7-46 | 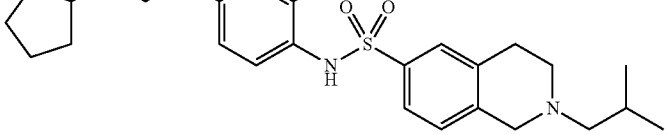 |
| 7-47 | 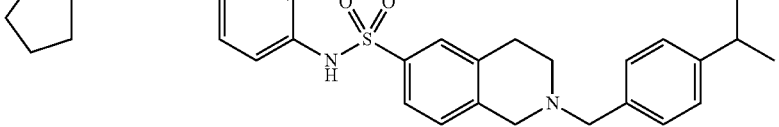 |

TABLE 22-4-continued
| Working Ex. | Structure |
|---|---|
| 7-48 | 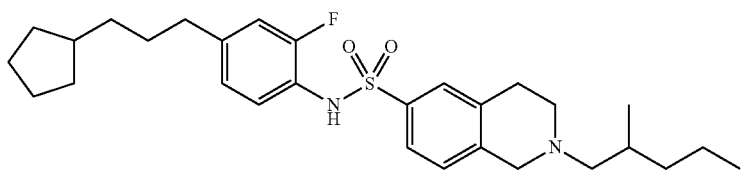 [SMILES: CCCC(C)CN1CCc2cc(S(=O)(=O)Nc3ccc(CCCC4CCCC4)cc3F)ccc2C1] |
| 7-49 | 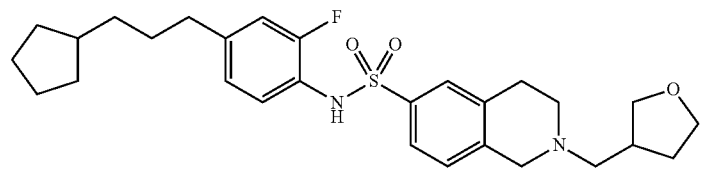 [SMILES: O=S(=O)(Nc1ccc(CCCC2CCCC2)cc1F)c1ccc2c(c1)CCN(CC1CCOC1)C2] |
| 7-50 | 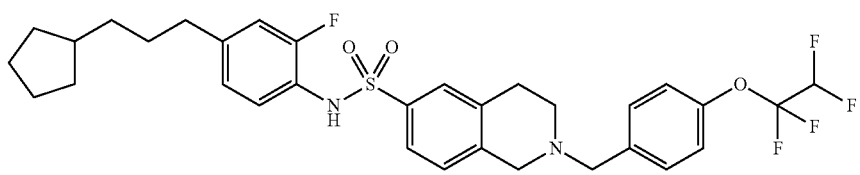 [SMILES: O=S(=O)(Nc1ccc(CCCC2CCCC2)cc1F)c1ccc2c(c1)CCN(Cc1ccc(OC(F)(F)C(F)F)cc1)C2] |
| 7-51 | 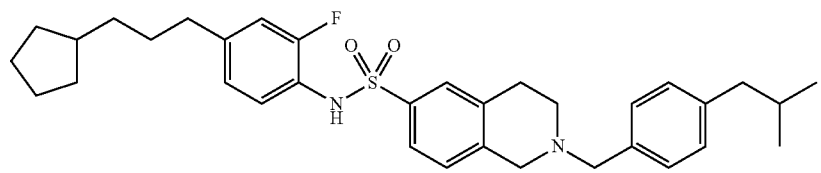 [SMILES: CC(C)Cc1ccc(CN2CCc3cc(S(=O)(=O)Nc4ccc(CCCC5CCCC5)cc4F)ccc3C2)cc1] |
| 7-52 | 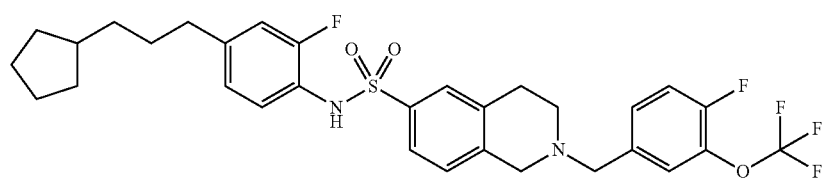 [SMILES: O=S(=O)(Nc1ccc(CCCC2CCCC2)cc1F)c1ccc2c(c1)CCN(Cc1ccc(F)c(OC(F)(F)F)c1)C2] |
| 7-53 | 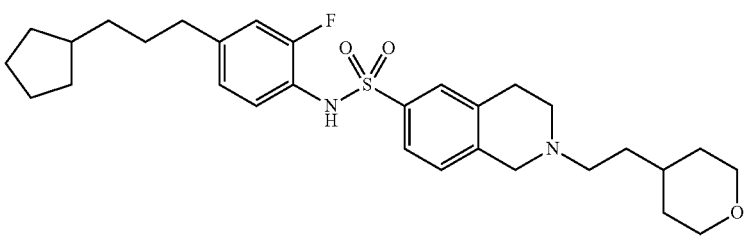 [SMILES: O=S(=O)(Nc1ccc(CCCC2CCCC2)cc1F)c1ccc2c(c1)CCN(CCC1CCOCC1)C2] |
| 7-54 | 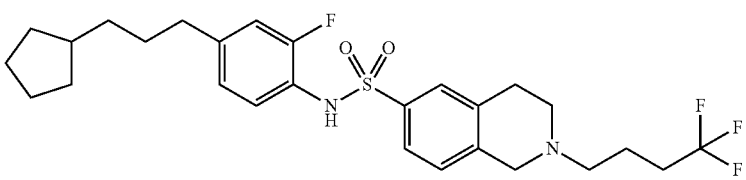 [SMILES: O=S(=O)(Nc1ccc(CCCC2CCCC2)cc1F)c1ccc2c(c1)CCN(CCCC(F)(F)F)C2] |

TABLE 22-5
| Working Ex. | Structure |
|---|---|
| 7-55 | 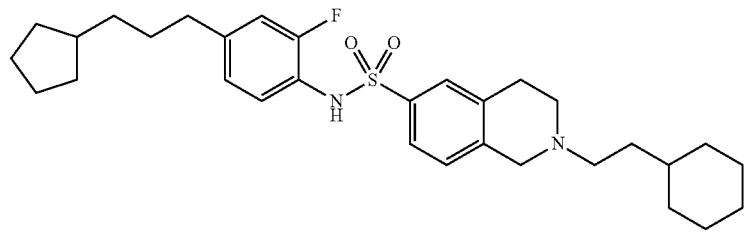 [SMILES: O=S(=O)(Nc1ccc(CCCC2CCCC2)cc1F)c1ccc2c(c1)CCN(CCC1CCCCC1)C2] |
| 7-56 | 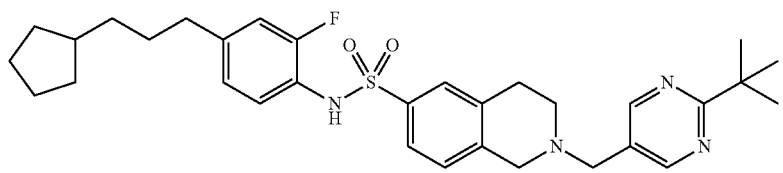 [SMILES: CC(C)(C)c1ncc(CN2CCc3cc(S(=O)(=O)Nc4ccc(CCCC5CCCC5)cc4F)ccc3C2)cn1] |
| 7-57 | 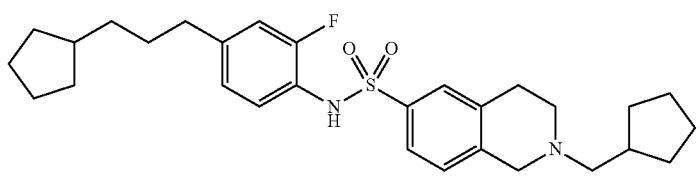 [SMILES: O=S(=O)(Nc1ccc(CCCC2CCCC2)cc1F)c1ccc2c(c1)CCN(CC1CCCC1)C2] |
| 7-58 | 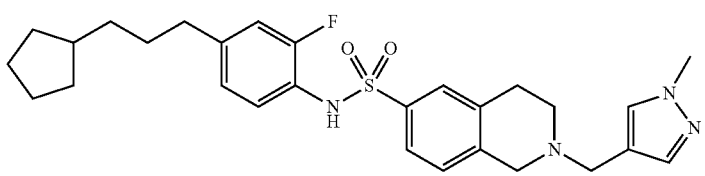 [SMILES: Cn1cc(CN2CCc3cc(S(=O)(=O)Nc4ccc(CCCC5CCCC5)cc4F)ccc3C2)cn1] |
| 7-59 | 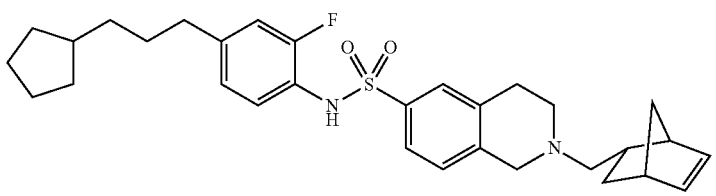 [SMILES: O=S(=O)(Nc1ccc(CCCC2CCCC2)cc1F)c1ccc2c(c1)CCN(CC1CC3C=CC1C3)C2] |
| 7-60 | 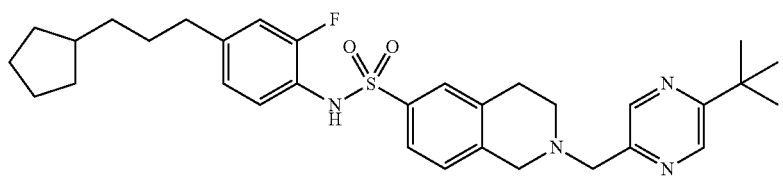 [SMILES: CC(C)(C)c1cnc(CN2CCc3cc(S(=O)(=O)Nc4ccc(CCCC5CCCC5)cc4F)ccc3C2)cn1] |
| 7-61 | 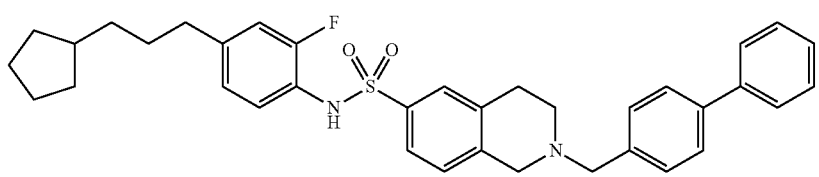 [SMILES: O=S(=O)(Nc1ccc(CCCC2CCCC2)cc1F)c1ccc2c(c1)CCN(Cc1ccc(-c3ccccc3)cc1)C2] |
| 7-62 | 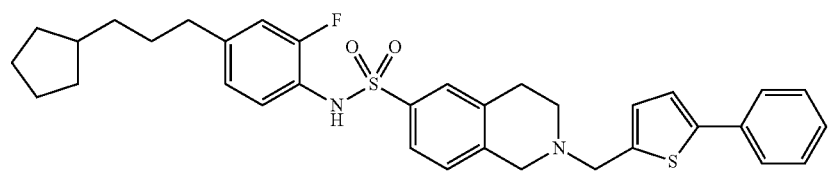 [SMILES: O=S(=O)(Nc1ccc(CCCC2CCCC2)cc1F)c1ccc2c(c1)CCN(Cc1ccc(-c3ccccc3)s1)C2] |

TABLE 22-5-continued

| Working Ex. | Structure |
|---|---|
| 7-63 | 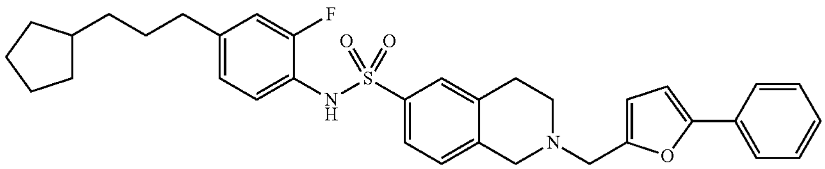 [SMILES: O=S(=O)(Nc1ccc(CCCC2CCCC2)cc1F)c1ccc2c(c1)CCN(Cc1ccc(-c3ccccc3)o1)C2] |
| 7-64 | 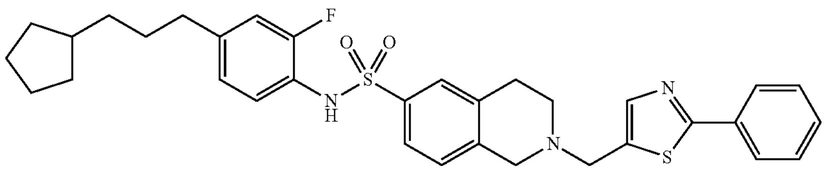 [SMILES: O=S(=O)(Nc1ccc(CCCC2CCCC2)cc1F)c1ccc2c(c1)CCN(Cc1cnc(-c3ccccc3)s1)C2] |
| 7-65 | 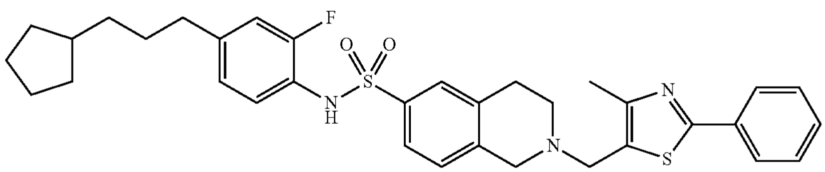 [SMILES: Cc1nc(-c2ccccc2)sc1CN1CCc2cc(S(=O)(=O)Nc3ccc(CCCC4CCCC4)cc3F)ccc2C1] |
| 7-66 | 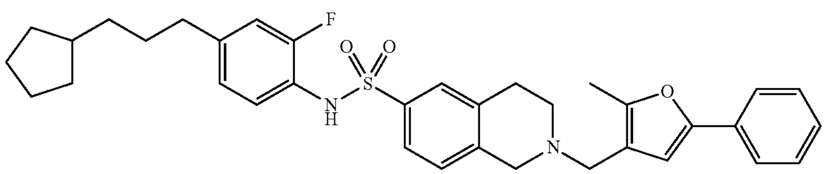 [SMILES: Cc1oc(-c2ccccc2)cc1CN1CCc2cc(S(=O)(=O)Nc3ccc(CCCC4CCCC4)cc3F)ccc2C1] |
| 7-67 | 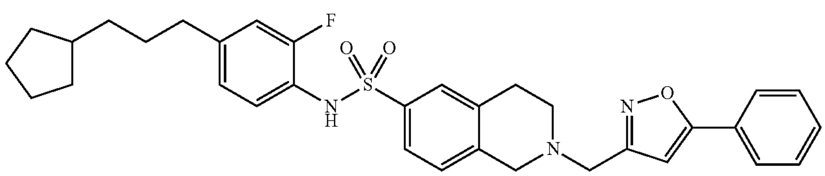 [SMILES: O=S(=O)(Nc1ccc(CCCC2CCCC2)cc1F)c1ccc2c(c1)CCN(Cc1cc(-c3ccccc3)on1)C2] |
| 7-68 | 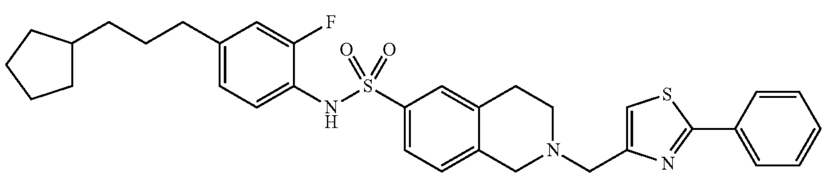 [SMILES: O=S(=O)(Nc1ccc(CCCC2CCCC2)cc1F)c1ccc2c(c1)CCN(Cc1csc(-c3ccccc3)n1)C2] |

TABLE 22-6

| Working Ex. | Structure |
|---|---|
| 7-69 | 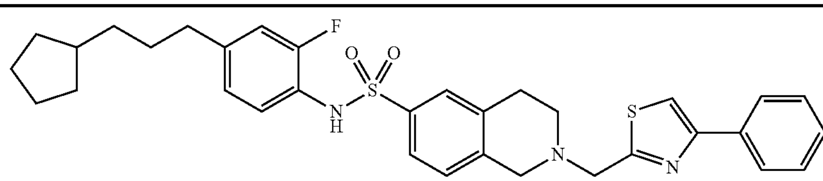 |
| 7-70 | 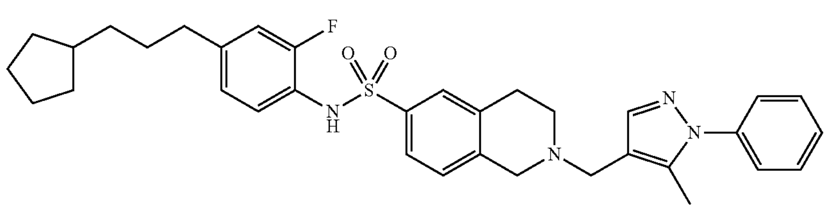 [SMILES: Cc1c(CN2CCc3cc(S(=O)(=O)Nc4ccc(CCCC5CCCC5)cc4F)ccc3C2)cnn1-c1ccccc1] |

US 9,035,059 B2
TABLE 22-6-continued
| Working Ex. | Structure |
|---|---|
| 7-71 | 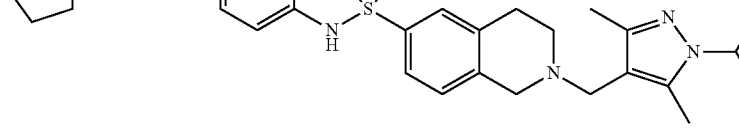 |
| 7-72 | 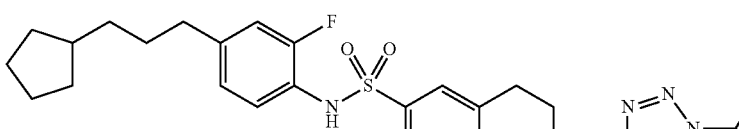 |
| 7-73 | 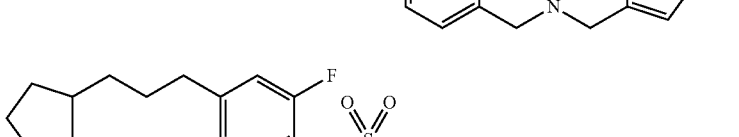 |
| 7-74 | 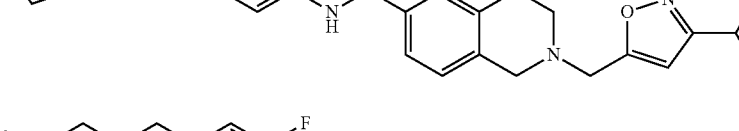 |
| 7-75 | 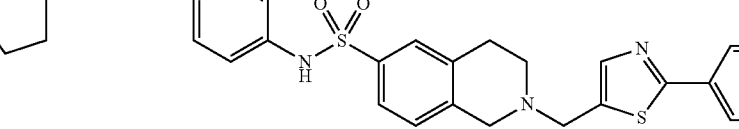 |
| 7-76 | 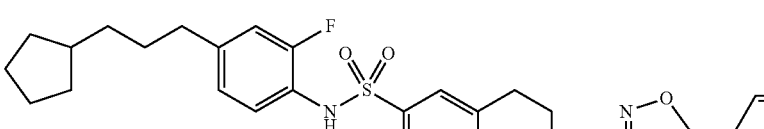 |
| 7-77 | 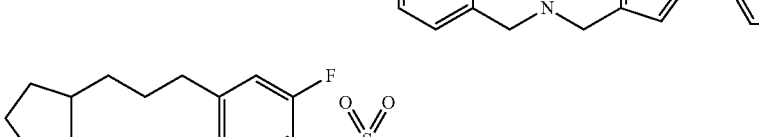 |
| 7-78 | 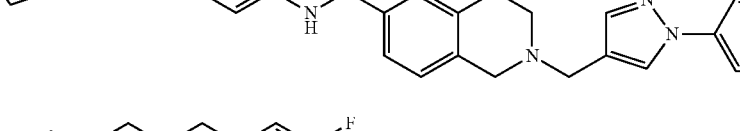 |

TABLE 22-6-continued
| Working Ex. | Structure |
|---|---|
| 7-79 | 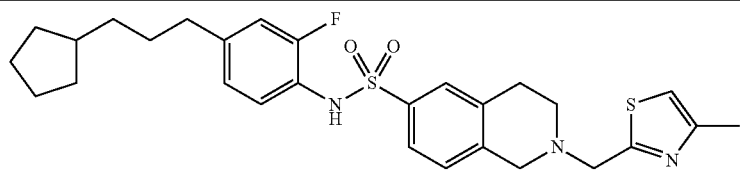 |
| 7-80 | 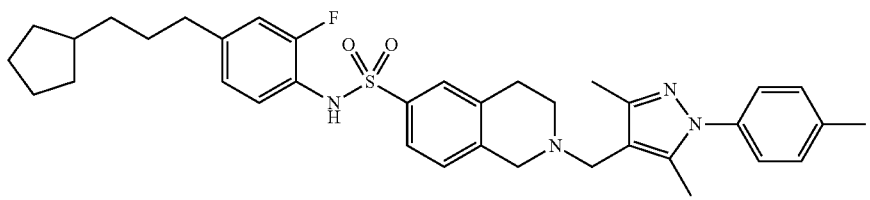 [SMILES: Cc1ccc(-n2nc(C)c(CN3CCc4cc(S(=O)(=O)Nc5ccc(CCCC6CCCC6)cc5F)ccc4C3)c2C)cc1] |
| 7-81 | 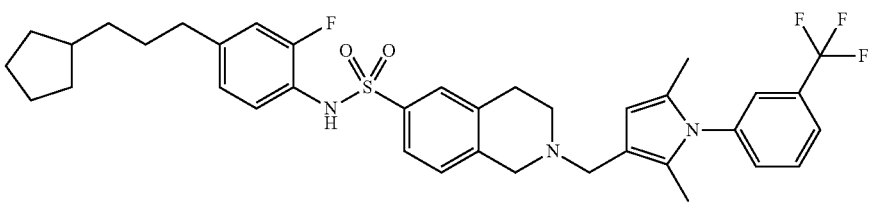 [SMILES: Cc1cc(CN2CCc3cc(S(=O)(=O)Nc4ccc(CCCC5CCCC5)cc4F)ccc3C2)c(C)n1-c1cccc(C(F)(F)F)c1] |
| 7-82 | 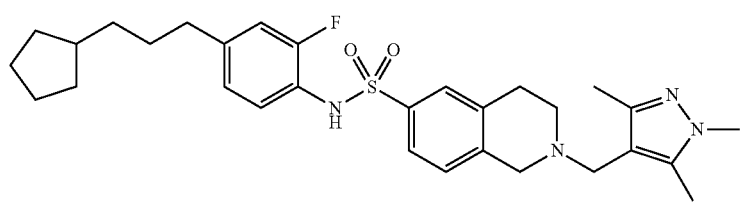 [SMILES: Cc1nn(C)c(C)c1CN1CCc2cc(S(=O)(=O)Nc3ccc(CCCC4CCCC4)cc3F)ccc2C1] |
TABLE 22-7
| Working Ex. | Structure |
|---|---|
| 7-83 | 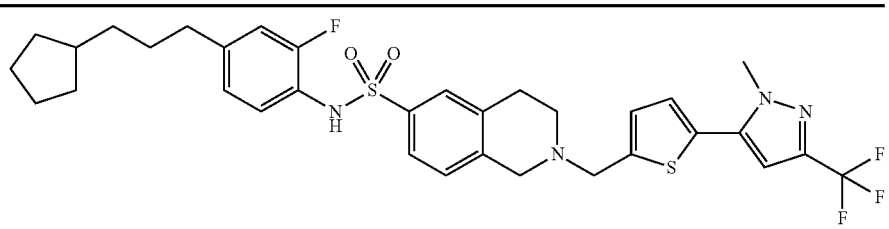 |
| 7-84 | 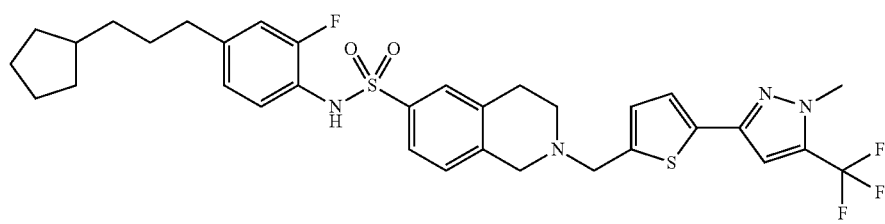 [SMILES: Cn1nc(-c2ccc(CN3CCc4cc(S(=O)(=O)Nc5ccc(CCCC6CCCC6)cc5F)ccc4C3)s2)cc1C(F)(F)F] |
| 7-85 | 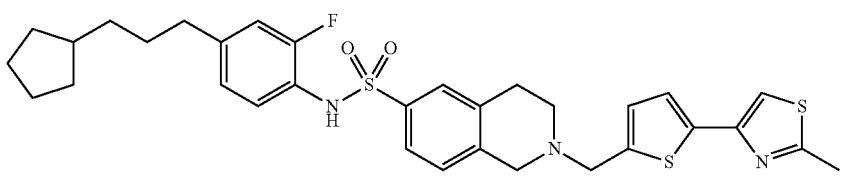 [SMILES: Cc1nc(-c2ccc(CN3CCc4cc(S(=O)(=O)Nc5ccc(CCCC6CCCC6)cc5F)ccc4C3)s2)cs1] |

TABLE 22-7-continued

| Working Ex. | Structure |
|---|---|
| 7-86 | 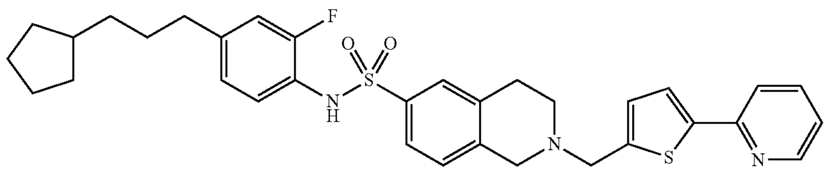 |
| 7-87 | 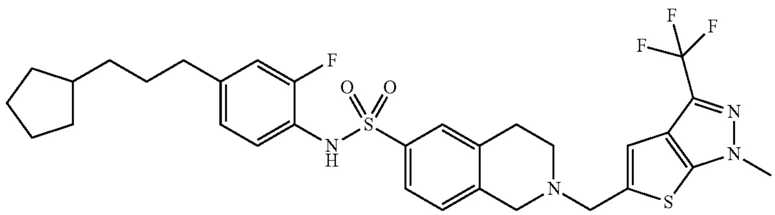 [SMILES: Cn1nc(C(F)(F)F)c2cc(CN3CCc4cc(S(=O)(=O)Nc5ccc(CCCC6CCCC6)cc5F)ccc4C3)sc21] |
| 7-88 | 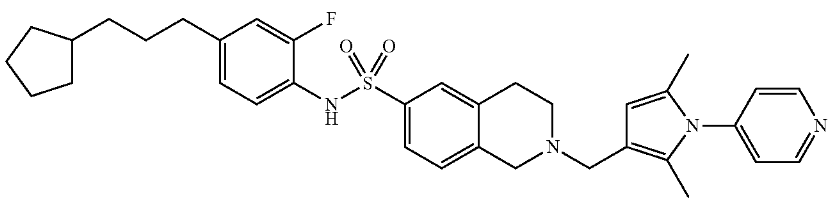 [SMILES: Cc1cc(CN2CCc3cc(S(=O)(=O)Nc4ccc(CCCC5CCCC5)cc4F)ccc3C2)c(C)n1-c1ccncc1] |
| 7-89 | 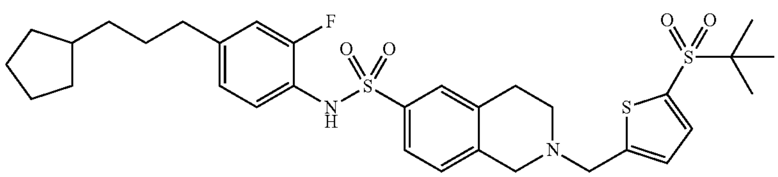 [SMILES: CC(C)(C)S(=O)(=O)c1ccc(CN2CCc3cc(S(=O)(=O)Nc4ccc(CCCC5CCCC5)cc4F)ccc3C2)s1] |
| 7-90 | 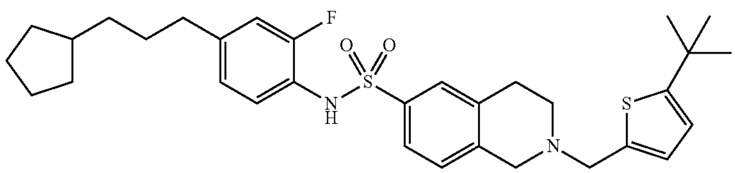 [SMILES: CC(C)(C)c1ccc(CN2CCc3cc(S(=O)(=O)Nc4ccc(CCCC5CCCC5)cc4F)ccc3C2)s1] |
| 7-91 | 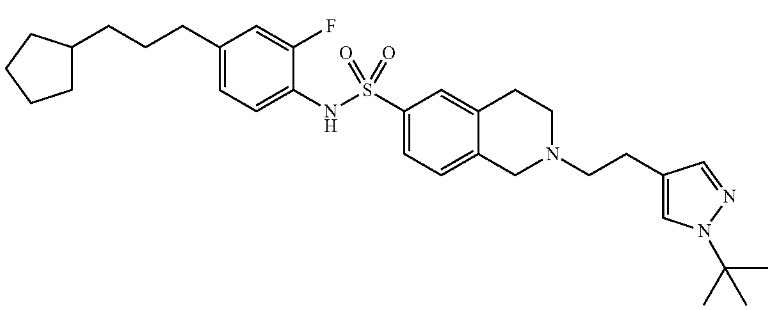 [SMILES: CC(C)(C)n1cc(CCN2CCc3cc(S(=O)(=O)Nc4ccc(CCCC5CCCC5)cc4F)ccc3C2)cn1] |

Working Example 8-1

2-[2-(4-tert-Butylphenyl)ethyl]-N-[2-fluoro-4-(4-phenylbutoxy)phenyl]-1,2,3,4-tetrahydroisoquinoline-6-sulfonamide

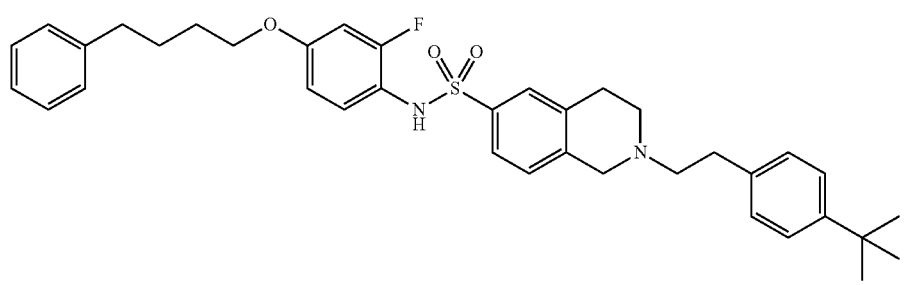

[Formula 62]

(1) To a 1,2-dichloroethane solution (10 mL) of compound 3-13 as obtained in Reference Example 3 (406 mg, 0.67 mmol) were added a 1,2-dichloroethane solution (5 mL) of the compound obtained in Reference Example 7-1 (130 mg, 0.74 mmol) and sodium triacetoxyborohydride (225 mg, 1.01 mmol) successively, and the mixture was stirred at room temperature for 1 hr. Saturated aqueous sodium hydrogen carbonate solution was added to the reaction mixture and the mixture was extracted with ethyl acetate. The organic layer was washed with brine and dried over anhydrous magnesium sulfate and then the desiccant was filtered off, followed by concentration under reduced pressure. The resulting residue was purified by silica gel column chromatography (hexane:ethyl acetate=65:35→chloroform:methanol=19:1) to afford 2-[2-(4-tert-butylphenyl)ethyl]-N-(2,4-dimethoxybenzyl)-N-[2-fluoro-4-(4-phenylbutoxy)phenyl]-1,2,3,4-tetrahydroisoquinoline-6-sulfonamide as a colorless amorphous substance (440 mg).

(2) Trifluoroacetic acid (1 mL) was added to a turbid solution of 2-[2-(4-tert-butylphenyl)ethyl]-N-(2,4-dimethoxybenzyl)-N-[2-fluoro-4-(4-phenylbutoxy)phenyl]-1,2,3,4-tetrahydroisoquinoline-6-sulfonamide obtained (440 mg) in anisole (5 mL) and chloroform (5 mL) while cooling in ice, and the mixture was stirred for 21 hr while cooling in ice. Saturated aqueous sodium hydrogen carbonate solution was added to the reaction mixture while cooling in ice and the mixture was extracted with ethyl acetate. The organic layer was washed with brine and dried over anhydrous magnesium sulfate and then the desiccant was filtered off, followed by concentration under reduced pressure. The resulting residue was purified by NH silica gel column chromatography (hexane:ethyl acetate=3:1→ethyl acetate only) to afford the title compound as a colorless amorphous substance (240 mg).

(3) To a solution of the title compound (240 mg) in ethyl acetate (4 mL) was added 4 mol/L hydrogen chloride-ethyl acetate (1 mL), and the mixture was stirred at room temperature for 14 hr. Diethyl ether (8 mL) was added to the reaction mixture and the mixture was stirred at room temperature for 1 hr. Thereafter, the resulting precipitate was collected by filtration and washed with diethyl ether to afford the monohydrochloride of the title compound as a colorless powder (214 mg).

$^1$H NMR (600 MHz, DMSO-$d_6$) δ ppm 1.27 (s, 9 H), 1.68 (dt, J=6.5, 3.4 Hz, 4 H), 2.58-2.65 (m, 2 H), 3.01-3.51 (m, 7 H), 3.75-3.84 (m, 1 H), 3.91-3.98 (m, 2 H), 4.39-4.50 (m, 1 H), 4.72 (d, J=15.1 Hz, 1 H), 6.66-6.81 (m, 2 H), 7.03-7.08 (m, 1 H), 7.14-7.24 (m, 5 H), 7.25-7.29 (m, 2 H), 7.35-7.42 (m, 3 H), 7.53-7.62 (m, 2 H), 9.89 (s, 1 H).

LCMS retention time: 5.59 min. (Condition 1-1-1)
MS (ESI posi) m/z: 615[M+H]$^+$.

The compounds of Working Examples 8-2 to 8-17 were obtained by using the corresponding compounds obtained in Reference Example 3 or 30 and the corresponding aldehydes obtained in Reference Examples 7-1, 9 and 10 in accordance with the process of Working Example 8-1.

Working Example 8-2

LCMS retention time: 5.43 min. (Condition 1-1-1)
MS (ESI posi) m/z: 601[M+H]$^+$.

Working Example 8-3

LCMS retention time: 5.60 min. (Condition 1-1-1)
MS (ESI posi) m/z: 567[M+H]$^+$.

Working Example 8-4

LCMS retention time: 3.61 min. (Condition 1-1-3)
MS (ESI posi) m/z: 483[M+H]$^+$.

Working Example 8-5

$^1$H NMR (600 MHz, DMSO-$d_6$) δ ppm 1.08-1.16 (m, 2 H), 1.27 (s, 9 H), 1.43-1.63 (m, 4 H), 1.66-1.78 (m, 4 H), 1.84-1.94 (m, 1 H), 3.03-3.49 (m, 7 H), 3.76-3.84 (m, 1 H), 3.93 (t, J=6.8 Hz, 2 H), 4.39-4.49 (m, 1 H), 4.68-4.79 (m, 1 H), 6.67-6.73 (m, 1 H), 6.75-6.81 (m, 1 H), 7.02-7.09 (m, 1 H), 7.20-7.26 (m, 2 H), 7.35-7.43 (m, 3 H), 7.54-7.61 (m, 2 H), 9.91 (s, 1 H).

LCMS retention time: 2.05 min. (Condition 3)
MS ESI/APCI Dual posi: 579[M+H]$^+$.

Working Example 8-6

$^1$H NMR (600 MHz, DMSO-$d_6$) δ ppm 1.27 (s, 9 H), 1.88-2.00 (m, 3 H), 2.97-3.23 (m, 4 H), 3.37-3.48 (m, 4 H), 3.77-3.83 (m, 1 H), 3.94-4.00 (m, 2 H), 4.41-4.51 (m, 1 H), 4.70-4.79 (m, 1 H), 6.63-6.77 (m, 2 H), 7.05-7.09 (m, 1 H), 7.19-7.23 (m, 2 H), 7.34-7.44 (m, 3 H), 7.52-7.62 (m, 2 H), 7.63-7.69 (m, 2 H), 7.73-7.79 (m, 1 H), 7.88-7.94 (m, 2 H), 9.95 (br. s., 1 H).

LCMS retention time: 1.08 min. (Condition 4-1)
MS (ESI posi) m/z: 665[M+H]$^+$.

Working Example 8-7

$^1$H NMR (600 MHz, DMSO-d$_6$) δ ppm 1.14-1.24 (m, 2 H), 1.37 (s, 9 H), 1.39-1.49 (m, 3 H), 1.58 (d, J=12.8 Hz, 1 H), 1.71-1.82 (m, 3 H), 3.04-3.44 (m, 5 H), 3.61-4.25 (m, 4 H), 4.33-4.62 (m, 3 H), 6.66-6.81 (m, 2 H), 7.03-7.09 (m, 1 H), 7.37-7.41 (m, 1 H), 7.47-7.64 (m, 3 H), 7.78-7.85 (m, 1 H), 8.66-8.70 (m, 1 H), 9.90 (br. s., 1 H).

LCMS retention time: 0.86 min. (Condition 5-1)
MS (ESI posi) m/z: 582[M+H]$^+$.

Working Example 8-8

$^1$H NMR (600 MHz, DMSO-d$_6$) δ ppm 1.12-1.21 (m, 1 H), 1.27 (s, 9 H), 1.32-1.55 (m, 4 H), 1.71-1.81 (m, 1 H), 3.01-3.50 (m, 11 H), 3.62-3.73 (m, 2 H), 3.75-3.87 (m, 2 H), 3.99-4.08 (m, 2 H), 4.40-4.51 (m, 1 H), 4.68-4.78 (m, 1 H), 6.67-6.75 (m, 1 H), 6.78-6.85 (m, 1 H), 7.03-7.11 (m, 1 H), 7.19-7.27 (m, 2 H), 7.34-7.44 (m, 3 H), 7.53-7.63 (m, 2 H), 9.93 (s, 1 H).

LCMS retention time: 0.82 min. (Condition 2)
MS (ESI posi) m/z: 625[M+H]$^+$.

Working Example 8-9

$^1$H NMR (600 MHz, DMSO-d$_6$) δ ppm 1.27 (s, 9 H), 1.43-1.55 (m, 1 H), 1.70-1.91 (m, 3 H), 3.02-3.27 (m, 4 H), 3.29-3.50 (m, 5 H), 3.56-3.64 (m, 1 H), 3.65-3.84 (m, 4 H), 3.86-3.95 (m, 1 H), 4.02-4.08 (m, 2 H), 4.40-4.51 (m, 1 H), 4.68-4.78 (m, 1 H), 6.68-6.76 (m, 1 H), 6.78-6.85 (m, 1 H), 7.03-7.12 (m, 1 H), 7.18-7.27 (m, 2 H), 7.34-7.44 (m, 3 H), 7.54-7.63 (m, 2 H), 9.93 (s, 1 H).

LCMS retention time: 0.77 min. (Condition 2)
MS (ESI posi) m/z: 611[M+H]$^+$.

Working Example 8-10

$^1$H NMR (600 MHz, DMSO-d$_6$) δ ppm 1.27 (s, 9 H), 1.45-1.56 (m, 1 H), 1.71-1.79 (m, 2 H), 1.95-2.05 (m, 1 H), 2.19-2.30 (m, 1 H), 3.04-3.49 (m, 8 H), 3.57-3.66 (m, 1 H), 3.69-3.83 (m, 3 H), 3.89-4.01 (m, 2 H), 4.39-4.50 (m, 1 H), 4.69-4.78 (m, 1 H), 6.68-6.74 (m, 1 H), 6.76-6.83 (m, 1 H), 7.03-7.11 (m, 1 H), 7.19-7.26 (m, 2 H), 7.34-7.44 (m, 3 H), 7.54-7.62 (m, 2 H), 9.92 (s, 1 H).

LCMS retention time: 0.78 min. (Condition 2)
MS (ESI posi) m/z: 581[M+H]$^+$.

Working Example 8-11

$^1$H NMR (600 MHz, DMSO-d$_6$) δ ppm 1.27 (s, 9 H), 1.43-1.59 (m, 2 H), 1.62-1.71 (m, 1 H), 1.78-1.97 (m, 2 H), 3.02-3.26 (m, 4 H), 3.29-3.52 (m, 5 H), 3.76-3.87 (m, 2 H), 3.89-4.07 (m, 3 H), 4.40-4.50 (m, 1 H), 4.52-4.65 (m, 1 H), 4.69-4.78 (m, 1 H), 6.68-6.75 (m, 1 H), 6.77-6.84 (m, 1 H), 7.03-7.12 (m, 1 H), 7.19-7.27 (m, 2 H), 7.34-7.44 (m, 3 H), 7.54-7.63 (m, 2 H), 9.93 (s, 1 H).

LCMS retention time: 0.81 min. (Condition 2)
MS (ESI posi) m/z: 613[M+H]$^+$.

Working Example 8-12

$^1$H NMR (600 MHz, DMSO-d$_6$) δ ppm 1.27 (s, 9 H), 1.90-2.00 (m, 2 H), 3.03-3.49 (m, 7 H), 3.67-3.74 (m, 1 H), 3.76-3.84 (m, 2 H), 3.93-4.10 (m, 4 H), 4.40-4.49 (m, 1H), 4.69-4.77 (m, 1 H), 6.68-6.83 (m, 2 H), 7.02-7.12 (m, 1 H), 7.19-7.27 (m, 2 H), 7.34-7.44 (m, 3 H), 7.53-7.63 (m, 2 H), 9.93 (s, 1 H).

LCMS retention time: 1.92 min. (Condition 3)
MS ESI/APCI Dual posi: 623[M+H]$^+$.

Working Example 8-13

$^1$H NMR (600 MHz, DMSO-d$_6$) δ ppm 1.10-1.25 (m, 5 H), 1.27 (s, 9 H), 1.42-1.53 (m, 1 H), 1.59-1.69 (m, 2 H), 1.77-1.87 (m, 2 H), 3.02-3.49 (m, 8 H), 3.64-3.72 (m, 2 H), 3.76-3.85 (m, 1 H), 3.98-4.07 (m, 2 H), 4.39-4.51 (m, 1 H), 4.68-4.78 (m, 1 H), 6.69-6.85 (m, 2 H), 7.02-7.11 (m, 1 H), 7.19-7.27 (m, 2 H), 7.34-7.44 (m, 3 H), 7.53-7.63 (m, 2 H), 9.93 (s, 1 H).

LCMS retention time: 1.96 min. (Condition 3)
MS ESI/APCI Dual posi: 609[M+H]$^+$.

Working Example 8-14

$^1$H NMR (600 MHz, DMSO-d$_6$) δ ppm 1.27 (s, 9 H), 1.40-1.69 (m, 8 H), 1.82-1.90 (m, 2 H), 3.02-3.26 (m, 4 H), 3.27-3.50 (m, 5 H), 3.76-3.88 (m, 2 H), 3.96 (t, J=6.4 Hz, 2 H), 4.40-4.51 (m, 1 H), 4.69-4.77 (m, 1 H), 6.67-6.83 (m, 2 H), 7.02-7.12 (m, 1 H), 7.19-7.27 (m, 2 H), 7.34-7.44 (m, 3 H), 7.54-7.63 (m, 2 H), 9.92 (s, 1 H).

LCMS retention time: 2.00 min. (Condition 3)
MS ESI/APCI Dual posi: 609[M+H]$^+$.

Working Example 8-15

$^1$H NMR (600 MHz, DMSO-d$_6$) δ ppm 1.27 (s, 9 H), 1.55-1.72 (m, 2 H), 1.79-1.94 (m, 2 H), 1.98-2.09 (m, 1 H), 3.05-3.18 (m, 3 H), 3.18-3.49 (m, 6 H), 3.70-3.85 (m, 2 H), 3.89-4.10 (m, 3 H), 4.25-4.39 (m, 1 H), 4.41-4.49 (m, 1 H), 4.67-4.78 (m, 1 H), 6.68-6.85 (m, 2 H), 7.02-7.12 (m, 1 H), 7.19-7.27 (m, 2 H), 7.33-7.45 (m, 3 H), 7.52-7.64 (m, 2 H), 9.93 (s, 1 H).

LCMS retention time: 0.82 min. (Condition 2)
MS (ESI posi) m/z: 613[M+H]$^+$.

Working Example 8-16

$^1$H NMR (600 MHz, DMSO-d$_6$) δ ppm 1.14-1.27 (m, 1 H), 1.31-1.49 (m, 11 H), 1.52-1.63 (m, 1 H), 1.71-1.82 (m, 3 H), 3.08-3.45 (m, 6 H), 3.49-3.90 (m, 6 H), 3.91-4.03 (m, 2 H), 4.39-4.52 (m, 1H), 4.65-4.76 (m, 1 H), 6.65-6.83 (m, 2 H), 7.00-7.12 (m, 1 H), 7.35-7.46 (m, 1 H), 7.53-7.88 (m, 4 H), 8.54-8.72 (m, 1 H), 9.92 (s, 1 H).

LCMS retention time: 1.39 min. (Condition 3)
MS ESI/APCI Dual posi: 596[M+H]$^+$.

Working Example 8-17

LCMS retention time: 0.98 min. (Condition 4-1)
MS (ESI posi) m/z: 497[M+H]$^+$.

The structures of the compounds of Working Examples 8-2 to 8-17 are shown in Tables 23-1 and 23-2.

TABLE 23-1
| Working Ex. | Structure |
|---|---|
| 8-2 | 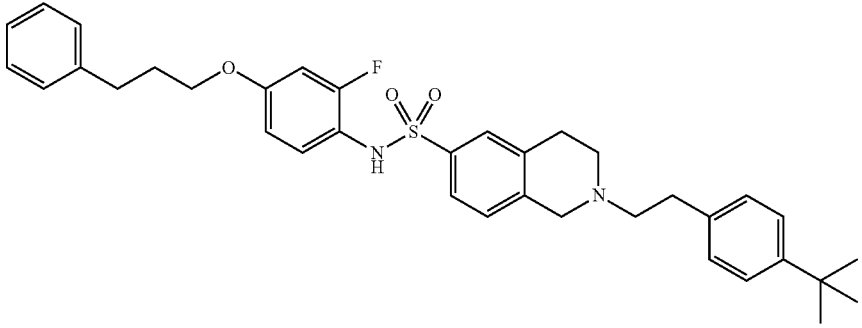 [SMILES: CC(C)(C)c1ccc(CCN2CCc3cc(S(=O)(=O)Nc4ccc(OCCCc5ccccc5)cc4F)ccc3C2)cc1] |
| 8-3 | 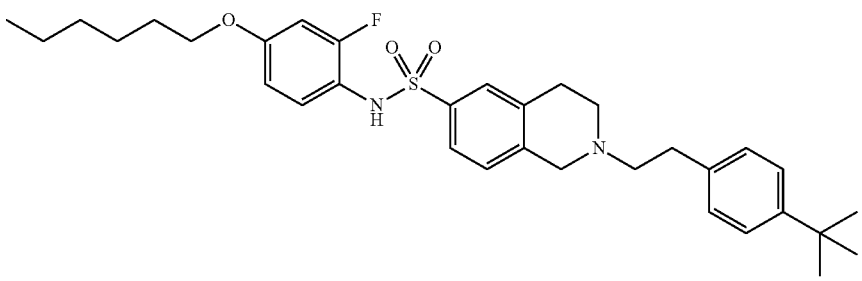 |
| 8-4 | 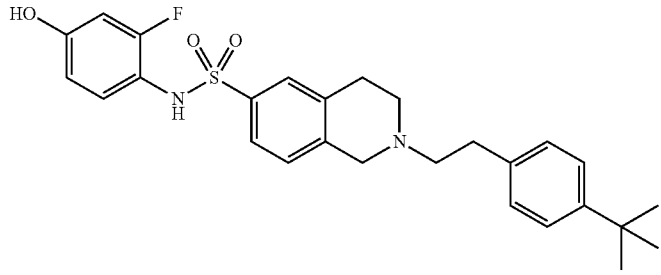 [SMILES: CC(C)(C)c1ccc(CCN2CCc3cc(S(=O)(=O)Nc4ccc(O)cc4F)ccc3C2)cc1] |
TABLE 23-2
| Working Ex. | Structure |
|---|---|
| 8-5 | 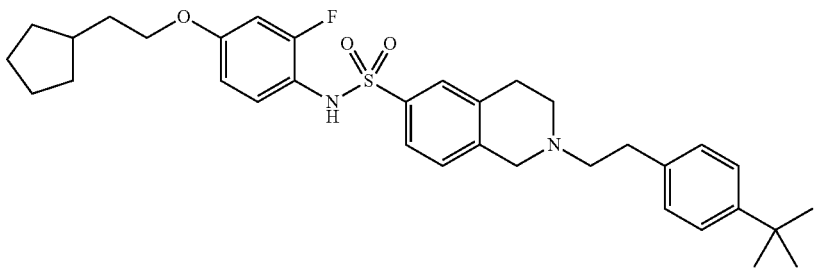 [SMILES: CC(C)(C)c1ccc(CCN2CCc3cc(S(=O)(=O)Nc4ccc(OCCC5CCCC5)cc4F)ccc3C2)cc1] |

TABLE 23-2-continued
| Working Ex. | Structure |
|---|---|
| 8-6 | 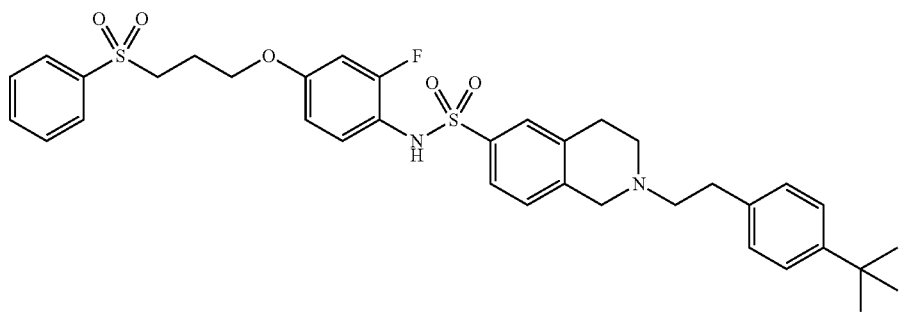 [SMILES: CC(C)(C)c1ccc(CCN2CCc3cc(S(=O)(=O)Nc4ccc(OCCCS(=O)(=O)c5ccccc5)cc4F)ccc3C2)cc1] |
| 8-7 | 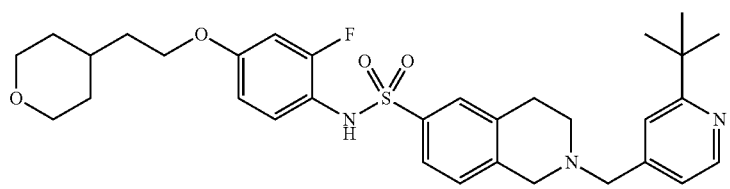 [SMILES: CC(C)(C)c1cc(CN2CCc3cc(S(=O)(=O)Nc4ccc(OCCC5CCOCC5)cc4F)ccc3C2)ccn1] |
| 8-8 | 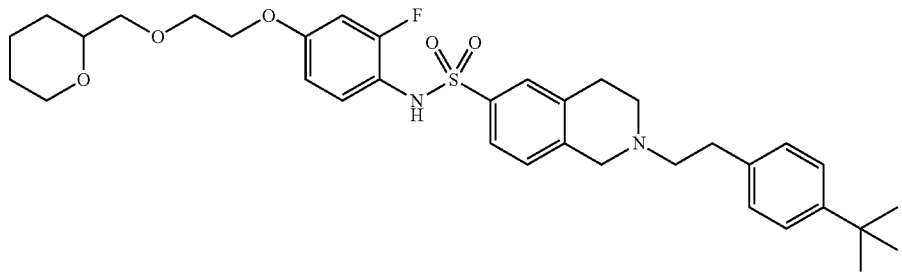 [SMILES: CC(C)(C)c1ccc(CCN2CCc3cc(S(=O)(=O)Nc4ccc(OCCOCC5CCCCO5)cc4F)ccc3C2)cc1] |
| 8-9 | 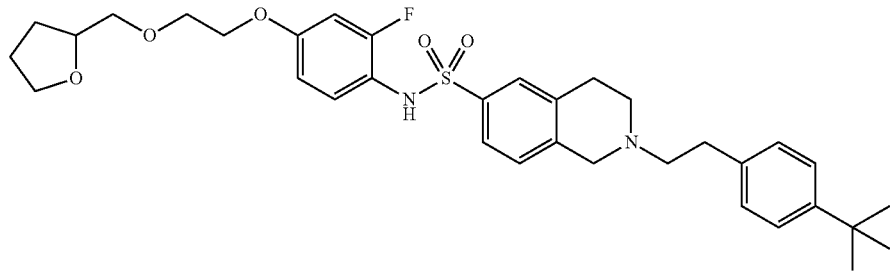 [SMILES: CC(C)(C)c1ccc(CCN2CCc3cc(S(=O)(=O)Nc4ccc(OCCOCC5CCCO5)cc4F)ccc3C2)cc1] |
| 8-10 | 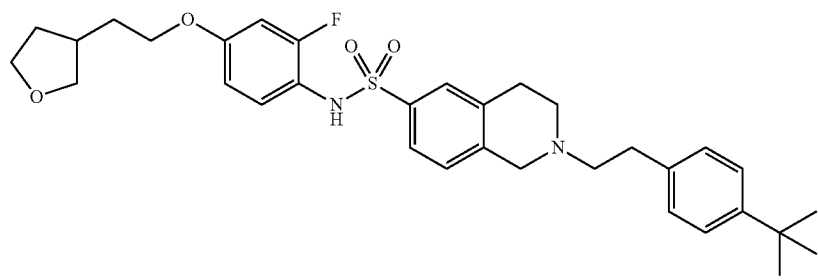 [SMILES: CC(C)(C)c1ccc(CCN2CCc3cc(S(=O)(=O)Nc4ccc(OCCC5CCOC5)cc4F)ccc3C2)cc1] |

TABLE 23-2-continued

| Working Ex. | Structure |
|---|---|
| 8-11 | 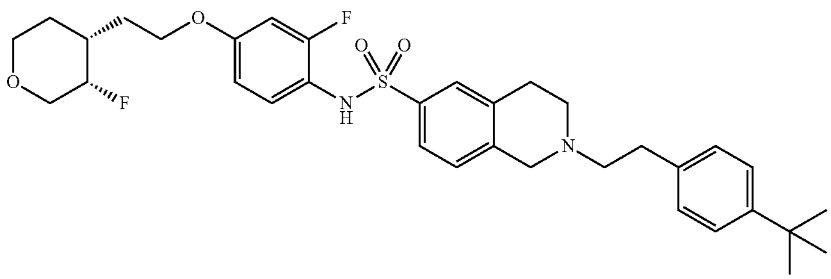 [SMILES: CC(C)(C)c1ccc(CCN2CCc3cc(S(=O)(=O)Nc4ccc(OCC[C@H]5CCOC[C@H]5F)cc4F)ccc3C2)cc1] |
| 8-12 | 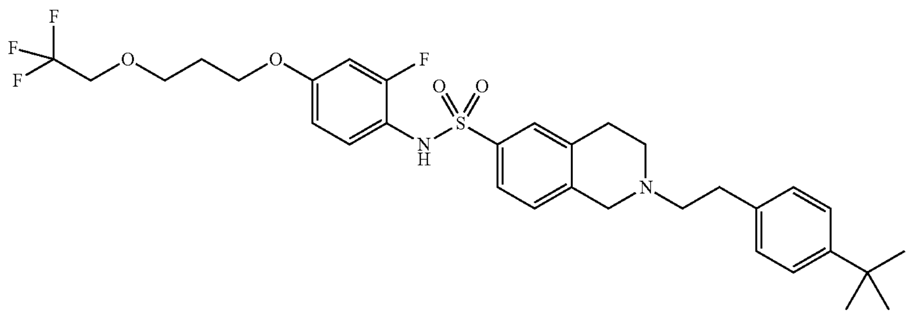 [SMILES: CC(C)(C)c1ccc(CCN2CCc3cc(S(=O)(=O)Nc4ccc(OCCCOCC(F)(F)F)cc4F)ccc3C2)cc1] |
| 8-13 | 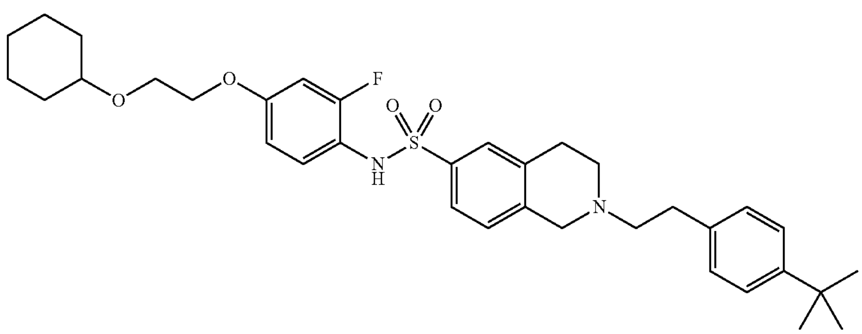 [SMILES: CC(C)(C)c1ccc(CCN2CCc3cc(S(=O)(=O)Nc4ccc(OCCOC5CCCCC5)cc4F)ccc3C2)cc1] |
| 8-14 | 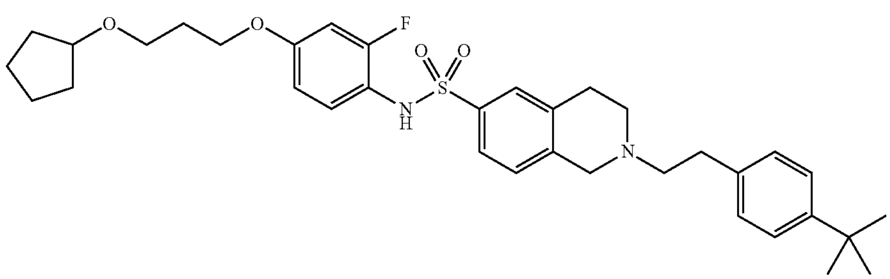 [SMILES: CC(C)(C)c1ccc(CCN2CCc3cc(S(=O)(=O)Nc4ccc(OCCCOC5CCCC5)cc4F)ccc3C2)cc1] |
| 8-15 | 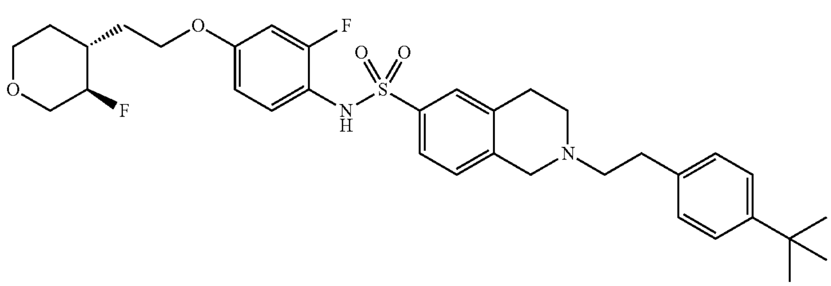 [SMILES: CC(C)(C)c1ccc(CCN2CCc3cc(S(=O)(=O)Nc4ccc(OCC[C@H]5CCOC[C@@H]5F)cc4F)ccc3C2)cc1] |

TABLE 23-2-continued

| Working Ex. | Structure |
|---|---|
| 8-16 | ![structure] |
| 8-17 | ![structure] |

Working Example 9-1

N-(4-Fluorophenyl)-2-(1-phenylethyl)-1,2,3,4-tetrahydroisoquinoline-6-sulfonamide

[Formula 63]

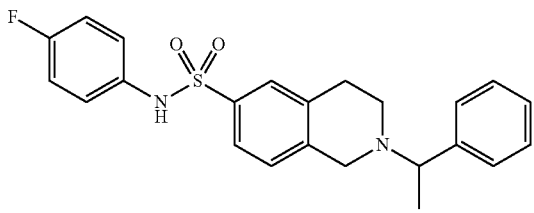

(1) To a solution of the compound obtained in Reference Example 3-1 (100 mg, 0.33 mmol) in methanol (5 mL) were added acetic acid (0.75 mL), acetophenone (76 µL, 0.65 mmol) and 2-picolineborane (70 mg, 0.65 mmol), and the mixture was heated to 65° C. and stirred for 8 hr. After cooling, saturated aqueous sodium hydrogen carbonate solution was added thereto and the mixture was extracted with ethyl acetate. The organic layer was washed with brine and dried over anhydrous magnesium sulfate and then the desiccant was filtered off, followed by concentration under reduced pressure. The resulting residue was purified by NH silica gel column chromatography (chloroform only→chloroform:methanol=19:1) to afford the title compound as a colorless amorphous substance (49 mg).

$^1$H NMR (300 MHz, CDCl$_3$) δ ppm 1.48 (d, J=6.7 Hz, 3 H), 2.57-2.69 (m, 1 H), 2.74-2.92 (m, 3 H), 3.53-3.65 (m, 2 H), 3.75-3.85 (m, 1 H), 6.56 (br. s., 1 H), 6.89-7.06 (m, 5 H), 7.25-7.35 (m, 5 H), 7.37-7.42 (m, 1 H), 7.44-7.47 (m, 1 H).

MS ESI/APCI Dual posi: 411[M+H]$^+$.

(2) The same process as that of Working Example 2-1(2) was performed using the title compound to afford the monohydrochloride of the title compound as a colorless powder (39 mg).

MS ESI/APCI Dual posi: 411[M+H]$^+$.

The compounds of Working Examples 9-2 to 9-4 were obtained by using the corresponding compounds obtained in Reference Example 3 and the ketone obtained in Reference Example 14-1(1) or the corresponding commercially available aldehydes or ketones in accordance with the process of Working Example 9-1(1).

Working Example 9-2

$^1$H NMR (300 MHz, DMSO-d$_6$) δ ppm 1.28 (s, 9 H), 1.33 (d, J=6.4 Hz, 3 H), 3.58-3.66 (m, 1 H), 3.67-3.75 (m, 2 H), 3.77-3.92 (m, 2 H), 7.04-7.10 (m, 4 H), 7.24-7.30 (m, 2 H), 7.32-7.38 (m, 3 H), 7.51-7.60 (m, 2 H).

MS ESI/APCI Dual posi: 453[M+H]$^+$.

Working Example 9-3

$^1$H NMR (300 MHz, DMSO-d$_6$) δ ppm 1.60-2.10 (m, 4 H), 2.64-2.88 (m, 2 H), 3.71-4.08 (m, 5 H), 6.99-7.20 (m, 7 H), 7.32-7.44 (m, 2 H), 7.50-7.62 (m, 2 H), 10.19 (br. s., 1 H).

MS ESI/APCI Dual posi: 423[M+H]$^+$.

Working Example 9-4

$^1$H NMR (300 MHz, DMSO-d$_6$) δ ppm 1.27 (s, 9 H), 2.60-2.68 (m, 2 (s, 2 H), 3.59 (s, 2 H), 7.04-7.09 (m, 4 H), 7.15-7.21 (m, 1 H), 7.22-7.28 (m, 2 H), 7.32-7.42 (m, 3 H), 7.45-7.48 (m, 1 H).

MS ESI/APCI Dual posi: 453[M+H]$^+$.

The compounds of Working Examples 9-5 to 9-24 were obtained by using the corresponding compounds obtained in Reference Example 3 and the compounds obtained in Reference Examples 7-1, 11 and 12 or the corresponding commercially available aldehydes or ketones in accordance with the processes of Working Example 9-1(1) and (2).

Working Example 9-5

MS ESI/APCI Dual posi: 481[M+H]$^+$.

Working Example 9-6

MS ESI/APCI Dual posi: 613[M+H]$^+$.

Working Example 9-7

$^1$H NMR (600 MHz, DMSO-d$_6$) δ ppm 0.72-0.81 (m, 3 H), 1.25-1.28 (m, 9 H), 1.61-1.73 (m, 1 H), 1.75-1.89 (m, 1 H), 2.75-2.94 (m, 2 H), 3.09-3.50 (m, 3 H), 3.58-3.81 (m, 2 H), 4.49-4.69 (m, 2 H), 7.05-7.15 (m, 4 H), 7.26 (dd, J=8.3, 4.1 Hz, 2 H), 7.32-7.43 (m, 3 H), 7.59-7.64 (m, 1 H), 7.67 (d, J=7.8 Hz, 1H), 10.34 (s, 1 H), 10.34 (s, 1 H).
LCMS retention time: 4.80 min. (Condition 1-1-1)
MS (ESI posi) m/z: 495[M+H]$^+$.

Working Example 9-8

$^1$H NMR (600 MHz, DMSO-d$_6$) δ ppm 0.68-0.79 (m, 3 H), 0.99-1.21 (m, 2 H), 1.23-1.29 (m, 9 H), 1.55-1.66 (m, 1 H), 1.74-1.83 (m, 1 H), 2.75-2.90 (m, 2 H), 3.08-3.27 (m, 3 H), 3.62-3.80 (m, 2 H), 4.51-4.67 (m, 2 H), 7.04-7.16 (m, 4 H), 7.25 (dd, J=8.3, 3.2 Hz, 2 H), 7.32-7.43 (m, 3 H), 7.58-7.64 (m, 1 H), 7.66 (d, J=6.4 Hz, 1 H), 10.34 (s, 1 H).
LCMS retention time: 5.03 min. (Condition 1-1-1)
MS (ESI posi) m/z: 509[M+H]$^+$.

Working Example 9-9

MS ESI/APCI Dual posi: 453[M+H]$^+$.

Working Example 9-10

MS ESI/APCI Dual posi: 397[M+H]$^+$.

Working Example 9-11

MS ESI/APCI Dual posi: 411[M+H]$^+$.

Working Example 9-12

MS ESI/APCI Dual posi: 481[M+H]$^+$.

Working Example 9-13

MS ESI/APCI Dual posi: 397[M+H]$^+$.

Working Example 9-14

$^1$H NMR (600 MHz, DMSO-d$_6$) δ ppm 3.02-3.33 (m, 3 H), 3.48 (s, 3 H), 3.63-3.76 (m, 1 H), 4.30-4.45 (m, 2 H), 4.47-4.65 (m, 2 H), 6.64-6.77 (m, 1 H), 6.80-6.87 (m, 1 H), 7.12-7.21 (m, 1 H), 7.30-7.41 (m, 1 H), 7.44-7.59 (m, 2 H), 7.80-7.94 (m, 4 H), 9.54 (br. s., 1 H), 11.25 (br. s., 1 H).
MS ESI/APCI Dual posi: 495[M+H]$^+$.

Working Example 9-15

$^1$H NMR (600 MHz, DMSO-d$_6$) δ ppm 3.04-3.51 (m, 6 H), 3.65-3.86 (m, 1 H), 4.29-4.75 (m, 4 H), 6.64-6.75 (m, 1 H), 6.78-6.89 (m, 1 H), 7.11-7.23 (m, 1 H), 7.27-7.40 (m, 1 H), 7.43-7.61 (m, 2 H), 7.97-8.15 (m, 1 H), 8.33-8.49 (m, 1 H), 8.94-9.06 (m, 1 H), 9.52 (br. s., 1 H), 11.51 (br. s., 1 H).
MS ESI/APCI Dual posi: 496[M+H]$^+$.

Working Example 9-16

$^1$H NMR (600 MHz, DMSO-d$_6$) δ ppm 1.34 (s, 9 H), 3.05-3.46 (m, 4 H), 3.52-3.69 (m, 2 H), 3.72-3.88 (m, 1 H), 3.95-4.50 (m, 2 H), 4.65-4.76 (m, 1 H), 7.04-7.16 (m, 4 H), 7.34-7.45 (m, 1 H), 7.56-7.69 (m, 2 H), 8.57 (s, 1 H), 8.68 (s, 1 H), 10.34 (s, 1 H), 10.97 (br. s., 1 H).
MS ESI/APCI Dual posi: 469[M+H]$^+$.

Working Example 9-17

$^1$H NMR (600 MHz, DMSO-d$_6$) δ ppm 1.33 (s, 9 H), 3.12-3.24 (m, 2 H), 3.39-3.74 (m, 6 H), 4.37-4.83 (m, 2 H), 7.03-7.16 (m, 4 H), 7.39 (d, J=8.3 Hz, 1 H), 7.56-7.70 (m, 2 H), 8.82 (s, 2 H), 10.32 (s, 1 H), 10.51 (br. s., 1 H).
MS ESI/APCI Dual posi: 469[M+H]$^+$.

Working Example 9-18

$^1$H NMR (600 MHz, DMSO-d$_6$) δ ppm 1.29 (s, 9 H), 3.14-3.25 (m, 2 H), 3.48 (t, J=7.8 Hz, 2 H), 3.58-3.90 (m, 4 H), 4.37-4.80 (m, 2 H), 7.05-7.15 (m, 4 H), 7.38 (d, J=8.3 Hz, 1 H), 7.45 (d, J=5.5 Hz, 1 H), 7.58-7.67 (m, 2 H), 8.68 (d, J=5.5 Hz, 1 H), 10.33 (s, 1 H), 10.72 (br. s., 1 H).
MS ESI/APCI Dual posi: 469[M+H]$^+$.

Working Example 9-19

$^1$H NMR (600 MHz, DMSO-d$_6$) δ ppm 1.35 (s, 9 H), 1.94-2.03 (m, 2 H), 2.67-2.73 (m, 2 H), 3.08-3.31 (m, 2 H), 3.33-3.46 (m, 3 H), 3.56-3.86 (m, 3 H), 3.92 (t, J=6.42 Hz, 2 H), 4.40-4.54 (m, 1 H), 4.68-4.79 (m, 1 H), 6.68-6.74 (m, 1 H), 6.76-6.82 (m, 1 H), 7.03-7.10 (m, 1 H), 7.15-7.24 (m, 3 H), 7.25-7.32 (m, 2 H), 7.38-7.43 (m, 1 H), 7.54-7.62 (m, 2 H), 8.56-8.60 (m, 1 H), 8.67-8.70 (m, 1 H), 9.91 (s, 1 H), 10.90 (br. s., H).
MS ESI/APCI Dual posi: 603[M+H]$^+$.

Working Example 9-20

$^1$H NMR (600 MHz, DMSO-d$_6$) δ ppm 0.83-0.90 (m, 3 H), 1.24-1.41 (m, 15 H), 1.62-1.70 (m, 2 H), 3.09-3.30 (m, 2 H), 3.34-3.45 (m, 3 H), 3.57-3.67 (m, 2 H), 3.79-4.03 (m, 3 H), 4.42-4.52 (m, 1 H), 4.68-4.77 (m, 1 H), 6.67-6.72 (m, 1 H), 6.75-6.80 (m, 1 H), 7.01-7.08 (m, 1 H), 7.40 (d, J=8.3 Hz, 1 H), 7.54-7.61 (m, 2 H), 8.56-8.60 (m, 1 H), 8.67-8.70 (m, 1 H), 9.90 (s, 1 H), 10.96 (br. s., 1 H).
MS ESI/APCI Dual posi: 569[M+H]$^+$.

Working Example 9-21

LCMS retention time: 5.04 min. (Condition 1-1-1)
MS (ESI posi) m/z: 569[M+H]$^+$.

Working Example 9-22

$^1$H NMR (600 MHz, DMSO-d$_6$) δ ppm 1.27 (s, 9 H), 2.30 (s, 3 H), 3.06-3.25 (m, 4 H), 3.33-3.49 (m, 3 H), 3.71-3.88 (m, 1 H), 4.35-4.52 (m, 1 H), 4.61-4.79 (m, 1 H), 6.15 (s, 1 H), 7.22 (d, J=8.3 Hz, 2 H), 7.37 (d, J=8.3 Hz, 2 H), 7.44-7.46 (m, 1 H), 7.72-7.75 (m, 1 H), 7.77 (s, 1 H).
LCMS retention time: 1.93 min. (Condition 1-2-1)
MS (ESI posi) m/z: 454[M+H]$^+$.

Working Example 9-23

$^1$H NMR (600 MHz, DMSO-d$_6$) δ ppm 0.96-1.06 (m, 2 H), 1.21-1.28 (m, 2 H), 1.35 (s, 9 H), 1.41-1.58 (m, 6 H), 1.65-1.76 (m, 3 H), 2.35-2.36 (m, 1 H), 3.09-3.28 (m, 2 H), 3.31-3.46 (m, 4H), 3.58-3.67 (m, 2H), 3.80-3.85 (m, 1 H), 4.43-4.52 (m, 1 H), 4.70-4.77 (m, 1 H), 6.93-6.96 (m, 1 H), 6.98-

7.02 (m, 1 H), 7.10-7.14 (m, 1 H), 7.39-7.42 (m, 1 H), 7.59-7.64 (m, 2 H), 8.57-8.59 (m, 1 H), 8.68-8.70 (m, 1 H), 10.12 (s, 1 H).
LCMS retention time: 0.96 min. (Condition 2)
MS (ESI posi) m/z: 579[M+H]$^+$.

Working Example 9-24

$^1$H NMR (600 MHz, DMSO-d$_6$) δ ppm 0.95-1.07 (m, 2 H), 1.19-1.29 (m, 2 H), 1.40-1.58 (m, 6 H), 1.64-1.77 (m, 3 H), 3.09-3.27 (m, 2 H), 3.36-3.89 (m, 8 H), 4.42-4.80 (m, 2 H), 6.92-7.04 (m, 2 H), 7.09-7.16 (m, 1 H), 7.36-7.43 (m, 1 H), 7.57-7.69 (m, 3 H), 8.19-8.27 (m, 1 H), 8.94 (s, 1 H), 10.12 (s, 1 H).
LCMS retention time: 0.94 min. (Condition 2)
MS (ESI posi) m/z: 590[M+H]$^+$.

The compounds of Working Examples 9-25 to 9-27 were obtained by using the corresponding compounds obtained in Reference Example 3 and the aldehyde obtained in Reference Example 7-1 in accordance with the process of Working Example 9-1(1).

Working Example 9-25

$^1$H NMR (600 MHz, DMSO-d$_6$) δ ppm 1.23 (s, 9 H), 1.25 (s, 9 H), 2.67-2.73 (m, 2 H), 2.75-2.81 (m, 4 H), 2.85-2.89 (m, 2 H), 3.67-3.75 (m, 2 H), 6.03 (s, 1 H), 7.17 (d, J=8.3 Hz, 2 H), 7.26-7.30 (m, 3 H), 7.57-7.61 (m, 2 H), 8.31 (s, 1 H).
LCMS retention time: 3.92 min. (Condition 1-2-1)
MS (ESI posi) m/z: 496[M+H]$^+$.

Working Example 9-26

$^1$H NMR (600 MHz, DMSO-d$_6$) δ ppm 1.10 (s, 9 H), 1.25 (s, 9 H), 2.64-2.70 (m, 2 H), 2.71-2.80 (m, 4 H), 2.82-2.88 (m, 2 H), 3.68 (s, 2 H), 5.17 (s, 1 H), 6.04 (s, 2 H), 7.16 (d, J=8.3 Hz, 2 H), 7.25-7.33 (m, 3 H), 7.57 (dd, J=8.3, 1.7 Hz, 1 H), 7.61 (s, 1 H).
LCMS retention time: 3.90 min. (Condition 1-2-1)
MS (ESI posi) m/z: 495[M+H]$^+$.

Working Example 9-27

$^1$H NMR (600 MHz, DMSO-d$_6$) δ ppm 1.18 (s, 9 H), 1.25 (s, 9 H), 2.66-2.71 (m, 2 H), 2.72-2.81 (m, 4 H), 2.85-2.89 (m, 2 H), 3.67 (s, 2 H), 6.34 (s, 1 H), 7.17 (d, J=8.3 Hz, 2 H), 7.22 (d, J=8.7 Hz, 1 H), 7.29 (d, J=8.3 Hz, 2 H), 7.51-7.56 (m, 2 H), 12.61 (br. s., 1 H).
LCMS retention time: 4.38 min. (Condition 1-2-1)
MS (ESI posi) m/z: 512[M+H]$^+$.

The structures of the compounds of Working Examples 9-2 to 9-27 are shown in Tables 24-1 to 24-3.

TABLE 24-1

| Working Ex. | Structure |
|---|---|
| 9-2 | (structure) |
| 9-3 | (structure) |
| 9-4 | (structure) |

TABLE 24-1-continued

| Working Ex. | Structure |
|---|---|
| 9-5 | 4-fluoro-N-phenyl sulfonamide of 2-(1-(4-tert-butylphenyl)propan-2-yl)-1,2,3,4-tetrahydroisoquinoline-6-sulfonamide |
| 9-6 | N-(4-(3-phenylpropoxy)-2-fluorophenyl)-2-(1-(4-(trifluoromethyl)phenyl)ethyl)-1,2,3,4-tetrahydroisoquinoline-6-sulfonamide |
| 9-7 | N-(4-fluorophenyl)-2-(1-(4-tert-butylphenyl)butan-2-yl)-1,2,3,4-tetrahydroisoquinoline-6-sulfonamide |
| 9-8 | N-(4-fluorophenyl)-2-(1-(4-tert-butylphenyl)pentan-2-yl)-1,2,3,4-tetrahydroisoquinoline-6-sulfonamide |
| 9-9 | N-(4-fluorophenyl)-2-(4-tert-butylbenzyl)-1,2,3,4-tetrahydroisoquinoline-7-sulfonamide |
| 9-10 | N-(4-fluorophenyl)-2-benzyl-1,2,3,4-tetrahydroisoquinoline-7-sulfonamide |

TABLE 24-1-continued
| Working Ex. | Structure |
|---|---|
| 9-11 | 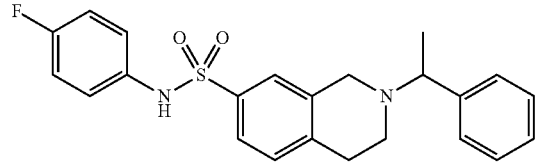 [SMILES: CC(c1ccccc1)N1CCc2ccc(S(=O)(=O)Nc3ccc(F)cc3)cc2C1] |
| 9-12 | 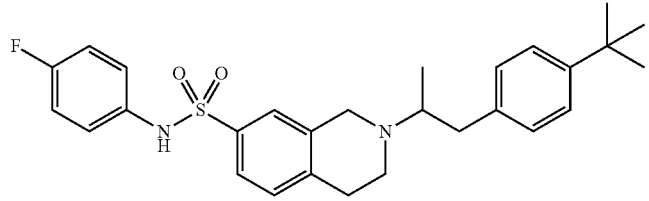 [SMILES: CC(Cc1ccc(C(C)(C)C)cc1)N1CCc2ccc(S(=O)(=O)Nc3ccc(F)cc3)cc2C1] |
| 9-13 | 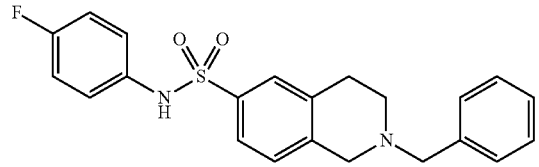 [SMILES: O=S(=O)(Nc1ccc(F)cc1)c1ccc2c(c1)CCN(Cc1ccccc1)C2] |
| 9-14 | 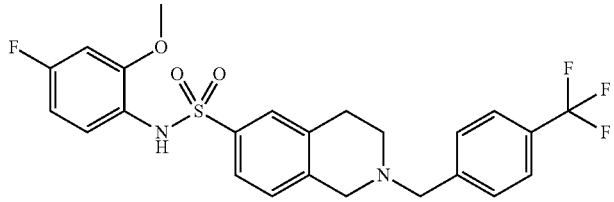 [SMILES: COc1cc(F)ccc1NS(=O)(=O)c1ccc2c(c1)CCN(Cc1ccc(C(F)(F)F)cc1)C2] |
| 9-15 | 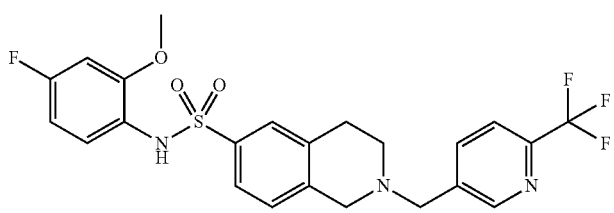 [SMILES: COc1cc(F)ccc1NS(=O)(=O)c1ccc2c(c1)CCN(Cc1ccc(C(F)(F)F)nc1)C2] |
TABLE 24-2
| Working Ex. | Structure |
|---|---|
| 9-16 | 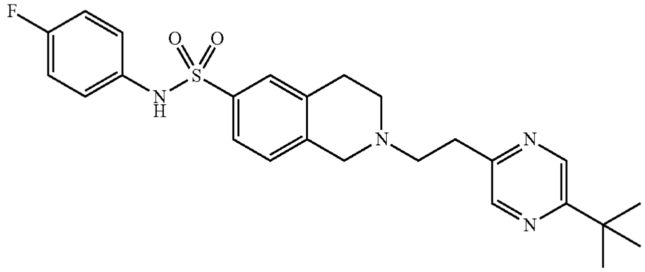 [SMILES: CC(C)(C)c1cnc(CCN2CCc3cc(S(=O)(=O)Nc4ccc(F)cc4)ccc3C2)cn1] |

TABLE 24-2-continued

| Working Ex. | Structure |
|---|---|
| 9-17 | 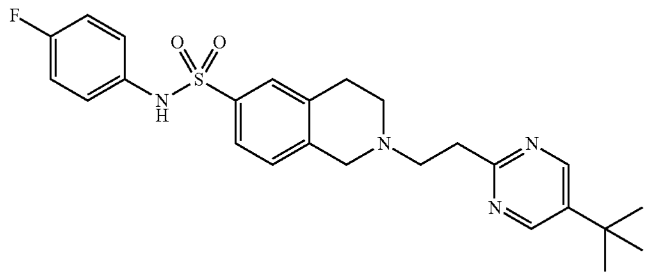 [SMILES: CC(C)(C)c1cnc(CCN2CCc3cc(S(=O)(=O)Nc4ccc(F)cc4)ccc3C2)nc1] |
| 9-18 | 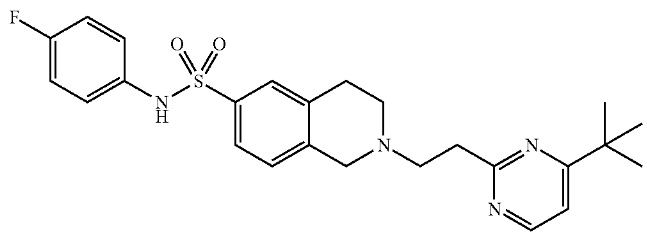 [SMILES: CC(C)(C)c1ccnc(CCN2CCc3cc(S(=O)(=O)Nc4ccc(F)cc4)ccc3C2)n1] |
| 9-19 | 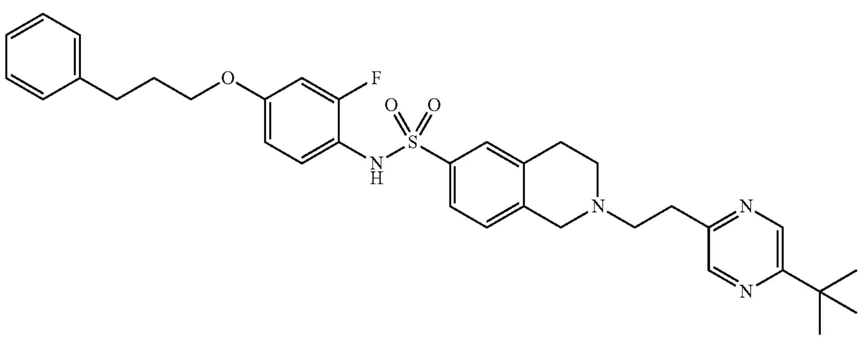 [SMILES: CC(C)(C)c1cnc(CCN2CCc3cc(S(=O)(=O)Nc4ccc(OCCCc5ccccc5)cc4F)ccc3C2)cn1] |
| 9-20 | 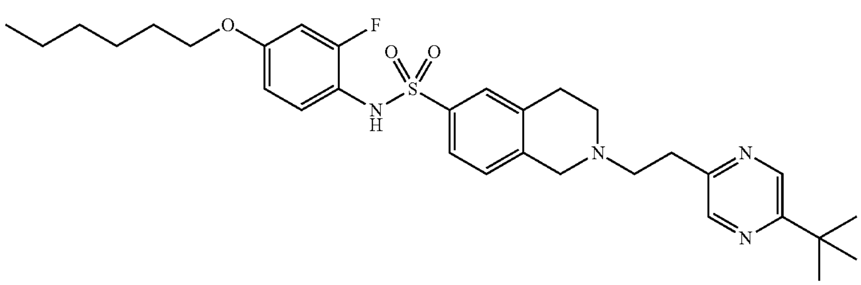 [SMILES: CCCCCCOc1ccc(NS(=O)(=O)c2ccc3c(c2)CCN(CCc2cnc(C(C)(C)C)cn2)C3)c(F)c1] |
| 9-21 | 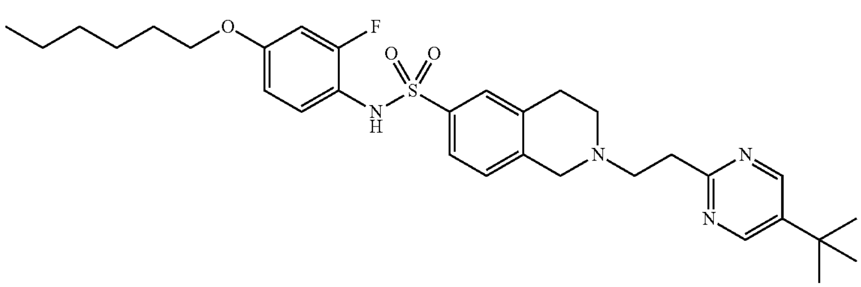 [SMILES: CCCCCCOc1ccc(NS(=O)(=O)c2ccc3c(c2)CCN(CCc2ncc(C(C)(C)C)cn2)C3)c(F)c1] |

TABLE 24-3
| Working Ex. | Structure |
|---|---|
| 9-22 | 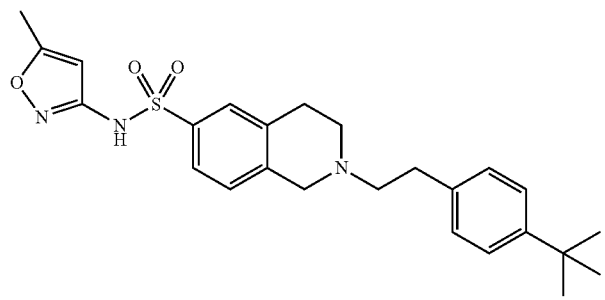 [SMILES: Cc1cc(NS(=O)(=O)c2ccc3c(c2)CCN(CCc2ccc(C(C)(C)C)cc2)C3)no1] |
| 9-23 | 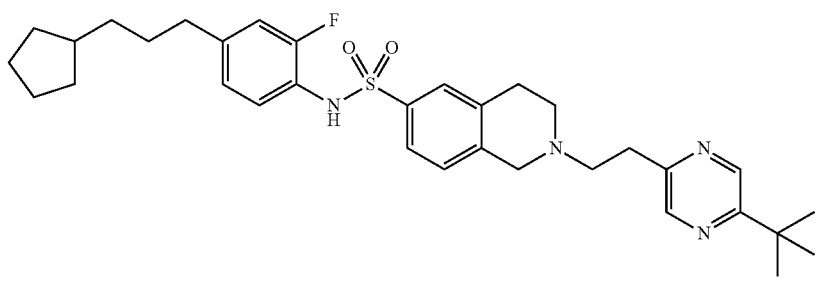 [SMILES: CC(C)(C)c1cnc(CCN2CCc3cc(S(=O)(=O)Nc4ccc(CCCC5CCCC5)cc4F)ccc3C2)cn1] |
| 9-24 | 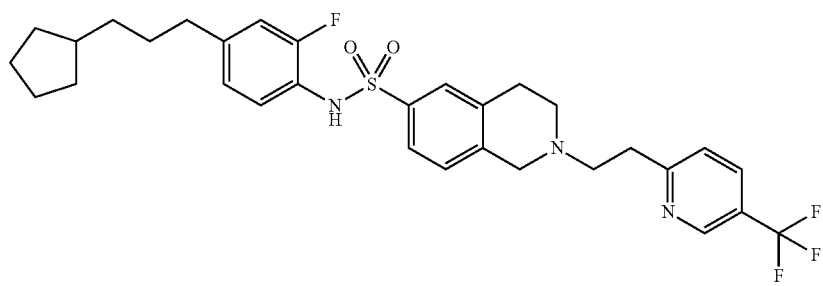 [SMILES: O=S(=O)(Nc1ccc(CCCC2CCCC2)cc1F)c1ccc2c(c1)CCN(CCc1ccc(C(F)(F)F)cn1)C2] |
| 9-25 | 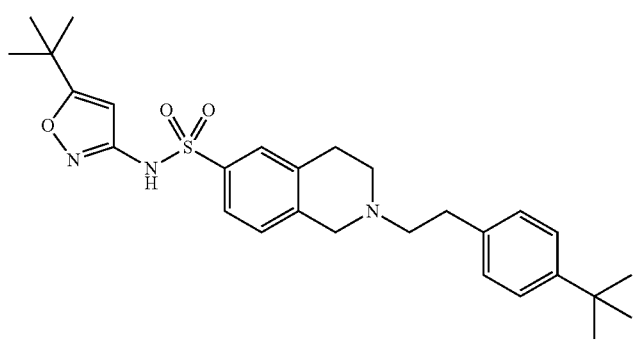 [SMILES: CC(C)(C)c1ccc(CCN2CCc3cc(S(=O)(=O)Nc4cc(C(C)(C)C)on4)ccc3C2)cc1] |
| 9-26 | 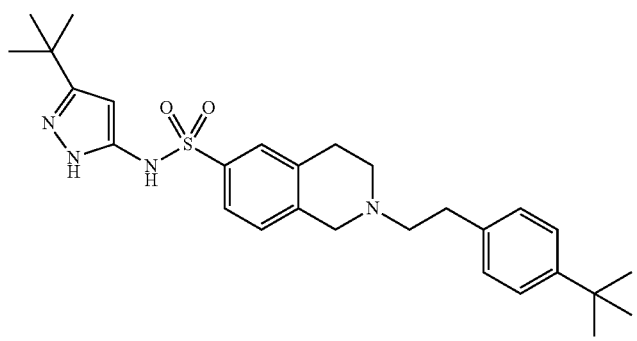 [SMILES: CC(C)(C)c1ccc(CCN2CCc3cc(S(=O)(=O)Nc4cc(C(C)(C)C)n[nH]4)ccc3C2)cc1] |

TABLE 24-3-continued

| Working Ex. | Structure |
|---|---|
| 9-27 | (structure shown) |

Working Examples 10-1 and 10-2

(R)-2-[1-(4-tert-Butylphenyl)propan-2-yl]-N-(4-fluorophenyl)-1,2,3,4-tetrahydroisoquinoline-6-sulfonamide and (S)-2-[1-(4-tert-butylphenyl)propan-2-yl]-N-(4-fluorophenyl)-1,2,3,4-tetrahydroisoquinoline-6-sulfonamide

[Formula 64]

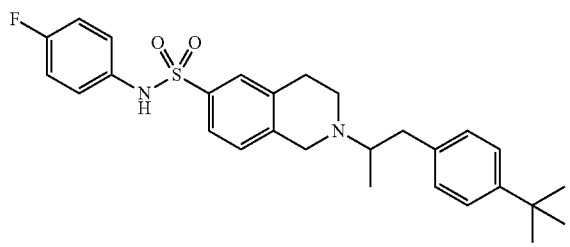

(1) Compound 9-5 as obtained in Working Example 9 (215 mg, 0.447 mmol) was separated by preparative HPLC (Daicel Corporation CHIRALPAK AD-H 5 μm 20×250 mm, 40° C., flow rate 14 mL/min, hexane:ethanol:diethylamine=90:10:0.1). A fraction eluted at a retention time of 18 min was concentrated to afford the compound of Working Example 10-1 as a brownish red amorphous substance (77.8 mg). A fraction eluted at a retention time of 22 min was concentrated to afford the compound of Working Example 10-2 as a pale yellow oil (82.8 mg).

(2) The same process as that of Working Example 2-1(2) was performed using the compounds of Working Examples 10-1 and 10-2 to afford the monohydrochloride of the compound of Working Example 10-1 as a colorless powder (42.9 mg) and the monohydrochloride of the compound of Working Example 10-2 as a brownish red powder (68.9 mg), respectively.

Monohydrochloride of the Compound of Working Example 10-1
  LCMS retention time: 4.70 min. (Condition 1-1-1)
  MS (ESI posi) m/z: 481[M+H]$^+$.

Monohydrochloride of the Compound of Working Example 10-2
  LCMS retention time: 4.71 min. (Condition 1-1-1)
  MS (ESI posi) m/z: 481 [M+H]$^+$.

Working Examples 10-3 and 10-4

(1) A compound obtained by the same process as that of Working Example 9-1(1) using compound 3-5 as obtained in Reference Example 3 and the ketone obtained in Reference Example 12-1 was separated by preparative HPLC in accordance with the process of Working Examples 10-1 and 10-2 (1). A fraction eluted at a retention time of 13 min was concentrated to afford the compound of Working Example 10-3 as a pale yellow amorphous substance (19.4 mg). A fraction eluted at a retention time of 16 min was concentrated to afford the compound of Working Example 10-4 as a pale yellow amorphous substance (18.8 mg).

(2) The same process as that of Working Example 2-1(2) was performed using the compounds of Working Examples 10-3 and 10-4 to afford the monohydrochloride of the compound of Working Example 10-3 as a pale yellow powder (13.7 mg) and the monohydrochloride of the compound of Working Example 10-4 as a pale yellow powder (10.3 mg), respectively.

Monohydrochloride of the Compound of Working Example 10-3
  LCMS retention time: 5.63 min. (Condition 1-1-1)
  MS (ESI posi) m/z: 581[M+F1]$^+$.

Monohydrochloride of the Compound of Working Example 10-4
  LCMS retention time: 5.64 min. (Condition 1-1-1)
  MS (ESI posi) m/z: 581[M+F1]$^+$.

Working Examples 10-5 and 10-6

(1) A compound obtained by the same process as that of Working Example 9-1(1) using compound 3-8 as obtained in Reference Example 3 and the ketone obtained in Reference Example 12-1 was separated by preparative HPLC in accordance with the process of Working Examples 10-1 and 10-2 (1). A fraction eluted at a shorter retention time was concentrated to afford the compound of Working Example 10-5 as a colorless oil (20 mg). A fraction eluted at a longer retention time was concentrated to afford the compound of Working Example 10-6 as a colorless oil (22 mg).

Working Example 10-5

HPLC retention time: 8.19 min. (Condition 6)

Working Example 10-6

HPLC retention time: 10.05 min. (Condition 6)

(2) The same process as that of Working Example 2-1(2) was performed using the compounds of Working Examples 10-5 and 10-6 to afford the monohydrochloride of the compound of Working Example 10-5 as a colorless powder (16 mg) and the monohydrochloride of the compound of Working Example 10-6 as a colorless powder (18 mg), respectively.

Monohydrochloride of the Compound of Working Example 10-5

LCMS retention time: 6.21 min. (Condition 1-1-1)
MS (ESI posi) m/z: 591[M+H]$^+$.

Monohydrochloride of the Compound of Working Example 10-6

LCMS retention time: 6.21 min. (Condition 1-1-1)
MS (ESI posi) m/z: 591[M+H]$^+$.

Working Examples 10-7 and 10-8

(1) A compound obtained by the same process as that of Working Example 9-1(1) using compound 3-9 as obtained in Reference Example 3 and the ketone obtained in Reference Example 12-1 was separated by preparative HPLC in accordance with the process of Working Examples 10-1 and 10-2 (1). A fraction eluted at a shorter retention time was concentrated to afford the compound of Working Example 10-7 as a colorless oil (23 mg). A fraction eluted at a longer retention time was concentrated to afford the compound of Working Example 10-8 as a colorless oil (23 mg).

Working Example 10-7

HPLC retention time: 7.13 min. (Condition 6)

Working Example 10-8

HPLC retention time: 8.33 min. (Condition 6)

(2) The same process as that of Working Example 2-1(2) was performed using the compounds of Working Examples 10-7 and 10-8 to afford the monohydrochloride of the compound of Working Example 10-7 as a colorless powder (19 mg) and the monohydrochloride of the compound of Working Example 10-8 as a colorless powder (24 mg), respectively.

Monohydrochloride of the compound of Working Example 10-7

LCMS retention time: 6.19 min. (Condition 1-1-1)
MS (ESI posi) m/z: 579[M+H]$^+$.

Monohydrochloride of the Compound of Working Example 10-8

LCMS retention time: 6.18 min. (Condition 1-1-1)
MS (ESI posi) m/z: 579[M+H]$^+$.

Working Examples 10-9 and 10-10

(1) A compound obtained by the same process as that of Working Example 9-1(1) using compound 3-22 as obtained in Reference Example 3 and the ketone obtained in Reference Example 12-1 was separated by preparative HPLC in accordance with the process of Working Examples 10-1 and 10-2 (1). A fraction eluted at a shorter retention time was concentrated to afford the compound of Working Example 10-9 as a pale yellow oil (137 mg). A fraction eluted at a longer retention time was concentrated to afford the compound of Working Example 10-10 as a pale yellow oil (136 mg).

Working Example 10-9

HPLC retention time: 7.92 min. (Condition 6)

Working Example 10-10

HPLC retention time: 9.48 min. (Condition 6)

(2) The same process as that of Working Example 2-1(2) was performed using the compounds of Working Examples 10-9 and 10-10 to afford the monohydrochloride of the compound of Working Example 10-9 as a colorless powder (124 mg) and the monohydrochloride of the compound of Working Example 10-10 as a colorless powder (124 mg), respectively.

Monohydrochloride of the Compound of Working Example 10-9

LCMS retention time: 6.31 min. (Condition 1-1-1)
MS (ESI posi) m/z: 609[M+H]$^+$.

Monohydrochloride of the Compound of Working Example 10-10

LCMS retention time: 6.31 min. (Condition 1-1-1)
MS (ESI posi) m/z: 609[M+H]$^+$.

Working Examples 10-11 and 10-12

(1) A compound obtained by the same process as that of Working Example 9-1(1) using compound 3-27 as obtained in Reference Example 3 and the ketone obtained in Reference Example 12-1 was separated by preparative HPLC in accordance with the process of Working Examples 10-1 and 10-2 (1). A fraction eluted at a shorter retention time was concentrated to afford the compound of Working Example 10-11 as a pale yellow amorphous substance (179 mg). A fraction eluted at a longer retention time was concentrated to afford the compound of Working Example 10-12 as a pale yellow amorphous substance (171 mg).

Working Example 10-11

HPLC retention time: 14.56 min. (Condition 6)

Working Example 10-12

HPLC retention time: 18.30 min. (Condition 6)

(2) The same process as that of Working Example 2-1(2) was performed using the compounds of Working Examples 10-11 and 10-12 to afford the monohydrochloride of the compound of Working Example 10-11 as a colorless powder (171 mg) and the monohydrochloride of the compound of Working Example 10-12 as a colorless powder (169 mg), respectively.

Monohydrochloride of the Compound of Working Example 10-11

LCMS retention time: 6.03 min. (Condition 1-1-1)
MS (ESI posi) m/z: 643[M+H]$^+$.

Monohydrochloride of the compound of Working Example 10-12

LCMS retention time: 6.03 min. (Condition 1-1-1)
MS (ESI posi) m/z: 643[M+H]$^+$.

Working Examples 10-13 and 10-14

(1) A compound obtained by the same process as that of Working Example 9-1(1) using compound 3-28 as obtained in Reference Example 3 and the ketone obtained in Reference Example 12-1 was separated by preparative HPLC in accordance with the process of Working Examples 10-1 and 10-2 (1). A fraction eluted at a shorter retention time was concentrated to afford the compound of Working Example 10-13 as a yellow oil (178 mg). A fraction eluted at a longer retention time was concentrated to afford the compound of Working Example 10-14 as a pale yellow amorphous substance (166 mg).

Working Example 10-13

HPLC retention time: 10.44 min. (Condition 6)

Working Example 10-14

HPLC retention time: 12.14 min. (Condition 6)

(2) The same process as that of Working Example 2-1(2) was performed using the compounds of Working Examples 10-13 and 10-14 to afford the monohydrochloride of the compound of Working Example 10-13 as a colorless powder (160 mg) and the monohydrochloride of the compound of Working Example 10-14 as a colorless powder (164 mg), respectively.

Monohydrochloride of the Compound of Working Example 10-13
  LCMS retention time: 1.86 min. (Condition 3)
  MS ESI/APCI Dual posi: 621[M+H]$^+$.

Monohydrochloride of the Compound of Working Example 10-14
  LCMS retention time: 1.87 min. (Condition 3)
  MS ESI/APCI Dual posi: 621 [M+H]$^+$.

Working Examples 10-15 and 10-16

(1) A compound obtained by the same process as that of Working Example 9-1(1) using compound 3-41 as obtained in Reference Example 3 and the ketone obtained in Reference Example 12-1 was separated by preparative HPLC in accordance with the process of Working Examples 10-1 and 10-2 (1). A fraction eluted at a shorter retention time was concentrated to afford the compound of Working Example 10-15 as a pale yellow oil (47 mg). A fraction eluted at a longer retention time was concentrated to afford the compound of Working Example 10-16 as a pale yellow oil (23 mg).

Working Example 10-15

HPLC retention time: 24.42 min. (Condition 6)

Working Example 10-16

HPLC retention time: 30.39 min. (Condition 6)

(2) The same process as that of Working Example 2-1(2) was performed using the compounds of Working Examples 10-15 and 10-16 to afford the monohydrochloride of the compound of Working Example 10-15 as a colorless powder (7 mg) and the monohydrochloride of the compound of Working Example 10-16 as a colorless powder (23 mg), respectively.

Monohydrochloride of the Compound of Working Example 10-15
  $^1$H NMR (600 MHz, DMSO-d$_6$) δ ppm 1.15-1.24 (m, 5 H), 1.28 (s, 9 H), 1.55-1.69 (m, 5 H), 2.69-2.82 (m, 1 H), 3.13-3.20 (m, 1 H), 3.23-3.29 (m, 4 H), 3.38-3.49 (m, 1 H), 3.72-3.84 (m, 4 H), 3.97 (t, J=6.4 Hz, 2 H), 4.54-4.65 (m, 2 H), 6.71 (dd, J=8.9, 2.4 Hz, 1 H), 6.80 (dd, J=12.0, 2.4 Hz, 1 H), 7.05-7.10 (m, 1 H), 7.22 (d, J=7.4 Hz, 2 H), 7.33-7.46 (m, 3 H), 7.54-7.65 (m, 2 H), 9.92 (br. s., 1 H).
  LCMS retention time: 4.11 min. (Condition 1-2-3)
  MS (ESI posi) m/z: 609[M+H]$^+$.

Monohydrochloride of the Compound of Working Example 10-16
  $^1$H NMR (600 MHz, DMSO-d$_6$) δ ppm 1.15-1.24 (m, 5 H), 1.28 (s, 9 H), 1.55-1.69 (m, 5 H), 2.69-2.82 (m, 1 H), 3.13-3.20 (m, 1 H), 3.23-3.29 (m, 4 H), 3.38-3.49 (m, 1 H), 3.72-3.84 (m, 4 H), 3.97 (t, J=6.4 Hz, 2 H), 4.54-4.65 (m, 2 H), 6.71 (dd, J=8.9, 2.4 Hz, 1 H), 6.80 (dd, J=12.0, 2.4 Hz, 1 H), 7.05-7.10 (m, 1 H), 7.22 (d, J=7.4 Hz, 2 H), 7.33-7.46 (m, 3 H), 7.54-7.65 (m, 2 H), 9.92 (br. s., 1 H).
  LCMS retention time: 4.11 min. (Condition 1-2-3)
  MS (ESI posi) m/z: 609[M+H]$^+$.

The structures of the compounds of Working Examples 10-3 to 10-16 are shown in Tables 25-1 and 25-2.

TABLE 25-1

| Working Ex. | Structure |
|---|---|
| 10-3<br>10-4 | 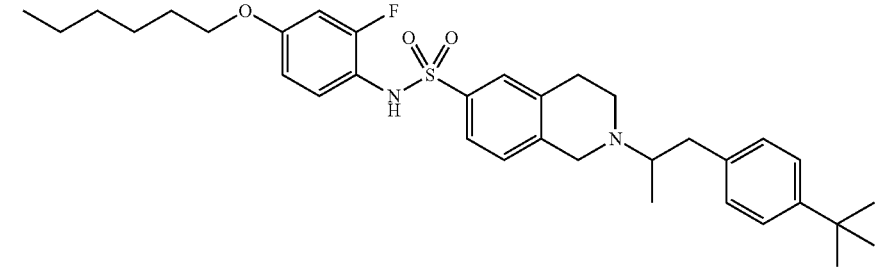 [SMILES: CCCCCCOc1ccc(NS(=O)(=O)c2ccc3c(c2)CCN(C(C)Cc2ccc(C(C)(C)C)cc2)C3)c(F)c1] |
| 10-5<br>10-6 | 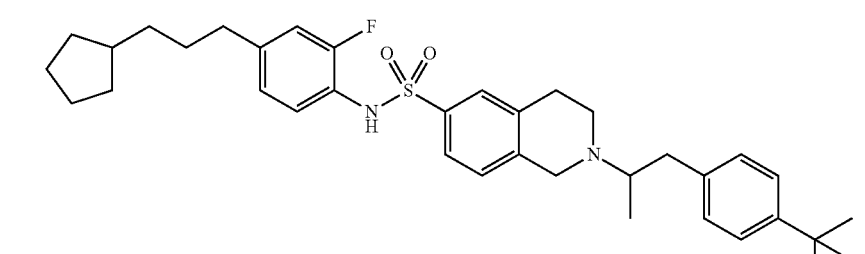 |

TABLE 25-1-continued

| Working Ex. | Structure |
|---|---|
| 10-7<br>10-8 | (4-heptyl-2-fluorophenyl sulfonamide of 2-(1-(4-tert-butylphenyl)propan-2-yl)-1,2,3,4-tetrahydroisoquinoline-6-sulfonamide) |
| 10-9<br>10-10 | (4-(heptyloxy)-2-fluorophenyl analog) |
| 10-11<br>10-12 | (4-(5-phenylpentyloxy)-2-fluorophenyl analog) |
| 10-13<br>10-14 | (4-(3-cyclohexylpropoxy)-2-fluorophenyl analog) |

TABLE 25-2

| Working Ex. | Structure |
|---|---|
| 10-15<br>10-16 | (4-(2-(tetrahydro-2H-pyran-4-yl)ethoxy)-2-fluorophenyl analog) |

Working Example 11-1

2-[1-(4-tert-Butylphenyl)ethyl]-N-(4-fluorophenyl)-1,2,3,4-tetrahydroisoquinoline-6-sulfonamide

[Formula 65]

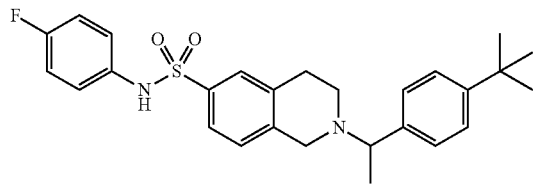

(1) The compound obtained in Reference Example 3-1 (180 mg, 0.59 mmol), N,N-dimethylformamide (1 mL) and the compound obtained in Reference Example 13-1 (149 mg, 0.62 mmol) were added to a suspension of sodium hydride (59 mg, 1.47 mmol) in tetrahydrofuran (4 mL) under an argon atmosphere while cooling in ice, and the mixture was warmed to room temperature and stirred for 15 hr. Saturated aqueous ammonium chloride solution was added to the reaction mixture and the mixture was extracted with ethyl acetate. The organic layer was washed with brine and dried over anhydrous magnesium sulfate and then the desiccant was filtered off, followed by concentration under reduced pressure. The resulting residue was purified by silica gel column chromatography (hexane:ethyl acetate=19:1→3:2) to afford the title compound as a colorless amorphous substance (165 mg).

$^1$H NMR (300 MHz, DMSO-$d_6$) δ ppm 1.27 (s, 9 H), 1.34 (d, J=6.8 Hz, 3 H), 2.60-2.80 (m, 3 H), 3.45-3.63 (m, 3 H), 3.67-3.76 (m, 1 H), 7.05-7.10 (m, 4 H), 7.16-7.21 (m, 1 H), 7.22-7.28 (m, 2 H), 7.31-7.46 (m, 4 H), 10.13 (br. s., 1 H).
MS ESI/APCI Dual posi: 467[M+H]$^+$.

(2) The same process as that of Working Example 2-1(2) was performed using the title compound to afford the monohydrochloride of the title compound as a colorless powder (112 mg).
MS ESI/APCI Dual posi: 467[M+H]$^+$.

The compounds of Working Examples 11-2 to 11-6 were obtained by using the corresponding compounds obtained in Reference Example 3 and the corresponding alkyl halides obtained in Reference Example 13 in accordance with the process of Working Example 11-1.

Working Example 11-2

LCMS retention time: 4.35 min. (Condition 1-1-3)
MS (ESI posi) m/z: 602[M+H]$^+$.

Working Example 11-3

LCMS retention time: 4.99 min. (Condition 1-1-3)
MS (ESI posi) m/z: 601[M+H]$^+$.

Working Example 11-4

LCMS retention time: 5.49 min. (Condition 1-1-2)
MS (ESI posi) m/z: 615[M+H]$^+$.

Working Example 11-5

LCMS retention time: 5.63 min. (Condition 1-1-2)
MS (ESI posi) m/z: 629[M+H]$^+$.

Working Example 11-6

MS ESI/APCI Dual posi: 467[M+H]$^+$.

The structures of the compounds of Working Examples 11-2 to 11-6 are shown in Table 26-1.

TABLE 26-1

| Working Ex. | Structure |
|---|---|
| 11-2 | (structure image) |
| 11-3 | (structure image) |

TABLE 26-1-continued

| Working Ex. | Structure |
|---|---|
| 11-4 | 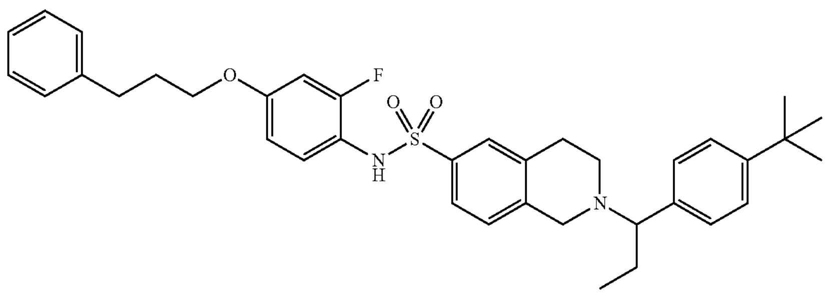 [SMILES: CCC(c1ccc(C(C)(C)C)cc1)N1CCc2cc(S(=O)(=O)Nc3ccc(OCCCc4ccccc4)cc3F)ccc2C1] |
| 11-5 | 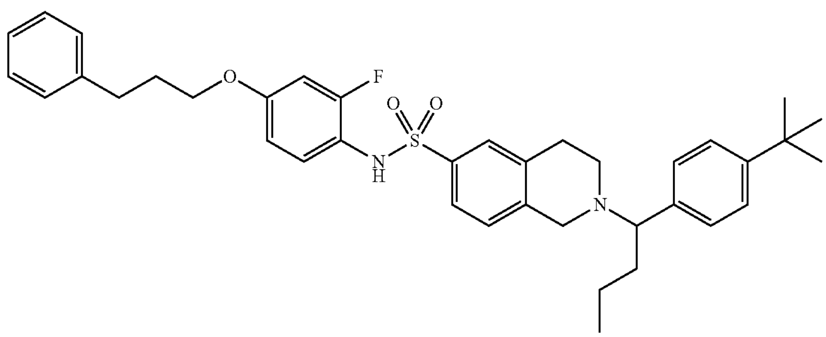 [SMILES: CCCC(c1ccc(C(C)(C)C)cc1)N1CCc2cc(S(=O)(=O)Nc3ccc(OCCCc4ccccc4)cc3F)ccc2C1] |
| 11-6 | 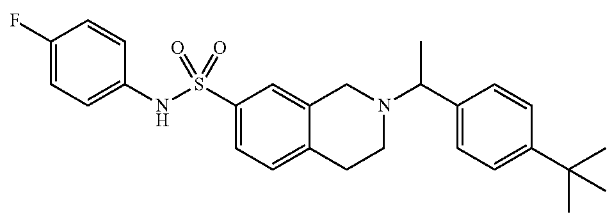 [SMILES: CC(c1ccc(C(C)(C)C)cc1)N1CCc2ccc(S(=O)(=O)Nc3ccc(F)cc3)cc2C1] |

Working Example 12-1

2-[2-(4-tert-butylphenyl)-2-oxoethyl]-N-(4-fluorophenyl)-1,2,3,4-tetrahydroisoquinoline-6-sulfonamide

[Formula 66]

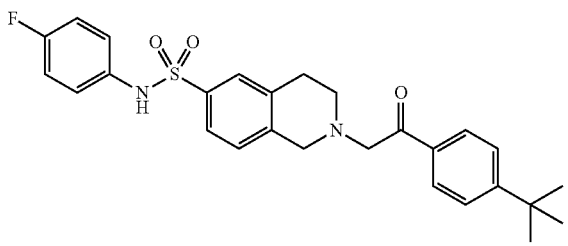

(1) N,N-Diisopropylethylamine (355 μL, 2.04 mmol) and the compound obtained in Reference Example 14-1 (260 mg, 1.02 mmol) were added successively to a solution of compound 3-6 as obtained in Reference Example 3 (310 mg, 0.68 mmol) in tetrahydrofuran (8 mL), and the mixture was stirred at room temperature for 3 hr. After concentration under reduced pressure, the resulting residue was purified by silica gel column chromatography (hexane:ethyl acetate=9:1→3:2) to afford 2-[2-(4-tert -butylphenyl)-2-oxoethyl]-N-(2,4-dimethoxybenzyl)-N-(4-fluorophenyl)-1,2,3,4-tetrahydroisoquinoline-6-sulfonamide (258 mg) as a pale yellow amorphous substance (258 mg).

(2) Anisole (3 mL) was added to a solution of 2-[2-(4-tert-butylphenyl)-2-oxoethyl]-N-(2,4-dimethoxybenzyl)-N-(4-fluorophenyl)-1,2,3,4-tetrahydroisoquinoline-6-sulfonamide obtained (258 mg) in chloroform (5 mL), and the mixture was cooled in ice. Trifluoroacetic acid (1 mL) was added thereto and the mixture was stirred at the same temperature for 2 hr. Saturated aqueous sodium hydrogen carbonate solution was added thereto and the mixture was extracted with chloroform. The organic layer was dried over anhydrous magnesium sulfate and then the desiccant was filtered off, followed by concentration under reduced pressure. The resulting residue was purified by silica gel column chromatography (hexane:ethyl acetate=19:1→3:2) to afford the title compound as a pale yellow amorphous substance (153 mg).

$^1$H NMR (300 MHz, CDCl$_3$) δ ppm 1.34 (s, 9 H), 2.87-2.98 (m, 4 H), 3.84 (s, 2 H), 4.01 (s, 2 H), 6.34 (s, 1 H), 6.90-7.09 (m, 5 H), 7.37-7.44 (m, 1 H), 7.44-7.52 (m, 3 H), 7.92-7.99 (m, 2 H).

MS ESI/APCI Dual posi: 481[M+H]$^+$.

(3) The same process as that of Working Example 2-1(2) was performed using the title compound to afford the monohydrochloride of the title compound as a pale yellow powder (125 mg).

MS ESI/APCI Dual posi: 481[M+H]$^+$.

Working Example 13-1

N-(4-Fluorophenyl)-2-phenyl-2,3-dihydro-1H-isoindole-5-sulfonamide

[Formula 67]

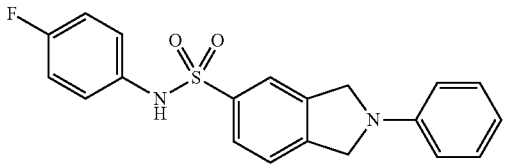

(1) Bromobenzene (53 μL, 0.50 mmol) was added to a suspension of compound 3-32 as obtained in Reference Example 3 (221 mg, 0.50 mmol), palladium acetate (11 mg, 0.05 mmol), 2,2'-bis(diphenylphosphino)-1,1'-binaphthyl (47 mg, 0.08 mmol) and cesium carbonate (244 mg, 0.75 mmol) in toluene (10 mL), and the mixture was stirred at 90° C. for 9 hr. After cooling, the mixture was filtered through Celite (registered trademark), followed by concentration under reduced pressure. The resulting residue was purified by NH silica gel column chromatography (hexane:ethyl acetate=9:1→1:1) to afford N-(2,4-dimethoxybenzyl)-N-(4-fluorophenyl)-2-phenyl-2,3-dihydro-1H-isoindole-5-sulfonamide (135 mg) as a pink powder (135 mg).

(2) Trifluoroacetic acid (0.5 mL) was added to a solution of N-(2,4-dimethoxybenzyl)-N-(4-fluorophenyl)-2-phenyl-2,3-dihydro-1H-isoindole-5-sulfonamide obtained (135 mg) in chloroform (4.5 mL) while cooling in ice, and the mixture was stirred at the same temperature for 2 hr. Saturated aqueous sodium hydrogen carbonate solution was added thereto and the mixture was extracted with ethyl acetate. The organic layer was washed with brine and dried over anhydrous magnesium sulfate and then the desiccant was filtered off, followed by concentration under reduced pressure. The resulting residue was purified by NH silica gel column chromatography (chloroform only→chloroform:methanol=19:1). To the resulting crude compound were added ethyl acetate, diethyl ether and hexane, and the mixture was powdered and then collected by filtration to afford the title compound as a light gray powder (74 mg).

$^1$H NMR (300 MHz, DMSO-$d_6$) δ ppm 4.61 (s, 4 H), 6.62-6.73 (m, 3 H), 7.06-7.12 (m, 4 H), 7.20-7.28 (m, 2 H), 7.54-7.58 (m, 1 H), 7.63-7.68 (m, 1 H), 7.74-7.77 (m, 1 H), 10.26 (br. s., 1 H).

MS ESI/APCI Dual posi: 369[M+H]$^+$.

Working Example 14-1

N-(4-tert-Butylphenyl)-6-[(4-fluorophenyl)sulfamoyl]-3,4-dihydroisoquinoline-2(1H)-carboxamide

[Formula 68]

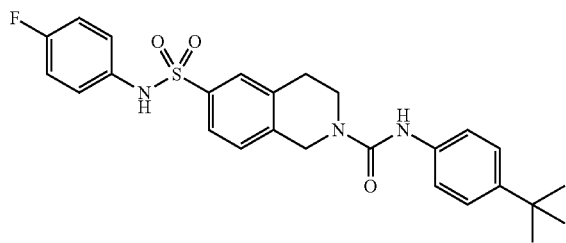

Potassium hydroxide (95.1 mg, 1.69 mmol) was added to a solution (5 mL) of the compound obtained in Reference Example 3-1(4) (341 mg, 0.847 mmol) in an ethanol/water mixture (4/1) at room temperature and the mixture was stirred overnight just after the addition. The reaction mixture was distilled off under reduced pressure and water was added to the residue. To the mixture was added 1 mol/L hydrochloric acid for neutralization and the mixture was extracted three times with ethyl acetate. The organic layer was dried over anhydrous magnesium sulfate and filtered and then the solvent was distilled off under reduced pressure to give a residue as a colorless amorphous substance (299 mg). The residue was dissolved in a chloroform/DMSO mixture (9/1) (5 mL), and triethylamine (118 μL, 0.847 mmol) and 4-tert-butylphenyl isocyanate (151 μL, 0.847 mmol) were added thereto at room temperature, followed by stirring for 2 hr. To the reaction mixture was added 1 mol/L hydrochloric acid, and the mixture was extracted three times with ethyl acetate. The organic layer was washed with brine, dried over anhydrous magnesium sulfate and filtered and then the solvent was distilled off under reduced pressure. The resulting residue was purified by silica gel column chromatography (hexane:ethyl acetate=2:1), powdered with hexane and then collected by filtration to afford the title compound as a colorless powder (262 mg).

$^1$H NMR (300 MHz, DMSO-$d_6$) δ ppm 1.25 (s, 9H), 2.83-2.93 (m, 2 H), 3.63-3.74 (m, 2 H), 4.66 (s, 2 H), 7.05-7.13 (m, 4 H), 7.21-7.28 (m, 2 H), 7.31-7.40 (m, 3 H), 7.48-7.54 (m, 1 H), 7.55-7.58 (m, 1 H), 8.50-8.55 (m, 1 H).

MS ESI/APCI Dual posi: 482[M+H]$^+$.

The compounds of Working Examples 14-2 to 14-36 were obtained by using the corresponding compounds obtained in Reference Examples 2 and 3-1(3) and (4) and the corresponding commercially available isocyanates in accordance with the process of Working Example 14-1.

Working Example 14-2

$^1$H NMR (300 MHz, DMSO-$d_6$) δ ppm 1.25 (s, 9 H), 2.81-2.88 (m, 2 H), 3.65-3.71 (m, 2 H), 4.64 (s, 2 H), 7.05-7.12 (m, 4 H), 7.21-7.27 (m, 2 H), 7.31-7.37 (m, 2 H), 7.65 (s, 1 H), 7.88 (s, 1 H), 8.55 (s, 1 H), 10.52 (s, 1 H).

MS ESI/APCI Dual posi: 560, 562[M+H]$^+$.

Working Example 14-3

$^1$H NMR (300 MHz, DMSO-$d_6$) δ ppm 0.81-0.93 (m, 6 H), 1.21-1.43 (m, 8 H), 1.45-1.58 (m, 2 H), 1.59-1.71 (m, 2 H), 2.83-2.92 (m, 2 H), 3.65-3.74 (m, 2 H), 3.90 (t, J=6.5 Hz, 2 H), 4.68 (s, 2 H), 6.64-6.71 (m, 1 H), 6.73-6.81 (m, 1 H), 6.99-7.08 (m, 3 H), 7.32-7.38 (m, 3 H), 7.45-7.52 (m, 2 H), 8.52 (s, 1 H), 9.76 (s, 1 H).

LCMS retention time: 2.33 min. (Condition 3)
MS ESI/APCI Dual posi: 582[M+H]$^+$.

Working Example 14-4

$^1$H NMR (300 MHz, DMSO-$d_6$) δ ppm 0.82-0.90 (m, 3 H), 1.23-1.43 (m, 15 H), 1.58-1.71 (m, 2 H), 2.83-2.92 (m, 2 H), 3.65-3.75 (m, 2 H), 3.90 (t, J=6.5 Hz, 2 H), 4.69 (s, 2 H), 6.64-6.71 (m, 1 H), 6.73-6.81 (m, 1 H), 6.99-7.08 (m, 1 H), 7.22-7.29 (m, 2 H), 7.32-7.40 (m, 3 H), 7.44-7.53 (m, 2 H), 8.54 (s, 1 H), 9.77 (s, 1 H).

LCMS retention time: 2.32 min. (Condition 3)
MS ESI/APCI Dual posi: 582[M+H]$^+$.

Working Example 14-5

$^1$H NMR (300 MHz, DMSO-$d_6$) δ ppm 1.26 (s, 9 H), 4.77 (s, 4 H), 7.07-7.12 (m, 4 H), 7.23-7.30 (m, 2 H), 7.41-7.47 (m, 2 H), 7.49-7.55 (m, 1 H), 7.61-7.67 (m, 1 H), 7.70 (s, 1 H), 8.30 (s, 1 H).

MS ESI/APCI Dual posi: 468[M+H]$^+$.

Working Example 14-6

$^1$H NMR (300 MHz, DMSO-d$_6$) δ ppm 1.26 (s, 9 H), 4.78 (s, 4 H), 7.21-7.34 (m, 4 H), 7.39-7.47 (m, 2 H), 7.51-7.64 (m, 3 H), 7.73-7.79 (m, 1 H), 7.83 (s, 1 H), 8.30 (s, 1 H).
MS ESI/APCI Dual posi: 518[M+H]$^+$.

Working Example 14-7

$^1$H NMR (300 MHz, DMSO-d$_6$) δ ppm 1.26 (s, 9 H), 2.80 (s, 6 H), 4.77 (s, 4 H), 6.33-6.42 (m, 2 H), 6.44-6.47 (m, 1 H), 6.95-7.02 (m, 1 H), 7.23-7.29 (m, 2 H), 7.41-7.46 (m, 2 H), 7.52 (d, J=8.1 Hz, 1 H), 7.69-7.74 (m, 1 H), 7.75-7.78 (m, 1 H), 8.30 (s, 1 H).
MS ESI/APCI Dual posi: 493[M+H]$^+$.

Working Example 14-8

$^1$H NMR (300 MHz, DMSO-d$_6$) δ ppm 1.26 (s, 9 H), 4.73-4.85 (m, 4 H), 6.98-7.09 (m, 1 H), 7.18-7.31 (m, 4 H), 7.41-7.48 (m, 2 H), 7.50-7.57 (m, 1 H), 7.60-7.70 (m, 2 H), 8.31 (s, 1 H), 10.14 (s, 1 H).
MS ESI/APCI Dual posi: 486[M+H]$^+$.

Working Example 14-9

$^1$H NMR (300 MHz, DMSO-d$_6$) δ ppm 1.26 (s, 9 H), 3.46 (s, 3 H), 4.74-4.82 (m, 4 H), 6.64-6.75 (m, 1 H), 6.78-6.88 (m, 1 H), 7.14-7.22 (m, 1 H), 7.23-7.30 (m, 2 H), 7.41-7.51 (m, 3 H), 7.56-7.66 (m, 2 H), 8.31 (s, 1 H).
MS ESI/APCI Dual posi: 498[M+H]$^+$.

Working Example 14-10

$^1$H NMR (300 MHz, DMSO-d$_6$) δ ppm 1.07 (t, J=6.9 Hz, 3 H), 1.26 (s, 9 H), 3.73 (q, J=6.9 Hz, 2 H), 4.67-4.84 (m, 4 H), 6.65-6.84 (m, 2 H), 7.18-7.31 (m, 3 H), 7.40-7.51 (m, 3 H), 7.55-7.64 (m, 2 H), 8.31 (s, 1 H).
MS ESI/APCI Dual posi: 512[M+H]$^+$.

Working Example 14-11

$^1$H NMR (300 MHz, DMSO-d$_6$) δ ppm 0.82 (t, J=7.5 Hz, 3 H), 1.26 (s, 9 H), 1.37-1.53 (m, 2 H), 3.62 (t, J=6.6 Hz, 2 H), 4.71-4.82 (m, 4 H), 6.64-6.75 (m, 1 H), 6.77-6.85 (m, 1 H), 7.18-7.30 (m, 3 H), 7.40-7.51 (m, 3 H), 7.53-7.63 (m, 2 H), 8.31 (s, 1 H).
MS ESI/APCI Dual posi: 526[M+H]$^+$.

Working Example 14-12

$^1$H NMR (300 MHz, DMSO-d$_6$) δ ppm 1.26 (s, 9 H), 4.74-4.87 (m, 4 H), 7.18-7.31 (m, 4 H), 7.41-7.49 (m, 2 H), 7.52-7.59 (m, 1 H), 7.62-7.72 (m, 2 H), 8.33 (s, 1 H), 10.0 (br. s., 1 H).
LCMS retention time: 5.81 min. (Condition 1-1-1)
MS (ESI posi) m/z: 504[M+H]$^+$.

Working Example 14-13

$^1$H NMR (300 MHz, DMSO-d$_6$) δ ppm 1.26 (s, 9 H), 2.02 (s, 3 H), 4.74-4.85 (m, 4 H), 6.89-6.96 (m, 2 H), 6.99-7.06 (m, 1 H), 7.27 (d, J=8.7 Hz, 2 H), 7.44 (d, J=8.7 Hz, 2 H), 7.49-7.62 (m, 3 H), 8.31 (s, 1 H), 9.57-9.62 (m, 1 H).
LCMS retention time: 5.98 min. (Condition 1-1-1)
MS (ESI posi) m/z: 482[M+H]$^+$.

Working Example 14-14

$^1$H NMR (300 MHz, DMSO-d$_6$) δ ppm 1.26 (s, 9 H), 4.75-4.84 (m, 4 H), 7.14-7.31 (m, 4 H), 7.40-7.48 (m, 3 H), 7.51-7.57 (m, 1 H), 7.60-7.69 (m, 2 H), 8.32 (s, 1 H), 10.1 (s, 1 H).
LCMS retention time: 6.04 min. (Condition 1-1-1)
MS (ESI posi) m/z: 502[M+H]$^+$.

Working Example 14-15

$^1$H NMR (300 MHz, DMSO-d$_6$) δ ppm 1.26 (s, 9 H), 3.40 (s, 3 H), 3.71 (s, 3 H), 4.74-4.82 (m, 4 H), 6.42-6.49 (m, 2 H), 7.04-7.11 (m, 1 H), 7.23-7.31 (m, 2 H), 7.41-7.51 (m, 3 H), 7.53-7.63 (m, 2 H), 8.31 (s, 1 H), 9.28 (br. s., 1 H).
LCMS retention time: 5.85 min. (Condition 1-1-1)
MS (ESI posi) m/z: 510[M+H]$^+$.

Working Example 14-16

$^1$H NMR (300 MHz, DMSO-d$_6$) δ ppm 1.26 (s, 9 H), 3.71 (s, 3 H), 4.75-4.83 (m, 4 H), 6.66-6.72 (m, 1 H), 6.76-6.83 (m, 1 H), 7.03-7.09 (m, 1 H), 7.27 (d, J=8.6 Hz, 2 H), 7.45 (d, J=8.6 Hz, 2 H), 7.49-7.55 (m, 1 H), 7.59-7.66 (m, 2 H), 8.32 (s, 1 H), 9.85 (br. s., 1 H).
LCMS retention time: 5.79 min. (Condition 1-1-1)
MS (ESI posi) m/z: 498[M+H]$^+$.

Working Example 14-17

LCMS retention time: 6.62 min. (Condition 1-1-1)
MS (ESI posi) m/z: 536[M+H]$^+$.

Working Example 14-18

LCMS retention time: 6.64 min. (Condition 1-1-1)
MS (ESI posi) m/z: 554[M+H]$^+$.

Working Example 14-19

$^1$H NMR (300 MHz, DMSO-d$_6$) δ ppm 0.98 (t, J=7.5 Hz, 3 H), 1.26 (s, 9 H), 4.75-4.84 (m, 4 H), 6.80-6.93 (m, 2 H), 7.02-7.08 (m, 1 H), 7.24-7.30 (m, 2 H), 7.42-7.47 (m, 2 H), 7.52-7.56 (m, 1 H), 7.59-7.63 (m, 2 H), 8.32 (s, 1 H), 9.60 (s, 1 H).
MS ESI/APCI Dual posi: 496[M+H]$^+$.

Working Example 14-20

$^1$H NMR (300 MHz, DMSO-d$_6$) δ ppm 0.79 (t, J=7.5 Hz, 3 H), 1.26 (s, 9 H), 1.30-1.40 (m, 2 H), 4.76-4.83 (m, 4 H), 6.82-6.96 (m, 2 H), 7.00-7.06 (m, 1 H), 7.25-7.30 (m, 2 H), 7.42-7.47 (m, 2 H), 7.52-7.56 (m, 1 H), 7.58-7.63 (m, 2 H), 8.32 (s, 1 H), 9.58 (s, 1 H).
MS ESI/APCI Dual posi: 510[M+H]$^+$.

Working Example 14-21

$^1$H NMR (300 MHz, DMSO-d$_6$) δ ppm 1.27 (s, 9 H), 3.37 (s, 3 H), 4.76-4.86 (m, 4 H), 6.71-6.91 (m, 2 H), 7.28 (d, J=8.6 Hz, 2 H), 7.46 (d, J=8.6 Hz, 2 H), 7.52 (d, J=8.6 Hz, 1 H), 7.59-7.67 (m, 2 H), 8.32 (s, 1 H), 9.45 (s, 1 H).
MS ESI/APCI Dual posi: 516[M+H]$^+$.

Working Example 14-22

$^1$H NMR (300 MHz, DMSO-d$_6$) δ ppm 1.26 (s, 9 H), 2.69 (s, 6 H), 4.77 (s, 4 H), 6.48-6.58 (m, 1 H), 6.62-6.69 (m, 1 H), 6.87-6.99 (m, 1 H), 7.26 (d, J=8.6 Hz, 2 H), 7.44 (d, J=8.6 Hz, 2 H), 7.52 (d, J=8.0 Hz, 1 H), 7.68 (d, J=8.0 Hz, 1 H), 7.72 (s, 1 H), 8.30 (s, 1 H), 10.12 (br. s., 1 H).

MS ESI/APCI Dual posi: 511[M+H]$^+$.

Working Example 14-23

LCMS retention time: 6.37 min. (Condition 1-1-2)
MS (ESI posi) m/z: 574[M+H]$^+$.

Working Example 14-24

LCMS retention time: 4.65 min. (Condition 1-1-1)
MS (ESI posi) m/z: 511[M+H]$^+$.

Working Example 14-25

$^1$H NMR (300 MHz, DMSO-d$_6$) δ ppm 1.26 (s, 9 H), 2.65 (s, 6 H), 3.41 (s, 3 H), 4.76 (s, 4 H), 6.60-6.68 (m, 1 H), 6.83-6.94 (m, 2 H), 7.26 (d, J=8.6 Hz, 2 H), 7.44 (d, J=8.6 Hz, 2 H), 7.51 (d, J=7.9 Hz, 1 H), 7.72-7.78 (m, 2 H), 8.30 (s, 1 H), 9.51 (br. s., 1 H).

MS ESI/APCI Dual posi: 523[M+H]$^+$.

Working Example 14-26

$^1$H NMR (300 MHz, DMSO-d$_6$) δ ppm 1.18 (d, J=7.0 Hz, 6 H), 2.77-2.90 (m, 1 H), 3.37 (s, 3 H), 4.77-4.85 (m, 4 H), 6.72-6.79 (m, 1 H), 6.81-6.92 (m, 1 H), 7.13 (d, J=8.6 Hz, 2 H), 7.45 (d, J=8.6 Hz, 2 H), 7.50-7.55 (m, 1 H), 7.59-7.66 (m, 2 H), 8.32 (s, 1 H), 9.44 (br. s., 1 H).

MS ESI/APCI Dual posi: 502[M+H]$^+$.

Working Example 14-27

$^1$H NMR (300 MHz, DMSO-d$_6$) δ ppm 0.76 (t, J=7.3 Hz, 3 H), 1.17 (d, J=7.0 Hz, 3 H), 1.45-1.59 (m, 2 H), 2.54 (m, 1 H), 3.37 (s, 3 H), 4.78-4.85 (m, 4 H), 6.72-6.79 (m, 1 H), 6.81-6.91 (m, 1 H), 7.08 (d, J=8.6 Hz, 2 H), 7.45 (d, J=8.6 Hz, 2 H), 7.52 (d, J=8.2 Hz, 1 H), 7.60-7.66 (m, 2 H), 8.31 (s, 1 H), 9.44 (br. s., 1 H).

MS ESI/APCI Dual posi: 516[M+H]$^+$.

Working Example 14-28

LCMS retention time: 5.71 min. (Condition 1-1-1)
MS (ESI posi) m/z: 528[M+H]$^+$.

Working Example 14-29

LCMS retention time: 5.51 min. (Condition 1-1-1)
MS (ESI posi) m/z: 529[M+H]$^+$.

Working Example 14-30

LCMS retention time: 5.55 min. (Condition 1-1-1)
MS (ESI posi) m/z: 535[M+H]$^+$.

Working Example 14-31

$^1$H NMR (300 MHz, DMSO-d$_6$) δ ppm 1.25 (s, 9 H), 2.80-2.95 (m, 2 H), 3.61-3.75 (m, 2 H), 4.64 (s, 2 H), 7.02-7.15 (m, 4 H), 7.21-7.28 (m, 2 H), 7.31-7.40 (m, 3 H), 7.46-7.57 (m, 2 H), 8.51 (s, 1 H).

MS ESI/APCI Dual posi: 482[M+H]$^+$.

Working Example 14-32

$^1$H NMR (600 MHz, DMSO-d$_6$) δ ppm 1.23 (s, 9 H), 1.25 (s, 9 H), 2.92 (t, J=5.8 Hz, 2 H), 3.70 (t, J=5.8 Hz, 2 H), 4.68 (s, 2 H), 6.05 (s, 1 H), 7.24 (d, J=8.9 Hz, 2 H), 7.36 (d, J=8.9 Hz, 2 H), 7.40 (d, J=8.0 Hz, 1 H), 7.67 (dd, J=8.0, 1.9 Hz, 1 H), 7.70 (s, 1 H), 8.52 (s, 1 H), 11.38 (br. s., 1 H).

LCMS retention time: 5.17 min. (Condition 1-2-1)
MS (ESI posi) m/z: 511[M+H]$^+$.

Working Example 14-33

$^1$H NMR (600 MHz, DMSO-d$_6$) δ ppm 1.10 (s, 9 H), 1.25 (s, 9 H), 2.91 (t, J=5.8 Hz, 2 H), 3.69 (t, J=5.8 Hz, 2 H), 4.69 (s, 2 H), 5.18 (s, 1 H), 6.05 (s, 2 H), 7.24 (d, J=8.5 Hz, 2 H), 7.35 (d, J=8.5 Hz, 2 H), 7.42 (d, J=8.3 Hz, 1 H), 7.65 (d, J=8.3 Hz, 1 H), 7.71 (s, 1 H), 8.53 (s, 1 H).

LCMS retention time: 5.20 min. (Condition 1-2-1)
MS (ESI posi) m/z: 510[M+H]$^+$.

Working Example 14-34

$^1$H NMR (600 MHz, DMSO-d$_6$) δ ppm 1.18 (s, 9 H), 1.25 (s, 9 H), 2.91 (t, J=5.9 Hz, 2 H), 3.70 (t, J=5.9 Hz, 2 H), 4.67 (s, 2 H), 6.35 (br. s., 1 H), 7.22-7.27 (m, 2 H), 7.31-7.40 (m, 3 H), 7.59-7.65 (m, 2 H), 8.52 (s, 1 H), 12.66 (br. s., 1 H).

LCMS retention time: 5.77 min. (Condition 1-2-1)
MS (ESI posi) m/z: 527[M+H]$^+$.

Working Example 14-35

$^1$H NMR (300 MHz, CDCl$_3$) δ ppm 1.30 (s, 9 H), 1.59-1.79 (m, 7 H), 2.93 (t, J=5.9 Hz, 2 H), 3.39 (dt, J=11.8, 2.3 Hz, 2 H), 3.70 (t, J=5.9 Hz, 2 H), 3.87-4.02 (m, 4 H), 4.70 (s, 2 H), 6.36 (d, J=12.6 Hz, 2 H), 6.50 (dd, J=12.0, 2.5 Hz, 1 H), 6.62-6.69 (m, 1 H), 7.20 (d, J=8.1 Hz, 1 H), 7.28-7.33 (m, 2 H), 7.40-7.59 (m, 3 H).

MS ESI/APCI Dual posi: 610[M+H]$^+$.

Working Example 14-36

$^1$H NMR (600 MHz, CDCl$_3$) δ ppm 0.99-1.20 (m, 5 H), 1.24-1.42 (m, 5 H), 1.47-1.65 (m, 6 H), 1.68-1.77 (m, 5 H), 1.92-2.00 (m, 2 H), 2.49-2.54 (m, 2 H), 2.83-2.87 (m, 2H), 3.53-3.58 (m, 2 H), 3.64-3.72 (m, 1 H), 4.25-4.30 (m, 1 H), 4.56 (s, 2 H), 6.52-6.55 (m, 1 H), 6.76-6.80 (m, 1 H), 6.91 (d, J=7.8 Hz, 1 H), 7.17 (d, J=7.8 Hz, 1 H), 7.43-7.48 (m, 1 H), 7.52-7.56 (m, 2 H).

LCMS retention time: 5.39 min. (Condition 1-2-3)
MS (ESI posi) m/z: 542[M+H]$^+$.

The structures of the compounds of Working Examples 14-2 to 14-36 are shown in Tables 27-1 to 27-4.

TABLE 27-1
| Working Ex. | Structure |
|---|---|
| 14-2 | 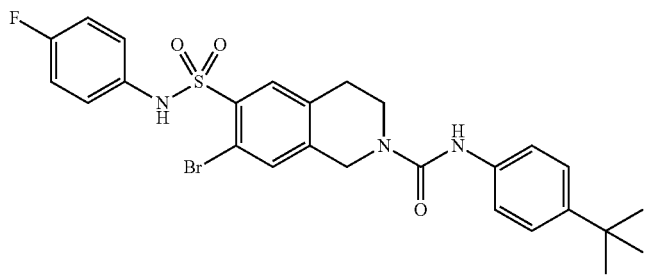 [SMILES: CC(C)(C)c1ccc(NC(=O)N2CCc3cc(S(=O)(=O)Nc4ccc(F)cc4)c(Br)cc3C2)cc1] |
| 14-3 | 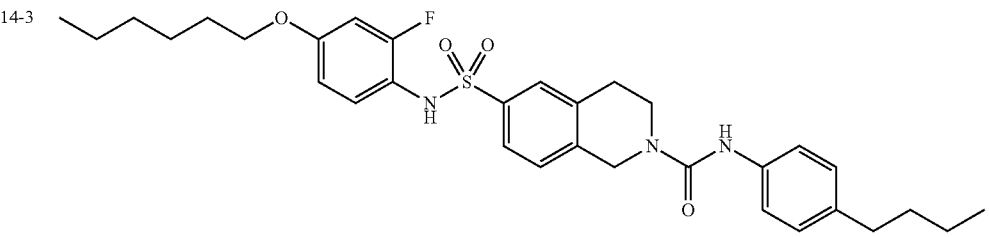 |
| 14-4 | 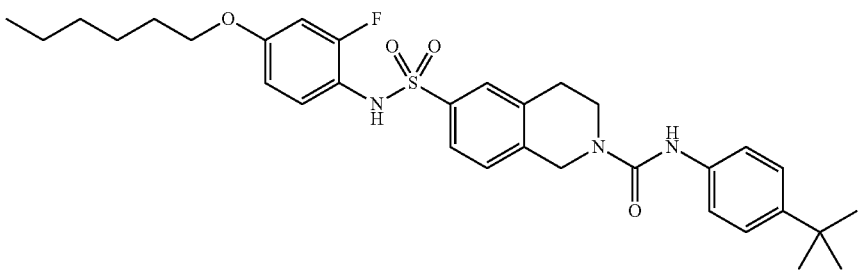 [SMILES: CCCCCCOc1ccc(NS(=O)(=O)c2ccc3c(c2)CCN(C(=O)Nc2ccc(C(C)(C)C)cc2)C3)c(F)c1] |
| 14-5 | 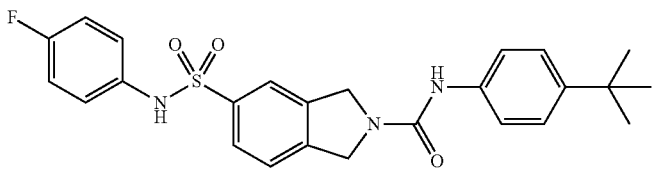 [SMILES: CC(C)(C)c1ccc(NC(=O)N2Cc3ccc(S(=O)(=O)Nc4ccc(F)cc4)cc3C2)cc1] |
| 14-6 | 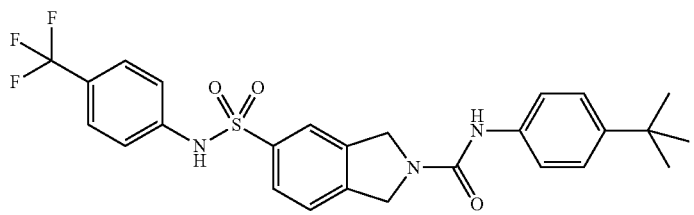 [SMILES: CC(C)(C)c1ccc(NC(=O)N2Cc3ccc(S(=O)(=O)Nc4ccc(C(F)(F)F)cc4)cc3C2)cc1] |
| 14-7 | 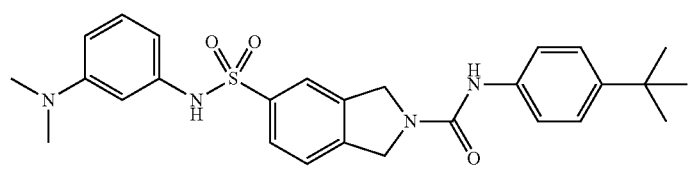 [SMILES: CN(C)c1cccc(NS(=O)(=O)c2ccc3c(c2)CN(C(=O)Nc2ccc(C(C)(C)C)cc2)C3)c1] |
| 14-8 | 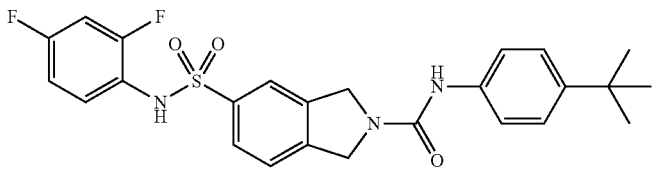 [SMILES: CC(C)(C)c1ccc(NC(=O)N2Cc3ccc(S(=O)(=O)Nc4ccc(F)cc4F)cc3C2)cc1] |

TABLE 27-1-continued
| Working Ex. | Structure |
|---|---|
| 14-9 | 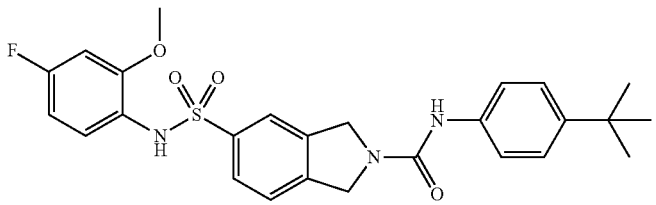 |
| 14-10 | 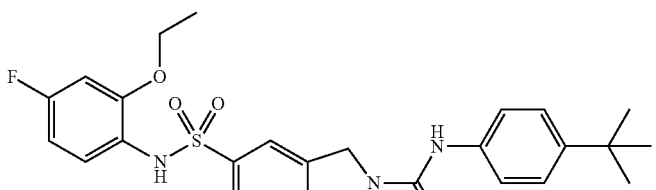 |
| 14-11 | 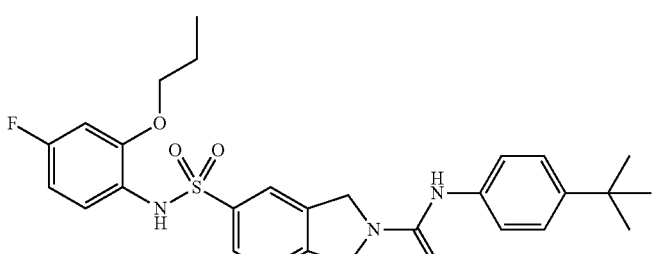 |
| 14-12 | 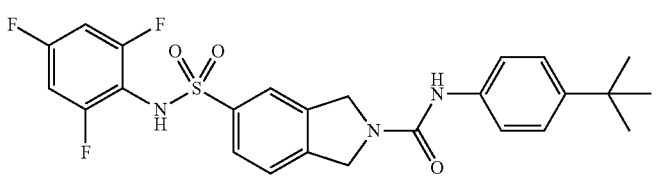 [SMILES: CC(C)(C)c1ccc(NC(=O)N2Cc3ccc(S(=O)(=O)Nc4c(F)cc(F)cc4F)cc3C2)cc1] |
| 14-13 | 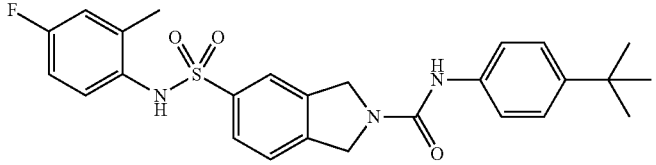 [SMILES: Cc1cc(F)ccc1NS(=O)(=O)c1ccc2c(c1)CN(C(=O)Nc1ccc(C(C)(C)C)cc1)C2] |
| 14-14 | 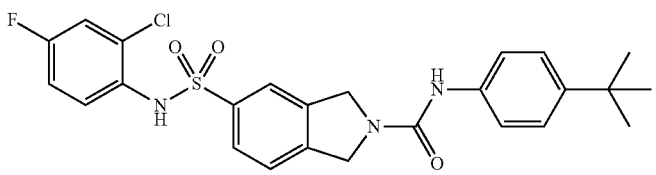 |
| 14-15 | 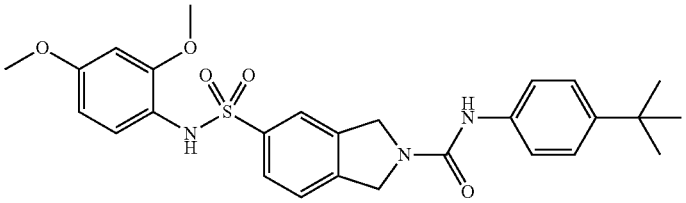 [SMILES: COc1ccc(NS(=O)(=O)c2ccc3c(c2)CN(C(=O)Nc2ccc(C(C)(C)C)cc2)C3)c(OC)c1] |

TABLE 27-2

| Working Ex. | Structure |
|---|---|
| 14-16 | (structure) |
| 14-17 | (structure) |
| 14-18 | (structure) |
| 14-19 | (structure) |
| 14-20 | (structure) |
| 14-21 | (structure) |
| 14-22 | (structure) |

TABLE 27-2-continued

| Working Ex. | Structure |
|---|---|
| 14-23 | 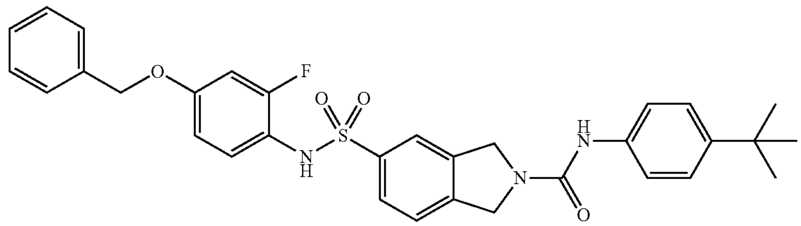 [SMILES: CC(C)(C)c1ccc(NC(=O)N2Cc3ccc(S(=O)(=O)Nc4ccc(OCc5ccccc5)cc4F)cc3C2)cc1] |
| 14-24 | 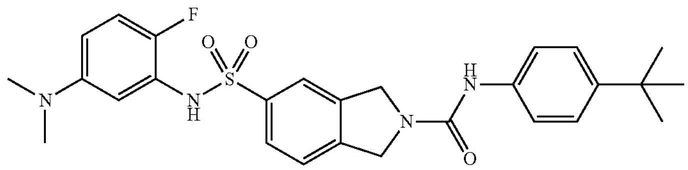 [SMILES: CN(C)c1ccc(F)c(NS(=O)(=O)c2ccc3c(c2)CN(C(=O)Nc2ccc(C(C)(C)C)cc2)C3)c1] |
| 14-25 | 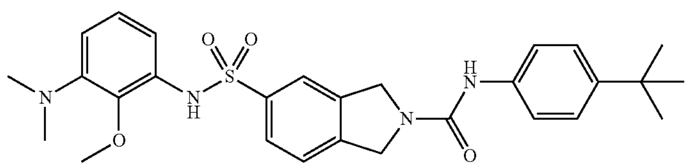 [SMILES: COc1c(NS(=O)(=O)c2ccc3c(c2)CN(C(=O)Nc2ccc(C(C)(C)C)cc2)C3)cccc1N(C)C] |
| 14-26 | 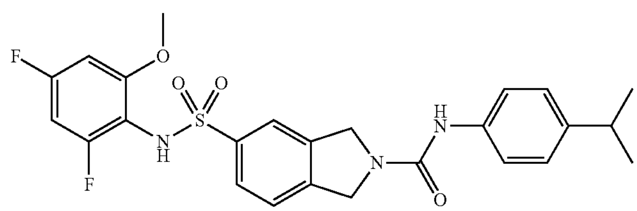 [SMILES: COc1cc(F)cc(F)c1NS(=O)(=O)c1ccc2c(c1)CN(C(=O)Nc1ccc(C(C)C)cc1)C2] |
| 14-27 | 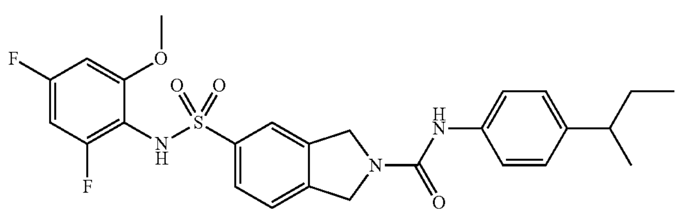 [SMILES: CCC(C)c1ccc(NC(=O)N2Cc3ccc(S(=O)(=O)Nc4c(F)cc(F)cc4OC)cc3C2)cc1] |
| 14-28 | 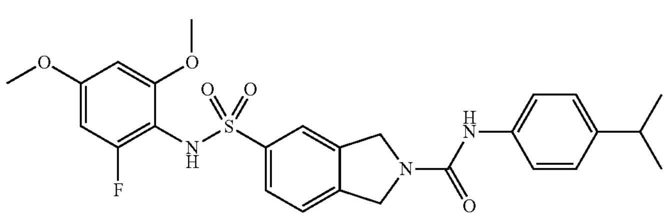 [SMILES: COc1cc(F)c(NS(=O)(=O)c2ccc3c(c2)CN(C(=O)Nc2ccc(C(C)C)cc2)C3)c(OC)c1] |
| 14-29 | 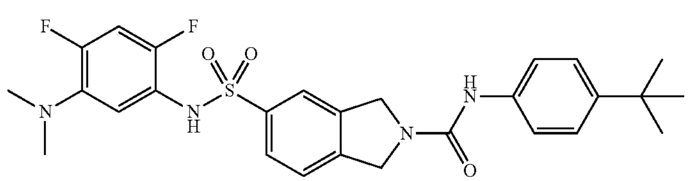 [SMILES: CN(C)c1cc(NS(=O)(=O)c2ccc3c(c2)CN(C(=O)Nc2ccc(C(C)(C)C)cc2)C3)c(F)cc1F] |

TABLE 27-3
| Working Ex. | Structure |
|---|---|
| 14-30 | 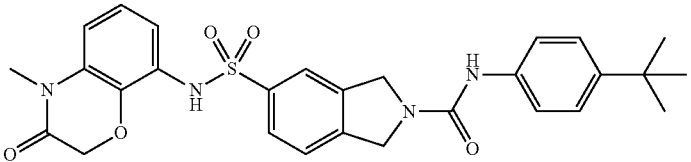 [SMILES: CN1C(=O)COc2c(NS(=O)(=O)c3ccc4c(c3)CN(C(=O)Nc3ccc(C(C)(C)C)cc3)C4)cccc21] |
| 14-31 | 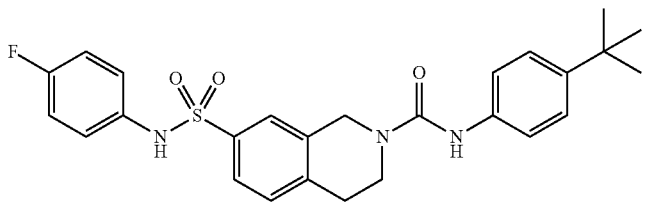 [SMILES: CC(C)(C)c1ccc(NC(=O)N2CCc3ccc(S(=O)(=O)Nc4ccc(F)cc4)cc3C2)cc1] |
TABLE 27-4
| Working Ex. | Structure |
|---|---|
| 14-32 | 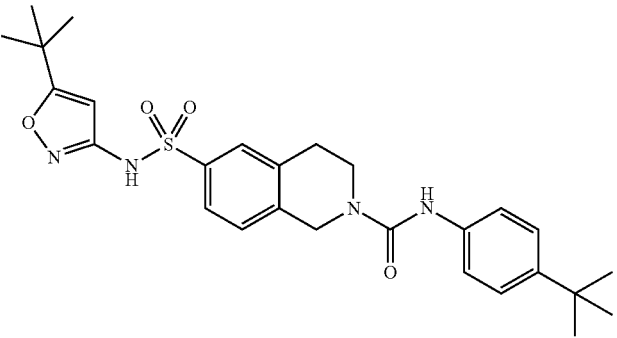 [SMILES: CC(C)(C)c1ccc(NC(=O)N2CCc3cc(S(=O)(=O)Nc4cc(C(C)(C)C)on4)ccc3C2)cc1] |
| 14-33 | 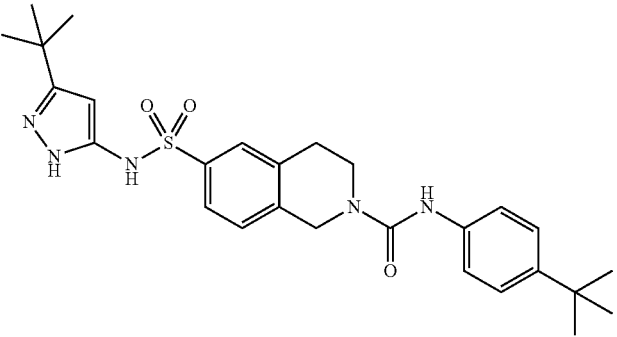 [SMILES: CC(C)(C)c1ccc(NC(=O)N2CCc3cc(S(=O)(=O)Nc4cc(C(C)(C)C)n[nH]4)ccc3C2)cc1] |
| 14-34 | 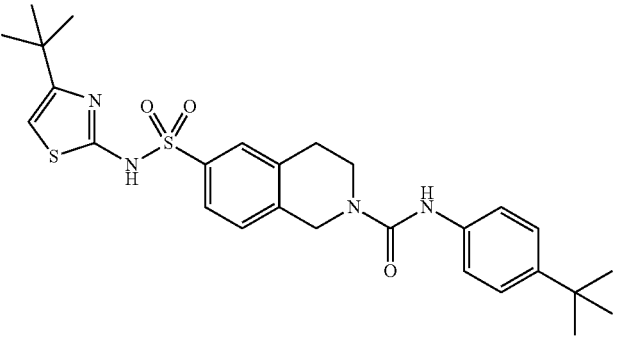 [SMILES: CC(C)(C)c1ccc(NC(=O)N2CCc3cc(S(=O)(=O)Nc4nc(C(C)(C)C)cs4)ccc3C2)cc1] |

TABLE 27-4-continued

| Working Ex. | Structure |
|---|---|
| 14-35 | (structure) |
| 14-36 | (structure) |

Working Example 15-1

N-(4-tert-Butylphenyl)-5-[(4-fluoro-2-hydroxyphenyl)sulfamoyl]-1,3-dihydro-2H-isoindole-2-carboxamide

[Formula 69]

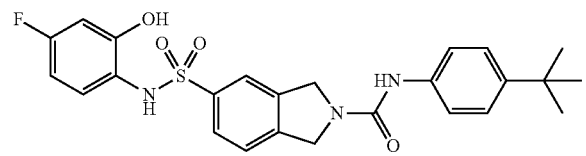

(1) The same process as that of Working Example 14-1 was performed using compound 2-8 as obtained in Reference Example 2 (898 mg, 1.82 mmol) to afford 5-{[2-(benzyloxy)-4-fluorophenyl]sulfamoyl}-N-(4-tert-butylphenyl)-1,3-dihydro-2H-isoindole-2-carboxamide as a colorless powder (298 mg).

(2) To a solution of 5-{[2-(benzyloxy)-4-fluorophenyl]sulfamoyl}-N-(4-tert-butylphenyl)-1,3-dihydro-2H-isoindole-2-carboxamide (150 mg, 0.261 mmol) in ethanol (10 mL) was added 10% palladium activated carbon (150 mg) at room temperature, and the mixture was stirred overnight under a hydrogen atmosphere. The reaction mixture was filtered through Celite (registered trademark) and the filtrate was concentrated under reduced pressure. The resulting residue was purified by silica gel column chromatography (chloroform:methanol=19:1), powdered with hexane, and then collected by filtration to afford the title compound as a brownish red powder (98.4 mg).

$^1$H NMR (300 MHz, DMSO-$d_6$) δ ppm 1.26 (s, 9 H), 4.73-4.81 (m, 4 H), 6.47-6.59 (m, 2 H), 7.05-7.12 (m, 1 H), 7.27 (d, J=8.7 Hz, 2 H), 7.41-7.51 (m, 3 H), 7.59-7.70 (m, 2 H), 8.31 (s, 1 H).

LCMS retention time: 5.60 min. (Condition 1-1-1)

MS (ESI posi) m/z: 484[M+H]$^+$.

The compound of Working Example 14-23 was used to afford the compound of Working Example 15-2 in accordance with the process of Working Example 15-1(2).

Working Example 15-2

LCMS retention time: 5.31 min. (Condition 1-1-2)

MS (ESI posi) m/z: 483[M+H]$^+$.

The structure of the compound of Working Example 15-2 is shown in Table 28-1.

TABLE 28-1

| Working Ex. | Structure |
|---|---|
| 15-2 | (structure) |

Working Example 17-1

2-[2-(4-tert-Butylphenyl)ethyl]-N-[2-fluoro-4-(heptyloxy)phenyl]-1,2,3,4-tetrahydroisoquinoline-6-sulfonamide

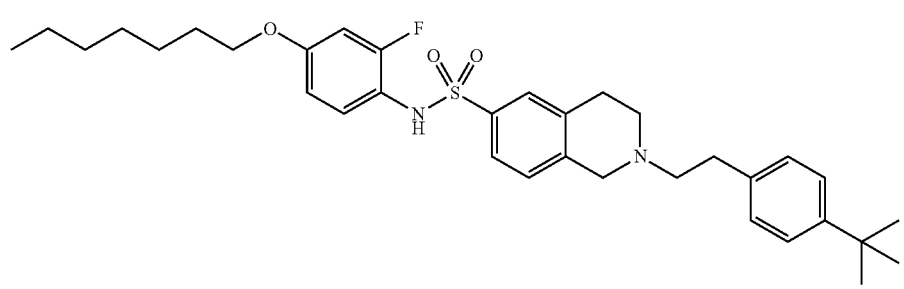

[Formula 70]

(1) Compound 3-2 as obtained in Reference Example 3 (400 mg, 0.70 mmol) was dissolved in N,N-dimethylformamide (1 mL), and 1-iodoheptane (207 mg, 0.92 mmol) and potassium carbonate (195 mg, 1.41 mmol) were added thereto, followed by stirring at room temperature overnight. The mixture was further stirred for 2 hr while heating at 85° C. To the reaction mixture were added ethyl acetate and saturated aqueous sodium hydrogen carbonate solution for separation into phases. The aqueous layer was extracted with ethyl acetate, and the combined organic layer was filtered through a phase separator. The solvent was distilled off from the filtrate under reduced pressure. The resulting residue was dissolved in ethanol (4.5 mL), aqueous potassium hydroxide solution (78 mg/0.5 mL) was added thereto, and the mixture was stirred at room temperature for 19 hr. The reaction mixture was concentrated under reduced pressure and the residue was diluted with water and ethyl acetate for separation into phases. The aqueous layer was extracted with ethyl acetate. The organic layer was filtered through a phase separator and the solvent was distilled off from the filtrate under reduced pressure. The residue was dissolved in chloroform (2 mL) and then aldehyde obtained in Reference Example 7-1 (64 mg, 0.36 mmol) and sodium triacetoxyborohydride (191 mg, 0.90 mmol) were added thereto, followed by stirring at room temperature for 19 hr. To the reaction mixture were added chloroform and saturated aqueous sodium hydrogen carbonate solution, and the mixture was stirred to thereby separate the organic layer therefrom. The aqueous layer was extracted with chloroform. The organic layer was filtered through a phase separator and the solvent was distilled off from the filtrate under reduced pressure. The residue was dissolved in chloroform (4 mL) and then anisole (4.1 mL) and trifluoroacetic acid (1 mL) were added thereto, and the mixture was stirred at room temperature for 3 hr. The reaction mixture was concentrated under reduced pressure and the residue was diluted with ethyl acetate and saturated aqueous sodium hydrogen carbonate solution for separation into phases. The organic layer was washed with brine and then filtered through a phase separator, and the solvent was distilled off from the filtrate under reduced pressure. The resulting residue was purified by silica gel column chromatography (hexane only→hexane:ethyl acetate=70:30) to afford the title compound as a colorless amorphous substance (78 mg).

(2) To a solution of the title compound in ethyl acetate (1 mL) was added 4 mol/L hydrogen chloride-ethyl acetate (0.34 mL), and the mixture was stirred at room temperature for 5 min. The solvent was distilled off under reduced pressure and the residue was suspended in ethyl acetate, collected by filtration and washed with ethyl acetate to afford the monohydrochloride of the title compound as a colorless powder (45 mg).

$^1$H NMR (600 MHz, DMSO-$d_6$) δ ppm 0.83-0.88 (m, 3 H), 1.22-1.32 (m, 17 H), 1.59-1.72 (m, 2 H), 3.04-3.49 (m, 7 H), 3.73-3.85 (m, 1 H), 3.86-3.98 (m, 2 H), 4.36-4.52 (m, 1 H), 4.64-4.79 (m, 1 H), 6.66-6.72 (m, 1 H), 6.72-6.80 (m, 1 H), 7.01-7.10 (m, 1 H), 7.19-7.27 (m, 2 H), 7.34-7.44 (m, 3 H), 7.52-7.64 (m, 2 H), 9.90 (br. s, 1 H), 10.69 (br. s, 1 H).

LCMS retention time: 5.01 min. (Condition 1-1-3)
MS (ESI posi) m/z: 581[M+H]$^+$.

The compounds of Working Examples 17-2 to 17-7 were obtained by using the corresponding commercially available alkyl halides in accordance with the process of Working Example 17-1.

Working Example 17-2

LCMS retention time: 5.14 min. (Condition 1-1-3)
MS (ESI posi) m/z: 595[M+H]$^+$.

Working Example 17-3

LCMS retention time: 4.08 min. (Condition 1-1-3)
MS (ESI posi) m/z: 599[M+H]$^+$.

Working Example 17-4

LCMS retention time: 4.66 min. (Condition 1-1-3)
MS (ESI posi) m/z: 553[M+H]$^+$.

Working Example 17-5

LCMS retention time: 4.92 min. (Condition 1-1-3)
MS (ESI posi) m/z: 629[M+H]$^+$.

Working Example 17-6

LCMS retention time: 5.17 min. (Condition 1-1-3)
MS (ESI posi) m/z: 607[M+H]$^+$.

Working Example 17-7

LCMS retention time: 4.24 min. (Condition 1-1-3)
MS (ESI posi) m/z: 595[M+H]$^+$.

The structures of the compounds of Working Examples 17-2 to 17-7 are shown in Table 29-1.

TABLE 29-1
| Working Ex. | Structure |
|---|---|
| 17-2 | 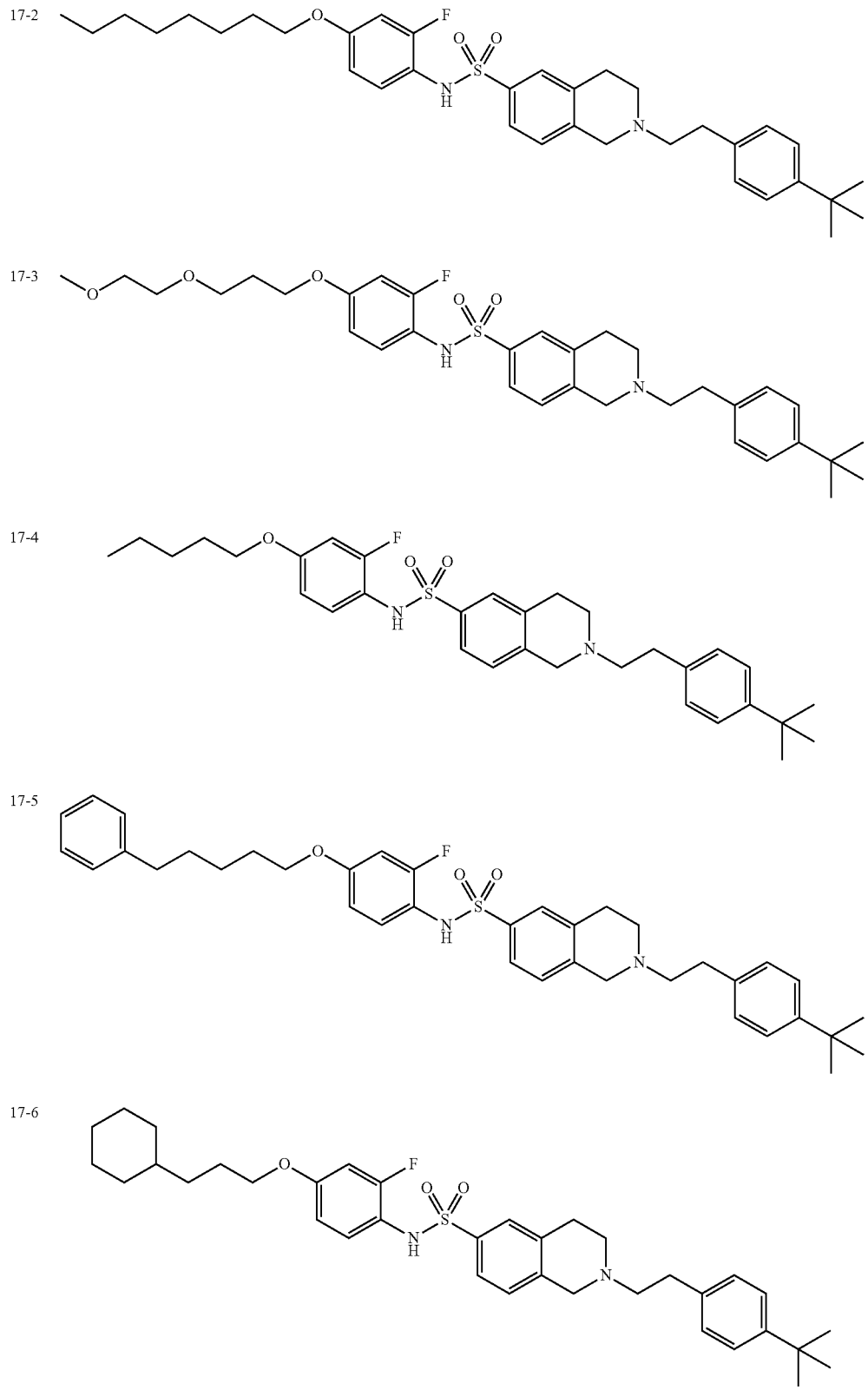 |
| 17-3 | 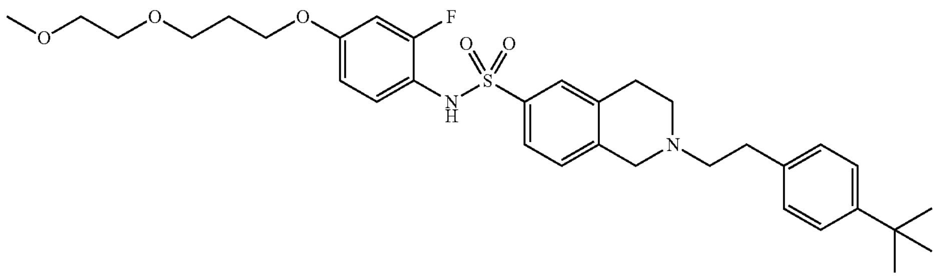 [SMILES: COCCOCCCOc1ccc(NS(=O)(=O)c2ccc3c(c2)CCN(CCc2ccc(C(C)(C)C)cc2)C3)c(F)c1] |
| 17-4 | 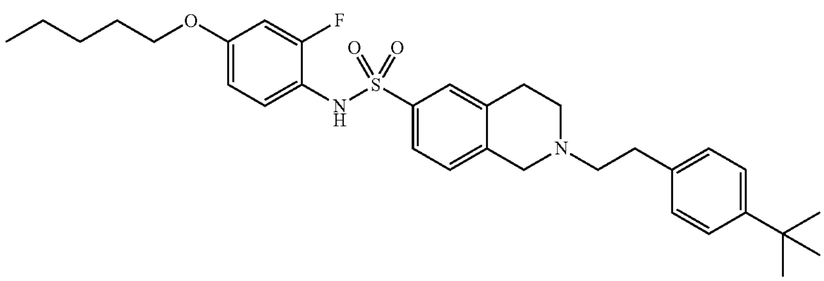 [SMILES: CCCCCOc1ccc(NS(=O)(=O)c2ccc3c(c2)CCN(CCc2ccc(C(C)(C)C)cc2)C3)c(F)c1] |
| 17-5 | 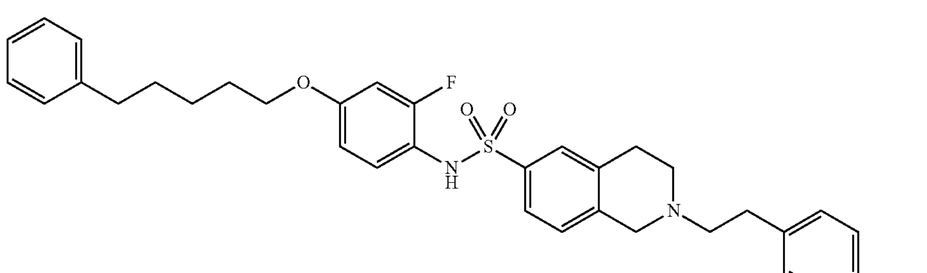 |
| 17-6 | 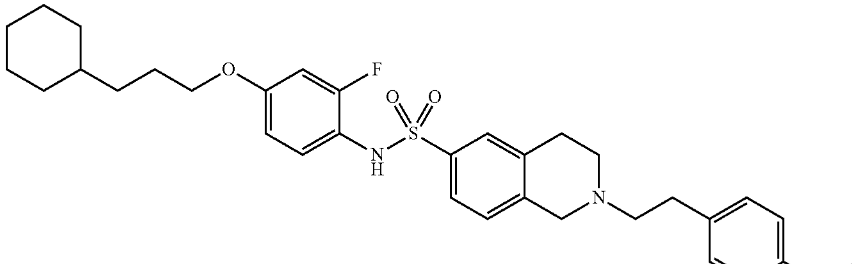 |

TABLE 29-1-continued

| Working Ex. | Structure |
|---|---|
| 17-7 | ![structure] |

Working Example 18-1

N-(4-tert-Butylphenyl)-5-[(2-fluoro-4-propoxyphenyl)sulfamoyl]-1,3-dihydro-2H-isoindole-2-carboxamide

[Formula 71]

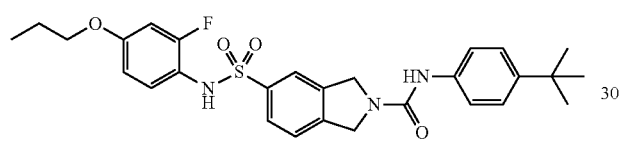

The compound obtained in Reference Example 5-1 (50 mg, 0.079 mmol) was dissolved in N,N-dimethylformamide (500 µL) and then 1-iodopropane (20 mg, 0.119 mmol) and potassium carbonate (16 mg, 0.119 mmol) were added thereto, followed by stirring at room temperature for 18 hr. To the reaction mixture were added ethyl acetate and water for separation into phases. The aqueous layer was extracted twice with ethyl acetate, and the combined organic layer was filtered through a phase separator. The solvent was distilled off from the filtrate under reduced pressure. The resulting residue was dissolved in chloroform (2.7 mL), trifluoroacetic acid (0.3 mL) was added thereto, and the mixture was left to stand at room temperature for 1 hr. The reaction mixture was concentrated under reduced pressure and the residue was diluted with dimethyl sulfoxide and then filtered. The filtrate was purified by HPLC to afford the title compound as a colorless powder (23 mg).

$^1$H NMR (300 MHz, DMSO-$d_6$) δ ppm 0.92-0.96 (m, 3 H), 1.26 (s, 9 H), 1.57-1.77 (m, 2 H), 3.79-3.94 (m, 2 H), 4.69-4.87 (m, 4 H), 6.64-6.84 (m, 2 H), 6.97-7.11 (m, 1 H), 7.20-7.33 (m, 2 H), 7.38-7.48 (m, 2 H), 7.49-7.57 (m, 1 H), 7.57-7.69 (m, 2 H), 8.24-8.39 (m, 1 H), 9.83 (br. s., 1 H).

LCMS retention time: 5.43 min. (Condition 1-1-2)
MS (ESI posi) m/z: 526[M+H]$^+$.

The compounds of Working Examples 18-2 to 18-35 were obtained by using the corresponding commercially available alkyl halides in accordance with the process of Working Example 18-1.

Working Example 18-2

LCMS retention time: 5.38 min. (Condition 1-1-2)
MS (ESI posi) m/z: 538[M+H]$^+$.

Working Example 18-3

LCMS retention time: 5.16 min. (Condition 1-1-2)
MS (ESI posi) m/z: 556[M+H]$^+$.

Working Example 18-4

LCMS retention time: 5.20 min. (Condition 1-1-2)
MS (ESI posi) m/z: 512[M+H]$^+$.

Working Example 18-5

LCMS retention time: 5.56 min. (Condition 1-1-2)
MS (ESI posi) m/z: 540[M+H]$^+$.

Working Example 18-6

LCMS retention time: 5.82 min. (Condition 1-1-2)
MS (ESI posi) m/z: 568[M+H]$^+$.

Working Example 18-7

LCMS retention time: 6.05 min. (Condition 1-1-2)
MS (ESI posi) m/z: 596[M+H]$^+$.

Working Example 18-8

LCMS retention time: 4.97 min. (Condition 1-1-2)
MS (ESI posi) m/z: 542[M+H]$^+$.

Working Example 18-9

LCMS retention time: 4.93 min. (Condition 1-1-2)
MS (ESI posi) m/z: 586[M+H]$^+$.

Working Example 18-10

LCMS retention time: 5.85 min. (Condition 1-1-2)
MS (ESI posi) m/z: 580[M+H]$^+$.

Working Example 18-11

LCMS retention time: 5.95 min. (Condition 1-1-2)
MS (ESI posi) m/z: 594[M+H]$^+$.

Working Example 18-12

LCMS retention time: 6.09 min. (Condition 1-1-2)
MS (ESI posi) m/z: 608[M+H]$^+$.

Working Example 18-13

LCMS retention time: 5.08 min. (Condition 1-1-2)
MS (ESI posi) m/z: 600[M+H]$^+$.

Working Example 18-14

LCMS retention time: 5.53 min. (Condition 1-1-3)
MS (ESI posi) m/z: 588[M+H]$^+$.

Working Example 18-15

LCMS retention time: 5.62 min. (Condition 1-1-3)
MS (ESI posi) m/z: 602[M+H]$^+$.

Working Example 18-16

LCMS retention time: 5.80 min. (Condition 1-1-3)
MS (ESI posi) m/z: 630[M+H]$^+$.

Working Example 18-17

LCMS retention time: 5.91 min. (Condition 1-1-3)
MS (ESI posi) m/z: 644[M+H]$^+$.

Working Example 18-18

LCMS retention time: 5.43 min. (Condition 1-1-3)
MS (ESI posi) m/z: 604[M+H]$^+$.

Working Example 18-19

LCMS retention time: 5.43 min. (Condition 1-1-3)
MS (ESI posi) m/z: 622[M+H]$^+$.

Working Example 18-20

LCMS retention time: 5.58 min. (Condition 1-1-3)
MS (ESI posi) m/z: 638[M+H]$^+$.

Working Example 18-21

LCMS retention time: 5.60 min. (Condition 1-1-3)
MS (ESI posi) m/z: 672[M+H]$^+$.

Working Example 18-22

LCMS retention time: 5.36 min. (Condition 1-1-3)
MS (ESI posi) m/z: 634[M+H]$^+$.

Working Example 18-23

LCMS retention time: 5.57 min. (Condition 1-1-3)
MS (ESI posi) m/z: 618[M+H]$^+$.

Working Example 18-24

LCMS retention time: 5.73 min. (Condition 1-1-3)
MS (ESI posi) m/z: 652[M+H]$^+$.

Working Example 18-25

LCMS retention time: 5.65 min. (Condition 1-1-3)
MS (ESI posi) m/z: 632[M+H]$^+$.

Working Example 18-26

LCMS retention time: 5.42 min. (Condition 1-1-3)
MS (ESI posi) m/z: 594[M+H]$^+$.

Working Example 18-27

LCMS retention time: 5.11 min. (Condition 1-1-3)
MS (ESI posi) m/z: 598[M+H]$^+$.

Working Example 18-28

LCMS retention time: 4.87 min. (Condition 1-1-3)
MS (ESI posi) m/z: 554[M+H]$^+$.

Working Example 18-29

LCMS retention time: 5.49 min. (Condition 1-1-3)
MS (ESI posi) m/z: 596[M+H]$^+$.

Working Example 18-30

LCMS retention time: 5.62 min. (Condition 1-1-3)
MS (ESI posi) m/z: 554[M+H]$^+$.

Working Example 18-31

LCMS retention time: 5.52 min. (Condition 1-1-3)
MS (ESI posi) m/z: 552[M+H]$^+$.

Working Example 18-32

LCMS retention time: 5.82 min. (Condition 1-1-3)
MS (ESI posi) m/z: 580[M+H]$^+$.

Working Example 18-33

LCMS retention time: 5.37 min. (Condition 1-1-3)
MS (ESI posi) m/z: 584[M+H]$^+$.

Working Example 18-34

LCMS retention time: 5.68 min. (Condition 1-1-3)
MS (ESI posi) m/z: 568[M+H]$^+$.

Working Example 18-35

LCMS retention time: 4.35 min. (Condition 1-1-3)
MS (ESI posi) m/z: 572[M+H]$^+$.

The structures of the compounds of Working Examples 18-2 to 18-35 are shown in Tables 30-1 to 30-3.

TABLE 30-1

| Working Ex. | Structure |
|---|---|
| 18-2 | (structure) |
| 18-3 | (structure) |
| 18-4 | (structure) |
| 18-5 | (structure) |
| 18-6 | (structure) |
| 18-7 | (structure) |
| 18-8 | (structure) |
| 18-9 | (structure) |

TABLE 30-1-continued
| Working Ex. | Structure |
|---|---|
| 18-10 | 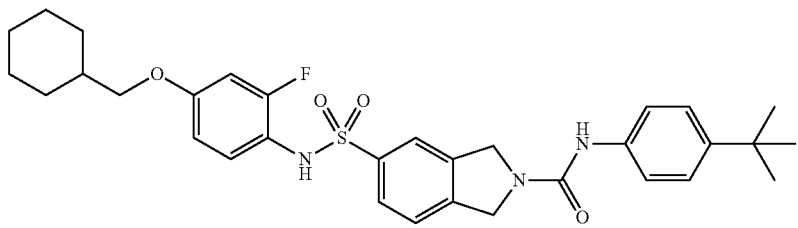 [SMILES: CC(C)(C)c1ccc(NC(=O)N2Cc3ccc(S(=O)(=O)Nc4ccc(OCC5CCCCC5)cc4F)cc3C2)cc1] |
| 18-11 | 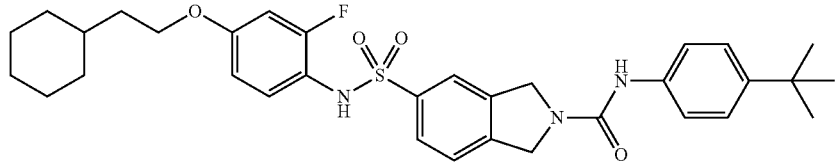 |
| 18-12 | 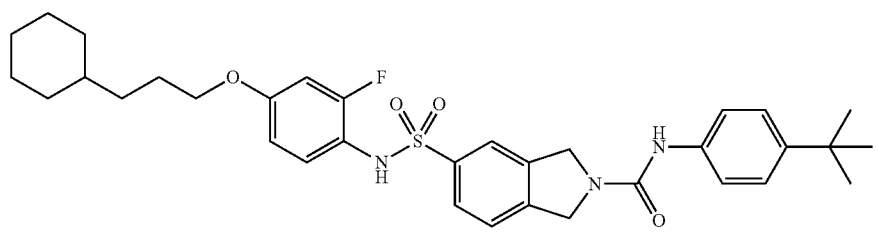 [SMILES: CC(C)(C)c1ccc(NC(=O)N2Cc3ccc(S(=O)(=O)Nc4ccc(OCCCC5CCCCC5)cc4F)cc3C2)cc1] |
| 18-13 | 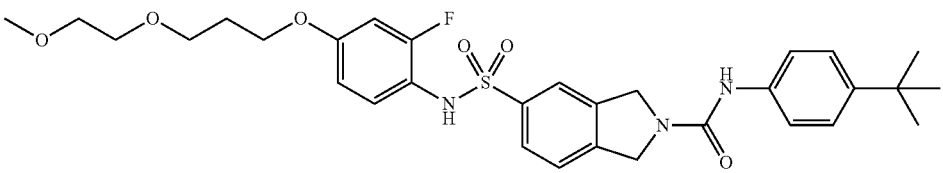 [SMILES: COCCOCCCOc1ccc(NS(=O)(=O)c2ccc3c(c2)CN(C(=O)Nc2ccc(C(C)(C)C)cc2)C3)c(F)c1] |
| 18-14 | 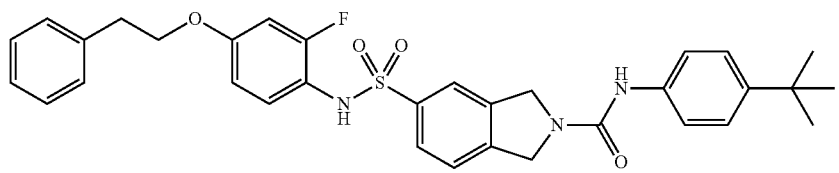 |
| 18-15 | 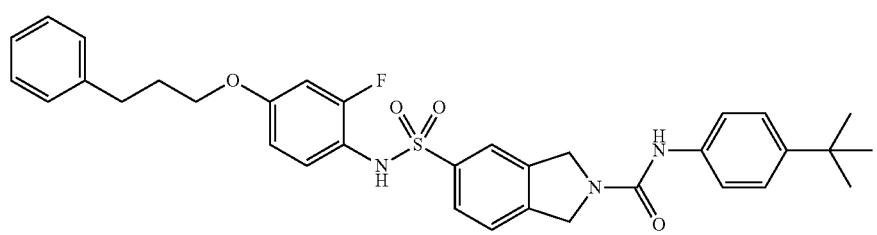 [SMILES: CC(C)(C)c1ccc(NC(=O)N2Cc3ccc(S(=O)(=O)Nc4ccc(OCCOc5ccccc5)cc4F)cc3C2)cc1] |

TABLE 30-2

| Working Ex. | Structure |
|---|---|
| 18-16 | (structure) |
| 18-17 | (structure) |
| 18-18 | (structure) |
| 18-19 | (structure) |
| 18-20 | (structure) |
| 18-21 | (structure) |
| 18-22 | (structure) |

TABLE 30-2-continued

| Working Ex. | Structure |
|---|---|
| 18-23 | (structure) |
| 18-24 | (structure) |
| 18-25 | (structure) |
| 18-26 | (structure) |
| 18-27 | (structure) |
| 18-28 | (structure) |
| 18-29 | (structure) |

TABLE 30-3

| Working Ex. | Structure |
|---|---|
| 18-30 | 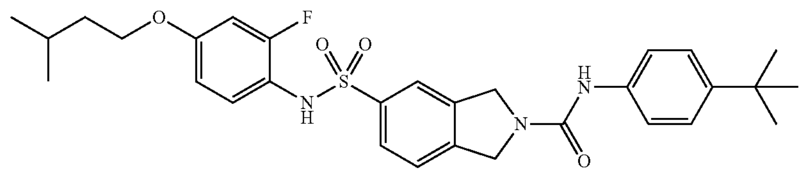 [SMILES: CC(C)CCOc1ccc(NS(=O)(=O)c2ccc3c(c2)CN(C(=O)Nc2ccc(C(C)(C)C)cc2)C3)c(F)c1] |
| 18-31 | 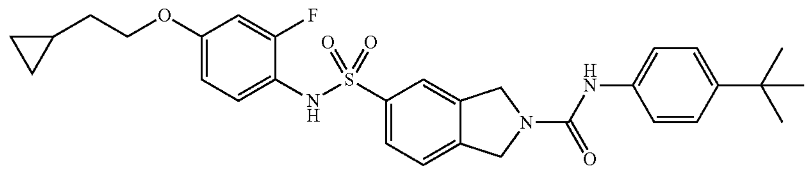 [SMILES: CC(C)(C)c1ccc(NC(=O)N2Cc3ccc(S(=O)(=O)Nc4ccc(OCCC5CC5)cc4F)cc3C2)cc1] |
| 18-32 | 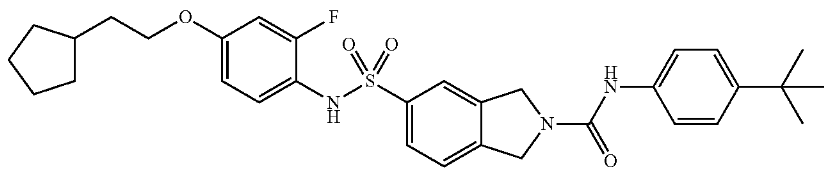 [SMILES: CC(C)(C)c1ccc(NC(=O)N2Cc3ccc(S(=O)(=O)Nc4ccc(OCCC5CCCC5)cc4F)cc3C2)cc1] |
| 18-33 | 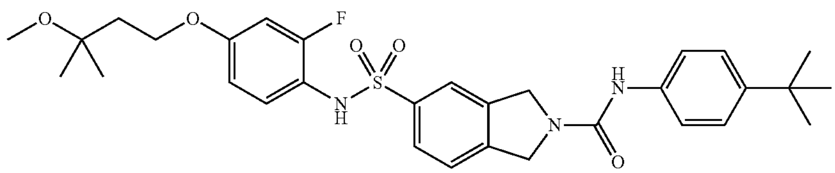 [SMILES: COC(C)(C)CCOc1ccc(NS(=O)(=O)c2ccc3c(c2)CN(C(=O)Nc2ccc(C(C)(C)C)cc2)C3)c(F)c1] |
| 18-34 | 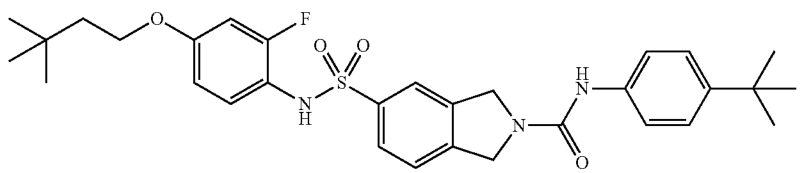 [SMILES: CC(C)(C)CCOc1ccc(NS(=O)(=O)c2ccc3c(c2)CN(C(=O)Nc2ccc(C(C)(C)C)cc2)C3)c(F)c1] |
| 18-35 | 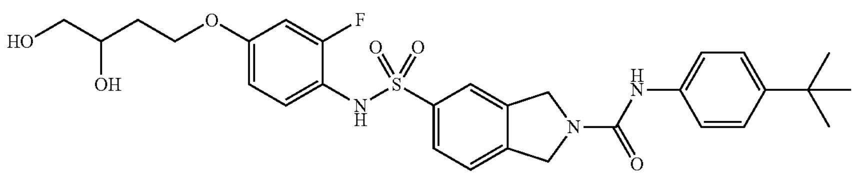 [SMILES: CC(C)(C)c1ccc(NC(=O)N2Cc3ccc(S(=O)(=O)Nc4ccc(OCCC(O)CO)cc4F)cc3C2)cc1] |

Working Example 19-1

N-(4-tert-Butylphenyl)-5-({2-fluoro-4-[3-(piperidin-1-yl)propoxy]phenyl}sulfamoyl)-1,3-dihydro-2H-isoindole-2-carboxamide The compound obtained in Reference Example 5-1 (50 mg, 0.079 mmol) was dissolved in tetrahydrofuran (1 mL) and then 1-piperidine propanol (24 µL, 0.16 mmol) and cyanomethylene tributylphosphorane (52 µL, 0.20 mmol) were added thereto. After stirring at room temperature for 4 days, the mixture was stirred for 2 hr while heating at 65° C. 1-Piperi-

[Formula 72]

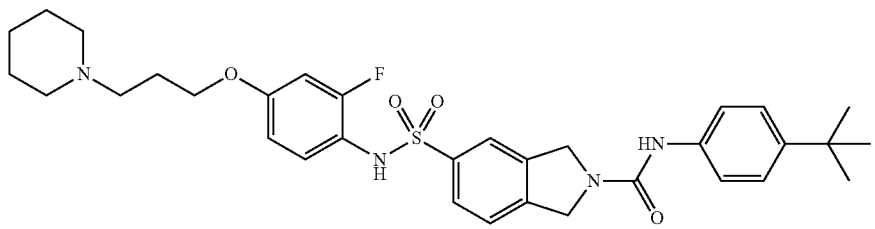

dine propanol (24 μL, 0.16 mmol) and cyanomethylene tributylphosphorane (52 μL, 0.20 mmol) were further added thereto and the mixture was stirred for 2 hr while heating at 65° C. Water was added to the reaction mixture and the solvent was distilled off under reduced pressure. The resulting residue was dissolved in chloroform (1.8 mL), trifluoroacetic acid (0.2 mL) was added thereto, and the mixture was left to stand at room temperature for 1 hr. The reaction mixture was concentrated under reduced pressure, the residue was diluted with dimethyl sulfoxide and then filtered. The filtrate was purified by HPLC to afford the trifluoroacetate of the title compound as a colorless powder (22 mg).

LCMS retention time: 3.97 min. (Condition 1-1-2)
MS (ESI posi) m/z: 609[M+H]$^+$.

The compounds of Working Examples 19-2 to 19-14 were obtained by using the corresponding commercially available alcohols in accordance with the process of Working Example 19-1.

Working Example 19-2

LCMS retention time: 5.71 min. (Condition 1-1-3)
MS (ESI posi) m/z: 616[M+H]$^+$.

Working Example 19-3

LCMS retention time: 5.92 min. (Condition 1-1-3)
MS (ESI posi) m/z: 594[M+H]$^+$.

Working Example 19-4

LCMS retention time: 5.82 min. (Condition 1-1-3)
MS (ESI posi) m/z: 594[M+H]$^+$.

Working Example 19-5

LCMS retention time: 5.25 min. (Condition 1-1-3)
MS (ESI posi) m/z: 614[M+H]$^+$.

Working Example 19-6

LCMS retention time: 5.56 min. (Condition 1-1-3)
MS (ESI posi) m/z: 642[M+H]$^+$.

Working Example 19-7

LCMS retention time: 5.74 min. (Condition 1-1-3)
MS (ESI posi) m/z: 568[M+H]$^+$.

Working Example 19-8

LCMS retention time: 5.89 min. (Condition 1-1-3)
MS (ESI posi) m/z: 582[M+H]$^+$.

Working Example 19-9

LCMS retention time: 4.74 min. (Condition 1-1-3)
MS (ESI posi) m/z: 609[M+H]$^+$.

Working Example 19-10

LCMS retention time: 6.22 min. (Condition 1-1-3)
MS (ESI posi) m/z: 622[M+H]$^+$.

Working Example 19-11

LCMS retention time: 5.62 min. (Condition 1-1-3)
MS (ESI posi) m/z: 566[M+H]$^+$.

Working Example 19-12

LCMS retention time: 3.87 min. (Condition 1-1-3)
MS (ESI posi) m/z: 589[M+H]$^+$.

Working Example 19-13

LCMS retention time: 3.87 min. (Condition 1-1-3)
MS (ESI posi) m/z: 589[M+H]$^+$.

Working Example 19-14

LCMS retention time: 3.87 min. (Condition 1-1-3)
MS (ESI posi) m/z: 589[M+H]$^+$.

The structures of the compounds of Working Examples 19-2 to 19-14 are shown in Table 31-1.

TABLE 31-1

| Working Ex. | Structure |
|---|---|
| 19-2 | (structure image) |
| 19-3 | (structure image) |

TABLE 31-1-continued
| Working Ex. | Structure |
|---|---|
| 19-4 | 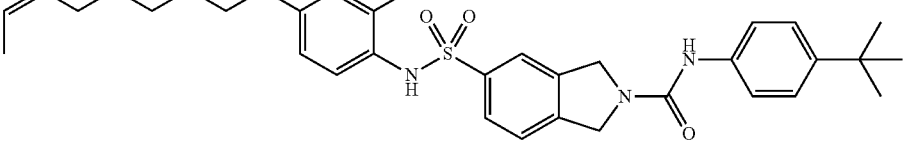 |
| 19-5 | 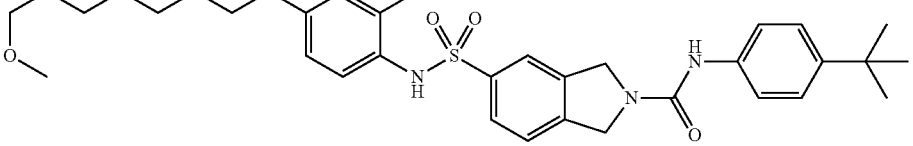 |
| 19-6 | 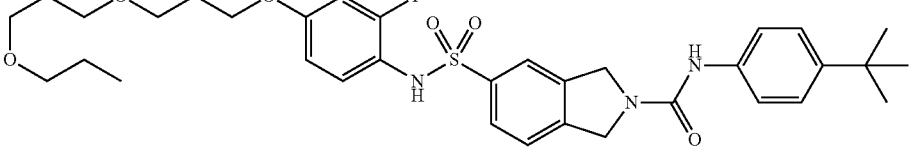 |
| 19-7 | 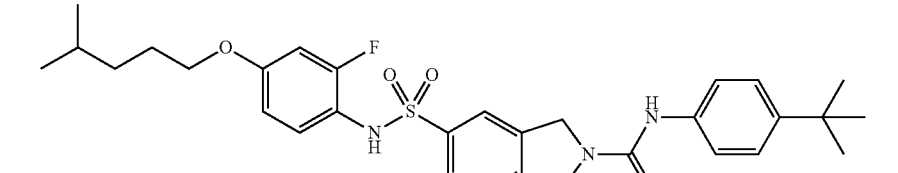 |
| 19-8 | 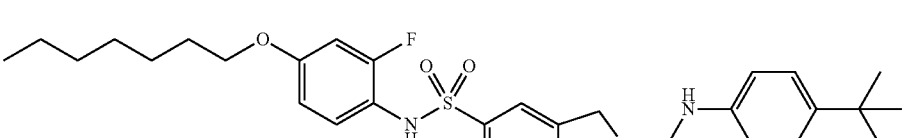 |
| 19-9 | 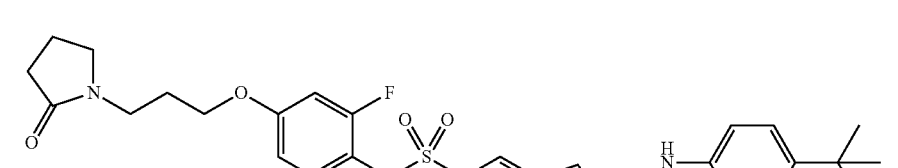 |
| 19-10 | 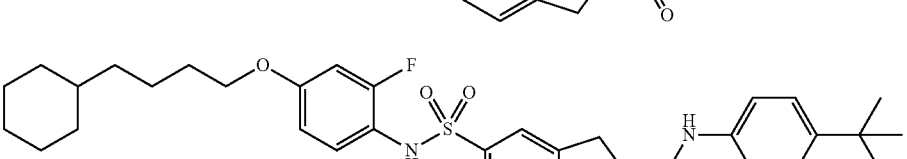 |
| 19-11 | 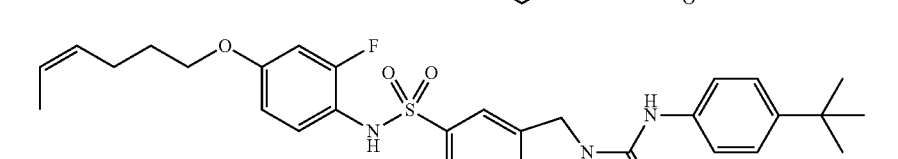 |

TABLE 31-1-continued

| Working Ex. | Structure |
|---|---|
| 19-12 | (structure) |
| 19-13 | (structure) |
| 19-14 | (structure) |

Working Example 20-1

2-[1-(4-tert-Butylphenyl)-2-methylpropan-2-yl]-N-(4-fluorophenyl)-1,2,3,4-tetrahydroisoquinoline-6-sulfonamide

[Formula 73]

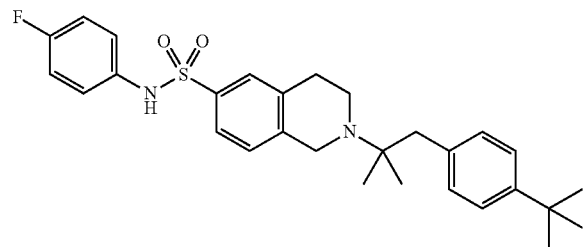

(1) The same process as that of Working Example 1-1 was performed using compound 3-6 as obtained in Reference Example 3 (500 mg, 1.10 mmol) to afford 2-[2-(4-tert-butylphenyl)ethyl]-N-(2,4-dimethoxybenzyl)-N-(4-fluorophenyl)-1,2,3,4-tetrahydroisoquinoline-6-sulfonamide as a colorless amorphous substance (448 mg).

(2) Titanium tetrachloride (17 μL, 0.16 mmol) was added to a solution of 2-[2-(4-tert-butylphenyl)ethyl]-N-(2,4-dimethoxybenzyl)-N-(4-fluorophenyl)-1,2,3,4-tetrahydroisoquinoline-6-sulfonamide obtained (100 mg) in tetrahydrofuran (3 mL) at −10° C. under a nitrogen atmosphere. After stirring at −10° C. for 30 min, methyl magnesium bromide (3 mol/L diethyl ether solution, 318 μL, 0.954 mmol) was added thereto and the mixture was slowly warmed to room temperature and stirred for 15 hr. Methyl magnesium bromide (3 mol/L diethyl ether solution, 318 μL, 0.954 mmol) was further added thereto and the mixture was stirred at room temperature for 4 hr and at 40° C. for 2.5 hr. Methyl magnesium bromide (3 mol/L diethyl ether solution, 318 μL, 0.954 mmol) was still further added thereto and the mixture was stirred at 40° C. for 17 hr. The mixture was cooled to room temperature, 30% aqueous sodium hydroxide solution was added to the reaction mixture, and the mixture was extracted with chloroform and ethyl acetate. The organic layer was washed with brine and dried over anhydrous magnesium sulfate and then the desiccant was filtered off, followed by concentration under reduced pressure. The resulting residue was purified by silica gel column chromatography (hexane:ethyl acetate=4:1) to afford 2-[1-(4-tert-butylphenyl)-2-methylpropan-2-yl]-N-(2,4-dimethoxybenzyl)-N-(4-fluorophenyl)-1,2,3,4-tetrahydroisoquinoline-6-sulfonamide as a yellow oil (22 mg).

(3) Trifluoroacetic acid (0.2 mL) was added to a solution of 2-[1-(4-tert-butylphenyl)-2-methylpropan-2-yl]-N-(2,4-dimethoxybenzyl)-N-(4-fluorophenyl)-1,2,3,4-tetrahydroisoquinoline-6-sulfonamide obtained (22 mg) in a mixture of anisole (1 mL) and chloroform (1 mL) while cooling in ice, and the mixture was stirred for 2.5 hr while cooling in ice. Saturated aqueous sodium hydrogen carbonate solution was added to the reaction mixture while cooling in ice and the mixture was extracted with chloroform. The organic layer was dried over anhydrous magnesium sulfate and then the desiccant was filtered off, followed by concentration under reduced pressure. The resulting residue was purified by NH silica gel column chromatography (chloroform:methanol=49:1) to afford the title compound as a colorless oil (8 mg).

(4) The same process as that of Working Example 2-1(2) was performed using the obtained title compound (6 mg) to afford the monohydrochloride of the title compound as a colorless powder (8 mg).

$^1$H NMR (600 MHz, DMSO-$d_6$) δ ppm 1.21-1.36 (m, 15 H), 2.97-3.12 (m, 2 H), 3.16-3.38 (m, 3 H), 3.95-4.03 (m, 1 H), 4.59-4.68 (m, 2 H), 7.06-7.16 (m, 4 H), 7.20 (d, J=7.8 Hz, 2 H), 7.37 (d, J=7.8 Hz, 2 H), 7.45 (d, J=8.7 Hz, 1 H), 7.63 (d, J=7.4 Hz, 1 H), 7.69 (br. s., 1 H), 10.33 (s, 1 H).

LCMS retention time: 5.07 min. (Condition 1-1-1)

MS (ESI posi) m/z: 495[M+H]$^+$.

The compounds of Working Examples 20-2 to 20-4 were obtained by using the compounds obtained in Reference Examples 29 and 30 and the compound obtained in Reference Example 12-1(1) or the corresponding commercially available carboxylic acids in accordance with the process of Working Example 20-1.

Working Example 20-2

¹H NMR (600 MHz, DMSO-d₆) δ ppm 0.97-1.06 (m, 2 H), 1.22-1.36 (m, 17 H), 1.41-1.58 (m, 6 H), 1.66-1.76 (m, 3 H), 2.45-2.54 (m, 2 H), 2.99-3.05 (m, 1 H), 3.08-3.20 (m, 2 H), 3.24-3.39 (m, 2 H), 3.96-4.02 (m, 1 H), 4.60-4.69 (m, 2 H), 6.93-7.04 (m, 2 H), 7.10-7.17 (m, 1 H), 7.19-7.23 (m, 2 H), 7.35-7.40 (m, 2 H), 7.43-7.49 (m, 1 H), 7.61-7.68 (m, 2 H), 10.13 (s, 1 H).
LCMS retention time: 2.16 min. (Condition 3)
MS ESI/APCI Dual posi: 605[M+H]⁺.

Working Example 20-3

¹H NMR (600 MHz, DMSO-d₆) δ ppm 1.16-1.35 (m, 15 H), 1.38-1.47 (m, 3 H), 1.56-1.61 (m, 1 H), 1.72-1.80 (m, 3 H), 2.99-3.05 (m, 1 H), 3.10-3.20 (m, 2 H), 3.24-3.40 (m, 5 H), 3.82-3.86 (m, 1 H), 3.94-4.02 (m, 3 H), 4.63-4.69 (m, 2 H), 6.69-6.73 (m, 1 H), 6.77-6.81 (m, 1 H), 7.05-7.09 (m, 1 H), 7.21 (d, J=8.3 Hz, 2 H), 7.38 (d, J=8.3 Hz, 2 H), 7.46 (d, J=8.3 Hz, 1 H), 7.58-7.64 (m, 2 H), 9.93 (s, 1 H).
LCMS retention time: 1.00 min. (Condition 5-2)
MS (ESI posi) m/z: 623[M+H]⁺.

Working Example 20-4

¹H NMR (600 MHz, DMSO-d₆) δ ppm 0.96-1.05 (m, 2 H), 1.21-1.27 (m, 2 H), 1.32-1.57 (m, 15 H), 1.63-1.75 (m, 3 H), 1.85-1.95 (m, 6 H), 3.00-3.14 (m, 2 H), 3.21-3.30 (m, 1 H), 3.59-4.08 (m, 3 H), 4.32-4.45 (m, 2 H), 6.89-7.03 (m, 2 H), 7.06-7.13 (m, 1 H), 7.33-7.40 (m, 1 H), 7.50-7.68 (m, 3 H), 8.17-8.30 (m, 1 H), 8.91 (s, 1 H), 10.09 (s, 1 H).
LCMS retention time: 0.99 min. (Condition 5-2)
MS (ESI posi) m/z: 592[M+H]⁺.

The structures of the compounds of Working Examples 20-2 to 20-4 are shown in Table 32-1.

TABLE 32-1

| Working Ex. | Structure |
|---|---|
| 20-2 | 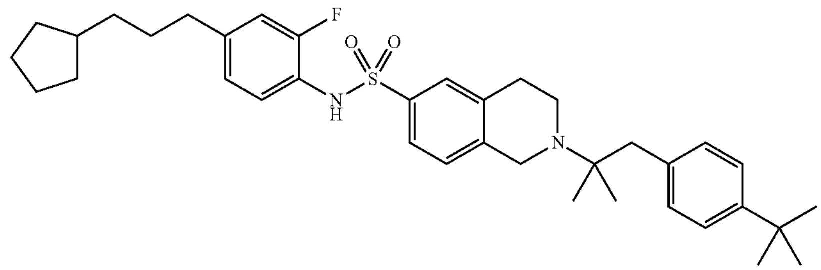 [SMILES: CC(C)(C)c1ccc(CC(C)(C)N2CCc3cc(S(=O)(=O)Nc4ccc(CCCC5CCCC5)cc4F)ccc3C2)cc1] |
| 20-3 | 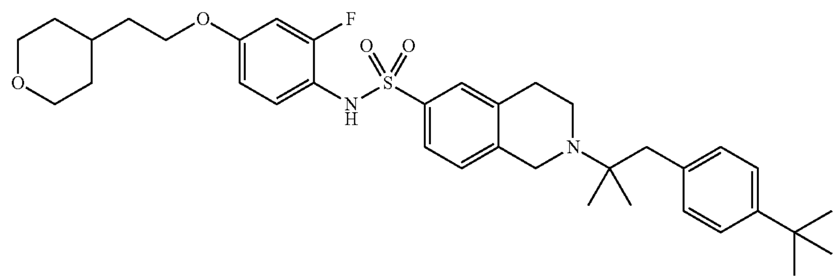 [SMILES: CC(C)(C)c1ccc(CC(C)(C)N2CCc3cc(S(=O)(=O)Nc4ccc(OCCC5CCOCC5)cc4F)ccc3C2)cc1] |
| 20-4 | 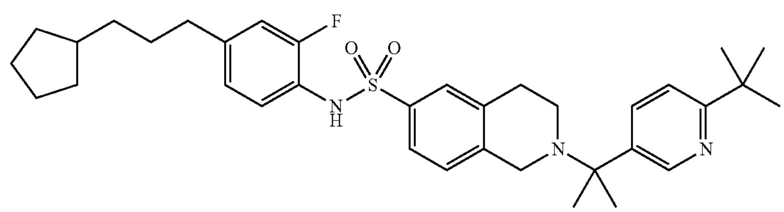 [SMILES: CC(C)(C)c1ccc(C(C)(C)N2CCc3cc(S(=O)(=O)Nc4ccc(CCCC5CCCC5)cc4F)ccc3C2)cn1] |

Working Example 21-1

N-(4-tert-Butylphenyl)-6-[(4-fluorophenyl)sulfamoyl]-7-methyl-3,4-dihydroisoquinoline-2(1H)-carboxamide

[Formula 74]

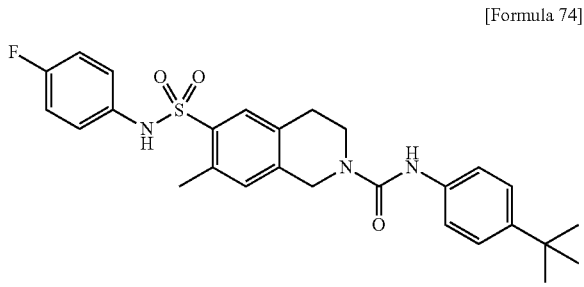 [SMILES: Cc1cc2c(cc1S(=O)(=O)Nc1ccc(F)cc1)CCN(C(=O)Nc1ccc(C(C)(C)C)cc1)C2]

To the compound of Working Example 14-2 (112 mg, 0.20 mmol), trimethylboroxine (42 μL, 0.30 mmol), tris(dibenzylideneacetone)dipalladium (18 mg, 0.02 mmol), tri(2-furyl)phosphine (28 mg, 0.12 mmol) and cesium carbonate (130 mg, 0.40 mmol) were added 1,4-dioxane (4 mL) and water (2 mL), and the mixture was stirred at an external temperature of 70° C. for 12 hr. The mixture was filtered through Celite (registered trademark), followed by concentration under reduced pressure. The resulting residue was purified by silica gel column chromatography (hexane:ethyl acetate=3:1→1:1), ethyl acetate, isopropyl ether and hexane were added thereto, and the mixture was powdered and then collected by filtration to afford the title compound as a colorless powder (23 mg).

$^1$H NMR (300 MHz, DMSO-d$_6$) δ ppm 1.25 (s, 9H), 2.78-2.87 (m, 2H), 3.63-3.71 (m, 2 H), 4.60 (s, 2 H), 7.04-7.08 (m, 4 H), 7.16 (s, 1 H), 7.21-7.27 (m, 2 H), 7.32-7.38 (m, 2 H), 7.68 (s, 1 H), 8.52 (s, 1 H), 10.30 (br. s., 1 H).

MS ESI/APCI Dual nega: 494[M−H]$^-$.

The compound of Working Example 21-2 was obtained by using the corresponding boronic acid in accordance with the process of Working Example 21-1.

Working Example 21-2

$^1$H NMR (300 MHz, DMSO-d$_6$) δ ppm 1.25 (s, 9 H), 2.88-2.95 (m, 2 H), 3.70-3.77 (m, 2 H), 4.67 (s, 2 H), 6.85-6.92 (m, 2 H), 6.99-7.10 (m, 3 H), 7.18-7.27 (m, 4 H), 7.32-7.40 (m, 5 H), 7.83 (s, 1 H), 8.54 (s, 1 H), 9.86 (br. s., 1 H).

MS ESI/APCI Dual posi: 558[M+H]$^+$.

The structure of the compound of Working Example 21-2 is shown in Table 33-1.

TABLE 33-1

| Working Ex. | Structure |
|---|---|
| 21-2 | 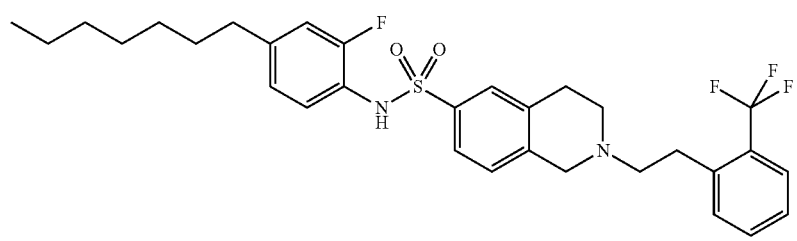 |

Working Example 22-1

N-(2-Fluoro-4-heptylphenyl)-2-{2-[2-(trifluoromethyl)phenyl]ethyl}-1,2,3,4-tetrahydroisoquinoline-6-sulfonamide A solution of Dess-Martin periodinane (236 mg, 556 μmol) in chloroform (1 mL) was added to a solution of 2-[2-(trifluoromethyl)phenyl]ethanol (17 μl, 111 μmol) in chloroform (3 mL) while cooling in ice, and the mixture was stirred at room temperature for 5 hr. To the reaction mixture was added 20 wt % aqueous sodium thiosulfate solution, the mixture was stirred for 30 min, and the aqueous layer was removed therefrom. To the organic layer was added 10 wt % aqueous potassium carbonate solution, the mixture was stirred for 30 min, and then the organic layer was filtered through a phase separator. To the filtrate were added compound 3-9 as obtained in Reference Example 3 (30 mg, 74 μmol) and sodium triacetoxyborohydride (31 mg, 148 μmol) successively. The mixture was stirred at room temperature overnight, saturated aqueous sodium hydrogen carbonate solution was added to the reaction mixture, and the mixture was extracted with chloroform. The organic layer was concentrated under reduced pressure and the residue was purified by HPLC to afford the title compound as a colorless powder (13 mg).

$^1$H NMR (600 MHz, DMSO-d$_6$) δ ppm 0.80-0.88 (m, 3 H), 1.18-1.29 (m, 8 H), 1.45-1.54 (m, 2 H), 3.10-3.30 (m, 5 H), 3.41-3.50 (m, 4 H), 3.80-3.89 (m, 1 H), 4.45-4.53 (m, 1 H), 4.75-4.82 (m, 1 H), 6.91-7.02 (m, 2 H), 7.10-7.16 (m, 1 H), 7.41-7.45 (m, 1 H), 7.50-7.54 (m, 1 H), 7.56-7.67 (m, 3 H), 7.68-7.80 (m, 2 H), 10.10 (br. s., 1 H).

LCMS retention time: 4.52 min. (Condition 1-2-3)

MS (ESI posi) m/z: 577[M+H]$^+$.

The compound of Working Example 22-2 was obtained by using Compound 3-8 as obtained in Reference Example 3 and the corresponding commercially available alcohol in accordance with the process of Working Example 21-1.

[Formula 75]

Working Example 22-2

$^1$H NMR (600 MHz, DMSO-d$_6$) δ ppm 0.97-1.06 (m, 2 H), 1.21-1.28 (m, 2 H), 1.40-1.59 (m, 6 H), 1.65-1.77 (m, 3 H), 3.06-3.18 (m, 3 H), 3.35-3.54 (m, 6 H), 3.70-3.83 (m, 1 H), 4.42-4.47 (m, 1 H), 4.70-4.74 (m, 1 H), 6.91-7.02 (m, 2 H), 7.09-7.16 (m, 1 H), 7.32-7.49 (m, 5 H), 7.57-7.67 (m, 2 H), 10.10 (br. s., 1 H).

LCMS retention time: 4.76 min. (Condition 1-2-3)
MS (ESI posi) m/z: 605[M+H]$^+$.

The structure of the compound of Working Example 22-2 is shown in Table 34-1.

due was purified by silica gel column chromatography (hexane only→hexane:ethyl acetate=3:2) to afford 2-[1-(6-tert-butylpyridin-3-yl)ethyl]-N-[4-(3-cyclopentylpropyl)-2-fluorophenyl]-N-(4-methoxybenzyl)-1,2,3,4-tetrahydroisoquinoline-6-sulfonamide as a pale yellow amorphous substance (621 mg).

(2) 2-[1-(6-tert-Butylpyridin-3-yl)ethyl]-N-[4-(3-cyclopentylpropyl)-2-fluorophenyl]-N-(4-methoxybenzyl)-1,2,3,4-tetrahydroisoquinoline-6-sulfonamide obtained (79 mg, 0.11 mmol) was used to afford the title compound as a colorless amorphous substance (60 mg) in accordance with the process of Working Example 8-1(2).

TABLE 34-1

| Working Ex. | Structure |
|---|---|
| 22-2 | 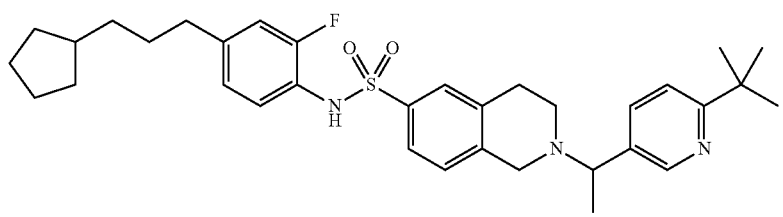 |

Working Example 23-1

2-[1-(6-tert-Butylpyridin-3-yl)ethyl]-N-[4-(3-cyclopentylpropyl)-2-fluorophenyl]-1,2,3,4-tetrahydroisoquinoline-6-sulfonamide

[Formula 76]

(1) Benzotriazole (137 mg, 1.15 mmol) and magnesium sulfate (180 mg, 2.00 mmol) were added to a solution of the compound obtained in Reference Example 29-1 (537 mg, 1.00 mmol) in chloroform (10 mL) under a nitrogen atmosphere, and the mixture was stirred at room temperature for 5 min. The compound obtained in Reference Example 9-1 (188 mg, 1.15 mmol) was added to the reaction mixture and the mixture was stirred at room temperature for 5 hr. The mixture was filtered through Celite (registered trademark), followed by concentration under reduced pressure. The residue was dissolved in tetrahydrofuran (10 mL), methyl magnesium bromide (diethyl ether solution, 3 mol/L, 0.67 mL, 2.00 mmol) was added dropwise thereto at 0° C. under a nitrogen atmosphere, and the mixture was gradually warmed to room temperature and stirred for 15 hr. Water and saturated aqueous ammonium chloride solution were added to the reaction mixture and the mixture was stirred. Thereafter, saturated aqueous sodium hydrogen carbonate solution was added thereto and the mixture was extracted with chloroform. The organic layer was concentrated under reduced pressure and the resi- (3) The dihydrochloride of the title compound was obtained as a colorless powder (49 mg) in accordance with the process of Working Example 2-1(2).

$^1$H NMR (600 MHz, DMSO-d$_6$) δ ppm 0.96-1.05 (m, 2 H), 1.20-1.26 (m, 2 H), 1.35 (s, 9 H), 1.41-1.57 (m, 6 H), 1.65-1.82 (m, 6 H), 2.99-3.23 (m, 3 H), 3.28-3.37 (m, 1 H), 3.89-3.96 (m, 1 H), 4.15-4.24 (m, 1 H), 4.30-4.42 (m, 1 H), 4.66-4.80 (m, 2 H), 6.93 (d, J=8.3 Hz, 1 H), 6.99 (d, J=11.6 Hz, 1 H), 7.05-7.13 (m, 1 H), 7.30-7.47 (m, 1 H), 7.51-7.68 (m, 3 H), 8.10-8.20 (m, 1 H), 8.72-8.79 (m, 1 H), 10.07 (s, 1 H).

LCMS retention time: 2.09 min. (Condition 3)
MS ESI/APCI Dual posi: 578[M+H]$^+$.

The compounds of Working Examples 23-2 to 23-6 were obtained by using the corresponding compounds obtained in Reference Example 29 and the aldehydes obtained in Reference Examples 9 and 34 or the corresponding commercially available aldehydes in accordance with the process of Working Example 23-1.

Working Example 23-2

$^1$H NMR (600 MHz, DMSO-d$_6$) δ ppm 1.32-1.43 (m, 11 H), 1.57-1.64 (m, 2 H), 1.66-1.73 (m, 2 H), 1.75-1.82 (m, 3 H), 2.54-2.61 (m, 2 H), 2.99-3.38 (m, 3 H), 3.85-3.95 (m, 2 H), 4.15-4.26 (m, 1 H), 4.30-4.43 (m, 1 H), 4.65-4.82 (m, 2 H), 6.65-6.69 (m, 1 H), 6.73-6.77 (m, 1 H), 6.99-7.05 (m, 1

H), 7.13-7.20 (m, 3 H), 7.23-7.35 (m, 3 H), 7.41-7.58 (m, 2 H), 7.61-7.68 (m, 1 H), 8.10-8.18 (m, 1 H), 8.73-8.78 (m, 1 H), 9.84-9.88 (m, 1 H).
LCMS retention time: 1.82 min. (Condition 3)
MS ESI/APCI Dual posi: 630[M+H]+.

Working Example 23-3

1H NMR (300 MHz, CDCl3) δ ppm 0.94-1.11 (m, 2 H), 1.22-1.32 (m, 2 H), 1.37 (s, 9 H), 1.40-1.61 (m, 9 H), 1.66-1.80 (m, 3 H), 2.47-2.62 (m, 3 H), 2.69-2.90 (m, 3 H), 3.51-3.60 (m, 2 H), 3.79-3.88 (m, 1 H), 6.51-6.54 (m, 1 H), 6.75-6.81 (m, 1 H), 6.87-6.92 (m, 1 H), 7.03-7.11 (m, 2 H), 7.29-7.32 (m, 1 H), 7.42-7.51 (m, 3 H), 8.51 (d, J=5.1 Hz, 1 H).
LCMS retention time: 2.13 min. (Condition 3)
MS ESI/APCI Dual posi: 578[M+H]+.

Working Example 23-4

1H NMR (300 MHz, CDCl3) δ ppm 0.95-1.11 (m, 2 H), 1.22-1.34 (m, 2 H), 1.40 (s, 9 H), 1.44-1.63 (m, 9 H), 1.65-1.80 (m, 3 H), 2.46-2.56 (m, 2 H), 2.66-2.89 (m, 4 H), 3.63-3.72 (m, 1 H), 3.81-3.94 (m, 2 H), 6.48-6.52 (m, 1 H), 6.74-6.81 (m, 1 H), 6.86-6.92 (m, 1 H), 7.04 (d, J=8.9 Hz, 1 H), 7.40-7.49 (m, 3 H), 8.53-8.62 (m, 2 H).
LCMS retention time: 2.14 min. (Condition 3)
MS ESI/APCI Dual posi: 579[M+H]+.

Working Example 23-5

1H NMR (300 MHz, CDCl3) δ ppm 0.94-1.11 (m, 2 H), 1.22-1.34 (m, 2 H), 1.44-1.65 (m, 9 H), 1.66-1.79 (m, 3 H), 2.46-2.55 (m, 2 H), 2.75-2.90 (m, 4 H), 3.69-3.79 (m, 1 H), 3.88-3.98 (m, 1 H), 4.16 (q, J=7.2 Hz, 1 H), 6.48-6.51 (m, 1 H), 6.72-6.81 (m, 1 H), 6.85-6.91 (m, 1 H), 7.01-7.07 (m, 1 H), 7.42-7.48 (m, 3 H), 8.97-9.00 (m, 2 H).
LCMS retention time: 2.11 min. (Condition 3)
MS ESI/APCI Dual posi: 591[M+H]+.

Working Example 23-6

1H NMR (300 MHz, CDCl3) δ ppm 0.95-1.11 (m, 2 H), 1.21-1.34 (m, 2 H), 1.41-1.63 (m, 9 H), 1.66-1.80 (m, 3 H), 2.47-2.86 (m, 6 H), 3.51-3.66 (m, 2 H), 3.71-3.82 (m, 1 H), 4.75 (q, J=8.6 Hz, 2 H), 6.49-6.54 (m, 1 H), 6.74-6.93 (m, 3 H), 7.03 (d, J=8.1 Hz, 1 H), 7.41-7.52 (m, 3 H), 7.64-7.71 (m, 1 H), 8.04-8.07 (m, 1 H).
LCMS retention time: 2.13 min. (Condition 3)
MS ESI/APCI Dual posi: 620[M+H]+.

The structures of the compounds of Working Examples 23-2 to 23-6 are shown in Table 35-1.

TABLE 35-1

| Working Ex. | Structure |
|---|---|
| 23-2 | 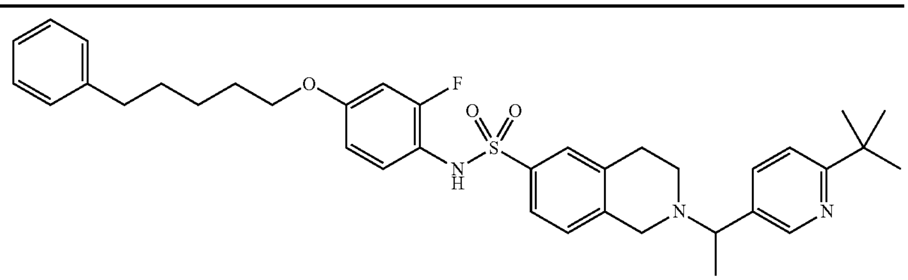 |
| 23-3 | 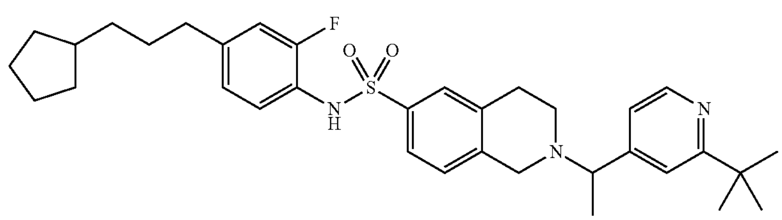 [SMILES: CC(c1ccnc(C(C)(C)C)c1)N1CCc2cc(S(=O)(=O)Nc3ccc(CCCC4CCCC4)cc3F)ccc2C1] |
| 23-4 | 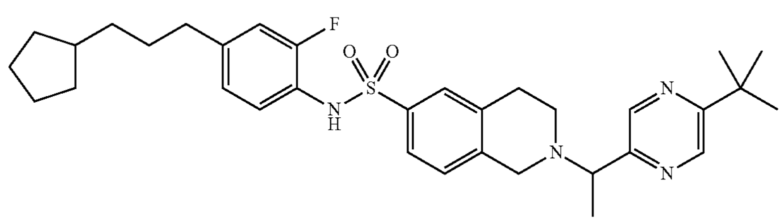 [SMILES: CC(c1cnc(C(C)(C)C)cn1)N1CCc2cc(S(=O)(=O)Nc3ccc(CCCC4CCCC4)cc3F)ccc2C1] |
| 23-5 | 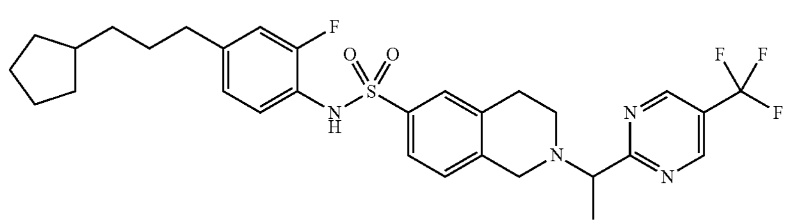 [SMILES: CC(c1ncc(C(F)(F)F)cn1)N1CCc2cc(S(=O)(=O)Nc3ccc(CCCC4CCCC4)cc3F)ccc2C1] |

TABLE 35-1-continued

| Working Ex. | Structure |
|---|---|
| 23-6 | 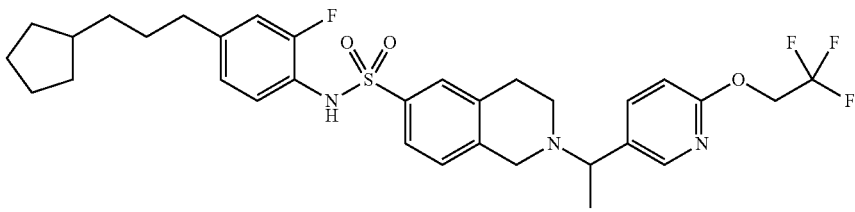 [SMILES: CC(c1ccc(OCC(F)(F)F)nc1)N1CCc2cc(S(=O)(=O)Nc3ccc(CCCC4CCCC4)cc3F)ccc2C1] |

Working Examples 24-1 and 24-2

2-[(1R)-1-(6-tert-Butylpyridin-3-yl)ethyl]-N-[4-(3-cyclopentylpropyl)-2-fluorophenyl]-1,2,3,4-tetrahydroisoquinoline-6-sulfonamide and 2-[(1S)-1-(6-tert-butylpyridin-3-yl)ethyl]-N-[4-(3-cyclopentylpropyl)-2-fluorophenyl]-1,2,3,4-tetrahydroisoquinoline-6-sulfonamide

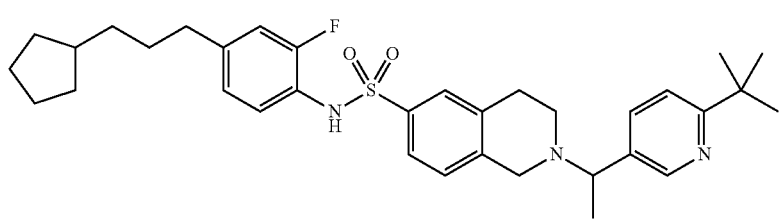 [SMILES: CC(c1cnc(C(C)(C)C)nc1)N1CCc2cc(S(=O)(=O)Nc3ccc(CCCC4CCCC4)cc3F)ccc2C1]

[Formula 77]

(1) The compounds obtained in Working Example 23-1(1) and (2) were separated by preparative HPLC (Daicel Corporation CHIRALPAK AD-H 5 μm 20×250 mm, 20° C., flow rate 5 mL/min, hexane:ethanol:diethylamine=50:50:0.1). A fraction eluted at a retention time of 20 min was concentrated, saturated aqueous ammonium chloride solution was added thereto, and the mixture was extracted with chloroform. The organic layer was dried over magnesium sulfate and then concentrated under reduced pressure to afford the compound of Working Example 24-1 as a brownish red oil (44 mg). A fraction eluted at a retention time of 28 min was concentrated and extracted in the same manner to afford the compound of Working Example 24-2 as a pale yellow oil (48 mg).

(2) The compounds of Working Examples 24-1 and 24-2 were used to afford the dihydrochloride of the compound of Working Example 24-1 as a colorless powder (39 mg) and the dihydrochloride of the compound of Working Example 24-2 as a colorless powder (37 mg), respectively, in accordance with the process of Working Example 2-1-(2).

Dihydrochloride of the Compound of Working Example 24-1

$^1$H NMR (600 MHz, DMSO-$d_6$) δ ppm 0.96-1.05 (m, 2 H), 1.20-1.26 (m, 2 H), 1.35 (s, 9 H), 1.41-1.57 (m, 6 H), 1.65-1.82 (m, 6 H), 2.99-3.23 (m, 3 H), 3.28-3.37 (m, 1 H), 3.89-3.96 (m, 1 H), 4.15-4.24 (m, 1 H), 4.30-4.42 (m, 1 H), 4.66-4.80 (m, 2 H), 6.93 (d, J=8.3 Hz, 1 H), 6.99 (d, J=11.6 Hz, 1 H), 7.05-7.13 (m, 1 H), 7.30-7.47 (m, 1 H), 7.51-7.68 (m, 3 H), 8.10-8.20 (m, 1 H), 8.72-8.79 (m, 1 H), 10.07 (s, 1 H).

LCMS retention time: 2.09 min. (Condition 3)
MS ESI/APCI Dual posi: 578[M+H]$^+$.

Dihydrochloride of the Compound of Working Example 24-2

$^1$H NMR (600 MHz, DMSO-$d_6$) δ ppm 0.96-1.05 (m, 2 H), 1.20-1.26 (m, 2 H), 1.35 (s, 9 H), 1.41-1.57 (m, 6 H), 1.65-1.82 (m, 6 H), 2.99-3.23 (m, 3 H), 3.28-3.37 (m, 1 H), 3.89-3.96 (m, 1 H), 4.15-4.24 (m, 1 H), 4.30-4.42 (m, 1 H), 4.66-4.80 (m, 2 H), 6.93 (d, J=8.3 Hz, 1 H), 6.99 (d, J=11.6 Hz, 1 H), 7.05-7.13 (m, 1 H), 7.30-7.47 (m, 1 H), 7.51-7.68 (m, 3 H), 8.10-8.20 (m, 1 H), 8.72-8.79 (m, 1 H), 10.07 (s, 1 H).

LCMS retention time: 2.09 min. (Condition 3)
MS ESI/APCI Dual posi: 578[M+H]$^+$.

Working Examples 24-3 and 24-4

(1) A compound obtained by the same processes as those of Working Example 23-1(1) and (2) using the compound obtained in Reference Example 29-1 or the corresponding commercially available aldehyde was separated by preparative HPLC in accordance with the process of Working Examples 24-1 and 24-2(1). A fraction eluted at a retention time of 25 min was concentrated to afford the compound of Working Example 24-3 as a pale yellow oil (48 mg). A fraction eluted at a retention time of 39 min was concentrated to afford the compound of Working Example 24-4 as a pale yellow oil (50 mg).

(2) The same process as that of Working Example 2-1(2) was performed using the compounds of Working Examples 24-3 and 24-4 to afford the monohydrochloride of the compound of Working Example 24-3 as a pale yellow powder (39 mg) and the monohydrochloride of the compound of Working Example 24-4 as a pale yellow powder (39 mg), respectively.

Monohydrochloride of the Compound of Working Example 24-3

¹H NMR (600 MHz, DMSO-d₆) δ ppm 0.94-1.06 (m, 2 H), 1.19-1.28 (m, 2 H), 1.37-1.58 (m, 6 H), 1.64-1.88 (m, 6 H), 2.99-3.66 (m, 4 H), 3.91-4.07 (m, 1 H), 4.19-4.48 (m, 2 H), 4.65-4.76 (m, 1 H), 4.85-4.96 (m, 1 H), 6.90-7.01 (m, 2 H), 7.07-7.14 (m, 1 H), 7.28-7.65 (m, 3 H), 8.01-8.13 (m, 1 H), 8.33-8.45 (m, 1 H), 8.91-9.05 (m, 1 H), 10.08 (s, 1 H).
LCMS retention time: 2.34 min. (Condition 3)
MS ESI/APCI Dual posi: 590[M+H]⁺.

Monohydrochloride of the Compound of Working Example 24-4

¹H NMR (600 MHz, DMSO-d₆) δ ppm 0.94-1.06 (m, 2 H), 1.19-1.28 (m, 2 H), 1.37-1.58 (m, 6 H), 1.64-1.88 (m, 6 H), 2.99-3.66 (m, 4 H), 3.91-4.07 (m, 1 H), 4.19-4.48 (m, 2 H), 4.65-4.76 (m, 1 H), 4.85-4.96 (m, 1 H), 6.90-7.01 (m, 2 H), 7.07-7.14 (m, 1 H), 7.28-7.65 (m, 3 H), 8.01-8.13 (m, 1 H), 8.33-8.45 (m, 1 H), 8.91-9.05 (m, 1 H), 10.08 (s, 1 H).
LCMS retention time: 2.34 min. (Condition 3)
MS ESI/APCI Dual posi: 590[M+H]⁺.

Working Examples 24-5 and 24-6

(1) A compound obtained by the same processes as those of Working Example 23-1(1) and (2) using the compound obtained in Reference Example 29-1 and the corresponding commercially available aldehyde was separated by preparative HPLC in accordance with the process of Working Examples 24-1 and 24-2(1). A fraction eluted at a retention time of 26 min was concentrated to afford the compound of Working Example 24-5 as a pale yellow oil (22 mg). A fraction eluted at a retention time of 31 min was concentrated to afford the compound of Working Example 24-6 as a pale yellow oil (17 mg).

(2) The same process as that of Working Example 2-1(2) was performed using the compounds of Working Examples 24-5 and 24-6 to afford the monohydrochloride of the compound of Working Example 24-5 as a pale yellow powder (12 mg) and the monohydrochloride of the compound of Working Example 24-6 as a pale yellow powder (10 mg), respectively.

Monohydrochloride of the Compound of Working Example 24-5

¹H NMR (600 MHz, DMSO-d₆) δ ppm 0.95-1.06 (m, 2 H), 1.20-1.27 (m, 2 H), 1.32-1.58 (m, 15 H), 1.63-1.84 (m, 6 H), 3.02-3.89 (m, 4 H), 4.18-4.65 (m, 4 H), 5.11-5.22 (m, 1 H), 6.90-7.02 (m, 2 H), 7.08-7.14 (m, 1 H), 7.35-7.46 (m, 1 H), 7.52-7.63 (m, 2 H), 7.84-8.00 (m, 1 H), 10.09 (s, 1 H).
LCMS retention time: 2.28 min. (Condition 3)
MS ESI/APCI Dual posi: 584[M+H]⁺.

Monohydrochloride of the Compound of Working Example 24-6

¹H NMR (600 MHz, DMSO-d₆) δ ppm 0.95-1.06 (m, 2 H), 1.20-1.27 (m, 2 H), 1.32-1.58 (m, 15 H), 1.63-1.84 (m, 6 H), 3.02-3.89 (m, 4 H), 4.18-4.65 (m, 4 H), 5.11-5.22 (m, 1 H), 6.90-7.02 (m, 2 H), 7.08-7.14 (m, 1 H), 7.35-7.46 (m, 1 H), 7.52-7.63 (m, 2 H), 7.84-8.00 (m, 1 H), 10.09 (s, 1 H).
LCMS retention time: 2.28 min. (Condition 3)
MS ESI/APCI Dual posi: 584[M+H]⁺.

Working Examples 24-7 and 24-8

(1) A compound obtained by the same processes as those of Working Example 23-1(1) and (2) using the compound obtained in Reference Example 29-1 and the corresponding commercially available aldehyde was separated by preparative HPLC in accordance with the process of Working Examples 24-1 and 24-2(1). A fraction eluted at a retention time of 25 min was concentrated to afford the compound of Working Example 24-7 as a pale yellow oil (18 mg). A fraction eluted at a retention time of 29 min was concentrated to afford the compound of Working Example 24-8 as a pale yellow oil (19 mg).

(2) The same process as that of Working Example 2-1(2) was performed using the compounds of Working Examples 24-7 and 24-8 to afford the monohydrochloride of the compound of Working Example 24-7 as a pale yellow powder (14 mg) and the monohydrochloride of the compound of Working Example 24-8 as a pale yellow powder (15 mg), respectively.

Monohydrochloride of the Compound of Working Example 24-7

¹H NMR (600 MHz, DMSO-d₆) δ ppm 0.95-1.06 (m, 2 H), 1.19-1.28 (m, 2 H), 1.37 (s, 9 H), 1.41-1.58 (m, 6 H), 1.63-1.85 (m, 6 H), 2.98-3.35 (m, 3 H), 3.41-3.94 (m, 2 H), 4.20-4.49 (m, 2 H), 4.58-4.84 (m, 2 H), 6.91-6.95 (m, 1 H), 6.96-7.01 (m, 1 H), 7.08-7.12 (m, 1 H), 7.32-7.45 (m, 1 H), 7.53-7.61 (m, 2 H), 8.97-9.04 (m, 2 H), 10.08 (s, 1 H).
LCMS retention time: 2.29 min. (Condition 3)
MS ESI/APCI Dual posi: 579[M+H]⁺.

Monohydrochloride of the Compound of Working Example 24-8

¹H NMR (600 MHz, DMSO-d₆) δ ppm 0.95-1.06 (m, 2 H), 1.19-1.28 (m, 2 H), 1.37 (s, 9 H), 1.41-1.58 (m, 6 H), 1.63-1.85 (m, 6 H), 2.98-3.35 (m, 3 H), 3.41-3.94 (m, 2 H), 4.20-4.49 (m, 2 H), 4.58-4.84 (m, 2 H), 6.91-6.95 (m, 1 H), 6.96-7.01 (m, 1 H), 7.08-7.12 (m, 1 H), 7.32-7.45 (m, 1 H), 7.53-7.61 (m, 2 H), 8.97-9.04 (m, 2 H), 10.08 (s, 1 H).
LCMS retention time: 2.29 min. (Condition 3)
MS ESI/APCI Dual posi: 579[M+H]⁺.

Working Examples 24-9 and 24-10

(1) A compound obtained by the same processes as those of Working Example 23-1(1) and (2) using the compound obtained in Reference Example 29-1 and the corresponding commercially available aldehyde was separated by preparative HPLC in accordance with the process of Working Examples 24-1 and 24-2(1). A fraction eluted at a retention time of 26 min was concentrated to afford the compound of Working Example 24-9 as a pale yellow oil (51 mg). A fraction eluted at a retention time of 35 min was concentrated to afford the compound of Working Example 24-10 as a pale yellow oil (45 mg).

(2) The same process as that of Working Example 2-1(2) was performed using the compounds of Working Examples 24-9 and 24-10 to afford the monohydrochloride of the compound of Working Example 24-9 as a pale yellow powder (37 mg) and the monohydrochloride of the compound of Working Example 24-10 as a pale yellow powder (37 mg), respectively.

Monohydrochloride of the Compound of Working Example 24-9

¹H NMR (600 MHz, DMSO-d₆) δ ppm 0.93-1.06 (m, 2 H), 1.18-1.29 (m, 2 H), 1.38-1.59 (m, 7 H), 1.63-1.94 (m, 5 H), 2.40-2.54 (m, 2 H), 2.96-4.06 (m, 4 H), 4.20-4.74 (m, 2 H), 4.85-5.05 (m, 1 H), 6.90-7.01 (m, 2 H), 7.07-7.13 (m, 1 H), 7.19-7.65 (m, 4 H), 9.18-9.40 (m, 1 H), 10.07 (s, 1 H).
LCMS retention time: 2.57 min. (Condition 3)
MS ESI/APCI Dual posi: 591[M+F1]⁺.

Monohydrochloride of the compound of Working Example 24-10

¹H NMR (600 MHz, DMSO-d₆) δ ppm 0.93-1.06 (m, 2H), 1.18-1.29 (m, 2 H), 1.38-1.59 (m, 7 H), 1.63-1.94 (m, 5 H), 2.40-2.54 (m, 2H), 2.96-4.06 (m, 4 H), 4.20-4.74 (m, 2 H), 4.85-5.05 (m, 1 H), 6.90-7.01 (m, 2 H), 7.07-7.13 (m, 1 H), 7.19-7.65 (m, 4 H), 9.18-9.40 (m, 1 H), 10.07 (s, 1 H).
LCMS retention time: 2.57 min. (Condition 3)
MS ESI/APCI Dual posi: 591[M+H]⁺.

Working Examples 24-11 and 24-12

(1) A compound obtained by the same processes as those of Working Example 23-1(1) and (2) using the compound obtained in Reference Example 29-1 and the corresponding commercially available aldehyde was separated by preparative HPLC in accordance with the process of Working Examples 24-1 and 24-2(1). A fraction eluted at a retention time of 31 min was concentrated to afford the compound of Working Example 24-11 as a pale yellow oil (16 mg). A fraction eluted at a retention time of 35 min was concentrated to afford the compound of Working Example 24-12 as a pale yellow oil (18 mg).

(2) The same process as that of Working Example 2-1(2) was performed using the compounds of Working Examples 24-11 and 24-12 to afford the monohydrochloride of the compound of Working Example 24-11 as a pale yellow powder (13 mg) and the monohydrochloride of the compound of Working Example 24-12 as a pale yellow powder (12 mg), respectively.

Monohydrochloride of the Compound of Working Example 24-11

$^1$H NMR (600 MHz, DMSO-$d_6$) δ ppm 0.96-1.06 (m, 2 H), 1.20-1.27 (m, 2 H), 1.41-1.58 (m, 6 H), 1.64-1.76 (m, 6 H), 2.44-2.53 (m, 2 H), 2.93-3.26 (m, 3 H), 3.63-3.75 (m, 1 H), 3.84-3.85 (m, 3 H), 4.09-4.29 (m, 1 H), 4.43-4.53 (m, 1 H), 4.67-4.77 (m, 1 H), 6.91-6.95 (m, 1 H), 6.97-7.00 (m, 1 H), 7.08-7.12 (m, 1 H), 7.35-7.40 (m, 1 H), 7.55-7.59 (m, 2 H), 7.66 (d, J=8.3 Hz, 1 H), 7.95 (s, 1 H), 10.09 (s, 1 H).

LCMS retention time: 1.85 min. (Condition 3)
MS ESI/APCI Dual posi: 525[M+H]$^+$.

Monohydrochloride of the Compound of Working Example 24-12

$^1$H NMR (600 MHz, DMSO-$d_6$) δ ppm 0.96-1.06 (m, 2 H), 1.20-1.27 (m, 2 H), 1.41-1.58 (m, 6 H), 1.64-1.76 (m, 6 H), 2.44-2.53 (m, 2 H), 2.93-3.26 (m, 3 H), 3.63-3.75 (m, 1 H), 3.84-3.85 (m, 3 H), 4.09-4.29 (m, 1 H), 4.43-4.53 (m, 1 H), 4.67-4.77 (m, 1 H), 6.91-6.95 (m, 1 H), 6.97-7.00 (m, 1 H), 7.08-7.12 (m, 1 H), 7.35-7.40 (m, 1 H), 7.55-7.59 (m, 2 H), 7.66 (d, J=8.3 Hz, 1 H), 7.95 (s, 1 H), 10.09 (s, 1 H).

LCMS retention time: 1.85 min. (Condition 3)
MS ESI/APCI Dual posi: 525[M+H]$^+$.

The structures of the compounds of Working Examples 24-3 to 24-12 are shown in Table 36-1.

TABLE 36-1

| Working Ex. | Structure |
|---|---|
| 24-3, 24-4 | (cyclopentyl-propyl-fluorophenyl-sulfonamide-tetrahydroisoquinoline-CH(CH₃)-pyridine-CF₃) |
| 24-5, 24-6 | (cyclopentyl-propyl-fluorophenyl-sulfonamide-tetrahydroisoquinoline-CH(CH₃)-thiazole-tBu) |
| 24-7, 24-8 | (cyclopentyl-propyl-fluorophenyl-sulfonamide-tetrahydroisoquinoline-CH(CH₃)-pyrimidine-tBu) |
| 24-9, 24-10 | (cyclopentyl-propyl-fluorophenyl-sulfonamide-tetrahydroisoquinoline-CH(CH₃)-pyrimidine-CF₃) |

| Working Ex. | Structure |
|---|---|
| 24-11<br>24-12 | 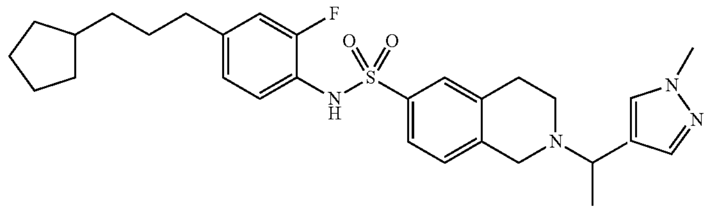 |

Working Example 25-1

2-[1-(4-tert-Butylbenzyl)cyclopropyl]-N-[4-(3-cy-clopentylpropyl)-2-fluorophenyl]-1,2,3,4-tetrahy-droisoquinoline-6-sulfonamide

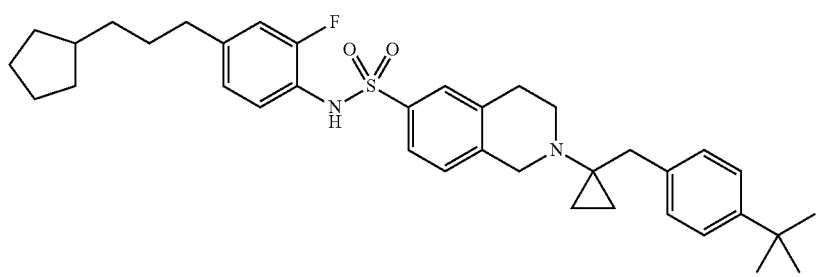

[Formula 78]

(1) In accordance with the process of Working Example 1-1, the compound obtained in Reference Example 29-1 (1.61 g, 3.00 mmol) was used to afford 2-[(4-tert-butylphenyl)acetyl]-N-[4-(3-cyclopentylpropyl)-2-fluorophenyl]-N-(4-methoxybenzyl)-1,2,3,4-tetrahydroisoquinoline-6-sulfonamide as a colorless amorphous substance (2.32 g).

(2) Tetraisopropyl orthotitanate (97 µL, 0.33 mmol) and ethyl magnesium bromide (diethyl ether solution, 3 mol/L, 0.25 mL, 0.75 mmol) were added to a solution of 2-[(4-tert-butylphenyl)acetyl]-N-[4-(3-cyclopentylpropyl)-2-fluorophenyl]-N-(4-methoxybenzyl)-1,2,3,4-tetrahydroisoquinoline-6-sulfonamide obtained (213 mg, 0.30 mmol) in tetrahydrofuran (5 mL) under a nitrogen atmosphere. The mixture was stirred at room temperature for 16 hr. Water and saturated aqueous ammonium chloride solution were added to the reaction mixture and the mixture was stirred and then filtered through Celite (registered trademark). The filtrate was concentrated under reduced pressure, 1 mol/mL aqueous sodium hydroxide solution was added thereto, and the mixture was extracted with ethyl acetate. The organic layer was washed with brine and dried over magnesium sulfate. The desiccant was filtered off, followed by concentration under reduced pressure. The residue was purified by silica gel column chromatography (hexane only→hexane:ethyl acetate=3:2) to afford 2-[1-(4-tert-butylbenzyl)cyclopropyl]-N-[4-(3-cyclopentylpropyl)-2-fluorophenyl]-N-(4-methoxybenzyl)-1,2,3,4-tetrahydroisoquinoline-6-sulfonamide as a pale yellow amorphous substance (142 mg).

(3) 2-[1-(4-tert-Butylbenzyl)cyclopropyl]-N-[4-(3-cyclopentylpropyl)-2-fluorophenyl]-N-(4-methoxybenzyl)-1,2,3,4-tetrahydroisoquinoline-6-sulfonamide obtained (142 mg, 0.20 mmol) was used to afford the title compound as a pale yellow oil (109 mg) in accordance with the process of Working Example 8-(2).

(4) The monohydrochloride of the title compound was obtained as a colorless powder (93 mg) in accordance with the process of Working Example 2-1-(2).

$^1$H NMR (600 MHz, DMSO-d$_6$) δ ppm 0.50-0.62 (m, 2 H), 0.96-1.05 (m, 2 H), 1.20-1.29 (m, 13 H), 1.41-1.58 (m, 6 H), 1.65-1.76 (m, 3 H), 2.44-2.55 (m, 2 H), 3.08-3.53 (m, 4 H), 3.63-3.82 (m, 2 H), 4.47-4.58 (m, 1 H), 4.80-4.92 (m, 1 H), 6.91-7.03 (m, 2 H), 7.09-7.22 (m, 3 H), 7.29-7.47 (m, 3 H), 7.56-7.67 (m, 2 H), 10.12 (s, 1 H).

LCMS retention time: 2.87 min. (Condition 3)

MS ESI/APCI Dual posi: 603[M+H]$^+$.

The compound of Working Example 25-2 was obtained by using the corresponding commercially available carboxylic acid in accordance with the process of Working Example 25-1.

Working Example 25-2

$^1$H NMR (600 MHz, DMSO-d$_6$) δ ppm 0.95-1.05 (m, 2 H), 1.15-1.28 (m, 6 H), 1.37 (s, 9 H), 1.41-1.57 (m, 6 H), 1.62-1.74 (m, 3 H), 2.46-2.52 (m, 2 H), 2.79-3.33 (m, 3 H), 3.69-4.99 (m, 3 H), 6.89-6.99 (m, 2 H), 7.04-7.09 (m, 1 H), 7.25-7.38 (m, 1 H), 7.44-7.55 (m, 2 H), 7.62-7.78 (m, 1 H), 8.09-8.31 (m, 1 H), 8.69-8.85 (m, 1 H), 10.02 (s, 1 H).

LCMS retention time: 1.05 min. (Condition 5-2)

MS (ESI posi) m/z: 590[M+H]$^+$.

The structure of the compound of Working Example 25-2 is shown in Table 37-1.

TABLE 37-1

| Working Ex. | Structure |
|---|---|
| 25-2 | 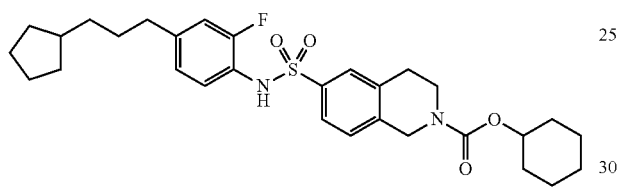 |

Working Example 26-1

Cyclohexyl 6-{[4-(3-cyclopentylpropyl)-2-fluorophenyl]sulfamoyl}-3,4-dihydroisoquinoline-2(1H)-carboxylate

[Formula 79]

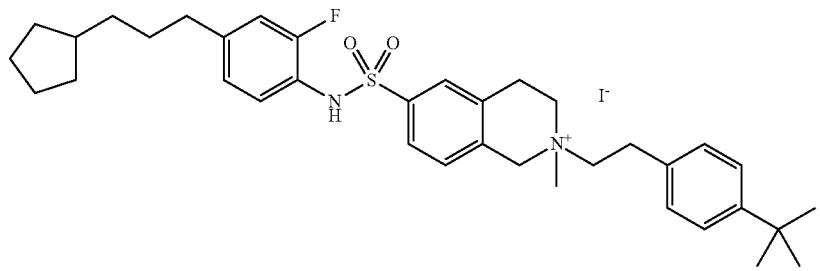

(1) Triphosgene (37.4 mg, 0.13 mmol) and triethylamine (84 μL, 0.60 mmol) were added to a solution of cyclohexanol (38 μL, 0.36 mmol) in chloroform (5 mL) at 0° C. under a nitrogen atmosphere, and the mixture was stirred at the same temperature for 30 min. To the reaction mixture were added the compound obtained in Reference Example 29-1 (161 mg, 0.30 mmol) and triethylamine (46 μL, 0.33 mmol), and the mixture was warmed to room temperature and stirred for 15 hr. Water and saturated aqueous sodium hydrogen carbonate solution were added thereto and the mixture was extracted with chloroform. The organic layer was concentrated under reduced pressure and the residue was purified by silica gel column chromatography (hexane:ethyl acetate=7:3) to afford cyclohexyl 6-{[4-(3-cyclopentylpropyl)-2-fluorophenyl](4-methoxybenzyl)sulfamoyl}-3,4-dihydroisoquinoline-2(1H)-carboxylate as a colorless oil (178 mg).

(2) Cyclohexyl 6-{[4-(3-cyclopentylpropyl)-2-fluorophenyl](4-methoxybenzyl)sulfamoyl}-3,4-dihydroisoquinoline-2(1H)-carboxylate obtained (178 mg, 0.27 mmol) was used to afford the title compound as a colorless oil (103 mg) in accordance with the process of Working Example 8-(2).

$^1$H NMR (300 MHz, CDCl$_3$) δ ppm 0.95-1.11 (m, 2 H), 1.22-1.62 (m, 14 H), 1.65-1.79 (m, 5 H), 1.82-1.92 (m, 2 H), 2.52 (t, J=7.7 Hz, 2 H), 2.82 (t, J=5.8 Hz, 2 H), 3.67 (t, J=5.8 Hz, 2 H), 4.63 (s, 2 H), 4.67-4.77 (m, 1 H), 6.51-6.56 (m, 1 H), 6.74-6.82 (m, 1 H), 6.88-6.94 (m, 1 H), 7.13-7.18 (m, 1 H), 7.41-7.57 (m, 3 H).

LCMS retention time: 5.88 min. (Condition 1-2-3)

MS (ESI posi) m/z: 543 [M+H]$^+$.

Working Example 27-1

2-[2-(4-tert-Butylphenyl)ethyl]-6-{[4-(3-cyclopentylpropyl)-2-fluorophenyl]sulfamoyl}-2-methyl-1,2,3,4-tetrahydroisoquinolinium iodide

[Formula 80]

Methyl iodide (248 μL, 4.00 mmol) was added to a solution of compound 6-17 as obtained in Working Example 6 (232 mg, 0.40 mmol) in acetonitrile (2 mL), and a reaction container used was shaded, followed by stirring at room temperature for 2 hr. The mixture was concentrated under reduced pressure, ethyl acetate and diethyl ether were added to the residue, and the mixture was stirred overnight. A precipitated powder was collected by filtration to afford the title compound as a colorless powder (245 mg).

$^1$H NMR (300 MHz, CDCl$_3$) δ ppm 0.95-1.11 (m, 2 H), 1.23-1.34 (m, 11 H), 1.44-1.62 (m, 6 H), 1.65-1.78 (m, 3 H), 2.48-2.56 (m, 2 H), 3.07-3.28 (m, 4 H), 3.51 (s, 3 H), 3.77-4.29 (m, 4 H), 4.94-5.18 (m, 2 H), 6.77-6.84 (m, 1 H), 6.88-6.94 (m, 1 H), 7.07-7.12 (m, 1 H), 7.18-7.25 (m, 3 H), 7.29-7.41 (m, 3 H), 7.60-7.65 (m, 1 H), 7.71-7.74 (m, 1 H).

LCMS retention time: 2.06 min. (Condition 3)

MS ESI/APCI Dual posi: 591 [M]$^+$.

Test Examples

The MGAT2 inhibitory action of the inventive compound may be evaluated in accordance with known methods such as those described in Test Examples below.

The MGAT2 inhibitory action of the inventive compound was measured by the methods described in Test Examples as shown below. The MGAT enzyme activity was measured based on the amount of an indicator, free Coenzyme A (CoA) which is generated by the reaction shown below, using a sulfhydryl reactive pigment (7-diethylamino-3-(4-maleimidophenyl)-4-methylcoumarin; hereinafter, sometimes abbreviated as CPM).

2-Monoacylglycerol+fatty acid CoA→diacylglycerol+free CoA

Test Example 1

Test of MGAT2 Inhibitory Action

A test for MGAT2 inhibitory action of test compounds was conducted in accordance with a partially modified version of the method described in John F. Lockwood et al., Am. J. Physiol. Endocrinol. Metab., 2003, 285, E927.

Bac-to-Bac Baculovirus Expression System (Life Technologies Japan) was used to express human MGAT2 in insect cells (Sf9) (Life Technologies Japan). These cells were sonicated and centrifuged at 100,000 g×1 hr to give a precipitate. The precipitate was used as a human MGAT2 enzyme fraction in this assay.

This test was conducted using a black flat-bottom 96-well plate (Corning). A buffer solution with final concentrations of 5 mM magnesium chloride, 100 mM sucrose and 100 mM Tris-HCl (pH=7.5) was prepared and test compounds prepared in various concentrations using dimethyl sulfoxide were added thereto to give a final dimethyl sulfoxide concentration of 1%. The MGAT2 enzyme fraction was added thereto to give a final concentration of 0.5 µg/ml and phosphatidylcholine, 2-monooleoyl glycerol and oleoyl-CoA were added thereto to give final concentrations of 7.5 µM, 0.78 µM and 5.3 µM, respectively, before starting a reaction. The reaction was performed at room temperature for 20 min.

After 20 min, a CPM-containing solution was added thereto to give a final concentration of 5 µM before stopping the MGAT reaction. After 1 hr, a fluorescence detector (Infinite 200 from Tecan Japan) was used to measure the CPM fluorescence value of each well (excitation 380 nm, emission 460 nm).

The fluorescence value of the well as measured without addition of the test compounds was taken as 100%, and the concentrations of the test compounds at which 50% of produced free CoA was inhibited in the presence of the test compounds ($IC_{50}$ values) were calculated by non-linear fitting.

As a result of the foregoing test, the inventive compounds had $IC_{50}$ values of 30000 nM or less. Among the compounds, those having $IC_{50}$ values of 300 nM or less are exemplified in Tables 38-1 and 38-2.

TABLE 38-1

| Working Ex. No. | Activity Value [nM] |
|---|---|
| 1-4 | 211 |
| 1-5 | 154 |
| 1-6 | 88 |
| 1-7 | 292 |
| 4-1 | 149 |
| 5-1 | 76 |
| 6-17 | 28 |
| 6-18 | 35 |
| 6-19 | 62 |
| 6-26 | 218 |
| 6-27 | 135 |
| 6-28 | 53 |
| 6-30 | 214 |
| 6-31 | 31 |
| 6-32 | 31 |
| 6-33 | 26 |
| 6-34 | 36 |
| 6-35 | 65 |
| 6-36 | 253 |
| 6-44 | 258 |
| 6-45 | 286 |
| 6-48 | 49 |
| 6-54 | 180 |
| 6-63 | 62 |
| 6-64 | 40 |
| 6-65 | 51 |
| 6-66 | 203 |
| 6-75 | 24 |
| 6-78 | 228 |
| 7-19 | 195 |
| 7-29 | 134 |
| 7-32 | 42 |
| 7-35 | 220 |
| 7-45 | 199 |
| 7-50 | 273 |
| 7-54 | 162 |
| 7-56 | 52 |
| 7-60 | 233 |
| 8-1 | 70 |
| 8-2 | 173 |
| 8-3 | 133 |
| 9-20 | 212 |
| 9-21 | 164 |
| 10-3 | 26 |
| 10-4 | 39 |
| 10-5 | 25 |
| 10-6 | 44 |
| 10-7 | 31 |
| 10-8 | 62 |
| 10-9 | 96 |
| 10-10 | 97 |
| 10-11 | 80 |
| 10-12 | 42 |
| 10-13 | 66 |
| 10-14 | 106 |
| 10-15 | 44 |

TABLE 38-2

| Working Ex. No. | Activity Value [nM] |
|---|---|
| 10-16 | 68 |
| 11-2 | 121 |
| 11-3 | 116 |
| 11-4 | 235 |
| 14-3 | 76 |
| 14-4 | 98 |
| 14-9 | 168 |
| 14-16 | 164 |
| 14-18 | 147 |
| 14-21 | 193 |
| 14-35 | 178 |
| 14-36 | 69 |
| 17-1 | 40 |
| 17-2 | 45 |
| 17-5 | 24 |
| 17-6 | 39 |
| 17-7 | 79 |

TABLE 38-2-continued

| Working Ex. No. | Activity Value [nM] |
|---|---|
| 18-6 | 43 |
| 18-7 | 7 |
| 18-10 | 230 |
| 18-11 | 29 |
| 18-12 | 26 |
| 18-14 | 127 |
| 18-15 | 56 |
| 18-16 | 10 |
| 18-18 | 136 |
| 18-19 | 125 |
| 18-21 | 59 |
| 18-22 | 120 |
| 18-23 | 92 |
| 18-24 | 62 |
| 18-25 | 33 |
| 18-26 | 185 |
| 18-29 | 128 |
| 18-31 | 266 |
| 18-32 | 58 |
| 19-2 | 30 |
| 19-3 | 4 |
| 19-4 | 2 |
| 19-7 | 99 |
| 19-8 | 28 |
| 19-11 | 128 |
| 19-12 | 23 |
| 22-2 | 256 |
| 23-1 | 13 |
| 23-2 | 14 |
| 26-1 | 217 |

Test Example 2

Test of MGAT2 Inhibitory Action

An MGAT2 inhibition test for test compounds was conducted in accordance with a partially modified version of the method described in John F. Lockwood et al., Am. J. Physiol. Endocrinol. Metab., 2003, 285, E927.

A 10 mg/mL microsomal fraction of human small intestine (duodenum- and jejunum-derived fraction purchased from Becton Dickinson Japan) was used as an enzyme source.

The test was conducted using a flat-bottom 96-well plate (Corning).

A buffer solution with final concentrations of 5 mM magnesium chloride, 1.25 mg/ml bovine serum albumin and 100 mM Tris-HCl (pH=7.5) was prepared and the microsomal fraction of human small intestine was added thereto to give a final concentration of 5 μg/ml. Test compounds prepared in various concentrations using dimethyl sulfoxide were added thereto to give a final dimethyl sulfoxide concentration of 1% and a reaction was performed at room temperature for 5 min. Thereafter, final concentrations of 5 mM magnesium chloride, 1.25 mg/ml bovine serum albumin, 100 mM Tris-HCl (pH=7.5), 4 μM oleoyl-CoA, 1.25 μM 2-monooleoyl glycerol and 0.125 μM $^3$H-labeled 2-monooleoyl glycerol (Muromachi Yakuhin Co., Ltd.) were added thereto to give a total volume of 100 μl. This mixture was reacted at room temperature for 30 min.

The reaction was stopped by adding an equal amount of isopropanol to the reaction mixture. The substrate contained in the reaction mixture ($^3$H-labeled 2-monooleoyl glycerol) and the reaction products ($^3$H-labeled dioleoyl glycerol and trioleoyl glycerol) were separated by adsorbing them onto an octadecylsilane resin (Wako gel 50C18) (Wako Pure Chemical Industries, Ltd.), removing the substrate by use of 80% isopropanol, and then eluting the reaction products with 100% isopropanol. The amounts of the reaction products were measured with MicroBeta (PerkinElmer Japan). The amounts of produced $^3$H-labeled dioleoyl glycerol and trioleoyl glycerol as measured without addition of the test compounds were taken as 100%, and the concentrations of the test compounds at which 50% of the products was inhibited in the presence of the test compounds ($IC_{50}$ values) were calculated by non-linear fitting.

As a result of the foregoing test, the inventive compounds had $IC_{50}$ values of 30000 nM or less. Among the compounds, those having $IC_{50}$ values of 300 nM or less are exemplified in Table 39-1.

TABLE 39-1

| Working Ex. No. | Activity Value [nM] |
|---|---|
| 2-4 | 92 |
| 2-5 | 180 |
| 2-6 | 174 |
| 2-7 | 234 |
| 2-8 | 213 |
| 2-9 | 142 |
| 2-10 | 198 |
| 6-82 | 182 |
| 6-83 | 193 |
| 6-84 | 248 |
| 6-85 | 71 |
| 6-88 | 248 |
| 6-90 | 164 |
| 7-65 | 118 |
| 7-70 | 81 |
| 7-71 | 57 |
| 7-74 | 105 |
| 7-76 | 16 |
| 7-80 | 66 |
| 7-81 | 45 |
| 7-82 | 189 |
| 7-88 | 145 |
| 7-91 | 140 |
| 8-5 | 29 |
| 8-6 | 35 |
| 8-7 | 235 |
| 8-8 | 178 |
| 8-9 | 160 |
| 8-10 | 148 |
| 8-11 | 169 |
| 8-12 | 158 |
| 8-13 | 137 |
| 8-14 | 68 |
| 8-15 | 204 |
| 9-23 | 46 |
| 9-24 | 46 |
| 20-2 | 14 |
| 20-3 | 223 |
| 20-4 | 5 |
| 23-3 | 13 |
| 23-6 | 115 |
| 24-1 | 4 |
| 24-2 | 29 |
| 24-3 | 42 |
| 24-4 | 185 |
| 24-5 | 10 |
| 24-6 | 75 |
| 24-7 | 57 |
| 24-8 | 34 |
| 24-9 | 131 |
| 24-10 | 100 |
| 24-11 | 159 |
| 25-1 | 200 |
| 25-2 | 60 |

Formulation Examples of the inventive compounds will be shown below.

Formulation Example 1

A granule comprising the following ingredients is produced:

| Ingredients | |
| --- | --- |
| Compound represented by formula (I) | 10 mg |
| Lactose | 700 mg |
| Corn starch | 274 mg |
| HPC-L | 16 mg |
| | 1000 mg |

A compound represented by formula (I) and lactose are passed through a 60-mesh sieve. Corn starch is passed through a 120-mesh sieve. These ingredients are mixed in a V-shaped mixer. To the mixed powder is added low-viscosity aqueous hydroxypropyl cellulose (HPC-L) solution, and the mixture is kneaded, granulated (extrusion granulation, pore size 0.5-1 mm) and then dried. The dried granule obtained is passed through a vibrating sieve (12/60 mesh) to give a granule.

Formulation Example 2

A powder for encapsulation comprising the following ingredients is produced.

| Ingredients | |
| --- | --- |
| Compound represented by formula (I) | 10 mg |
| Lactose | 79 mg |
| Corn starch | 10 mg |
| Magnesium stearate | 1 mg |
| | 100 mg |

A compound represented by formula (I) and lactose are passed through a 60-mesh sieve. Corn starch is passed through a 120-mesh sieve. These ingredients and magnesium stearate are mixed in a V-shaped mixer. A No. 5 hard gelatin capsule is filled with 100 mg of the 10% powder.

Formulation Example 3

A granule for encapsulation comprising the following ingredients is produced.

| Ingredients | |
| --- | --- |
| Compound represented by formula (I) | 15 mg |
| Lactose | 90 mg |
| Corn starch | 42 mg |
| HPC-L | 3 mg |
| | 150 mg |

A compound represented by formula (I) and lactose are passed through a 60-mesh sieve. Corn starch is passed through a 120-mesh sieve. These ingredients are mixed in a V-shaped mixer. To the mixed powder is added low-viscosity aqueous hydroxypropyl cellulose (HPC-L) solution, and the mixture is kneaded, granulated and then dried. The dried granule obtained is passed and size-regulated through a vibrating sieve (12/60 mesh) and a No. 4 hard gelatin capsule is filled with 150 mg of the granule.

Formulation Example 4

A tablet comprising the following ingredients is produced.

| Ingredients | |
| --- | --- |
| Compound represented by formula (I) | 10 mg |
| Lactose | 90 mg |
| Microcrystalline cellulose | 30 mg |
| Magnesium stearate | 5 mg |
| CMC-Na | 15 mg |
| | 150 mg |

A compound represented by formula (I), lactose, microcrystalline cellulose and CMC-Na (sodium carboxymethylcellulose) are passed through a 60-mesh sieve and mixed. To the mixed powder is added magnesium stearate to give a mixed powder for formulation. The powder is directly compressed to give 150 mg of a tablet.

Industrial Applicability

Since the inventive compounds have superior MGAT2 inhibitory activity, thus enabling the provision of pharmaceutical products effective in the prevention or treatment of diseases attributable to lipid metabolism abnormality, in particular, obesity, hyperlipidemia, diseases derived therefrom, and the like.

The invention claimed is:
1. A compound represented by the following formula (I) or a pharmaceutically acceptable salt thereof:

[Formula 1]

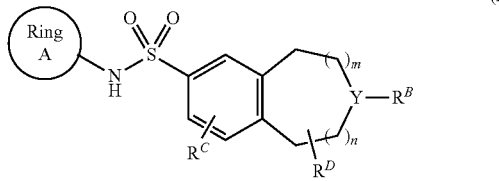

(I)

wherein

Ring A represents a partially saturated heteroaryl group which may be substituted by 1 or 2 substituents, which may be the same or different, selected from the group consisting of:
  a $C_{1-8}$ alkyl group, and
  an oxo group,
an aryl group or a heteroaryl group, which aryl group and heteroaryl group may be each substituted by 1 to 3 substituents, which may be the same or different, selected from the group consisting of (i) to (vii) below:
  (i) a halogen atom,
  (ii) a hydroxy group,
  (iii) a $C_{1-8}$ alkyl group which may be substituted by 1 to 3 substituents, which may be the same or different, selected from the group consisting of:
    a hydroxy group,
    a halogen atom,
    a $C_{1-8}$ alkoxy group which may be substituted by one saturated heterocyclyl group,
    a $C_{3-8}$ cycloalkyl group,
    a saturated heterocyclyl group, and
    an aryl group, (iv) a $C_{1-8}$ alkoxy group which may be substituted by 1 to 3 substituents, which may be the same or different, selected from the group consisting of:
(iv-1) a halogen atom,
(iv-2) an oxo group,
(iv-3) a $C_{3-8}$ cycloalkyl group,
(iv-4) a saturated heterocyclyl group which may be substituted by 1 or 2 substituents, which may be the same or different, selected from the group consisting of:
a halogen atom,
a $C_{1-8}$ alkyl group, and
an oxo group,
(iv-5) an aryl group,
(iv-6) a heteroaryl group,
(iv-7) a $C_{1-8}$ alkoxy group which may be substituted by 1 to 3 substituents, which may be the same or different, selected from the group consisting of:
a halogen atom,
a saturated heterocyclyl group, and
a $C_{1-8}$ alkoxy group,
(iv-8) a $C_{3-8}$ cycloalkyloxy group,
(iv-9) an aryloxy group which may be substituted by one substituent selected from the group consisting of:
a halogen atom,
a $C_{1-8}$ alkyl group which may be substituted by 1 to 3 halogen atoms, and
a $C_{1-8}$ alkoxy group,
(iv-10) a $C_{1-8}$ alkylsulfonyl group, and
(iv-11) an arylsulfonyl group,
(v) a $C_{2-8}$ alkenyloxy group,
(vi) a mono$C_{1-8}$ alkylamino group which may be substituted by one aryl group, and
(vii) a di$C_{1-8}$ alkylamino group,
$R^B$ represents a $C_{4-18}$ alkyl group which may be substituted by 1 to 3 substituents, which may be the same or different, selected from the group consisting of:
a halogen atom, and
a $C_{3-8}$ cycloalkyl group,
a $C_{3-8}$ cycloalkyl group,
a partially saturated aryl group,
an aryl group, or
the following formula (II):

[Formula 2]

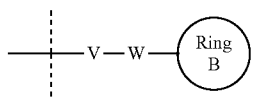

(II)

wherein
V represents the formula —$CR^{11}R^{12}$— (wherein $R^{11}$ and $R^{12}$, which may be the same or different, each represent a hydrogen atom or a $C_{1-4}$ alkyl group, or $R^{11}$ and $R^{12}$, taken together with the adjacent carbon atom, may form $C_{3-6}$ cycloalkane), —CO—, —CO—O— or —CO—NH—,
W represents a single bond or
either a $C_{1-3}$ alkylene group which may be substituted by 1 or 2 substituents, which may be the same or different, selected from the group consisting of:
a fluorine atom,
an amino group which may be substituted by one $C_{1-4}$ alkyl group, and
an oxo group, or a $C_{1-3}$ alkylene group in which one carbon atom that forms the $C_{1-3}$ alkylene group may form a $C_{3-6}$ cycloalkane-1,1-diyl group, and
Ring B represents a $C_{3-8}$ cycloalkyl group which may be substituted by one $C_{1-8}$ alkyl group, a $C_{3-8}$ cycloalkenyl group which may be crosslinked with a $C_{1-4}$ alkanediyl group or may be substituted by one $C_{1-8}$ alkyl group,
a partially saturated heteroaryl group which may be substituted by 1 or 2 halogen atoms,
a saturated heterocyclyl group,
an aryl group or a heteroaryl group, which aryl group and heteroaryl group may be each substituted by 1 to 3 substituents, which may be the same or different, selected from the group consisting of:
(a) a halogen atom,
(b) a hydroxy group,
(c) a $C_{1-8}$ alkyl group and a $C_{1-8}$ alkoxy group, which $C_{1-8}$ alkyl group and $C_{1-8}$ alkoxy group may be each substituted by 1 to 4 substituents, which may be the same or different, selected from the group consisting of:
a halogen atom,
a hydroxy group,
a $C_{3-8}$ cycloalkyl group, and
an aryl group,
(d) a $C_{3-8}$ cycloalkyl group,
(e) an aryl group and a heteroaryl group, which aryl group and heteroaryl group may be each substituted by 1 or 2 substituents, which may be the same or different, selected from the group consisting of:
a halogen atom, and
a $C_{1-8}$ alkyl group which may be substituted by 1 to 3 halogen atoms, and
(f) a $C_{1-8}$ alkylsulfonyl group,
$R^C$ represents a hydrogen atom,
a halogen atom,
a $C_{1-4}$ alkyl group which may be substituted by 1 to 3 halogen atoms,
an aryl group, or
a heteroaryl group,
$R^D$ represents a hydrogen atom or a $C_{1-4}$ alkyl group which may be substituted by 1 to 3 halogen atoms,
Y represents a nitrogen atom or the formula $N^+(R^F)$,
$R^F$ represents a $C_{1-4}$ alkyl group,
m represents an integer of 0 or 1, and n is 0 provided that the following compounds are excluded:
2-(4-fluorobenzoyl)—N—(thiazol-2-yl)isoindoline-5-sulfonamide,
2-(2-(1H-indol-1-yl)propanoyl)—N—(thiazol-2-yl)isoindoline-5-sulfonamide,
2-(2-(6-chloro-3,4-dihydroquinolin-1(2H)-yl)acetyl)—N—(pyrimidin-4-yl)isoindoline-5-sulfonamide,
2-(2-(7-chloro-1H-indol-yl)acetyl)—N—(pyrimidin-4-yl)isoindoline-5-sulfonamide,
2-(2-(6-chloro-3,4-dihydroquinolin-1(2H)-yl)propanoyl)—N—(1,2,4-thiadiazol-5-yl)isoindoline-5-sulfonamide,
(R)—N—(6-chloropyridazin-3-yl)-2-(2-(4-fluoro-1H-indol-1-yl)propanoyl)isoindoline-5-sulfonamide,
(R)-2-(2-(4-fluoro-1H-indol-1-yl)propanoyl)—N—(1,2,4-thiadiazol-5-yl)isoindoline-5-sulfonamide,
(S)-2-(2-(6-chloro-3,4-dihydroquinolin-1(2H)-yl)propanoyl)—N—(5-methyl-1,3,4-thiadiazol-2-yl)isoindoline-5-sulfonamide,
(R)—N—(5-ethyl-1,3,4-thiadiazol-2-yl)-2-(2-(4-fluoro-1H-indol-yl)propanoyl)isoindoline-5-sulfonamide, 2-(2-(6-chloro-3,4-dihydroquinolin-1(2H)-yl)acetyl)—N—(1,2,4-thiadiazol-5-yl)isoindoline-5-sulfonamide,
(S)-2-(2-(4-fluoro-1H-indol-1-yl)propanoyl)—N—(1,2,4-thiadiazol-5-yl)isoindoline-5-sulfonamide,
2-(3-(5-chloro-1H-indol-1-yl)propanoyl)—N—(1,2,4-thiadiazol-5-yl)isoindoline-5-sulfonamide,
2-(2-(6-chloro-3,4-dihydroquinolin-1(2H)-yl)propanoyl)-N-(5-ethyl-1,3,4-thiadiazol-2-yl)isoindoline-5-sulfonamide,
(S)-2-(2-(6-chloro-3,4-dihydroquinolin-1(2H)-yl)propanoyl)-N-(6-chloropyridazin-3-yl)isoindoline-5-sulfonamide,
(S)-2-(2-(1H-indol-1-yl)propanoyl)-N-(1,2,4-thiadiazol-5-yl)isoindoline-5-sulfonamide,
2-(3-(5-chloro-1H-indol-1-yl)propanoyl)-N-(thiazol-2-yl)isoindoline-5-sulfonamide,
2-(2-(4-methoxyphenyl)acetyl)-N-(thiazol-2-yl)isoindoline-5-sulfonamide,
(S)-2-(2-(4-fluoro-1H-indol-1-yl)propanoyl)-N-(pyrimidin-4-yl)isoindoline-5-sulfonamide,
(R)-2-(2-(1H-indol-1-yl)propanoyl)-N-(1,2,4-thiadiazol-5-yl)isoindoline-5-sulfonamide,
2-(2-(7-chloro-1H-indol-1-yl)acetyl)-N-(thiazol-2-yl)-1,2,3,4-tetrahydroisoquinoline-7-sulfonamide,
2-(2,4-difluorobenzoyl)-N-(thiazol-2-yl)-1,2,3,4-tetrahydroisoquinoline-7-sulfonamide,
2-(2,5-difluorobenzoyl)-N-(thiazol-2-yl)-1,2,3,4-tetrahydroisoquinoline-7-sulfonamide,
2-(4-fluorobenzoyl)-N-(thiazol-2-yl)-1,2,3,4-tetrahydroisoquinoline-7-sulfonamide,
2-(3-(5-chloro-1H-indol-1-yl)propanoyl)-N-(thiazol-2-yl)-1,2,3,4-tetrahydroisoquinoline-7-sulfonamide,
2-(2-fluorobenzoyl)-N-(thiazol-2-yl)-1,2,3,4-tetrahydroisoquinoline-7-sulfonamide,
2-(2,4-dichlorobenzoyl)-N-(thiazol-2-yl)-1,2,3,4-tetrahydroisoquinoline-7-sulfonamide, and
2-(4-methoxybenzoyl)-N-(thiazol-2-yl)-1,2,3,4-tetrahydroisoquinoline-7-sulfonamide.

2. The compound of the formula (I) or pharmaceutically acceptable salt thereof according to claim 1, wherein
Ring A is a partially saturated heteroaryl group which may be substituted by 1 or 2 substituents, which may be the same or different, selected from the group consisting of:
a $C_{1-8}$ alkyl group, and
an oxo group,
an aryl group or a heteroaryl group, which aryl group and heteroaryl group may be each substituted by 1 to 3 substituents, which may be the same or different, selected from the group consisting of:
a halogen atom,
a hydroxy group,
a $C_{1-8}$ alkyl group which may be substituted by 1 to 3 substituents, which may be the same or different, selected from the group consisting of:
a halogen atom,
a $C_{3-8}$ cycloalkyl group, and
an aryl group,
a $C_{1-8}$ alkoxy group which may be substituted by 1 to 3 substituents, which may be the same or different, selected from the group consisting of:
a halogen atom,
an oxo group,
a $C_{3-8}$ cycloalkyl group,
a saturated heterocyclyl group which may be substituted by 1 or 2 substituents, which may be the same or different, selected from the group consisting of a $C_{1-8}$ alkyl group, and an oxo group,
an aryl group,
a heteroaryl group,
a $C_{1-8}$ alkoxy group which may be substituted by one $C_{1-8}$ alkoxy group,
a $C_{3-8}$ cycloalkyloxy group, and
an aryloxy group which may be substituted by one substituent selected from the group consisting of a halogen atom, a $C_{1-8}$ alkyl group which may be substituted by 1 to 3 halogen atoms, and a $C_{1-8}$ alkoxy group,
a $C_{2-8}$ alkenyloxy group,
a mono$C_{1-8}$ alkylamino group which may be substituted by one aryl group, and
a di$C_{1-8}$ alkylamino group, and
$R^B$ is a $C_{4-18}$ alkyl group, a $C_{3-8}$ cycloalkyl group, a partially saturated aryl group, an aryl group, or the following formula (II):

[Formula 3]

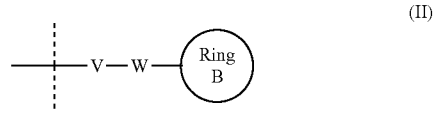

(II)

wherein
V represents the formula —$CR^{11}R^{12}$—(wherein $R^{11}$ and $R^{12}$ each represent a hydrogen atom or a $C_{1-4}$ alkyl group), —CO— or —CO—NH—,
W represents a single bond or
either a $C_{1-3}$ alkylene group which may be substituted by 1 or 2 substituents, which may be the same or different, selected from the group consisting of:
a fluorine atom,
an amino group which may be substituted by one $C_{1-4}$ alkyl group, and
an oxo group, or
a $C_{1-3}$ alkylene group in which one carbon atom that forms the $C_{1-3}$ alkylene group may form a $C_{3-6}$ cycloalkane-1,1-diyl group, and
Ring B represents a $C_{3-8}$ cycloalkyl group,
a partially saturated heteroaryl group,
an aryl group or a heteroaryl group, which aryl group and heteroaryl group may be each substituted by 1 to 3 substituents, which may be the same or different, selected from the group consisting of:
a halogen atom,
a $C_{1-8}$ alkyl group and a $C_{1-8}$ alkoxy group, which $C_{1-8}$ alkyl group and $C_{1-8}$ alkoxy group may be each substituted by 1 to 3 substituents, which may be the same or different, selected from the group consisting of a halogen atom, a hydroxy group, and an aryl group,
an aryl group, and
a heteroaryl group, and
Y is a nitrogen atom.

3. The compound of the formula (I) or pharmaceutically acceptable salt thereof according to claim 1, wherein $R^B$ is the formula (II).

4. The compound of the formula (I) or pharmaceutically acceptable salt thereof according to claim 1, wherein
$R^B$ is the formula (II),
V is the formula —$CR^{11}R^{12}$—, wherein $R^{11}$ and $R^{12}$, which may be the same or different, each represent a hydrogen atom or a $C_{1-4}$ alkyl group, or $R^{11}$ and $R^{12}$, taken together with the adjacent carbon atom, may form $C_{3-6}$ cycloalkane, and
m is 1.

5. The compound of the formula (I) or pharmaceutically acceptable salt thereof according to claim 3, wherein
V is the formula —$CR^{11}R^{12}$—, wherein $R^{11}$ and $R^{12}$, which may be the same or different, each represent a hydrogen atom or a $C_{1-4}$ alkyl group, and
m is 1.

6. The compound of the formula (I) or pharmaceutically acceptable salt thereof according to claim 3, wherein
V is the formula —CO—NH—,
W is a single bond, and
m is 1.

7. The compound of the formula (I) or pharmaceutically acceptable salt thereof according to claim 3, wherein
V is the formula —CO—NH—,
W is a single bond, and
m is 0.

8. The compound of the formula (I) or pharmaceutically acceptable salt thereof according to claim 1, wherein
Ring A is an aryl group which may be substituted by 1 to 3 substituents, which may be the same or different, selected from the group consisting of (i) to (vii) below:
(i) a halogen atom,
(ii) a hydroxy group,
(iii) a $C_{1-8}$ alkyl group which may be substituted by 1 to 3 substituents, which may be the same or different, selected from the group consisting of:
a hydroxy group,
a halogen atom,
a $C_{1-8}$ alkoxy group which may be substituted by one saturated heterocyclyl group,
a $C_{3-8}$ cycloalkyl group,
a saturated heterocyclyl group, and
an aryl group,
(iv) a $C_{1-8}$ alkoxy group which may be substituted by 1 to 3 substituents, which may be the same or different, selected from the group consisting of:
(iv-1) a halogen atom,
(iv-2) an oxo group,
(iv-3) a $C_{3-8}$ cycloalkyl group,
(iv-4) a saturated heterocyclyl group which may be substituted by 1 or 2 substituents,
which may be the same or different, selected from the group consisting of:
a halogen atom,
a $C_{1-8}$ alkyl group, and
an oxo group,
(iv-5) an aryl group,
(iv-6) a heteroaryl group,
(iv-7) a $C_{1-8}$ alkoxy group which may be substituted by 1 to 3 substituents, which may be the same or different, selected from the group consisting of:
a halogen atom,
a saturated heterocyclyl group, and
a $C_{1-8}$ alkoxy group,
(iv-8) a $C_{3-8}$ cycloalkyloxy group,
(iv-9) an aryloxy group which may be substituted by one substituent selected from the group consisting of:
a halogen atom,
a $C_{1-8}$ alkyl group which may be substituted by 1 to 3 halogen atoms, and
a $C_{1-8}$ alkoxy group,
(iv-10) a $C_{1-8}$ alkylsulfonyl group, and
(iv-11) an arylsulfonyl group,
(v) a $C_{2-8}$ alkenyloxy group,
(vi) a mono$C_{1-8}$ alkylamino group which may be substituted by one aryl group, and
(vii) a di$C_{1-8}$ alkylamino group.

9. The compound of the formula (I) or pharmaceutically acceptable salt thereof according to claim 1, wherein
Ring A is an aryl group which may be substituted by 1 to 3 substituents, which may be the same or different, selected from the group consisting of:
a halogen atom,
a hydroxy group,
a $C_{1-8}$ alkyl group which may be substituted by 1 to 3 substituents, which may be the same or different, selected from the group consisting of:
a halogen atom,
a $C_{3-8}$ cycloalkyl group, and
an aryl group,
a $C_{1-8}$ alkoxy group which may be substituted by 1 to 3 substituents, which may be the same or different, selected from the group consisting of:
a halogen atom,
an oxo group,
a $C_{3-8}$ cycloalkyl group,
a saturated heterocyclyl group which may be substituted by 1 or 2 substituents, which may be the same or different, selected from the group consisting of a $C_{1-8}$ alkyl group, and an oxo group,
an aryl group,
a heteroaryl group,
a $C_{1-8}$ alkoxy group which may be substituted by one $C_{1-8}$ alkoxy group,
a $C_{3-8}$ cycloalkyloxy group, and
an aryloxy group which may be substituted by one substituent selected from the group consisting of a halogen atom, a $C_{1-8}$ alkyl group which may be substituted by 1 to 3 halogen atoms, and a $C_{1-8}$ alkoxy group,
a $C_{2-8}$ alkenyloxy group, and
a di$C_{1-8}$ alkylamino group.

10. The compound of the formula (I) or pharmaceutically acceptable salt thereof according to claim 1, wherein $R^c$ is a hydrogen atom or a $C_{1-4}$ alkyl group.

11. A pharmaceutical composition comprising the compound or pharmaceutically acceptable salt thereof according to claim 1 and a pharmaceutically acceptable carrier or diluent.

12. A method for inhibiting monoacylglycerol acyltransferase 2 comprising administering to a subject in need of inhibiting monoacylglycerol acyltransferase 2 an effective amount of the compound or pharmaceutically acceptable salt thereof according to claim 1.

13. A method for inhibiting fat absorption comprising administering to a subject in need of inhibiting fat absorption an effective amount of the compound or pharmaceutically acceptable salt thereof according to claim 1.

14. A method treatment of obesity comprising administering to a subject in need of said treatment an effective amount of the compound or pharmaceutically acceptable salt thereof according to claim 1.

15. A method for treatment of lipid metabolism abnormality comprising administering to a subject in need of said treatment an effective amount of the compound or pharmaceutically acceptable salt thereof according to claim 1.

* * * * *